US012441689B2

(12) United States Patent
Nakache et al.

(10) Patent No.: US 12,441,689 B2
(45) Date of Patent: Oct. 14, 2025

(54) ACSS2 INHIBITORS AND METHODS OF USE THEREOF

(71) Applicant: EpiVario, Inc., Philadelphia, PA (US)

(72) Inventors: Philippe Nakache, Ness Ziona (IL); Omri Erez, Rehovot (IL); Simone Botti, Rehovot (IL); Andreas Goutopoulos, Boston, MA (US); Harry Finch, Bedfordshire (GB)

(73) Assignee: EpiVario, Inc., Philadelphia, PA (US)

( * ) Notice: Subject to any disclaimer, the term of this patent is extended or adjusted under 35 U.S.C. 154(b) by 925 days.

(21) Appl. No.: 17/609,392

(22) PCT Filed: May 14, 2020

(86) PCT No.: PCT/IL2020/050524

§ 371 (c)(1),
(2) Date: Nov. 7, 2021

(87) PCT Pub. No.: WO2020/230134

PCT Pub. Date: Nov. 19, 2020

(65) Prior Publication Data

US 2023/0084752 A1 Mar. 16, 2023

Related U.S. Application Data

(63) Continuation of application No. 16/411,168, filed as application No. PCT/IL2020/050524 on May 14, 2020, now Pat. No. 10,851,064.

(Continued)

(51) Int. Cl.

| | |
|---|---|
| ***C07D 231/22*** | (2006.01) |
| ***A61K 31/4152*** | (2006.01) |
| ***A61K 31/4155*** | (2006.01) |
| ***A61K 31/4184*** | (2006.01) |
| ***A61K 31/422*** | (2006.01) |
| ***A61K 31/427*** | (2006.01) |
| ***A61K 31/4439*** | (2006.01) |

(Continued)

(52) U.S. Cl.

CPC ........ *C07D 231/22* (2013.01); *A61K 31/4152* (2013.01); *A61K 31/4155* (2013.01); *A61K 31/4184* (2013.01); *A61K 31/422* (2013.01); *A61K 31/427* (2013.01); *A61K 31/4439* (2013.01); *A61K 31/454* (2013.01); *A61K 31/497* (2013.01); *A61K 31/506* (2013.01); *A61K 45/06* (2013.01); *A61P 3/00* (2018.01); *A61P 25/00* (2018.01); *A61P 29/00* (2018.01); *A61P 31/12* (2018.01); *A61P 35/00* (2018.01); *A61P 37/02* (2018.01); *C07D 231/20* (2013.01); *C07D 231/26* (2013.01); *C07D 233/70* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 403/12* (2013.01); *C07D 405/04* (2013.01); *C07D 405/10* (2013.01); *C07D 405/12* (2013.01); *C07D 405/14* (2013.01); *C07D 409/04* (2013.01); *C07D 409/12* (2013.01); *C07D 413/10* (2013.01); *C07D 413/12* (2013.01); *C07D 413/14* (2013.01); *C07D 417/12* (2013.01); *C07F 5/025* (2013.01)

(58) Field of Classification Search

CPC .. C07D 231/22; C07D 231/20; C07D 401/04; C07D 401/10; C07D 401/12; C07D 403/12; C07D 405/04; C07D 405/12; C07D 405/14; C07D 409/04; C07D 409/12; C07D 413/10; C07D 413/12; C07D 413/14; C07D 417/12; A61K 2300/00; A61K 31/4152; A61K 31/4155; A61K 31/4178; A61K 31/4184; A61K 31/4196; A61K 31/422; A61K 31/427; A61K 31/4439; A61K 31/454; A61K 31/4709; A61K 31/497; A61K 31/506; A61K 31/69; A61K 45/06

See application file for complete search history.

(56) References Cited

U.S. PATENT DOCUMENTS

| | | | |
|---|---|---|---|
| 3,905,997 | A | 9/1975 | Zinnes et al. |
| 4,207,317 | A | 6/1980 | Walker |

(Continued)

FOREIGN PATENT DOCUMENTS

| | | | |
|---|---|---|---|
| CA | 2984073 | | 4/2019 |
| DE | 2324893 | A1 | 12/1974 |

(Continued)

OTHER PUBLICATIONS

Gaffer, et al, Synthesis and Antioxidant Activity of Some New Thiazolyl-Pyrazolone Derivatives, J. Heterocyclic Chem., 54, 331 (2017). (Year: 2017).*

(Continued)

*Primary Examiner* — Erich A Leeser

(74) *Attorney, Agent, or Firm* — Meunier Carlin & Curfman LLC

(57) ABSTRACT

The present invention relates to novel ACSS2 inhibitors having activity as anti-cancer therapy, treatment of alcoholism, and viral infection (e.g., CMV), composition and methods of preparation thereof, and uses thereof for treating viral infection, alcoholism, alcoholic steatohepatitis (ASH), non-alcoholic steatohepatitis (NASH), obesity/weight gain, anxiety, depression, post-traumatic stress disorder, inflammatory/autoimmune conditions and cancer, including metastatic cancer, advanced cancer, and dmg resistant cancer of various types.

13 Claims, No Drawings

Related U.S. Application Data

(60) Provisional application No. 62/847,348, filed on May 14, 2019.

(51) Int. Cl.

| | |
|---|---|
| ***A61K 31/454*** | (2006.01) |
| ***A61K 31/497*** | (2006.01) |
| ***A61K 31/506*** | (2006.01) |
| ***A61K 45/06*** | (2006.01) |
| ***A61P 3/00*** | (2006.01) |
| ***A61P 25/00*** | (2006.01) |
| ***A61P 29/00*** | (2006.01) |
| ***A61P 31/12*** | (2006.01) |
| ***A61P 35/00*** | (2006.01) |
| ***A61P 37/02*** | (2006.01) |
| ***C07D 231/20*** | (2006.01) |
| ***C07D 231/26*** | (2006.01) |
| ***C07D 233/70*** | (2006.01) |
| ***C07D 401/04*** | (2006.01) |
| ***C07D 401/10*** | (2006.01) |
| ***C07D 401/12*** | (2006.01) |
| ***C07D 401/14*** | (2006.01) |
| ***C07D 403/04*** | (2006.01) |
| ***C07D 403/10*** | (2006.01) |
| ***C07D 403/12*** | (2006.01) |
| ***C07D 405/04*** | (2006.01) |
| ***C07D 405/10*** | (2006.01) |
| ***C07D 405/12*** | (2006.01) |
| ***C07D 405/14*** | (2006.01) |
| ***C07D 409/04*** | (2006.01) |
| ***C07D 409/12*** | (2006.01) |
| ***C07D 413/10*** | (2006.01) |
| ***C07D 413/12*** | (2006.01) |
| ***C07D 413/14*** | (2006.01) |
| ***C07D 417/12*** | (2006.01) |
| ***C07F 5/02*** | (2006.01) |

(56) References Cited

U.S. PATENT DOCUMENTS

| | | | |
|---|---|---|---|
| 2017/0190689 | A1 | 7/2017 | Sparks et al. |
| 2019/0263758 | A1 | 8/2019 | Nakache et al. |

FOREIGN PATENT DOCUMENTS

| | | | |
|---|---|---|---|
| DE | 140966 | A1 | 4/1980 |
| JP | H11291635 | A | 10/1999 |
| WO | WO 2003/013484 | A2 | 2/2003 |
| WO | WO 2003/024448 | A2 | 3/2003 |
| WO | WO 2007/026215 | A1 | 3/2007 |
| WO | WO 2011/143425 | A2 | 11/2011 |
| WO | WO 2013/159224 | A1 | 10/2013 |
| WO | WO 2015/175845 | A1 | 11/2015 |
| WO | WO 2019/067528 | A1 | 4/2019 |
| WO | WO 2019/097515 | A1 | 5/2019 |
| WO | WO 2020/230134 | A1 | 11/2020 |

OTHER PUBLICATIONS

Banerjee et al. "Small molecule ACSS2 inhibitors target acetate metabolizing tumor cells in hypoxic conditions" 2018: 78(13)3510-3510.

Björnson et al. "Stratification of hepatocellular carcinoma patients based on acetate utilization" Cell reports. Dec. 1, 2015;13(9):2014-26.

Bulusu et al. "Acetate recapturing by nuclear acetyl-CoA synthetase 2 prevents loss of histone acetylation during oxygen and serum limitation" Cell reports. Jan. 17, 2017;18(3):647-58.

"Cancer facts & figures: American Cancer Society", The Society; 2008.

CAS Registry No. 373639-90-8; CA Index Name: Benzamide, N-[4,5-dihydro-5-oxo-1-(2,4,6-trichlorophenyl)-1H-pyrazol-4-yl]-3-nitro-; Entered STN: Dec. 5, 2001. Also published in URL: <http://www.chemspider.com/Chemical-Structure.514218.html>, and as PubChem CID: 591511 ("3-Nitro-N-[5-oxo-1-(2,4,6-trichlorophenyl)-4,5-dihydro-1H-pyrazol-4-yl]benzamide"; Create date: Mar. 27, 2005. URL: <https://pubchem.ncbi.nlm.nih.gov/compound/591511>). Dec. 5, 2001 (Dec. 5, 2001).

CAS Registry No. 373639-87-3; CA Index Name: Benzamide, 3-amino-N-[4,5-dihydro-5-oxo-1-(2,4,6-trichlorophenyl)-1H-pyrazol-4-yl]-; Entered STN: Dec. 5, 2001. Dec. 5, 2001 (Dec. 5, 2001).

CAS Registry No. 97635-51-3; CA Index Name: Benzamide, 3-amino-N-[2,5-dihydro-5-oxo-1-(2,4,5-trichlorophenyl)-1H-pyrazol-4-yl]-; Entered STN: Aug. 18, 1985. See URL: <http://www.ichemistry.cn/chemistry/97635-51-3.htm> or URL: <http://www.chemspider.com/Chemical-Structure.2290805.html>. Aug. 18, 1985 (Aug. 18, 1985) & Commercially available online, such as in URL: <http://www.chembuyersguide.com/partners/sage-493.html>.

CAS Registry No. 1808705-10-3, CA Index Name: 1H-Pyrazole-4-carboxamide, 1-(4,6-dimethyl-2-pyrimidinyl)-4,5-dihydro-3-methyl-N-[2-(1-methylethyl)phenyl]-5-oxo-, Entered STN: Sep. 30, 2015.

CAS Registry No. 1791350-17-8, CA Index Name: 1H-Pyrazole-4-carboxamide, 1-(2,4-dimethylphenyl)-4,5-dihydro-3-methyl-N-[1-(1-methylethyl)-1H-pyrazol-5-yl]-5-oxo-, Entered STN: Jun. 30, 2015.

CAS Registry No. 1787906-31-3, CA Index Name: 1H-Pyrazole-4-carboxamide, 4,5-dihydro-3-methyl-N-[3-methyl-1-(phenylmethyl)-1H-pyrazol-5-yl]-5-oxo-1-phenyl-, Entered STN: Jun. 25, 2015.

CAS Registry No. 1444619-19-5, CA Index Name: 1H-Pyrazole-4-carboxamide, 1-(4-fluorophenyl)-4,5-dihydro-3-methyl-5-oxo-N-(tetrahydro-1,1-dioxido-3-thienyl)-, Entered STN: Jul. 16, 2013.

CAS Registry No. 1444612-86-5, CA Index Name: 1H-Pyrazole-4-carboxamide, 1-(3-chlorophenyl)-4,5-dihydro-3-methyl-5-oxo-N-(tetrahydro-1,1-dioxido-3-thienyl)-, Entered STN: Jun. 16, 2013.

CAS Registry No. 1444608-50-7, CA Index Name: 1H-Pyrazole-4-carboxamide, 1-(2,4-dimethylphenyl)-4,5-dihydro-3-methyl-5-oxo-N-(tetrahydro-1,1-dioxido-3-thienyl)-, Entered STN: Jul. 16, 2013.

CAS Registry No. 1427938-63-3, CA Index Name: 1H-Pyrazole-4-carboxamide, 4,5-dihydro-3-methyl-5-oxo-N-2-pyridinyl-1-(tetrahydro-1,1-dioxido-3-thienyl)-, Entered STN: Apr. 11, 2013.

CAS Registry No. 1424277-15-5, CA Index Name: 1H-Pyrazole-4-carboxamide, 4,5-dihydro-3-methyl-5-oxo-1-(tetrahydro-1,1-dioxido-3-thienyl)-N-2-thiazolyl, Entered STN: Mar. 15, 2013.

CAS Registry No. 1424179-52-1, CA Index Name: 1H-Pyrazole-4-carboxamide, 4,5-dihydro-3-methyl-5-oxo-1-(tetrahydro-1,1-dioxido-3-thienyl)-N-1,3,4-thiadiazol-2-yl, Entered STN: Mar. 15, 2013.

CAS Registry No. 1424083-43-1, CA Index Name: 1H-Pyrazole-4-carboxamide, 4,5-dihydro-3-methyl-5-oxo-N-3-pyridinyl-1-(tetrahydro-1,1-dioxido-3-thienyl), Entered STN: Mar. 15, 2013.

CAS Registry No. 1423725-39-6, CA Index Name: 1H-Pyrazole-4-carboxamide, N-1,3-benzodioxol-5-yl-4,5-dihydro-3-methyl-5-oxo-1-(tetrahydro-1,1-dioxido-3-thienyl)—Entered STN: Mar. 14, 2013.

CAS Registry No. 1423670-51-2, CA Index Name: 1H-Pyrazole-4-carboxamide, 4,5-dihydro-3-methyl-5-oxo-N-phenyl-1-(tetrahydro-1,1-dioxido-3-thienyl), Entered STN: Mar. 14, 2013.

CAS Registry No. 1423624-35-4, CA Index Name: 1H-Pyrazole-4-carboxamide, N-(2-chloro-3-pyridinyl)-4,5-dihydro-3-methyl-5-oxo-1-(tetrahydro-1,1-dioxido-3- thienyl)-, Entered STN: Mar. 14, 2013.

CAS Registry No. 1376380-77-6, CA Index Name: 1H-Pyrazole-4-carboxamide, N-[4-(3-fluorophenyl)-2-thiazolyl]-4,5-dihydro-3-methyl-5-oxo-1-(tetrahydro-1,1-dioxido-3-thienyl)-, Entered STN: Jun. 7, 2012.

CAS Registry No. 1375980-06-5, CA Index Name: 1H-Pyrazole-4-carboxamide, N-(6-ethyl-2-benzothiazolyl)-4,5-dihydro-3-methyl-5-oxo-1-(tetrahydro-1,1-dioxido-3-thienyl)-, Entered STN: Jun. 7, 2012.

(56) References Cited

OTHER PUBLICATIONS

CAS Registry No. 483276-32-0, CA Index Name: 1H-Pyrazole-4-carbothioamide, 1-[4-(4-chiorophenyl)-2-thiazolyl]-4,5-dihydro-5-oxo-N,3-diphenyl-, Entered STN: Jan. 30, 2003.
CAS Registry No. 483276-31-9, CA Index Name: 1H-Pyrazole-4-carboxamide, N-(4-chlorophenyl)-1-[4-(4-chlorophenyl)-2-thiazolyl]-4,5-dihydro-5-oxo-3-phenyl-, Entered STN: Jan. 30, 2003.
Chen et al. "Coordinate regulation of stress signaling and epigenetic events by Acss2 and HIF-2 in cancer cells" PLoS One. Dec. 27, 2017;12(12):e0190241.
Chen et al. "The acetate/ACSS2 switch regulates HIF-2 stress signaling in the tumor cell microenvironment" PloS one. Feb. 17, 2015;10(2):e0116515.
Chen et al. "TM6SF2 E167K variant, a novel genetic susceptibility variant, contributing to nonalcoholic fatty liver disease" Journal of clinical and translational hepatology. Dec. 28, 2015;3(4):265.
Collisson et al. "Comprehensive molecular profiling of lung adenocarcinoma: The cancer genome atlas research network" Nature. 2014;511(7511):543-50.
Comerford et al. "Acetate dependence of tumors" Cell. Dec. 18, 2014;159(7):1591-602.
Dey et al. "ATF4-dependent induction of heme oxygenase 1 prevents anoikis and promotes metastasis" The Journal of clinical investigation. Jul. 1, 2015;125(7):2592-608.
El-Desoky et al. "Utility of isothiocyanates in heterocyclic synthesis" Sulfur Letters. Jan. 1, 2002;25(5):199-205.
Ertel et al. "Synthese von 1-Hydroxyimidazolen und 1-Hydroxyimidazol-3-oxiden" Justus Liebigs Annalen der Chemie. Oct. 17, 1974;1974(9):1399-406.
Fang et al. "In vivo antitumor activity of pegylated zinc protoporphyrin: targeted inhibition of heme oxygenase in solid tumor" Cancer Research. Jul. 1, 2003;63(13):3567-74.
Gaffer et al. "Synthesis and antioxidant activity of some new thiazolyl-pyrazolone derivatives" Journal of Heterocyclic Chemistry. Jan. 2017;54(1):331-40.
Gao et al. "Acetate functions as an epigenetic metabolite to promote lipid synthesis under hypoxia. Nature communications" Jun. 30, 2016;7:11960.
Gräff et al. "Histone acetylation: molecular mnemonics on the chromatin" Nature Reviews Neuroscience. Feb. 2013;14(2):97-111.
Harriman et al. "Acetyl-CoA carboxylase inhibition by ND-630 reduces hepatic steatosis, improves insulin sensitivity, and modulates dyslipidemia in rats" Proceedings of the National Academy of Sciences. Mar. 29, 2016;113(13):E1796-805.
Hosios et al. "Acetate metabolism in cancer cells" Cancer & metabolism. Dec. 2014;2(1):27.
Huang et al. "ACSS2 promotes systemic fat storage and utilization through selective regulation of genes involved in lipid metabolism" Proceedings of the National Academy of Sciences. Oct. 2, 2018;115(40):E9499-506.
International Search Report for PCT Application No. PCT/IL2020/050524 dated Sep. 7, 2020.
International Search Report for PCT Application No. PCT/IL2021/050541 dated Jul. 28, 2021.
Kamphorst et al. "Quantitative analysis of acetyl-CoA production in hypoxic cancer cells reveals substantial contribution from acetate" Cancer & metabolism. Dec. 2014;2(1):23.
Kort et al. "Subtype-selective Nav1. 8 sodium channel blockers: Identification of potent, orally active nicotinamide derivatives" Bioorganic & medicinal chemistry letters. Nov. 15, 2010;20(22):6812-5.
Lakhter et al. "Glucose-independent acetate metabolism promotes melanoma cell survival and tumor growth" Journal of Biological Chemistry. Oct. 14, 2016;291(42):21869-79.
Li et al. "Nucleus-translocated ACSS2 promotes gene transcription for lysosomal biogenesis and autophagy" Molecular cell. Jun. 1, 2017;66(5):684-97.
Linchenko et al. "Cyclizations in the reactions of isocyanates with compounds containing active methylene groups in the presence of triethylamine" Russian chemical bulletin. May 2006;55(5):873-8.
Lyssiotis et al. "Acetate fuels the cancer engine. Cell" Dec. 18, 2014;159(7):1492-4.
Márquez et al. "Tricarboxylic Acid Cycle Activity and Remodeling of Glycerophosphocholine Lipids Support Cytokine Induction in Response to Fungal Patterns" Cell reports. Apr. 9, 2019;27(2):525-36.
Marzouk et al. "Synthesis and characterization of novel pyrazolone derivatives" European Journal of Chemistry. Mar. 31, 2014;5(1):24-32.
Mashimo et al. "Acetate is a bioenergetic substrate for human glioblastoma and brain metastases" Cell. Dec. 18, 2014;159(7):1603-14.
McKnight SL. "A hypothetical means of treating or preventing cancer" Cancer & metabolism. May 2014;2(1):07.
Mews et al. "Acetyl-CoA synthetase regulates histone acetylation and hippocampal memory" Nature. Jun. 2017;546(7658):381-6.
Nikitina et al. "Synthesis and antiviral activity of 1-hydroxy-2-(2-hydroxyphenyl) imidazoles against vaccinia virus" Russian Chemical Bulletin. Mar. 2019;68(3):634-7.
Pinheiro et al. "Pd-catalyzed carbonylative α-arylation of azlactones: A formal four-component coupling route to α, α-disubstituted amino acids" Journal of Catalysis. Aug. 1, 2018;364:366-70.
PubChem Compound CID 137186565. National Center for Biotechnology Information. Create date: Jan. 25, 2019. URL: <https://pubchem.ncbi.nlm.nih.gov/compound/137186565>. & Zinc604419253. URL: <http://zinc.docking.org/substances/ZINC000604419253/>. Jan. 25, 2019 (Jan. 25, 2019).
Ribeiro et al. "Possible involvement of ACSS2 gene in alcoholism" Journal of Neural Transmission. Sep. 1, 2017;124(9):1151-8.
Saeed et al. "Synthesis, characterization and biological evaluation of N-(2, 3-dimethyl-5-oxo-1-phenyl-2, 5-dihydro-1 H-pyrazol-4-yl) benzamides" RSC advances. 2015;5(105):86428-39.
Santeusanio et al. "Divergent approach to thiazolylidene derivatives: a perspective on the synthesis of a heterocyclic skeleton from β-amidothioamides reactivity" The Journal of organic chemistry. Sep. 15, 2017;82(18):9773-8.
Schug et al. "Acetyl-CoA synthetase 2 promotes acetate utilization and maintains cancer cell growth under metabolic stress" Cancer cell. Jan. 12, 2015;27(1):57-71.
Schug et al. "The metabolic fate of acetate in cancer" Nature Reviews Cancer. Nov. 2016;16(11):708.
Shang et al. "ZnPPIX inhibits peritoneal metastasis of gastric cancer via its antiangiogenic activity" Biomedicine & Pharmacotherapy. Apr. 1, 2015;71:240-6.
Vysochan et al. "ACSS2-mediated acetyl-CoA synthesis from acetate is necessary for human cytomegalovirus infection" Proceedings of the National Academy of Sciences. Feb. 21, 2017;114(8):E1528-35.
Wakil et al. "Fatty acid metabolism: target for metabolic syndrome" Journal of lipid research. Jan. 1, 2009;50:S138-43.
Wen et al. "Glucose-derived acetate and ACSS2 as key players in cisplatin resistance in bladder cancer" Biochimica et Biophysica Acta (BBA)-Molecular and Cell Biology of Lipids. Mar. 1, 2019;1864(3):413-21.
Yoshii et al. "Cytosolic acetyl-CoA synthetase affected tumor cell survival under hypoxia: the possible function in tumor acetyl-CoA/acetate metabolism" Cancer science. May 2009:100(5):821-7.
Yoshii et al. "Tumor uptake of radiolabeled acetate reflects the expression of cytosolic acetyl-CoA synthetase: implications for the mechanism of acetate PET" Nuclear medicine and biology. Oct. 1, 2009;36(7):771-7.
Yoshii et al. "Acetate/acetyl-CoA metabolism associated with cancer fatty acid synthesis: overview and application" Cancer letters. Jan. 28, 2015;356(2):211-6.
Yun et al. "The importance of acetyl coenzyme A synthetase for 11C-acetate uptake and cell survival in hepatocellular carcinoma" Journal of nuclear medicine. Aug. 1, 2009:50(8):1222-8.
Zhao et al. "ATP-citrate lyase controls a glucose-to-acetate metabolic switch" Cell reports. Oct. 18, 2016;17(4):1037-52.
Zlotorynski E. "Gene expression: ACSS2 boosts local histone acetylation" Nature Reviews Molecular Cell Biology. Jun. 7, 2017;18(7):405.

* cited by examiner

ACSS2 INHIBITORS AND METHODS OF USE THEREOF

CROSS-REFERENCE TO RELATED APPLICATIONS

This application is a National Phase Application of PCT International Application No. PCT/IL2020/050524, filed May 14, 2020, which claims the benefit of U.S. patent application Ser. No. 16/411,168, filed May 14, 2019, and of U.S. Provisional Application No. 62/847,348, filed May 14, 2019, all of which are hereby incorporated by reference.

FIELD OF THE INVENTION

The present invention relates to novel ACSS2 inhibitors, composition and methods of preparation thereof, and uses thereof for treating viral infection (e.g. CMV), alcoholism, alcoholic steatohepatitis (ASH), non-alcoholic steatohepatitis (NASH), metabolic disorders including: obesity, weight gain and hepatic steatosis, neuropsychiatric diseases including: anxiety, depression, schizophrenia, autism and post-traumatic stress disorder, inflammatory/autoimmune conditions and cancer, including metastatic cancer, advanced cancer, and drug resistant cancer of various types.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (*Cancer Facts & Figures* American Cancer Society: Atlanta, GA (2008)). The rate of new cancer cases decreased by an average 0.6% per year among men between 2000 and 2009 and stayed the same for women. From 2000 through 2009, death rates from all cancers combined decreased on average 1.8% per year among men and 1.4% per year among women. This improvement in survival reflects progress in diagnosing at an earlier stage and improvements in treatment. Discovering highly effective anticancer agents with low toxicity is a primary goal of cancer research.

Cell growth and proliferation are intimately coordinated with metabolism. Potentially distinct differences in metabolism between normal and cancerous cells have sparked a renewed interest in targeting metabolic enzymes as an approach to the discovery of new anticancer therapeutics.

It is now appreciated that cancer cells within metabolically stressed microenvironments, herein defined as those with low oxygen and low nutrient availability (i.e., hypoxia conditions), adopt many tumour-promoting characteristics, such as genomic instability, altered cellular bioenergetics and invasive behaviour. In addition, these cancer cells are often intrinsically resistant to cell death and their physical isolation from the vasculature at the tumour site can compromise successful immune responses, drug delivery and therapeutic efficiency, thereby promoting relapse and metastasis, which ultimately translates into drastically reduced patient survival. Therefore, there is an absolute requirement to define therapeutic targets in metabolically stressed cancer cells and to develop new delivery techniques to increase therapeutic efficacy. For instance, the particular metabolic dependence of cancer cells on alternative nutrients (such as acetate) to support energy and biomass production may offer opportunities for the development of novel targeted therapies.

Acetyl-CoA Synthetase Enzyme, ACSS2 as a Target for Cancer Treatment

Acetyl-CoA represents a central node of carbon metabolism that plays a key role in bioenergetics, cell proliferation, and the regulation of gene expression. Highly glycolytic or hypoxic tumors must produce sufficient quantities of this metabolite to support cell growth and survival under nutrient-limiting conditions. Acetate is an important source of acetyl-CoA in hypoxia. Inhibition of acetate metabolism may impair tumor growth. The nucleocytosolic acetyl-CoA synthetase enzyme, ACSS2, supplies a key source of acetyl-CoA for tumors by capturing acetate as a carbon source. Despite exhibiting no gross deficits in growth or development, adult mice lacking ACSS2 exhibit a significant reduction in tumor burden in two different models of hepatocellular carcinoma. ACSS2 is expressed in a large proportion of human tumors, and its activity is responsible for the majority of cellular acetate uptake into both lipids and histones. Further, ACSS2 was identified in an unbiased functional genomic screen as a critical enzyme for the growth and survival of breast and prostate cancer cells cultured in hypoxia and low serum. High expression of ACSS2 is frequently found in invasive ductal carcinomas of the breast, triple-negative breast cancer, glioblastoma, ovarian cancer, pancreatic cancer and lung cancer, and often directly correlates with higher-grade tumours and poorer survival compared with tumours that have low ACSS2 expression. These observations may qualify ACSS2 as a targetable metabolic vulnerability of a wide spectrum of tumors.

Due to the nature of tumorigenesis, cancer cells constantly encounter environments in which nutrient and oxygen availability is severely compromised. In order to survive these harsh conditions, cancer cell transformation is often coupled with large changes in metabolism to satisfy the demands for energy and biomass imposed by continued cellular proliferation. Several recent reports discovered that acetate is used as an important nutritional source by some types of breast, prostate, liver and brain tumors in an acetyl-CoA synthetase 2 (ACSS2)-dependent manner. It was shown that acetate and ACSS2 supplied a significant fraction of the carbon within the fatty acid and phospholipid pools (Comerford et. al. Cell 2014; Mashimo et. al. Cell 2014; Schug et al Cancer Cell 2015*). High levels of ACSS2 due to copy-number gain or high expression were found to correlate with disease progression in human breast prostate and brain tumors. Furthermore, ACSS2, which is essential for tumor growth under hypoxic conditions, is dispensable for the normal growth of cells, and mice lacking ACSS2 demonstrated normal phenotype (Comerford et. al. 2014). The switch to increased reliance on ACSS2 is not due to genetic alterations, but rather due to metabolic stress conditions in the tumor microenvironment. Under normal oxidative conditions, acetyl-CoA is typically produced from citrate via citrate lyase activity. However, under hypoxia, when cells adapt to anaerobic metabolism, acetate becomes a key source for acetyl-CoA and hence, ACSS2 becomes essential and is, defacto, synthetically lethal with hypoxic conditions (see Schug et. al., *Cancer Cell,* 2015, 27:1, pp. 57-71). The accumulative evidences from several studies suggest that ACSS2 may be a targetable metabolic vulnerability of a wide spectrum of tumors.

In certain tumors expressing ACSS2, there is a strict dependency on acetate for their growth or survival, then selective inhibitors of this nonessential enzyme might represent an unusually ripe opportunity for the development of new anticancer therapeutics. If the normal human cells and tissues are not heavily reliant on the activity of the ACSS2 enzyme, it is possible that such agents might inhibit the growth of ACSS2-expressing tumors with a favorable therapeutic window.

Non-alcoholic steatohepatitis (NASH) and alcoholic steatohepatitis (ASH) have a similar pathogenesis and histopathology but a different etiology and epidemiology. NASH and ASH are advanced stages of non-alcoholic fatty liver disease (NAFLD) and alcoholic fatty liver disease (AFLD). NAFLD is characterized by excessive fat accumulation in the liver (steatosis), without any other evident causes of chronic liver diseases (viral, autoimmune, genetic, etc.), and with an alcohol consumption ≤20-30 g/day. On the contrary, AFLD is defined as the presence of steatosis and alcohol consumption >20-30 g/day.

Hepatocyte ethanol metabolism produces free acetate as its endproduct which, largely in other tissues, can be incorporated into acetyl-coenzyme A (acetylcoA) for use in Krebs cycle oxidation, fatty acid synthesis, or as a substrate for protein acetylation. This conversion is catalyzed by the acyl-coenzyme A synthetase short-chain family members 1 and 2 (ACSS1 and ACSS2). The role of acetyl-coA synthesis in control of inflammation opens a novel field of study into the relationship between cellular energy supply and inflammatory disease. It has been shown that ethanol enhances macrophage cytokine production by uncoupling gene transcription from its normal regulatory mechanisms through increased histone acetylation, and that the conversion of the ethanol metabolite acetate to acetyl-coA is crucial to this process.

It was suggested that inflammation is enhanced in acute alcoholic hepatitis in which acetyl-coA synthetases are upregulated and convert the ethanol metabolite acetate to an excess of acetyl-coA which increases proinflammatory cytokine gene histone acetylation by increased substrate concentration and histone deacetylases (HDAC) inhibition, leading to enhanced gene expression and perpetuation of the inflammatory response. The clinical implication of these findings is that modulation of HDAC or ACSS activity might affect the clinical course of alcoholic liver injury in humans. If inhibitors of ACSS1 and 2 can modulate ethanol-associated histone changes without affecting the flow of acetyl-coA through the normal metabolic pathways, then they have the potential to become much needed effective therapeutic options in acute alcoholic hepatitis. Therefore, synthesis of metabolically available acetyl-coA from acetate is critical to the increased acetylation of proinflammatory gene histones and consequent enhancement of the inflammatory response in ethanol-exposed macrophages. This mechanism is a potential therapeutic target in acute alcoholic hepatitis.

Cytosolic acetyl-CoA is the precursor of multiple anabolic reactions including de-novo fatty acids (FA) synthesis. Inhibition of FA synthesis may favorably affect the morbidity and mortality associated with Fatty-liver metabolic syndromes (Wakil S J, Abu-Elheiga L A. 2009. 'Fatty acid metabolism: Target for metabolic syndrome'. *J. Lipid Res.*) and because of the pivotal role of Acetyl-CoA Carboxylase (ACC) in regulating fatty acid metabolism, ACC inhibitors are under investigation as clinical drug targets in several metabolic diseases, including nonalcoholic fatty liver disease (NAFLD) and nonalcoholic steatohepatitis (NASH). Inhibition of ACSS2 is expected to directly reduce fatty-acid accumulation in the liver through its effect on Acetyl-CoA flux from acetate that is present in the liver at high levels due to the hepatocyte ethanol metabolism. Furthermore, ACSS2 inhibitors are expected to have a better safety profile than ACC inhibitors since they are expected only to affect the flux from Acetate that is not a major source for Ac-CoA in normal conditions (Harriman G et. al., 2016. "Acetyl-CoA carboxylase inhibition by ND-630 reduces hepatic steatosis, improves insulin sensitivity, and modulates dyslipidemia in rats" PNAS). In addition, mice lacking ACSS2 showed reduced body weight and hepatic steatosis in a diet-induced obesity model (Z. Huang et al., ACSS2 promotes systemic fat storage and utilization through selective regulation of genes involved in lipid metabolism PNAS 115, (40), E9499-E9506, 2018).

ACSS2 is also shown to enter the nucleus under certain condition (hypoxia, high fat etc.) and to affect histone acetylation and crotonylation by making available acetyl-CoA and crotonyl-CoA and thereby regulate gene expression. For example, ACSS2 decrease is shown to lower levels of nuclear acetyl-CoA and histone acetylation in neurons affecting the expression of many neuronal genes. In the hippocampus such reductions in ACSS2 lead to effects on memory and neuronal plasticity (Mews P, et al., Nature, Vol 546, 381, 2017). Such epigenetic modifications are implicated in neuropsychiatric diseases such as anxiety, PTSD, depression etc. (Graff, J et al. Histone acetylation: molecular mnemonics on chromatin. Nat Rev. Neurosci. 14, 97-111 (2013)). Thus, an inhibitor of ACSS2 may find useful application in these conditions.

Nuclear ACSS2 is also shown to promote lysosomal biogenesis, autophagy and to promote brain tumorigenesis by affecting Histone H3 acetylation (Li, X et al.: Nucleus-Translocated ACSS2 Promotes Gene Transcription for Lysosomal Biogenesis and Autophagy, Molecular Cell 66, 1-14, 2017). In addition, nuclear ACSS2 is shown to activate HIF-2alpha by acetylation and thus accelerate growth and metastasis of HIF2alpha-driven cancers such as certain Renal Cell Carcinoma and Glioblastomas (Chen, R. et al. Coordinate regulation of stress signaling and epigenetic events by ACSS2 and HIF-2 in cancer cells, Plos One, 12 (12) 1-31, 2017).

SUMMARY OF THE INVENTION

This invention provides a compound or its pharmaceutically acceptable salt, optical isomer, tautomer, hydrate, N-oxide, reverse amide analog, prodrug, isotopic variants (e.g., deuterated analog), PROTAC, pharmaceutical product or any combination thereof, represented by the structure of formula I-III(a), and by the structures listed in Table 1, as defined herein below. In various embodiments, the compound is an Acyl-CoA Synthetase Short-Chain Family Member 2 (ACSS2) inhibitor.

This invention further provides a pharmaceutical composition comprising a compound or its pharmaceutically acceptable salt, optical isomer, tautomer, hydrate, N-oxide, reverse amide analog, prodrug, isotopic variants (e.g., deuterated analog), PROTAC, pharmaceutical product or any combination thereof, represented by the structure of formula I-III(a), and by the structures listed in Table 1, as defined herein below, and a pharmaceutically acceptable carrier.

This invention further provides a method of treating, suppressing, reducing the severity, reducing the risk of developing or inhibiting cancer comprising administering a compound represented by the structure of formula I-III(a), and by the structures listed in Table 1, as defined herein below, to a subject suffering from cancer under conditions effective to treat, suppress, reduce the severity, reduce the risk of developing, or inhibit said cancer. In various embodiments, the cancer is selected from the list of: hepatocellular carcinoma, melanoma (e.g., BRAF mutant melanoma), glioblastoma, breast cancer (e.g., invasive ductal carcinomas of the breast, triple-negative breast cancer), prostate cancer, liver cancer, brain cancer, ovarian cancer, lung cancer, Lewis lung carcinoma (LLC), colon carcinoma, pancreatic cancer, renal cell carcinoma and mammary carcinoma. In various embodiments, the cancer is early cancer, advanced cancer, invasive cancer, metastatic cancer, drug resistant cancer or any combination thereof. In various embodiments, the subject has been previously treated with chemotherapy, immunotherapy, radiotherapy, biological therapy, surgical intervention, or any combination thereof. In various embodiments, the compound is administered in combination with an anti-cancer therapy. In various embodiments, the anti-cancer therapy is chemotherapy, immunotherapy, radiotherapy, biological therapy, surgical intervention, or any combination thereof.

This invention further provides a method of suppressing, reducing or inhibiting tumour growth in a subject, comprising administering a compound represented by the structure of formula I-III(a), and by the structures listed in Table 1, as defined herein below, to a subject suffering from cancer under conditions effective to suppress, reduce or inhibit said tumour growth in said subject. In various embodiments, the tumor growth is enhanced by increased acetate uptake by cancer cells of said cancer. In various embodiments, the increased acetate uptake is mediated by ACSS2. In various embodiments, the cancer cells are under hypoxic stress. In various embodiments, the tumor growth is suppressed due to suppression of lipid (e.g., fatty acid) synthesis and/or histones synthesis induced by ACSS2 mediated acetate metabolism to acetyl-CoA. In various embodiments, the tumor growth is suppressed due to suppressed regulation of histones acetylation and function induced by ACSS2 mediated acetate metabolism to acetyl-CoA.

This invention further provides a method of suppressing, reducing or inhibiting lipid synthesis and/or regulating histones acetylation and functioning a cell, comprising contacting a compound represented by the structure of formula I-III(a), and by the structures listed in Table 1, as defined herein below, with a cell under conditions effective to suppress, reduce or inhibit lipid synthesis and/or regulating histones acetylation and function in said cell. In various embodiments, the cell is a cancer cell.

This invention further provides a method of binding an ACSS2 inhibitor compound to an ACSS2 enzyme, comprising the step of contacting an ACSS2 enzyme with an ACSS2 inhibitor compound represented by the structure of formula I-III(a), and by the structures listed in Table 1, as defined herein below, in an amount effective to bind the ACSS2 inhibitor compound to the ACSS2 enzyme.

This invention further provides a method of suppressing, reducing or inhibiting acetyl-CoA synthesis from acetate in a cell, comprising contacting a compound represented by the structure of formula I-III(a), and by the structures listed in Table 1, as defined herein below, with a cell, under conditions effective to suppress, reduce or inhibit acetyl-CoA synthesis from acetate in said cell. In various embodiments, the cell is a cancer cell. In various embodiments, the synthesis is mediated by ACSS2.

This invention further provides a method of suppressing, reducing or inhibiting acetate metabolism in a cancer cell, comprising contacting a compound represented by the structure of formula I-III(a), and by the structures listed in Table 1, as defined herein below, with a cancer cell, under conditions effective to suppress, reduce or inhibit acetate metabolism in said cells. In various embodiments, the acetate metabolism is mediated by ACSS2. In various embodiments, the cancer cell is under hypoxic stress.

This invention further provides a method of treating, suppressing, reducing the severity, reducing the risk of developing or inhibiting human alcoholism in a subject, comprising administering a compound represented by the structure of formula I-III(a), and by the structures listed in Table 1, as defined herein below, to a subject suffering from alcoholism under conditions effective to treat, suppress, reduce the severity, reduce the risk of developing, or inhibit alcoholism in said subject.

This invention further provides a method of treating, suppressing, reducing the severity, reducing the risk of developing or inhibiting a viral infection in a subject, comprising administering a compound represented by the structure of formula I-III(a), and by the structures listed in Table 1, as defined herein below, to a subject suffering from a viral infection under conditions effective to treat, suppress, reduce the severity, reduce the risk of developing, or inhibit the viral infection in said subject. In various embodiments, the viral infection is human cytomegalovirus (HCMV) infection.

This invention further provides a method of treating, suppressing, reducing the severity, reducing the risk of developing or inhibiting a non-alcoholic steatohepatitis (NASH) in a subject, comprising administering a compound represented by the structure of formula I-III(a), and by the structures listed in Table 1, as defined herein below, to a subject suffering from non-alcoholic steatohepatitis (NASH) under conditions effective to treat, suppress, reduce the severity, reduce the risk of developing, or inhibit the non-alcoholic steatohepatitis (NASH) in said subject.

This invention further provides a method of treating, suppressing, reducing the severity, reducing the risk of developing or inhibiting an alcoholic steatohepatitis (ASH) in a subject, comprising administering a compound represented by the structure of formula I-III(a), and by the structures listed in Table 1, as defined herein below, to a subject suffering from an alcoholic steatohepatitis (ASH) under conditions effective to treat, suppress, reduce the severity, reduce the risk of developing, or inhibit the alcoholic steatohepatitis (ASH) in said subject.

This invention further provides a method of treating, suppressing, reducing the severity, reducing the risk of developing or inhibiting a metabolic disorder in a subject, comprising administering a compound represented by the structure of formula I-III(a), and by the structures listed in Table 1, as defined herein below, to a subject suffering from metabolic disorder under conditions effective to treat, suppress, reduce the severity, reduce the risk of developing, or inhibit metabolic disorder in said subject. In various embodiment, the metabolic disorder is selected from: obesity, weight gain, hepatic steatosis and fatty liver disease.

This invention further provides a method of treating, suppressing, reducing the severity, reducing the risk of developing or inhibiting a neuropsychiatric disease or disorder in a subject, comprising administering a compound represented by the structure of formula I-III(a), and by the structures listed in Table 1, as defined herein below, to a subject suffering from neuropsychiatric disease or disorder under conditions effective to treat, suppress, reduce the severity, reduce the risk of developing, or inhibit neuropsychiatric disease or disorder in said subject. In some embodiments, the neuropsychiatric disease or disorder is selected from: anxiety, depression, schizophrenia, autism and post-traumatic stress disorder.

This invention further provides a method of treating, suppressing, reducing the severity, reducing the risk of developing or inhibiting inflammatory condition in a subject, comprising administering a compound represented by the structure of formula I-III(a), and by the structures listed in Table 1, as defined herein below, to a subject suffering from inflammatory condition under conditions effective to treat, suppress, reduce the severity, reduce the risk of developing, or inhibit inflammatory condition in said subject.

This invention further provides a method of treating, suppressing, reducing the severity, reducing the risk of developing or inhibiting an autoimmune disease or disorder in a subject, comprising administering a compound represented by the structure of formula I-III(a), and by the structures listed in Table 1, as defined herein below, to a subject suffering from an autoimmune disease or disorder under conditions effective to treat, suppress, reduce the severity, reduce the risk of developing, or inhibit the autoimmune disease or disorder in said subject.

DETAILED DESCRIPTION OF THE INVENTION

In various embodiments, this invention is directed to a compound represented by the structure of formula (I):

(I)

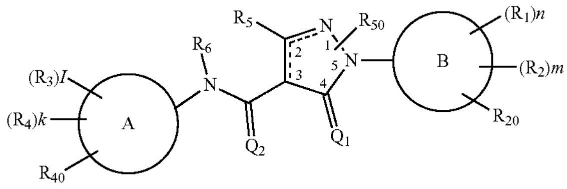

wherein

A and B rings are each independently a single or fused aromatic or heteroaromatic ring system (e.g., phenyl, indole, benzofuran, 2-, 3- or 4-pyridine, naphthalene, thiazole, thiophene, imidazole, 1-methylimidazole, benzimidazole,), or a single or fused $C_3$-$C_{10}$ cycloalkyl (e.g. cyclohexyl) or a single or fused $C_3$-$C_{10}$ heterocyclic ring (e.g., benzofuran-2(3H)-one, benzo[d][1,3] dioxole, tetrahydrothiophene 1,1-dioxide, piperidine, 1-methylpiperidine, isoquinoline, and 1,3-dihydroisobenzofuran);

$R_1$, $R_2$ and $R_{20}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl) (e.g., cyclohexyl), $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—$N(CH_3)_2$), $R_9$—$R_8$—N($R_{10}$)($R_{11}$) (e.g., C≡C—$CH_2$—$NH_2$), $B(OH)_2$, —OC(O)$CF_3$, —$OCH_2$Ph, NHC(O)—$R_{10}$ (e.g., NHC(O)$CH_3$), NHCO—N($R_{10}$)($R_{11}$) (e.g., NHC(O)N$(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N$(CH_3)_2$), $SO_2$R, $SO_2$N($R_{10}$)($R_{11}$) (e.g., $SO_2N(CH_3)_2$, $SO_2$NHC(O)$CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═C$(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), CH($CF_3$)(NH—$R_{10}$);

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$, $R_4$ and $R_{40}$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—$N(CH_3)_2$) $R_9$—$R_8$—N($R_{10}$)($R_{11}$), $B(OH)_2$, —OC(O)$CF_3$, —$OCH_2$Ph, —NHCO—$R_{10}$ (e.g., NHC(O)$CH_3$), NHCO—N($R_{10}$)($R_{11}$) (e.g., NHC(O)N$(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N$(CH_3)_2$), $SO_2$R, $SO_2$N($R_{10}$)($R_{11}$) (e.g., $SO_2N(CH_3)_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), $CH(CF_3)(NH—R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_5$ is H, $C_1$-$C_5$ linear or branched, substituted or unsubstituted alkyl (e.g., methyl, $CH_2SH$, ethyl, iso-propyl), $C_2$-$C_5$ linear or branched, substituted or unsubstituted alkenyl, $C_2$-$C_5$ linear or branched, substituted or unsubstituted alkynyl (e.g., CCH), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)—CH(CH_3)_2$), $R_8$-aryl (e.g., $CH_2$-Ph), $C(=CH_2)—R_{10}$ (e.g., $C(=CH_2)—C(O)—OCH_3$, $C(=CH_2)—CN$) substituted or unsubstituted aryl (e.g., phenyl), substituted or unsubstituted heteroaryl (e.g., pyridine (2, 3, and 4-pyridine), (wherein substitutions include: F, Cl, Br, I, OH, SH, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_{50}$ is H, F, Cl, Br, I, $C_1$-$C_5$ linear or branched, substituted or unsubstituted alkyl (e.g., methyl, $CH_2SH$, ethyl, propyl, iso-propyl, benzyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)—CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), substituted or unsubstituted benzyl, (wherein substitutions include: F, Cl, Br, I, OH, SH, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof);

wherein $R_{50}$ is attached either to $N_1$ or to $C_3$ and if $R_{50}$ is attached to $N_1$ than $N_1—C_2$ is a single bond and $C_2$-$C_3$ is a double bond, and if $R_{50}$ is attached to $C_3$ than $N_1—C_2$ is a double bond and $C_2$-$C_3$ is a single bond;

$R_6$ is H, $C_1$-$C_5$ linear or branched alkyl (e.g., methyl), C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl (e.g., methyl, ethyl), C(O)R (e.g., $C(O)(OCH_3)$), or $S(O)_2R$; or $R_{10}$ and $R_{11}$ are joint to form a substituted or unsubstituted $C_3$-$C_8$ heterocyclic ring (e.g., piperazine, piperidine), wherein substitutions include: F, Cl, Br, I, OH, $C_1$-$C_5$ linear or branched alkyl, $C_1$-$C_5$ linear or branched alkyl-OH (e.g., $C(CH_3)_2CH_2—OH$, $CH_2CH_2—OH$), $C_3$-$C_8$ heterocyclic ring (e.g., piperidine), alkoxy, $N(R)_2$, $CF_3$, aryl, phenyl, halophenyl, (benzyloxy)phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m, n, l and k are each independently an integer between 0 and 4 (e.g., 0, 1 or 2);

$Q_1$ and $Q_2$ are each independently S, O, N—OH, $CH_2$, $C(R)_2$ or N—OMe;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if $R_{50}$ is H then neither one of $R_1$, $R_2$ or $R_{20}$ is H, and n and m are not 0.

In various embodiments, this invention is directed to a compound represented by the structure of formula I(a)

I(a)

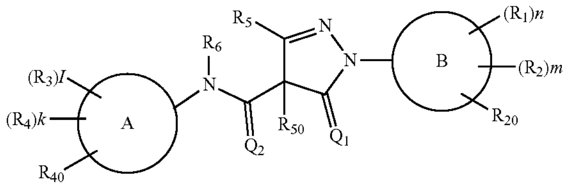

wherein

A and B rings are each independently a single or fused aromatic or heteroaromatic ring system (e.g., phenyl, indole, benzofuran, 2-, 3- or 4-pyridine, naphthalene, thiazole, thiophene, imidazole, 1-methylimidazole, benzimidazole,), or a single or fused $C_3$-$C_{10}$ cycloalkyl (e.g. cyclohexyl) or a single or fused $C_3$-$C_{10}$ heterocyclic ring (e.g., benzofuran-2(3H)-one, benzo[d][1,3]dioxole, tetrahydrothiophene 1,1-dioxide, piperidine, 1-methylpiperidine, isoquinoline, and 1,3-dihydroisobenzofuran);

$R_1$, $R_2$ and $R_{20}$ are each independently H, F, Cl, Br, I, OH, SH, $R_8—OH$ (e.g., $CH_2—OH$), $R_8—SH$, $—R_8—O—R_{10}$, (e.g., $—CH_2—O—CH_3$), $R_8—(C_3$-$C_8$ cycloalkyl) (e.g., cyclohexyl), $R_8—(C_3$-$C_8$ heterocyclic ring) (e.g., $CH_2$-imidazole, $CH_2$-indazole), $CF_3$, $CD_3$, $OCD_3$, CN, $NO_2$, $—CH_2CN$, $—R_8CN$, $NH_2$, NHR, $N(R)_2$, $R_8—N(R_{10})(R_{11})$ (e.g., $CH_2—NH_2$, $CH_2—N(CH_3)_2$), $R_9—R_8—N(R_{10})(R_{11})$ (e.g., $C≡C—CH_2—NH_2$), $B(OH)_2$, $—OC(O)CF_3$, $—OCH_2Ph$, $NHC(O)—R_{10}$ (e.g., $NHC(O)CH_3$), $NHCO—N(R_{10})(R_{11})$ (e.g., $NHC(O)N(CH_3)_2$), COOH, —C(O)Ph, $C(O)O—R_{10}$ (e.g. $C(O)O—CH_3$, $C(O)O—CH(CH_3)_2$, $C(O)O—CH_2CH_3$), $R_8—C(O)—R_{10}$ (e.g., $CH_2C(O)CH_3$), C(O)H, $C(O)—R_{10}$ (e.g., $C(O)—CH_3$, $C(O)—CH_2CH_3$, $C(O)—CH_2CH_2CH_3$), $C_1$-$C_5$ linear or branched C(O)-haloalkyl (e.g., $C(O)—CF_3$), $—C(O)NH_2$, C(O)NHR, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2—C_6H_4—Cl$, ethyl, propyl, iso-propyl, t-Bu, iso-butyl, pentyl, benzyl), $C_1$-$C_5$ linear or branched, substituted or unsubstituted alkenyl (e.g., $CH=C(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)—CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), $CH(CF_3)(NH—R_{10})$;

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$, $R_4$ and $R_{40}$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—N$(R_{10})(R_{11})$ (e.g., $CH_2$—$NH_2$, $CH_2$—$N(CH_3)_2$) $R_9$—$R_8$—N$(R_{10})(R_{11})$, $B(OH)_2$, —OC(O)$CF_3$, —$OCH_2$Ph, —NHCO—$R_{10}$ (e.g., NHC(O)$CH_3$), NHCO—N$(R_{10})(R_{11})$ (e.g., NHC(O)N$(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N$(R_{10})(R_{11})$ (e.g., C(O)N$(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, C(OH)$(CH_3)$(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), $CH(CF_3)(NH—R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_5$ is H, $C_1$-$C_5$ linear or branched, substituted or unsubstituted alkyl (e.g., methyl, $CH_2SH$, ethyl, iso-propyl), $C_2$-$C_5$ linear or branched, substituted or unsubstituted alkenyl, $C_2$-$C_5$ linear or branched, substituted or unsubstituted alkynyl (e.g., CCH), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), C(=$CH_2$)—$R_{10}$ (e.g., C(=$CH_2$)—C(O)—$OCH_3$, C(=$CH_2$)—CN), substituted or unsubstituted aryl (e.g., phenyl), substituted or unsubstituted heteroaryl (e.g., pyridine (2, 3, and 4-pyridine), (wherein substitutions include: F, Cl, Br, I, OH, SH, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_{50}$ is H, F, Cl, Br, I, $C_1$-$C_5$ linear or branched, substituted or unsubstituted alkyl (e.g., methyl, $CH_2SH$, ethyl, propyl, iso-propyl, benzyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), substituted or unsubstituted benzyl, (wherein substitutions include: F, Cl, Br, I, OH, SH, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof);

$R_6$ is H, $C_1$-$C_5$ linear or branched alkyl (e.g., methyl), C(O)R, or $S(O)_2R$;

$R_8$ is $[CH_2]_p$
wherein p is between 1 and 10;

$R_9$ is $[CH]_q$, $[C]_q$
wherein q is between 2 and 10;

$R_{10}$ and $R_{11}$ are each independently H, CN, $C_1$-$C_5$ linear or branched alkyl (e.g., methyl, ethyl), C(O)R (e.g., C(O)$(OCH_3)$), or $S(O)_2R$; or $R_{10}$ and $R_{11}$ are joint to form a substituted or unsubstituted $C_3$-$C_8$ heterocyclic ring (e.g., piperazine, piperidine),
wherein substitutions include: F, Cl, Br, I, OH, $C_1$-$C_5$ linear or branched alkyl, $C_1$-$C_5$ linear or branched alkyl-OH (e.g., $C(CH_3)_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy)phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m, n, l and k are each independently an integer between 0 and 4 (e.g., 0, 1 or 2);

$Q_1$ and $Q_2$ are each independently S, O, N—OH, $CH_2$, $C(R)_2$ or N—OMe;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if $R_{50}$ is H then neither one of $R_1$, $R_2$ or $R_{20}$ is H, and n and m are not 0.

In various embodiments, this invention is directed to a compound represented by the structure of formula I(b):

I(b)

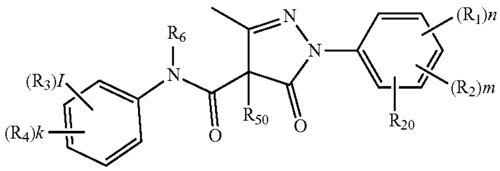

wherein $R_1$, $R_2$ and $R_{20}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl) (e.g., cyclohexyl), $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—N($CH_3$)$_2$), $R_9$—$R_8$—N($R_{10}$)($R_{11}$) (e.g., C≡C—$CH_2$—$NH_2$), $B(OH)_2$, —OC(O)$CF_3$, —$OCH_2$Ph, NHC(O)—$R_{10}$ (e.g., NHC(O)$CH_3$), NHCO—N($R_{10}$)($R_{11}$) (e.g., NHC(O)N($CH_3$)$_2$), COOH, —C(O)Ph, C(O)O—$R_{10}$ (e.g. C(O)O—$CH_3$, C(O)O—CH($CH_3$)$_2$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N($CH_3$)$_2$), $SO_2$R, $SO_2$N($R_{10}$)($R_{11}$) (e.g., $SO_2$N($CH_3$)$_2$, $SO_2$NHC(O)$CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═C(Ph)$_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2$CH($CH_3$)$_2$, CF($CH_3$)—CH($CH_3$)$_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), CH($CF_3$)(NH—$R_{10}$);

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$, and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—N($CH_3$)$_2$) $R_9$—$R_8$—N($R_{10}$)($R_{11}$), $B(OH)_2$, —OC(O)$CF_3$, —$OCH_2$Ph, —NHCO—$R_{10}$ (e.g., NHC(O)$CH_3$), NHCO—N($R_{10}$)($R_{11}$) (e.g., NHC(O)N($CH_3$)$_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N($CH_3$)$_2$), $SO_2$R, $SO_2$N($R_{10}$)($R_{11}$) (e.g., $SO_2$N($CH_3$)$_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2$CH($CH_3$)$_2$, CF($CH_3$)—CH($CH_3$)$_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), CH($CF_3$)(NH—$R_{10}$);

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_{50}$ is H, F, Cl, Br, I, $C_1$-$C_5$ linear or branched, substituted or unsubstituted alkyl (e.g., methyl, $CH_2$SH, ethyl, propyl, iso-propyl, benzyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2$CH($CH_3$)$_2$, CF($CH_3$)—CH($CH_3$)$_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), substituted or unsubstituted benzyl, (wherein substitutions include: F, Cl, Br, I, OH, SH, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof);

$R_6$ is H, $C_1$-$C_5$ linear or branched alkyl (e.g., methyl), C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl (e.g., methyl, ethyl), C(O)R (e.g., C(O)($OCH_3$)), or $S(O)_2R$; or $R_{10}$ and $R_{11}$ are joint to form a substituted or unsubstituted $C_3$-$C_8$ heterocyclic ring (e.g., piperazine, piperidine), wherein substitutions include: F, Cl, Br, I, OH, $C_1$-$C_5$ linear or branched alkyl, $C_1$-$C_5$ linear or branched alkyl-OH (e.g., C($CH_3$)$_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy)phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m, n, l and k are each independently an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if $R_{50}$ is H then neither one of $R_1$, $R_2$ or $R_{20}$ is H, and n and m are not 0.

In various embodiments, this invention is directed to a compound represented by the structure of formula (II):

(II)

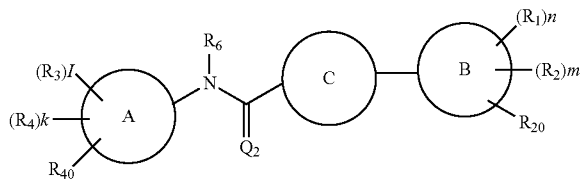

wherein

A and B rings are each independently a single or fused aromatic or heteroaromatic ring system (e.g., phenyl, indole, benzofuran, 2-, 3- or 4-pyridine, naphthalene, thiazole, thiophene, imidazole, 1-methylimidazole, benzimidazole,), or a single or fused $C_3$-$C_{10}$ cycloalkyl (e.g. cyclohexyl) or a single or fused $C_3$-$C_{10}$ heterocyclic ring (e.g., benzofuran-2(3H)-one, benzo[d][1,3] dioxole, tetrahydrothiophene 1,1-dioxide, piperidine, 1-methylpiperidine, isoquinoline, and 1,3-dihydroisobenzofuran);

C ring is selected from the following (wavy line represents a connection point):

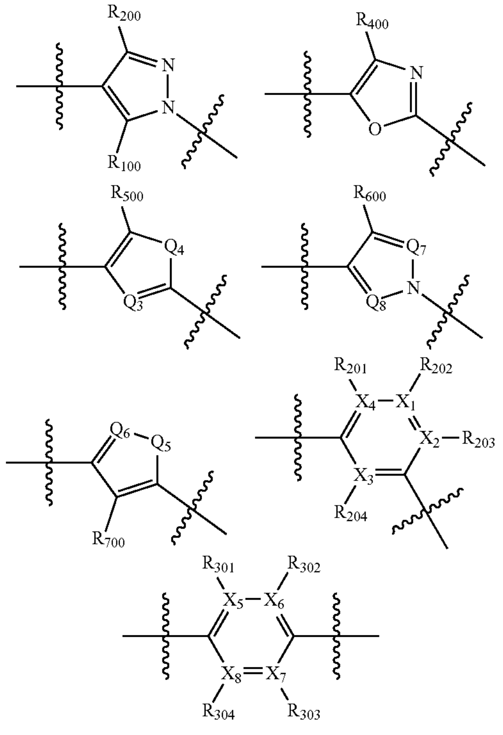

wherein $X_1$, $X_2$, $X_3$, $X_4$, $X_5$, $X_6$, $X_7$ and $X_8$ are each independently N, N—O, or C, wherein at least one of $X_1$, $X_2$, $X_3$, $X_4$, $X_5$, $X_6$, $X_7$ or $X_8$ is N, and wherein if $X_1$, $X_2$, $X_3$, $X_4$, $X_5$, $X_6$, $X_7$ or $X_8$ is N than its respective substituent is nothing;

$Q_3$, $Q_6$, $Q_7$ and $Q_8$ are each independently N, N—O, CH or C(R);

$Q_4$ and $Q_5$ are each independently O, NH or N(R);

$R_{200}$, $R_{400}$, $R_{500}$, and $R_{600}$ are each independently H or a $C_1$-$C_5$ linear or branched, substituted or unsubstituted alkyl (e.g., methyl, ethyl, propyl, iso-propyl, t-Bu, iso-butyl, pentyl, benzyl);

$R_{201}$, $R_{202}$, $R_{203}$, $R_{204}$, $R_{301}$, $R_{302}$, $R_{303}$, and $R_{304}$ are each independently nothing, H or a $C_1$-$C_5$ linear or branched, substituted or unsubstituted alkyl (e.g., methyl, ethyl, propyl, iso-propyl, t-Bu, iso-butyl, pentyl, benzyl);

$R_{100}$ and $R_{700}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl), $R_8$—($C_3$-$C_8$ heterocyclic ring) (e.g., $CH_2$-imidazole, indazole), $CF_3$, $CD_3$, $OCD_3$, CN, $NO_2$, —$CH_2CN$, —$R_8CN$, $NH_2$, NHR (e.g., $NHCH_3$), $N(R)_2$ (e.g., $N(CH_3)_2$), $R_8$—$N(R_{10})(R_{11})$ (e.g., $CH_2$—$NH_2$, $CH_2$—$N(CH_3)_2$), $R_9$—$R_8$—N$(R_{10})(R_{11})$ (e.g., C≡C—$CH_2$—$NH_2$), $B(OH)_2$, —OC(O)—$N(R_{10})(R_{11})$ (e.g. OC(O)-piperidine-$C(Me)_2CH_2OH$, OC(O)-piperazine-$CH_2CH_2OH$, OC(O)-piperidine-piperidine), —$OC(O)CF_3$, —$OCH_2Ph$, NHC(O)—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —$C(O)NH_2$, C(O)NHR, C(O)$N(R_{10})(R_{11})$ (e.g., $C(O)N(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═$C(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, $C_3$-$C_8$ cycloalkyl, halophenyl, (benzyloxy)phenyl, CN, $NO_2$ or any combination thereof), $CH(CF_3)(NH—R_{10})$;

$R_1$, $R_2$ and $R_{20}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl) (e.g., cyclohexyl), $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2$CN, —$R_8$CN, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —OC(O)$CF_3$, —$OCH_2$Ph, NHC(O)—$R_{10}$ (e.g., NHC(O)$CH_3$), NHCO—$N(R_{10})(R_{11})$ (e.g., NHC(O)$N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)$N(CH_3)_2$), $SO_2R$, $SO_2N(R_{10})(R_{11})$ (e.g., $SO_2N(CH_3)_2$, $SO_2$NHC(O)$CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═C(Ph)$_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), $CH(CF_3)(NH—R_{10})$;

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$, $R_4$ and $R_{40}$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2$CN, —$R_8$CN, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$, $B(OH)_2$, —OC(O)$CF_3$, —$OCH_2$Ph, —NHCO—$R_{10}$ (e.g., NHC(O)$CH_3$), NHCO—$N(R_{10})(R_{11})$ (e.g., NHC(O)$N(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)$N(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), $CH(CF_3)(NH—R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_6$ is H, $C_1$-$C_5$ linear or branched alkyl (e.g., methyl), C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl (e.g., methyl, ethyl), C(O)R (e.g., C(O)($OCH_3$)), or $S(O)_2R$; or $R_{10}$ and $R_{11}$ are joint to form a substituted or unsubstituted $C_3$-$C_8$ heterocyclic ring (e.g., piperazine, piperidine), wherein substitutions include: F, Cl, Br, I, OH, $C_1$-$C_5$ linear or branched alkyl, $C_1$-$C_5$ linear or branched alkyl-OH (e.g., $C(CH_3)_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy)phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m, n, l and k are each independently an integer between 0 and 4 (e.g., 0, 1 or 2);

$Q_2$ is S, O, N—OH, $CH_2$, CH(R), $C(R)_2$ or N—OMe;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula II(a)

II(a)

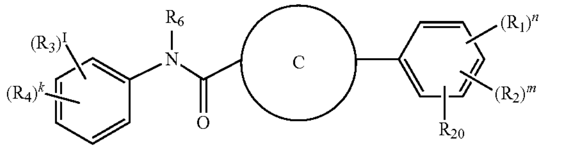

wherein

C ring is selected from the following (wavy line represents a connection point):

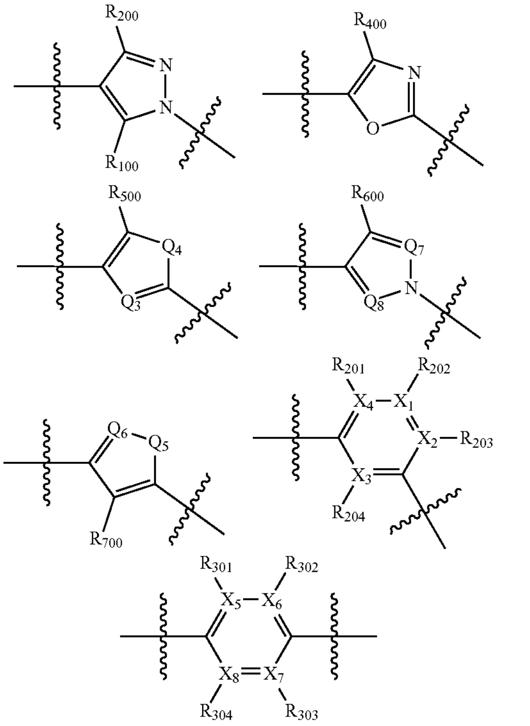

wherein $X_1$, $X_2$, $X_3$, $X_4$, $X_5$, $X_6$, $X_7$ and $X_8$ are each independently N, N—O, or C, wherein at least one of $X_1$, $X_2$, $X_3$, $X_4$, $X_5$, $X_6$, $X_7$ or $X_8$ is N, and wherein if $X_1$, $X_2$, $X_3$, $X_4$, $X_5$, $X_6$, $X_7$ or $X_8$ is N than its respective substituent is nothing;

$Q_3$, $Q_6$, $Q_7$ and $Q_8$ are each independently N, N—O, CH or C(R);

$Q_4$ and $Q_5$ are each independently O, NH or N(R);

$R_{200}$, $R_{400}$, $R_{500}$, and $R_{600}$ are each independently H or a $C_1$-$C_5$ linear or branched, substituted or unsubstituted alkyl (e.g., methyl, ethyl, propyl, iso-propyl, t-Bu, iso-butyl, pentyl, benzyl);

$R_{201}$, $R_{202}$, $R_{203}$, $R_{204}$, $R_{301}$, $R_{302}$, $R_{303}$, and $R_{304}$ are each independently nothing, H or a $C_1$-$C_5$ linear or branched, substituted or unsubstituted alkyl (e.g., methyl, ethyl, propyl, iso-propyl, t-Bu, iso-butyl, pentyl, benzyl);

$R_{100}$ and $R_{700}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl), $R_8$—($C_3$-$C_8$ heterocyclic ring) (e.g., $CH_2$-imidazole, indazole), $CF_3$, $CD_3$, $OCD_3$, CN, $NO_2$, —$CH_2CN$, —$R_8$CN, $NH_2$, NHR (e.g., $NHCH_3$), $N(R)_2$ (e.g., $N(CH_3)_2$), $R_8$—$N(R_{10})(R_{11})$ (e.g., $CH_2$—$NH_2$, $CH_2$—$N(CH_3)_2$), $R_9$—$R_8$—N$(R_{10})(R_{11})$ (e.g., C≡C—$CH_2$—$NH_2$), $B(OH)_2$, —OC(O)—$N(R_{10})(R_{11})$ (e.g. OC(O)-piperidine-$C(Me)_2CH_2OH$, OC(O)-piperazine-$CH_2CH_2OH$, OC(O)-piperidine-piperidine), —$OC(O)CF_3$, —$OCH_2Ph$, NHC(O)—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —$C(O)NH_2$, C(O)NHR, C(O)$N(R_{10})(R_{11})$ (e.g., $C(O)N(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═C(Ph)$_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, $C_3$-$C_8$ cycloalkyl, halophenyl, (benzyloxy)phenyl, CN, $NO_2$ or any combination thereof), $CH(CF_3)(NH$—$R_{10})$;

$R_1$, $R_2$ and $R_{20}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl) (e.g., cyclohexyl), $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2CN$, —$R_8$CN, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, NHC(O)—$R_{10}$ (e.g., $NHC(O)CH_3$), NHCO—$N(R_{10})(R_{11})$ (e.g., NHC(O)$N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)- haloalkyl (e.g., C(O)—$CF_3$), —$C(O)NH_2$, C(O)NHR, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH=$C(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), $CH(CF_3)(NH$—$R_{10})$;

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$, $B(OH)_2$, —$OC(O)CF_3$, —$OCH_2Ph$, —NHCO—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —$C(O)NH_2$, C(O)NHR, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), $CH(CF_3)(NH$—$R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_6$ is H, $C_1$-$C_5$ linear or branched alkyl (e.g., methyl), C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl (e.g., methyl, ethyl), C(O)R (e.g., $C(O)(OCH_3)$), or $S(O)_2R$; or $R_{10}$ and $R_{11}$ are joint to form a substituted or unsubstituted $C_3$-$C_8$ heterocyclic ring (e.g., piperazine, piperidine), wherein substitutions include: F, Cl, Br, I, OH, $C_1$-$C_5$ linear or branched alkyl, $C_1$-$C_5$ linear or branched alkyl-OH (e.g., $C(CH_3)_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy) phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m, n, l and k are each independently an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula II(b)

II(b)

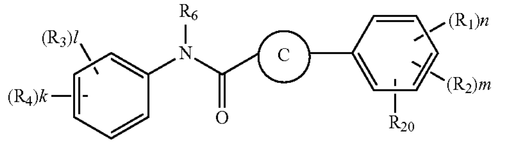

wherein

C ring is selected from the following (wavy line represents a connection point):

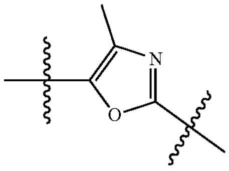

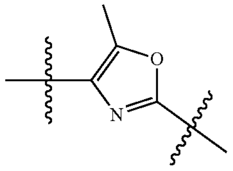

-continued

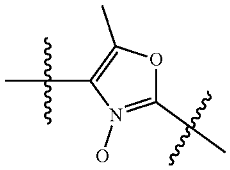
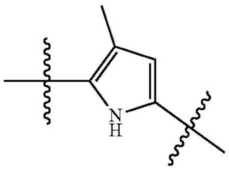
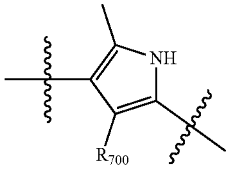
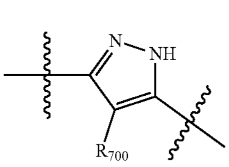
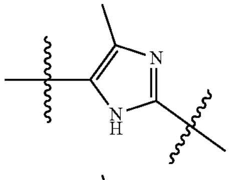
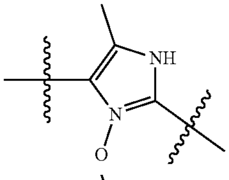
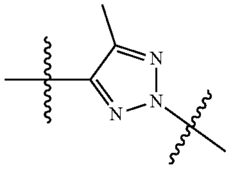
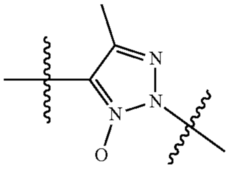
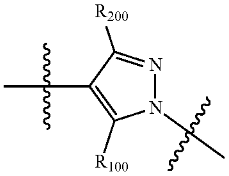
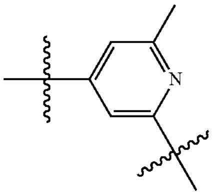
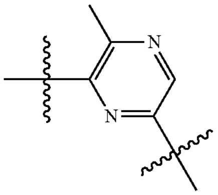
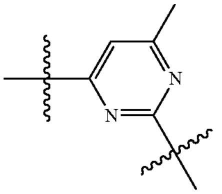
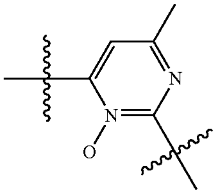
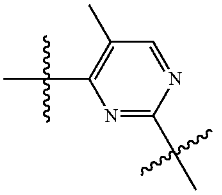
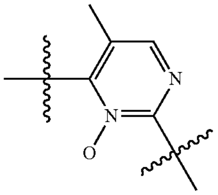
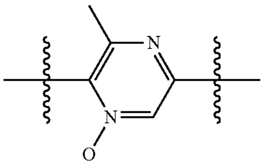
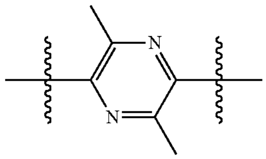
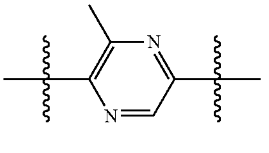
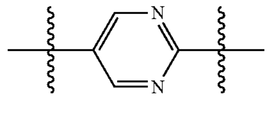

-continued

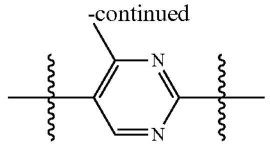

wherein $R_{200}$ is H or a $C_1$-$C_5$ linear or branched, substituted or unsubstituted alkyl (e.g., methyl, ethyl, propyl, iso-propyl, t-Bu, iso-butyl, pentyl, benzyl);

$R_{100}$ and $R_{700}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl), $R_8$—($C_3$-$C_8$ heterocyclic ring) (e.g., $CH_2$-imidazole, indazole), $CF_3$, $CD_3$, $OCD_3$, CN, $NO_2$, —$CH_2CN$, —$R_8CN$, $NH_2$, NHR (e.g., $NHCH_3$), $N(R)_2$ (e.g., $N(CH_3)_2$), $R_8$—$N(R_{10})(R_{11})$ (e.g., $CH_2$—$NH_2$, $CH_2$—$N(CH_3)_2$), $R_9$—$R_8$—N($R_{10}$)($R_{11}$) (e.g., C≡C—$CH_2$—$NH_2$), $B(OH)_2$, —OC(O)—N($R_{10}$)($R_{11}$) (e.g. OC(O)-piperidine-$C(Me)_2CH_2OH$, OC(O)-piperazine-$CH_2CH_2OH$, OC(O)-piperidine-piperidine), —$OC(O)CF_3$, —$OCH_2Ph$, NHC(O)—$R_{10}$ (e.g., $NHC(O)CH_3$), NHCO—N($R_{10}$)($R_{11}$) (e.g., $NHC(O)N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —$C(O)NH_2$, C(O)NHR, C(O)N($R_{10}$)($R_{11}$) (e.g., $C(O)N(CH_3)_2$), $SO_2R$, $SO_2N$($R_{10}$)($R_{11}$) (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═$C(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, $C_3$-$C_8$ cycloalkyl, halophenyl, (benzyloxy)phenyl, CN, $NO_2$ or any combination thereof), $CH(CF_3)$(NH—$R_{10}$);

$R_1$, $R_2$ and $R_{20}$ are each independently H, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl) (e.g., cyclohexyl), $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—$N(CH_3)_2$), $R_9$—$R_8$—N($R_{10}$)($R_{11}$) (e.g., C≡C—$CH_2$—$NH_2$), $B(OH)_2$, —OC(O)$CF_3$, —$OCH_2$Ph, NHC(O)—$R_{10}$ (e.g., NHC(O)$CH_3$), NHCO—N($R_{10}$)($R_{11}$) (e.g., NHC(O)N$(CH_3)_2$), COOH, —C(O)Ph, C(O)O—$R_{10}$ (e.g. C(O)O—$CH_3$, C(O)O—CH$(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N$(CH_3)_2$), $SO_2R$, $SO_2$N($R_{10}$)($R_{11}$) (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═C$(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, CF$(CH_3)$—CH$(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), CH($CF_3$)(NH—$R_{10}$);

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—$N(CH_3)_2$) $R_9$—$R_8$—N($R_{10}$)($R_{11}$), $B(OH)_2$, —OC(O)$CF_3$, —$OCH_2$Ph, —NHCO—$R_{10}$ (e.g., NHC(O)$CH_3$), NHCO—N($R_{10}$)($R_{11}$) (e.g., NHC(O)N$(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N$(CH_3)_2$), $SO_2R$, $SO_2$N($R_{10}$)($R_{11}$) (e.g., $SO_2N(CH_3)_2$), $C_1$-$C_5$ linear or branched, substituted or unsubstituted alkyl (e.g., methyl, C(OH)$(CH_3)$(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, CF$(CH_3)$—CH$(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), CH($CF_3$)(NH—$R_{10}$);

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_6$ is H, $C_1$-$C_5$ linear or branched alkyl (e.g., methyl), C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl (e.g., methyl, ethyl), C(O)R (e.g., C(O)($OCH_3$)), or $S(O)_2R$; or $R_{10}$ and $R_{11}$ are joint to form a substituted or unsubstituted $C_3$-$C_8$ heterocyclic ring (e.g., piperazine, piperidine), wherein substitutions include: F, Cl, Br, I, OH, $C_1$-$C_5$ linear or branched alkyl, $C_1$-$C_5$ linear or branched alkyl-OH (e.g., $C(CH_3)_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy)phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m, n, l and k are each independently an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

[Three Substituents on Ring B]

In various embodiments, this invention is directed to a compound represented by the structure of formula III:

III

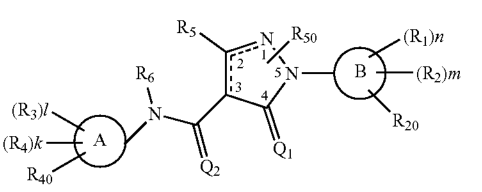

wherein

A and B rings are each independently a single or fused aromatic or heteroaromatic ring system (e.g., phenyl, indole, benzofuran, 2-, 3- or 4-pyridine, naphthalene, thiazole, thiophene, imidazole, 1-methylimidazole, benzimidazole,), or a single or fused $C_3$-$C_{10}$ cycloalkyl (e.g. cyclohexyl) or a single or fused $C_3$-$C_{10}$ heterocyclic ring (e.g., benzofuran-2(3H)-one, benzo[d][1,3] dioxole, tetrahydrothiophene 1,1-dioxide, piperidine, 1-methylpiperidine, isoquinoline, and 1,3-dihydroisobenzofuran);

$R_1$, $R_2$ and $R_{20}$ are each independently F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl) (e.g., cyclohexyl), $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—$N(CH_3)_2$), $R_9$—$R_8$—N($R_{10}$)($R_{11}$) (e.g., C≡C—$CH_2$—$NH_2$), $B(OH)_2$, —OC(O)$CF_3$, —$OCH_2$Ph, NHC(O)—$R_{10}$ (e.g., NHC(O)$CH_3$), NHCO—N($R_{10}$)($R_{11}$) (e.g., NHC(O)$N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)$N(CH_3)_2$), $SO_2R$, $SO_2$N($R_{10}$)($R_{11}$) (e.g., $SO_2N(CH_3)_2$, $SO_2$NHC(O)$CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═C(Ph)$_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), CH($CF_3$)(NH—$R_{10}$);

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$, $R_4$ and $R_{40}$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2$CN, —$R_8$CN, $NH_2$, NHR, $N(R)_2$, $R_8$—N($R_{10}$)($R_{11}$) (e.g., $CH_2$—$NH_2$, $CH_2$—$N(CH_3)_2$) $R_9$—$R_8$—N($R_{10}$)($R_{11}$), $B(OH)_2$, —OC(O)$CF_3$, —$OCH_2$Ph, —NHCO—$R_{10}$ (e.g., NHC(O)$CH_3$), NHCO—N($R_{10}$)($R_{11}$) (e.g., NHC(O)$N(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)$N(CH_3)_2$), $SO_2R$, $SO_2$N($R_{10}$)($R_{11}$) (e.g., $SO_2N(CH_3)_2$), $C_1$-$C_5$ linear or branched, substituted or unsubstituted alkyl (e.g., methyl, C(OH)($CH_3$)(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), CH($CF_3$)(NH—$R_{10}$);

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_5$ is H, $C_1$-$C_5$ linear or branched, substituted or unsubstituted alkyl (e.g., methyl, $CH_2$SH, ethyl, iso-propyl), $C_2$-$C_5$ linear or branched, substituted or unsubstituted alkenyl, $C_2$-$C_5$ linear or branched, substituted or unsubstituted alkynyl (e.g., CCH), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), C(═$CH_2$)—$R_{10}$ (e.g., C(═$CH_2$)—C(O)—$OCH_3$, C(═$CH_2$)—CN) substituted or unsubstituted aryl (e.g., phenyl), substituted or unsubstituted heteroaryl (e.g., pyridine (2, 3, and 4-pyridine), (wherein substitutions include: F, Cl, Br, I, OH, SH, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_{50}$ is H, F, Cl, Br, I, $C_1$-$C_5$ linear or branched, substituted or unsubstituted alkyl (e.g., methyl, $CH_2$SH, ethyl, propyl, iso-propyl, benzyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), substituted or unsubstituted benzyl, (wherein substitutions include: F, Cl, Br, I, OH, SH, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof);

wherein $R_{50}$ is attached either to $N_1$ or to $C_3$ and if $R_{50}$ is attached to $N_1$ than $N_1$—$C_2$ is a single bond and $C_2$-$C_3$ is a double bond, and if $R_{50}$ is attached to $C_3$ than $N_1$—$C_2$ is a double bond and $C_2$-$C_3$ is a single bond;

$R_6$ is H, $C_1$-$C_5$ linear or branched alkyl (e.g., methyl), C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl (e.g., methyl, ethyl), C(O)R (e.g., $C(O)(OCH_3)$), or $S(O)_2R$; or $R_{10}$ and $R_{11}$ are joint to form a substituted or unsubstituted $C_3$-$C_8$ heterocyclic ring (e.g., piperazine, piperidine), wherein substitutions include: F, Cl, Br, I, OH, $C_1$-$C_5$ linear or branched alkyl, $C_1$-$C_5$ linear or branched alkyl-OH (e.g., $C(CH_3)_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy) phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m and, n, are each independently an integer between 1 and 4 (e.g., 1 or 2);

l and k are each independently an integer between 0 and 4 (e.g., 0, 1 or 2);

$Q_1$ and $Q_2$ are each independently S, O, N—OH, $CH_2$, $C(R)_2$ or N—OMe;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula III(a):

III(a)

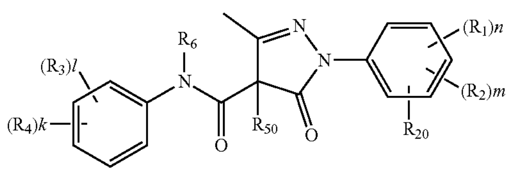

wherein $R_1$, $R_2$ and $R_{20}$ are each independently F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl) (e.g., cyclohexyl), $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2CN$, —$R_8CN$, $NH_2$, NHR, $N(R)_2$, $R_8$—N$(R_{10})(R_{11})$ (e.g., $CH_2$—$NH_2$, $CH_2$—$N(CH_3)_2$), $R_9$—$R_8$—N$(R_{10})(R_{11})$ (e.g., C≡C—$CH_2$—$NH_2$), $B(OH)_2$, —OC(O)$CF_3$, —$OCH_2$Ph, NHC(O)—$R_{10}$ (e.g., NHC(O)$CH_3$), NHCO—N$(R_{10})(R_{11})$ (e.g., NHC(O)N$(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N$(R_{10})(R_{11})$ (e.g., C(O)N$(CH_3)_2$), $SO_2R$, $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═C$(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), (wherein substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, $NO_2$ or any combination thereof), $CH(CF_3)(NH$—$R_{10})$;

or $R_2$ and $R_1$ are joint together to form a 5 or 6 membered substituted or unsubstituted, aliphatic or aromatic, carbocyclic or heterocyclic ring (e.g., pyrrol, [1,3]dioxole, furan-2(3H)-one, benzene, pyridine);

$R_3$, $R_4$ and $R_{40}$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—N$(R_{10})(R_{11})$ (e.g., $CH_2$—$NH_2$, $CH_2$—$N(CH_3)_2$) $R_9$—$R_8$—N$(R_{10})(R_{11})$, $B(OH)_2$, —OC(O)$CF_3$, —$OCH_2$Ph, —NHCO—$R_{10}$ (e.g., NHC(O)$CH_3$), NHCO—N$(R_{10})(R_{11})$ (e.g., NHC(O)N$(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N$(R_{10})(R_{11})$ (e.g., C(O)N$(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, C(OH)$(CH_3)$(Ph), ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof), $CH(CF_3)(NH$—$R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole);

$R_{50}$ is H, F, Cl, Br, I, $C_1$-$C_5$ linear or branched, substituted or unsubstituted alkyl (e.g., methyl, $CH_2SH$, ethyl, propyl, iso-propyl, benzyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), substituted or unsubstituted aryl (e.g., phenyl), substituted or unsubstituted heteroaryl (e.g., pyridine (2, 3, and 4-pyridine), substituted or unsubstituted benzyl, (wherein substitutions include: F, Cl, Br, I, OH, SH, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof);

$R_6$ is H, $C_1$-$C_5$ linear or branched alkyl (e.g., methyl), C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl (e.g., methyl, ethyl), C(O)R (e.g., $C(O)(OCH_3)$), or $S(O)_2R$; or $R_{10}$ and $R_{11}$ are joint to form a substituted or unsubstituted $C_3$-$C_8$ heterocyclic ring (e.g., piperazine, piperidine), wherein substitutions include: F, Cl, Br, I, OH, $C_1$-$C_5$ linear or branched alkyl, $C_1$-$C_5$ linear or branched alkyl-OH (e.g., $C(CH_3)_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy) phenyl, CN, $NO_2$ or any combination thereof)

R is H, $C_1$-$C_5$ linear or branched alkyl (e.g., methyl, ethyl), $C_1$-$C_5$ linear or branched alkoxy (e.g., methoxy), phenyl, aryl or heteroaryl, or two gem R substituents are joint together to form a 5 or 6 membered heterocyclic ring;

m and, n, are each independently an integer between 1 and 4 (e.g., 1 or 2);

l and k are each independently an integer between 0 and 4 (e.g., 0, 1 or 2);

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In some embodiments, A of formula I, I(a), II, and/or III is a phenyl. In other embodiments, A is pyridinyl. In other embodiments, A is 2-pyridinyl. In other embodiments, A is 3-pyridinyl. In other embodiments, A is 4-pyridinyl. In other embodiments, A is naphthyl. In other embodiments, A is benzothiazolyl. In other embodiments, A is benzimidazolyl. In other embodiments, A is quinolinyl. In other embodiments, A is isoquinolinyl. In other embodiments, A is indolyl. In other embodiments, A is tetrahydronaphthyl. In other embodiments, A is indenyl. In other embodiments, A is benzofuran-2(3H)-one. In other embodiments, A is benzo [d][1,3]dioxole. In other embodiments, A is naphthalene. In other embodiments, A is tetrahydrothiophene1,1-dioxide. In other embodiments, A is thiazole. In other embodiments, A is benzimidazole. In others embodiment, A is piperidine. In other embodiments, A is 1-methylpiperidine. In other embodiments, A is imidazole. In other embodiments, A is 1-methylimidazole. In other embodiments, A is thiophene. In other embodiments, A is isoquinoline. In other embodiments, A is indole. In other embodiments, A is 1,3-dihydroisobenzofuran. In other embodiments, A is benzofuran. In other embodiments, A is single or fused $C_3$-$C_{10}$ cycloalkyl ring. In other embodiments, A is cyclohexyl.

In some embodiments, B of formula I, I(a), II, and/or III is a phenyl ring. In other embodiments, B is pyridinyl. In other embodiments, B is 2-pyridinyl. In other embodiments, B is 3-pyridinyl. In other embodiments, B is 4-pyridinyl. In other embodiments, B is naphthyl. In other embodiments, B is indolyl. In other embodiments, B is benzimidazolyl. In other embodiments, B is benzothiazolyl. In other embodiments, B is quinoxalinyl. In other embodiments, B is tetrahydronaphthyl. In other embodiments, B is quinolinyl. In other embodiments, B is isoquinolinyl. In other embodiments, B is indenyl. In other embodiments, B is naphthalene. In other embodiments, B is tetrahydrothiophene1,1-dioxide. In other embodiments, B is thiazole. In other embodiments, B is benzimidazole. In other embodiments, B is piperidine. In other embodiments, B is 1-methylpiperidine. In other embodiments, B is imidazole. In other embodiments, B is 1-methylimidazole. In other embodiments, B is thiophene. In other embodiments, B is isoquinoline. In other embodiments, B is indole. In other embodiments, B is 1,3-dihydroisobenzofuran. In other embodiments, B is benzofuran. In other embodiments, B is single or fused $C_3$-$C_{10}$ cycloalkyl ring. In other embodiments, B is cyclohexyl.

In some embodiments, C of formula II, and/or II(a) is

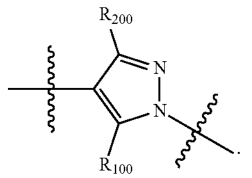

In other embodiments, C is

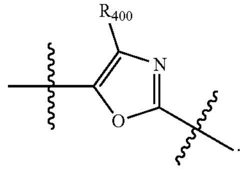

In other embodiments, C is
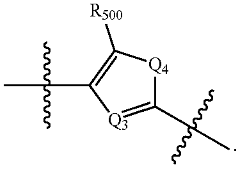
In other embodiments, C is
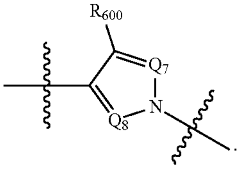
In other embodiments, C is
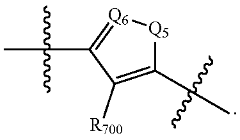
In other embodiments, C is
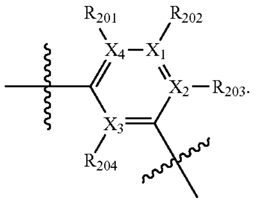
In other embodiments, C is
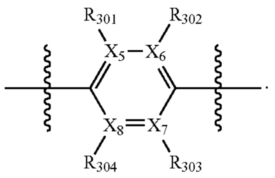
In other embodiments, C is
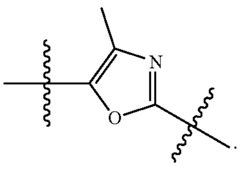 [SMILES: *c1nc(C)c(*)o1]
In other embodiments, C is
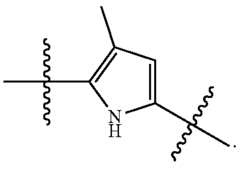 [SMILES: *c1cc(C)c(*)[nH]1]
In other embodiments, C is
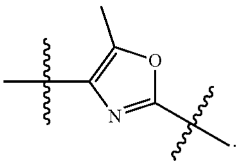 [SMILES: *c1nc(*)c(C)o1]
In other embodiments, C is
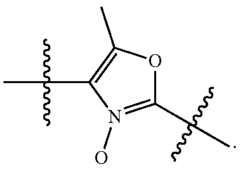
In other embodiments, C is
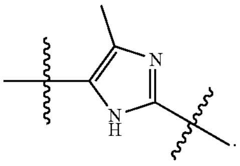 [SMILES: *c1nc(C)c(*)[nH]1]
In other embodiments, C is
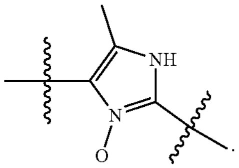
In other embodiments, C is
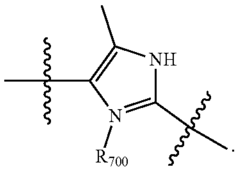

In other embodiments, C is
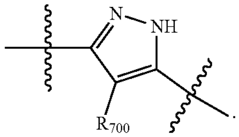
In other embodiments, C is
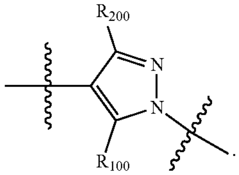
In other embodiments, C is
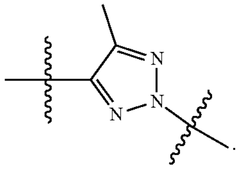 [SMILES: *c1nn(*)nc1C]
In other embodiments, C is
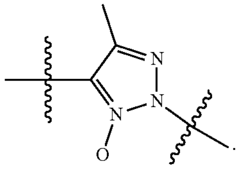
In other embodiments, C is
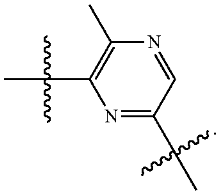 [SMILES: *c1cnc(C)c(*)n1]
In other embodiments, C is
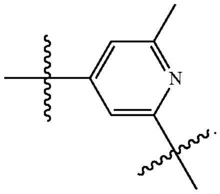 [SMILES: *c1cc(*)nc(C)c1]
In other embodiments, C is
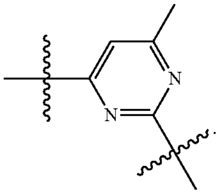 [SMILES: *c1cc(C)nc(*)n1]
In other embodiments, C is
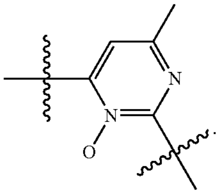
In other embodiments, C is
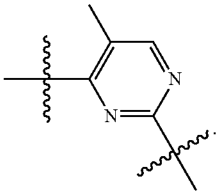 [SMILES: *c1ncc(C)c(*)n1]
In other embodiments, C is
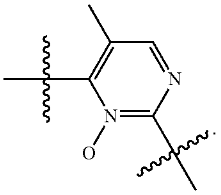
In other embodiments, C is
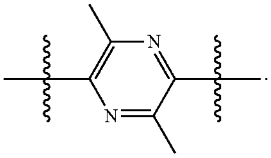 [SMILES: *c1nc(C)c(*)nc1C]
In other embodiments, C is
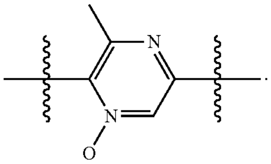

In other embodiments, C is
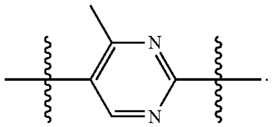
In other embodiments, C is
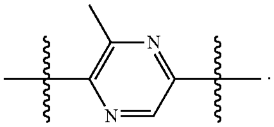
In other embodiments, C is
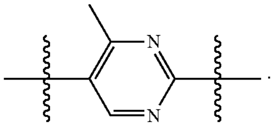 [SMILES: *c1ncc(*)c(C)n1]
In some embodiments, C of formula II(b) is
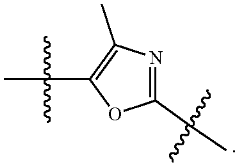 [SMILES: *c1nc(C)c(*)o1]
In other embodiments, C is
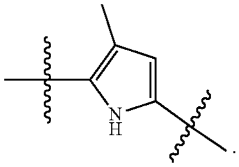 [SMILES: *c1cc(C)c(*)[nH]1]
In other embodiments, C is
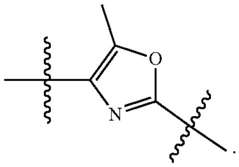 [SMILES: *c1nc(*)c(C)o1]
In other embodiments, C is
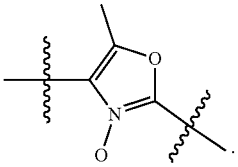
In other embodiments, C is
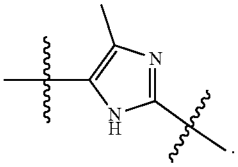 [SMILES: *c1nc(C)c(*)[nH]1]
In other embodiments, C is
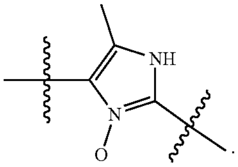
In other embodiments, C is
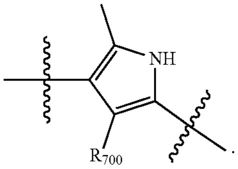
In other embodiments, C is
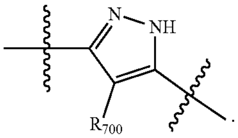
In other embodiments, C is
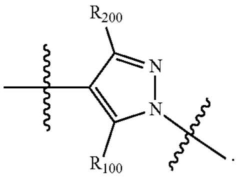

In other embodiments, C is
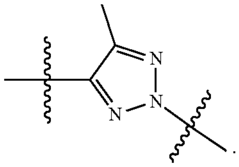 [SMILES: *c1nn(*)nc1C]
In other embodiments, C is
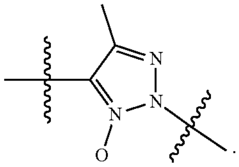
In other embodiments, C is
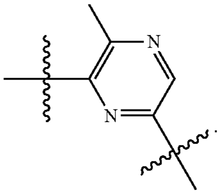 [SMILES: *c1cnc(C)c(*)n1]
In other embodiments, C is
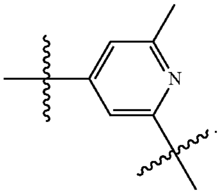 [SMILES: *c1cc(*)nc(C)c1]
In other embodiments, C is
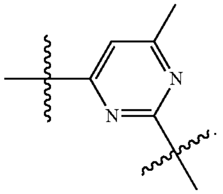 [SMILES: *c1cc(C)nc(*)n1]
In other embodiments, C is
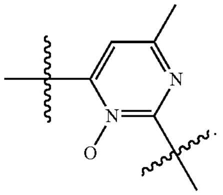
In other embodiments, C is
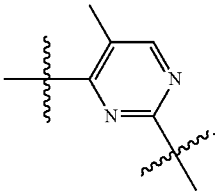 [SMILES: *c1ncc(C)c(*)n1]
In other embodiments, C is
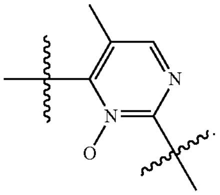
In other embodiments, C is
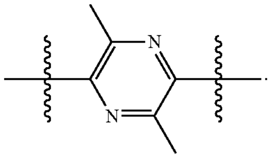 [SMILES: *c1nc(C)c(*)nc1C]
In other embodiments, C is
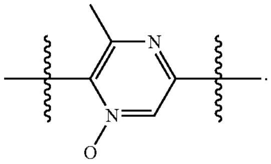
In other embodiments, C is
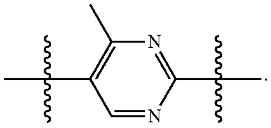 [SMILES: *c1ncc(*)c(C)n1]
In other embodiments, C is
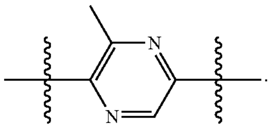 [SMILES: *c1cnc(*)c(C)n1]

In other embodiments, C is

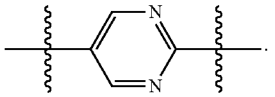 [SMILES: *c1cnc(*)nc1]

In some embodiments, $X_1$ of compound of formula II and/or II(a) is C. In other embodiments, $X_1$ is N. In other embodiments, $X_1$ is N—O (i.e., N-oxide).

In some embodiments, $X_2$ of compound of formula II and/or II(a) is C. In other embodiments, $X_2$ is N. In other embodiments, $X_2$ is N—O (i.e., N-oxide).

In some embodiments, $X_3$ of compound of formula II and/or II(a) is C. In other embodiments, $X_3$ is N. In other embodiments, $X_3$ is N—O (i.e., N-oxide).

In some embodiments, $X_4$ of compound of formula II and/or II(a) is C. In other embodiments, $X_4$ is N. In other embodiments, $X_4$ is N—O (i.e., N-oxide).

In some embodiments, $X_5$ of compound of formula II and/or II(a) is C. In other embodiments, $X_5$ is N. In other embodiments, $X_5$ is N—O (i.e., N-oxide).

In some embodiments, $X_6$ of compound of formula II and/or II(a) is C. In other embodiments, $X_6$ is N. In other embodiments, $X_6$ is N—O (i.e., N-oxide).

In some embodiments, $X_7$ of compound of formula II and/or II(a) is C. In other embodiments, $X_7$ is N. In other embodiments, $X_7$ is N—O (i.e., N-oxide).

In some embodiments, $X_8$ of compound of formula II and/or II(a) is C. In other embodiments, $X_8$ is N. In other embodiments, $X_8$ is N—O (i.e., N-oxide).

In some embodiments, $R_{200}$ of compound of formula II, II(a) and/or II(b) is H. In other embodiments, $R_{200}$ is a $C_1$-$C_5$ linear or branched, substituted or unsubstituted alkyl. In other embodiments, $R_{200}$ is methyl. In other embodiments, $R_{200}$ is ethyl. In other embodiments, $R_{200}$ is propyl. In other embodiments, $R_{200}$ is iso-propyl. In other embodiments, $R_{200}$ is t-Bu. In other embodiments, $R_{200}$ is iso-butyl. In other embodiments, $R_{200}$ is pentyl. In other embodiments, $R_{200}$ is benzyl.

In some embodiments, $R_{400}$ of compound of formula II and/or II(a) is H. In other embodiments, $R_{400}$ is a $C_1$-$C_5$ linear or branched, substituted or unsubstituted alkyl. In other embodiments, $R_{400}$ is methyl. In other embodiments, $R_{400}$ is ethyl. In other embodiments, $R_{400}$ is propyl. In other embodiments, $R_{400}$ is iso-propyl. In other embodiments, $R_{400}$ is t-Bu. In other embodiments, $R_{400}$ is iso-butyl. In other embodiments, $R_{400}$ is pentyl. In other embodiments, $R_{400}$ is benzyl.

In some embodiments, $R_{500}$ of compound of formula II and/or II(a) is H. In other embodiments, $R_{500}$ is a $C_1$-$C_5$ linear or branched, substituted or unsubstituted alkyl. In other embodiments, $R_{500}$ is methyl. In other embodiments, $R_{500}$ is ethyl. In other embodiments, $R_{500}$ is propyl. In other embodiments, $R_{500}$ is iso-propyl. In other embodiments, $R_{500}$ is t-Bu. In other embodiments, $R_{500}$ is iso-butyl. In other embodiments, $R_{500}$ is pentyl. In other embodiments, $R_{500}$ is benzyl.

In some embodiments, $R_{600}$ of compound of formula II and/or II(a) is H. In other embodiments, $R_{600}$ is a $C_1$-$C_5$ linear or branched, substituted or unsubstituted alkyl. In other embodiments, $R_{600}$ is methyl. In other embodiments, $R_{600}$ is ethyl. In other embodiments, $R_{600}$ is propyl. In other embodiments, $R_{600}$ is iso-propyl. In other embodiments, $R_{600}$ is t-Bu. In other embodiments, $R_{600}$ is iso-butyl. In other embodiments, $R_{600}$ is pentyl. In other embodiments, $R_{600}$ is benzyl.

In some embodiments, $R_{201}$ of formula II and/or II(a) is nothing. In other embodiments, $R_{201}$ is H. In other embodiments, $R_{201}$ is a $C_1$-$C_5$ linear or branched, substituted or unsubstituted alkyl. In other embodiments, $R_{201}$ is methyl. In other embodiments, $R_{201}$ is ethyl. In other embodiments, $R_{201}$ is propyl. In other embodiments, $R_{201}$ is iso-propyl. In other embodiments, $R_{201}$ is t-Bu. In other embodiments, $R_{201}$ is iso-butyl. In other embodiments, $R_{201}$ is pentyl. In other embodiments, $R_{201}$ is benzyl.

In some embodiments, $R_{202}$ of formula II and/or II(a) is nothing. In other embodiments, $R_{202}$ is H. In other embodiments, $R_{202}$ is a $C_1$-$C_5$ linear or branched, substituted or unsubstituted alkyl. In other embodiments, $R_{202}$ is methyl. In other embodiments, $R_{202}$ is ethyl. In other embodiments, $R_{202}$ is propyl. In other embodiments, $R_{202}$ is iso-propyl. In other embodiments, $R_{202}$ is t-Bu. In other embodiments, $R_{201}$ is iso-butyl. In other embodiments, $R_{202}$ is pentyl. In other embodiments, $R_{202}$ is benzyl.

In some embodiments, $R_{203}$ of formula II and/or II(a) is nothing. In other embodiments, $R_{203}$ is H. In other embodiments, $R_{203}$ is a $C_1$-$C_5$ linear or branched, substituted or unsubstituted alkyl. In other embodiments, $R_{203}$ is methyl. In other embodiments, $R_{203}$ is ethyl. In other embodiments, $R_{203}$ is propyl. In other embodiments, $R_{203}$ is iso-propyl. In other embodiments, $R_{203}$ is t-Bu. In other embodiments, $R_{201}$ is iso-butyl. In other embodiments, $R_{203}$ is pentyl. In other embodiments, $R_{203}$ is benzyl.

In some embodiments, $R_{204}$ of formula II and/or II(a) is nothing. In other embodiments, $R_{204}$ is H. In other embodiments, $R_{204}$ is a $C_1$-$C_5$ linear or branched, substituted or unsubstituted alkyl. In other embodiments, $R_{204}$ is methyl. In other embodiments, $R_{204}$ is ethyl. In other embodiments, $R_{204}$ is propyl. In other embodiments, $R_{204}$ is iso-propyl. In other embodiments, $R_{204}$ is t-Bu. In other embodiments, $R_{204}$ is iso-butyl. In other embodiments, $R_{204}$ is pentyl. In other embodiments, $R_{204}$ is benzyl.

In some embodiments, $R_{301}$ of formula II and/or II(a) is nothing. In other embodiments, $R_{301}$ is H. In other embodiments, $R_{301}$ is a $C_1$-$C_5$ linear or branched, substituted or unsubstituted alkyl. In other embodiments, $R_{301}$ is methyl. In other embodiments, $R_{301}$ is ethyl. In other embodiments, $R_{301}$ is propyl. In other embodiments, $R_{301}$ is iso-propyl. In other embodiments, $R_{301}$ is t-Bu. In other embodiments, $R_{301}$ is iso-butyl. In other embodiments, $R_{301}$ is pentyl. In other embodiments, $R_{301}$ is benzyl.

In some embodiments, $R_{302}$ of formula II and/or II(a) is nothing. In other embodiments, $R_{302}$ is H. In other embodiments, $R_{302}$ is a $C_1$-$C_5$ linear or branched, substituted or unsubstituted alkyl. In other embodiments, $R_{302}$ is methyl. In other embodiments, $R_{302}$ is ethyl. In other embodiments, $R_{302}$ is propyl. In other embodiments, $R_{302}$ is iso-propyl. In other embodiments, $R_{302}$ is t-Bu. In other embodiments, $R_{302}$ is iso-butyl. In other embodiments, $R_{302}$ is pentyl. In other embodiments, $R_{302}$ is benzyl.

In some embodiments, $R_{303}$ of formula II and/or II(a) is nothing. In other embodiments, $R_{303}$ is H. In other embodiments, $R_{303}$ is a $C_1$-$C_5$ linear or branched, substituted or unsubstituted alkyl. In other embodiments, $R_{303}$ is methyl. In other embodiments, $R_{303}$ is ethyl. In other embodiments, $R_{303}$ is propyl. In other embodiments, $R_{303}$ is iso-propyl. In other embodiments, $R_{303}$ is t-Bu. In other embodiments, $R_{303}$ is iso-butyl. In other embodiments, $R_{303}$ is pentyl. In other embodiments, $R_{303}$ is benzyl.

In some embodiments, $R_{304}$ of formula II and/or II(a) is nothing. In other embodiments, $R_{304}$ is H. In other embodiments, $R_{304}$ is a $C_1$-$C_5$ linear or branched, substituted or unsubstituted alkyl. In other embodiments, $R_{304}$ is methyl. In other embodiments, $R_{304}$ is ethyl. In other embodiments, $R_{304}$ is propyl. In other embodiments, $R_{304}$ is iso-propyl. In other embodiments, $R_{304}$ is t-Bu. In other embodiments, $R_{304}$ is iso-butyl. In other embodiments, $R_{304}$ is pentyl. In other embodiments, $R_{304}$ is benzyl.

In some embodiments, $R_{100}$ of formula II, II(a) and/or II(b) is H. In other embodiments, $R_{100}$ is F. In other embodiments, $R_{100}$ is Cl. In other embodiments, $R_{100}$ is Br. In other embodiments, $R_{100}$ is I. In other embodiments, $R_{100}$ is OH. In other embodiments, $R_{100}$ is SH. In other embodiments, $R_{100}$ is $R_8$—OH. In other embodiments, $R_{100}$ is $CH_2$—OH. In other embodiments, $R_{100}$ is $R_8$—SH. In other embodiments, $R_{100}$ is —$R_8$—O—$R_{10}$. In other embodiments, $R_{100}$ is —$CH_2$—O—$CH_3$. In other embodiments, $R_{100}$ is $R_8$—($C_3$-$C_8$ cycloalkyl). In other embodiments, $R_{100}$ is $R_8$—($C_3$-$C_8$ heterocyclic ring). In other embodiments, $R_{100}$ is $CH_2$-imidazole. In other embodiments, $R_{100}$ is indazole. In other embodiments, $R_{100}$ is $CF_3$. In other embodiments, $R_{100}$ is $CD_3$. In other embodiments, $R_{100}$ is $OCD_3$. In other embodiments, $R_{100}$ is CN. In other embodiments, $R_{100}$ is $NO_2$. In other embodiments, $R_{100}$ is —$CH_2CN$. In other embodiments, $R_{100}$ is —$R_8$CN. In other embodiments, $R_{100}$ is $NH_2$. In other embodiments, $R_{100}$ is NHR. In other embodiments, $R_{100}$ is $NHCH_3$. In other embodiments, $R_{100}$ is $N(R)_2$. In other embodiments, $R_{100}$ is $N(CH_3)_2$. In other embodiments, $R_{100}$ is $R_8$—$N(R_{10})(R_{11})$. In other embodiments, $R_{100}$ is $CH_2$—$NH_2$. In other embodiments, $R_{100}$ is $CH_2$—$N(CH_3)_2$. In other embodiments, $R_{100}$ is $R_9$—$R_8$—$N(R_{10})(R_{11})$. In other embodiments, $R_{100}$ is C≡C—$CH_2$—$NH_2$. In other embodiments, $R_{100}$ is $B(OH)_2$. In other embodiments, $R_{100}$ is —OC(O)—$N(R_{10})(R_{11})$. In other embodiments, $R_{100}$ is OC(O)-piperidine-$C(Me)_2CH_2OH$. In other embodiments, $R_{100}$ is OC(O)-piperazine-$CH_2CH_2OH$. In other embodiments, $R_{100}$ is OC(O)-piperidine-piperidine. In other embodiments, $R_{100}$ is —$OC(O)CF_3$. In other embodiments, $R_{100}$ is —$OCH_2Ph$. In other embodiments, $R_{100}$ is NHC(O)—$R_{10}$. In other embodiments, $R_{100}$ is $NHC(O)CH_3$). In other embodiments, $R_{100}$ is NHCO—$N(R_{10})(R_{11})$. In other embodiments, $R_{100}$ is $NHC(O)N(CH_3)_2$. In other embodiments, $R_{100}$ is COOH. In other embodiments, $R_{100}$ is —C(O)Ph. In other embodiments, $R_{100}$ is C(O)O—$R_{10}$. In other embodiments, $R_{100}$ is C(O)O—$CH_3$. In other embodiments, $R_{100}$ is C(O)O—$CH(CH_3)_2$. In other embodiments, $R_{100}$ is C(O)O—$CH_2CH_3$). In other embodiments, $R_{100}$ is $R_8$—C(O)—$R_{10}$. In other embodiments, $R_{100}$ is $CH_2C(O)CH_3$. In other embodiments, $R_{100}$ is C(O)H. In other embodiments, $R_{100}$ is C(O)—$R_{10}$. In other embodiments, $R_{100}$ is C(O)—$CH_3$. In other embodiments, $R_{100}$ is C(O)—$CH_2CH_3$. In other embodiments, $R_{100}$ is C(O)—$CH_2CH_2CH_3$. In other embodiments, $R_{100}$ is $C_1$-$C_5$ linear or branched C(O)-haloalkyl. In other embodiments, $R_{100}$ is C(O)—$CF_3$. In other embodiments, $R_{100}$ is —$C(O)NH_2$. In other embodiments, $R_{100}$ is C(O)NHR. In other embodiments, $R_{100}$ is $C(O)N(R_{10})(R_{11})$. In other embodiments, $R_{100}$ is $C(O)N(CH_3)_2$. In other embodiments, $R_{100}$ is $SO_2R$. In other embodiments, $R_{100}$ is $SO_2N(R_{10})(R_1)$. In other embodiments, $R_{100}$ is $SO_2N(CH_3)_2$. In other embodiments, $R_{100}$ is $SO_2NHC(O)CH_3$. In other embodiments, $R_{100}$ is $C_1$-$C_5$ linear or branched, substituted or unsubstituted alkyl. In other embodiments, $R_{100}$ is methyl. In other embodiments, $R_{100}$ is 2, 3, or 4-$CH_2$—$C_6H_4$—Cl. In other embodiments, $R_{100}$ is ethyl. In other embodiments, $R_{100}$ is propyl. In other embodiments, $R_{100}$ is iso-propyl. In other embodiments, $R_{100}$ is t-Bu. In other embodiments, $R_{100}$ is iso-butyl. In other embodiments, $R_{100}$ is pentyl. In other embodiments, $R_{100}$ is benzyl. In other embodiments, $R_{100}$ is $C_1$-$C_5$ linear or branched, substituted or unsubstituted alkenyl. In other embodiments, $R_{100}$ is $CH{=}C(Ph)_2$. In other embodiments, $R_{100}$ is $C_1$-$C_5$ linear, branched or cyclic haloalkyl. In other embodiments, $R_{100}$ is $CF_3$. In other embodiments, $R_{100}$ is $CF_2CH_3$. In other embodiments, $R_{100}$ is $CH_2CF_3$, $CF_2CH_2CH_3$, $CH_2CH_2CF_3$, $CF_2CH(CH_3)_2$, or $CF(CH_3)$—$CH(CH_3)_2$; each is a separate embodiment according to this invention. In other embodiments, $R_{100}$ is $C_1$-$C_5$ linear, branched or cyclic alkoxy. In other embodiments, $R_{100}$ is methoxy, ethoxy, propoxy, isopropoxy, O—$CH_2$-cyclopropyl, O-cyclobutyl, O-cyclopentyl, O-cyclohexyl, 1-butoxy, 2-butoxy, or 0-tBu; each is a separate embodiment according to this invention. In other embodiments, $R_{100}$ is $C_1$-$C_5$ linear or branched thioalkoxy. In other embodiments, $R_{100}$ is $C_1$-$C_5$ linear or branched haloalkoxy. In other embodiments, $R_{100}$ is $OCF_3$. In other embodiments, $R_{100}$ is $OCHF_2$. In other embodiments, $R_{100}$ is $C_1$-$C_5$ linear or branched alkoxyalkyl. In other embodiments, $R_{100}$ is substituted or unsubstituted $C_3$-$C_8$ cycloalkyl. In other embodiments, $R_{100}$ is cyclopropyl. In other embodiments, $R_{100}$ is cyclopentyl. In other embodiments, $R_{100}$ is substituted or unsubstituted $C_3$-$C_8$ heterocyclic ring. In other embodiments, $R_{100}$ is 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide; each is a separate embodiment according to this invention. In other embodiments, $R_{100}$ is substituted or unsubstituted aryl. In other embodiments, $R_{100}$ is phenyl. In other embodiments, $R_{100}$ is substituted or unsubstituted benzyl. In other embodiments, $R_{100}$ is. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, $C_3$-$C_8$ cycloalkyl, halophenyl, (benzyloxy)phenyl, CN, $NO_2$ or any combination thereof. In other embodiments, $R_{100}$ is $CH(CF_3)(NH$—$R_{10})$.

In some embodiments, $R_{700}$ of formula II, II(a) and/or II(b) is H. In other embodiments, $R_{700}$ is F. In other embodiments, $R_{700}$ is Cl. In other embodiments, $R_{700}$ is Br. In other embodiments, $R_{700}$ is I. In other embodiments, $R_{700}$ is OH. In other embodiments, $R_{700}$ is SH. In other embodiments, $R_{700}$ is $R_8$—OH. In other embodiments, $R_{700}$ is $CH_2$—OH. In other embodiments, $R_{700}$ is $R_8$—SH. In other embodiments, $R_{700}$ is —$R_8$—O—$R_{10}$. In other embodiments, $R_{700}$ is —$CH_2$—O—$CH_3$. In other embodiments, $R_{700}$ is $R_8$—($C_3$-$C_8$ cycloalkyl). In other embodiments, $R_{700}$ is $R_8$—($C_3$-$C_8$ heterocyclic ring). In other embodiments, $R_{700}$ is $CH_2$-imidazole. In other embodiments, $R_{700}$ is indazole. In other embodiments, $R_{700}$ is $CF_3$. In other embodiments, $R_{700}$ is $CD_3$. In other embodiments, $R_{700}$ is $OCD_3$. In other embodiments, $R_{700}$ is CN. In other embodiments, $R_{700}$ is $NO_2$. In other embodiments, $R_{700}$ is —$CH_2CN$. In other embodiments, $R_{700}$ is —$R_8$CN. In other embodiments, $R_{700}$ is $NH_2$. In other embodiments, $R_{700}$ is NHR. In other embodiments, $R_{700}$ is $NHCH_3$. In other embodiments, $R_{700}$ is $N(R)_2$. In other embodiments, $R_{700}$ is $N(CH_3)_2$. In other embodiments, $R_{700}$ is $R_8$—$N(R_{10})(R_{11})$. In other embodiments, $R_{700}$ is $CH_2$—$NH_2$. In other embodiments, $R_{700}$ is $CH_2$—$N(CH_3)_2$. In other embodiments, $R_{700}$ is $R_9$—$R_8$—$N(R_{10})(R_{11})$. In other embodiments, $R_{700}$ is C≡C—$CH_2$—$NH_2$. In other embodiments, $R_{700}$ is $B(OH)_2$. In other embodiments, $R_{700}$ is —OC(O)—$N(R_{10})(R_{11})$. In other embodiments, $R_{700}$ is OC(O)-piperidine-$C(Me)_2CH_2OH$. In other embodiments, $R_{700}$ is OC(O)-piperazine-$CH_2CH_2OH$. In other embodiments, $R_{700}$ is OC(O)-piperidine-piperidine. In other embodiments, $R_{700}$ is —OC(O)$CF_3$. In other embodiments, $R_{700}$ is —$OCH_2$Ph. In other embodiments, $R_{700}$ is NHC(O)—$R_{10}$. In other embodiments, $R_{700}$ is NHC(O)$CH_3$). In other embodiments, $R_{700}$ is NHCO—N($R_{10}$)($R_{11}$). In other embodiments, $R_{700}$ is NHC(O)N$(CH_3)_2$. In other embodiments, $R_{700}$ is COOH. In other embodiments, $R_{700}$ is —C(O)Ph. In other embodiments, $R_{700}$ is C(O)O—$R_{10}$. In other embodiments, $R_{700}$ is C(O)O—$CH_3$. In other embodiments, $R_{700}$ is C(O)O—CH$(CH_3)_2$. In other embodiments, $R_{700}$ is C(O)O—$CH_2CH_3$). In other embodiments, $R_{700}$ is $R_8$—C(O)—$R_{10}$. In other embodiments, $R_{700}$ is $CH_2$C(O)$CH_3$. In other embodiments, $R_{700}$ is C(O)H. In other embodiments, $R_{700}$ is C(O)—$R_{10}$. In other embodiments, $R_{700}$ is C(O)—$CH_3$. In other embodiments, $R_{700}$ is C(O)—$CH_2CH_3$. In other embodiments, $R_{700}$ is C(O)—$CH_2CH_2CH_3$. In other embodiments, $R_{700}$ is $C_1$-$C_5$ linear or branched C(O)-haloalkyl. In other embodiments, $R_{700}$ is C(O)—$CF_3$. In other embodiments, $R_{700}$ is —C(O)$NH_2$. In other embodiments, $R_{700}$ is C(O)NHR. In other embodiments, $R_{700}$ is C(O)N($R_{10}$)($R_{11}$). In other embodiments, $R_{700}$ is C(O)N$(CH_3)_2$. In other embodiments, $R_{700}$ is $SO_2$R. In other embodiments, $R_{700}$ is $SO_2$N($R_{10}$)($R_{11}$). In other embodiments, $R_{700}$ is $SO_2$N$(CH_3)_2$. In other embodiments, $R_{100}$ is $SO_2$NHC(O)$CH_3$. In other embodiments, $R_{700}$ is $C_1$-$C_5$ linear or branched, substituted or unsubstituted alkyl. In other embodiments, $R_{700}$ is methyl. In other embodiments, $R_{700}$ is 2, 3, or 4-$CH_2$—$C_6H_4$—Cl. In other embodiments, $R_{700}$ is ethyl. In other embodiments, $R_{700}$ is propyl. In other embodiments, $R_{700}$ is iso-propyl. In other embodiments, $R_{700}$ is t-Bu. In other embodiments, $R_{700}$ is iso-butyl. In other embodiments, $R_{700}$ is pentyl. In other embodiments, $R_{700}$ is benzyl. In other embodiments, $R_{700}$ is $C_1$-$C_5$ linear or branched, substituted or unsubstituted alkenyl. In other embodiments, $R_{700}$ is CH═C$(Ph)_2$. In other embodiments, $R_{100}$ is $C_1$-$C_5$ linear, branched or cyclic haloalkyl. In other embodiments, $R_{700}$ is $CF_3$. In other embodiments, $R_{700}$ is $CF_2CH_3$. In other embodiments, $R_{700}$ is $CH_2CF_3$, $CF_2CH_2CH_3$, $CH_2CH_2CF_3$, $CF_2CH(CH_3)_2$, or CF($CH_3$)—CH$(CH_3)_2$; each is a separate embodiment according to this invention. In other embodiments, $R_{700}$ is $C_1$-$C_5$ linear, branched or cyclic alkoxy. In other embodiments, $R_{700}$ is methoxy, ethoxy, propoxy, isopropoxy, O—$CH_2$-cyclopropyl, O-cyclobutyl, O-cyclopentyl, O-cyclohexyl, 1-butoxy, 2-butoxy, or 0-tBu; each is a separate embodiment according to this invention. In other embodiments, $R_{700}$ is $C_1$-$C_5$ linear or branched thioalkoxy. In other embodiments, $R_{700}$ is $C_1$-$C_5$ linear or branched haloalkoxy. In other embodiments, $R_{700}$ is $OCF_3$. In other embodiments, $R_{700}$ is $OCHF_2$. In other embodiments, $R_{700}$ is $C_1$-$C_5$ linear or branched alkoxyalkyl. In other embodiments, $R_{700}$ is substituted or unsubstituted $C_3$-$C_8$ cycloalkyl. In other embodiments, $R_{700}$ is cyclopropyl. In other embodiments, $R_{700}$ is cyclopentyl. In other embodiments, $R_{700}$ is substituted or unsubstituted $C_3$-$C_8$ heterocyclic ring. In other embodiments, $R_{700}$ is 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), pyrimidine, pyrazine, oxacyclobutane (1 or 2-oxacyclobutane), indole, protonated or deprotonated pyridine oxide; each is a separate embodiment according to this invention. In other embodiments, $R_{700}$ is substituted or unsubstituted aryl. In other embodiments, $R_{700}$ is phenyl. In other embodiments, $R_{700}$ is substituted or unsubstituted benzyl. In other embodiments, $R_{700}$ is. In other embodiments, substitutions include: F, Cl, Br, I, $C_1$-$C_5$ linear or branched alkyl (e.g. methyl, ethyl), OH, alkoxy, N$(R)_2$, $CF_3$, aryl, phenyl, $C_3$-$C_8$ cycloalkyl, halophenyl, (benzyloxy)phenyl, CN, $NO_2$ or any combination thereof. In other embodiments, $R_{700}$ is CH($CF_3$)(NH—$R_{10}$).

In some embodiments, $R_1$ of formula I, I(a), I(b), II, II(a) and II(b) is H.

In other embodiments, $R_1$ of formula I, I(a), I(b), II, II(a), II(b), III and III(a) is F. In other embodiments, $R_1$ is Cl. In other embodiments, $R_1$ is Br. In other embodiments, $R_1$ is I. In other embodiments, $R_1$ is $R_8$—($C_3$-$C_8$ cycloalkyl). In other embodiments, $R_1$ is $CH_2$-cyclohexyl. In other embodiments, $R_1$ is $R_8$—($C_3$-$C_8$ heterocyclic ring). In other embodiments, $R_1$ is $CH_2$-imidazole. In other embodiments, $R_1$ is $CH_2$-indazole. In other embodiments, $R_1$ is $CF_3$. In other embodiments, $R_1$ is $CF_2CH_2CH_3$. In other embodiments, $R_1$ is $CH_2CH_2CF_3$. In other embodiments, $R_1$ is $CF_2CH(CH_3)_2$. In other embodiments, $R_1$ is CF($CH_3$)—CH$(CH_3)_2$. In other embodiments, $R_1$ is $OCD_3$. In other embodiments, $R_1$ is $NO_2$. In other embodiments, $R_1$ is $NH_2$. In other embodiments, $R_1$ is $R_8$—N($R_{10}$)($R_{11}$). In other embodiments, $R_1$ is $CH_2$—$NH_2$. In other embodiments, $R_1$ is $CH_2$—N$(CH_3)_2$). In other embodiments, $R_1$ is $R_9$—$R_8$—N($R_{10}$)($R_{11}$). In other embodiments, $R_1$ is C≡C—$CH_2$—$NH_2$. In other embodiments, $R_1$ is B$(OH)_2$. In other embodiments, $R_1$ is NHC(O)—$R_{10}$. In other embodiments, $R_1$ is NHC(O)$CH_3$. In other embodiments, $R_1$ is NHCO—N($R_{10}$)($R_{11}$). In other embodiments, $R_1$ is NHC(O)N$(CH_3)_2$. In other embodiments, $R_1$ is COOH. In other embodiments, $R_1$ is C(O)O—$R_{10}$. In other embodiments, $R_1$ is C(O)O—CH$(CH_3)_2$. In other embodiments, $R_1$ is C(O)O—$CH_3$. In other embodiments, $R_1$ is $SO_2$N($R_{10}$)($R_{11}$). In other embodiments, $R_1$ is $SO_2$N$(CH_3)_2$. In other embodiments, $R_1$ is $SO_2$NHC(O)$CH_3$. In other embodiments, $R_1$ is $C_1$-$C_5$ linear or branched, substituted or unsubstituted alkyl. In other embodiments, $R_1$ is methyl. In other embodiments, $R_1$ is ethyl. In other embodiments, $R_1$ is iso-propyl. In other embodiments, $R_1$ is t-Bu. In other embodiments, $R_1$ is iso-butyl. In other embodiments, $R_1$ is pentyl. In other embodiments, $R_1$ is propyl. In other embodiments, $R_1$ is benzyl. In other embodiments, $R_1$ is $C_1$-$C_5$ linear or branched, substituted or unsubstituted alkenyl. In other embodiments, $R_1$ is CH═C$(Ph)_2$. In other embodiments, $R_1$ is 2-$CH_2$—$C_6H_4$—Cl. In other embodiments, $R_1$ is 3-$CH_2$—$C_6H_4$—Cl. In other embodiments, $R_1$ is 4-$CH_2$—$C_6H_4$—Cl. In other embodiments, $R_1$ is ethyl. In other embodiments, $R_1$ is iso-propyl. In other embodiments, $R_1$ is t-Bu. In other embodiments, $R_1$ is iso-butyl. In other embodiments, $R_1$ is pentyl. In other embodiments, $R_1$ is substituted or unsubstituted $C_3$-$C_5$ cycloalkyl (e.g., cyclopropyl, cyclopentyl). In other embodiments, $R_1$ is $C_1$-$C_5$ linear, branched or cyclic alkoxy. In other embodiments, $R_1$ is methoxy. In other embodiments, $R_1$ is ethoxy. In other embodiments, $R_1$ is propoxy. In other embodiments, $R_1$ is isopropoxy. In other embodiments, $R_1$ is 0-$CH_2$-cyclopropyl. In other embodiments, $R_1$ is O-cyclobutyl. In other embodiments, $R_1$ is O-cyclopentyl. In other embodiments, $R_1$ is O-cyclohexyl. In other embodiments, $R_1$ is O-1-oxacyclobutyl. In other embodiments, $R_1$ is O-2-oxacyclobutyl. In other embodiments, $R_1$ is 1-butoxy. In other embodiments, $R_1$ is 2-butoxy. In other embodiments, $R_1$ is O-tBu. In other embodiments, $R_1$ is $C_1$-$C_5$ linear, branched or cyclic alkoxy wherein at least one methylene group ($CH_2$) in the alkoxy is replaced with an oxygen atom (O). In other embodiments, $R_1$ is O-1-oxacyclobutyl. In other embodiments, $R_1$ is O-2-oxacyclobutyl. In other embodiments, $R_1$ is $C_1$-$C_5$ linear or branched haloalkoxy. In other embodiments, $R_1$ is $OCF_3$. In other embodiments, $R_1$ is $OCHF_2$. In other embodiments, $R_1$ is substituted or unsubstituted $C_3$-$C_8$ heterocyclic ring. In other embodiments, $R_1$ is oxazole. In other embodiments, $R_1$ is methyl substituted oxazole. In other embodiments, $R_1$ is oxadiazole. In other embodiments, $R_1$ is methyl substituted oxadiazole. In other embodiments, $R_1$ is imidazole. In other embodiments, $R_1$ is methyl substituted imidazole. In other embodiments, $R_1$ is pyridine. In other embodiments, $R_1$ is 2-pyridine. In other embodiments, $R_1$ is 3-pyridine. In other embodiments, $R_1$ is 3-methyl-2-pyridine. In other embodiments, $R_1$ is 4-pyridine. In other embodiments, $R_1$ is tetrazole. In other embodiments, $R_1$ is pyrimidine. In other embodiments, $R_1$ is pyrazine. In other embodiments, $R_1$ is oxacyclobutane. In other embodiments, $R_1$ is 1-oxacyclobutane. In other embodiments, $R_1$ is 2-oxacyclobutane. In other embodiments, $R_1$ is indole. In other embodiments, $R_1$ is pyridine oxide. In other embodiments, $R_1$ is protonated pyridine oxide. In other embodiments, $R_1$ is deprotonated pyridine oxide. In other embodiments, $R_1$ is 3-methyl-4H-1,2,4-triazole. In other embodiments, $R_1$ is 5-methyl-1,2,4-oxadiazole. In other embodiments, $R_1$ is substituted or unsubstituted aryl. In other embodiments, $R_1$ is phenyl. In other embodiments, $R_1$ is bromophenyl. In other embodiments, $R_1$ is 2-bromophenyl. In other embodiments, $R_1$ is 3-bromophenyl. In other embodiments, $R_1$ is 4-bromophenyl. In other embodiments, $R_1$ is substituted or unsubstituted benzyl. In other embodiments, $R_1$ is 4-Cl-benzyl. In other embodiments, $R_1$ is 4-OH-benzyl. In other embodiments, $R_1$ is benzyl. In other embodiments, $R_1$ is $R_8$—$N(R_{10})(R_{11})$. In other embodiments, $R_1$ is $CH_2$—$NH_2$. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, and/or $NO_2$, each is a separate embodiment according to this invention.

In some embodiments, $R_2$ of formula I, I(a), I(b), II, II(a) and II(b) is H.

In some embodiments, $R_2$ of formula I, I(a), I(b), II, II(a), II(b), III and III(a) is F. In other embodiments, $R_2$ is Cl. In other embodiments, $R_2$ is Br. In other embodiments, $R_2$ is I. In other embodiments, $R_2$ is $R_8$—($C_3$-$C_8$ cycloalkyl). In other embodiments, $R_2$ is $CH_2$-cyclohexyl. In other embodiments, $R_2$ is $R_8$—($C_3$-$C_8$ heterocyclic ring). In other embodiments, $R_2$ is $CH_2$-imidazole. In other embodiments, $R_2$ is $CF_3$. In other embodiments, $R_2$ is $CF_2CH_2CH_3$. In other embodiments, $R_2$ is $CH_2CH_2CF_3$. In other embodiments, $R_2$ is $CF_2CH(CH_3)_2$. In other embodiments, $R_2$ is $CF(CH_3)$—$CH(CH_3)_2$. In other embodiments, $R_2$ is $OCD_3$. In other embodiments, $R_2$ is $NO_2$. In other embodiments, $R_2$ is $NH_2$. In other embodiments, $R_2$ is $R_8$—$N(R_{10})(R_{11})$. In other embodiments, $R_2$ is $CH_2$—$NH_2$. In other embodiments, $R_2$ is $CH_2$—$N(CH_3)_2$). In other embodiments, $R_2$ is $R_9$—$R_8$—$N(R_{10})(R_{11})$. In other embodiments, $R_2$ is C≡C—$CH_2$—$NH_2$. In other embodiments, $R_2$ is $B(OH)_2$. In other embodiments, $R_2$ is NHC(O)—$R_{10}$. In other embodiments, $R_2$ is $NHC(O)CH_3$. In other embodiments, $R_2$ is NHCO—$N(R_{10})(R_{11})$. In other embodiments, $R_2$ is $NHC(O)N(CH_3)_2$. In other embodiments, $R_2$ is COOH. In other embodiments, $R_2$ is C(O)O—$R_{10}$. In other embodiments, $R_2$ is C(O)O—$CH(CH_3)_2$. In other embodiments, $R_2$ is C(O)O—$CH_3$. In other embodiments, $R_2$ is $SO_2N(R_{10})(R_{11})$. In other embodiments, $R_2$ is $SO_2N(CH_3)_2$. In other embodiments, $R_2$ is $SO_2NHC(O)CH_3$. In other embodiments, $R_2$ is $C_1$-$C_5$ linear or branched, substituted or unsubstituted alkyl. In other embodiments, $R_2$ is methyl. In other embodiments, $R_2$ is ethyl. In other embodiments, $R_2$ is iso-propyl. In other embodiments, $R_2$ is t-Bu. In other embodiments, $R_2$ is iso-butyl. In other embodiments, $R_2$ is pentyl. In other embodiments, $R_2$ is propyl. In other embodiments, $R_2$ is benzyl. In other embodiments, $R_2$ is $C_1$-$C_5$ linear or branched, substituted or unsubstituted alkenyl. In other embodiments, $R_2$ is $CH{=}C(Ph)_2$. In other embodiments, $R_2$ is 2-$CH_2$—$C_6H_4$—Cl. In other embodiments, $R_2$ is 3-$CH_2$—$C_6H_4$—Cl. In other embodiments, $R_2$ is 4-$CH_2$—$C_6H_4$—Cl. In other embodiments, $R_2$ is ethyl. In other embodiments, $R_2$ is iso-propyl. In other embodiments, $R_2$ is t-Bu. In other embodiments, $R_2$ is iso-butyl. In other embodiments, $R_2$ is pentyl. In other embodiments, $R_2$ is substituted or unsubstituted $C_3$-$C_8$ cycloalkyl (e.g., cyclopropyl, cyclopentyl). In other embodiments, $R_2$ is $C_1$-$C_5$ linear, branched or cyclic alkoxy. In other embodiments, $R_2$ is methoxy. In other embodiments, $R_2$ is ethoxy. In other embodiments, $R_2$ is propoxy. In other embodiments, $R_2$ is isopropoxy. In other embodiments, $R_2$ is O—$CH_2$-cyclopropyl. In other embodiments, $R_2$ is O-cyclobutyl. In other embodiments, $R_2$ is O-cyclopentyl. In other embodiments, $R_2$ is O-cyclohexyl. In other embodiments, $R_2$ is O-1-oxacyclobutyl. In other embodiments, $R_2$ is O-2-oxacyclobutyl. In other embodiments, $R_2$ is 1-butoxy. In other embodiments, $R_2$ is 2-butoxy. In other embodiments, $R_2$ is 0-tBu. In other embodiments, $R_2$ is $C_1$-$C_5$ linear or branched haloalkoxy. In other embodiments, $R_2$ is $OCF_3$. In other embodiments, $R_2$ is $OCHF_2$. In other embodiments, $R_2$ is substituted or unsubstituted $C_3$-$C_8$ heterocyclic ring. In other embodiments, $R_2$ is oxazole or methyl substituted oxazole. In other embodiments, $R_2$ is oxadiazole or methyl substituted oxadiazole. In other embodiments, $R_2$ is imidazole or methyl substituted imidazole. In other embodiments, $R_2$ is pyridine. In other embodiments, $R_2$ is 2-pyridine. In other embodiments, $R_2$ is 3-pyridine. In other embodiments, $R_2$ is 4-pyridine. In other embodiments, $R_2$ is 3-methyl-2-pyridine. In other embodiments, $R_2$ is tetrazole. In other embodiments, $R_2$ is pyrimidine. In other embodiments, $R_2$ is pyrazine. In other embodiments, $R_2$ is oxacyclobutane. In other embodiments, $R_2$ is 1-oxacyclobutane. In other embodiments, $R_2$ is 2-oxacyclobutane. In other embodiments, $R_2$ is indole. In other embodiments, $R_2$ is pyridine oxide. In other embodiments, $R_2$ is protonated pyridine oxide. In other embodiments, $R_2$ is deprotonated pyridine oxide. In other embodiments, $R_2$ is 3-methyl-4H-1,2,4-triazole. In other embodiments, $R_2$ is 5-methyl-1,2,4-oxadiazole. In other embodiments, $R_2$ is substituted or unsubstituted aryl. In other embodiments, $R_2$ is phenyl. In other embodiments, $R_2$ is bromophenyl. In other embodiments, $R_2$ is 2-bromophenyl. In other embodiments, $R_2$ is 3-bromophenyl. In other embodiments, $R_2$ is 4-bromophenyl. In other embodiments, $R_2$ is substituted or unsubstituted benzyl. In other embodiments, $R_2$ is benzyl. In other embodiments, $R_1$ is 4-Cl-benzyl. In other embodiments, $R_1$ is 4-OH-benzyl. In other embodiments, $R_2$ is $R_8$—$N(R_{10})(R_{11})$. In other embodiments, $R_2$ is $CH_2$—$NH_2$. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, and/or $NO_2$, each is a separate embodiment according to this invention.

In some embodiments, $R_1$ and $R_2$ of formula I, I(a), I(b), II, II(a), II(b), III and III(a) are joint together to form a pyrrol ring. In some embodiments, $R_1$ and $R_2$ are joint together to form a [1,3]dioxole ring. In some embodiments, $R_1$ and $R_2$ are joint together to form a furanone ring (e.g., furan-2(3H)-one). In some embodiments, $R_1$ and $R_2$ are joint together to form a benzene ring. In some embodiments, $R_1$ and $R_2$ are joint together to form a pyridine ring.

In some embodiments, $R_{20}$ of formula I, I(a), I(b), II, II(a) and II(b) is H.

In some embodiments, $R_{20}$ of formula I, I(a), I(b), II, II(a), II(b), III and III(a) is F. In other embodiments, $R_{20}$ is Cl. In other embodiments, $R_{20}$ is Br. In other embodiments, $R_{20}$ is I. In other embodiments, $R_{20}$ is $R_8$—($C_3$-$C_8$ cycloalkyl). In other embodiments, $R_{20}$ is $CH_2$-cyclohexyl. In other embodiments, $R_{20}$ is $R_8$—($C_3$-$C_8$ heterocyclic ring). In other embodiments, $R_{20}$ is $CH_2$-imidazole. In other embodiments, $R_{20}$ is $CF_3$. In other embodiments, $R_{20}$ is $CF_2CH_2CH_3$. In other embodiments, $R_{20}$ is $CH_2CH_2CF_3$. In other embodiments, $R_{20}$ is $CF_2CH(CH_3)_2$. In other embodiments, $R_{20}$ is $CF(CH_3)$—$CH(CH_3)_2$. In other embodiments, $R_{20}$ is $OCD_3$. In other embodiments, $R_{20}$ is $NO_2$. In other embodiments, $R_{20}$ is $NH_2$. In other embodiments, $R_{20}$ is $R_8$—$N(R_{10})(R_{11})$. In other embodiments, $R_{20}$ is $CH_2$—$NH_2$. In other embodiments, $R_{20}$ is $CH_2$—$N(CH_3)_2$). In other embodiments, $R_{20}$ is $R_9$—$R_8$—$N(R_{10})(R_{11})$. In other embodiments, $R_{20}$ is C≡C—$CH_2$—$NH_2$. In other embodiments, $R_{20}$ is $B(OH)_2$. In other embodiments, $R_{20}$ is NHC(O)—$R_{10}$. In other embodiments, $R_{20}$ is $NHC(O)CH_3$. In other embodiments, $R_{20}$ is NHCO—$N(R_{10})(R_{11})$. In other embodiments, $R_{20}$ is NHC(O) $N(CH_3)_2$. In other embodiments, $R_{20}$ is COOH. In other embodiments, $R_{20}$ is C(O)O—$R_{10}$. In other embodiments, $R_{20}$ is C(O)O—$CH(CH_3)_2$. In other embodiments, $R_{20}$ is C(O)O—$CH_3$. In other embodiments, $R_{20}$ is $SO_2N(R_{10})$ $(R_{11})$. In other embodiments, $R_{20}$ is $SO_2N(CH_3)_2$. In other embodiments, $R_{20}$ is $SO_2NHC(O)CH_3$. In other embodiments, $R_{20}$ is $C_1$-$C_5$ linear or branched, substituted or unsubstituted alkyl. In other embodiments, $R_{20}$ is methyl. In other embodiments, $R_{20}$ is ethyl. In other embodiments, $R_{20}$ is iso-propyl. In other embodiments, $R_{20}$ is t-Bu. In other embodiments, $R_{20}$ is iso-butyl. In other embodiments, $R_{20}$ is pentyl. In other embodiments, $R_{20}$ is propyl. In other embodiments, $R_{20}$ is benzyl. In other embodiments, $R_{20}$ is $C_1$-$C_5$ linear or branched, substituted or unsubstituted alkenyl. In other embodiments, $R_{20}$ is CH═$C(Ph)_2$. In other embodiments, $R_{20}$ is 2-$CH_2$—$C_6H_4$—Cl. In other embodiments, $R_{20}$ is 3-$CH_2$—$C_6H_4$—Cl. In other embodiments, $R_{20}$ is 4-$CH_2$—$C_6H_4$—Cl. In other embodiments, $R_{20}$ is ethyl. In other embodiments, $R_{20}$ is iso-propyl. In other embodiments, $R_{20}$ is t-Bu. In other embodiments, $R_{20}$ is iso-butyl. In other embodiments, $R_{20}$ is pentyl. In other embodiments, $R_{20}$ is substituted or unsubstituted $C_3$-$C_8$ cycloalkyl (e.g., cyclopropyl, cyclopentyl). In other embodiments, $R_{20}$ is $C_1$-$C_5$ linear, branched or cyclic alkoxy. In other embodiments, $R_{20}$ is methoxy. In other embodiments, $R_{20}$ is ethoxy. In other embodiments, $R_{20}$ is propoxy. In other embodiments, $R_{20}$ is isopropoxy. In other embodiments, $R_{20}$ is O—$CH_2$-cyclopropyl. In other embodiments, $R_{20}$ is O-cyclobutyl. In other embodiments, $R_{20}$ is O-cyclopentyl. In other embodiments, $R_{20}$ is O-cyclohexyl. In other embodiments, $R_{20}$ is O-1-oxacyclobutyl. In other embodiments, $R_{20}$ is O-2-oxacyclobutyl. In other embodiments, $R_{20}$ is 1-butoxy. In other embodiments, $R_{20}$ is 2-butoxy. In other embodiments, $R_{20}$ is O-tBu. In other embodiments, $R_{20}$ is $C_1$-$C_5$ linear, branched or cyclic alkoxy wherein at least one methylene group ($CH_2$) in the alkoxy is replaced with an oxygen atom (O). In other embodiments, $R_{20}$ is O-1-oxacyclobutyl. In other embodiments, $R_{20}$ is O-2-oxacyclobutyl. In other embodiments, $R_{20}$ is $C_1$-$C_5$ linear or branched haloalkoxy. In other embodiments, $R_{20}$ is $OCF_3$. In other embodiments, $R_{20}$ is $OCHF_2$. In other embodiments, $R_{20}$ is substituted or unsubstituted $C_3$-$C_8$ heterocyclic ring. In other embodiments, $R_{20}$ is oxazole. In other embodiments, $R_{20}$ is methyl substituted oxazole. In other embodiments, $R_{20}$ is oxadiazole. In other embodiments, $R_{20}$ is methyl substituted oxadiazole. In other embodiments, $R_{20}$ is imidazole. In other embodiments, $R_{20}$ is methyl substituted imidazole. In other embodiments, $R_{20}$ is pyridine. In other embodiments, $R_{20}$ is 2-pyridine. In other embodiments, $R_{20}$ is 3-pyridine. In other embodiments, $R_{20}$ is 4-pyridine. In other embodiments, $R_{20}$ is 3-methyl-2-pyridine. In other embodiments, $R_{20}$ is tetrazole. In other embodiments, $R_{20}$ is pyrimidine. In other embodiments, $R_{20}$ is pyrazine. In other embodiments, $R_{20}$ is oxacyclobutane. In other embodiments, $R_{20}$ is 1-oxacyclobutane. In other embodiments, $R_{20}$ is 2-oxacyclobutane. In other embodiments, $R_{20}$ is indole. In other embodiments, $R_{20}$ is pyridine oxide. In other embodiments, $R_{20}$ is protonated pyridine oxide. In other embodiments, $R_{20}$ is deprotonated pyridine oxide. In other embodiments, $R_{20}$ is 3-methyl-4H-1,2,4-triazole. In other embodiments, $R_{20}$ is 5-methyl-1,2,4-oxadiazole. In other embodiments, $R_{20}$ is substituted or unsubstituted aryl. In other embodiments, $R_{20}$ is phenyl. In other embodiments, $R_{20}$ is bromophenyl. In other embodiments, $R_{20}$ is 2-bromophenyl. In other embodiments, $R_{20}$ is 3-bromophenyl. In other embodiments, $R_{20}$ is 4-bromophenyl. In other embodiments, $R_{20}$ is substituted or unsubstituted benzyl. In other embodiments, $R_{20}$ is benzyl. In other embodiments, $R_1$ is 4-Cl-benzyl. In other embodiments, $R_1$ is 4-OH-benzyl. In other embodiments, $R_{20}$ is $R_8$—$N(R_{10})(R_{11})$. In other embodiments, $R_{20}$ is $CH_2$—$NH_2$. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole) $C_3$-$C_8$ cycloalkyl (e.g., cyclohexyl), halophenyl, (benzyloxy)phenyl, CN, and/or $NO_2$, each is a separate embodiment according to this invention.

In some embodiments, $R_3$ of formula I, I(a), I(b), II, II(a), II(b), III and III(a) is H. In other embodiments, $R_3$ is Cl. In other embodiments, $R_3$ is I. In other embodiments, $R_3$ is F. In other embodiments, $R_3$ is Br. In other embodiments, $R_3$ is OH. In other embodiments, $R_3$ is $CD_3$. In other embodiments, $R_3$ is $OCD_3$. In other embodiments, $R_3$ is $R_8$—OH. In other embodiments, $R_3$ is $CH_2$—OH. In other embodiments, $R_3$ is —$R_8$—O—$R_{10}$. In other embodiments, $R_3$ is $CH_2$—O—$CH_3$. In other embodiments, $R_3$ is $R_8$—$N(R_{10})(R_{11})$. In other embodiments, $R_3$ is $CH_2$—$NH_2$. In other embodiments, $R_3$ is $CH_2$—$N(CH_3)_2$. In other embodiments, $R_3$ is COOH. In other embodiments, $R_3$ is C(O)O—$R_{10}$. In other embodiments, $R_3$ is C(O)O—$CH_2CH_3$. In other embodiments, $R_3$ is $R_8$—C(O)—$R_{10}$. In other embodiments, $R_3$ is $CH_2C(O)CH_3$. In other embodiments, $R_3$ is C(O)—$R_{10}$. In other embodiments, $R_3$ is C(O)—$CH_3$. In other embodiments, $R_3$ is C(O)—$CH_2CH_3$. In other embodiments, $R_3$ is C(O)—$CH_2CH_2CH_3$. In other embodiments, $R_3$ is $C_1$-$C_5$ linear or branched C(O)-haloalkyl. In other embodiments, $R_3$ is C(O)—$CF_3$. In other embodiments, $R_3$ is $C(O)N(R_{10})$ $(R_{11})$. In other embodiments, $R_3$ is $C(O)N(CH_3)_2$). In other embodiments, $R_3$ is $SO_2N(R_{10})(R_{11})$. In other embodiments, $R_3$ is $SO_2N(CH_3)_2$. In other embodiments, $R_3$ is $C_1$-$C_5$ linear or branched, substituted or unsubstituted alkyl. In other embodiments, $R_3$ is methyl. In other embodiments, $R_3$ is $C(OH)(CH_3)(Ph)$. In other embodiments, $R_3$ is ethyl. In other embodiments, $R_3$ is propyl. In other embodiments, $R_3$ is iso-propyl. In other embodiments, $R_3$ is t-Bu. In other embodiments, $R_3$ is iso-butyl. In other embodiments, $R_3$ is pentyl. In other embodiments, $R_3$ is $C_1$-$C_5$ linear, branched or cyclic haloalkyl. In other embodiments, $R_3$ is $CF_2CH_3$. In other embodiments, $R_3$ is $CF_2$-cyclobutyl. In other embodiments, $R_3$ is $CH_2CF_3$. In other embodiments, $R_3$ is $CF_2CH_2CH_3$. In other embodiments, $R_3$ is $CF_3$. In other embodiments, $R_3$ is $CF_2CH_2CH_3$. In other embodiments, $R_3$ is $CH_2CH_2CF_3$. In other embodiments, $R_3$ is $CF_2CH(CH_3)_2$. In other embodiments, $R_3$ is $CF(CH_3)$—$CH(CH_3)_2$. In other embodiments, $R_3$ is $C_1$-$C_5$ linear, branched or cyclic alkoxy.

In other embodiments, $R_3$ is methoxy. In other embodiments, $R_3$ is isopropoxy. In other embodiments, $R_3$ is substituted or unsubstituted $C_3$-$C_8$ cycloalkyl. In other embodiments, $R_3$ is cyclopropyl. In other embodiments, $R_3$ is cyclopentyl. In other embodiments, $R_3$ is substituted or unsubstituted $C_3$-$C_8$ heterocyclic ring. In other embodiments, $R_3$ is thiophene. In other embodiments, $R_3$ is oxazole. In other embodiments, $R_3$ is isoxazole. In other embodiments, $R_3$ is imidazole. In other embodiments, $R_3$ is furane. In other embodiments, $R_3$ is triazole. In other embodiments, $R_3$ is pyridine. In other embodiments, $R_3$ is 2-pyridine. In other embodiments, $R_3$ is 3-pyridine. In other embodiments, $R_3$ is 4-pyridine. In other embodiments, $R_3$ is pyrimidine. In other embodiments, $R_3$ is pyrazine. In other embodiments, $R_3$ is oxacyclobutane. In other embodiments, $R_3$ is 1-oxacyclobutane. In other embodiments, $R_3$ is 2-oxacyclobutane. In other embodiments, $R_3$ is indole. In other embodiments, $R_3$ is 3-methyl-4H-1,2,4-triazole. In other embodiments, $R_3$ is 5-methyl-1,2,4-oxadiazole. In other embodiments, $R_3$ is substituted or unsubstituted aryl. In other embodiments, $R_3$ is phenyl. In other embodiments, $R_3$ is $CH(CF_3)(NH—R_{10})$.

In some embodiments, $R_4$ of formula I, I(a), I(b), II, II(a), II(b), III and III(a) is H. In other embodiments, $R_4$ is Cl. In other embodiments, $R_4$ is I. In other embodiments, $R_4$ is F. In other embodiments, $R_4$ is Br. In other embodiments, $R_4$ is OH. In other embodiments, $R_4$ is $CD_3$. In other embodiments, $R_4$ is $OCD_3$. In other embodiments, $R_4$ is $R_8$—OH. In other embodiments, $R_4$ is $CH_2$—OH. In other embodiments, $R_4$ is —$R_8$—O—$R_{10}$. In other embodiments, $R_4$ is $CH_2$—O—$CH_3$. In other embodiments, $R_4$ is $R_8$—$N(R_{10})(R_{11})$. In other embodiments, $R_4$ is $CH_2$—$NH_2$. In other embodiments, $R_4$ is $CH_2$—$N(CH_3)_2$. In other embodiments, $R_4$ is COOH. In other embodiments, $R_4$ is C(O)O—$R_{10}$. In other embodiments, $R_4$ is C(O)O—$CH_2CH_3$. In other embodiments, $R_4$ is $R_8$—C(O)—$R_{10}$. In other embodiments, $R_4$ is $CH_2C(O)CH_3$. In other embodiments, $R_4$ is C(O)—$R_{10}$. In other embodiments, $R_4$ is C(O)—$CH_3$. In other embodiments, $R_4$ is C(O)—$CH_2CH_3$. In other embodiments, $R_4$ is C(O)—$CH_2CH_2CH_3$. In other embodiments, $R_4$ is $C_1$-$C_5$ linear or branched C(O)-haloalkyl. In other embodiments, $R_4$ is C(O)—$CF_3$. In other embodiments, $R_4$ is $C(O)N(R_{10})(R_{11})$. In other embodiments, $R_4$ is $C(O)N(CH_3)_2$). In other embodiments, $R_4$ is $SO_2N(R_{10})(R_{11})$. In other embodiments, $R_4$ is $SO_2N(CH_3)_2$. In other embodiments, $R_4$ is $C_1$-$C_5$ linear or branched, substituted or unsubstituted alkyl. In other embodiments, $R_4$ is methyl. In other embodiments, $R_4$ is $C(OH)(CH_3)(Ph)$. In other embodiments, $R_4$ is ethyl. In other embodiments, $R_4$ is propyl. In other embodiments, $R_4$ is iso-propyl. In other embodiments, $R_4$ is t-Bu. In other embodiments, $R_4$ is iso-butyl. In other embodiments, $R_4$ is pentyl. In other embodiments, $R_4$ is $C_1$-$C_5$ linear, branched or cyclic haloalkyl. In other embodiments, $R_3$ is $CF_2CH_3$. In other embodiments, $R_3$ is $CF_2$-cyclobutyl. In other embodiments, $R_4$ is $CH_2CF_3$. In other embodiments, $R_4$ is $CF_2CH_2CH_3$. In other embodiments, $R_4$ is $CF_3$. In other embodiments, $R_4$ is $CF_2CH_2CH_3$. In other embodiments, $R_4$ is $CH_2CH_2CF_3$. In other embodiments, $R_4$ is $CF_2CH(CH_3)_2$. In other embodiments, $R_4$ is $CF(CH_3)$—$CH(CH_3)_2$. In other embodiments, $R_4$ is $C_1$-$C_5$ linear, branched or cyclic alkoxy. In other embodiments, $R_4$ is methoxy. In other embodiments, $R_4$ is isopropoxy. In other embodiments, $R_4$ is substituted or unsubstituted $C_3$-$C_8$ cycloalkyl. In other embodiments, $R_4$ is cyclopropyl. In other embodiments, $R_4$ is cyclopentyl. In other embodiments, $R_4$ is substituted or unsubstituted $C_3$-$C_8$ heterocyclic ring. In other embodiments, $R_4$ is thiophene. In other embodiments, $R_4$ is oxazole. In other embodiments, $R_4$ is isoxazole. In other embodiments, $R_4$ is imidazole. In other embodiments, $R_4$ is furane. In other embodiments, $R_4$ is triazole. In other embodiments, $R_4$ is pyridine. In other embodiments, $R_4$ is 2-pyridine. In other embodiments, $R_4$ is 3-pyridine. In other embodiments, $R_4$ is 4-pyridine. In other embodiments, $R_4$ is pyrimidine. In other embodiments, $R_4$ is pyrazine. In other embodiments, $R_4$ is oxacyclobutane. In other embodiments, $R_4$ is 1-oxacyclobutane. In other embodiments, $R_4$ is 2-oxacyclobutane. In other embodiments, $R_4$ is indole. In other embodiments, $R_4$ is 3-methyl-4H-1,2,4-triazole. In other embodiments, $R_4$ is 5-methyl-1,2,4-oxadiazole. In other embodiments, $R_4$ is substituted or unsubstituted aryl. In other embodiments, $R_4$ is phenyl. In other embodiments, $R_4$ is $CH(CF_3)(NH—R_{10})$.

In some embodiments, $R_3$ and $R_4$ of formula I, I(a), I(b), II, II(a), II(b), III and III(a) are joint together to form a [1,3]dioxole ring. In some embodiments, $R_3$ and $R_4$ are joint together to form a furanone ring (e.g., furan-2(3H)-one). In some embodiments, $R_3$ and $R_4$ are joint together to form a benzene ring. In some embodiments, $R_3$ and $R_4$ are joint together to form a cyclopentene ring. In some embodiments, $R_3$ and $R_4$ are joint together to form an imidazole ring.

In some embodiments, $R_{40}$ of formula I, I(a), II and III is H. In other embodiments, $R_{40}$ is Cl. In other embodiments, $R_{40}$ is I. In other embodiments, $R_{40}$ is F. In other embodiments, $R_{40}$ is Br. In other embodiments, $R_{40}$ is OH. In other embodiments, $R_{40}$ is $CD_3$. In other embodiments, $R_{40}$ is $OCD_3$. In other embodiments, $R_{40}$ is $R_8$—OH. In other embodiments, $R_{40}$ is $CH_2$—OH. In other embodiments, $R_{40}$ is —$R_8$—O—$R_{10}$. In other embodiments, $R_{40}$ is $CH_2$—O—$CH_3$. In other embodiments, $R_{40}$ is $R_8$—$N(R_{10})(R_{11})$. In other embodiments, $R_{40}$ is $CH_2$—$NH_2$. In other embodiments, $R_{40}$ is $CH_2$—$N(CH_3)_2$. In other embodiments, $R_{40}$ is COOH. In other embodiments, $R_{40}$ is C(O)O—$R_{10}$. In other embodiments, $R_{40}$ is C(O)O—$CH_2CH_3$. In other embodiments, $R_{40}$ is $R_8$—C(O)—$R_{10}$. In other embodiments, $R_{40}$ is $CH_2C(O)CH_3$. In other embodiments, $R_{40}$ is C(O)—$R_{10}$. In other embodiments, $R_{40}$ is C(O)—$CH_3$. In other embodiments, $R_{40}$ is C(O)—$CH_2CH_3$. In other embodiments, $R_{40}$ is C(O)—$CH_2CH_2CH_3$. In other embodiments, $R_{40}$ is $C_1$-$C_5$ linear or branched C(O)-haloalkyl. In other embodiments, $R_{40}$ is C(O)—$CF_3$. In other embodiments, $R_{40}$ is $C(O)N(R_{10})(R_{11})$. In other embodiments, $R_{40}$ is $C(O)N(CH_3)_2$). In other embodiments, $R_{40}$ is $SO_2N(R_{10})(R_{11})$. In other embodiments, $R_{40}$ is $SO_2N(CH_3)_2$. In other embodiments, $R_{40}$ is $C_1$-$C_5$ linear or branched, substituted or unsubstituted alkyl. In other embodiments, $R_{40}$ is methyl. In other embodiments, $R_{40}$ is $C(OH)(CH_3)(Ph)$. In other embodiments, $R_{40}$ is ethyl. In other embodiments, $R_{40}$ is propyl. In other embodiments, $R_{40}$ is iso-propyl. In other embodiments, $R_{40}$ is t-Bu. In other embodiments, $R_{40}$ is iso-butyl. In other embodiments, $R_{40}$ is pentyl. In other embodiments, $R_{40}$ is $C_1$-$C_5$ linear, branched or cyclic haloalkyl. In other embodiments, $R_{40}$ is $CF_2CH_3$. In other embodiments, $R_{40}$ is $CF_2$-cyclobutyl. In other embodiments, $R_{40}$ is $CH_2CF_3$. In other embodiments, $R_{40}$ is $CF_2CH_2CH_3$. In other embodiments, $R_{40}$ is $CF_3$. In other embodiments, $R_{40}$ is $CF_2CH_2CH_3$. In other embodiments, $R_{40}$ is $CH_2CH_2CF_3$. In other embodiments, $R_{40}$ is $CF_2CH(CH_3)_2$. In other embodiments, $R_{40}$ is $CF(CH_3)$—$CH(CH_3)_2$. In other embodiments, $R_{40}$ is $C_1$-$C_5$ linear, branched or cyclic alkoxy. In other embodiments, $R_{40}$ is methoxy. In other embodiments, $R_{40}$ is isopropoxy. In other embodiments, $R_{40}$ is substituted or unsubstituted $C_3$-$C_8$ cycloalkyl. In other embodiments, $R_{40}$ is cyclopropyl. In other embodiments, $R_{40}$ is cyclopentyl. In other embodiments, $R_{40}$ is substituted or unsubstituted $C_3$-$C_8$ heterocyclic ring. In other embodiments, $R_{40}$ is thiophene. In other embodiments, $R_{40}$ is oxazole. In other embodiments, $R_{40}$ is isoxazole. In other embodiments, $R_{40}$ is imidazole. In other embodiments, $R_{40}$ is furane. In other embodiments, $R_{40}$ is triazole. In other embodiments, $R_{40}$ is pyridine. In other embodiments, $R_{40}$ is 2-pyridine. In other embodiments, $R_{40}$ is 3-pyridine. In other embodiments, $R_{40}$ is 4-pyridine. In other embodiments, $R_{40}$ is pyrimidine. In other embodiments, $R_{40}$ is pyrazine. In other embodiments, $R_{40}$ is oxacyclobutane. In other embodiments, $R_{40}$ is 1-oxacyclobutane. In other embodiments, $R_{40}$ is 2-oxacyclobutane. In other embodiments, $R_{40}$ is indole. In other embodiments, $R_{40}$ is 3-methyl-4H-1,2,4-triazole. In other embodiments, $R_{40}$ is 5-methyl-1,2,4-oxadiazole. In other embodiments, $R_{40}$ is substituted or unsubstituted aryl. In other embodiments, $R_{40}$ is phenyl. In other embodiments, $R_{40}$ is $CH(CF_3)(NH—R_{10})$.

In some embodiments, $R_5$ of formula I, I(a) and III is H. In other embodiments, $R_5$ is $C_1$-$C_5$ linear or branched, substituted or unsubstituted alkyl. In other embodiments, $R_5$ is methyl. In other embodiments, $R_5$ is $CH_2SH$. In other embodiments, $R_5$ is ethyl. In other embodiments, $R_5$ is iso-propyl. In other embodiments, $R_5$ is $CH_2SH$. In other embodiments, $R_5$ is $C_2$-$C_5$ linear or branched, substituted or unsubstituted alkenyl. In other embodiments, $R_5$ is $C_2$-$C_5$ linear or branched, substituted or unsubstituted alkynyl. In other embodiments, $R_5$ is C(CH). In other embodiments, $R_5$ is $C_1$-$C_5$ linear or branched haloalkyl. In other embodiments, $R_5$ is $CF_2CH_3$. In other embodiments, $R_5$ is $CH_2CF_3$. In other embodiments, $R_5$ is $CF_2CH_2CH_3$. In other embodiments, $R_5$ is $CF_3$. In other embodiments, $R_5$ is $CF_2CH_2CH_3$. In other embodiments, $R_5$ is $CH_2CH_2CF_3$. In other embodiments, $R_5$ is $CF_2CH(CH_3)_2$. In other embodiments, $R_5$ is $CF(CH_3)—CH(CH_3)_2$. In other embodiments, $R_5$ is $R_8$-aryl. In other embodiments, $R_5$ is $CH_2$-Ph (i.e., benzyl). In other embodiments, $R_5$ is substituted or unsubstituted aryl. In other embodiments, $R_5$ is phenyl. In other embodiments, $R_5$ is substituted or unsubstituted heteroaryl. In other embodiments, $R_5$ is pyridine. In other embodiments, $R_5$ is 2-pyridine. In other embodiments, $R_5$ is 3-pyridine. In other embodiments, $R_5$ is 4-pyridine. In other embodiments, substitutions include: F, Cl, Br, I, OH, SH, $C_1$-$C_5$ linear or branched alkyl, OH, alkoxy, $N(R)_2$, $CF_3$, phenyl, halophenyl, (benzyloxy)phenyl, CN, $NO_2$ or any combination thereof; each represents a separate embodiment according to this invention.

In some embodiments, $R_{50}$ of formula I, I(a), I(b), III and III(a) is H. In other embodiments, $R_{50}$ is F. In other embodiments, $R_{50}$ is Cl. In other embodiments, $R_{50}$ is Br. In other embodiments, $R_{50}$ is I. In other embodiments, $R_{50}$ is $C_1$-$C_5$ linear or branched, substituted or unsubstituted alkyl. In other embodiments, $R_{50}$ is $C_1$-$C_5$ linear or branched, alkyl, substituted with phenyl. In other embodiments, $R_{50}$ is methyl. In other embodiments, $R_{50}$ is $CH_2SH$. In other embodiments, $R_{50}$ is ethyl. In other embodiments, $R_{50}$ is propyl. In other embodiments, $R_{50}$ is iso-propyl. In other embodiments, $R_{50}$ is benzyl. In other embodiments, $R_{50}$'s substitutions include phenyl.

In some embodiments, $R_{50}$ of formula I and III is connected to the N atom in position indicated as 1 in the structure (i.e., $N_1$). In other embodiments, $R_{50}$ is connected to the C atom in position indicated as 3 in the structure (i.e., $C_3$).

In some embodiments, if $R_{50}$ of formula I, I(a), I(b) is H then neither one of $R_1$, $R_2$ or $R_{20}$ is H, and n and m are not 0.

In some embodiments, $R_6$ of formula I, I(a), I(b), II, II(a), II(b), III and III(a) is H. In other embodiments, $R_6$ is $C_1$-$C_5$ linear or branched alkyl. In other embodiments, $R_6$ is methyl.

In some embodiments, $R_8$ of formula I, I(a), I(b), II, II(a), II(b), III and III(a) is $CH_2$. In other embodiments, $R_8$ is $CH_2CH_2$. In other embodiments, $R_8$ is $CH_2CH_2CH_2$.

In some embodiments, p of formula I, I(a), I(b), II, II(a), II(b), III and III(a) is 1. In other embodiments, p is 2. In other embodiments, p is 3.

In some embodiments, $R_9$ of formula I, I(a), I(b), II, II(a), II(b), III and III(a) is $C{\equiv}C$.

In some embodiments, q of formula I, I(a), I(b), II, II(a), II(b), III and III(a) is 2.

In some embodiments, $R_{10}$ of formula I, I(a), I(b), II, II(a), II(b), III and III(a) is $C_1$-$C_5$ linear or branched alkyl. In other embodiments, $R_{10}$ is H. In other embodiments, $R_{10}$ is $CH_3$. In other embodiments, $R_{10}$ is $CH_2CH_3$. In other embodiments, $R_{10}$ is $CH_2CH_2CH_3$. In other embodiments, $R_{10}$ is CN. In other embodiments, $R_{10}$ is C(O)R. In other embodiments, $R_{10}$ is $C(O)(OCH_3)$.

In some embodiments, $R_{11}$ of formula I, I(a), I(b), II, II(a), II(b), III and III(a) is $C_1$-$C_5$ linear or branched alkyl. In other embodiments, $R_{10}$ is H. In other embodiments, $R_{11}$ is $CH_3$. In other embodiments, $R_{11}$ is CN. In other embodiments, $R_{11}$ is C(O)R. In other embodiments, $R_{11}$ is $C(O)(OCH_3)$.

In some embodiments, $R_{10}$ and $R_{11}$ of formula I, I(a), I(b), II, II(a), II(b), III and III(a) are joint to form a substituted or unsubstituted $C_3$-$C_8$ heterocyclic ring. In other embodiments, $R_{10}$ and $R_{11}$ are joint to form a piperazine ring. In other embodiments, $R_{10}$ and $R_{11}$ are joint to form a piperidine ring. In some embodiments, substitutions include: F, Cl, Br, I, OH, $C_1$-$C_5$ linear or branched alkyl, $C_1$-$C_5$ linear or branched alkyl-OH (e.g., $C(CH_3)_2CH_2—OH$, $CH_2CH_2—OH$), $C_3$-$C_8$ heterocyclic ring (e.g., piperidine), alkoxy, $N(R)_2$, $CF_3$, aryl, phenyl, halophenyl, (benzyloxy)phenyl, CN, $NO_2$ or any combination thereof; each represents a separate embodiment according to this invention.

In some embodiments, R of formula I, I(a), I(b), II, II(a), II(b), III and III(a) is H. In other embodiments, R is $C_1$-$C_5$ linear or branched alkyl. In other embodiments, R is methyl. In other embodiments, R is ethyl. In other embodiments, R is $C_1$-$C_5$ linear or branched alkoxy. In other embodiments, R is methoxy.

In some embodiments, m of formula I, I(a), I(b), II, II(a), II(b), III and III(a) is 1. In some embodiments, m of formula I, I(a), I(b), II, II(a), and II(b), is 0.

In some embodiments, n of formula I, I(a), I(b), II, II(a), II(b), III and III(a) is 1. In other embodiments, n is 0.

In some embodiments, k of formula I, I(a), I(b), II, II(a) and II(b) is 1. In other embodiments, k is 0.

In some embodiments, 1 of formula I, I(a), I(b), II, II(a) and II(b) is 1. In other embodiments, 1 is 0.

In some embodiments, $Q_1$ of formula I, I(a), II and III is 0.

In some embodiments, $Q_2$ of formula I, I(a), II and III is 0.

In some embodiments, $Q_3$ of formula II and II(a) is N. In some embodiments, $Q_3$ is CH. In some embodiments, $Q_3$ is C(R). In some embodiments, $Q_3$ is NO (N-oxide).

In some embodiments, $Q_6$ of formula II and II(a) is N. In some embodiments, $Q_6$ is CH. In some embodiments, $Q_6$ is C(R). In some embodiments, $Q_6$ is NO (N-oxide).

In some embodiments, $Q_7$ of formula II and II(a) is N. In some embodiments, $Q_7$ is CH. In some embodiments, $Q_7$ is C(R). In some embodiments, $Q_7$ is NO (N-oxide).

In some embodiments, $Q_8$ of formula II and II(a) is N. In some embodiments, $Q_8$ is CH. In some embodiments, $Q_8$ is C(R). In some embodiments, $Q_8$ is NO (N-oxide).

In some embodiments, $Q_4$ of formula II and II(a) is O. In some embodiments, $Q_4$ is NH. In some embodiments, $Q_4$ is N(R).

In some embodiments, $Q_5$ of formula II and II(a) is O. In some embodiments, $Q_5$ is NH. In some embodiments, $Q_5$ is N(R).

In various embodiments, this invention is directed to the compounds presented in Table 1, pharmaceutical compositions and/or method of use thereof:

TABLE 1

| Compound Number | Compound Structure |
|---|---|
| 100 | 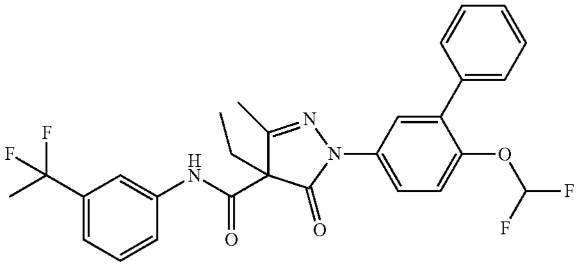 [SMILES: CCC1(C(=O)Nc2cccc(C(C)(F)F)c2)C(=O)N(c2ccc(OC(F)F)c(-c3ccccc3)c2)N=C1C] |
| 101 | 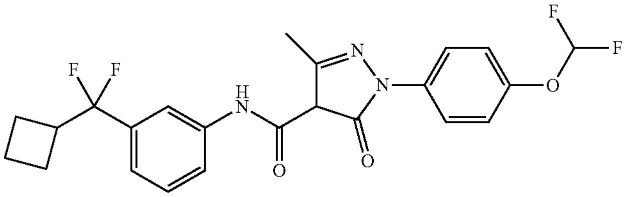 [SMILES: CC1=NN(c2ccc(OC(F)F)cc2)C(=O)C1C(=O)Nc1cccc(C(F)(F)C2CCC2)c1] |
| 102 | 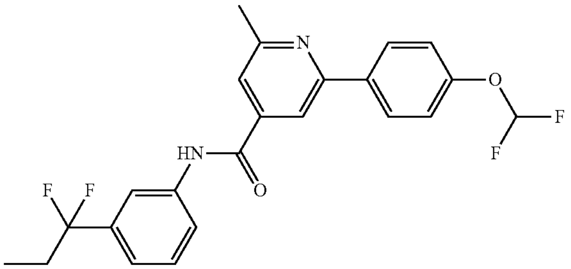 [SMILES: CCC(F)(F)c1cccc(NC(=O)c2cc(C)nc(-c3ccc(OC(F)F)cc3)c2)c1] |
| 103 | 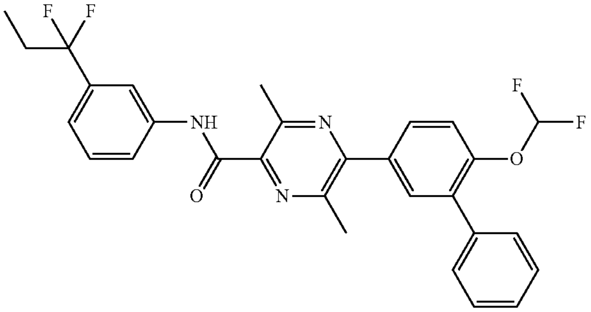 [SMILES: CCC(F)(F)c1cccc(NC(=O)c2nc(C)c(-c3ccc(OC(F)F)c(-c4ccccc4)c3)nc2C)c1] |
| 104 | 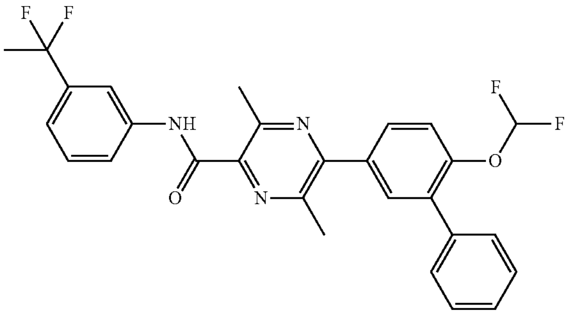 |

TABLE 1-continued
| Compound Number | Compound Structure |
| --- | --- |
| 105 | 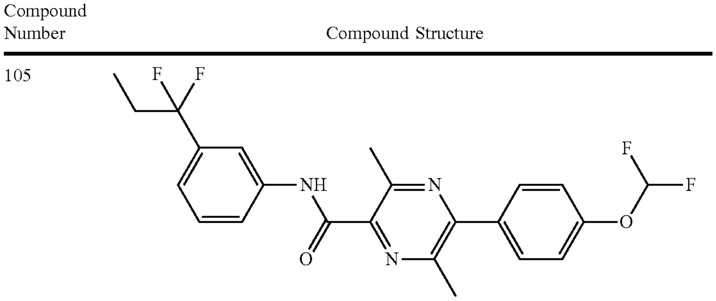 |
| 106 | 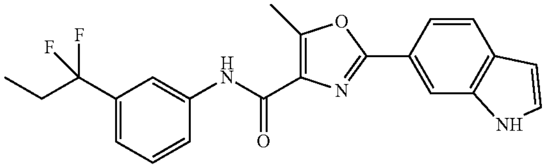 [SMILES: CCC(F)(F)c1cccc(NC(=O)c2nc(-c3ccc4cc[nH]c4c3)oc2C)c1] |
| 107 | 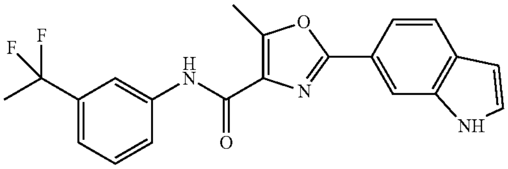 [SMILES: Cc1oc(-c2ccc3cc[nH]c3c2)nc1C(=O)Nc1cccc(C(C)(F)F)c1] |
| 108 | 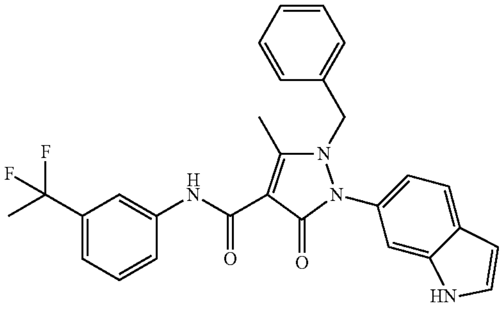 [SMILES: Cc1c(C(=O)Nc2cccc(C(C)(F)F)c2)c(=O)n(-c2ccc3cc[nH]c3c2)n1Cc1ccccc1] |
| 109 | 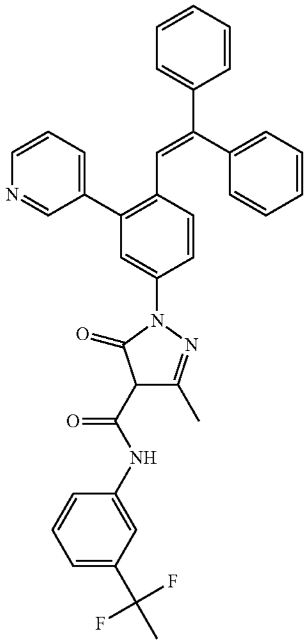 [SMILES: CC1=NN(c2ccc(C=C(c3ccccc3)c3ccccc3)c(-c3cccnc3)c2)C(=O)C1C(=O)Nc1cccc(C(C)(F)F)c1] |

TABLE 1-continued
| Compound Number | Compound Structure |
| --- | --- |
| 110 | 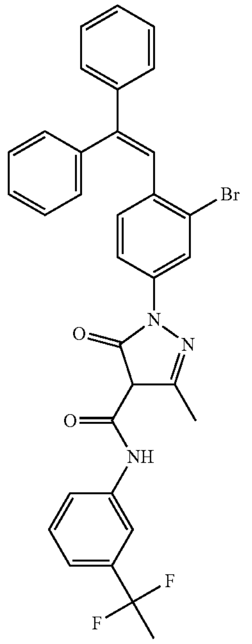 [SMILES: CC1=NN(c2ccc(C=C(c3ccccc3)c3ccccc3)c(Br)c2)C(=O)C1C(=O)Nc1cccc(C(C)(F)F)c1] |
| 111 | 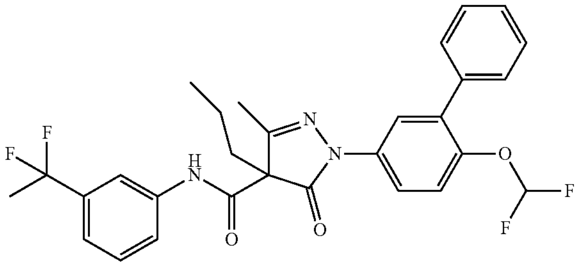 [SMILES: CCCC1(C(=O)Nc2cccc(C(C)(F)F)c2)C(=O)N(c2ccc(OC(F)F)c(-c3ccccc3)c2)N=C1C] |
| 112 | 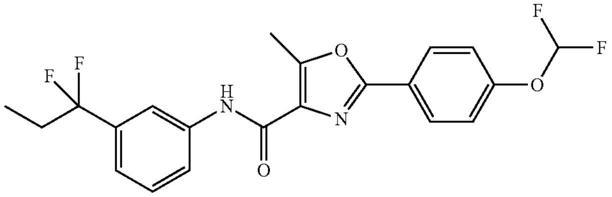 [SMILES: CCC(F)(F)c1cccc(NC(=O)c2nc(-c3ccc(OC(F)F)cc3)oc2C)c1] |
| 113 | 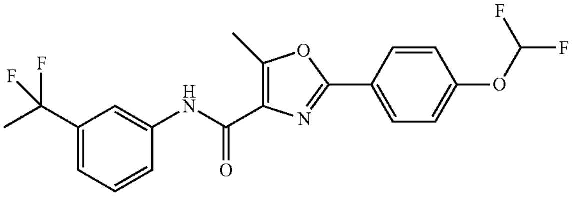 [SMILES: Cc1oc(-c2ccc(OC(F)F)cc2)nc1C(=O)Nc1cccc(C(C)(F)F)c1] |
| 114 | 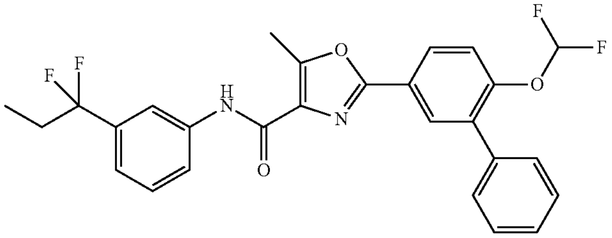 [SMILES: CCC(F)(F)c1cccc(NC(=O)c2nc(-c3ccc(OC(F)F)c(-c4ccccc4)c3)oc2C)c1] |

TABLE 1-continued
| Compound Number | Compound Structure |
|---|---|
| 115 | 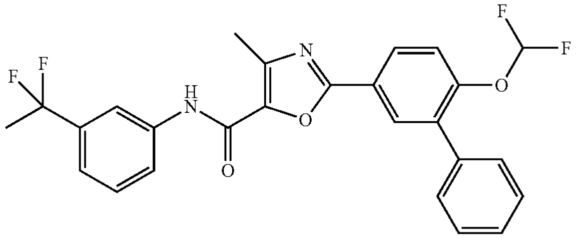 [SMILES: Cc1nc(-c2ccc(OC(F)F)c(-c3ccccc3)c2)oc1C(=O)Nc1cccc(C(C)(F)F)c1] |
| 116 | 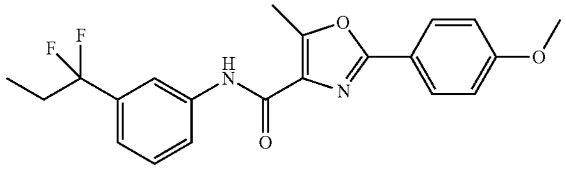 [SMILES: CCC(F)(F)c1cccc(NC(=O)c2nc(-c3ccc(OC)cc3)oc2C)c1] |
| 117 | 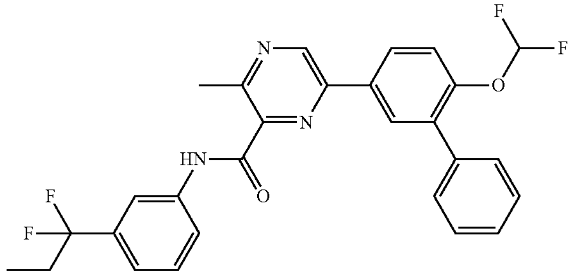 [SMILES: CCC(F)(F)c1cccc(NC(=O)c2nc(-c3ccc(OC(F)F)c(-c4ccccc4)c3)cnc2C)c1] |
| 118 | 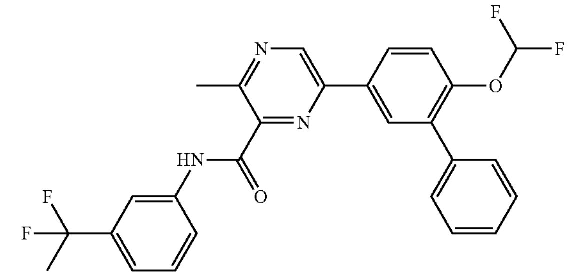 [SMILES: Cc1ncc(-c2ccc(OC(F)F)c(-c3ccccc3)c2)nc1C(=O)Nc1cccc(C(C)(F)F)c1] |
| 119 | 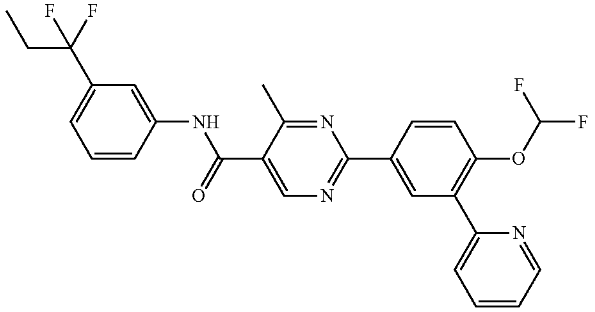 [SMILES: CCC(F)(F)c1cccc(NC(=O)c2cnc(-c3ccc(OC(F)F)c(-c4ccccn4)c3)nc2C)c1] |

TABLE 1-continued
| Compound Number | Compound Structure |
|---|---|
| 120 | 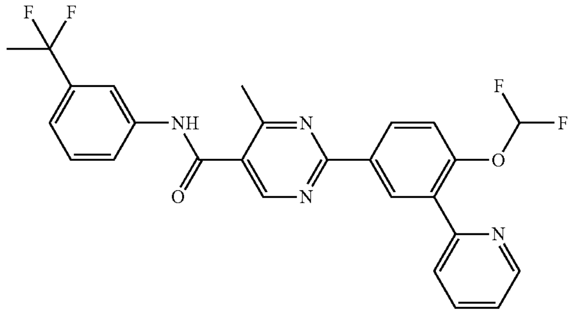 [SMILES: Cc1nc(-c2ccc(OC(F)F)c(-c3ccccn3)c2)ncc1C(=O)Nc1cccc(C(C)(F)F)c1] |
| 121 | 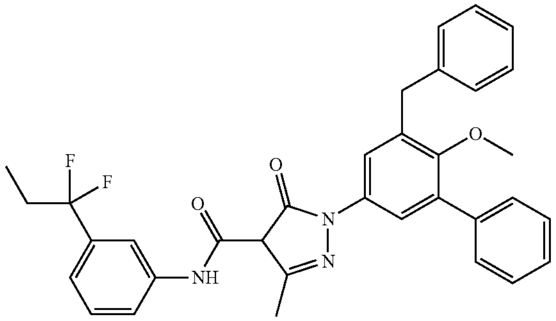 [SMILES: CCC(F)(F)c1cccc(NC(=O)C2C(=O)N(c3cc(Cc4ccccc4)c(OC)c(-c4ccccc4)c3)N=C2C)c1] |
| 122 | 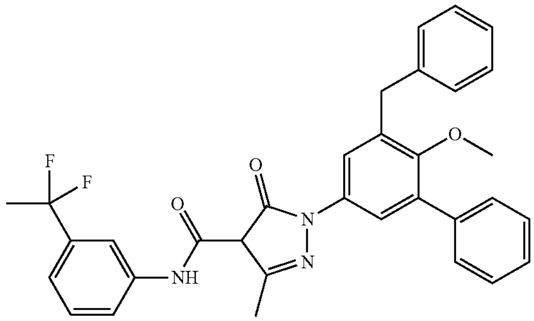 [SMILES: COc1c(Cc2ccccc2)cc(N2N=C(C)C(C(=O)Nc3cccc(C(C)(F)F)c3)C2=O)cc1-c1ccccc1] |
| 123 | 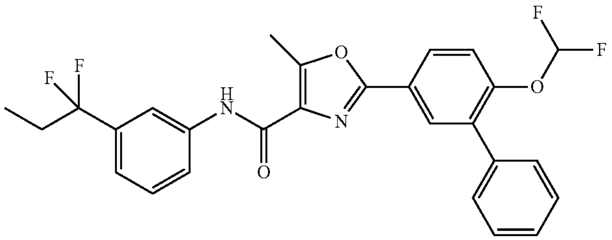 [SMILES: CCC(F)(F)c1cccc(NC(=O)c2nc(-c3ccc(OC(F)F)c(-c4ccccc4)c3)oc2C)c1] |
| 124 | 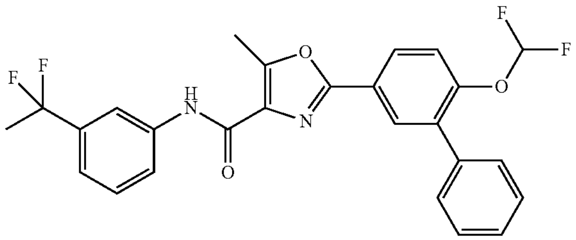 [SMILES: Cc1oc(-c2ccc(OC(F)F)c(-c3ccccc3)c2)nc1C(=O)Nc1cccc(C(C)(F)F)c1] |

TABLE 1-continued
| Compound Number | Compound Structure |
|---|---|
| 125 | 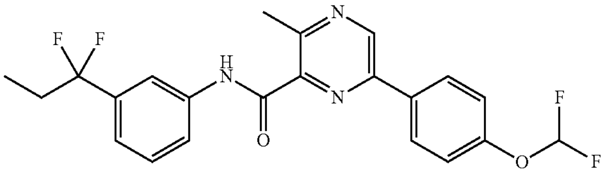 [SMILES: CCC(F)(F)c1cccc(NC(=O)c2nc(-c3ccc(OC(F)F)cc3)cnc2C)c1] |
| 126 | 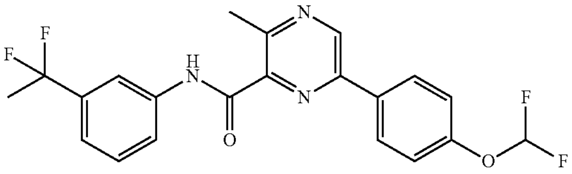 [SMILES: Cc1ncc(-c2ccc(OC(F)F)cc2)nc1C(=O)Nc1cccc(C(C)(F)F)c1] |
| 127 | 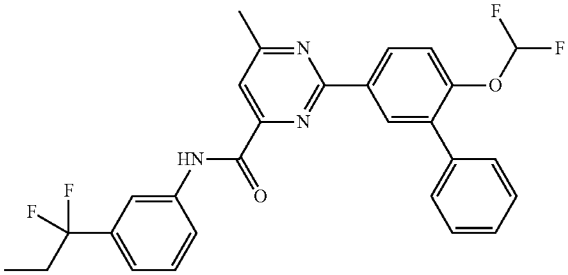 [SMILES: CCC(F)(F)c1cccc(NC(=O)c2cc(C)nc(-c3ccc(OC(F)F)c(-c4ccccc4)c3)n2)c1] |
| 128 | 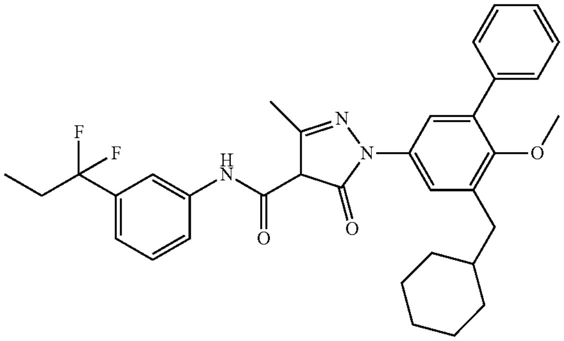 [SMILES: CCC(F)(F)c1cccc(NC(=O)C2C(=O)N(c3cc(CC4CCCCC4)c(OC)c(-c4ccccc4)c3)N=C2C)c1] |
| 129 | 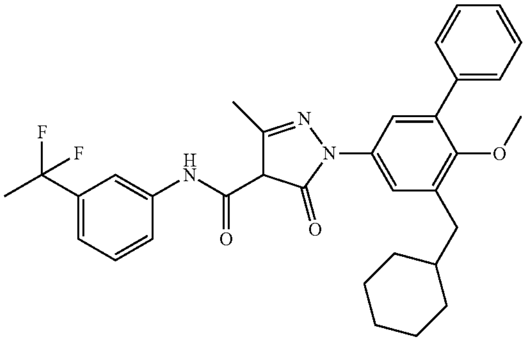 [SMILES: COc1c(CC2CCCCC2)cc(N2N=C(C)C(C(=O)Nc3cccc(C(C)(F)F)c3)C2=O)cc1-c1ccccc1]

TABLE 1-continued
| Compound Number | Compound Structure |
|---|---|
| 130 | 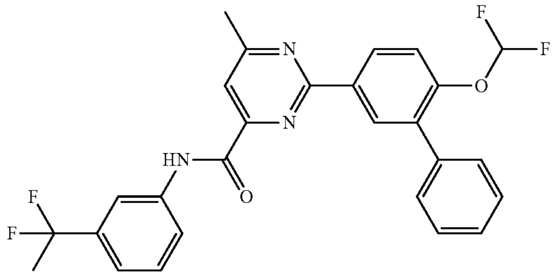 [SMILES: Cc1cc(C(=O)Nc2cccc(C(C)(F)F)c2)nc(-c2ccc(OC(F)F)c(-c3ccccc3)c2)n1] |
| 131 | 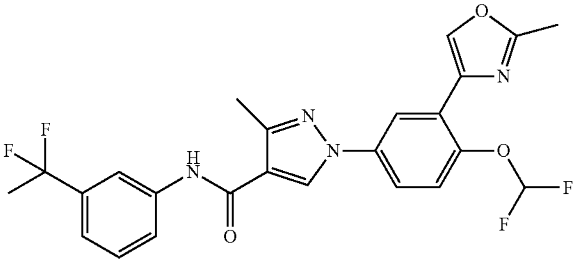 [SMILES: Cc1nc(-c2cc(-n3cc(C(=O)Nc4cccc(C(C)(F)F)c4)c(C)n3)ccc2OC(F)F)co1] |
| 132 | 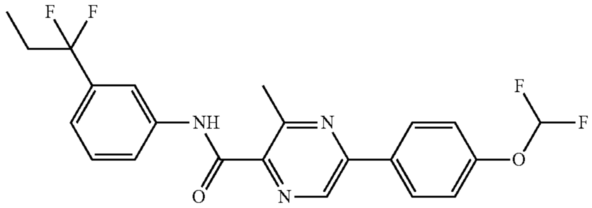 [SMILES: CCC(F)(F)c1cccc(NC(=O)c2ncc(-c3ccc(OC(F)F)cc3)nc2C)c1] |
| 133 | 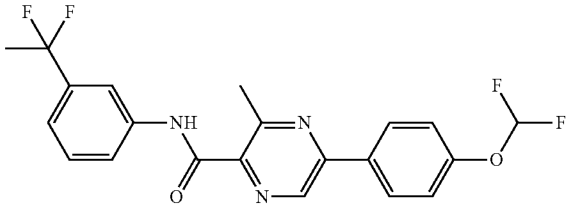 |
| 134 | 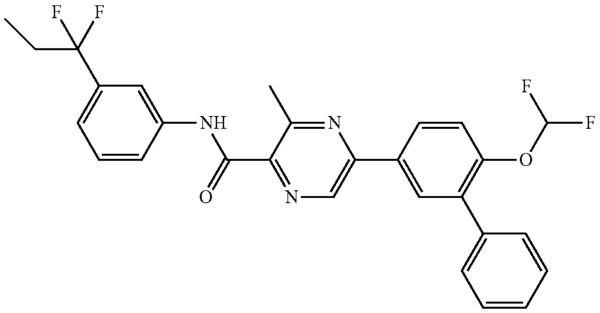 [SMILES: CCC(F)(F)c1cccc(NC(=O)c2ncc(-c3ccc(OC(F)F)c(-c4ccccc4)c3)nc2C)c1] |

TABLE 1-continued
| Compound Number | Compound Structure |
| --- | --- |
| 135 | 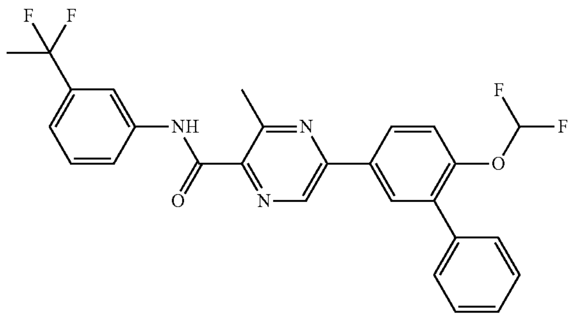 [SMILES: Cc1nc(-c2ccc(OC(F)F)c(-c3ccccc3)c2)cnc1C(=O)Nc1cccc(C(C)(F)F)c1] |
| 136 | 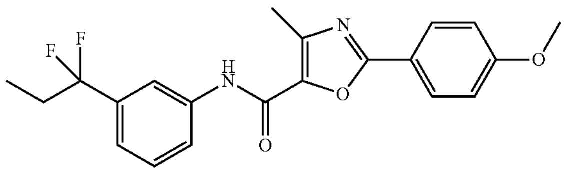 [SMILES: CCC(F)(F)c1cccc(NC(=O)c2oc(-c3ccc(OC)cc3)nc2C)c1] |
| 137 | 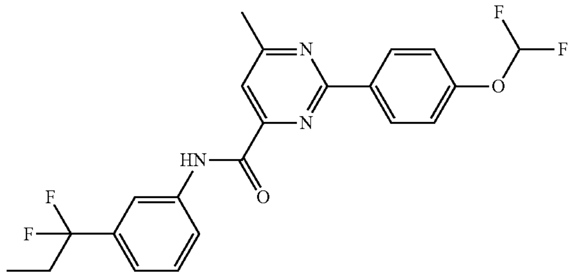 [SMILES: CCC(F)(F)c1cccc(NC(=O)c2cc(C)nc(-c3ccc(OC(F)F)cc3)n2)c1] |
| 138 | 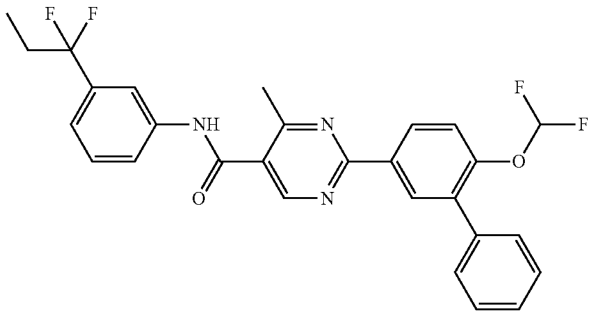 |
| 139 | 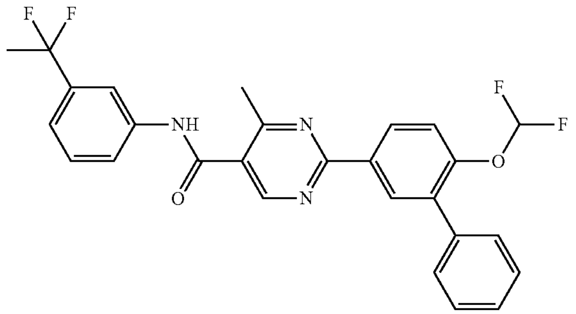 |

TABLE 1-continued
| Compound Number | Compound Structure |
|---|---|
| 140 | 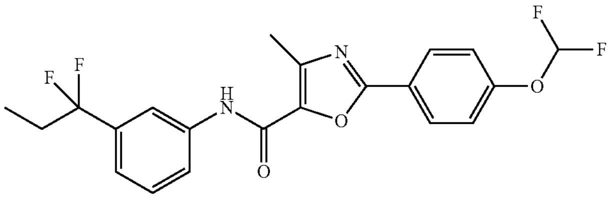 [SMILES: CCC(F)(F)c1cccc(NC(=O)c2oc(-c3ccc(OC(F)F)cc3)nc2C)c1] |
| 141 | 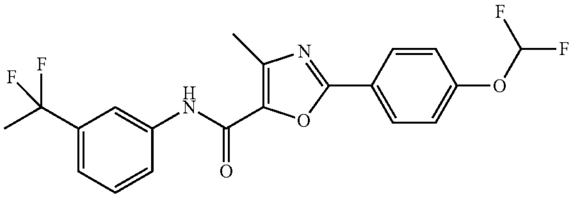 [SMILES: Cc1nc(-c2ccc(OC(F)F)cc2)oc1C(=O)Nc1cccc(C(C)(F)F)c1] |
| 142 | 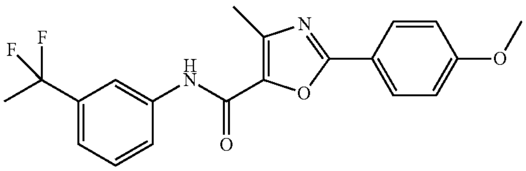 [SMILES: COc1ccc(-c2nc(C)c(C(=O)Nc3cccc(C(C)(F)F)c3)o2)cc1] |
| 143 | 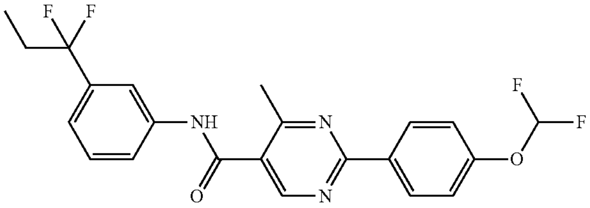 [SMILES: CCC(F)(F)c1cccc(NC(=O)c2cnc(-c3ccc(OC(F)F)cc3)nc2C)c1] |
| 144 | 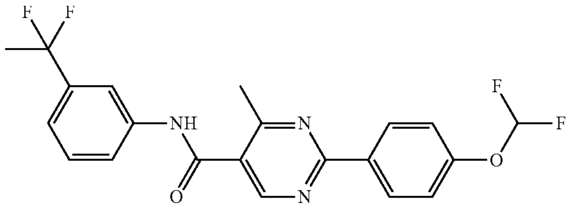 [SMILES: Cc1nc(-c2ccc(OC(F)F)cc2)ncc1C(=O)Nc1cccc(C(C)(F)F)c1] |
| 145 | 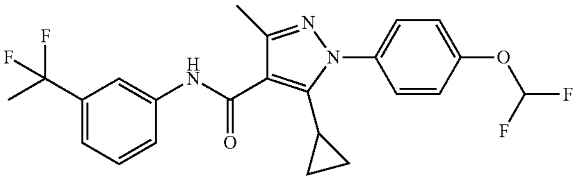 [SMILES: Cc1nn(-c2ccc(OC(F)F)cc2)c(C2CC2)c1C(=O)Nc1cccc(C(C)(F)F)c1] |
| 146 | 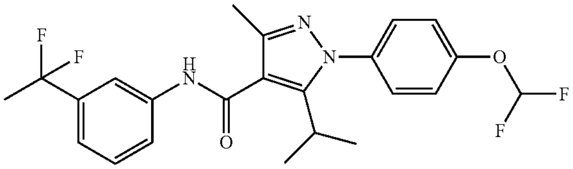 [SMILES: Cc1nn(-c2ccc(OC(F)F)cc2)c(C(C)C)c1C(=O)Nc1cccc(C(C)(F)F)c1] |

TABLE 1-continued
| Compound Number | Compound Structure |
| --- | --- |
| 147 | 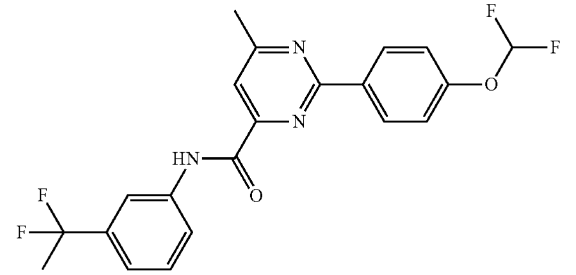 [SMILES: Cc1cc(C(=O)Nc2cccc(C(C)(F)F)c2)nc(-c2ccc(OC(F)F)cc2)n1] |
| 148 | 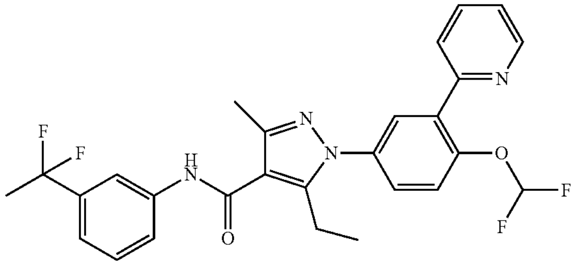 |
| 149 | 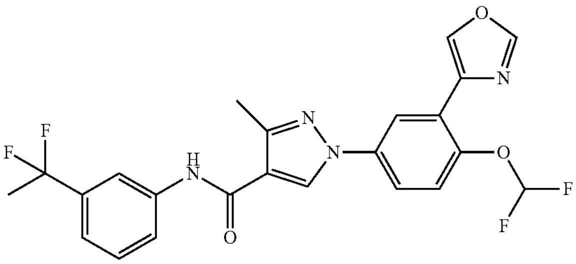 [SMILES: Cc1nn(-c2ccc(OC(F)F)c(-c3cocn3)c2)cc1C(=O)Nc1cccc(C(C)(F)F)c1] |
| 150 | 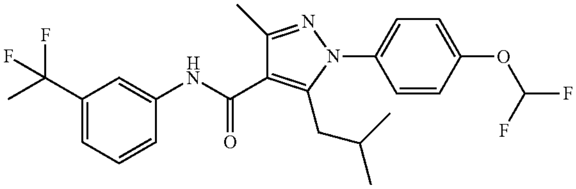 [SMILES: Cc1nn(-c2ccc(OC(F)F)cc2)c(CC(C)C)c1C(=O)Nc1cccc(C(C)(F)F)c1] |
| 151 | 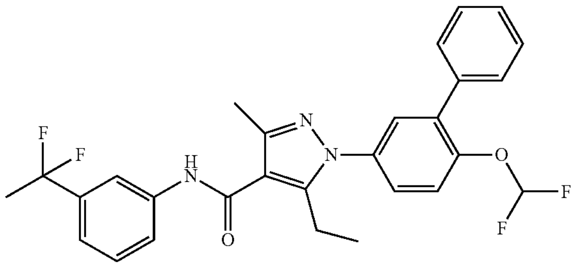 |
| 152 | 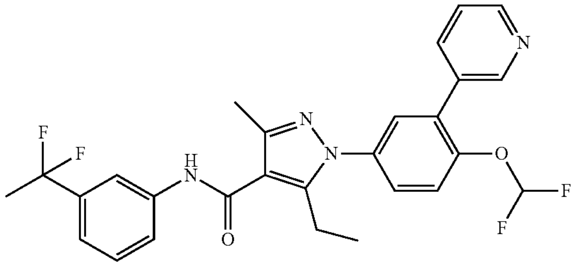 [SMILES: CCc1c(C(=O)Nc2cccc(C(C)(F)F)c2)c(C)nn1-c1ccc(OC(F)F)c(-c2cccnc2)c1] |

TABLE 1-continued
| Compound Number | Compound Structure |
|---|---|
| 153 | 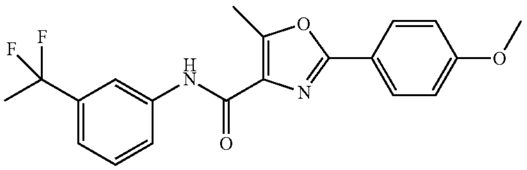 [SMILES: COc1ccc(-c2nc(C(=O)Nc3cccc(C(C)(F)F)c3)c(C)o2)cc1] |
| 154 | 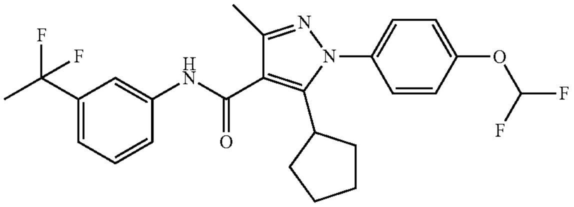 [SMILES: Cc1nn(-c2ccc(OC(F)F)cc2)c(C2CCCC2)c1C(=O)Nc1cccc(C(C)(F)F)c1] |
| 155 | 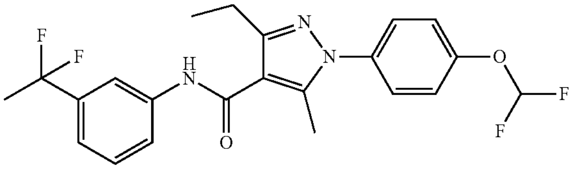 [SMILES: CCc1nn(-c2ccc(OC(F)F)cc2)c(C)c1C(=O)Nc1cccc(C(C)(F)F)c1] |
| 156 | 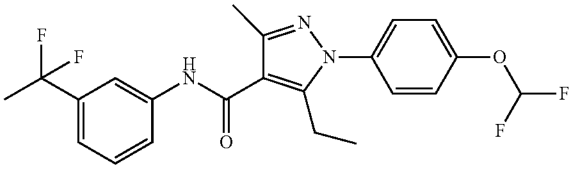 [SMILES: CCc1c(C(=O)Nc2cccc(C(C)(F)F)c2)c(C)nn1-c1ccc(OC(F)F)cc1] |
| 157 | 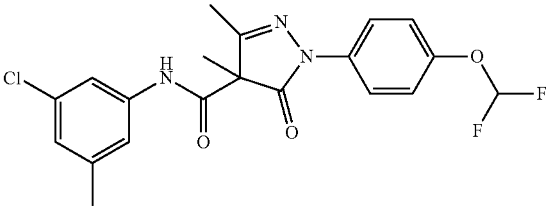 [SMILES: CC1=NN(c2ccc(OC(F)F)cc2)C(=O)C1(C)C(=O)Nc1cc(C)cc(Cl)c1] |
| 158 | 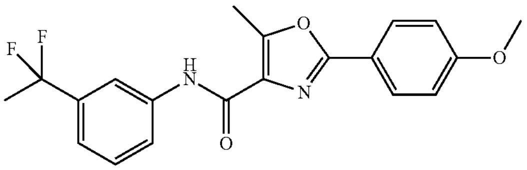 [SMILES: COc1ccc(-c2nc(C(=O)Nc3cccc(C(C)(F)F)c3)c(C)o2)cc1] |
| 159 | 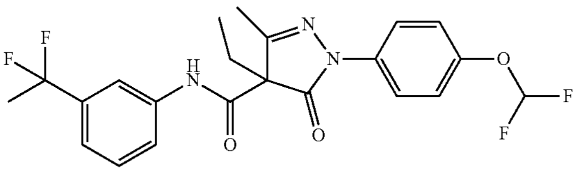 [SMILES: CCC1(C(=O)Nc2cccc(C(C)(F)F)c2)C(=O)N(c2ccc(OC(F)F)cc2)N=C1C] |

TABLE 1-continued
| Compound Number | Compound Structure |
|---|---|
| 160 | 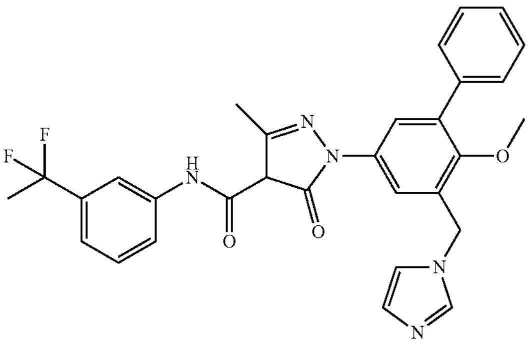 [SMILES: COc1c(Cn2ccnc2)cc(N2N=C(C)C(C(=O)Nc3cccc(C(C)(F)F)c3)C2=O)cc1-c1ccccc1] |
| 161 | 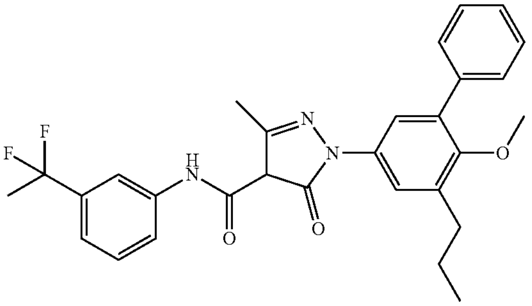 [SMILES: CCCc1cc(N2N=C(C)C(C(=O)Nc3cccc(C(C)(F)F)c3)C2=O)cc(-c2ccccc2)c1OC] |
| 162 | 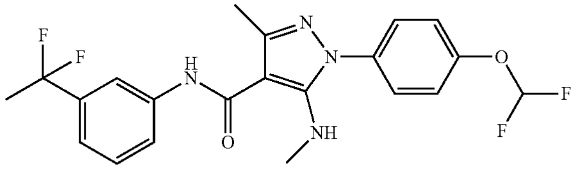 [SMILES: CNc1c(C(=O)Nc2cccc(C(C)(F)F)c2)c(C)nn1-c1ccc(OC(F)F)cc1] |
| 163 | 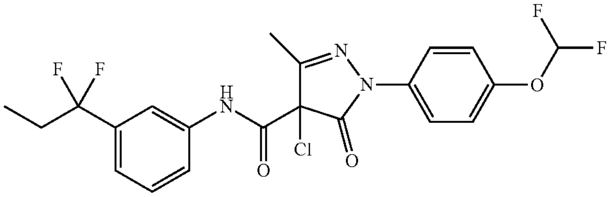 [SMILES: CCC(F)(F)c1cccc(NC(=O)C2(Cl)C(=O)N(c3ccc(OC(F)F)cc3)N=C2C)c1] |
| 164 | 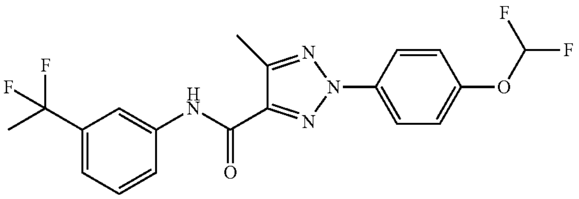 [SMILES: Cc1nn(-c2ccc(OC(F)F)cc2)nc1C(=O)Nc1cccc(C(C)(F)F)c1] |
| 165 | 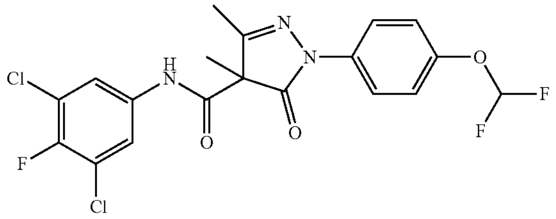 [SMILES: CC1=NN(c2ccc(OC(F)F)cc2)C(=O)C1(C)C(=O)Nc1cc(Cl)c(F)c(Cl)c1] |

TABLE 1-continued
| Compound Number | Compound Structure |
| --- | --- |
| 166 | 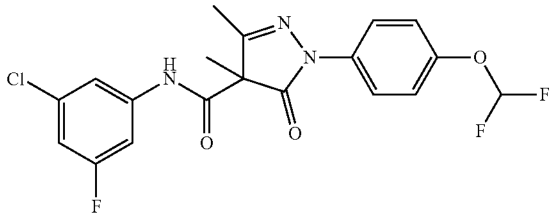 [SMILES: CC1=NN(c2ccc(OC(F)F)cc2)C(=O)C1(C)C(=O)Nc1cc(F)cc(Cl)c1] |
| 167 | 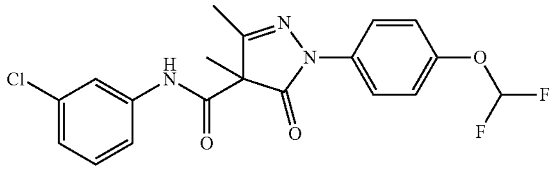 [SMILES: CC1=NN(c2ccc(OC(F)F)cc2)C(=O)C1(C)C(=O)Nc1cccc(Cl)c1] |
| 168 | 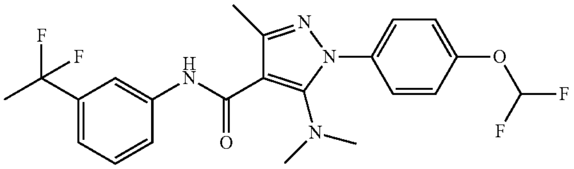 [SMILES: Cc1nn(-c2ccc(OC(F)F)cc2)c(N(C)C)c1C(=O)Nc1cccc(C(C)(F)F)c1] |
| 169 | 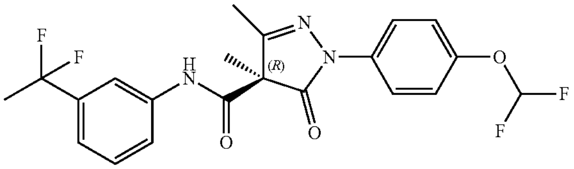 |
| 170 | 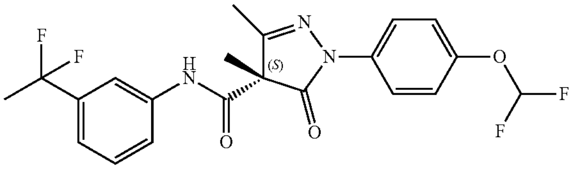 |
| 171 | 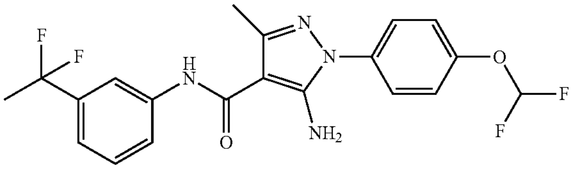 [SMILES: Cc1nn(-c2ccc(OC(F)F)cc2)c(N)c1C(=O)Nc1cccc(C(C)(F)F)c1] |
| 172 | 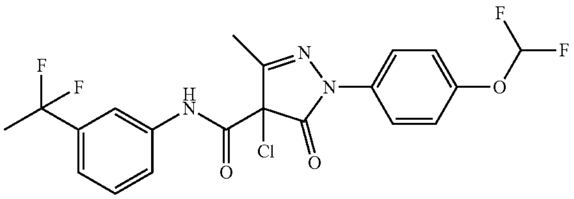 [SMILES: CC1=NN(c2ccc(OC(F)F)cc2)C(=O)C1(Cl)C(=O)Nc1cccc(C(C)(F)F)c1] |

TABLE 1-continued
| Compound Number | Compound Structure |
|---|---|
| 173 | 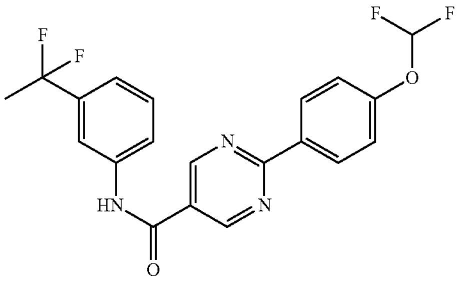 [SMILES: CC(F)(F)c1cccc(NC(=O)c2cnc(-c3ccc(OC(F)F)cc3)nc2)c1] |
| 174 | 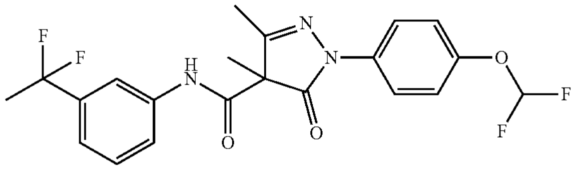 [SMILES: CC1=NN(c2ccc(OC(F)F)cc2)C(=O)C1(C)C(=O)Nc1cccc(C(C)(F)F)c1] |
| 175 | 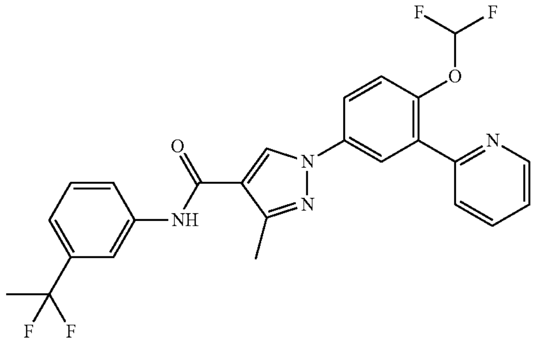 [SMILES: Cc1nn(-c2ccc(OC(F)F)c(-c3ccccn3)c2)cc1C(=O)Nc1cccc(C(C)(F)F)c1] |
| 176 | 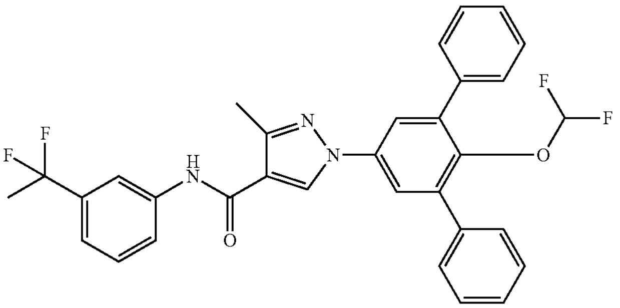 [SMILES: Cc1nn(-c2cc(-c3ccccc3)c(OC(F)F)c(-c3ccccc3)c2)cc1C(=O)Nc1cccc(C(C)(F)F)c1] |
| 177 | 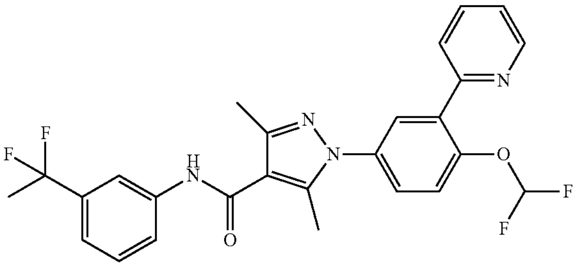 [SMILES: Cc1nn(-c2ccc(OC(F)F)c(-c3ccccn3)c2)c(C)c1C(=O)Nc1cccc(C(C)(F)F)c1] |

TABLE 1-continued
| Compound Number | Compound Structure |
|---|---|
| 178 | 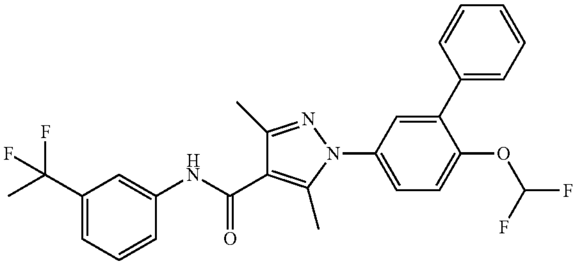 [SMILES: Cc1nn(-c2ccc(OC(F)F)c(-c3ccccc3)c2)c(C)c1C(=O)Nc1cccc(C(C)(F)F)c1] |
| 179 | 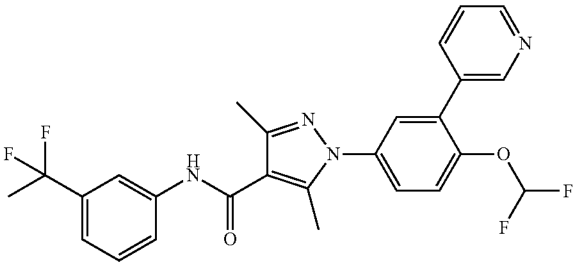 [SMILES: Cc1nn(-c2ccc(OC(F)F)c(-c3cccnc3)c2)c(C)c1C(=O)Nc1cccc(C(C)(F)F)c1] |
| 180 | 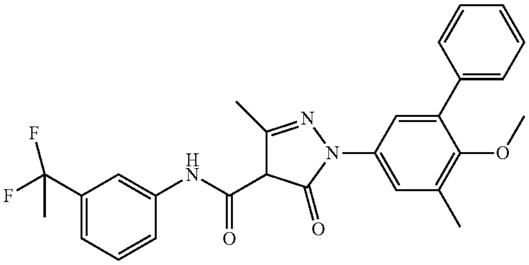 [SMILES: COc1c(C)cc(N2N=C(C)C(C(=O)Nc3cccc(C(C)(F)F)c3)C2=O)cc1-c1ccccc1] |
| 181 | 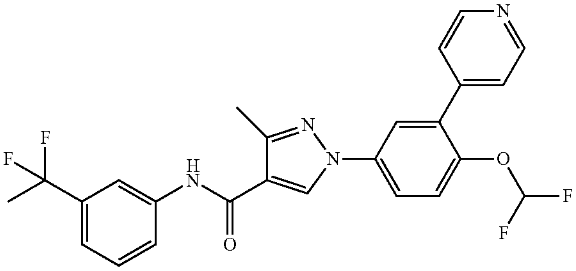 [SMILES: Cc1nn(-c2ccc(OC(F)F)c(-c3ccncc3)c2)cc1C(=O)Nc1cccc(C(C)(F)F)c1] |
| 182 | 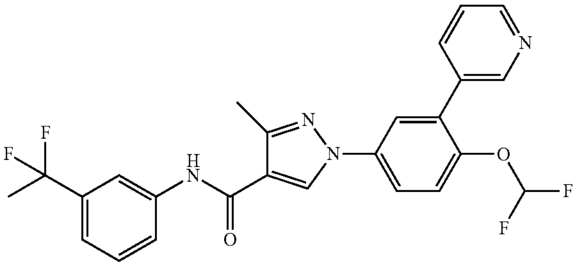 [SMILES: Cc1nn(-c2ccc(OC(F)F)c(-c3cccnc3)c2)cc1C(=O)Nc1cccc(C(C)(F)F)c1] |

TABLE 1-continued
| Compound Number | Compound Structure |
|---|---|
| 183 | 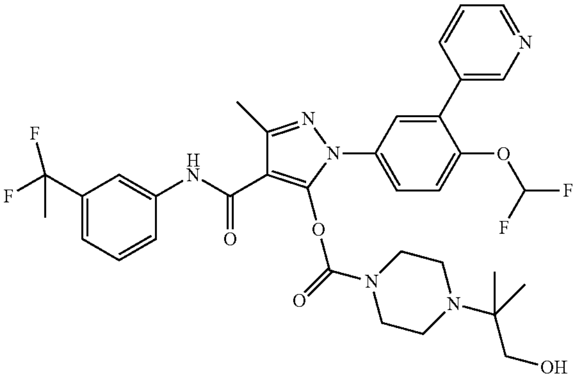 [SMILES: Cc1nn(-c2ccc(OC(F)F)c(-c3cccnc3)c2)c(OC(=O)N2CCN(C(C)(C)CO)CC2)c1C(=O)Nc1cccc(C(C)(F)F)c1] |
| 184 | 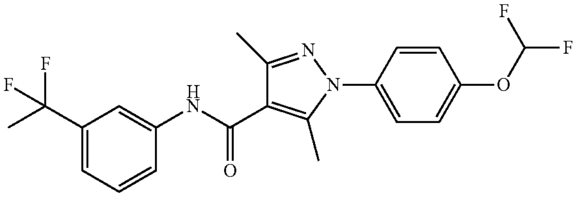 [SMILES: Cc1nn(-c2ccc(OC(F)F)cc2)c(C)c1C(=O)Nc1cccc(C(C)(F)F)c1] |
| 185 | 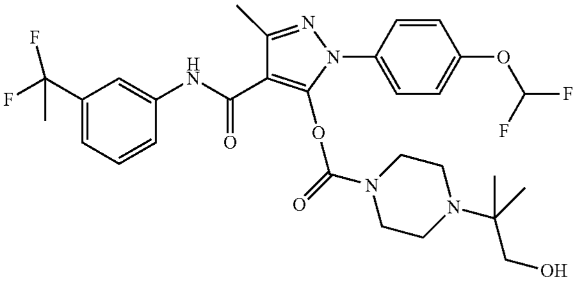 [SMILES: Cc1nn(-c2ccc(OC(F)F)cc2)c(OC(=O)N2CCN(C(C)(C)CO)CC2)c1C(=O)Nc1cccc(C(C)(F)F)c1] |
| 186 | 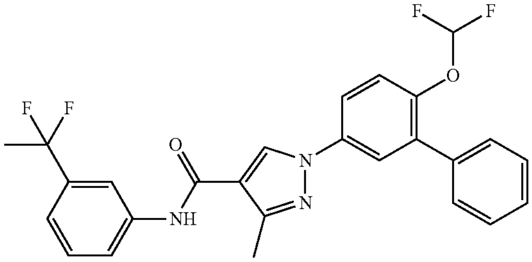 [SMILES: Cc1nn(-c2ccc(OC(F)F)c(-c3ccccc3)c2)cc1C(=O)Nc1cccc(C(C)(F)F)c1] |
| 187 | 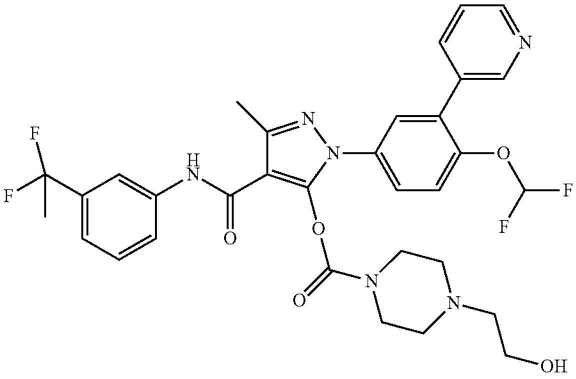 [SMILES: Cc1nn(-c2ccc(OC(F)F)c(-c3cccnc3)c2)c(OC(=O)N2CCN(CCO)CC2)c1C(=O)Nc1cccc(C(C)(F)F)c1] |

TABLE 1-continued
| Compound Number | Compound Structure |
|---|---|
| 188 | 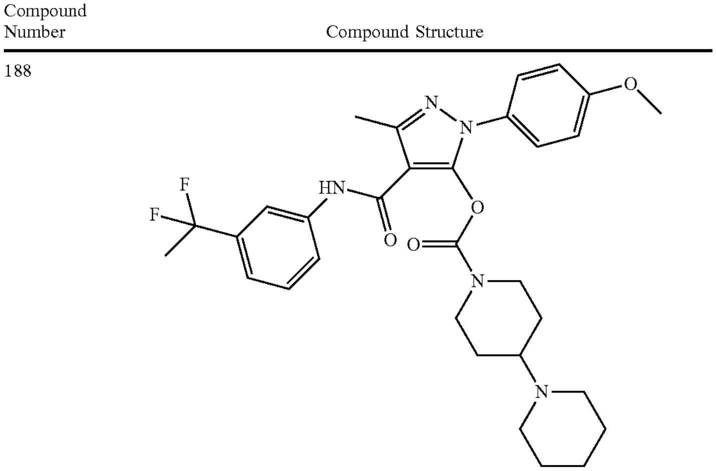 |
| 189 | 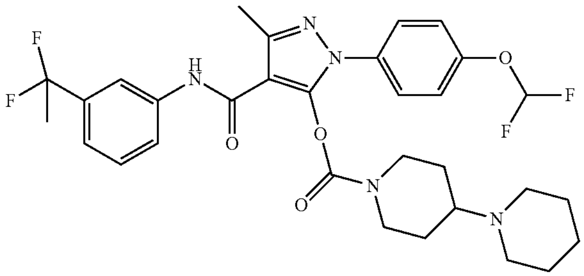 [SMILES: Cc1nn(-c2ccc(OC(F)F)cc2)c(OC(=O)N2CCC(N3CCCCC3)CC2)c1C(=O)Nc1cccc(C(C)(F)F)c1] |
| 190 | 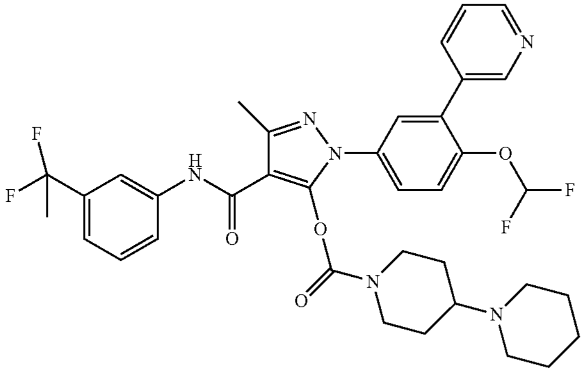 [SMILES: Cc1nn(-c2ccc(OC(F)F)c(-c3cccnc3)c2)c(OC(=O)N2CCC(N3CCCCC3)CC2)c1C(=O)Nc1cccc(C(C)(F)F)c1] |
| 191 | 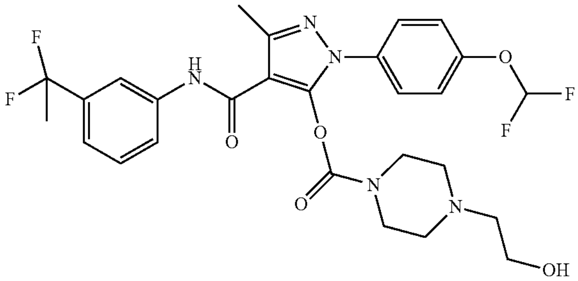 [SMILES: Cc1nn(-c2ccc(OC(F)F)cc2)c(OC(=O)N2CCN(CCO)CC2)c1C(=O)Nc1cccc(C(C)(F)F)c1] |
| 192 | 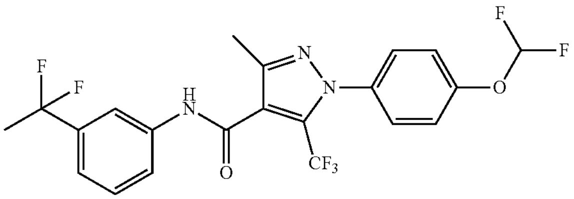 [SMILES: Cc1nn(-c2ccc(OC(F)F)cc2)c(C(F)(F)F)c1C(=O)Nc1cccc(C(C)(F)F)c1] |

TABLE 1-continued
| Compound Number | Compound Structure |
|---|---|
| 193 | 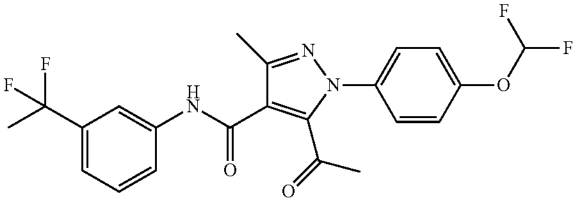 [SMILES: CC(=O)c1c(C(=O)Nc2cccc(C(C)(F)F)c2)c(C)nn1-c1ccc(OC(F)F)cc1] |
| 194 | 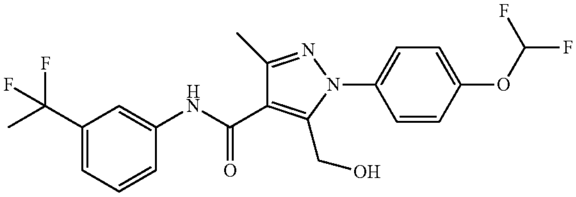 [SMILES: Cc1nn(-c2ccc(OC(F)F)cc2)c(CO)c1C(=O)Nc1cccc(C(C)(F)F)c1] |
| 195 | 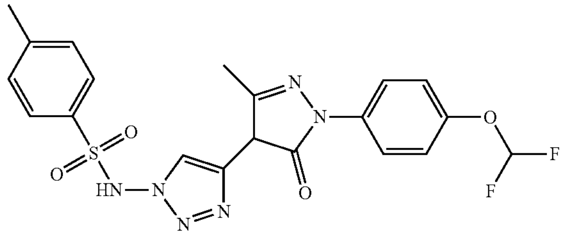 [SMILES: CC1=NN(c2ccc(OC(F)F)cc2)C(=O)C1c1cn(NS(=O)(=O)c2ccc(C)cc2)nn1] |
| 196 | 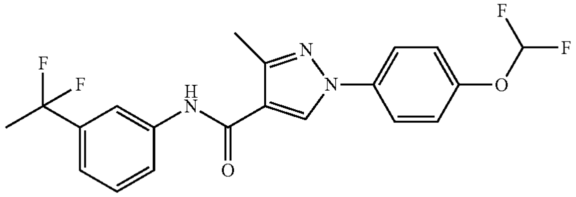 [SMILES: Cc1nn(-c2ccc(OC(F)F)cc2)cc1C(=O)Nc1cccc(C(C)(F)F)c1] |
| 197 | 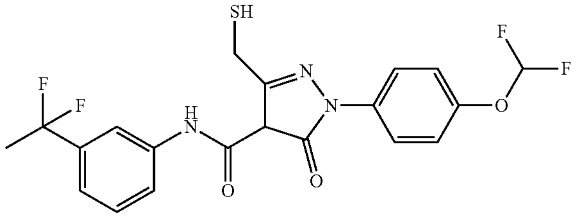 [SMILES: CC(F)(F)c1cccc(NC(=O)C2C(=O)N(c3ccc(OC(F)F)cc3)N=C2CS)c1] |
| 198 | 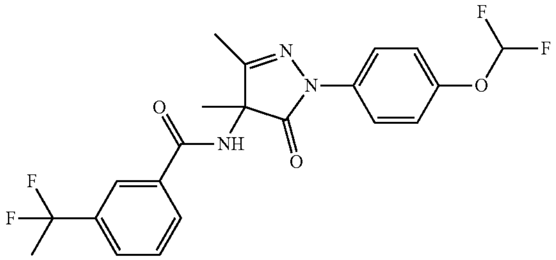 [SMILES: CC1=NN(c2ccc(OC(F)F)cc2)C(=O)C1(C)NC(=O)c1cccc(C(C)(F)F)c1] |
| 199 | 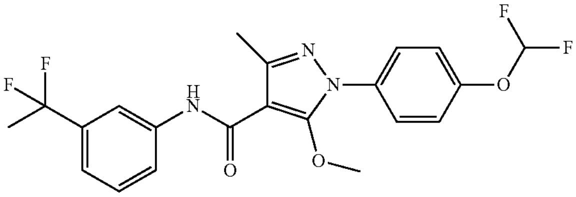 [SMILES: COc1c(C(=O)Nc2cccc(C(C)(F)F)c2)c(C)nn1-c1ccc(OC(F)F)cc1] |

TABLE 1-continued
| Compound Number | Compound Structure |
|---|---|
| 200 | 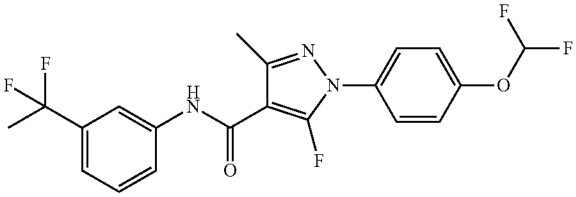 [SMILES: Cc1nn(-c2ccc(OC(F)F)cc2)c(F)c1C(=O)Nc1cccc(C(C)(F)F)c1] |
| 201 | 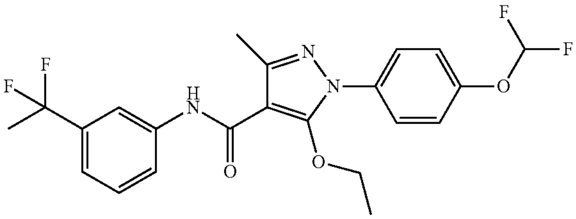 [SMILES: CCOc1c(C(=O)Nc2cccc(C(C)(F)F)c2)c(C)nn1-c1ccc(OC(F)F)cc1] |
| 202 | 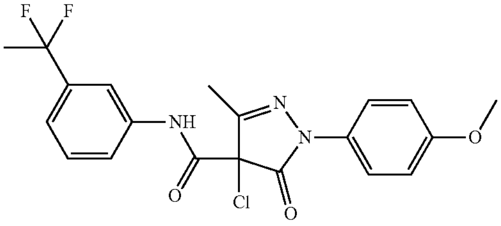 [SMILES: COc1ccc(N2N=C(C)C(Cl)(C(=O)Nc3cccc(C(C)(F)F)c3)C2=O)cc1] |
| 203 | 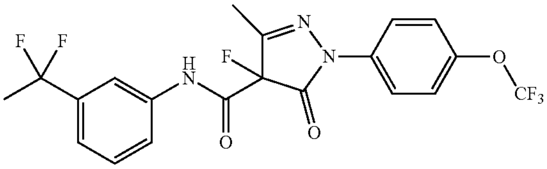 [SMILES: CC1=NN(c2ccc(OC(F)(F)F)cc2)C(=O)C1(F)C(=O)Nc1cccc(C(C)(F)F)c1] |
| 204 | 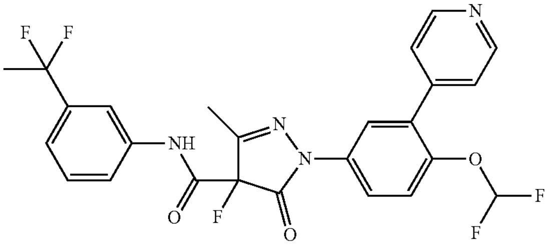 [SMILES: CC1=NN(c2ccc(OC(F)F)c(-c3ccncc3)c2)C(=O)C1(F)C(=O)Nc1cccc(C(C)(F)F)c1] |
| 205 | 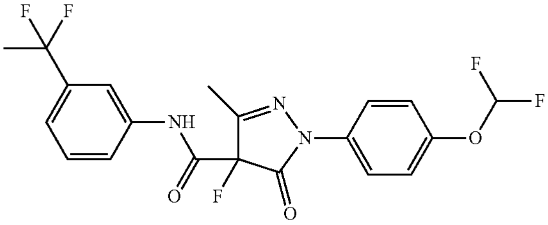 [SMILES: CC1=NN(c2ccc(OC(F)F)cc2)C(=O)C1(F)C(=O)Nc1cccc(C(C)(F)F)c1] |
| 206 | 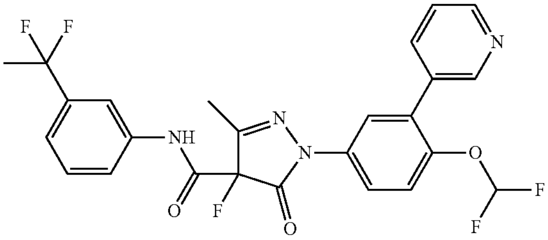 [SMILES: CC1=NN(c2ccc(OC(F)F)c(-c3cccnc3)c2)C(=O)C1(F)C(=O)Nc1cccc(C(C)(F)F)c1]

TABLE 1-continued
| Compound Number | Compound Structure |
| --- | --- |
| 207 | 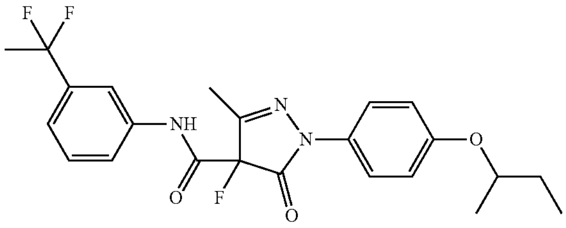 [SMILES: CCC(C)Oc1ccc(N2N=C(C)C(F)(C(=O)Nc3cccc(C(C)(F)F)c3)C2=O)cc1] |
| 208 | 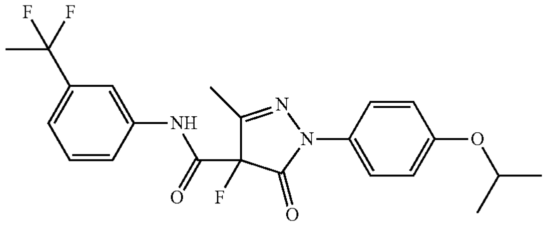 [SMILES: CC1=NN(c2ccc(OC(C)C)cc2)C(=O)C1(F)C(=O)Nc1cccc(C(C)(F)F)c1] |
| 209 | 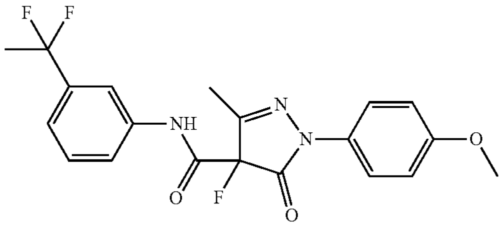 [SMILES: COc1ccc(N2N=C(C)C(F)(C(=O)Nc3cccc(C(C)(F)F)c3)C2=O)cc1] |
| 210 | 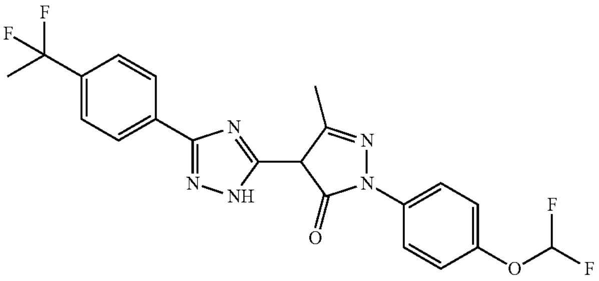 [SMILES: CC1=NN(c2ccc(OC(F)F)cc2)C(=O)C1c1nc(-c2ccc(C(C)(F)F)cc2)n[nH]1] |
| 211 | 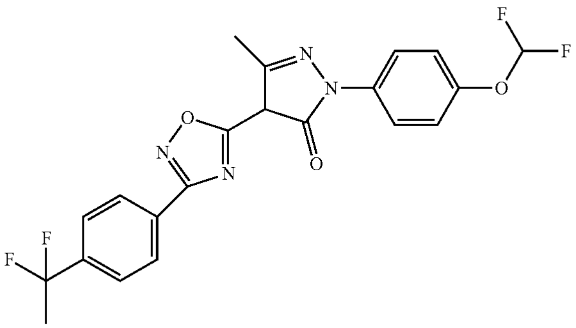 [SMILES: CC1=NN(c2ccc(OC(F)F)cc2)C(=O)C1c1nc(-c2ccc(C(C)(F)F)cc2)no1] |

TABLE 1-continued
| Compound Number | Compound Structure |
| --- | --- |
| 212 | 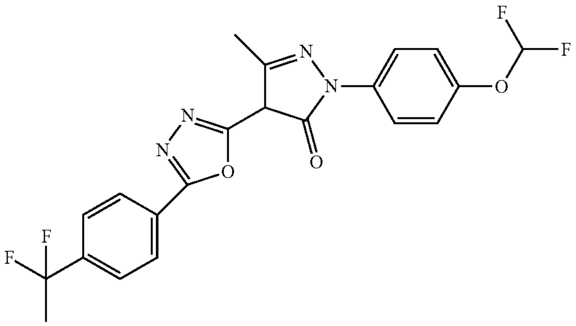 [SMILES: CC1=NN(c2ccc(OC(F)F)cc2)C(=O)C1c1nnc(-c2ccc(C(C)(F)F)cc2)o1] |
| 213 | 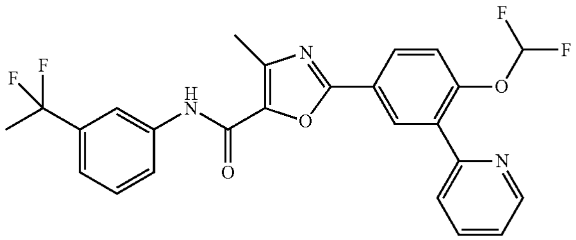 [SMILES: Cc1nc(-c2ccc(OC(F)F)c(-c3ccccn3)c2)oc1C(=O)Nc1cccc(C(C)(F)F)c1] |
| 214 | 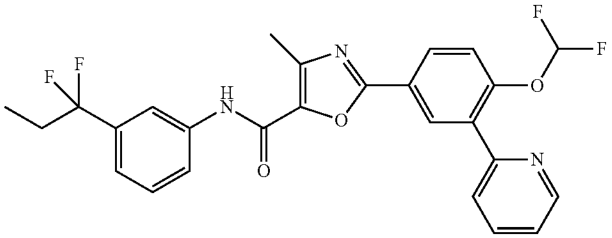 [SMILES: CCC(F)(F)c1cccc(NC(=O)c2oc(-c3ccc(OC(F)F)c(-c4ccccn4)c3)nc2C)c1] |
| 215 | 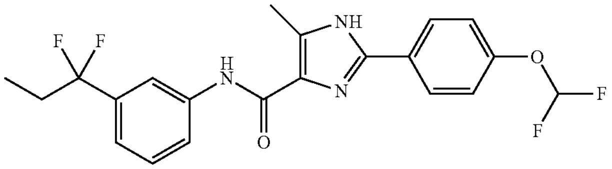 [SMILES: CCC(F)(F)c1cccc(NC(=O)c2nc(-c3ccc(OC(F)F)cc3)[nH]c2C)c1] |
| 216 | 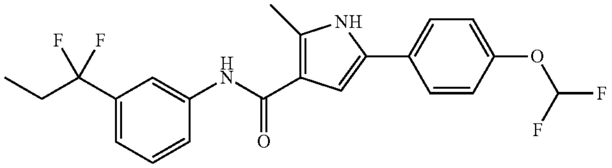 [SMILES: CCC(F)(F)c1cccc(NC(=O)c2cc(-c3ccc(OC(F)F)cc3)[nH]c2C)c1] |
| 217 | 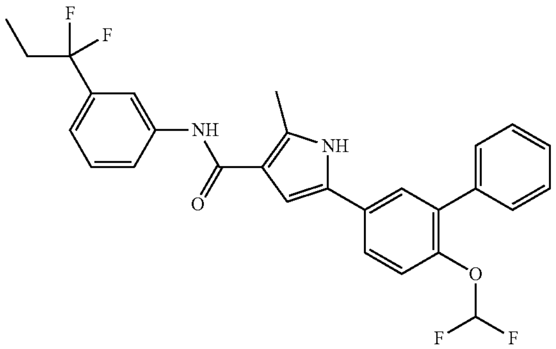 [SMILES: CCC(F)(F)c1cccc(NC(=O)c2cc(-c3ccc(OC(F)F)c(-c4ccccc4)c3)[nH]c2C)c1] |

TABLE 1-continued
| Compound Number | Compound Structure |
|---|---|
| 218 | 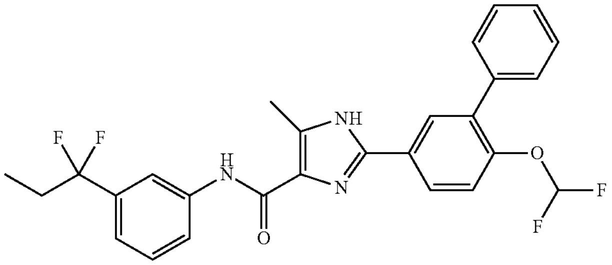 [SMILES: CCC(F)(F)c1cccc(NC(=O)c2nc(-c3ccc(OC(F)F)c(-c4ccccc4)c3)[nH]c2C)c1] |
| 219 | 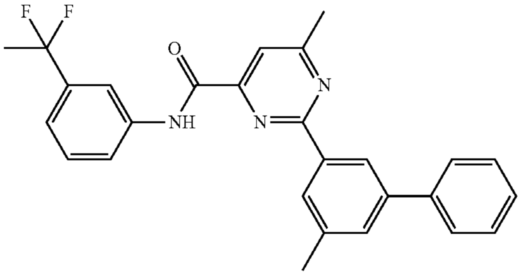 [SMILES: Cc1cc(-c2ccccc2)cc(-c2nc(C)cc(C(=O)Nc3cccc(C(C)(F)F)c3)n2)c1] |
| 220 | 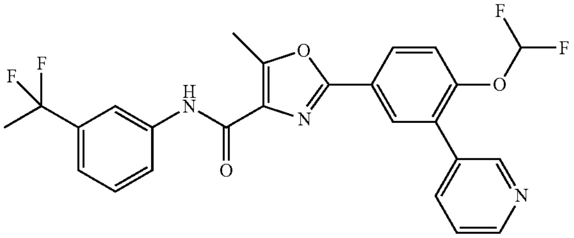 [SMILES: Cc1oc(-c2ccc(OC(F)F)c(-c3cccnc3)c2)nc1C(=O)Nc1cccc(C(C)(F)F)c1] |
| 221 | 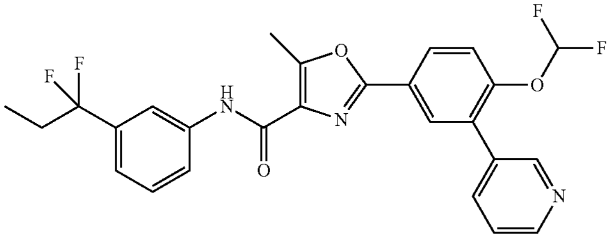 |
| 222 | 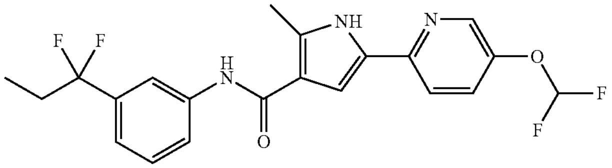 [SMILES: CCC(F)(F)c1cccc(NC(=O)c2cc(-c3ccc(OC(F)F)cn3)[nH]c2C)c1] |
| 223 | 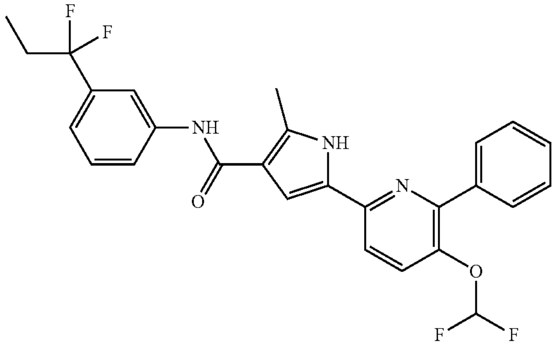 [SMILES: CCC(F)(F)c1cccc(NC(=O)c2cc(-c3ccc(OC(F)F)c(-c4ccccc4)n3)[nH]c2C)c1] |

TABLE 1-continued
| Compound Number | Compound Structure |
|---|---|
| 224 | 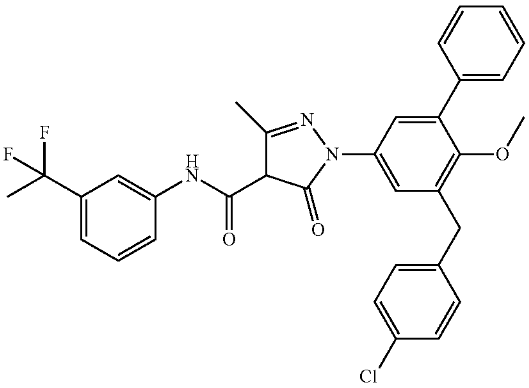 [SMILES: COc1c(Cc2ccc(Cl)cc2)cc(N2N=C(C)C(C(=O)Nc3cccc(C(C)(F)F)c3)C2=O)cc1-c1ccccc1] |
| 225 | 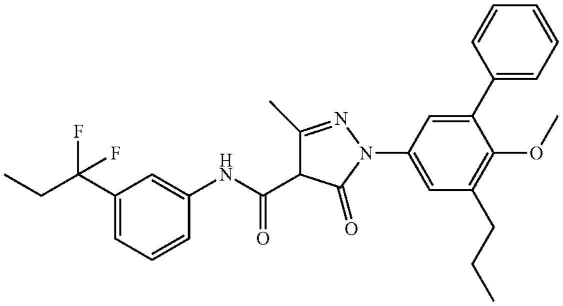 [SMILES: CCCc1cc(N2N=C(C)C(C(=O)Nc3cccc(C(F)(F)CC)c3)C2=O)cc(-c2ccccc2)c1OC] |
| 226 | 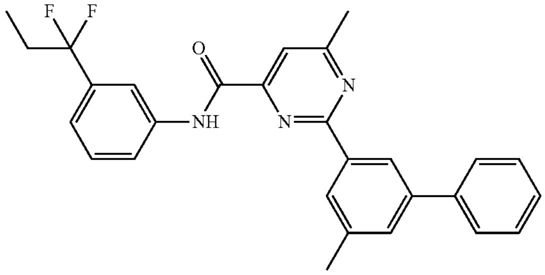 [SMILES: CCC(F)(F)c1cccc(NC(=O)c2cc(C)nc(-c3cc(C)cc(-c4ccccc4)c3)n2)c1] |
| 227 | 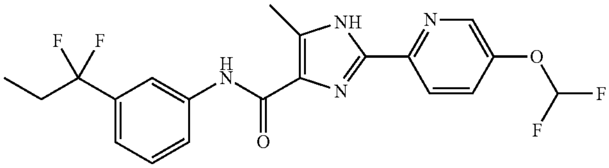 [SMILES: CCC(F)(F)c1cccc(NC(=O)c2nc(-c3ccc(OC(F)F)cn3)[nH]c2C)c1] |
| 228 | 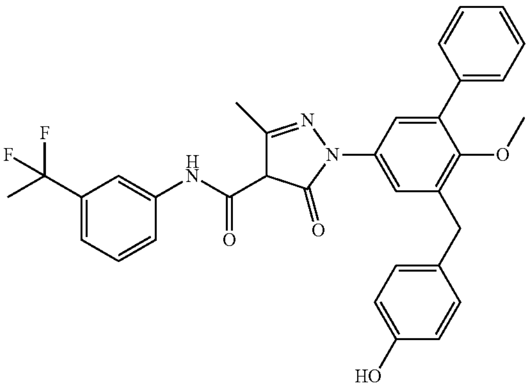 [SMILES: COc1c(Cc2ccc(O)cc2)cc(N2N=C(C)C(C(=O)Nc3cccc(C(C)(F)F)c3)C2=O)cc1-c1ccccc1] |

TABLE 1-continued
| Compound Number | Compound Structure |
|---|---|
| 229 | 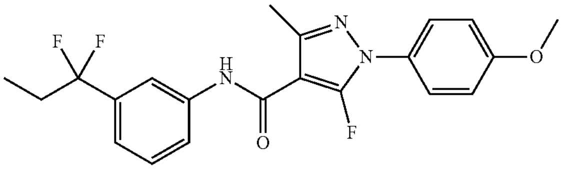 [SMILES: CCC(F)(F)c1cccc(NC(=O)c2c(C)nn(-c3ccc(OC)cc3)c2F)c1] |
| 230 | 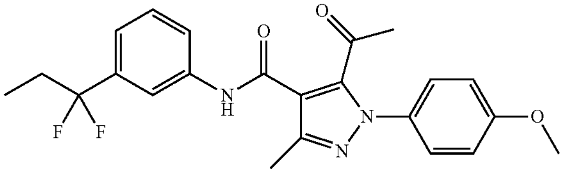 [SMILES: CCC(F)(F)c1cccc(NC(=O)c2c(C)nn(-c3ccc(OC)cc3)c2C(C)=O)c1] |
| 231 | 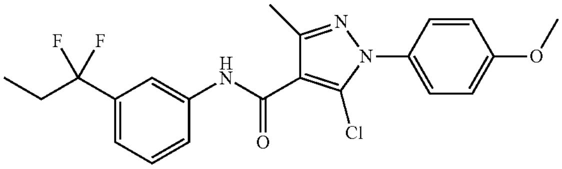 [SMILES: CCC(F)(F)c1cccc(NC(=O)c2c(C)nn(-c3ccc(OC)cc3)c2Cl)c1] |
| 232 | 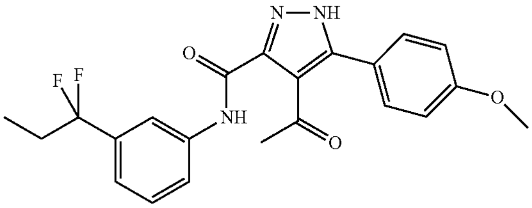 [SMILES: CCC(F)(F)c1cccc(NC(=O)c2n[nH]c(-c3ccc(OC)cc3)c2C(C)=O)c1] |
| 233 | 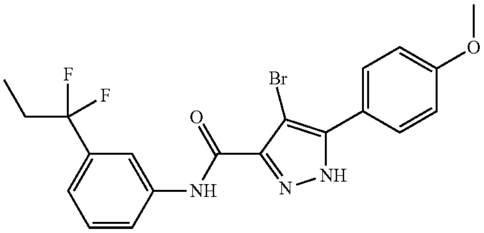 [SMILES: CCC(F)(F)c1cccc(NC(=O)c2n[nH]c(-c3ccc(OC)cc3)c2Br)c1] |
| 234 | 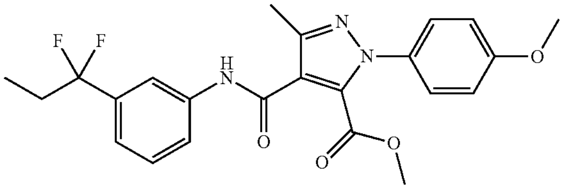 [SMILES: CCC(F)(F)c1cccc(NC(=O)c2c(C)nn(-c3ccc(OC)cc3)c2C(=O)OC)c1] |
| 235 | 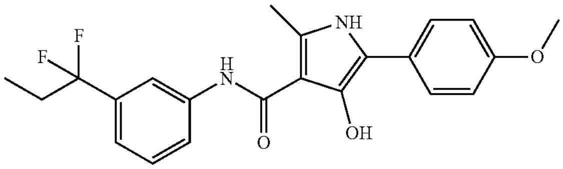 [SMILES: CCC(F)(F)c1cccc(NC(=O)c2c(C)[nH]c(-c3ccc(OC)cc3)c2O)c1] |

TABLE 1-continued
| Compound Number | Compound Structure |
|---|---|
| 236 | 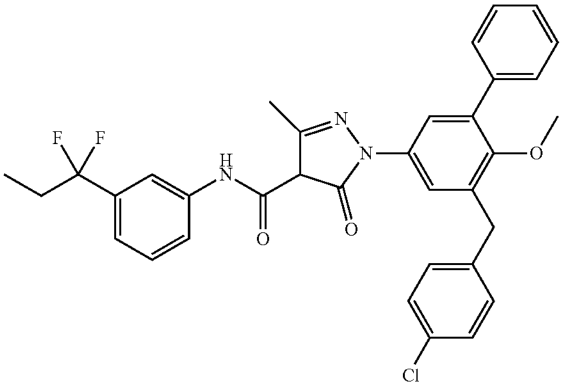 [SMILES: CCC(F)(F)c1cccc(NC(=O)C2C(=O)N(c3cc(Cc4ccc(Cl)cc4)c(OC)c(-c4ccccc4)c3)N=C2C)c1] |
| 237 | 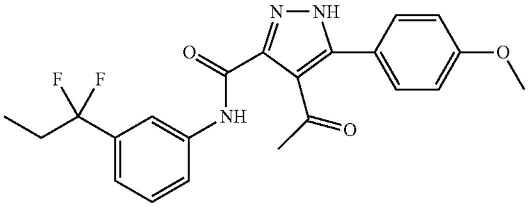 [SMILES: CCC(F)(F)c1cccc(NC(=O)c2n[nH]c(-c3ccc(OC)cc3)c2C(C)=O)c1] |
| 238 | 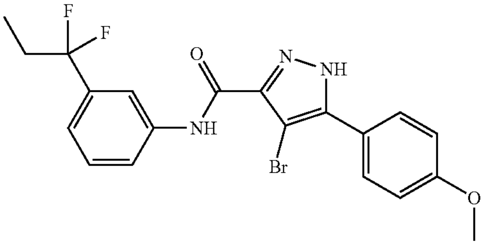 [SMILES: CCC(F)(F)c1cccc(NC(=O)c2n[nH]c(-c3ccc(OC)cc3)c2Br)c1] |
| 239 | 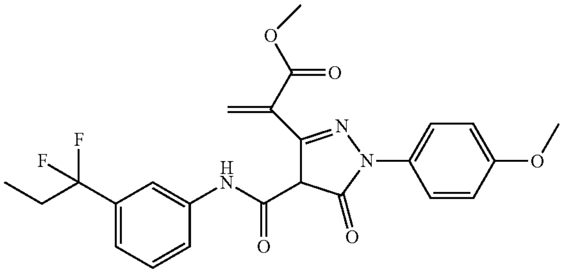 [SMILES: C=C(C(=O)OC)C1=NN(c2ccc(OC)cc2)C(=O)C1C(=O)Nc1cccc(C(F)(F)CC)c1] |
| 240 | 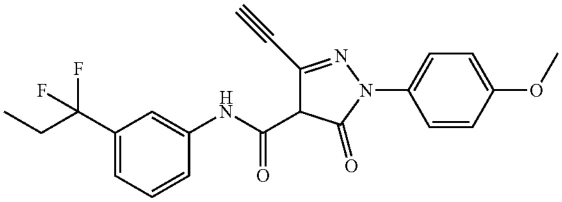 [SMILES: C#CC1=NN(c2ccc(OC)cc2)C(=O)C1C(=O)Nc1cccc(C(F)(F)CC)c1] |

TABLE 1-continued
| Compound Number | Compound Structure |
|---|---|
| 241 | 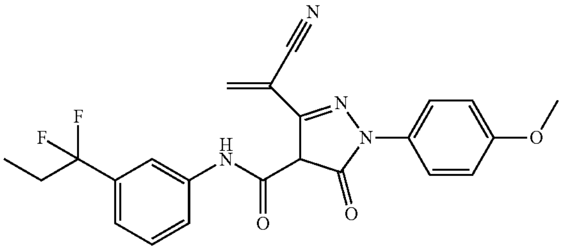 [SMILES: C=C(C#N)C1=NN(c2ccc(OC)cc2)C(=O)C1C(=O)Nc1cccc(C(F)(F)CC)c1] |
| 242 | 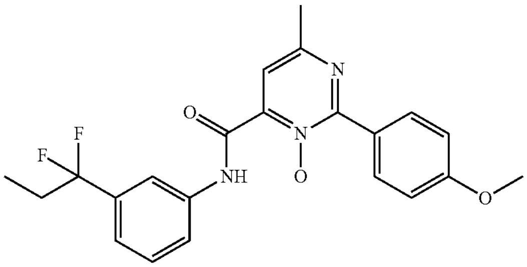 |
| 243 | 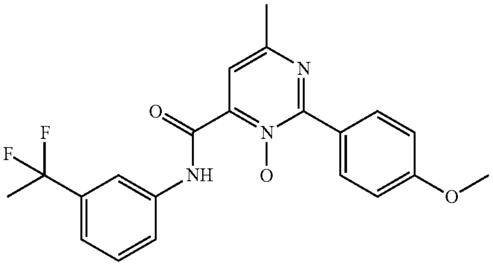 |
| 244 | 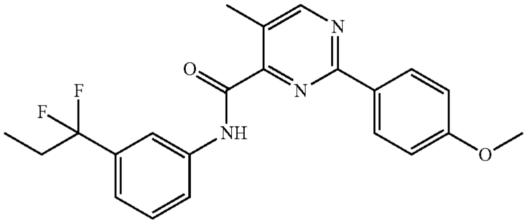 [SMILES: CCC(F)(F)c1cccc(NC(=O)c2nc(-c3ccc(OC)cc3)ncc2C)c1] |
| 245 | 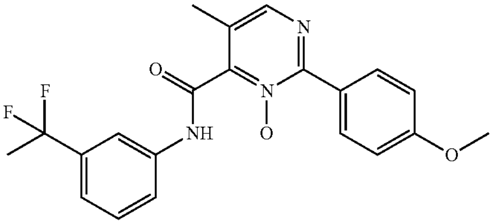 |
| 246 | 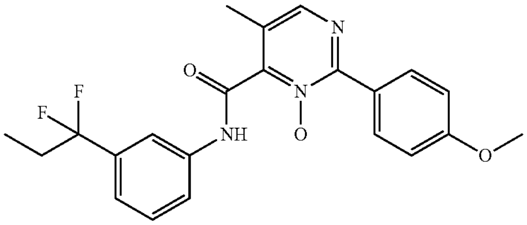 |

TABLE 1-continued
| Compound Number | Compound Structure |
| --- | --- |
| 247 | 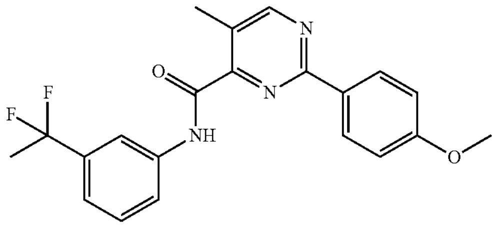 [SMILES: COc1ccc(-c2ncc(C)c(C(=O)Nc3cccc(C(C)(F)F)c3)n2)cc1] |
| 248 | 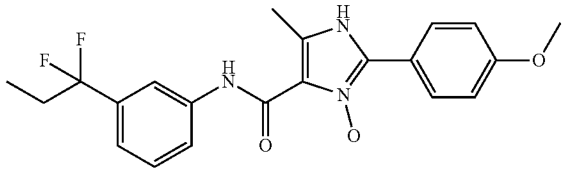 |
| 249 | 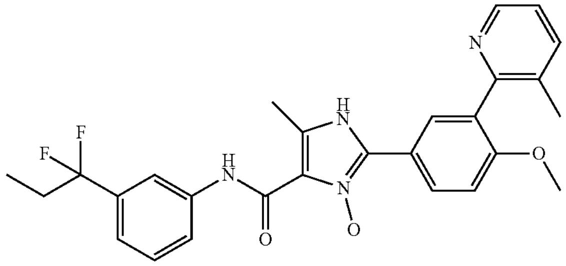 |
| 250 | 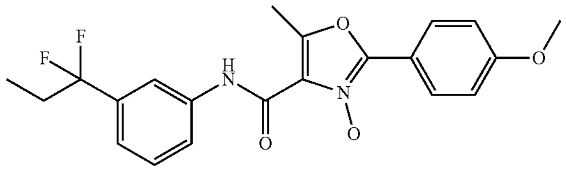 |
| 251 | 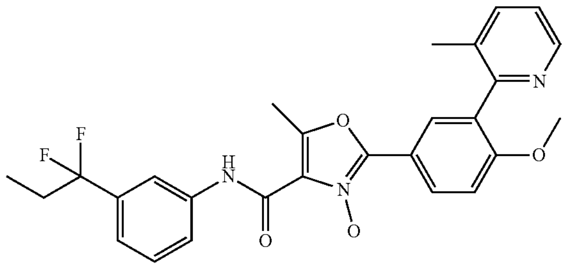 |
| 252 | 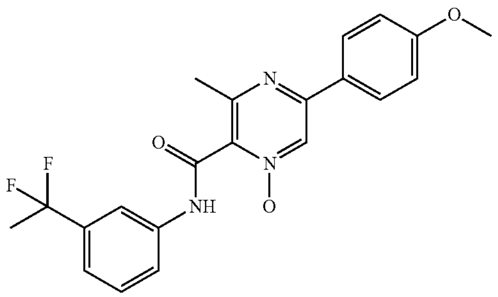 |

TABLE 1-continued
| Compound Number | Compound Structure |
|---|---|
| 253 | 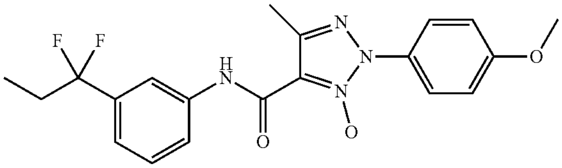 |
| 254 | 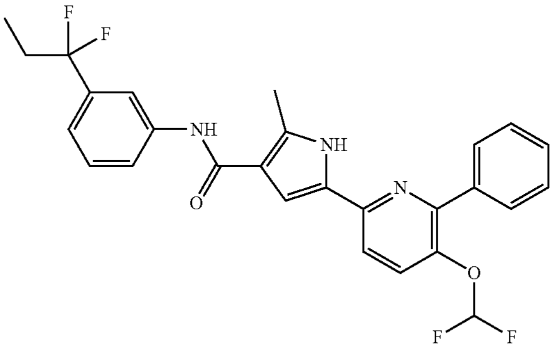 [SMILES: CCC(F)(F)c1cccc(NC(=O)c2cc(-c3ccc(OC(F)F)c(-c4ccccc4)n3)[nH]c2C)c1] |
| 255 | 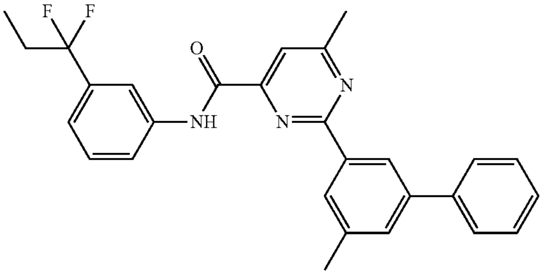 [SMILES: CCC(F)(F)c1cccc(NC(=O)c2cc(C)nc(-c3cc(C)cc(-c4ccccc4)c3)n2)c1] |
| 256 | 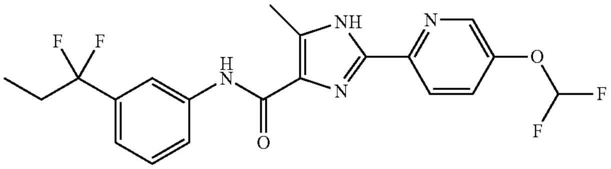 [SMILES: CCC(F)(F)c1cccc(NC(=O)c2nc(-c3ccc(OC(F)F)cn3)[nH]c2C)c1] |
| 257 | 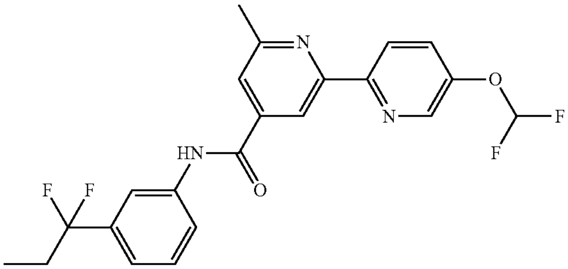 [SMILES: CCC(F)(F)c1cccc(NC(=O)c2cc(C)nc(-c3ccc(OC(F)F)cn3)c2)c1] |
| 258 | 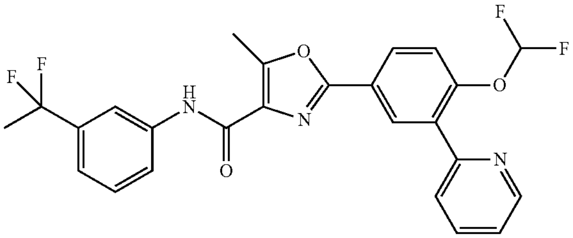 [SMILES: Cc1oc(-c2ccc(OC(F)F)c(-c3ccccn3)c2)nc1C(=O)Nc1cccc(C(C)(F)F)c1] |

TABLE 1-continued

| Compound Number | Compound Structure |
|---|---|
| 259 | 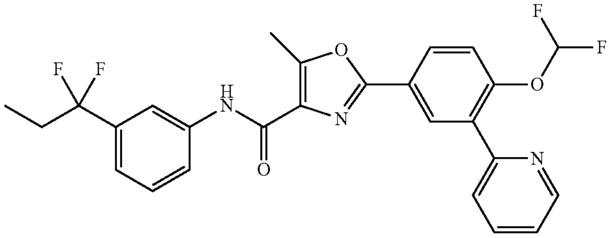 [SMILES: CCC(F)(F)c1cccc(NC(=O)c2nc(-c3ccc(OC(F)F)c(-c4ccccn4)c3)oc2C)c1] |
| 260 | 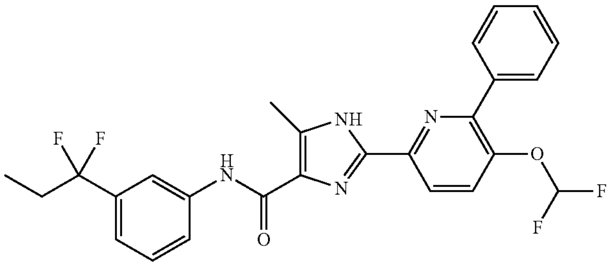 [SMILES: CCC(F)(F)c1cccc(NC(=O)c2nc(-c3ccc(OC(F)F)c(-c4ccccc4)n3)[nH]c2C)c1] |
| 268 | 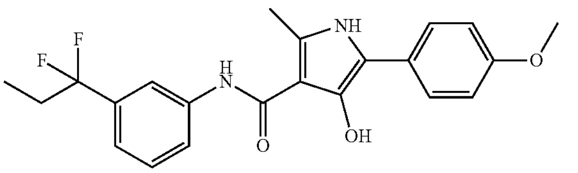 [SMILES: CCC(F)(F)c1cccc(NC(=O)c2c(C)[nH]c(-c3ccc(OC)cc3)c2O)c1] |

It is well understood that in structures presented in this invention wherein the carbon atom has less than 4 bonds, H atoms are present to complete the valence of the carbon. It is well understood that in structures presented in this invention wherein the nitrogen atom has less than 3 bonds, H atoms are present to complete the valence of the nitrogen.

In some embodiments, this invention is directed to the compounds listed hereinabove, pharmaceutical compositions and/or method of use thereof, wherein the compound is pharmaceutically acceptable salt, optical isomer, tautomer, hydrate, N-oxide, reverse amide analog, prodrug, isotopic variant (deuterated analog), PROTAC, pharmaceutical product or any combination thereof. In some embodiments, the compounds are Acyl-CoA Synthetase Short-Chain Family Member 2 (ACSS2) inhibitors.

In various embodiments, the A ring of formula I, I(a), II and III is phenyl, naphthyl, pyridinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, isoquinoline, pyrazolyl, pyrrolyl, furanyl, thiophene-yl, isoquinolinyl, indolyl, 1H-indole, isoindolyl, naphthyl, anthracenyl, benzimidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, cinnolinyl, phthalazinyl, quinolinyl, isoquinolinyl, 2,3-dihydroindenyl, indenyl, tetrahydronaphthyl, 3,4-dihydro-2H-benzo[b][1,4]dioxepine, benzo[d][1,3]dioxole, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, benzo[d][1,3]dioxole, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, each definition is a separate embodiment according to this invention; or A is $C_3$-$C_8$ cycloalkyl (e.g. cyclohexyl) or $C_3$-$C_8$ heterocyclic ring including but not limited to: tetrahydropyran, piperidine, 1-methylpiperidine, tetrahydrothiophene 1,1-dioxide, 1-(piperidin-1-yl)ethanone or morpholine.

In various embodiments, the B ring of formula I, I(a), II and/or III is phenyl, naphthyl, pyridinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, isoquinoline, pyrazolyl, pyrrolyl, furanyl, thiophene-yl, isoquinolinyl, indolyl, 1H-indole, isoindolyl, naphthyl, anthracenyl, benzimidazolyl, 2,3-dihydro-1H-benzo[d]imidazolyl, tetrahydronaphthyl 3,4-dihydro-2H-benzo[b][1,4]dioxepine, benzofuran-2(3H)-one, benzo[d][1,3]dioxole, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, cinnolinyl, phthalazinyl, quinolinyl, isoquinolinyl, acridinyl, benzofuranyl, 1-benzofuran, isobenzofuranyl, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 3H-imidazo[4,5-b]pyridine, 3H-imidazo[4,5-c]pyridine, pyrazolo[1,5-a]pyridine, imidazo[1,2-a]pyrazine, imidazo[1,2-a]pyrimidine, pyrido[2,3-b]pyrazin or pyrido[2,3-b]pyrazin-3(4H)-one, 4H-thieno[3,2-b]pyrrole, quinoxalin-2(1H)-one, 1,2,3,4-tetrahydroquinoxaline, 1-(pyridin-1(2H)-yl)ethanone, 1H-pyrrolo[2,3-b]pyridine, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, $C_3$-$C_8$ cycloalkyl, or $C_3$-$C_8$ heterocyclic ring including but not limited to: tetrahydropyran, piperidine, 1-methylpiperidine, tetrahydrothiophene 1,1-dioxide, 1-(piperidin-1-yl)ethanone or morpholine; each definition is a separate embodiment according to this invention.

In various embodiments, compound of formula I, I(a), II and/or III is substituted by $R_1$, $R_2$ and $R_{20}$. Single substituents can be present at the ortho, meta, or para positions.

In various embodiments, $R_1$, $R_2$ and $R_{20}$ of formula I-II(b) are each independently H.

In various embodiments, $R_1$, $R_2$ and $R_{20}$ of formula I-III(a) are each independently F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$—($C_3$-$C_8$ cycloalkyl), $CH_2$-cyclohexyl, $R_8$—($C_3$-$C_8$ heterocyclic ring) (e.g., $CH_2$-imidazole, $CH_2$-indazole), $CF_3$, $CD_3$, $OCD_3$, CN, $NO_2$, —$CH_2$CN, —$R_8$CN, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —OC(O)$CF_3$, —$OCH_2$Ph, NHC(O)—$R_{10}$ (e.g., NHC(O)$CH_3$), NHCO—$N(R_{10})(R_{11})$ (e.g., NHC(O)$N(CH_3)_2$), COOH, —C(O)Ph, C(O)O—$R_{10}$ (e.g. C(O)O—$CH_3$, C(O)O—$CH(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)$N(CH_3)_2$), $SO_2R$, $SO_2N(R_{10})(R_{11})$ (e.g., $SO_2N(CH_3)_2$, $SO_2$NHC(O)$CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, t-Bu, iso-butyl, pentyl, benzyl), $C_1$-$C_5$ linear or branched, substituted or unsubstituted alkenyl (e.g., CH═$C(Ph)_2$)), $C_1$-$C_5$ linear, branched or cyclic haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy, $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 3-methyl-2-pyridine, pyrimidine, pyrazine, oxacyclobutane (1 or 2-oxacyclobutane), indole, protonated or deprotonated pyridine oxide), substituted or unsubstituted aryl (e.g., phenyl), substituted or unsubstituted benzyl (e.g., benzyl, 4-Cl-benzyl, 4-OH-benzyl), or $CH(CF_3)$(NH—$R_{10}$); each is a separate embodiment according to this invention. In other embodiments substitutions include: F, Cl, Br, I, $C_1$-$C_5$ linear or branched alkyl (e.g. methyl, ethyl), OH, alkoxy, $N(R)_2$, $CF_3$, aryl, phenyl, heteroaryl (e.g., imidazole), $C_3$-$C_8$ cycloalkyl, halophenyl, (benzyloxy)phenyl, CN, $NO_2$ or any combination thereof; each is a separate embodiment according to this invention.

In some embodiments, $R_1$ and $R_2$ are joint together to form a 5 or 6 membered substituted or unsubstituted, aliphatic or aromatic, carbocyclic or heterocyclic ring. In some embodiments, $R_1$ and $R_2$ are joined together to form a 5 or 6 membered heterocyclic ring. In some embodiments, $R_1$ and $R_2$ are joined together to form a pyrrol ring. In some embodiments, $R_1$ and $R_2$ are joined together to form a [1,3]dioxole ring. In some embodiments, $R_1$ and $R_2$ are joined together to form a furan-2(3H)-one ring. In some embodiments, $R_1$ and $R_2$ are joint together to form a benzene ring. In some embodiments, $R_1$ and $R_2$ are joined together to form a pyridine ring. In some embodiments, $R_1$ and $R_2$ are joined together to form a morpholine ring. In some embodiments, $R_1$ and $R_2$ are joined together to form a piperazine ring. In some embodiments, $R_1$ and $R_2$ are joined together to form an imidazole ring. In some embodiments, $R_1$ and $R_2$ are joined together to form a pyrrole ring. In some embodiments, $R_1$ and $R_2$ are joined together to form a cyclohexene ring. In some embodiments, $R_1$ and $R_2$ are joined together to form a pyrazine ring.

In various embodiments, compound of formula I-III(a) is substituted by $R_3$ and $R_4$. Single substituents can be present at the ortho, meta, or para positions. In various embodiments, compound of formula I, I(a), II, and III is substituted by $R_{40}$. Single substituents can be present at the ortho, meta, or para positions.

In various embodiments, $R_3$ and $R_4$ of formula I-III(a) are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2$CN, —$R_8$CN, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$, $B(OH)_2$, —OC(O)$CF_3$, —$OCH_2$Ph, —NHCO—$R_{10}$ (e.g., NHC(O)$CH_3$), NHCO—$N(R_{10})(R_{11})$ (e.g., NHC(O)$N(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)$N(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, $C(OH)(CH_3)(Ph)$, ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), $CH(CF_3)$(NH—$R_{10}$); each represents a separate embodiment of this invention. In some embodiments, substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof; each represents a separate embodiment of this invention.

In some embodiments, $R_3$ and $R_4$ are joint together to form a 5 or 6 membered substituted or unsubstituted, aliphatic or aromatic, carbocyclic or heterocyclic ring. In some embodiments, $R_3$ and $R_4$ are joint together to form a 5 or 6 membered carbocyclic ring. In some embodiments, $R_3$ and $R_4$ are joined together to form a 5 or 6 membered heterocyclic ring. In some embodiments, $R_3$ and $R_4$ are joined together to form a dioxole ring. [1,3]dioxole ring. In some embodiments, $R_3$ and $R_4$ are joined together to form a dihydrofuran-2(3H)-one ring. In some embodiments, $R_3$ and $R_4$ are joined together to form a furan-2(3H)-one ring. In some embodiments, $R_3$ and $R_4$ are joined together to form a benzene ring. In some embodiments, $R_3$ and $R_4$ are joint together to form an imidazole ring. In some embodiments, $R_3$ and $R_4$ are joined together to form a pyridine ring. In some embodiments, $R_3$ and $R_4$ are joined together to form a pyrrole ring. In some embodiments, $R_3$ and $R_4$ are joined together to form a cyclohexene ring. In some embodiments, $R_3$ and $R_4$ are joined together to form a cyclopentene ring. In some embodiments, $R_4$ and $R_3$ are joint together to form a dioxepine ring.

In various embodiments, $R_{40}$ of formula I, I(a), II and III is H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$) $R_9$—$R_8$—$N(R_{10})(R_{11})$, $B(OH)_2$, —$OC(O)CF_3$, —$OCH_2Ph$, —NHCO—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —$C(O)NH_2$, C(O)NHR, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$), $C_1$-$C_5$ linear or branched, substituted or unsubstituted alkyl (e.g., methyl, $C(OH)(CH_3)(Ph)$, ethyl, propyl, iso-propyl, t-Bu, iso-butyl, pentyl), $C_1$-$C_5$ linear, branched or cyclic haloalkyl (e.g., $CF_3$, $CF_2CH_3$, $CF_2$-cyclobutyl, $CH_2CF_3$, $CF_2CH_2CH_3$, $CH_2CH_2CF_3$, $CF_2CH(CH_3)_2$, $CF(CH_3)$—$CH(CH_3)_2$), $C_1$-$C_5$ linear, branched or cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, triazole, pyridine (2, 3, or 4-pyridine), pyrimidine, pyrazine, oxacyclobutane (1 or 2-oxacyclobutane), indole), substituted or unsubstituted aryl (e.g., phenyl), $CH(CF_3)$ (NH—$R_{10}$); each represents a separate embodiment of this invention. In some embodiments, substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof; each represents a separate embodiment of this invention.

In various embodiments, $R_5$ of compound of formula I, I(a) and III is H, $C_1$-$C_5$ linear or branched, substituted or unsubstituted alkyl (e.g., methyl, $CH_2SH$, ethyl, iso-propyl), $C_2$-$C_5$ linear or branched, substituted or unsubstituted alkenyl, $C_2$-$C_5$ linear or branched, substituted or unsubstituted alkynyl (e.g., C(CH)), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), substituted or unsubstituted aryl (e.g., phenyl), or substituted or unsubstituted heteroaryl (e.g., pyridine (2, 3, and 4-pyridine); each represents a separate embodiment of this invention. In other embodiments, substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof; each represents a separate embodiment of this invention.

In some embodiments, $R_{50}$ of formula I, I(a), I(b), III and III(a) is H. In other embodiments, $R_{50}$ is F. In other embodiments, $R_{50}$ is Cl. In other embodiments, $R_{50}$ is Br. In other embodiments, $R_{50}$ is I. In other embodiments, $R_{50}$ is $C_1$-$C_5$ linear or branched, substituted or unsubstituted alkyl. In other embodiments, $R_{50}$ is $C_1$-$C_5$ linear or branched, alkyl, substituted with phenyl. In other embodiments, $R_{50}$ is methyl. In other embodiments, $R_{50}$ is $CH_2SH$. In other embodiments, $R_{50}$ is ethyl. In other embodiments, $R_{50}$ is propyl. In other embodiments, $R_{50}$ is iso-propyl. In other embodiments, $R_{50}$ is benzyl. In other embodiments, $R_{50}$'s substitutions include phenyl.

In some embodiments, $R_{50}$ of formula I and III is connected to the N atom in position indicated as 1 in the structure (i.e., $N_1$). In other embodiments, $R_{50}$ is connected to the C atom in position indicated as 3 in the structure (i.e., $C_3$).

In some embodiments, if $R_{50}$ of formula I, I(a), I(b) is H then neither one of $R_1$, $R_2$ or $R_{20}$ is H, and n and m are not 0.

In various embodiments, n of compound of formula I-II(b) is 0. In some embodiments, n is 0 or 1. In some embodiments, n of compound of formula I-III(a) is between 1 and 3. In some embodiments, n of compound of formula I-III(a) is between 1 and 4. In some embodiments, n of compound of formula I-II(b) is between 0 and 2. In some embodiments, n of compound of formula I-II(b) is between 0 and 3. In some embodiments, n of compound of formula I-II(b) is between 0 and 4. In some embodiments, n of compound of formula I-III(a) is 1. In some embodiments, n of compound of formula I-III(a) is 2. In some embodiments, n of compound of formula I-III(a) is 3. In some embodiments, n of compound of formula I-III(a) is 4.

In various embodiments, m of compound of formula I-II(b) is 0. In some embodiments, m is 0 or 1. In some embodiments, m of compound of formula I-III(a) is between 1 and 3. In some embodiments, m of compound of formula I-III(a) is between 1 and 4. In some embodiments, m of compound of formula I-II(b) is between 0 and 2. In some embodiments, m of compound of formula I-II(b) is between 0 and 3. In some embodiments, m of compound of formula I-II(b) is between 0 and 4. In some embodiments, m of compound of formula I-III(a) is 1. In some embodiments, m of compound of formula I-III(a) is 2. In some embodiments, m of compound of formula I-III(a) is 3. In some embodiments, m of compound of formula I-III(a) is 4.

In various embodiments, l of compound of formula I-III (a) is 0. In some embodiments, l is 0 or 1. In some embodiments, l is between 1 and 3. In some embodiments, l is between 1 and 4. In some embodiments, l is between 0 and 2. In some embodiments, l is between 0 and 3. In some embodiments, l is between 0 and 4. In some embodiments, l is 1. In some embodiments, l is 2. In some embodiments, l is 3. In some embodiments, l is 4.

In various embodiments, k of compound of formula I-III(a) is 0. In some embodiments, k is 0 or 1. In some embodiments, k is between 1 and 3. In some embodiments, k is between 1 and 4. In some embodiments, k is between 0 and 2. In some embodiments, k is between 0 and 3. In some embodiments, k is between 0 and 4. In some embodiments, k is 1. In some embodiments, k is 2. In some embodiments, k is 3. In some embodiments, k is 4.

It is understood that for heterocyclic rings, n, m, l and/or k are limited to the number of available positions for substitution, i.e. to the number of CH or NH groups minus one. Accordingly, if A and/or B rings are, for example, furanyl, thiophenyl or pyrrolyl, n, m, l and k are between 0 and 2; and if A and/or B rings are, for example, oxazolyl, imidazolyl or thiazolyl, n, m, l and k are either 0 or 1; and if A and/or B rings are, for example, oxadiazolyl or thiadiazolyl, n, m, l and k are 0.

In various embodiments, $R_6$ of compound of formula I-III(a) is H. In some embodiments, $R_6$ is $C_1$-$C_5$ linear or branched alkyl. In some embodiments, $R_6$ is methyl. In some embodiments, $R_6$ is ethyl. In some embodiments, $R_6$ is C(O)R wherein R is $C_1$-$C_5$ linear or branched alkyl, $C_1$-$C_5$ linear or branched alkoxy, phenyl, aryl or heteroaryl. In some embodiments, $R_6$ is $S(O)_2R$ wherein R is $C_1$-$C_5$ linear or branched alkyl, $C_1$-$C_5$ linear or branched alkoxy, phenyl, aryl or heteroaryl.

In various embodiments, $R_8$ of compound of formula I-III(a) is $CH_2$. In some embodiments, $R_8$ is $CH_2CH_2$. In some embodiments, $R_8$ is $CH_2CH_2CH_2$. In some embodiments, $R_8$ is $CH_2CH_2CH_2CH_2$.

In various embodiments, p of compound of formula I-III(a) is 1. In some embodiments, p is 2. In some embodiments, p is 3. In some embodiments, p is 4. In some embodiments, p is 5. In some embodiments, p is between 1 and 3. In some embodiments, p is between 1 and 5. In some embodiments, p is between 1 and 10.

In some embodiments, $R_9$ of compound of formula I-III (a) is C≡C. In some embodiments, $R_9$ is C≡C—C≡C. In some embodiments, $R_9$ is CH═CH. In some embodiments, $R_9$ is CH═CH—CH═CH.

In some embodiments, q of compound of formula I-III(a) is 2. In some embodiments, q is 4. In some embodiments, q is 6. In some embodiments, q is 8. In some embodiments, q is between 2 and 6.

In various embodiments, $R_{10}$ of compound of formula I-III(a) is H. In some embodiments, $R_{10}$ is $C_1$-$C_5$ linear or branched alkyl. In some embodiments, $R_{10}$ is methyl. In some embodiments, $R_{10}$ is ethyl. In some embodiments, $R_{10}$ is propyl. In some embodiments, $R_{10}$ is isopropyl. In some embodiments, $R_{10}$ is butyl. In some embodiments, $R_{10}$ is isobutyl. In some embodiments, $R_{10}$ is t-butyl. In some embodiments, $R_{10}$ is cyclopropyl. In some embodiments, $R_{10}$ is pentyl. In some embodiments, $R_{10}$ is isopentyl. In some embodiments, $R_{10}$ is neopentyl. In some embodiments, $R_{10}$ is benzyl. In some embodiments, $R_{10}$ is C(O)R. In other embodiments, $R_{10}$ is $C(O)(OCH_3)$. In other embodiments, $R_{10}$ is CN. In some embodiments, $R_{10}$ is $S(O)_2R$.

In various embodiments, $R_{11}$ of compound of formula I-III(a) is H. In some embodiments, $R_{11}$ is $C_1$-$C_5$ linear or branched alkyl. In some embodiments, $R_{11}$ is methyl. In some embodiments, $R_{11}$ is ethyl. In some embodiments, $R_{11}$ is propyl. In some embodiments, $R_{11}$ is isopropyl. In some embodiments, $R_{11}$ is butyl. In some embodiments, $R_{11}$ is isobutyl. In some embodiments, $R_{11}$ is t-butyl. In some embodiments, $R_{11}$ is cyclopropyl. In some embodiments, $R_{11}$ is pentyl. In some embodiments, $R_{11}$ is isopentyl. In some embodiments, $R_{11}$ is neopentyl. In some embodiments, $R_{11}$ is benzyl. In some embodiments, $R_{11}$ is C(O)R. In other embodiments, $R_{11}$ is $C(O)(OCH_3)$. In other embodiments, $R_{11}$ is CN. In some embodiments, $R_{11}$ is $S(O)_2R$.

In some embodiments, $R_{10}$ and $R_{11}$ of formula I, I(a), I(b), II, II(a), II(b), III and III(a) are joint to form a substituted or unsubstituted $C_3$-$C_8$ heterocyclic ring. In other embodiments, $R_{10}$ and $R_{11}$ are joint to form a piperazine ring. In other embodiments, $R_{10}$ and $R_{11}$ are joint to form a piperidine ring. In some embodiments, substitutions include: F, Cl, Br, I, OH, $C_1$-$C_5$ linear or branched alkyl, $C_1$-$C_5$ linear or branched alkyl-OH (e.g., $C(CH_3)_2CH_2$—OH, $CH_2CH_2$—OH), $C_3$-$C_8$ heterocyclic ring (e.g., piperidine), alkoxy, $N(R)_2$, $CF_3$, aryl, phenyl, halophenyl, (benzyloxy)phenyl, CN, $NO_2$ or any combination thereof; each represents a separate embodiment according to this invention.

In various embodiments, R of compound of formula I-III(a) is H. In other embodiments, R is $C_1$-$C_5$ linear or branched alkyl. In other embodiments, R is methyl. In other embodiments, R is ethyl. In other embodiments, R is $C_1$-$C_5$ linear or branched alkoxy. In other embodiments, R is methoxy. In other embodiments, R is phenyl. In other embodiments, R is aryl. In other embodiments, R is heteroaryl. In other embodiments, two gem R substituents are joint together to form a 5 or 6 membered heterocyclic ring.

In various embodiments, $Q_1$ of compound of formula I, I(a), II and/or III is O. In other embodiments, $Q_1$ is S. In other embodiments, $Q_1$ is N—OH. In other embodiments, $Q_1$ is $CH_2$. In other embodiments, $Q_1$ is $C(R)_2$. In other embodiments, $Q_1$ is N—OMe.

In various embodiments, $Q_2$ of compound of formula I, I(a), II and/or III is O. In other embodiments, $Q_2$ is S. In other embodiments, $Q_2$ is N—OH. In other embodiments, $Q_2$ is $CH_2$. In other embodiments, $Q_2$ is $C(R)_2$. In other embodiments, $Q_2$ is N—OMe.

In some embodiments, $Q_3$ of formula II and II(a) is N. In some embodiments, $Q_3$ is CH. In some embodiments, $Q_3$ is C(R). In some embodiments, $Q_3$ is NO (N-oxide).

In some embodiments, $Q_6$ of formula II and II(a) is N. In some embodiments, $Q_6$ is CH. In some embodiments, $Q_6$ is C(R). In some embodiments, $Q_6$ is NO (N-oxide).

In some embodiments, $Q_7$ of formula II and II(a) is N. In some embodiments, $Q_7$ is CH. In some embodiments, $Q_7$ is C(R). In some embodiments, $Q_7$ is NO (N-oxide).

In some embodiments, $Q_8$ of formula II and II(a) is N. In some embodiments, $Q_8$ is CH. In some embodiments, $Q_8$ is C(R). In some embodiments, $Q_8$ is NO (N-oxide).

In some embodiments, $Q_4$ of formula II and II(a) is O. In some embodiments, $Q_4$ is NH. In some embodiments, $Q_4$ is N(R).

In some embodiments, $Q_5$ of formula II and II(a) is O. In some embodiments, $Q_5$ is NH. In some embodiments, $Q_5$ is N(R).

As used herein, "single or fused aromatic or heteroaromatic ring systems" can be any such ring, including but not limited to phenyl, naphthyl, pyridinyl, (2-, 3-, and 4-pyridinyl), quinolinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, pyrazolyl, pyrrolyl, furanyl, thiophene-yl, quinolinyl, isoquinolinyl, 2,3-dihydroindenyl, indenyl, tetrahydronaphthyl, 3,4-dihydro-2H-benzo[b][1,4]dioxepine benzodioxolyl, benzo[d][1,3]dioxole, tetrahydronaphthyl, indolyl, 1H-indole, isoindolyl, anthracenyl, benzimidazolyl, 2,3-dihydro-1H-benzo[d]imidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, 1,2,3,4-tetrahydroquinoxaline, 1-(pyridin-1(2H)-yl)ethanone, cinnolinyl, phthalazinyl, quinolinyl, isoquinolinyl, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, 3-methyl-4H-1,2,4-triazole, 5-methyl-1,2,4-oxadiazole, etc.

As used herein, the term “alkyl” can be any straight- or branched-chain alkyl group containing up to about 30 carbons unless otherwise specified. In various embodiments, an alkyl includes $C_1$-$C_5$ carbons. In some embodiments, an alkyl includes $C_1$-$C_6$ carbons. In some embodiments, an alkyl includes $C_1$-$C_5$ carbons. In some embodiments, an alkyl includes $C_1$-$C_{10}$ carbons. In some embodiments, an alkyl is a $C_1$-$C_{12}$ carbons. In some embodiments, an alkyl is a $C_1$-$C_{20}$ carbons. In some embodiments, branched alkyl is an alkyl substituted by alkyl side chains of 1 to 5 carbons. In various embodiments, the alkyl group may be unsubstituted. In some embodiments, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, N(alkyl)$_2$, —OC(O)$CF_3$, —$OCH_2$Ph, —NHCO-alkyl, —C(O)Ph, C(O)O-alkyl, C(O)H, —C(O)$NH_2$ or any combination thereof.

The alkyl group can be a sole substituent, or it can be a component of a larger substituent, such as in an alkoxy, alkoxyalkyl, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, 2, 3, or 4-$CH_2$—$C_6H_4$—Cl, C(OH)($CH_3$)(Ph), etc.

As used herein, the term “alkenyl” can be any straight- or branched-chain alkenyl group containing up to about 30 carbons as defined hereinabove for the term “alkyl” and at least one carbon-carbon double bond. Accordingly, the term alkenyl as defined herein includes also alkadienes, alkatrienes, alkatetraenes, and so on. In some embodiments, the alkenyl group contains one carbon-carbon double bond. In some embodiments, the alkenyl group contains two, three, four, five, six, seven or eight carbon-carbon double bonds; each represents a separate embodiment according to this invention. Non limiting examples of alkenyl groups include: Ethenyl, Propenyl, Butenyl (i.e., 1-Butenyl, trans-2-Butenyl, cis-2-Butenyl, and Isobutylenyl), Pentene (i.e., 1-Pentenyl, cis-2-Pentenyl, and trans-2-Pentenyl), Hexene (e.g., 1-Hexenyl, (E)-2-Hexenyl, (Z)-2-Hexenyl, (E)-3-Hexenyl, (Z)-3-Hexenyl, 2-Methyl-1-Pentene, etc.), which may all be substituted as defined herein above for the term “alkyl”.

As used herein, the term “alkynyl” can be any straight- or branched-chain alkynyl group containing up to about 30 carbons as defined hereinabove for the term “alkyl” and at least one carbon-carbon triple bond. Accordingly, the term alkynyl as defined herein includes also alkadiynes, alkatriynes, alkatetraynes, and so on. In some embodiments, the alkynyl group contains one carbon-carbon triple bond. In some embodiments, the alkynyl group contains two, three, four, five, six, seven or eight carbon-carbon triple bonds; each represents a separate embodiment according to this invention. Non limiting examples of alkynyl groups include: acetylenyl, Propynyl, Butynyl (i.e., 1-Butynyl, 2-Butynyl, and Isobutylynyl), Pentyne (i.e., 1-Pentynyl, 2-Pentenyl), Hexyne (e.g., 1-Hexynyl, 2-Hexeynyl, 3-Hexynyl, etc.), which may all be substituted as defined herein above for the term “alkyl”.

As used herein, the term “aryl” refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, indolyl, phenylmethyl, phenylethyl, phenylamino, phenylamido, 3-methyl-4H-1,2,4-triazolyl, 5-methyl-1,2,4-oxadiazolyl, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, phenyl, halophenyl, (benzyloxy)phenyl, CN, $NO_2$, —$CH_2CN$, $NH_2$, NH-alkyl, N(alkyl)$_2$, hydroxyl, —OC(O)$CF_3$, —$OCH_2$Ph, —NHCO-alkyl, COOH, —C(O)Ph, C(O)O-alkyl, C(O)H, —C(O)$NH_2$ or any combination thereof.

As used herein, the term “alkoxy” refers to an ether group substituted by an alkyl group as defined above. Alkoxy refers both to linear and to branched alkoxy groups. Nonlimiting examples of alkoxy groups are methoxy, ethoxy, propoxy, iso-propoxy, tert-butoxy.

As used herein, the term “aminoalkyl” refers to an amine group substituted by an alkyl group as defined above. Aminoalkyl refers to monoalkylamine, dialkylamine or trialkylamine. Nonlimiting examples of aminoalkyl groups are —N(Me)$_2$, —NHMe, —$NH_3$.

A “haloalkyl” group refers, in some embodiments, to an alkyl group as defined above, which is substituted by one or more halogen atoms, e.g. by F, Cl, Br or I. The term “haloalkyl” include but is not limited to fluoroalkyl, i.e., to an alkyl group bearing at least one fluorine atom. Nonlimiting examples of haloalkyl groups are $CF_3$, $CF_2CF_3$, $CF_2CH_3$, $CH_2CF_3$, $CF_2CH_2CH_3$, $CH_2CH_2CF_3$, $CF_2CH(CH_3)_2$ and $CF(CH_3)$—$CH(CH_3)_2$.

A “haloalkenyl” group refers, in some embodiments, to an alkenyl group as defined above, which is substituted by one or more halogen atoms, e.g. by F, Cl, Br or I. The term “haloalkenyl” include but is not limited to fluoroalkenyl, i.e., to an alkenyl group bearing at least one fluorine atom, as well as their respective isomers if applicable (i.e., E, Z and/or cis and trans). Nonlimiting examples of haloalkenyl groups are $CFCF_2$, CF═CH—$CH_3$, $CFCH_2$, $CHCF_2$, $CFCHCH_3$, $CHCHCF_3$, and CF═C—$(CH_3)_2$ (both E and Z isomers where applicable).

A “halophenyl” group refers, in some embodiments, to a phenyl substituent which is substituted by one or more halogen atoms, e.g. by F, Cl, Br or I. In one embodiment, the halophenyl is 4-chlorophenyl.

An "alkoxyalkyl" group refers, in some embodiments, to an alkyl group as defined above, which is substituted by alkoxy group as defined above, e.g. by methoxy, ethoxy, propoxy, i-propoxy, t-butoxy etc. Nonlimiting examples of alkoxyalkyl groups are $—CH_2—O—CH_3$, $—CH_2—O—CH(CH_3)_2$, $—CH_2—O—C(CH_3)_3$, $—CH_2—CH_2—O—CH_3$, $—CH_2—CH_2—O—CH(CH_3)_2$, $—CH_2—CH_2—O—C(CH_3)_3$.

A "cycloalkyl" or "carbocyclic" group refers, in various embodiments, to a ring structure comprising carbon atoms as ring atoms, which may be either saturated or unsaturated, substituted or unsubstituted, single or fused. In some embodiments the cycloalkyl is a 3-10 membered ring. In some embodiments the cycloalkyl is a 3-12 membered ring. In some embodiments the cycloalkyl is a 6 membered ring. In some embodiments the cycloalkyl is a 5-7 membered ring. In some embodiments the cycloalkyl is a 3-8 membered ring. In some embodiments, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, $—CH_2CN$, $NH_2$, NH-alkyl, $N(alkyl)_2$, $—OC(O)CF_3$, $—OCH_2Ph$, —NHCO-alkyl, —C(O)Ph, C(O)O-alkyl, C(O)H, $—C(O)NH_2$ or any combination thereof. In some embodiments, the cycloalkyl ring may be fused to another saturated or unsaturated cycloalkyl or heterocyclic 3-8 membered ring. In some embodiments, the cycloalkyl ring is a saturated ring. In some embodiments, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclobutyl, cyclobutenyl, cycloctyl, cycloctadienyl (COD), cycloctaene (COE) etc.

A "heterocycle" or "heterocyclic" group refers, in various embodiments, to a ring structure comprising in addition to carbon atoms, sulfur, oxygen, nitrogen or any combination thereof, as part of the ring. A "heteroaromatic ring" refers in various embodiments, to an aromatic ring structure comprising in addition to carbon atoms, sulfur, oxygen, nitrogen or any combination thereof, as part of the ring. In some embodiments the heterocycle or heteroaromatic ring is a 3-10 membered ring. In some embodiments the heterocycle or heteroaromatic ring is a 3-12 membered ring. In some embodiments the heterocycle or heteroaromatic ring is a 6 membered ring. In some embodiments the heterocycle or heteroaromatic ring is a 5-7 membered ring. In some embodiments the heterocycle or heteroaromatic ring is a 3-8 membered ring. In some embodiments, the heterocycle group or heteroaromatic ring may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, $—CH_2CN$, $NH_2$, NH-alkyl, $N(alkyl)_2$, $—OC(O)CF_3$, $—OCH_2Ph$, —NHCO-alkyl, —C(O)Ph, C(O)O-alkyl, C(O)H, $—C(O)NH_2$ or any combination thereof. In some embodiments, the heterocycle ring or heteroaromatic ring may be fused to another saturated or unsaturated cycloalkyl or heterocyclic 3-8 membered ring. In some embodiments, the heterocyclic ring is a saturated ring. In some embodiments, the heterocyclic ring is an unsaturated ring. Non limiting examples of a heterocyclic ring or heteroaromatic ring systems comprise pyridine, piperidine, morpholine, piperazine, thiophene, pyrrole, benzodioxole, benzofuran-2(3H)-one, benzo[d][1,3]dioxole, indole, oxazole, isoxazole, imidazole and 1-methylimidazole, furane, triazole, pyrimidine, pyrazine, oxacyclobutane (1 or 2-oxacyclobutane), naphthalene, tetrahydrothiophene 1,1-dioxide, thiazole, benzimidazole, piperidine, 1-methylpiperidine, isoquinoline, 1,3-dihydroisobenzofuran, benzofuran, 3-methyl-4H-1,2,4-triazole, 5-methyl-1,2,4-oxadiazole, or indole.

In various embodiments, this invention provides a compound of this invention or its isomer, metabolite, pharmaceutically acceptable salt, pharmaceutical product, tautomer, hydrate, N-oxide, prodrug, isotopic variant (deuterated analog), PROTAC, polymorph, or crystal or combinations thereof. In various embodiments, this invention provides an isomer of the compound of this invention. In some embodiments, this invention provides a metabolite of the compound of this invention. In some embodiments, this invention provides a pharmaceutically acceptable salt of the compound of this invention. In some embodiments, this invention provides a pharmaceutical product of the compound of this invention. In some embodiments, this invention provides a tautomer of the compound of this invention. In some embodiments, this invention provides a hydrate of the compound of this invention. In some embodiments, this invention provides an N-oxide of the compound of this invention. In some embodiments, this invention provides a reverse amide analog of the compound of this invention. In some embodiments, this invention provides a prodrug of the compound of this invention. In some embodiments, this invention provides an isotopic variant (including but not limited to deuterated analog) of the compound of this invention. In some embodiments, this invention provides a PROTAC (Proteolysis targeting chimera) of the compound of this invention. In some embodiments, this invention provides a polymorph of the compound of this invention. In some embodiments, this invention provides a crystal of the compound of this invention. In some embodiments, this invention provides composition comprising a compound of this invention, as described herein, or, In some embodiments, a combination of an isomer, metabolite, pharmaceutically acceptable salt, pharmaceutical product, tautomer, hydrate, N-oxide, prodrug, isotopic variant (deuterated analog), PROTAC, polymorph, or crystal of the compound of this invention.

In various embodiments, the term "isomer" includes, but is not limited to, optical isomers and analogs, structural isomers and analogs, conformational isomers and analogs, and the like. In some embodiments, the isomer is an optical isomer.

In various embodiments, this invention encompasses the use of various optical isomers of the compounds of the invention. It will be appreciated by those skilled in the art that the compounds of the present invention may contain at least one chiral center. Accordingly, the compounds used in the methods of the present invention may exist in, and be isolated in, optically-active or racemic forms. Accordingly, the compounds according to this invention may exist as optically-active isomers (enantiomers or diastereomers, including but not limited to: the (R), (S), (R)(R), (R)(S), (S)(S), (S)(R), (R)(R)(R), (R)(R)(S), (R)(S)(R), (S)(R)(R), (R)(S)(S), (S)(R)(S), (S)(S)(R) or (S)(S)(S) isomers); as racemic mixtures, or as enantiomerically enriched mixtures. Some compounds may also exhibit polymorphism. It is to be understood that the present invention encompasses any racemic, optically-active, polymorphic, or stereoisomeric form, or mixtures thereof, which form possesses properties useful in the treatment of the various conditions described herein.

It is well known in the art how to prepare optically-active forms (for example, by resolution of the racemic form by recrystallization techniques, by synthesis from optically-active starting materials, by chiral synthesis, or by chromatographic separation using a chiral stationary phase).

The compounds of the present invention can also be present in the form of a racemic mixture, containing substantially equivalent amounts of stereoisomers. In some embodiments, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

Compounds of the present invention can also be in the form of a hydrate, which means that the compound further includes a stoichiometric or non-stoichiometric amount of water bound by non-covalent intermolecular forces.

As used herein, when some chemical functional group (e.g. alkyl or aryl) is said to be "substituted", it is herein defined that one or more substitutions are possible.

Compounds of the present invention may exist in the form of one or more of the possible tautomers and depending on the conditions it may be possible to separate some or all of the tautomers into individual and distinct entities. It is to be understood that all of the possible tautomers, including all additional enol and keto tautomers and/or isomers are hereby covered. For example, the following tautomers, but not limited to these, are included:

Tautomerization of the imidazole ring

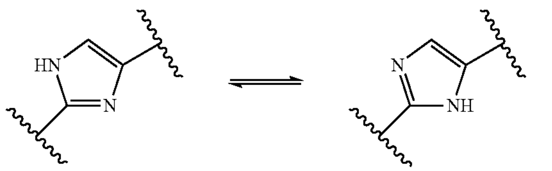

Tautomerization of the pyrazolone ring:

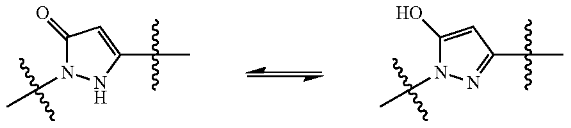

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds the compounds of this invention may be prepared from an inorganic acid or from an organic acid. In various embodiments, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In various embodiments, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In various embodiments, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In some embodiments, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In various embodiments, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In some embodiments, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In various embodiments, the compounds of this invention are administered in combination with an anti-cancer agent. In various embodiments, the anti-cancer agent is a monoclonal antibody. In some embodiments, the monoclonal antibodies are used for diagnosis, monitoring, or treatment of cancer. In various embodiments, monoclonal antibodies react against specific antigens on cancer cells. In various embodiments, the monoclonal antibody acts as a cancer cell receptor antagonist. In various embodiments, monoclonal antibodies enhance the patient's immune response. In various embodiments, monoclonal antibodies act against cell growth factors, thus blocking cancer cell growth. In various embodiments, anti-cancer monoclonal antibodies are conjugated or linked to anti-cancer drugs, radioisotopes, other biologic response modifiers, other toxins, or a combination thereof. In various embodiments, anti-cancer monoclonal antibodies are conjugated or linked to a compound of this invention as described hereinabove.

In various embodiments, the compounds of this invention are administered in combination with an agent treating Alzheimer's disease.

In various embodiments, the compounds of this invention are administered in combination with an anti-viral agent.

In various embodiments, the compounds of this invention are administered in combination with at least one of the following: chemotherapy, molecularly-targeted therapies, DNA damaging agents, hypoxia-inducing agents, or immunotherapy, each possibility represents a separate embodiment of this invention.

Yet another aspect of the present invention relates to a method of treating cancer that includes selecting a subject in need of treatment for cancer and administering to the subject a pharmaceutical composition comprising a compound according to the first aspect of the present invention and a pharmaceutically acceptable carrier under conditions effective to treat cancer.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

In various embodiments, the invention provides compounds and compositions, including any embodiment described herein, for use in any of the methods of this invention. In various embodiments, use of a compound of this invention or a composition comprising the same, will have utility in inhibiting, suppressing, enhancing or stimulating a desired response in a subject, as will be understood by one skilled in the art. In some embodiments, the compositions may further comprise additional active ingredients, whose activity is useful for the particular application for which the compound of this invention is being administered.

Acetate is an important source of acetyl-CoA in hypoxia. Inhibition of acetate metabolism may impair tumor growth. The nucleocytosolic acetyl-CoA synthetase enzyme, ACSS2, supplies a key source of acetyl-CoA for tumors by capturing acetate as a carbon source. Despite exhibiting no gross deficits in growth or development, adult mice lacking ACSS2 exhibit a significant reduction in tumor burden in two different models of hepatocellular carcinoma. ACSS2 is expressed in a large proportion of human tumors, and its activity is responsible for the majority of cellular acetate uptake into both lipids and histones. Further, ACSS2 was identified in an unbiased functional genomic screen as a critical enzyme for the growth and survival of breast and prostate cancer cells cultured in hypoxia and low serum. Indeed, high expression of ACSS2 is frequently found in invasive ductal carcinomas of the breast, triple-negative breast cancer, glioblastoma, ovarian cancer, pancreatic cancer and lung cancer, and often directly correlates with higher-grade tumours and poorer survival compared with tumours that have low ACSS2 expression. These observations may qualify ACSS2 as a targetable metabolic vulnerability of a wide spectrum of tumors.

Therefore, in various embodiments, this invention is directed to a method of treating, suppressing, reducing the severity, reducing the risk of developing or inhibiting cancer comprising administering a compound of this invention to a subject suffering from cancer under conditions effective to treat, suppress, reduce the severity, reduce the risk of developing, or inhibit the cancer. In some embodiments, the compound is an ACSS2 inhibitor. In some embodiments, the cancer is early cancer. In some embodiments, the cancer is advanced cancer. In some embodiments, the cancer is invasive cancer. In some embodiments, the cancer is metastatic cancer. In some embodiments, the cancer is drug resistant cancer. In some embodiments, the cancer is selected from the list presented below:

| |
|---|
| Cancer, bladder (urothelial carcinoma) |
| Myelodysplasia |
| Cancer, breast (inflammatory) |
| Cancer, cervix |
| Cancer, endometrium |
| Cancer, esophagus |
| Cancer, head and neck (squamous cell carcinoma) |
| Cancer, kidney (renal cell carcinoma) |
| Cancer, kidney (renal cell carcinoma, clear cell) |
| Cancer, liver (hepatocellular carcinoma) |
| Cancer, lung (non-small cell) (NSCLC) |
| Cancer, metastatic (to brain) |
| Cancer, nasopharynx |
| Cancer, solid tumor |
| Cancer, stomach |
| Carcinoma, adrenocortical |
| Glioblastoma multiforme |
| Leukemia, acute myeloid |
| Leukemia, chronic lymphocytic |
| Lymphoma, Hodgkin's (classical) |
| Lymphoma, diffuse large B-cell |
| Lymphoma, primary central nervous system |
| Melanoma, malignant |
| Melanoma, uveal |
| Meningioma |
| Multiple myeloma |
| Cancer, breast |
| Cancer |
| Cancer, anus |
| Cancer, anus (squamous cell) |
| Cancer, biliary |
| Cancer, bladder, muscle invasive urothelial carcinoma |
| Cancer, breast metastatic |
| Cancer, colorectal |
| Cancer, colorectal metastatic |
| Cancer, fallopian tube |
| Cancer, gastroesophageal junction |
| Cancer, gastroesophageal junction (adenocarcinoma) |
| Cancer, larynx (squamous cell) |
| Cancer, lung (non-small cell) (NSCLC) (squamous cell carcinoma) |

-continued

| |
|---|
| Cancer, lung (non-small cell) (NSCLC) metastatic |
| Cancer, lung (small cell) (SCLC) |
| Cancer, lung (small cell) (SCLC) (extensive) |
| Cancer, merkel cell |
| Cancer, mouth |
| Cancer, ovary |
| Cancer, ovary (epithelial) |
| Cancer, pancreas |
| Cancer, pancreas (adenocarcinoma) |
| Cancer, pancreas metastatic |
| Cancer, penis |
| Cancer, penis (squamous cell carcinoma) |
| Cancer, peritoneum |
| Cancer, prostate (castration-resistant) |
| Cancer, prostate (castration-resistant), metastatic |
| Cancer, rectum |
| Cancer, skin (basal cell carcinoma) |
| Cancer, skin (squamous cell carcinoma) |
| Cancer, small intestine (adenocarcinoma) |
| Cancer, testis |
| Cancer, thymus |
| Cancer, thyroid, anaplastic |
| Cholangiocarcinoma |
| Chordoma |
| Cutaneous T-cell lymphoma |
| Digestive-gastrointestinal cancer |
| Familial pheochromocytoma-paraganglioma |
| Glioma |
| HTLV-1-associated adult T-cell leukemia-lymphoma |
| Hematologic-blood cancer |
| Hepatitis C (HCV) |
| Infection, papillomaviral respiratory |
| Leiomyosarcoma, uterine |
| Leukemia, acute lymphocytic |
| Leukemia, chronic myeloid |
| Lymphoma, T-cell |
| Lymphoma, follicular |
| Lymphoma, primary mediastinal large B-cell |
| Lymphoma, testicular, diffuse large B-cell |
| Melanoma |
| Mesothelioma, malignant |
| Mesothelioma, pleural |
| Mycosis fungoides |
| Neuroendocrine cancer |
| Oral epithelial dysplasia |
| Sarcoma |
| Sepsis, severe |
| Sezary syndrome |
| Smoldering myeloma |
| Soft tissue sarcoma |
| T-cell lymphoma, nasal natural killer (NK) cell |
| T-cell lymphoma, peripheral |

In some embodiments, the cancer is selected from the list of: hepatocellular carcinoma, melanoma (e.g., BRAF mutant melanoma), glioblastoma, breast cancer, prostate cancer, liver cancer, brain cancer, Lewis lung carcinoma (LLC), colon carcinoma, pancreatic cancer, renal cell carcinoma, and mammary carcinoma. In some embodiments, the cancer is selected from the list of: melanoma, non-small cell lung cancer, kidney cancer, bladder cancer, head and neck cancers, Hodgkin lymphoma, Merkel cell skin cancer (Merkel cell carcinoma), esophagus cancer; gastroesophageal junction cancer; liver cancer, (hepatocellular carcinoma); lung cancer, (small cell) (SCLC); stomach cancer; upper urinary tract cancer, (urothelial carcinoma); multiforme Glioblastoma; Multiple myeloma; anus cancer, (squamous cell); cervix cancer; endometrium cancer; nasopharynx cancer; ovary cancer; metastatic pancreas cancer; solid tumor cancer; adrenocortical Carcinoma; HTLV-1-associated adult T-cell leukemia-lymphoma; uterine Leiomyosarcoma; acute myeloid Leukemia; chronic lymphocytic Leukemia; diffuse large B-cell Lymphoma; follicular Lymphoma; uveal Melanoma; Meningioma; pleural Mesothelioma; Myelodysplasia; Soft tissue sarcoma; breast cancer; colon cancer; Cutaneous T-cell lymphoma; and peripheral T-cell lymphoma. In some embodiments, the cancer is selected from the list of: glioblastoma, melanoma, lymphoma, breast cancer, ovarian cancer, glioma, digestive system cancer, central nervous system cancer, hepatocellular cancer, hematological cancer, colon cancer or any combination thereof. In some embodiments, the compound is any one of the compounds listed in Table 1; each compound represents a separate embodiment according to this invention.

It has been shown that glucose-independent acetate metabolism promotes melanoma cell survival and tumor growth. Glucose-starved melanoma cells are highly dependent on acetate to sustain ATP levels, cell viability and proliferation. Conversely, depletion of ACSS1 or ACSS2 reduced melanoma tumor growth in mice. Collectively, this data demonstrates acetate metabolism as a liability in melanoma.

Accordingly, in various embodiments, this invention is directed to a method of treating, suppressing, reducing the severity, reducing the risk of developing or inhibiting melanoma comprising administering a compound of this invention to a subject suffering from melanoma under conditions effective to treat, suppress, reduce the severity, reduce the risk of developing, or inhibit the melanoma. In some embodiments, the melanoma is early melanoma. In some embodiments, the melanoma is advanced melanoma. In some embodiments, the melanoma is invasive melanoma. In some embodiments, the melanoma is metastatic melanoma. In some embodiments, the melanoma is drug resistant melanoma. In some embodiments, the melanoma is BRAF mutant melanoma. In some embodiments, the compound is an ACSS2 inhibitor. In some embodiments, the compound is any one of the compounds listed in Table 1; each compound represents a separate embodiment according to this invention.

Acetyl-CoA synthetases that catalyse the conversion of acetate to acetyl-CoA have now been implicated in the growth of hepatocellular carcinoma, glioblastoma, breast cancer and prostate cancer.

Hepatocellular carcinoma (HCC) is a deadly form of liver cancer, and it is currently the second leading cause of cancer-related deaths worldwide (European Association For The Study Of The Liver; European Organisation For Research And Treatment Of Cancer, 2012). Despite a number of available treatment strategies, the survival rate for HCC patients is low. Considering its rising prevalence, more targeted and effective treatment strategies are highly desirable for HCC.

In various embodiments, this invention is directed to a method of treating, suppressing, reducing the severity, reducing the risk of developing or inhibiting hepatocellular carcinoma (HCC) comprising administering a compound of this invention to a subject suffering from hepatocellular carcinoma (HCC) under conditions effective to treat, suppress, reduce the severity, reduce the risk of developing, or inhibit the hepatocellular carcinoma (HCC). In some embodiments, the hepatocellular carcinoma (HCC) is early hepatocellular carcinoma (HCC). In some embodiments, the hepatocellular carcinoma (HCC) is advanced hepatocellular carcinoma (HCC). In some embodiments, the hepatocellular carcinoma (HCC) is invasive hepatocellular carcinoma (HCC). In some embodiments, the hepatocellular carcinoma (HCC) is metastatic hepatocellular carcinoma (HCC). In some embodiments, the hepatocellular carcinoma (HCC) is drug resistant hepatocellular carcinoma (HCC). In some embodiments, the compound is an ACSS2 inhibitor. In some embodiments, the compound is any one of the compounds listed in Table 1; each compound represents a separate embodiment according to this invention.

ACSS2-mediated acetate metabolism contributes to lipid synthesis and aggressive growth in glioblastoma and breast cancer.

Nuclear ACSS2 is shown to activate HIF-2alpha by acetylation and thus accelerate growth and metastasis of HIF2alpha-driven cancers such as certain Renal Cell Carcinoma and Glioblastomas (Chen, R. et al. Coordinate regulation of stress signaling and epigenetic events by Acss2 and HIF-2 in cancer cells, Plos One, 12 (12) 1-31, 2017).

Therefore, and in various embodiments, this invention is directed to a method of treating, suppressing, reducing the severity, reducing the risk of developing or inhibiting glioblastoma comprising administering a compound of this invention to a subject suffering from glioblastoma under conditions effective to treat, suppress, reduce the severity, reduce the risk of developing, or inhibit the glioblastoma. In some embodiments, the glioblastoma is early glioblastoma. In some embodiments, the glioblastoma is advanced glioblastoma. In some embodiments, the glioblastoma is invasive glioblastoma. In some embodiments, the glioblastoma is metastatic glioblastoma. In some embodiments, the glioblastoma is drug resistant glioblastoma. In some embodiments, the compound is an ACSS2 inhibitor. In some embodiments, the compound is any one of the compounds listed in Table 1; each compound represents a separate embodiment according to this invention.

Therefore, and in various embodiments, this invention is directed to a method of treating, suppressing, reducing the severity, reducing the risk of developing or inhibiting Renal Cell Carcinoma comprising administering a compound of this invention to a subject suffering from Renal Cell Carcinoma under conditions effective to treat, suppress, reduce the severity, reduce the risk of developing, or inhibit the Renal Cell Carcinoma. In some embodiments, the Renal Cell Carcinoma is early Renal Cell Carcinoma. In some embodiments, the Renal Cell Carcinoma is advanced Renal Cell Carcinoma. In some embodiments, the Renal Cell Carcinoma is invasive Renal Cell Carcinoma. In some embodiments, the Renal Cell Carcinoma is metastatic Renal Cell Carcinoma. In some embodiments, the Renal Cell Carcinoma is drug resistant Renal Cell Carcinoma. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting breast cancer comprising administering a compound of this invention to a subject suffering from breast cancer under conditions effective to treat, suppress, reduce the severity, reduce the risk of developing, or inhibit the breast cancer. In some embodiments, the breast cancer is early breast cancer. In some embodiments, the breast cancer is advanced breast cancer. In some embodiments, the breast cancer is invasive breast cancer. In some embodiments, the breast cancer is metastatic breast cancer. In some embodiments, the breast cancer is drug resistant breast cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting prostate cancer comprising administering a compound of this invention to a subject suffering from prostate cancer under conditions effective to treat, suppress, reduce the severity, reduce the risk of developing, or inhibit the prostate cancer. In some embodiments, the prostate cancer is early prostate cancer. In some embodiments, the prostate cancer is advanced prostate cancer. In some embodiments, the prostate cancer is invasive prostate cancer. In some embodiments, the prostate cancer is metastatic prostate cancer. In some embodiments, the prostate cancer is drug resistant prostate cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting liver cancer comprising administering a compound of this invention to a subject suffering from liver cancer under conditions effective to treat, suppress, reduce the severity, reduce the risk of developing, or inhibit the liver cancer. In some embodiments, the liver cancer is early liver cancer. In some embodiments, the liver cancer is advanced liver cancer. In some embodiments, the liver cancer is invasive liver cancer. In some embodiments, the liver cancer is metastatic liver cancer. In some embodiments, the liver cancer is drug resistant liver cancer. In some embodiments, the compound is an ACSS2 inhibitor. In some embodiments, the compound is any one of the compounds listed in Table 1; each compound represents a separate embodiment according to this invention.

Nuclear ACSS2 is also shown to promote lysosomal biogenesis, autophagy and to promote brain tumorigenesis by affecting Histone H3 acetylation (Li, X et al.: Nucleus-Translocated ACSS2 Promotes Gene Transcription for Lysosomal Biogenesis and Autophagy, *Molecular Cell* 66, 1-14, 2017).

In various embodiments, this invention is directed to a method of treating, suppressing, reducing the severity, reducing the risk of developing or inhibiting brain cancer comprising administering a compound of this invention to a subject suffering from brain cancer under conditions effective to treat, suppress, reduce the severity, reduce the risk of developing, or inhibit the brain cancer. In some embodiments, the brain cancer is early brain cancer. In some embodiments, the brain cancer is advanced brain cancer. In some embodiments, the brain cancer is invasive brain cancer. In some embodiments, the brain cancer is metastatic brain cancer. In some embodiments, the brain cancer is drug resistant brain cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting pancreatic cancer comprising administering a compound of this invention to a subject suffering from pancreatic cancer under conditions effective to treat, suppress, reduce the severity, reduce the risk of developing, or inhibit the pancreatic cancer. In some embodiments, the pancreatic cancer is early pancreatic cancer. In some embodiments, the pancreatic cancer is advanced pancreatic cancer. In some embodiments, the pancreatic cancer is invasive pancreatic cancer. In some embodiments, the pancreatic cancer is metastatic pancreatic cancer. In some embodiments, the pancreatic cancer is drug resistant pancreatic cancer. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting Lewis lung carcinoma (LLC) comprising administering a compound of this invention to a subject suffering from Lewis lung carcinoma (LLC) under conditions effective to treat, suppress, reduce the severity, reduce the risk of developing, or inhibit the Lewis lung carcinoma (LLC). In some embodiments, the Lewis lung carcinoma (LLC) is early Lewis lung carcinoma (LLC). In some embodiments, the Lewis lung carcinoma (LLC) is advanced Lewis lung carcinoma (LLC). In some embodiments, the Lewis lung carcinoma (LLC) is invasive Lewis lung carcinoma (LLC). In some embodiments, the Lewis lung carcinoma (LLC) is metastatic Lewis lung carcinoma (LLC). In some embodiments, the Lewis lung carcinoma (LLC) is drug resistant Lewis lung carcinoma (LLC). In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colon carcinoma comprising administering a compound of this invention to a subject suffering from colon carcinoma under conditions effective to treat, suppress, reduce the severity, reduce the risk of developing, or inhibit the colon carcinoma. In some embodiments, the colon carcinoma is early colon carcinoma. In some embodiments, the colon carcinoma is advanced colon carcinoma. In some embodiments, the colon carcinoma is invasive colon carcinoma. In some embodiments, the colon carcinoma is metastatic colon carcinoma. In some embodiments, the colon carcinoma is drug resistant colon carcinoma. In some embodiments, the compound is a 'program cell death receptor 1' (PD-1) modulator. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting mammary carcinoma comprising administering a compound of this invention to a subject suffering from mammary carcinoma under conditions effective to treat, suppress, reduce the severity, reduce the risk of developing, or inhibit the mammary carcinoma. In some embodiments, the mammary carcinoma is early mammary carcinoma. In some embodiments, the mammary carcinoma is advanced mammary carcinoma. In some embodiments, the mammary carcinoma is invasive mammary carcinoma. In some embodiments, the mammary carcinoma is metastatic mammary carcinoma. In some embodiments, the mammary carcinoma is drug resistant mammary carcinoma. In some embodiments, the compound is an ACSS2 inhibitor. In some embodiments, the compound is any one of the compounds listed in Table 1; each compound represents a separate embodiment according to this invention.

In various embodiments, this invention is directed to a method of suppressing, reducing or inhibiting tumour growth in a subject, comprising administering a compound according to this invention, to a subject suffering from a proliferative disorder (e.g., cancer) under conditions effective to suppress, reduce or inhibit said tumour growth in said subject. In some embodiments, the tumor growth is enhanced by increased acetate uptake by cancer cells. In some embodiments, the increase in acetate uptake is mediated by ACSS2. In some embodiments, the cancer cells are under hypoxic stress. In some embodiments, the compound is an ACSS2 inhibitor. In some embodiments, the tumor growth is suppressed due to suppression of lipid synthesis (e.g., fatty acid) induced by ACSS2 mediated acetate metabolism to acetyl-CoA. In some embodiments, the tumor growth is suppressed due to suppression of the regulation of histones acetylation and function induced by ACSS2 mediated acetate metabolism to acetyl-CoA. In some embodiments, the synthesis is suppressed under hypoxia (hypoxic stress). In some embodiments, the compound is any one of the compounds listed in Table 1; each compound represents a separate embodiment according to this invention.

In various embodiments, this invention is directed to a method of suppressing, reducing or inhibiting lipid synthesis and/or regulating histones acetylation and function in a cell, comprising contacting a compound of this invention, with a cell under conditions effective to suppress, reduce or inhibit lipid synthesis and/or regulating histones acetylation and function in said cell. In various embodiments, the method is carried out in vitro. In various embodiments, the method is carried out in vivo. In various embodiments, the lipid synthesis is induced by ACSS2 mediated acetate metabolism to acetyl-CoA. In various embodiments, regulating histones acetylation and function is induced by ACSS2 mediated acetate metabolism to acetyl-CoA. In various embodiments, the cell is cancer cell. In various embodiments, the lipid is fatty acid. In various embodiments, the acetate metabolism to acetyl-CoA is carried out under hypoxia (i.e., hypoxic stress). In some embodiments, the compound is an ACSS2 inhibitor. In some embodiments, the compound is any one of the compounds listed in Table 1; each compound represents a separate embodiment according to this invention.

In various embodiments, this invention is directed to a method of suppressing, reducing or inhibiting fatty-acid accumulation in the liver, comprising administering a compound of this invention to a subject in need thereof, under conditions effective to suppress, reduce or inhibit fatty-acid accumulation in the liver of said subject. In various embodiments, the fatty-acid accumulation is induced by ACSS2 mediated acetate metabolism to acetyl-CoA. In various embodiments, the subject suffers from a fatty liver condition. In various embodiments, the acetate metabolism to acetyl-CoA in the liver is carried out under hypoxia (i.e., hypoxic stress). In some embodiments, the compound is an ACSS2 inhibitor. In some embodiments, the compound is any one of the compounds listed in Table 1; each compound represents a separate embodiment according to this invention.

In various embodiments, this invention is directed to a method of binding an ACSS2 inhibitor compound to an ACSS2 enzyme, comprising the step of contacting an ACSS2 enzyme with an ACSS2 inhibitor compound of this invention, in an amount effective to bind the ACSS2 inhibitor compound to the ACSS2 enzyme. In some embodiments, the method is carried out in vitro. In another embodiment, the method is carried out in vivo. In some embodiments, the compound is any one of the compounds listed in Table 1; each compound represents a separate embodiment according to this invention.

In various embodiments, this invention is directed to a method of suppressing, reducing or inhibiting acetyl-CoA synthesis from acetate in a cell, comprising contacting a compound according to this invention with a cell, under conditions effective to suppress, reduce or inhibit acetyl-CoA synthesis from acetate in said cell. In some embodiments, the cell is a cancer cell. In some embodiments, the method is carried out in vitro. In another embodiment, the method is carried out in vivo. In some embodiments, the synthesis is mediated by ACSS2. In some embodiments, the compound is an ACSS2 inhibitor. In some embodiments, the cell is under hypoxic stress. In some embodiments, the compound is any one of the compounds listed in Table 1; each compound represents a separate embodiment according to this invention.

In various embodiments, this invention is directed to a method of suppressing, reducing or inhibiting acetate metabolism in a cancer cell, comprising contacting a compound according to this invention with a cancer cell, under conditions effective to suppress, reduce or inhibit acetate metabolism in said cell. In some embodiments, the acetate metabolism is mediated by ACSS2. In some embodiments, the compound is an ACSS2 inhibitor. In some embodiments, the cancer cell is under hypoxic stress. In some embodiments, the compound is any one of the compounds listed in Table 1; each compound represents a separate embodiment according to this invention.

In various embodiments, this invention provides methods for treating, suppressing, reducing the severity, reducing the risk, or inhibiting metastatic cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for increasing the survival of a subject suffering from metastatic cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for treating, suppressing, reducing the severity, reducing the risk, or inhibiting advanced cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for increasing the survival of a subject suffering from advanced cancer comprising the step of administering to said subject a compound of this invention and/or an isomer, metabolite, pharmaceutically acceptable salt, pharmaceutical product, tautomer, hydrate, N-oxide, prodrug, isotopic variant (e.g., deuterated analog), PROTAC, polymorph, or crystal of said compound, or any combination thereof. In some embodiments, the compound is an ACSS2 inhibitor. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

The compounds of the present invention are useful in the treatment, reducing the severity, reducing the risk, or inhibition of cancer, metastatic cancer, advanced cancer, drug resistant cancer, and various forms of cancer. In a preferred embodiment the cancer is hepatocellular carcinoma, melanoma (e.g., BRAF mutant melanoma), glioblastoma, breast cancer, prostate cancer, liver cancer, brain cancer, pancreatic cancer, Lewis lung carcinoma (LLC), colon carcinoma, renal cell carcinoma, and/or mammary carcinoma; each represents a separate embodiment according to this invention. Based upon their believed mode of action, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In various embodiments, other types of cancers that may be treatable with the ACSS2 inhibitors according to this invention include: adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, hepatocellular cancer, hematological cancer or any combination thereof. In some embodiments the cancer is invasive. In some embodiments the cancer is metastatic cancer. In some embodiments the cancer is advanced cancer. In some embodiments the cancer is drug resistant cancer.

In various embodiments "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In various embodiments "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism; g) Cells and tumors with activating RAS mutations are relatively resistant to most anti-cancer agents. Thus, the resistance to anticancer agents used in chemotherapy is the main cause of treatment failure in malignant disorders, provoking tumors to become resistant. Drug resistance is the major cause of cancer chemotherapy failure.

In various embodiments "resistant cancer" refers to drug-resistant cancer as described herein above. In some embodiments "resistant cancer" refers to cancer cells that acquire resistance to any treatment such as chemotherapy, radiotherapy or biological therapy.

In various embodiments, this invention is directed to treating, suppressing, reducing the severity, reducing the risk, or inhibiting cancer in a subject, wherein the subject has been previously treated with chemotherapy, radiotherapy or biological therapy.

In various embodiments "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In various embodiments, "Radiotherapy" (also referred herein as "Radiation therapy") refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In various embodiments "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

It is this kind of metabolic plasticity—the ability to exploit and survive on a variety of nutritional sources—that confers resistance to many of the current cancer metabolism drugs as monotherapies. Interestingly, ACSS2 is highly expressed in many cancer tissues, and its upregulation by hypoxia and low nutrient availability indicates that it is an important enzyme for coping with the typical stresses within the tumour microenvironment and, as such, a potential Achilles heel. Moreover, highly stressed regions of tumours have been shown to select for apoptotic resistance and promote aggressive behaviour, treatment resistance and relapse. In this way, the combination of ACSS2 inhibitors with a therapy that specifically targets well-oxygenated regions of tumours (for example, radiotherapy) could prove to be an effective regimen.

Accordingly, and in various embodiments, the compound according to this invention, is administered in combination with an anti-cancer therapy. Examples of such therapies include but are not limited to: chemotherapy, immunotherapy, radiotherapy, biological therapy, surgical intervention, and combinations thereof. In some embodiments, the compound according to this invention is administered in combination with a therapy that specifically targets well-oxygenated regions of tumours. In some embodiments, the compound according to this invention is administered in combination with radiotherapy.

In various embodiments, the compound is administered in combination with an anti-cancer agent by administering the compounds as herein described, alone or in combination with other agents.

In various embodiments, the composition for cancer treatment of the present invention can be used together with existing chemotherapy drugs or be made as a mixture with them. Such a chemotherapy drug includes, for example, alkylating agents, nitrosourea agents, antimetabolites, antitumor antibiotics, alkaloids derived from plant, topoisomerase inhibitors, hormone therapy medicines, hormone antagonists, aromatase inhibitors, P-glycoprotein inhibitors, platinum complex derivatives, other immunotherapeutic drugs, and other anticancer agents. Further, they can be used together with hypoleukocytosis (neutrophil) medicines that are cancer treatment adjuvant, thrombopenia medicines, antiemetic drugs, and cancer pain medicines for patient's QOL recovery or be made as a mixture with them.

In various embodiments, this invention is directed to a method of destroying a cancerous cell comprising: providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture).

In some embodiments, the cancer is selected from the group consisting of melanoma, non-small cell lung cancer, kidney cancer, bladder cancer, head and neck cancers, Hodgkin lymphoma, glioblastoma, renal cell carcinoma, Merkel cell skin cancer (Merkel cell carcinoma), and combinations thereof. In some embodiments, the cancer is selected from the group consisting of: melanoma, non-small cell lung cancer, kidney cancer, bladder cancer, head and neck cancers, Hodgkin lymphoma, glioblastoma, Merkel cell skin cancer (Merkel cell carcinoma), esophagus cancer; gastroesophageal junction cancer; liver cancer, (hepatocellular carcinoma); lung cancer, (small cell) (SCLC); stomach cancer; upper urinary tract cancer, (urothelial carcinoma); multiforme Glioblastoma; Multiple myeloma; anus cancer, (squamous cell); cervix cancer; endometrium cancer; nasopharynx cancer; ovary cancer; metastatic pancreas cancer; solid tumor cancer; adrenocortical Carcinoma; HTLV-1-associated adult T-cell leukemia-lymphoma; uterine Leiomyosarcoma; acute myeloid Leukemia; chronic lymphocytic Leukemia; diffuse large B-cell Lymphoma; follicular Lymphoma; uveal Melanoma; Meningioma; pleural Mesothelioma; Myelodysplasia; Soft tissue sarcoma; breast cancer; colon cancer; pancreatic cancer, Cutaneous T-cell lymphoma; peripheral T-cell lymphoma or any combination thereof.

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to other embodiments, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

ACSS2 gene has recently been suggested to be associated with human alcoholism and ethanol intake. Accordingly, in various embodiments, this invention is directed to a method of treating, suppressing, reducing the severity, reducing the risk of developing or inhibiting human alcoholism in a subject, comprising administering a compound of this invention, to a subject suffering from alcoholism under conditions effective to treat, suppress, reduce the severity, reduce the risk of developing, or inhibit alcoholism in said subject. In some embodiments, the compound is an ACSS2 inhibitor. In some embodiments, the compound is any one of the compounds listed in Table 1; each compound represents a separate embodiment according to this invention.

Non-alcoholic steatohepatitis (NASH) and alcoholic steatohepatitis (ASH) have a similar pathogenesis and histopathology but a different etiology and epidemiology. NASH and ASH are advanced stages of non-alcoholic fatty liver disease (NAFLD) and alcoholic fatty liver disease (AFLD). NAFLD is characterized by excessive fat accumulation in the liver (steatosis), without any other evident causes of chronic liver diseases (viral, autoimmune, genetic, etc.), and with an alcohol consumption ≤20-30 g/day. On the contrary, AFLD is defined as the presence of steatosis and alcohol consumption >20-30 g/day.

It has been shown that synthesis of metabolically available acetyl-coA from acetate is critical to the increased acetylation of proinflammatory gene histones and consequent enhancement of the inflammatory response in ethanol-exposed macrophages. This mechanism is a potential therapeutic target in acute alcoholic hepatitis.

Accordingly, in various embodiments, this invention is directed to a method of treating, suppressing, reducing the severity, reducing the risk of developing or inhibiting alcoholic steatohepatitis (ASH) in a subject, comprising administering a compound of this invention, to a subject suffering from alcoholic steatohepatitis (ASH) under conditions effective to treat, suppress, reduce the severity, reduce the risk of developing, or inhibit alcoholic steatohepatitis (ASH) in said subject. In some embodiments, the compound is an ACSS2 inhibitor. In some embodiments, the compound is any one of the compounds listed in Table 1; each compound represents a separate embodiment according to this invention.

Accordingly, in various embodiments, this invention is directed to a method of treating, suppressing, reducing the severity, reducing the risk of developing or inhibiting non alcoholic fatty liver disease (NAFLD) in a subject, comprising administering a compound of this invention, to a subject suffering from non alcoholic fatty liver disease (NAFLD) under conditions effective to treat, suppress, reduce the severity, reduce the risk of developing, or inhibit non alcoholic fatty liver disease (NAFLD) in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting non-alcoholic steatohepatitis (NASH) in a subject, comprising administering a compound of this invention, to a subject suffering from non-alcoholic steatohepatitis (NASH) under conditions effective to treat, suppress, reduce the severity, reduce the risk of developing, or inhibit non-alcoholic steatohepatitis (NASH) in said subject. In some embodiments, the compound is an ACSS2 inhibitor. In some embodiments, the compound is any one of the compounds listed in Table 1; each compound represents a separate embodiment according to this invention.

ACSS2-mediated acetyl-CoA synthesis from acetate has also been shown to be necessary for human cytomegalovirus infection. It has been shown that glucose carbon can be converted to acetate and used to make cytosolic acetyl-CoA by acetyl-CoA synthetase short-chain family member 2 (ACSS2) for lipid synthesis, which is important for HCMV-induced lipogenesis and the viral growth. Accordingly, ACSS2 inhibitors are expected to be useful as an antiviral therapy, and in the treatment of HCMV infection.

Therefore, in various embodiments, this invention is directed to a method of treating, suppressing, reducing the severity, reducing the risk of developing or inhibiting a viral infection in a subject, comprising administering a compound of this invention, to a subject suffering from a viral infection under conditions effective to treat, suppress, reduce the severity, reduce the risk of developing, or inhibit the viral infection in said subject. In some embodiments, the viral infection is HCMV. In some embodiments, the compound is an ACSS2 inhibitor. In some embodiments, the compound is any one of the compounds listed in Table 1; each compound represents a separate embodiment according to this invention.

It was found that mice lacking ACSS2 showed reduced body weight and hepatic steatosis in a diet-induced obesity model (Z. Huang et al., "ACSS2 promotes systemic fat storage and utilization through selective regulation of genes involved in lipid metabolism" *PNAS* 115, (40), E9499-E9506, 2018).

Accordingly, in various embodiments, this invention is directed to a method of treating, suppressing, reducing the severity, reducing the risk of developing or inhibiting a metabolic disorder in a subject, comprising administering a compound of this invention, to a subject suffering from a metabolic disorder under conditions effective to treat, suppress, reduce the severity, reduce the risk of developing, or inhibit the metabolic disorder in said subject. In some embodiments, the metabolic disorder is obesity. In other embodiments, the metabolic disorder is weight gain. In other embodiments, the metabolic disorder is hepatic steatosis. In other embodiments, the metabolic disorder is fatty liver disease. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting obesity in a subject, comprising administering a compound of this invention, to a subject suffering from obesity under conditions effective to treat, suppress, reduce the severity, reduce the risk of developing, or inhibit the obesity in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting weight gain in a subject, comprising administering a compound of this invention, to a subject suffering from weight gain under conditions effective to treat, suppress, reduce the severity, reduce the risk of developing, or inhibit the weight gain in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting hepatic steatosis in a subject, comprising administering a compound of this invention, to a subject suffering from hepatic steatosis under conditions effective to treat, suppress, reduce the severity, reduce the risk of developing, or inhibit the hepatic steatosis in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting fatty liver disease in a subject, comprising administering a compound of this invention, to a subject suffering from fatty liver disease under conditions effective to treat, suppress, reduce the severity, reduce the risk of developing, or inhibit the fatty liver disease in said subject. In some embodiments, the compound is an ACSS2 inhibitor. In some embodiments, the compound is any one of the compounds listed in Table 1; each compound represents a separate embodiment according to this invention.

ACSS2 is also shown to enter the nucleus under certain condition (hypoxia, high fat etc.) and to affect histone acetylation and crotonylation by making available acetyl-CoA and crotonyl-CoA and thereby regulate gene expression. For example, ACSS2 decrease is shown to lower levels of nuclear acetyl-CoA and histone acetylation in neurons affecting the expression of many neuronal genes. In the hippocampus such redIt was found that uctions in ACSS2 lead to effects on memory and neuronal plasticity (Mews P, et al., Nature, Vol 546, 381, 2017). Such epigenetic modifications are implicated in neuropsychiatric diseases such as anxiety, PTSD, depression etc. (Graff, J et al. Histone acetylation: molecular mnemonics on chromatin. Nat Rev. Neurosci. 14, 97-111 (2013)). Thus, an inhibitor of ACSS2 may find useful application in these conditions.

Accordingly, in various embodiments, this invention is directed to a method of treating, suppressing, reducing the severity, reducing the risk of developing or inhibiting neuropsychiatric disease or disorder in a subject, comprising administering a compound of this invention, to a subject suffering from neuropsychiatric disease or disorder under conditions effective to treat, suppress, reduce the severity, reduce the risk of developing, or inhibit the neuropsychiatric disease or disorder in said subject. In some embodiments, the neuropsychiatric disease or disorder is selected from: anxiety, depression, schizophrenia, autism and/or or post-traumatic stress disorder; each represents a separate embodiment according to this invention. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting anxiety in a subject, comprising administering a compound of this invention, to a subject suffering from anxiety under conditions effective to treat, suppress, reduce the severity, reduce the risk of developing, or inhibit the anxiety in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting depression disorder in a subject, comprising administering a compound of this invention, to a subject suffering from depression under conditions effective to treat, suppress, reduce the severity, reduce the risk of developing, or inhibit the depression in said subject. In some embodiments, the compound is an ACSS2 inhibitor. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting post-traumatic stress disorder in a subject, comprising administering a compound of this invention, to a subject suffering from post-traumatic stress disorder under conditions effective to treat, suppress, reduce the severity, reduce the risk of developing, or inhibit the post-traumatic stress disorder in said subject. In some embodiments, the compound is an ACSS2 inhibitor. In some embodiments, the compound is any one of the compounds listed in Table 1; each compound represents a separate embodiment according to this invention.

In some embodiments, this invention is directed to a method of treating, suppressing, reducing the severity, reducing the risk of developing or inhibiting inflammatory condition in a subject, comprising administering a compound of this invention, to a subject suffering from inflammatory condition under conditions effective to treat, suppress, reduce the severity, reduce the risk of developing, or inhibit the inflammatory condition in said subject. In some embodiments, the compound is an ACSS2 inhibitor. In some embodiments, the compound is any one of the compounds listed in Table 1; each compound represents a separate embodiment according to this invention.

In some embodiments, this invention is directed to a method of treating, suppressing, reducing the severity, reducing the risk of developing or inhibiting an autoimmune disease or disorder in a subject, comprising administering a compound of this invention, to a subject suffering from an autoimmune disease or disorder under conditions effective to treat, suppress, reduce the severity, reduce the risk of developing, or inhibit the autoimmune disease or disorder in said subject. In some embodiments, the compound is an ACSS2 inhibitor. In some embodiments, the compound is any one of the compounds listed in Table 1; each compound represents a separate embodiment according to this invention.

As used herein, subject or patient refers to any mammalian patient, including without limitation, humans and other primates, dogs, cats, horses, cows, sheep, pigs, rats, mice, and other rodents. In various embodiments, the subject is male. In some embodiments, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The following examples are presented in order to more fully illustrate the preferred embodiments of the invention. They should in no way, however, be construed as limiting the broad scope of the invention.

EXAMPLES

Example 1

Synthetic Details for Compounds of the Invention

General Procedure I: Synthesis of hydrazine 2

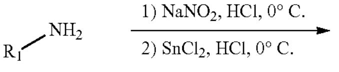

1

-continued

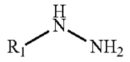

2

To a round-bottom flask equipped with a magnetic stir bar were added amine 1 (1.0 eq), water and hydrochloride acid (12 M, 10 eq). Then a saturated solution of sodium nitrite (1.2 eq) in water was added into the previous solution at 0° C. The mixture was stirred at 0~5° C. for 0.5 h. Then a solution of tin(II) chloride dihydrate (2.2 eq) in hydrochloride acid (12 M, 15.0 eq) was added at 0~5° C. dropwise. The mixture was stirred at 5° C. for 0.5 h. The resulting precipitate was collected by filtration to afford 2 as hydrochloride. Sometimes, the hydrazine was dissolved in water and needed to be extracted from the aqueous layer after neutralized the reaction solution.

General Procedure II: The general synthesis of pyrazol 4

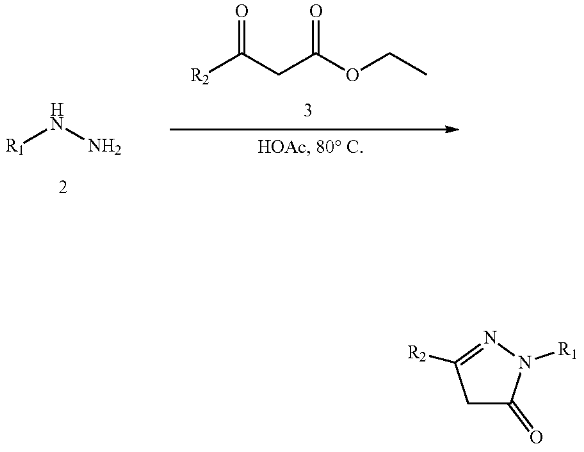

To a round-bottom flask equipped with a magnetic stir bar was added compound 3 (1.0 eq) followed by the addition of acetic acid. Then compound 2 (1.0 eq) was added into the mixture. The mixture was stirred at 80° C. under an atmosphere of nitrogen for 3~10 h. The solution was concentrated and the residue was triturated with ethyl acetate or ethanol to give compound 4.

Scheme III: The general synthesis of active ester 6

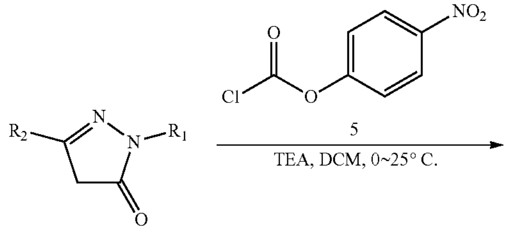

-continued

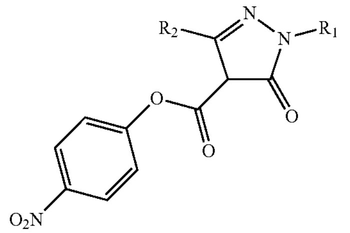

6

To a round-bottom flask equipped with a magnetic stir bar were added compound 4 (1.0 eq) and dichloromethane. Then triethylamine (2.0 eq) was added to the solution and the reaction mixture was stirred at 25° C. for 0.5 h. Compound 5 (1.0 eq) was added and the solution was stirred at 25° C. for 2.5 h under an atmosphere of nitrogen. The reaction solution was concentrated in vacuum to give compound 6 which was used directly for next step.

General Procedure IV: The general synthesis of target

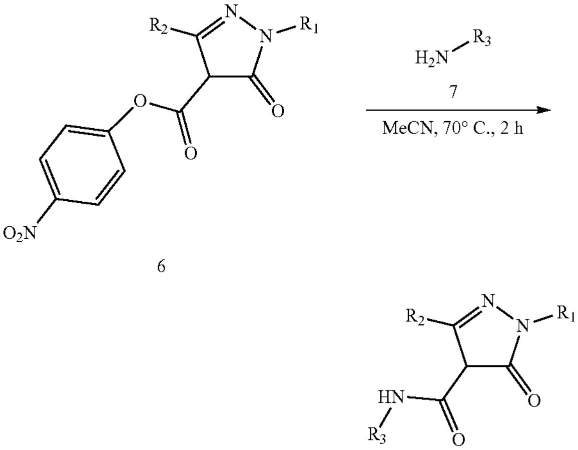

$R_1$ $R_2$ $R_3$ = aryl or alkyl

To a round-bottom flask equipped with a magnetic stir bar was added compound 6 (1.80 eq) in acetonitrile. Then benzotriazol-1-ol (2.0 eq), amine 7 (1.0 eq) and diisopropylethylamine (3.0 eq) were added. The mixture was stirred at 70° C. for 2 h before concentrated. The residue was purified by prep-HPLC to afford target compounds.

General Procedure V: The general synthesis of target

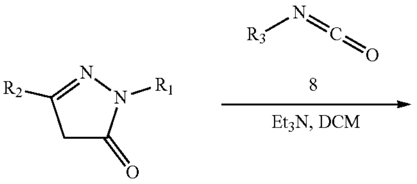

-continued

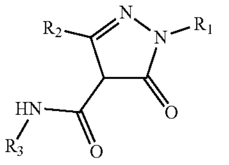

$R_1$ $R_2$ $R_3$ = aryl or alkyl

To a solution of compound 4 (1.0 eq) in dichloromethane (1~10 mL) was added triethylamine (2.0 eq) with stirring. Compound 8 (1.00 eq) was added and the mixture was stirred at 20° C. for 10 h. The reaction mixture was concentrated under vacuum, and the residue was purified by prep-HPLC to give compounds.

Compounds were synthesized according to the general schemes outlined above unless disclosed otherwise.

Synthetic Details and Analytical Data for Compound of the Invention

N-(3-(1,1-difluoroethyl)phenyl)-1-(4-methoxyphenyl)-3-methyl-5-oxo-4,5-dihydro-1H-pyrazole-4-carboxamide Compound ID: 265i

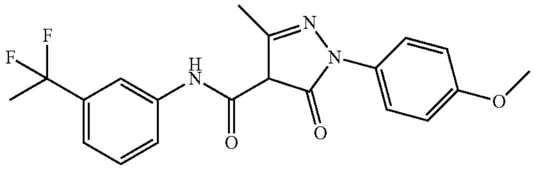

Compound 265i was obtained via general procedure IV from 1-(4-methoxyphenyl)-3-methyl-5-oxo-4,5-dihydro-1H-pyrazole-4-carboxylate and 3-(1,1-difluoroethyl)aniline.

LCMS: (ESI) m/z 388.2 $[M+H]^+$.

$^1$H NMR: (400 MHz, MeOD-$d_4$) δ: 7.90 (s, 1H), 7.62 (d, J=8.0 Hz, 1H), 7.52-7.48 (m, 2H), 7.40 (t, J=8.0 Hz, 1H), 7.24 (d, J=7.6 Hz, 1H), 7.10-7.06 (m, 2H), 3.85 (s, 3H), 2.60 (s, 3H), 1.92 (t, J=18.4 Hz, 3H).

N-(3-(1,1-difluoroethyl)phenyl)-4-fluoro-1-(4-methoxyphenyl)-3-methyl-5-oxo-4,5-dihydro-1H-pyrazole-4-carboxamide (Compound 209)

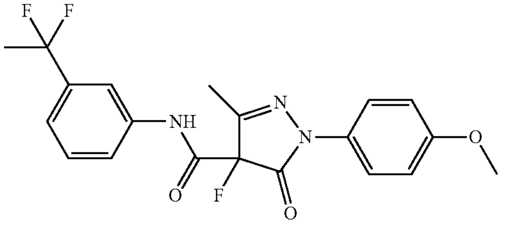 [SMILES: COc1ccc(N2N=C(C)C(F)(C(=O)Nc3cccc(C(C)(F)F)c3)C2=O)cc1]

To a solution of N-(3-(1,1-difluoroethyl)phenyl)-1-(4-methoxyphenyl)-3-methyl-5-oxo-4,5-dihydro-1H-pyrazole-4-carboxamide (Compound 265i) (200 mg, 508 umol, 1.0 eq) in toluene (4 mL) was added 1,4-diazabicyclo[2,2,2,] octane (86.9 mg, 774 umol, 1.5 eq) followed by N-fluorobenzenesulfonimide (244 mg, 774 umol, 1.5 eq). The solution was stirred at 25° C. for 12 hours. The solution was filtered and the filtrate was concentrated. The residue was purified by prep-HPLC (column: Phenomenex Synergi C18 150*25*10 um; mobile phase: [water (0.225% FA)-ACN]; B %: 48%-78%, 10 min) to give 90.0 mg (44% yield) of Compound 209 as a yellow solid.

LCMS: (ESI) m/z: 406.0 $[M+H]^+$.

$^1$H NMR (400 MHz, DMSO-d) δ: 11.03 (s, 1H), 7.98 (s, 1H), 7.84 (d, J=8.0 Hz, 1H), 7.66-7.64 (m, 2H), 7.51 (t, J=8.0 Hz, 1H), 7.39 (d, J=8.4 Hz, 1H), 7.07-7.04 (m, 2H), 3.79 (s, 3H), 2.23 (d, J=1.6 Hz, 3H), 1.95 (t, J=18.8 Hz, 3H).

Synthesis of 4-chloro-N-(3-(1,1-difluoroethyl)phenyl)-1-(4-methoxyphenyl)-3-methyl-5-oxo-4,5-dihydro-1H-pyrazole-4-carboxamide Compound ID: 202

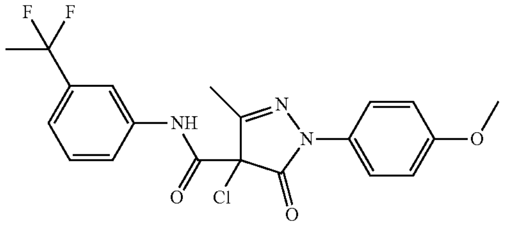

A mixture of 265i (100 mg, 254 umol, 1.0 eq), 1-chloropyrrolidine-2,5-dione (50.0 mg, 381 umol, 1.5 eq) and 1,4-diazabicyclo[2.2.2]octane (42.0 mg, 381 umol, 1.5 eq) in toluene (2 mL) was stirred at 25° C. for 12 h. The mixture was concentrated in vacuum to give a brown solid. The solid was purified by prep-HPLC (column: Phenomenex Synergi C18 150*25*10 um; mobile phase: [0.225% formic acid]; B %: 70%-88%, 6 min) to give 20.0 mg (18% yield) of Compound 202 as a yellow gum.

LCMS: (ESI) m/z 444.0 $[M+Na]^+$.

$^1$H NMR: (400 MHz, DMSO-d) δ: 10.56 (s, 1H), 7.86 (s, 1H), 7.79 (d, J=8.0 Hz, 1H), 7.68 (d, J=8.8 Hz, 2H), 7.50 (t, J=8.0 Hz, 1H), 7.40 (d, J=8.0 Hz, 1H), 7.06 (d, J=9.2 Hz, 2H), 3.79 (s, 3H), 2.26 (s, 3H), 1.96 (t, J=18.8 Hz, 3H).

N-[3-(1,1-difluoroethyl)phenyl]-1-(4-isopropoxyphenyl)-3-methyl-5-oxo-4H-pyrazole-4-carboxamide Compound ID: 447i

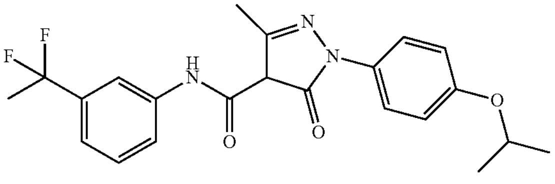

Compound 447i was obtained via general procedure IV from (4-nitrophenyl) 1-(4-isopropoxyphenyl)-3-methyl-5-oxo-4H-pyrazole-4-carboxylate and 3-(1,1-difluoroethyl) aniline.

LCMS: (ESI) m/z 416.0 $[M+H]^+$.

$^1$H NMR: (400 MHz, DMSO-d) δ: 11.32 (s, 1H), 8.66 (s, 1H), 8.39 (d, J=8.0 Hz, 1H), 8.20 (s, 1H), 8.01 (d, J=7.6 Hz,

1H), 7.71 (s, 2H), 7.58 (t, J=8.0 Hz, 1H), 7.54-7.45 (m, 2H), 7.34 (d, J=7.6 Hz, 1H), 2.63 (s, 6H), 2.30 (s, 3H).

Synthesis of N-(3-(1,1-difluoroethyl)phenyl)-4-fluoro-1-(4-isopropoxyphenyl)-3-methyl-5-oxo-4,5-dihydro-1H-pyrazole-4-carboxamide Compound ID: 208

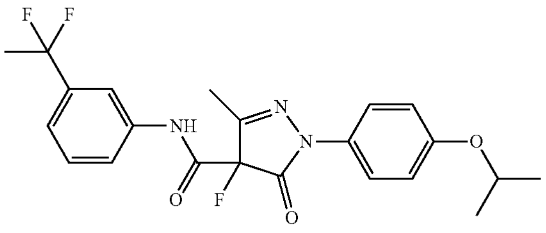

To a solution of N-[3-(1,1-difluoroethyl)phenyl]-1-(4-isopropoxyphenyl)-3-methyl-5-oxo-4H-pyrazole-4-carboxamide (447i) (50.0 mg, 120 umol, 1.0 eq) in toluene (3 mL) was added 1,4-diazabicyclo[2,2,2,]octane (27.0 mg, 241 umol, 2.0 eq), followed by N-fluorobenzenesulfonimide (56.9 mg, 181 umol, 1.5 eq). The solution was stirred at 25° C. for 12 h. The solution was concentrated. The residue was purified by prep-HPLC (column: Phenomenex Synergi C18 150*25*10 um; mobile phase: [water(0.225% FA)-ACN]; B %: 70%-100%, 9 min) to give 25 mg (48% yield) of Compound 208 as a yellow gum.

LCMS: (ESI) m/z: 434.0 $[M+H]^+$;

$^1$H NMR: (400 MHz, MeOD-$d_4$) δ: 7.88 (s, 1H), 7.68 (d, J=2.4 Hz, 1H), 7.67 (d, J=2.0 Hz, 2H), 7.46-7.43 (m, 1H), 7.39-7.37 (m, 1H), 6.97-6.94 (m, 2H), 4.64-4.54 (m, 1H), 2.23 (s, 3H), 1.94 (t, J=18.0 Hz, 3H), 1.35 (d, J=6.0 Hz, 6H).

N-[3-(1,1-difluoroethyl)phenyl]-3-methyl-5-oxo-1-(4-sec-butoxyphenyl)-4H-pyrazole-4-carboxamide Compound ID: 444i

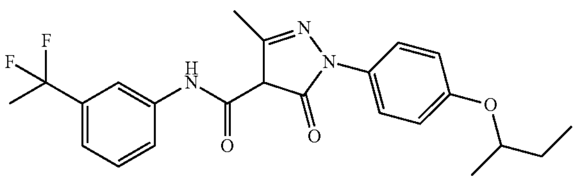

Compound 444i was obtained via general procedure IV from (4-nitrophenyl) 3-methyl-5-oxo-1-(4-sec-butoxyphenyl)-4H-pyrazole-4-carboxylate and 3-(1,1-difluoroethyl) aniline.

LCMS: (ESI) m/z 430.2 $[M+H]^+$.

$^1$H NMR: (400 MHz, DMSO-d) δ: 7.90 (s, 1H), 7.62 (d, J=8.0 Hz, 1H), 7.51 (d, J=8.8 Hz, 2H), 7.39 (t, J=8.0 Hz, 1H), 7.22 (d, J=73.6 Hz, 1H), 7.02 (d, J=9.2 Hz, 1H), 4.45-4.34 (m, 1H), 2.55 (s, 3H), 1.92 (t, J=18.4 Hz, 3H), 1.75-1.64 (m, 2H), 1.29 (d, J=6.4 Hz, 3H), 1.00 (t, J=7.2 Hz, 3H).

Synthesis of N-[3-(1,1-difluoroethyl)phenyl]-4-fluoro-3-methyl-5-oxo-1-(4-sec-butoxyphenyl)pyrazole-4-carboxamide Compound ID:207

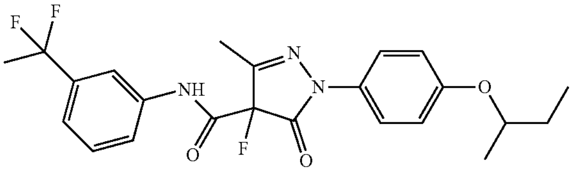

To a solution of N-[3-(1,1-difluoroethyl)phenyl]-3-methyl-5-oxo-1-(4-sec-butoxyphenyl)-4H-pyrazole-4-carboxamide (444i) (35.0 mg, 80.3 umol, 1.0 eq) in toluene (2 mL) was added 1,4-diazabicyclo[2,2,2,]octane (18.0 mg, 161 umol, 2.0 eq), followed by N-fluorobenzenesulfonimide (38.0 mg, 120 umol, 1.5 eq). The solution was stirred at 25° C. for 12 h. The solution was concentrated. The residue was purified by prep-HPLC (column: Phenomenex Synergi C18 150*25*10 um; mobile phase: [water(0.225% FA)-ACN]; B %: 70%-100%, 9 min) to give 28 mg (78% yield) of Compound 207 as a yellow gum.

LCMS: (ESI) m/z: 448.1 $[M+H]^+$;

$^1$H NMR: (400 MHz, MeOD-$d_4$) δ: 7.88 (s, 1H), 7.69 (d, J=2.4 Hz, 1H), 7.67 (d, J=2.4 Hz, 2H), 7.47-7.44 (m, 1H), 7.39-7.37 (m, 1H), 6.98-6.95 (m, 2H), 4.41-4.32 (m, 1H), 2.23 (s, 3H), 1.91 (t, J=18.0 Hz, 3H), 1.73-1.62 (m, 2H), 1.27 (d, J=6.0 Hz, 3H), 0.99 (t, J=7.6 Hz, 3H).

N-(3-(1,1-difluoroethyl)phenyl)-1-(4-(difluoromethoxy)-3-(pyridin-3-yl)phenyl)-3-methyl-5-oxo-4,5-dihydro-1H-pyrazole-4-carboxamide Compound ID: 455i

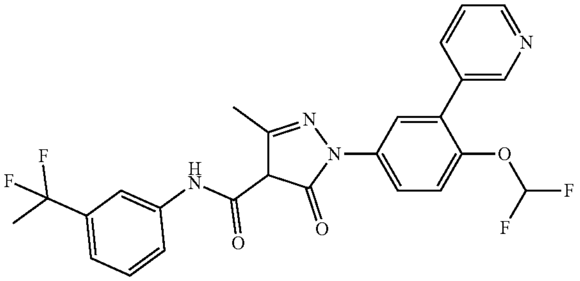

Compound 455i was obtained via general procedure IV from 4-nitrophenyl 1-(4-(difluoromethoxy)-3-(pyridin-3-yl) phenyl)-3-methyl-5-oxo-4,5-dihydro-1H-pyrazole-4-carboxylate and 3-(1, 1-difluoroethyl)aniline.

LCMS: (ESI) m/z 501.1 $[M+H]^+$.

$^1$H NMR: (400 MHz, MeOD-$d_4$) δ: 8.80 (s, 1H), 8.63-8.61 (m, 1H), 8.19-8.15 (m, 1H), 7.90 (d, J=2.4 Hz, 2H), 7.82 (d, J=2.4 Hz, 1H), 7.65-7.62 (m, 2H), 7.49 (d, J=8.8 Hz, 1H), 7.41-7.35 (m, 1H), 7.25-7.20 (m, 1H), 6.87 (t, J=73.2 Hz, 1H), 2.60 (s, 3H), 1.92 (t, J=13.2 Hz, 3H).

Synthesis of N-(3-(1,1-difluoroethyl)phenyl)-1-(4-(difluoromethoxy)-3-(pyridin-3-yl)phenyl)-4-fluoro-3-methyl-5-oxo-4,5-dihydro-1H-pyrazole-4-carboxamide Compound ID:206

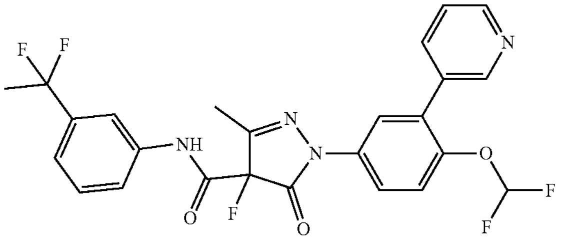

To a solution of N-(3-(1,1-difluoroethyl)phenyl)-1-(4-(difluoromethoxy)-3-(pyridin-3-yl)phenyl)-3-methyl-5-oxo-4,5-dihydro-1H-pyrazole-4-carboxamide (455i) (30.0 mg, 58.5 umol, 1.0 eq) in toluene (2.0 mL) was added 1,4-diazabicyclo[2.2.2]octane (13.1 mg, 117 umol, 2.0 eq) followed by N-fluoro-N-(phenylsulfonyl)benzenesulfonamide (27.7 mg, 87.7 umol, 1.5 eq). The solution was stirred at 25° C. for 12 h. The solution was concentrated. The residue was purified by prep-HPLC (column: Phenomenex Synergi C18150*25*10 um; mobile phase: [water(0.225% FA)-ACN]; B %: 55%-85%, 9 min) to give 9.50 mg (31% yield) of Compound 206 as a white solid.

LCMS: (ESI) m/z 519.0 $[M+H]^+$.

$^1$H NMR: (400 MHz, MeOD-$d_4$) δ: 8.85 (s, 1H), 8.69 (s, 1H), 8.31 (d, J=8.0 Hz, 1H), 8.06-8.01 (m, 2H), 7.90 (s, 1H), 7.80-7.76 (m, 2H), 7.49-7.40 (m, 3H), 6.87 (t, J=73.2 Hz, 1H), 2.30 (s, 3H), 1.93 (t, 18.4 Hz, 3H).

$^{19}$F NMR: (400 MHz, MeOD) δ: −83.405, −88.945, −173.954.

N-(3-(1,1-difluoroethyl)phenyl)-1-(4-(difluoromethoxy)phenyl)-3-methyl-5-oxo-4,5-dihydro-1H-pyrazole-4-carboxamide Compound ID:298i

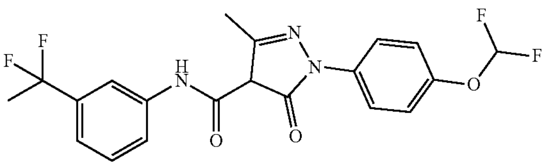

Compound 298i was obtained via general procedure IV from 1-(4-(difluoromethoxy)phenyl)-3-methyl-5-oxo-4,5-dihydro-1H-pyrazole-4-carboxylate and 3-(1,1-difluoroethyl)aniline.

LCMS: (ESI) m/z: 424.2 $[M+H]^+$.

$^1$H NMR: (400 MHz, MeOD-$d_4$) δ: 7.90 (s, 1H), 7.69-7.66 (m, 2H), 7.62 (d, J=8.0 Hz, 1H), 7.40 (t, J=8.0 Hz, 1H), 7.32-7.30 (m, 2H), 7.24 (d, J=7.6 Hz, 1H), 6.89 (t, J=72.0 Hz, 1H), 2.61 (d, J=3.6 Hz, 3H), 1.92 (t, J=18.0 Hz, 3H).

N-(3-(1,1-difluoroethyl)phenyl)-1-(4-(difluoromethoxy)phenyl)-4-fluoro-3-methyl-5-oxo-4,5-dihydro-1H-pyrazole-4-carboxamide Compound ID:205

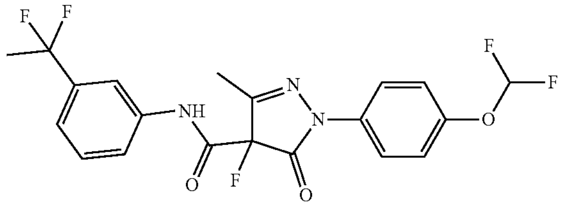

Compound 205 was obtained via similar procedure of Compound 209 from N-(3-(1,1-difluoroethyl)phenyl)-1-(4-(difluoromethoxy)phenyl)-3-methyl-5-oxo-4,5-dihydro-1H-pyrazole-4-carboxamide (298i).

LCMS: (ESI) m/z: 464.1 $[M+Na]^+$.

$^1$H NMR (400 MHz, MeOD-$d_4$) δ: 7.86-7.89 (m, 3H), 7.76 (d, J=8.4 Hz, 1H), 7.47 (t, J=8.0 Hz, 1H), 7.38 (d, J=8.0 Hz, 1H), 7.25-7.23 (m, 2H), 6.84 (t, J=74.0 Hz, 1H), 2.26 (d, J=2.0 Hz, 3H), 1.92 (t, J=18.4 Hz, 3H).

$^{19}$F NMR (400 MHz, MeOD-$d_4$) δ: −83.49, −88.98, −173.95.

N-(3-(1,1-difluoroethyl)phenyl)-3-methyl-5-oxo-1-(4-(trifluoromethoxy)phenyl)-4,5-dihydro-1H-pyrazole-4-carboxamide Compound ID:226i

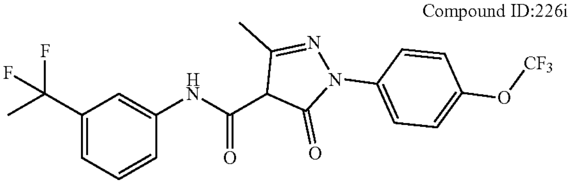

Compound 226i was obtained via general procedure IV from 3-methyl-5-oxo-1-(4-(trifluoromethoxy)phenyl)-4,5-dihydro-1H-pyrazole-4-carboxylate and 3-(1,1-difluoroethyl)aniline.

LCMS: (ESI) m/z 442.1 $[M+H]^+$.

$^1$H NMR: (400 MHz, DMSO-d) δ: 10.77 (s, 1H), 7.94 (s, 1H), 7.91-7.84 (m, 2H), 7.65-7.58 (m, 1H), 7.53 (d, J=8.0 Hz, 2H), 7.42 (t, J=8.0 Hz, 1H), 7.24-7.18 (m, 1H), 2.54 (s, 3H), 1.96 (t, J=18.8 Hz, 3H).

N-(3-(1,1-difluoroethyl)phenyl)-4-fluoro-3-methyl-5-oxo-1-(4-(trifluoromethoxy)phenyl)-4,5-dihydro-1H-pyrazole-4-carboxamide Compound ID: 203

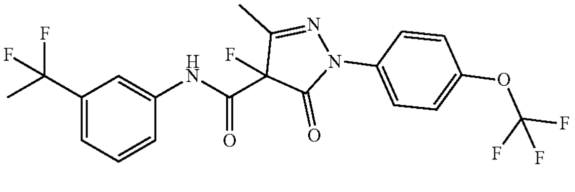

To a solution of N-(3-(1,1-difluoroethyl)phenyl)-3-methyl-5-oxo-1-(4-(trifluoromethoxy)phenyl)-4,5-dihydro-1H-pyrazole-4-carboxamide (226i) (20.0 mg, 45.3 umol, 1.0 eq) in toluene (1 mL) was added N-fluorobis(benzenesulfon)imide (21.4 mg, 67.9 umol, 1.5 eq) and 1,4-diazabicyclo[2.2.2]octane (7.6 mg, 67.9 umol, 1.5 eq). The mixture was stirred at 25° C. for 12 h. The mixture was concentrated under reduced pressure. The residue was purified by prep-HPLC(column: Phenomenex Synergi C18 150*25*10 um; mobile phase: [water(0.225% FA)-ACN]; B %: 55%-85%, 10 min) to give 10 mg (48% yield) of Compound 203 as a white solid.

LCMS: (ESI) m/z: 459.9 $[M+H]^+$.

$^1$H NMR: (400 MHz, MeOD-d4) δ: 8.00-7.93 (m, 2H), 7.87 (s, 1H), 7.77 (br d, J=8.0 Hz, 1H), 7.47 (t, J=8.0 Hz, 1H), 7.38 (br d, J=9.2 Hz, 3H), 2.27 (d, J=1.6 Hz, 3H), 1.92 (t, J=18.4 Hz, 3H).

N-(3-(1,1-difluoroethyl)phenyl)-1-(4-(difluoromethoxy)-3-(pyridin-4-yl)phenyl)-3-methyl-5-oxo-4,5-dihydro-1H-pyrazole-4-carboxamide Compound ID:315i

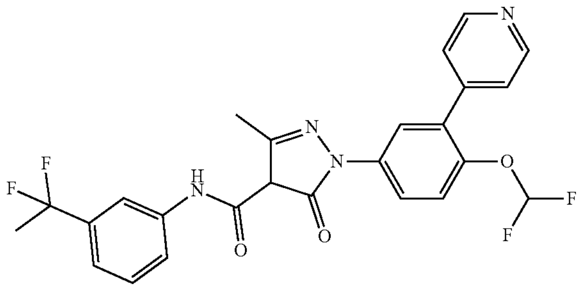

Compound 315i was obtained via general procedure IV from 4-nitrophenyl 1-(4-(difluoromethoxy)-3-(pyridin-4-yl)phenyl)-3-methyl-5-oxo-4,5-dihydro-1H-pyrazole-4-carboxylate and 3-(1,1-difluoroethyl)aniline.

LCMS: (ESI) m/z: 501.1 $[M+H]^+$.

$^1$H NMR: (400 MHz, MeOD-$d_4$) δ: 8.67 (d, J=5.6 Hz, 2H), 8.01 (d, J=2.4 Hz, 1H), 7.93-7.90 (m, 2H), 7.78 (d, J=5.6 Hz, 2H), 7.63 (d, J=8.0 Hz, 1H), 7.45 (d, J=9.2 Hz, 1H), 7.39 (t, J=7.6 Hz, 1H), 7.20 (d, J=7.6 Hz, 1H), 6.85 (t, J=73.2 Hz, 1H), 2.53 (s, 3H), 1.92 (t, J=18.0 Hz, 3H).

Synthesis of N-(3-(1,1-difluoroethyl)phenyl)-1-(4-(difluoromethoxy)-3-(pyridin-4-yl)phenyl)-4-fluoro-3-methyl-5-oxo-4,5-dihydro-1H-pyrazole-4-carboxamide Compound ID:204

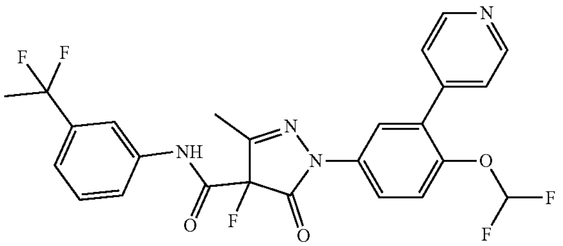

Compound 204 was obtained via similar procedure of Compound 209 from N-(3-(1,1-difluoroethyl)phenyl)-1-(4-(difluoromethoxy)-3-(pyridin-4-yl)phenyl)-3-methyl-5-oxo-4,5-dihydro-1H-pyrazole-4-carboxamide (315i).

LCMS: (ESI) m/z: 519.1 $[M+H]^+$.

$^1$H NMR (400 MHz, MeOD-$d_4$) δ: 8.63 (s, 2H), 8.01-7.98 (m, 2H), 7.88 (s, 1H), 7.76 (d, J=8.0 Hz, 1H), 7.61 (d, J=5.6 Hz, 2H), 7.49-7.43 (m, 2H), 7.39-7.37 (m, 1H), 6.82 (t, J=73.2 Hz, 1H), 2.28 (d, J=1.2 Hz, 3H), 1.92 (t, J=18.4 Hz, 3H).

$^{19}$F NMR (400 MHz, MeOD-$d_4$) δ: −83.37, −88.99, −173.93.

Synthesis of N-(3-(1,1-difluoroethyl)phenyl)-1-(4-(difluoromethoxy)phenyl)-5-ethoxy-3-methyl-1H-pyrazole-4-carboxamide Compound ID:201

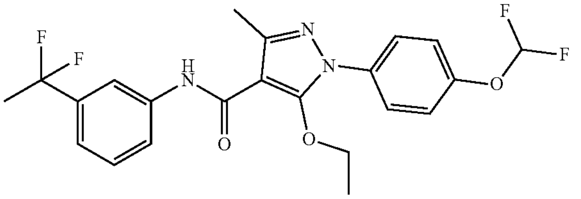

A mixture of 1-(4-(difluoromethoxy)phenyl)-5-ethoxy-3-methyl-1H-pyrazole-4-carboxylic acid (50.0 mg, 142 umol, 1.0 eq), triethylamine (43.1 mg, 425 umol, 3.0 eq), [dimethylamino(triazolo[4,5-b]pyridin-3-yloxy)methylidene]-dimethylazanium; hexafluorophosphate (108 mg, 284 umol, 2.0 eq) in dichloromethane (5 mL) was stirred at 25° C. for 30 min. To the mixture was added 3-(1,1-difluoroethyl)aniline (33.4 mg, 213 umol, 1.5 eq). The mixture was stirred at 50° C. for 11.5 h. The mixture was concentrated under reduced pressure to give a residue. The residue was purified by prep-HPLC (column: Phenomenex luna C18 150*25 10 u; mobile phase: [water (0.225% FA)-ACN]; B %: 54%-84%, 10 min) to give 24.0 mg (37% yield) of Compound 201 as a brown solid.

LCMS: (ESI) m/z: 452.1 $[M+H]^+$.

$^1$H NMR (400 MHz, MeOD-$d_4$) δ: 7.91 (s, 1H), 7.71-7.69 (m, 3H), 7.44 (t, J=8.0 Hz, 1H), 7.32-7.28 (m, 3H), 6.91 (t, J=74.0 Hz, 1H), 4.14 (q, J=7.2 Hz, 2H), 2.43 (s, 3H), 1.92 (t, J=18.0 Hz, 3H), 1.27 (t, J=7.2 Hz, 3H).

Synthesis of N-(3-(1,1-difluoroethyl)phenyl)-1-(4-(difluoromethoxy)phenyl)-5-fluoro-3-methyl-1H-pyrazole-4-carboxamide Compound ID:200

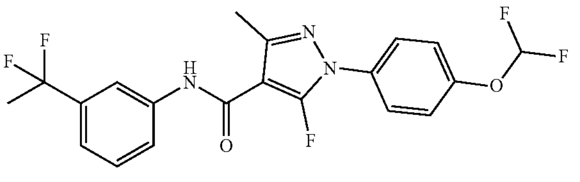

To a solution of 1-(3-(1,1-difluoroethyl)phenyl)-3-oxo-2-(trifluoromethyl)butanamide (300 mg, 970 umol, 1.0 eq) and

[4-(difluoromethoxy)phenyl]hydrazine (163 mg, 776 umol, 0.8 eq, HCl) in ethyl alcohol (5 mL) was added triethylamine (294 mg, 2.91 mmol, 3.0 eq). The mixture was stirred at 80° C. for 1 h. The mixture was concentrated under reduced pressure to give a brown oil. The residue was purified by prep-HPLC (column: Phenomenex luna C18 150*25 10 u; mobile phase: [water(0.225% aqueous formic acid solution)-acetonitrile]; B %:52%-82%, 10 min) to give 25 mg (6% yield) of Compound 200 as a yellow solid.

LCMS: (ESI) m/z 426.1 $[M+H]^+$.

$^1$H NMR: (400 MHz, MeOD-$d_4$) δ: 7.87 (s, 1H), 7.71 (br d, J=7.6 Hz, 3H), 7.44 (t, J=8.0 Hz, 1H), 7.37-7.28 (m, 3H), 6.92 (t, J=65.6 Hz, 1H), 2.47 (s, 3H), 1.93 (t, J=18.0 Hz, 3H).

Synthesis of N-(3-(1,1-difluoroethyl)phenyl)-1-(4-(difluoromethoxy)phenyl)-5-methoxy-3-methyl-1H-pyrazole-4-carboxamide Compound ID:199

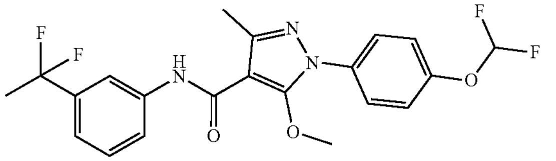

Compound 199 was obtained via similar procedure of Compound 201 from 1-(4-(difluoromethoxy)phenyl)-5-methoxy-3-methyl-1H-pyrazole-4-carboxylic acid and 3-(1,1-difluoroethyl)aniline.

LCMS: (ESI) m/z: 438.1 $[M+H]^+$.

$^1$H NMR (400 MHz, MeOD-$d_4$) δ: 7.91 (s, 1H), 7.72-7.67 (m, 3H), 7.45 (t, J=8.0 Hz, 1H), 7.32-7.30 (m, 3H), 6.91 (t, J=72.4 Hz, 1H), 3.95 (s, 3H), 2.43 (s, 3H), 1.93 (t, J=18.4 Hz, 3H).

Synthesis of 3-(1,1-difluoroethyl)-N-(1-(4-(difluoromethoxy)phenyl)-3,4-dimethyl-5-oxo-4,5-dihydro-1H-pyrazol-4-yl)benzamide Compound ID:198

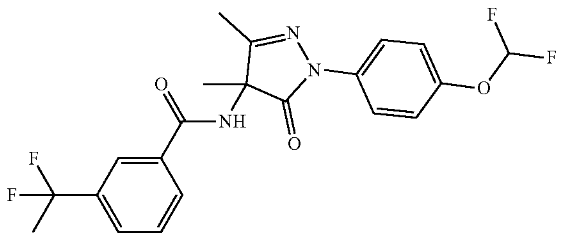

To a solution of 3-(1,1-difluoroethyl)benzoic acid (98.2 mg, 484 umol, 1.0 eq) in pyridine (4 mL) was added 1-ethyl-(3-(3-dimethylamino)propyl)-carbodiimide hydrochloride (102 mg, 531 umol, 1.1 eq). The mixture was stirred at 25° C. for 10 min. Then 4-amino-1-(4-(difluoromethoxy)phenyl)-3,4-dimethyl-1H-pyrazol-5(4H)-one (130 mg, 483 umol, 1 eq) was added to the mixture. The mixture was stirred at 25° C. for 2 hr. The mixture was concentrated under reduced pressure to give a yellow oil. The yellow oil was purified by prep-HPLC (column: Shim-pack C18

150*25*10 um; mobile phase: [water(0.225% FA)-ACN]; B %: 46%-76%, 10 min) to give 54.7 mg (26% yield) of Compound 198 as a white solid.

LCMS: (ESI) m/z: 437.9$[M+H]^+$.

$^1$H NMR: (400 MHz, DMSO-d) δ: =9.42 (s, 1H), 8.10 (s, 1H), 8.03 (d, J=7.6 Hz, 1H), 7.91-7.84 (m, 2H), 7.78 (d, J=8.0 Hz, 1H), 7.67-7.60 (m, 1H), 7.27 (d, J=8.8 Hz, 2H), 7.22 (t, J=74.4 Hz, 1H), 2.07-1.95 (m, 6H), 1.53 (s, 3H).

Synthesis of N-(3-(1,1-difluoroethyl)phenyl)-1-(4-(difluoromethoxy)phenyl)-3-methyl-1H-pyrazole-4-carboxamide Compound ID:196

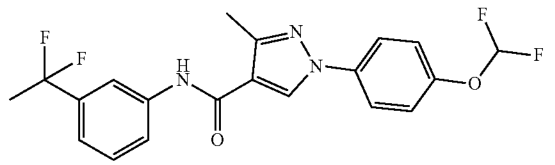

Compound 196 was obtained via similar procedure of Compound 201 and 3-(1,1-difluoroethyl)aniline.

LCMS: (ESI) m/z: 408.0 $[M+H]^+$.

$^1$H NMR (400 MHz, MeOD-$d_4$) δ: 8.78 (s, 1H), 7.90 (s, 1H), 7.82-7.78 (m, 2H), 7.77-7.72 (m, 1H), 7.43 (t, J=8.0 Hz, 1H), 7.33-7.26 (m, 3H), 6.88 (t, J=73.6 Hz, 1H), 2.55 (s, 3H), 1.93 (t, J=18.0 Hz, 3H).

Synthesis of 1-(4-(difluoromethoxy)phenyl)-3-methyl-4-(1-((4-(methylsulfonyl)phenyl)amino)-1H-1,2,3-triazol-4-yl)-1H-pyrazol-5(4H)-one (195)

Compound ID:195

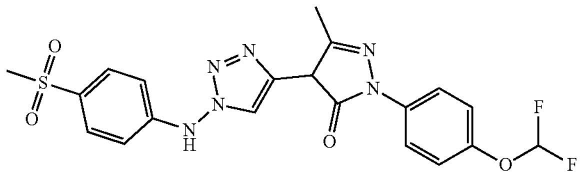

To a 50 mL round-bottom flask equipped with a magnetic stir bar was added 4-(2,2-dichloroacetyl)-1-(4-(difluoromethoxy)phenyl)-3-methyl-1H-pyrazol-5(4H)-one (100 mg, 285 umol, 1.0 eq) followed by the addition of methanol (3 mL). Then reagent tosylhydrazine (106 mg, 570 umol, 2.0 eq) and acetic acid (1.71 mg, 28.5 umol, 0.10 eq) was added into the mixture at 25° C. The mixture was stirred at 25° C. for 21 h to afford solution A.

To another 50 mL round-bottom flask equipped with a magnetic stir bar was added 4-(1,1-difluoroethyl)aniline (66.2 mg, 342 umol, 1.2 eq, hydrochloride) followed by the addition of methanol (3 mL). Then diisopropylethylamine (221 mg, 1.71 mmol, 6.0 eq) was added into the mixture at 25° C. before the addition of the previous solution A. The reaction was stirred at 25° C. for 2 h. The solution was concentrated and the residue was purified by prep-HPLC (Waters Xbridge: flow rate: 25 mL/min; gradient: 1%-24% B over 10 min; mobile phase A: 0.05% aqueous ammonia hydroxide (v/v)) to afford 24.6 mg (18% yield) of 195 as a white solid.

LCMS: (ESI) m/z: 477.3 $[M+H]^+$.

$^1H$ NMR (400 MHz, MeOD-$d_4$) δ: 7.77 (d, J=8.8 Hz, 2H), 7.52 (s, 1H), 7.40-7.24 (m, 4H), 7.08 (d, J=8.0 Hz, 1H), 7.11-6.67 (t, J=74.0 Hz, 1H), 2.35 (s, 3H), 2.00 (s, 3H).

Synthesis of N-[3-(1,1-difluoroethyl)phenyl]-1-[4-(difluoromethoxy) phenyl]-5-(hydroxymethyl)-3-methyl-pyrazole-4-carboxamide (194)

Compound ID:194

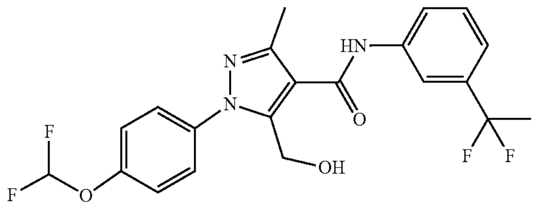

To a solution of 1-[4-(difluoromethoxy)phenyl]-5-(hydroxymethyl)-3-methyl-pyrazole-4-carboxylic acid (150 mg, 501 umol, 1.0 eq) and 3-(1,1-difluoroethyl) aniline (119 mg, 754 umol, 1.5 eq) in dichloromethane (5 mL) was added 1H-benzo[d][1,2,3]triazol-1-ol (102 mg, 754 umol, 1.5 eq) and N1-((ethylimino) methylene)-N3,N3-dimethylpropane-1,3-diamine hydrochloride (145 mg, 754 umol, 1.5 eq), the mixture was stirred at 25° C. for 2 hr. The mixture was concentrated under reduced pressure affording the crude product as light yellow oil. The crude product was purified by silica gel column chromatography (petroleum ether/ethyl acetate, from 10/1 to 0/1) to give a crude product. The crude product was purified by preparative HPLC: (Phenomenex Gemini C18 column: Waters Xbridge 150*25 5 u; mobile phase: [water (0.05% ammonia hydroxide v/v)-acetonitrile]; B %: 42%-72%, 10 min) to give 100 mg (46% yield) of 194 as a white solid.

LCMS: (ESI) m/z: 438.1 $[M+H]^+$.

$^1H$ NMR: (400 MHz, $CDCl_3$-d) δ: 8.23 (br s, 1H), 7.73-7.63 (m, 2H), 7.49-7.34 (m, 3H), 7.27 (s, 3H), 6.75-6.30 (m, 1H), 4.66 (br d, J=4.4 Hz, 2H), 4.31 (br s, 1H), 2.58 (s, 3H), 2.00-1.83 (m, 4H).

Synthesis of 5-acetyl-N-(3-(1,1-difluoroethyl)phenyl)-1-(4-(difluoromethoxy)phenyl)-3-methyl-1H-pyrazole-4-carboxamide (193)

Compound ID:193

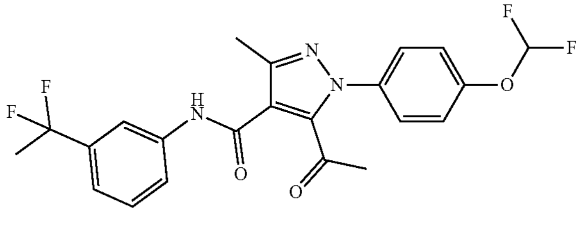

To a solution of 5-acetyl-1-(4-(difluoromethoxy)phenyl)-3-methyl-1H-pyrazole-4-carboxylic acid (298 mg, 869 umol, 1.0 eq) in N, N-dimethyl-formamide (15 mL) was added triethylamine (194 mg, 1.92 mmol, 2.2 eq) and 2-(3H-[1,2,3] triazolo[4,5-b]pyridin-3-yl)-1,1,3,3-tetramethylisouronium (438 mg, 1.15 mmol, 1.3 eq), the reaction mixture was stirred at 25° C. for 15 min. Then 3-(1,1-difluoroethyl) aniline (226 mg, 1.44 mmol, 1.7 eq) was added to the mixture and the solution was stirred at 25° C. for 20 min. The mixture was concentrated under reduced pressure affording a residue. The residue was purified by silica gel column chromatography (petroleum ether/ethyl acetate, from 10/1 to 1/1) to give a crude product. The crude product was purified by preparative HPLC: (Phenomenex Gemini C18 column: Waters Xbridge 150*25 5 u; mobile phase: [water (0.05% ammonia hydroxide v/v)-acetonitrile]; B %: 42%-72%, 10 min) to give 150 mg (38% yield) of 193 was obtained as a white solid.

LCMS: (ESI) m/z: 450.3 $[M+H]^+$.

$^1H$ NMR: (400 MHz, $CDCl_3$-d) δ: 9.66 (br s, 1H), 7.83 (s, 1H), 7.72 (br d, J=8.2 Hz, 1H), 7.48-7.33 (m, 3H), 7.27 (s, 3H), 6.79-6.31 (m, 1H), 2.59 (s, 3H), 2.16 (s, 3H), 1.91 (t, J=18.2 Hz, 3H).

N-(3-(1,1-difluoroethyl)phenyl)-1-(4-(difluoromethoxy)phenyl)-3-methyl-5-(trifluoromethyl)-1H-pyrazole-4-carboxamide (192)

Compound ID : 192

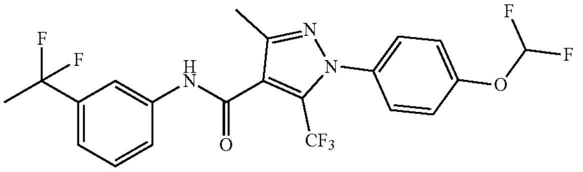

192 was obtained via similar procedure of 186 from 1-(4-(difluoromethoxy)phenyl)-3-methyl-5-(trifluoromethyl)-1H-pyrazole-4-carboxylic acid and 3-(1,1-difluoroethyl)aniline LCMS: (ESI) m/z: 476.0 $[M+H]^+$.

$^1H$ NMR (400 MHz, MeOD-$d_4$) δ: 7.90 (s, 1H)), 7.75-7.73 (d, J=8 Hz, 1H), 7.57-7.55 (d, J=8.8 Hz, 1H), 7.48 (t, J=7.6 Hz, 1H), 7.37-7.35 (d, J=8.8 Hz, 3H), 6.991 (t, J=73.2, 1H), 2.428 (s, 3H), 1.953 (t, J=18.4 Hz, 3H).

Synthesis of 4-((3-(1,1-difluoroethyl)phenyl)carbamoyl)-1-(4-(difluoromethoxy)phenyl)-3-methyl-1H-pyrazol-5-yl 4-(2-hydroxyethyl)piperazine-1-carboxylate (191)

Compound ID : 191

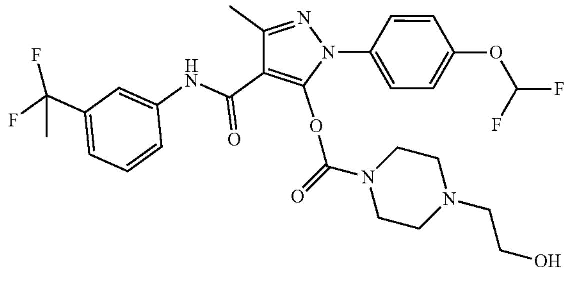

191 was obtained via similar procedure of 189 from 4-((3-(1,1-difluoroethyl)phenyl)carbamoyl)-1-(4-(difluoromethoxy)phenyl)-3-methyl-1H-pyrazol-5-yl (2,2,2-trichloroethyl) carbonate and 2-(piperazin-1-yl)ethanol.

LCMS: (ESI) m/z: 580.5 $[M+H]^+$.

$^1$H NMR (400 MHz, MeOD-$d_4$) δ: 7.74 (d, J=8.8 Hz, 2H), 7.52-7.46 (m, 1H), 7.45-7.40 (m, 1H), 7.32 (s, 1H), 7.26 (br d, J=8.4 Hz, 1H), 7.16 (d, J=8.8 Hz, 2H), 6.97 (s, 1H), 6.79 (s, 1H), 6.60 (s, 1H), 3.83-3.75 (m, 2H), 3.75-3.45 (m, 4H), 3.18-2.87 (m, 6H), 2.32 (s, 3H), 1.98-1.87 (m, 3H).

Synthesis of N-(3-(1,1-difluoroethyl)phenyl)-1-(4-(difluoromethoxy)-3-(pyridin-3-yl)phenyl)-3-methyl-5-oxo-4,5-dihydro-1H-pyrazole-4-carboxamide (310i)

Compound ID: 310i

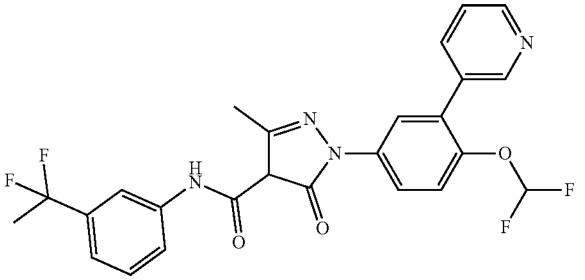

Compound 310i was obtained via general procedure IV from 4-nitrophenyl 1-(4-(difluoromethoxy)-3-(pyridin-3-yl)phenyl)-3-methyl-5-oxo-4,5-dihydro-1H-pyrazole-4-carboxylate and 3-(1, 1-difluoroethyl)aniline.

LCMS: (ESI) m/z 501.1 $[M+H]^+$.

$^1$H NMR: (400 MHz, MeOD-$d_4$) δ: 8.80 (s, 1H), 8.63-8.61 (m, 1H), 8.19-8.15 (m, 1H), 7.90 (d, J=2.4 Hz, 2H), 7.82 (d, J=2.4 Hz, 1H), 7.65-7.62 (m, 2H), 7.49 (d, J=8.8 Hz, 1H), 7.41-7.35 (m, 1H), 7.25-7.20 (m, 1H), 6.87 (t, J=73.2 Hz, 1H), 2.60 (s, 3H), 1.92 (t, J=13.2 Hz, 3H).

Synthesis of 4-((3-(1,1-difluoroethyl)phenyl)carbamoyl)-1-(4-(difluoromethoxy)-3-(pyridin-3-yl)phenyl)-3-methyl-1H-pyrazol-5-yl [1,4'-bipiperidine]-1'-carboxylate (190)

Compound ID: 190

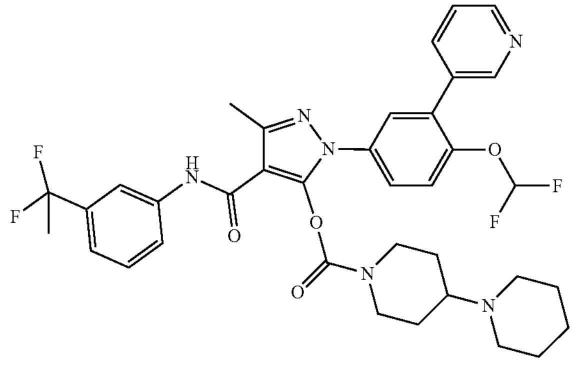

To a 50 mL round-bottom flask equipped with a magnetic stir bar was added 310i (50.0 mg, 97.9 umol, 1.0 eq) followed by the addition of dichloromethane (5 mL). The solution was cooled to 0° C. Next, triethylamine (39.6 mg, 391 umol, 4.0 eq) followed by 2,2,2-trichloroethyl carbonochloridate (35.3 mg, 166 umol, 1.7 eq) was added dropwise. The mixture was allowed to warm to 25° C. and stir for 2 h. Then 1-(4-piperidyl)piperidine (41.2 mg, 245 umol, 2.5 eq) was added. The solution was stirred at 25° C. for 12 h. The mixture was concentrated under reduced pressure affording the crude product as black oil. The crude product was purified by prep-HPLC (column: Xtimate C18 150*25 mm*5 um; mobile phase: [water (0.05% ammonia hydroxide v/v)-acetonitrile]; B %: 20%-50%, 10 min) to give a white solid. The white solid was triturated with acetonitrile (0.5 mL) to give 4.00 mg (6% yield) of 190 as a white solid.

LCMS: (ESI) m/z: 695.4 $[M+H]^+$.

$^1$H NMR: (400 MHz, MeOD-$d_4$) δ: 8.74 (d, J=1.6 Hz, 1H), 8.54 (d, J=1.6 Hz, 1H), 8.04 (d, J=8.8 Hz, 1H), 7.95 (s, 1H), 7.86 (d, J=8.8 Hz, 1H), 7.65-7.55 (m, 1H), 7.46 (d, J=7.6 Hz, 1H), 7.42-7.40 (m, 1H), 7.33-7.32 (m, 2H), 7.31 (d, J=3.6 Hz, 1H), 6.74 (t, J=74.0 Hz, 1H), 4.20 (d, J=13.2 Hz, 2H), 2.87-2.80 (m, 4H), 2.33 (s, 3H), 1.91 (t, J=18.4 Hz, 3H), 1.81-1.80 (m, 2H), 1.80-1.78 (m, 4H), 1.70-1.69 (m, 2H), 1.69-1.29 (m, 5H).

Synthesis of 4-((3-(1,1-difluoroethyl)phenyl)carbamoyl)-1-(4-(difluoromethoxy)phenyl)-3-methyl-1H-pyrazol-5-yl [1,4'-bipiperidine]-1'-carboxylate (189)

Compound ID : 189

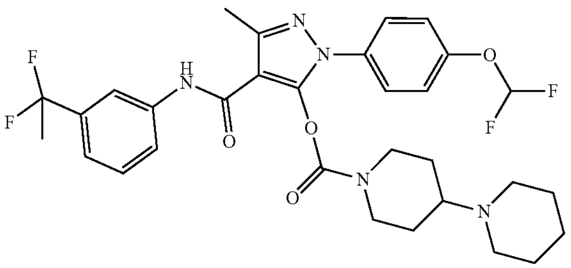

To a 10 mL round-bottom as equipped with a magnetic stir bar was added 4-((3-(1,1-difluoroethyl)phenyl)carbamoyl)-1-(4-(difluoromethoxy)phenyl)-3-methyl-1H-pyrazol-5-yl (2,2,2-trichloroethyl) carbonate (220 mg, 367 umol, 1.0 eq), triethylamine (112 mg, 1.10 mmol, 3.0 eq) followed by the addition of dichloromethane (2 mL). Then reagent 1-(4-piperidyl)piperidine (74.2 mg, 441 umol, 1.2 eq) was added into the mixture at 25° C. The mixture was stirred at 25° C. for 1 hr. The mixture was concentrated under reduced pressure to give a crude product as a brown oil. The crude product was purified by preparative HPLC: (column: Shim-pack C18 150*25*10 um; mobile phase: [Water-acetonitrile]; B %: 22%-52%, 10 min) to give 79.0 mg (33% yield) of 189 as an off-white solid.

LCMS: (ESI) m/z: 618.5 $[M+H]^+$.

$^1$H NMR (400 MHz, MeOD-$d_4$) δ: 7.77-7.80 (m, 2H), 7.49 (t, J=7.6 Hz, 1H), 7.41-7.423 (m, 1H), 7.33 (s, 1H), 7.27 (d, J=8.0 Hz, 1H), 7.15 (d, J=9.2 Hz, 2H), 6.79 (t, J=74.0 Hz, 1H), 4.20 (d, J=14.4 Hz, 2H), 3.04-3.20 (m, 5H), 3.14 (t, J=12.8 Hz, 2H), 2.33 (s, 3H), 1.93 (t, J=18.4 Hz, 3H), 1.78-1.89 (m, 6H), 1.63 (s, 2H), 1.48 (d, J=9.2 Hz, 2H).

Synthesis of 4-((3-(1,1-difluoroethyl)phenyl)carbamoyl)-1-(4-methoxyphenyl)-3-methyl-1H-pyrazol-5-yl [1,4'-bipiperidine]-1'-carboxylate (188)

Compound ID : 188

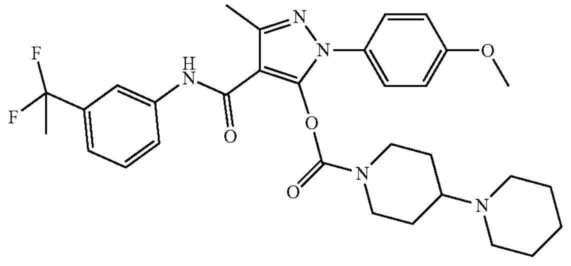

188 was obtained via similar procedure of 189 from 4-((3-(1,1-difluoroethyl)phenyl)carbamoyl)-1-(4-methoxyphenyl)-3-methyl-1H-pyrazol-5-yl (2,2,2-trichloroethyl) carbonate and 1-(4-piperidyl)piperidine LCMS: (ESI) m/z: 582.4 $[M+H]^+$.

$^1$H NMR (400 MHz, MeOD-$d_4$) δ: 7.54-7.58 (m, 2H), 7.43 (t, J=7.6 Hz, 1H), 7.39-7.41 (m, 1H), 7.31 (s, 1H), 7.26 (d, J=8.0 Hz, 1H), 6.92-6.95 (m, 2H), 4.20 (d, J=12.4 Hz, 2H), 3.80 (s, 3H), 3.02-3.14 (m, 5H), 2.81 (t, J=12.0 Hz, 2H), 2.30 (s, 3H), 1.93 (t, J=11.2 Hz, 3H) 1.76-1.83 (m, 6H), 1.60 (s, 2H), 1.43 (d, J=8.8 Hz, 2H).

Synthesis of 4-((3-(1,1-difluoroethyl)phenyl)carbamoyl)-1-(4-(difluoromethoxy)-3-(pyridin-3-yl)phenyl)-3-methyl-1H-pyrazol-5-yl 4-(2-hydroxyethyl)piperazine-1-carboxylate (187)

Compound ID: 187

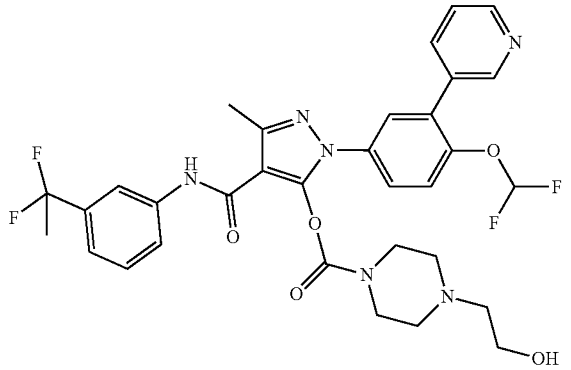

187 was obtained via the similar synthetic method of 190 from 310i and 2-(piperazin-1-yl)ethanol.

LCMS: (ESI) m/z: 657.6 $[M+H]^+$.

$^1$H NMR: (400 MHz, MeOD-$d_4$) δ: 8.74 (d, J=1.6 Hz, 1H), 8.53 (d, J=1.6 Hz, 1H), 8.12 (d, J=1.6 Hz, 1H), 8.05 (d, J=8.0 Hz, 1H), 7.96 (d, J=1.6 Hz, 1H), 7.60-7.55 (m, 1H), 7.53 (d, J=8.0 Hz, 1H), 7.46 (d, J=8.0 Hz, 1H), 7.40-7.30 (m, 2H), 7.32 (d, J=8.0 Hz, 1H), 6.74 (t, J=73.6 Hz, 1H), 3.72-3.59 (m, 6H), 3.30-2.40 (m, 6H), 2.82 (s, 3H), 1.91 (t, J=18.4 Hz, 3H).

Synthesis of ethyl 1-(3-bromo-4-(difluoromethoxy)phenyl)-3-methyl-1H-pyrazole-4-carboxylate (186)

Compound ID : 186

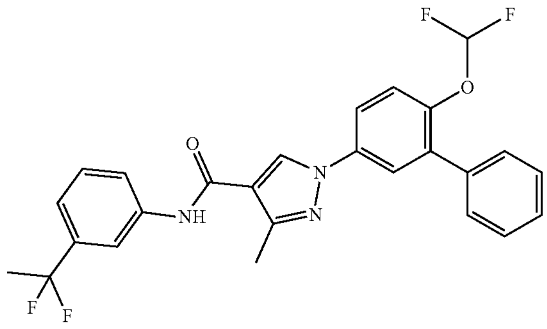

To a 8 mL round-bottom flask equipped with a magnetic stir bar was added 1-(6-(difluoromethoxy)-[1,1'-biphenyl]-3-yl)-3-methyl-1H-pyrazole-4-carboxylic acid (30.0 mg, 74.9 umol, 1.0 eq) and N-[3-(dimethylamino)propyl]-N-ethylcarbodiimide hydrochloride (16.6 mg, 87.0 umol, 1.1 eq) followed by the addition of pyridine (2 mL). Then reagent 3-(1,1-difluoroethyl)aniline (16.3 mg, 104 umol, 1.4 eq) was added into the mixture at 25° C. The mixture was stirred at 25° C. for 2 h. The mixture was concentrated under reduced pressure affording the crude product as yellow oil. The crude product was purified by preparative HPLC: (column: Phenomenex Synergi C18 150*25*10 um; mobile phase: [water (0.225% formic acid)-acetonitrile]; B %: 60%-90%, 10 min) to give 16.0 mg (43% yield) of 186 as a yellow solid.

LCMS: (ESI) m/z: 484.1 $[M+H]^+$.

$^1$H NMR (400 MHz, MeOD-$d_4$) δ: 8.87 (s, 1H)), 7.94 (s, 1H), 7.87 (d, J=2.8 Hz, 1H), 7.83 (dd, J=2.8, 8.8 Hz, 1H), 7.78 (d, J=8.8 Hz, 1H), 7.64-7.58 (m, 2H), 7.54-7.43 (m, 5H), 7.32 (d, J=7.8 Hz, 1H), 6.973 (t, J=68.0, 1H), 2.60 (s, 3H), 1.97 (t, J=18.4 Hz, 3H)

Synthesis of 4-((3-(1,1-difluoroethyl)phenyl)carbamoyl)-1-(4-(difluoromethoxy)phenyl)-3-methyl-1H-pyrazol-5-yl 4-(1-hydroxy-2-methylpropan-2-yl)piperazine-1-carboxylate (185)

Compound ID : 185

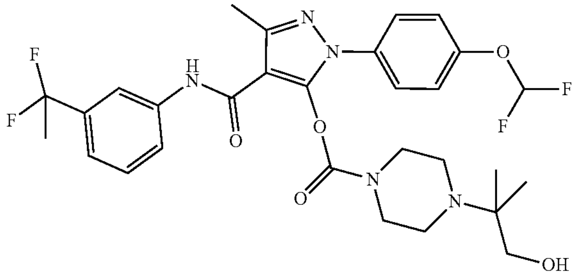

185 was obtained via similar procedure of 189

LCMS: (ESI) m/z: 608.4 $[M+H]^+$.

$^1$H NMR (400 MHz, MeOD-$d_4$) δ: 7.78 (d, J=8.8 Hz, 2H), 7.42-7.52 (m, 2H), 7.32 (s, 1H), 7.26 (d, J=8.0 Hz, 1H), 7.14

(d, J=8.8 Hz, 2H), 6.78 (t, J=74.4, 1H), 4.13 (s, 2H), 3.58 (s, 2H), 3.20 (s, 6H), 2.33 (s, 3H), 1.93 (t, J=18.4 Hz, 3H),1.29 (s, 6H).

Synthesis of N-(3-(1,1-difluoroethyl)phenyl)-1-(4-(difluoromethoxy)phenyl)-3,5-dimethyl-1H-pyrazole-4-carboxamide (184)

Compound ID : 184

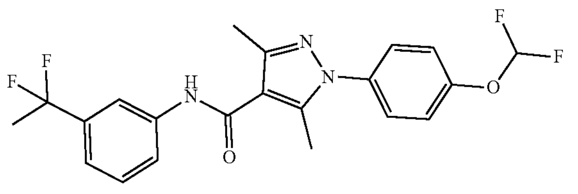

To a solution of 1-(4-(difluoromethoxy)phenyl)-3,5-dimethyl-1H-pyrazole-4-carboxylic acid (150 mg, 531 umol, 1.0 eq) in pyridine (5 mL) was added N-[3-(dimethylamino) propyl]-N-ethylcarbodiimide hydrochloride (132 mg, 691 umol, 1.3 eq). The solution was stirred at 25° C. for 5 min and then 3-(1,1-difluoroethyl)aniline (108 mg, 691 umol, 1.3 eq) was added. The solution was stirred at 25° C. for 30 min and then stirred at 60° C. for 2 h. The solution was concentrated. The residue was purified by prep-HPLC (column: Phenomenex Synergi Max-RP 150*50 mm*10 um; mobile phase: [water (0.225% formic acid)-acetonitrile]; B %: 55%-85%, 11 min) to give 84.9 mg (38% yield) of 184 as a yellow solid.

LCMS: (ESI) m/z: 422.0 $[M+H]^+$.

$^1$H NMR: (400 MHz, MeOD-$d_4$) δ: 7.91 (s, 1H), 7.74 (d, J=8.0 Hz, 1H), 7.54 (d, J=8.8 Hz, 2H), 7.47 (t, J=7.6 Hz, 1H), 7.40-7.30 (m, 3H), 6.96 (t, J=74.0 Hz, 1H), 2.46 (s, 3H), 2.45 (s, 3H), 1.95 (t, J=18.0 Hz, 3H)

Synthesis of 4-((3-(1,1-difluoroethyl)phenyl)carbamoyl)-1-(4-(difluoromethoxy)-3-(pyridin-3-yl) phenyl)-3-methyl-1H-pyrazol-5-yl 4-(1-hydroxy-2-methylpropan-2-yl)piperazine-1-carboxylate (183)

Compound ID: 183

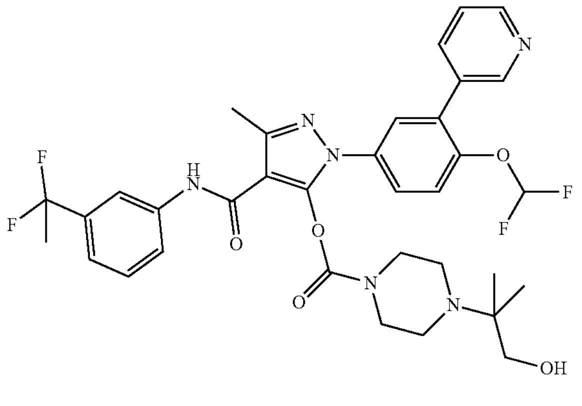

183 was obtained via the similar synthetic method of 190 from 310i and 2-methyl-2-(piperazin-1-yl)propan-1-ol.

LCMS: (ESI) m/z: 685.6 $[M+H]^+$.

$^1$H NMR: (400 MHz, MeOD-$d_4$) δ: 8.73 (s, 1H), 8.53 (dd, J=1.2 Hz, 4.8 Hz, 1H), 8.05-8.02 (m, 2H), 7.99 (d, J=2.4 Hz, 1H), 7.56-7.45 (m, 2H), 7.47 (d, J=8.0 Hz, 1H), 7.44-7.38 (m, 2H), 7.34-7.28 (m, 1H), 6.73 (t, J=74.0 Hz, 1H), 3.74 (br s, 2H), 3.58-3.42 (m, 4H), 3.21-2.83 (m, 4H), 2.33 (s, 3H), 1.91 (t, J=18.0 Hz, 3H), 1.13 (s, 6H).

Synthesis of 182

N-(3-(1,1-difluoroethyl)phenyl)-1-(4-(difluoromethoxy)-3-(pyridin-3-yl)phenyl)-3-methyl-1H-pyrazole-4-carboxamide (182)

Compound ID : 182

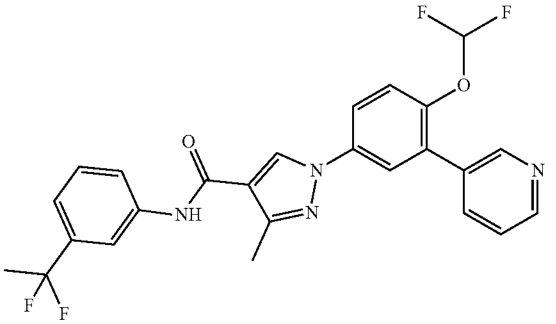

182 was obtained via similar procedure of 186 from 1-(4-(difluoromethoxy)-3-(pyridin-3-yl)phenyl)-3-methyl-1H-pyrazole-4-carboxylic acid and 3-(1,1-difluoroethyl)aniline LCMS: (ESI) m/z: 485.2 $[M+H]^+$.

$^1$H NMR (400 MHz, MeOD-$d_4$) δ: 8.89 (s, 1H), 8.76 (d, J=1.6 Hz, 1H), 8.63-8.56 (m, 1H), 8.08 (d, J=8.4 Hz, 1H), 7.95-7.86 (m, 3H), 7.75 (d, J=7.6 Hz, 1H), 7.58-7.50 (m, 1H), 7.51 (d, J=8.8 Hz, 1H), 7.44 (t, J=7.6 Hz, 1H), 7.29 (d, J=8.4 Hz, 1H), 6.86 (t, J=73.6 Hz, 1H), 2.57 (s, 3H), 1.93 (t, J=18.0 Hz, 3H).

N-(3-(1,1-difluoroethyl)phenyl)-1-(4-(difluoromethoxy)-3-(pyridin-4-yl)phenyl)-3-methyl-1H-pyrazole-4-carboxamide (181)

Compound ID: 181

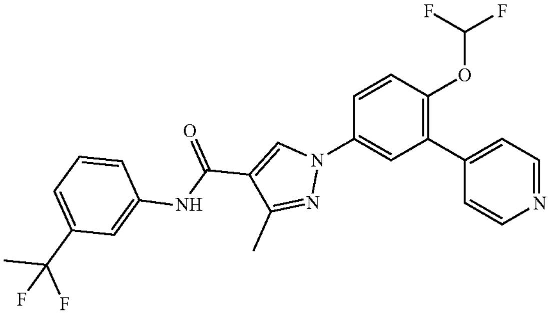

181 was obtained via similar procedure of 186 from 1-(4-(difloromethoxy)-3-(pyridin-4-yl)phenyl)-3-methyl-1H-pyrazole-4-carboxylic acid and 3-(1,1-difluoroethyl)aniline LCMS: (ESI) m/z: 485.2[M+H]$^+$.

$^1$H NMR (400 MHz, MeOD-$d_4$) δ: 8.89 (s, 1H), 8.66 (d, J=5.6 Hz, 2H), 7.95-7.90 (m, 3H), 7.75 (d, J=7.6 Hz, 1H), 7.67 (d, J=6.0 Hz, 2H), 7.51 (d, J=8.8 Hz, 1H), 7.43 (t, J=8.0 Hz, 1H), 7.28 (d, J=7.6 Hz, 1H), 6.87 (t, J=73.2 Hz, 1H), 2.56 (s, 3H), 1.93 (t, J=18.0 Hz, 3H).

Synthesis of N-[3-(1,1-difluoroethyl)phenyl]-1-(4-methoxy-3-methyl-5-phenyl-phenyl)-3-methyl-5-oxo-4H-pyrazole-4-carboxamide (180)

Compound ID: 180

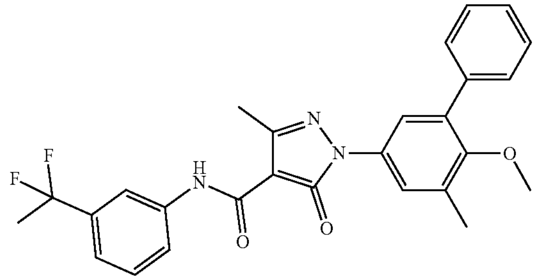

180 was obtained via general procedure IV from (4-nitrophenyl) 1-(4-methoxy-3-methyl-5-phenyl-phenyl)-3-methyl-5-oxo-4H-pyrazole-4-carboxylate LCMS: (ESI) m/z: 478.3 [M+H]$^+$.

$^1$H NMR: (400 MHz, $CDCl_3$-d) δ: 7.77 (s, 1H), 7.58 (d, J=8.0 Hz, 1H), 7.47 (d, J=7.2 Hz, 7.36-7.30 (m, 5H), 7.23-7.21 (m, 2H), 3.32 (s, 3H), 2.49 (s, 3H), 2.27 (s, 3H), 1.90 (t, J=18.0 Hz, 3H).

Synthesis of N-(3-(1,1-difluoroethyl)phenyl)-1-(4-(difluoromethoxy)-3-(pyridin-3-yl)phenyl)-3,5-dimethyl-1H-pyrazole-4-carboxamide (179)

Compound ID : 179

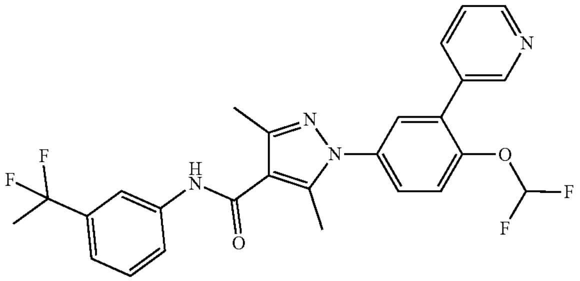

To a 10 mL round-bottom flask equipped with a magnetic stir bar was added 1-(4-(difluoromethoxy)-3-(pyridin-3-yl)phenyl)-3,5-dimethyl-1H-pyrazole-4-carboxylic acid (105 mg, 271 umol, 1.0 eq), N-(3-dimethylaminopropyl)-N-ethylcarbodiimide hydrochloride (78.0 mg, 406 umol, 1.5 eq) followed by the addition of pyridine (5 mL). Then 3-(1,1-difluoroethyl)aniline (85.2 mg, 542 umol, 2.0 eq) was added into the mixture at 25° C. The mixture was stirred at 25° C. for 12 h. The mixture was concentrated under reduced pressure to give a residue. The residue was purified by prep-HPLC (column: Phenomenex Gemini 150*25 mm*10 um; mobile phase: [water (0.225% formic acid)-acetonitrile]; B %: 35%-65%, min) to give 14.6 mg (11% yield) of 179 as a yellow solid.

LCMS: (ESI) m/z: 499.1 [M+H]$^+$.

$^1$H NMR (400 MHz, MeOD-$d_4$) δ: 8.74 (s, 1H), 8.58 (d, J=4.4 Hz, 1H), 7.96 (d, J=8.0 Hz, 1H), 7.71 (s, 1H), 7.64 (d, J=8.4 Hz, 1H), 7.63-7.59 (m, 4H), 7.54 (t, J=8.8 Hz, 1H), 7.44-7.31 (m, 1H), 6.92 (t, J=73.2 Hz, 1H), 1.93 (d, J=16.4 Hz, 6H), 1.93 (t, J=18.4 Hz, 3H).

Synthesis of 178

Step 1: Synthesis of ethyl 1-(6-(difluoromethoxy)-[1,1'-biphenyl]-3-yl)-3,5-dimethyl-1H-pyrazole-4-carboxylate (178-A)

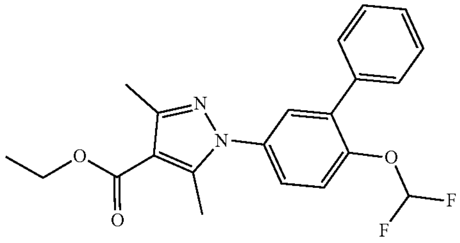 [SMILES: CCOC(=O)c1c(C)nn(-c2ccc(OC(F)F)c(-c3ccccc3)c2)c1C]

178-A was obtained via similar procedure of 2-(difluoromethoxy)-5-nitro-1,1'-biphenyl from 179-C and phenylboronic acid.

LCMS: (ESI) m/z: 387.1 [M+H

Step 2: Synthesis of 1-(6-(difluoromethoxy)-[1,1'-biphenyl]-3-yl)-3,5-dimethyl-1H-pyrazole-4-carboxylic acid (178-B)

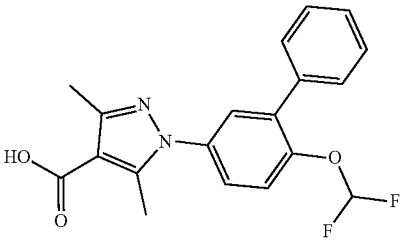 [SMILES: Cc1nn(-c2ccc(OC(F)F)c(-c3ccccc3)c2)c(C)c1C(=O)O]

178-B was obtained via similar procedure of 179-E from 178-A

LCMS: (ESI) m/z: 359.1 [M+H]$^+$.

Step 3: Synthesis of N-(3-(1,1-difluoroethyl)phenyl)-1-(4-(difluoromethoxy)-3-(pyridin-3-yl)phenyl)-3,5-dimethyl-1H-pyrazole-4-carboxamide (178)

Compound ID : 178

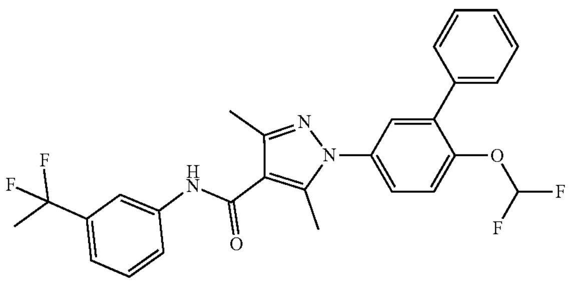

178 was obtained via similar procedure of 179 from 178-B and 3-(1,1-difluoroethyl)aniline LCMS: (ESI) m/z: 498.2 $[M+H]^+$.

$^1$H NMR (400 MHz, MeOD-$d_4$) δ:7.89 (s, 1H), 7.72 (d, J=7.6 Hz, 1H), 7.38-7.58 (m, 9H), 7.30 (d, J=8.0 Hz, 1H), 6.80 (t, J=73.6 Hz, 1H), 2.47 (d, J=13.6 Hz, 6H), 1.93 (t, J=18.4 Hz, 3H).

Synthesis of 177

Step 1: ethyl ethyl 1-(4-(difluoromethoxy)-3-(4,4,5,5-tetramethyl-1,3,2-dioxaborolan-2-yl)phenyl)-3,5-dimethyl-1H-pyrazole-4-carboxylate (177-A)

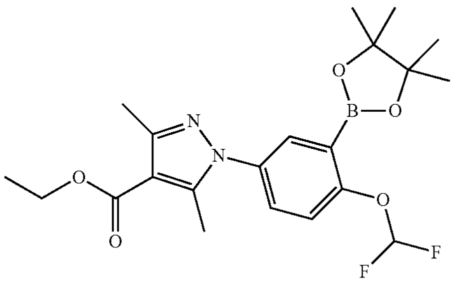 [SMILES: CCOC(=O)c1c(C)nn(-c2ccc(OC(F)F)c(B3OC(C)(C)C(C)(C)O3)c2)c1C]

To a 50 mL round-bottom flask equipped with a magnetic stir bar and a reflux condenser was added 179-C (200 mg, 497 umol, 1.0 eq), 4,4,5,5-tetramethyl-2-(4,4,5,5-tetramethyl-1,3,2-dioxaborolan-2-yl)-1,3,2-dioxaborolane (252 mg, 993 umol, 2.0 eq), 1,1-bis(diphenylphosphino)ferrocene]dichloropalladium(II) (36.3 mg, 49.6 umol, 0.10 eq) followed by the addition of dioxane (15 mL). Then potassium acetate (97.5 mg, 994 umol, 2.0 eq) was added into the mixture at 25° C. The mixture was heated to 85° C. and stirred for 12 h under nitrogen protection. The mixture was filtered, the filtrate was concentrated under reduced pressure to give a residue. The residue was purified by silica gel column chromatography (petroleum ether/ethyl acetate, from 100/1 to 60/1) to give 210 mg (crude) of 177-A as a brown oil.

LCMS: (ESI) m/z: 355.1 $[M+H]^+$.

Step 2: ethyl 1-(4-(difluoromethoxy)-3-(pyridin-2-yl)phenyl)-3,5-dimethyl-1H-pyrazole-4-carboxylate (177-B)

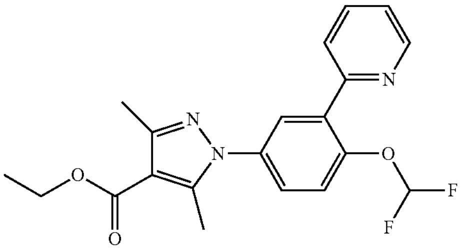 [SMILES: CCOC(=O)c1c(C)nn(-c2ccc(OC(F)F)c(-c3ccccn3)c2)c1C]

To a 50 mL round-bottom flask equipped with a magnetic stir bar was added 177-A (210 mg, 593 umol, 1.0 eq), 2-bromopyridine (114. mg, 722 umol, 1.2 eq), sodium bicarbonate (121 mg, 1.40 mmol, 2.4 eq) followed by the addition of dioxane (12 mL) and water (4 mL). Then 1,1-bis(diphenylphosphino)ferrocene]dichloropalladium(II) (70.4 mg, 96.2 umol, 1.62e-1 eq) was added into the mixture at 25° C. The flask was then evacuated and backfilled with nitrogen for three times. The mixture was stirred at 85° C. under an atmosphere of nitrogen for 12 h. The mixture was filtered, the filtrate was concentrated under reduced pressure to give a residue. The residue was purified by silica gel column chromatography (petroleum ether/ethyl acetate, from 20/1 to 5/1) to give 160 mg (60% yield) of 177-B as a light yellow oil.

LCMS: (ESI) m/z: 388.0 $[M+H]^+$.

Step 3: ethyl 1-(4-(difluoromethoxy)-3-(pyridin-2-yl)phenyl)-3,5-dimethyl-1H-pyrazole-4-carboxylic acid (177-C)

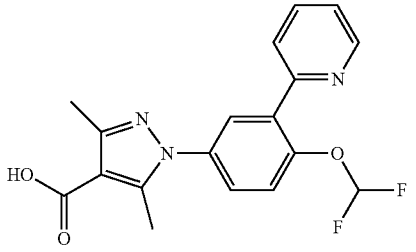 [SMILES: Cc1nn(-c2ccc(OC(F)F)c(-c3ccccn3)c2)c(C)c1C(=O)O]

To a 10 mL round-bottom flask equipped with a magnetic stir bar and a reflux condenser was added 177-B (160 mg, 353 umol, 1.0 eq) followed by the addition of solvent ethanol (5 mL) and water (1 mL). Then sodium hydroxide (42.4 mg, 1.06 mmol, 3.0 eq) was added into the mixture at 25° C. The mixture was heated to 50° C. and stirred for 4 h. To the mixture was added sodium hydroxide (141 mg, 3.53 mmol, 10 eq) again, and the mixture was stirred at 80° C. for 4 hr. The mixture was concentrated under reduced pressure to give a residue. The residue was dissolved in water (10 mL). The pH of the mixture was adjusted to 6. The mixture was extracted with ethyl acetate (10 mL×3). The combined organic layer was washed with brine (15 mL), dried over sodium sulfate, filtered and concentrated to give 140 mg (89% yield) of 177-C as a yellow solid.

LCMS: (ESI) m/z: 360.1 $[M+H]^+$.

Step 4: N-(3-(1,1-difluoroethyl)phenyl)-1-(4-(difluoromethoxy)-3-(pyridin-2-yl)phenyl)-3,5-dimethyl-1H-pyrazole-4-carboxamide (177)

Compound ID: 177

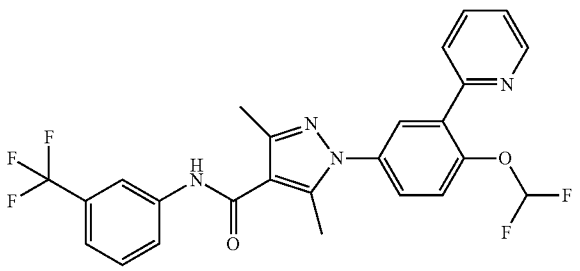

177 was obtained via similar procedure of 186 from 177-C and 3-(1,1-difluoroethyl)aniline LCMS: (ESI) m/z: 499.3 $[M+H]^+$.

$^1$H NMR (400 MHz, MeOD-$d_4$) δ: 8.67 (d, J=4.4 Hz, 1H), 7.82-7.96 (m, 4H), 7.72 (d, J=8.4 Hz, 1H), 7.62 (dd, J=2.4, 8.8 Hz, 1H), 7.43-7.52 (m, 3H), 7.30 (d, J=7.6 Hz, 1H), 6.94 (t, J=73.2 Hz 1H), 2.48 (d, J=19.8 Hz, 6H), 1.93 (t, J=18.0 Hz, 3H).

Synthesis of 176

Step 1: 2,6-dibromo-4-nitrophenol (176-A)

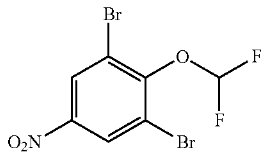

To a 250 mL round-bottom flask equipped with a magnetic stir bar was added 2,6-dibromo-4-nitro-phenol (8.00 g, 27.0 mmol, 1.0 eq) followed by the addition of acetonitrile (100 mL), potassium carbonate (7.45 g, 53.9 mmol, 2.0 eq) was added. The solution was cooled to 0° C. Next, ethyl 2-bromo-2,2-difluoro-acetate (8.20 g, 40.4 mmol, 1.5 eq) was added dropwise. The mixture was heated to 80° C. and stirred for 12 h. The mixture was filtered. The filtrate was concentrated. The residue was partitioned between ethyl acetate (200 mL) and water (200 mL). The aqueous layer was extracted with ethyl acetate (100 mL×2). The combined organic layer was washed with brine (200 mL), dried over anhydrous sodium sulfate, filtered, and concentrated under reduced pressure affording the residue as a brown oil. The crude product was purified by silica gel column chromatography (petroleum ether/ethyl acetate, 20/1) to give 15.0 g (80% yield) of 176-A as a brown oil.

$^1$H NMR (400 MHz, MeOD-$d_4$) δ: 8.40 (s, 2H), 6.64 (t, J=73.2 Hz, 1H).

Step 2: 1,3-dibromo-2-(difluoromethoxy)-5-nitrobenzene (176-B)

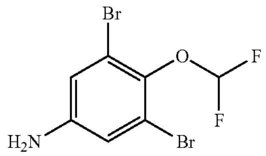 [SMILES: O=[N+]([O-])c1cc(Br)c(OC(F)F)c(Br)c1]

To a 50 mL round-bottom flask equipped with a magnetic stir bar and a reflux condenser was added 176-A (500 mg, 1.44 mmol, 1.0 eq) followed by the addition of water (1 mL) and methanol (5 mL). Then ammonium chloride (771 mg, 14.4 mmol, 10 eq) and iron powder (804 mg, 14.4 mmol, 10 eq) were added into the mixture at 25° C. The mixture was heated to 80° C. and stirred for 2 h. The mixture was diluted by slow addition of water (30 mL). The resulting mixture was transferred to a separatory funnel, and the aqueous layer mixture was extracted with ethyl acetate (20 mL×3). The combined organic layer was washed with brine (20 mL), dried over anhydrous sodium sulfate, filtered, and concentrated under reduced pressure affording the residue to give 400 mg (64% yield) of 176-B as a yellow solid.

LCMS: (ESI) m/z: 317.8$[M+H]^+$.

Step 3: 3,5-dibromo-4-(difluoromethoxy)aniline (176-C)

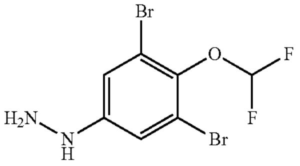 [SMILES: NNc1cc(Br)c(OC(F)F)c(Br)c1]

176-C was obtained via general procedure I from 176-B

LCMS: (ESI) m/z: 296.1 $[M+H]^+$.

Step 4: (3,5-dibromo-4-(difluoromethoxy)phenyl)hydrazine (176-D)

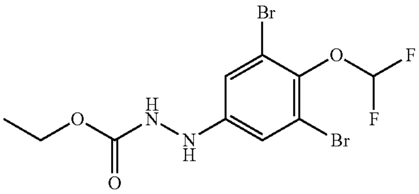 [SMILES: CCOC(=O)NNc1cc(Br)c(OC(F)F)c(Br)c1]

176-D was obtained via similar procedure of 186-A from 176-C and ethyl carbonochloridate LCMS: (ESI) m/z: 404.9$[M+H]^+$.

Step 5: ethyl 2-(3,5-dibromo-4-(difluoromethoxy) phenyl)hydrazinecarboxylate (176-E)

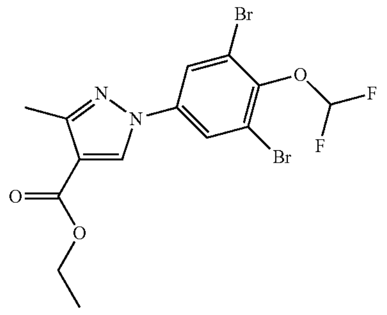 [SMILES: CCOC(=O)c1cn(-c2cc(Br)c(OC(F)F)c(Br)c2)nc1C]

176-E was obtained via similar procedure of 186-B from 176-D and ethyl (2E)-2-(methoxymethylene)-3-oxo-butanoate LCMS: (ESI) m/z: 454.9 $[M+H]^+$.

Step 6: ethyl 1-(3,5-dibromo-4-(difluoromethoxy) phenyl)-3-methyl-1H-pyrazole-4-carboxylate (176-F)

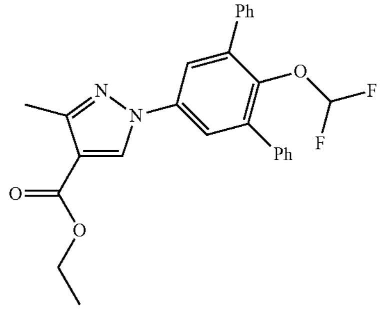 [SMILES: CCOC(=O)c1cn(-c2cc(-c3ccccc3)c(OC(F)F)c(-c3ccccc3)c2)nc1C]

176-F was obtained via similar procedure of 186-C from 176-E and phenylboronic acid LCMS: (ESI) m/z: 449.0$[M+H]^+$.

Step 7: 1-(2'-(difluoromethoxy)-[1,1':3',1"-terphenyl]-5'-yl)-3-methyl-1H-pyrazole-4-carboxylic acid (176-G)

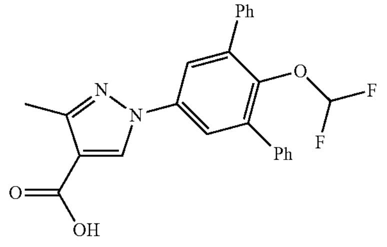 [SMILES: Cc1nn(-c2cc(-c3ccccc3)c(OC(F)F)c(-c3ccccc3)c2)cc1C(=O)O]

176-G was obtained via similar procedure of 186-D from 176-F and sodium hydroxide LCMS: (ESI) m/z: 421.1 $[M+H]^+$.

Spectra

Step 8: N-(3-(1,1-difluoroethyl)phenyl)-1-(2'-(difluoromethoxy)-[1,1':3',1"-terphenyl]-5'-yl)-3-methyl-1H-pyrazole-4-carboxamide (176)

Compound ID: 176

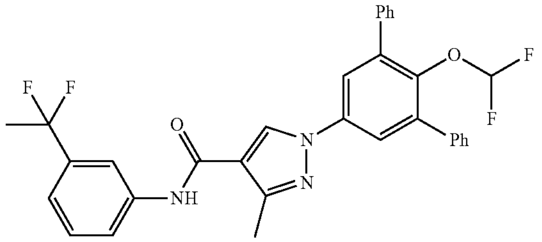

176 was obtained via similar procedure of 186 from 176-G and 3-(1,1-difluoroethyl)aniline LCMS: (ESI) m/z: 559.19$[M+H]^+$.

$^1$H NMR (400 MHz, MeOD-$d_4$) δ: 8.95 (s, 1H), 7.90 (s, 1H), 7.83 (s, 2H), 7.74 (d, J=8.4 Hz, 1H), 7.68-7.61 (m, 4H), 7.55-7.47 (m, 4H), 7.47-7.38 (m, 3H), 7.28 (d, J=7.6 Hz, 1H), 5.90 (t, J=73.2 Hz, 1H), 2.57 (s, 3H), 1.93 (t, J=18.0 Hz, 3H).

Synthesis of 175

Step 1: Synthesis of ethyl 1-[4-(difluoromethoxy)-3-(4,4,5,5-tetramethyl-1,3,2-dioxaborolan-2-yl)phenyl]-3-methyl-pyrazole-4-carboxylate (175-A)

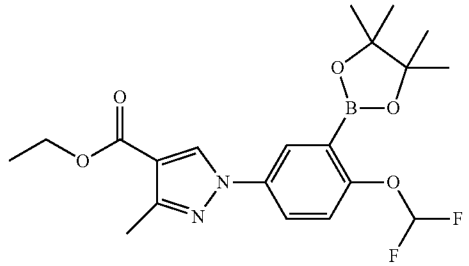 [SMILES: CCOC(=O)c1cn(-c2ccc(OC(F)F)c(B3OC(C)(C)C(C)(C)O3)c2)nc1C]

To a 100 mL round-bottom flask equipped with a magnetic stir bar was added 186-B (0.400 g, 1.02 mmol, 1.0 eq) followed by the addition of dioxane (15 mL). Then potassium acetate (200 mg, 2.04 mmol, 2.0 eq), 4,4,5,5-tetramethyl-2-(4,4,5,5-tetramethyl-1,3,2-dioxaborolan-2-yl)-1,3,2-dioxaborolane (517 mg, 2.04 mmol, 2.0 eq) and 1,1-bis (diphenylphosphino)ferrocene]dichloropalladium(II) (74.5 mg, 102 umol, 0.10 eq) were added into the mixture at 20° C. The flask was then evacuated and backfilled with nitrogen for three times. The mixture was stirred at 90° C. under an atmosphere of nitrogen for 12 h. The mixture was diluted with water (20 mL), and then extracted with ethyl acetate (15 mL×3). The combined organic layer was washed with brine (20 mL), dried over anhydrous sodium sulfate, filtered and concentrated under reduced pressure to give a residue. The residue was purified by silica gel column chromatography (petroleum ether/ethyl acetate, from 30/1 to 5/1) to give 410 mg (78% yield) of 175-A as a white solid.

LCMS: (ESI) m/z: 423.1 $[M+H]^+$.

Step 2: Synthesis of ethyl 1-[4-(difluoromethoxy)-3-(2-pyridyl)phenyl]-3-methyl-pyrazole-4-carboxylate (175-B)

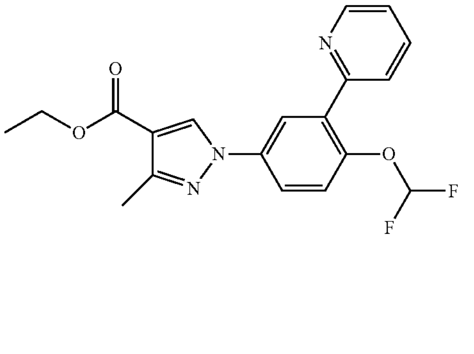 [SMILES: CCOC(=O)c1cn(-c2ccc(OC(F)F)c(-c3ccccn3)c2)nc1C]

A mixture of 175-A (410 mg, 796 umol, 1.0 eq), 2-bromopyridine (230 mg, 1.46 mmol, 1.8 eq), sodium bicarbonate (163 mg, 1.94 mmol, 2.4 eq) and 1,1-bis(diphenylphosphino)ferrocene]dichloropalladium(II) (71.0 mg, 97.0 umol, 1.2e-1.0 eq) in dioxane (8 mL) and water (2 mL) was degassed and purged with nitrogen for 3 times. And then the mixture was stirred at 90° C. for 4 hr under nitrogen atmosphere. The mixture was diluted with water (40 mL), and extracted with ethyl acetate (30 mL×3). The combined organic layer was washed with brine (50 mL), dried over anhydrous sodium sulfate, filtered and concentrated under reduced pressure to give a residue. The residue was purified by silica gel column chromatography (petroleum ether/ethyl acetate, from 30/1 to 3/1) to give 300 mg (75% yield) of 175-B as a white solid.

LCMS: (ESI) m/z: 374.1 $[M+H]^+$.

Step 3: Synthesis of 1-[4-(difluoromethoxy)-3-(2-pyridyl)phenyl]-3-methyl-pyrazole-4-carboxylic acid (175-C)

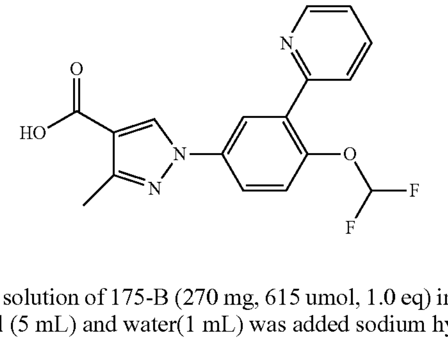

To a solution of 175-B (270 mg, 615 umol, 1.0 eq) in ethyl alcohol (5 mL) and water(1 mL) was added sodium hydroxide (73.8 mg, 1.84 mmol, 3.0 eq). The mixture was heated to 50° C. and stirred for 2 hr. The mixture was concentrated in vacuum. The residue was diluted with water (20 mL), and washed with methyl tertiary butyl ether (10 mL). The pH of aqueous phase was adjusted to 5-6, then extracted with ethyl acetate (15 mL×2). The combined organic layer was washed with brine (20 mL), dried over anhydrous, filtered and concentrated under reduced pressure to give 140 mg (54% yield) of 175-C as a white solid.

LCMS: (ESI) m/z: 344.2 $[M+H]^+$.

Step 4: Synthesis of N-[3-(1,1-difluoroethyl)phenyl]-1-[4-(difluoromethoxy)-3-(2-pyridyl)phenyl]-3-methyl-pyrazole-4-carboxamide (175)

Compound ID: 175

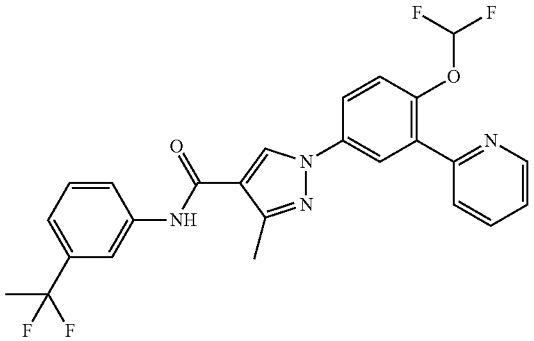

To a solution of 175-C and 3-(1,1-difluoroethyl)aniline (41.4 mg, 263 umol, 1.0 eq) in pyridine (10 mL) was added N-[3-(dimethylamino)propyl]-N-ethylcarbodiimide hydrochloride (75.8 mg, 395 umol, 1.5 eq). The mixture was stirred at 25° C. for 2 hr. The mixture was concentrated in vacuum. The residue was diluted with water (20 mL), and extracted with ethyl acetate (15 mL×3). The combined organic layer was washed with brine (20 mL), dried over anhydrous sodium sulfate, filtered and concentrated under reduced pressure to give a residue. The residue was purified by prep-HPLC (column: Waters Xbridge 150*25 5 u; mobile phase: [water (10 mM ammonium hydrogen carbonate)-acetonitrile]; B %: 48%-78%, 10 min), then freeze-dried to give 53.9 mg (35% yield) of 175 as a white solid LCMS: (ESI) m/z: 485.2$[M+H]^+$.

$^1H$ NMR: (400 MHz, MeOD-$d_4$) δ: 8.87 (s, 1H), 8.71-8.69 (m, 1H), 8.13 (d, J=3.2 Hz, 1H), 7.97-7.89 (m, 3H), 7.84 (d, J=8.0 Hz, 1H), 7.75 (d, J=8.4 Hz, 1H), 7.50-7.41 (m, 3H), 7.29 (d, J=8.0 Hz, 1H), 6.87 (t, J=73.6 Hz, 1H), 2.56 (s, 3H), 1.93 (t, J=18.4 Hz, 3H).

Synthesis of 174

Step 1: Synthesis of N-(3-(1,1-difluoroethyl)phenyl)-1-(4-(difluoromethoxy)phenyl)-3,4-dimethyl-5-oxo-4,5-dihydro-1H-pyrazole-4-carboxamide (174)

Compound ID: 174

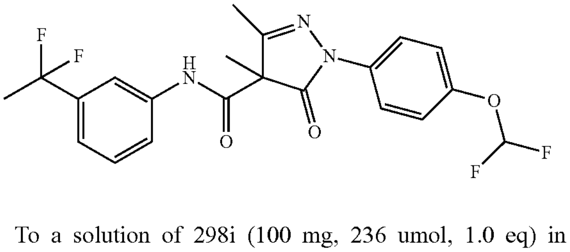

To a solution of 298i (100 mg, 236 umol, 1.0 eq) in tetrahydrofuran (2 mL) was added tetra-butyl ammonium fluoride (1 M in tetrahydrofuran, 283 uL, 1.2 eq) and iodomethane (50.0 mg, 354 umol, 1.5 eq). The mixture was stirred at 25° C. for 12 h. The mixture was concentrated. The residue was purified by prep-TLC (petroleum ether/ethyl acetate=3/1) to give 6.70 mg (6% yield) of 174 as yellow gum.

LCMS: (ESI) m/z: 438.2 $[M+H]^+$.

$^1H$ NMR: (400 MHz, MeOD-$d_4$) δ: 7.97 (d, J=9.2 Hz, 2H), 7.78 (s, 1H), 7.64 (d, J=8.0 Hz, 1H), 7.42 (t, J=8.0 Hz, 1H), 7.31 (d, J=7.6 Hz, 1H), 7.21 (d, J=9.2 Hz, 2H), 6.82 (t, J=74.4 Hz, 1H), 2.30 (s, 3H), 1.90 (t, J=18.4 Hz, 3H), 1.76 (s, 3H).

Synthesis of 173

Step 1: Synthesis of 2-(4-(difluoromethoxy)phenyl)-4,4,5,5-tetramethyl-1,3,2-dioxaborolane (173-A)

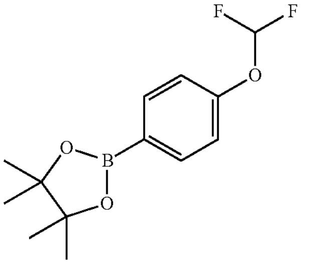 [SMILES: CC1(C)OB(c2ccc(OC(F)F)cc2)OC1(C)C]

To a 50 mL round-bottom flask equipped with a magnetic stir bar was added 1-bromo-4-(difluoromethoxy)benzene (500 mg, 2.24 mmol, 1.0 eq), 4,4,5,5-tetramethyl-2-(4,4,5,5-tetramethyl-1,3,2-dioxaborolan-2-yl)-1,3,2-dioxaborolane (1.14 g, 4.48 mmol, 2.0 eq), potassium acetate (440 mg, 4.48 mmol, 2.0 eq) followed by the addition of dioxane (20 mL). Then 1,1-bis(diphenylphosphino)ferrocene]dichloropalladium(II) (164 mg, 224 umol, 0.10 eq) was added into the mixture at 25° C. The flask was then evacuated and back-filled with nitrogen for three times. The mixture was stirred at 85° C. under an atmosphere of nitrogen for 12 hr. The mixture was filtered, the filtrate was concentrated under reduced pressure to give a residue. The residue was purified by silica gel column chromatography (petroleum ether/ethyl acetate, from 50/1 to 25/1) to give 500 mg (71% yield) of 173-A as a colorless oil.

LCMS: (ESI) m/z: 271.1 $[M+H]^+$.

Step 2: Synthesis of methyl 2-chloropyrimidine-5-carboxylate (173-B)

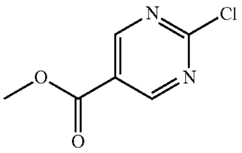

To a 100 mL round-bottom flask equipped with a magnetic stir bar was added 2-chloropyrimidine-5-carboxylic acid (1.00 g, 6.31 mmol, 1.0 eq) followed by the addition of toluene (30 mL) and methanol (12 mL). Then diazomethyl (trimethyl)silane (2 M, 6.31 mL, 2.0 eq) was added into the mixture at 25° C. The mixture was stirred at 25° C. for 0.5 hr. The mixture was concentrated under reduced pressure to give a residue. The residue was purified by silica gel column chromatography (petroleum ether/ethyl acetate, from 30/1 to 25/1) to give 0.700 g (61% yield) of 173-B as a white solid.

LCMS: (ESI) m/z: 173.0 $[M+H]^+$.

Step 3: Synthesis of 2-(4-(difluoromethoxy)phenyl) pyrimidine-5-carboxylic acid (173-C)

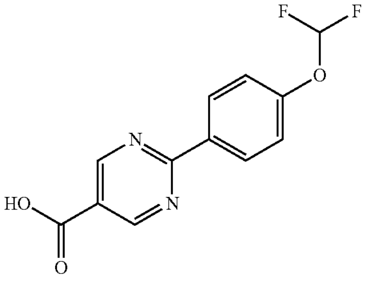 [SMILES: O=C(O)c1cnc(-c2ccc(OC(F)F)cc2)nc1]

To a 50 mL round-bottom flask equipped with a magnetic stir bar and a reflux condenser was added 173-B (224 mg, 1.24 mmol, 1.3 eq), 173-A (250 mg, 792 umol, 8.3e-1 eq), sodium bicarbonate (240 mg, 2.86 mmol, 3.0 eq) followed by the addition of dioxane (12 mL) and water (4 mL). Then 1,1-bis(diphenylphosphino)ferrocene]dichloropalladium(II) (69.8 mg, 95.4 umol, 0.10 eq) was added into the mixture at 25° C. The mixture was heated to 85° C. and stirred for 12 hr. The mixture was filtered, the filtrate was diluted with water (10 ml). The resulting mixture was transferred to a separatory funnel, and the aqueous layer mixture was extracted with ethyl acetate (20 mL). The pH of the aqueous phase was adjusted to 4. The mixture was extracted with ethyl acetate (10 mL×3). The combined organic layer was washed with brine (15 mL), dried over anhydrous sodium sulfate, filtered and concentrated to give 250 mg (88% yield) of 173-C as a yellow solid.

LCMS: (ESI) m/z: 267.1 $[M+H]^+$.

Step 4: Synthesis of N-(3-(1,1-difluoroethyl)phenyl)-2-(4-(difluoromethoxy)phenyl)pyrimidine-5-carboxamide (173)

Compound ID: 173

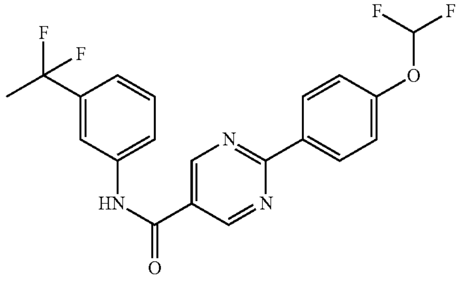

173 was obtained via similar procedure of 179 from 173-C and 3-(1,1-difluoroethyl)aniline LCMS: (ESI) m/z 406.1 $[M+H]^+$.

1H NMR (400 MHz, MeOD-$d_4$) δ: 9.32 (s, 2H), 8.56-8.58 (m, 2H), 7.97 (s, 1H), 7.83 (d, J=8.00 Hz, 1H), 7.48 (t, J=7.6 Hz, 1H), 7.35 (d, J=7.2 Hz, 1H), 7.29 (d, J=8.8 Hz, 2H), 6.97 (t, J=73.6 Hz, 1H), 1.94 (t, J=18.4 Hz, 3H).

Synthesis of 172

Step 1: Synthesis of 4-chloro-N-(3-(1,1-difluoroethyl)phenyl)-1-(4-(difluoromethoxy)phenyl)-3-methyl-5-oxo-4,5-dihydro-1H-pyrazole-4-carboxamide (172)

Compound ID: 172

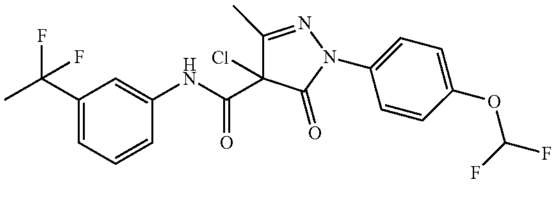

To a solution of 298i (0.100 g, 236 umol, 1.0 eq) in tetrahydrofuran (2 mL) was added dropwise a solution of 1-chloropyrrolidine-2,5-dione (47.3 mg, 354 umol, 1.5 eq) in tetrahydrofuran (2 mL) at 0° C. The mixture was stirred at 0° C. for 5 min. The mixture was concentrated in vacuo. The residue was purified by prep-HPLC (column: Phenomenex Synergi C18 150*25*10 um; mobile phase: [water (0.225% formic acid)-acetonitrile]; B %: 68%-98%, 9 min) to give 39.7 mg (34% yield) of 172 as a yellow oil.

LCMS: (ESI) m/z: 480.0 $[M+Na]^+$.

$^1$H NMR (400 MHz, $CDCl_3$-d) δ: 8.82 (br s, 1H), 7.91 (d, J=9.2 Hz, 2H), 7.73 (s, 1H), 7.64 (d, J=8.0 Hz, 1H), 7.44 (t, J=8.0 Hz, 1H), 7.36 (d, J=8.0 Hz, 1H), 7.21 (d, J=9.2 Hz, 2H), 6.52 (t, J=73.6 Hz, 1H), 2.47 (s, 3H), 1.93 (t, J=18.4 Hz, 3H).

Synthesis of 171

Step 1: Synthesis of ethyl 2-cyano-3-oxobutanoate (171-A)

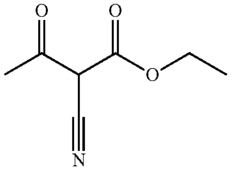

To a solution of ethyl 5-methylisoxazole-4-carboxylate (9.00 g, 58.0 mmol, 1.0 eq) in ethanol (100 mL) was added sodium ethoxide (7.89 g, 116 mmol, 2.0 eq) slowly at 0° C., then the solution was stirred at 20° C. for 12 h. The solution was diluted with water (50 mL), adjusted to pH=1 with hydrochloric acid (1 M), extracted with ethyl acetate (100 mL×3). The combined organic phase was washed with brine (100 mL), dried with anhydrous sodium sulfate, filtered and concentrated to give 8.50 g (94% yield) of 171-A as a yellow oil.

$^1$H NMR: (400 MHz, $CDCl_3$-d) δ: 13.62 (s, 1H), 4.33 (dd, J=14.4 Hz, 7.2 Hz, 2H), 2.34 (s, 3H), 1.36 (t, J=7.2 Hz, 3H).

Step 2: Synthesis of ethyl 5-amino-1-(4-(difluoromethoxy)phenyl)-3-methyl-1H-pyrazole-4-carboxylate (171-B)

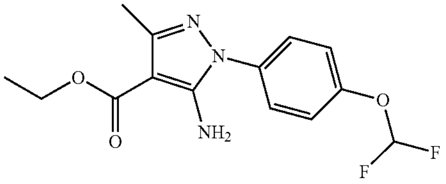 [SMILES: CCOC(=O)c1c(C)nn(-c2ccc(OC(F)F)cc2)c1N]

To a mixture of 171-A (2.00 g, 12.9 mmol, 1.0 eq) and (4-(difluoromethoxy)phenyl)hydrazine.

(2.24 g, 12.9 mmol, 1.0 eq) in ethyl acetate (20 mL) was added propylphosphonic anhydride (16.4 g, 25.8 mmol, 50% purity, 2.0 eq), the suspension was stirred at 50° C. for 12 h. The solution was poured into water (20 mL), extracted with ethyl acetate (20 mL×3). The combined organic phase was washed with saturated sodium bicarbonate solution (20 mL) and then brine (20 mL), dried with anhydrous sodium sulfate, filtered and concentrated. The residue was purified by silica gel column chromatography (petroleum ether/ethyl acetate, from 10/1 to 5/1) to give 600 mg (15% yield) of 171-B as a red solid.

LCMS: (ESI) m/z: 311.9 $[M+H]^+$.

Step 3: Synthesis of 5-amino-1-(4-(difluoromethoxy)phenyl)-3-methyl-1H-pyrazole-4-carboxylic acid (171-C)

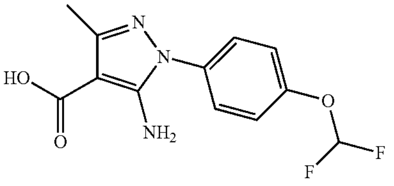 [SMILES: Cc1nn(-c2ccc(OC(F)F)cc2)c(N)c1C(=O)O]

To a solution of 171-B (200 mg, 643 umol, 1.0 eq) in methanol (3 mL)/water (1 mL) was added lithium hydroxide hydrate (135 mg, 3.21 mmol, 5.0 eq), the solution was stirred at 50° C. for 30 mins. The solution was concentrated. The residue was diluted with water (3 mL). The filtrated was adjusted to pH=3 with hydrochloric acid (1 M). The suspension was filtered and washed with water (5 mL×3). The filter cake was dried under vacuum to give 100 mg (53% yield) of 171-C as a white solid.

LCMS: (ESI) m/z: 284.0 $[M+H]^+$.

Step 4: Synthesis of 5-amino-N-(3-(1,1-difluoroethyl)phenyl)-1-(4-(difluoromethoxy)phenyl)-3-methyl-1H-pyrazole-4-carboxamide (171)

Compound ID: 171

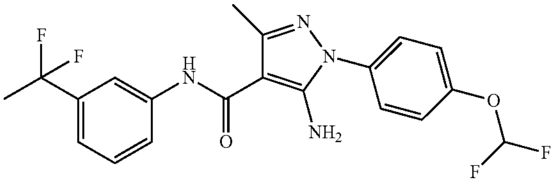

To a solution of 171-C (100 mg, 337 umol, 1.0 eq) and 3-1,1-difluoroethyl)aniline (79.55 mg, 506.14 umol, 1.5 eq) in pyridine (5 mL) was added N-[3-(dimethylamino)propyl]-N-ethylcarbodiimide hydrochloride (97.0 mg, 506 umol, 1.5 eq), the solution was stirred at 50° C. for 12 h. The solution was concentrated. The residue was purified by silica gel column chromatography (petroleum ether/ethyl acetate, from 5/1 to 1/1) to afford a gray solid. The solid was purified by preparative HPLC (column: Waters Xbridge 150*25 5 u; mobile phase: [water (10 mM ammonium bicarbonate)-acetonitrile]; B %: 42%-72%, 10 min) to give 11.2 mg (8% yield) of 171 as a white solid.

LCMS: (ESI) m/z: 423.2 $[M+H]^+$.

$^1$H NMR (400 MHz, DMSO-d) δ: 8.92 (s, 1H), 7.91 (s, 1H), 7.73 (d, J=8.4 Hz, 1H), 7.62-7.59 (m, 2H), 7.44 (t, J=7.6 Hz, 1H), 7.31 (d, J=4.4 Hz, 2H), 7.23 (d, J=7.6 Hz, 1H), 7.34 (t, J=60.4 Hz, 1H), 6.29 (s, 2H), 2.44 (s, 3H), 1.97 (t, J=18.8 Hz, 3H).

Synthesis of 170

Step 1: Synthesis of (4S)—N-(3-(1,1-difluoroethyl)phenyl)-1-(4-(difluoromethoxy)phenyl)-3,4-dimethyl-5-oxo-4,5-dihydro-1H-pyrazole-4-carboxamide (170)

Compound ID: 170

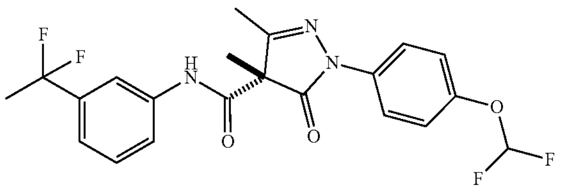

15.0 mg of 174 was purified by SFC (column: DAICEL CHIRALCEL OJ-H (250 mm*30 mm, 5 um); mobile phase: [Neu-methanol]; B %: 20%-20%, 3.7 min; 50 min) to give 3.90 mg (27% yield) of 170 as yellow oil.

LCMS: (ESI) m/z: 438.3 $[M+H]^+$.

$^1$H NMR: (400 MHz, MeOD-$d_4$) δ: 7.97 (d, J=9.2 Hz, 2H), 7.78 (s, 1H), 7.64 (d, J=8.0 Hz, 1H), 7.42 (t, J=8.0 Hz, 1H), 7.31 (d, J=7.6 Hz, 1H), 7.21 (d, J=9.2 Hz, 2H), 6.82 (t, J=74.4 Hz, 1H), 2.30 (s, 3H), 1.90 (t, J=18.4 Hz, 3H), 1.76 (s, 3H).

Synthesis of 169

Step 1: Synthesis of (4R)—N-(3-(1,1-difluoroethyl)phenyl)-1-(4-(difluoromethoxy)phenyl)-3,4-dimethyl-5-oxo-4,5-dihydro-1H-pyrazole-4-carboxamide (169)

Compound ID: 169

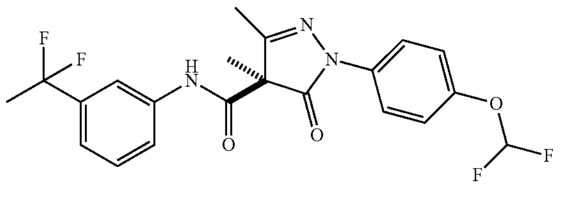

15.0 mg of 174 was purified by SFC (column: DAICEL CHIRALCEL OJ-H (250 mm*30 mm, 5 um); mobile phase: [Neu-methanol]; B %: 20%-20%, 3.7 min; 50 min min) to give 5.50 mg (38% yield) of 169 as yellow oil.

LCMS: (ESI) m/z: 438.3 $[M+H]^+$.

$^1$H NMR: (400 MHz, MeOD-$d_4$) δ: 7.97 (d, J=9.2 Hz, 2H), 7.78 (s, 1H), 7.64 (d, J=8.0 Hz, 1H), 7.42 (t, J=8.0 Hz, 1H), 7.31 (d, J=7.6 Hz, 1H), 7.21 (d, J=9.2 Hz, 2H), 6.82 (t, J=74.4 Hz, 1H), 2.30 (s, 3H), 1.90 (t, J=18.4 Hz, 3H), 1.76 (s, 3H).

Synthesis of 168

Step 1: Synthesis of ethyl 1-(4-(difluoromethoxy)phenyl)-5-(dimethylamino)-3-methyl-1H-pyrazole-4-carboxylate (168-A)

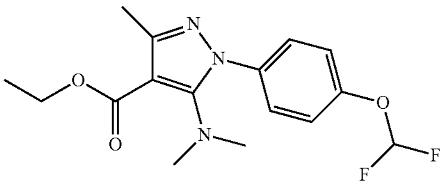 [SMILES: CCOC(=O)c1c(C)nn(-c2ccc(OC(F)F)cc2)c1N(C)C]

To a solution of 171-B (160 mg, 514 umol, 1.0 eq) in N,N-dimethylformamide (5 mL) was added sodium hydride (41.1 mg, 1.03 mmol, 60% purity, 2.0 eq) at 0° C. The solution was stirred at 0° C. for 30 mins. Then iodomethane (80.2 mg, 565 umol, 1.1 eq) was added into the solution and the reaction mixture was stirred at 25° C. for stirred for 2 h. The solution was poured into water (10 mL), extracted with ethyl acetate (10 mL×3). The combined organic phase was washed with brine (20 mL), dried with anhydrous sodium sulfate, filtered and concentrated. The residue was purified by silica gel column chromatography (petroleum ether/ethyl acetate, from 10/1 to 2/1) to afford 60.0 mg (30% yield) of 168-A as a white solid.

LCMS: (ESI) m/z: 340.1 $[M+H]^+$.

Step 2: Synthesis of 1-(4-(difluoromethoxy)phenyl)-5-(dimethylamino)-3-methyl-1H-pyrazole-4-carboxylic acid (168-B)

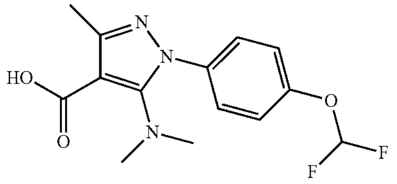 [SMILES: Cc1nn(-c2ccc(OC(F)F)cc2)c(N(C)C)c1C(=O)O]

168-B was obtained via similar procedure of 171-C from 168-A and sodium hydroxide.

LCMS: (ESI) m/z: 312.2 $[M+H]^+$.

Step 3: Synthesis of N-(3-(1,1-difluoroethyl)phenyl)-1-(4-(difluoromethoxy)phenyl)-5-(dimethylamino)-3-methyl-1H-pyrazole-4-carboxamide (168)

Compound ID: 168

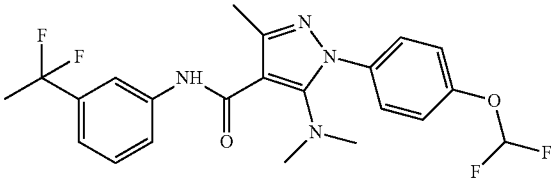

168 was obtained via similar procedure of 171 from 168-B.

LCMS: (ESI) m/z: 451.2 $[M+H]^+$.

$^1$H NMR: (400 MHz, DMSO-d) δ: 10.22 (s, 1H), 7.99 (s, 1H), 7.73 (d, J=7.2 Hz, 1H), 7.65-7.63 (m, 2H), 7.44 (t, J=8.0 Hz, 1H), 7.33-7.30 (m, 2H), 7.31 (t, J=74.0 Hz, 1H), 7.26 (d, J=7.6 Hz, 1H), 2.70-2.65 (m, 6H), 2.28 (s, 3H), 1.96 (t, J=18.8 Hz, 3H).

Synthesis of 167

Step 1: Synthesis of N-(3-chlorophenyl)-1-[4-(difluoromethoxy)phenyl]-3-methyl-5-oxo-4H-pyrazole-4-carboxamide (167-A)

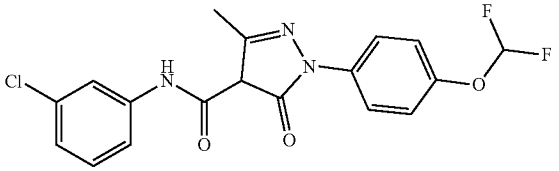 [SMILES: CC1=NN(c2ccc(OC(F)F)cc2)C(=O)C1C(=O)Nc1cccc(Cl)c1]

167-A was obtained via general procedure IV from 4-nitrophenyl 1-(4-(difluoromethoxy)phenyl)-3-methyl-5-oxo-4,5-dihydro-1H-pyrazole-4-carboxylate and 3-chloroaniline.

LCMS: (ESI) m/z: 394.1 $[M+H]^+$.

Step 2: Synthesis of N-(3-chlorophenyl)-1-[4-(difluoromethoxy)phenyl]-3,4-dimethyl-5-oxo-pyrazole-4-carboxamide (167)

Compound ID: 167

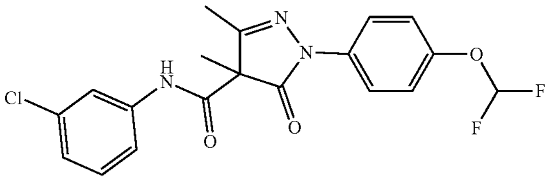

To a solution of 167-A (55.0 mg, 135 umol, 1.0 eq) in tetrahydrofuran (5 mL) was added iodomethane (28.8 mg, 203 umol, 1.5 eq) and tetrabutylammonium fluoride (1 M, 203 uL, 1.5 eq). It was stirred at 25° C. for 12 h. The mixture was concentrated under reduced pressure to give a residue. It was purified by Prep-TLC (petroleum ether/ethyl acetate=5/1) to afford a crude product. The crude product was further purified by prep-HPLC (column: Phenomenex Synergi C18 150*30 mm*4 um; mobile phase: [water (0.225% formic acid)-acetonitrile]; B %: 50%-80%, 10 min) to give 1.10 mg (2% yield) of 167 as a white solid.

LCMS: (ESI) m/z: 408.2 $[M+H]^+$.

$^1$H NMR (400 MHz, MeOD-$d_4$) δ: 7.96 (d, J=9.2 Hz, 2H), 7.72 (t, J=2.0 Hz, 1H), 7.46-7.44 (m, 1H), 7.30 (t, J=8.0 Hz, 1H), 7.21 (d, J=9.2 Hz, 2H), 7.16-7.14 (m, 1H), 6.82 (t, J=74.0 Hz, 1H), 2.29 (s, 3H), 1.75 (s, 3H).

Synthesis of 166

Step 1: Synthesis of N-(3-chloro-5-fluoro-phenyl)-1-[4-(difluoromethoxy)phenyl]-3-methyl-5-oxo-4H-pyrazole-4-carboxamide (166-A)

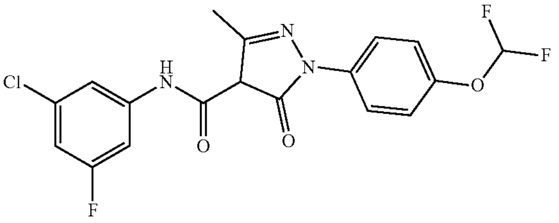 [SMILES: CC1=NN(c2ccc(OC(F)F)cc2)C(=O)C1C(=O)Nc1cc(F)cc(Cl)c1]

166-A was obtained via general procedure IV from 4-nitrophenyl 1-(4-(difluoromethoxy)phenyl)-3-methyl-5-oxo-4,5-dihydro-1H-pyrazole-4-carboxylate and 3-chloro-5-fluoro-aniline.

LCMS: (ESI) m/z: 434.1 $[M+H]^+$.

Step 2: Synthesis of N-(3-chloro-5-fluoro-phenyl)-1-[4-(difluoromethoxy)phenyl]-3,4-dimethyl-5-oxo-pyrazole-4-carboxamide (166)

Compound ID: 166

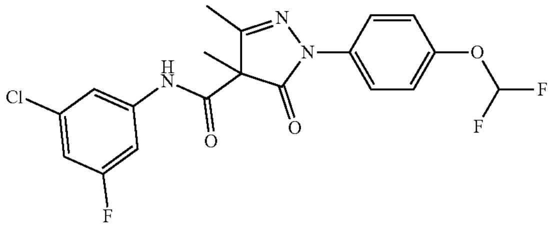

166 was obtained via similar procedure of 167 from 166-A and iodomethane

LCMS: (ESI) m/z: 425.9 $[M+H]^+$.

$^1$H NMR (400 MHz, MeOD-$d_4$) δ: 7.95 (d, J=8.8 Hz, 2H), 7.51 (s, 1H), 7.46-7.43 (m, 1H), 7.21 (d, J=8.8 Hz, 2H), 6.98-6.96 (m, 1H), 6.82 (t, J=74.0 Hz, 1H), 2.28 (s, 3H), 1.75 (s, 3H)

Synthesis of 165

Step 1: Synthesis of N-(3,5-dichloro-4-fluoro-phenyl)-1-[4-(difluoromethoxy)phenyl]-3-methyl-5-oxo-4H-pyrazole-4-carboxamide (165-A)

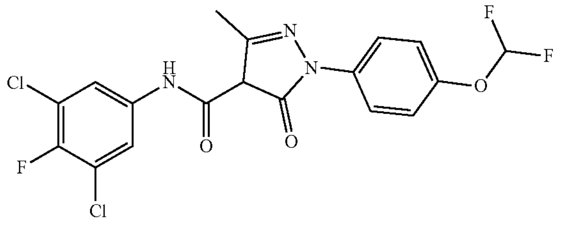 [SMILES: CC1=NN(c2ccc(OC(F)F)cc2)C(=O)C1C(=O)Nc1cc(Cl)c(F)c(Cl)c1]

165-A was obtained via general procedure IV from 4-nitrophenyl 1-(4-(difluoromethoxy)phenyl)-3-methyl-5-oxo-4,5-dihydro-1H-pyrazole-4-carboxylate and 3,5-dichloro-4-fluoro-aniline.

LCMS: (ESI) m/z: 446.1 $[M+H]^+$.

Step 2: Synthesis of N-(3,5-dichloro-4-fluoro-phenyl)-1-[4-(difluoromethoxy)phenyl]-3,4-dimethyl-5-oxo-pyrazole-4-carboxamide (165)

Compound ID: 165

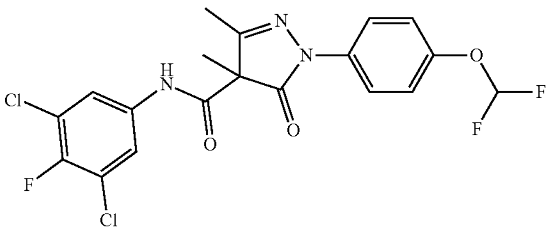

165 was obtained via similar procedure of 167 from 165-A and iodomethane

LCMS: (ESI) m/z: 460.1 $[M+H]^+$.

$^1H$ NMR (400 MHz, MeOD-$d_4$) δ: 7.95 (d, J=9.2 Hz, 2H), 7.75 (s, 1H), 7.73 (s, 1H), 7.21 (d, J=9.2 Hz, 2H), 6.82 (t, J=74.0 Hz, 1H), 2.28 (s, 3H), 1.74 (s, 3H).

Synthesis of 164

Step 1: Synthesis of N-(3-(1,1-difluoroethyl)phenyl)-3-oxobutanamide (164-A)

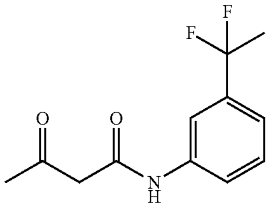 [SMILES: CC(=O)CC(=O)Nc1cccc(C(C)(F)F)c1]

To a mixture of 3-(1,1-difluoroethyl)aniline (6.23 g, 39.7 mmol, 1.0 eq) in dichloromethane (50 mL) was added 4-methyleneoxetan-2-one (5.00 g, 59.5 mmol, 1.5 eq). The mixture was stirred at 25° C. for 3 hr. The mixture was concentrated under reduced pressure to give a residue. The residue was purified by column chromatography on silica gel (petroleum ether/ethyl acetate, from 5/1 to 4/1) to give 9.60 g (96% yield) of 164-A as a brown solid.

LCMS: (ESI) m/z: 242.5 $[M+H]^+$.

Step 2: Synthesis of (Z)—N-(3-(1,1-difluoroethyl)phenyl)-2-(hydroxyimino)-3-oxobutanamide (164-B)

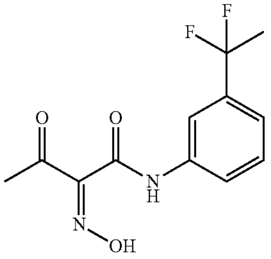 [SMILES: CC(=O)/C(=N/O)C(=O)Nc1cccc(C(C)(F)F)c1]

To a 50 mL round-bottom 11 as equipped with a magnetic stir bar was added 164-A (1.00 g, 3.98 mmol, 1.0 eq) followed by the addition of acetic acid (10 mL). The solution was cooled to 0° C. Next, a solution of sodium nitrite (412 mg, 5.97 mmol, 1.5 eq) in water (2 mL) was added dropwise. The mixture was allowed to warm to 25° C. and stir for 12 h. The mixture was diluted by water (30 mL), the resulting mixture was transferred to a separatory funnel, and the aqueous layer mixture was extracted with ethyl acetate (20 mL×3). The combined organic layer was washed with brine (30 mL), dried over anhydrous sodium sulfate, filtered, and concentrated under reduced pressure to give 0.960 g (75% yield) of 164-B as a yellow oil.

LCMS: (ESI) m/z: 271.1 $[M+H]^+$.

Step 3: Synthesis of (2Z,3E)-N-(3-(1,1-difluoroethyl)phenyl)-3-(2-(4-(difluoromethoxy)phenyl)hydrazono)-2-(hydroxyimino)butanamide (164-C)

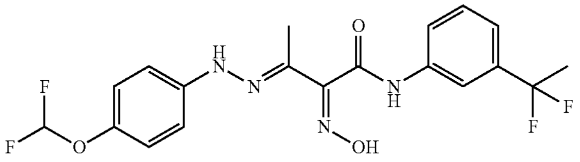 [SMILES: CC(=N\Nc1ccc(OC(F)F)cc1)/C(=N/O)C(=O)Nc1cccc(C(C)(F)F)c1]

To a 10 mL round-bottom flask equipped with a magnetic stir bar and a reflux condenser was added 164-B (130 mg, 405 umol, 1.0 eq) and (4-(difluoromethoxy)phenyl)hydrazine (106 mg, 562 umol, 1.4 eq) followed by the addition of ethanol (4 mL). The mixture was heated to 80° C. and stirred for 0.5 hr. The mixture was concentrated under reduced pressure to give 180 mg (crude) of 164-C as a brown oil.

LCMS: (ESI) m/z: 427.1 $[M+H]^+$.

Step 4: Synthesis of (2Z,3E)-2-(acetoxyimino)-N-(3-(1,1-difluoroethyl)phenyl)-3-(2-(4-(difluoromethoxy)phenyl)hydrazono butanamide (164-D)

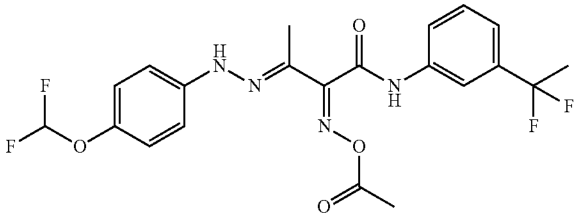 [SMILES: CC(=O)O/N=C(C(=O)Nc1cccc(C(C)(F)F)c1)/C(C)=N/Nc1ccc(OC(F)F)cc1]

A mixture of 164-C (180 mg, 422 umol, 1.0 eq) in acetic anhydride (3 mL) was stirred at 50° C. for 2 hr. The mixture was quenched by slow addition of methanol (10 mL). The mixture was concentrated under reduced pressure to give a residue. The residue was purified by prep-HPLC (column: Phenomenex Gemini 150*25 mm*10 um; mobile phase: [water (0.225% formic acid)-acetonitrile]; B %: 44%-74%, 10 min) to give 40.0 mg (20% yield) of 164-D as a yellow solid.

LCMS: (ESI) m/z: 469.3 $[M+H]^+$.

Step 4: Synthesis of N-(3-(1,1-difluoroethyl)phenyl)-2-(4-(difluoromethoxy)phenyl)-5-methyl-2H-1,2,3-triazole-4-carboxamide (164)

Compound ID : 164

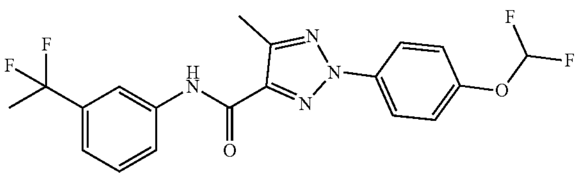

To a 10 mL round-bottom flask equipped with a magnetic stir bar and a reflux condenser was added 164-D (35.0 mg, 73.8 umol, 1.0 eq) followed by the addition of N, N-dimethylformamide (2 mL). Then potassium carbonate (102 mg, 738 umol, 10 eq) was added into the mixture. The mixture was heated to 50° C. and stirred for 1 hr. The mixture was filtered to give a filtrate. The filtrate was purified by prep-HPLC (column: Phenomenex Synergi C18 150*25*10 um; mobile phase: [water (0.225% formic acid)-acetonitrile]; B %: 65%-95%, 9 min) to give 20.0 mg (67% yield) of 164 as a white solid.

LCMS: (ESI) m/z: 409.0 $[M+H]^+$.

$^1$H NMR (400 MHz, DMSO-d) δ: 10.54 (s, 1H), 8.15-8.19 (m, 2H), 8.08 (s, 1H), 7.95 (d, J=8.0 Hz, 1H), 7.49 (t, J=7.6 Hz, 1H), 7.44 (d, J=9.2 Hz, 2H), 7.35 (t, J=73.6 Hz, 1H), 7.32 (d, J=8.0 Hz, 1H), 2.59 (s, 3H), 1.98 (t, J=18.8 Hz, 3H).

Synthesis of 163

Step 1: 1-(4-(difluoromethoxy)phenyl)-N-(3-(1,1-difluoropropyl)phenyl)-3-methyl-5-oxo-4,5-dihydro-1H-pyrazole-4-carboxamide (163-A)

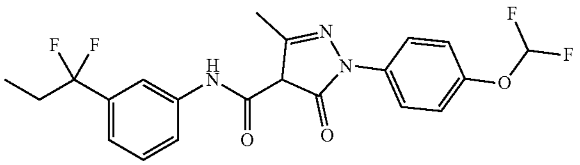 [SMILES: CCC(F)(F)c1cccc(NC(=O)C2C(=O)N(c3ccc(OC(F)F)cc3)N=C2C)c1]

163-A was obtained via general procedure IV from 4-nitrophenyl 1-(4-(difluoromethoxy)phenyl)-3-methyl-5-oxo-4,5-dihydro-1H-pyrazole-4-carboxylate and 3-(1,1-difluoropropyl)aniline LCMS: (ESI) m/z: 438.1 $[M+H]^+$.

$^1$H NMR (400 MHz, MeOD-$d_4$) δ: 7.88 (s, 1H), 7.68-7.73 (m, 2H), 7.66 (br d, J=8.4 Hz, 1H), 7.43 (t, J=8.0 Hz, 1H), 7.35 (d, J=8.8 Hz, 2H), 7.22 (d, J=8.0 Hz, 1H), 6.71-7.13 (m, 1H), 2.65 (s, 3H), 2.10-2.31 (m, 2H), 1.00 (t, J=7.2 Hz, 3H).

Step 2: 4-chloro-1-(4-(difluoromethoxy)phenyl)-N-(3-(1,1-difluoropropyl)phenyl)-3-methyl-5-oxo-4,5-dihydro-1H-pyrazole-4-carboxamide (163)

Compound ID : 163

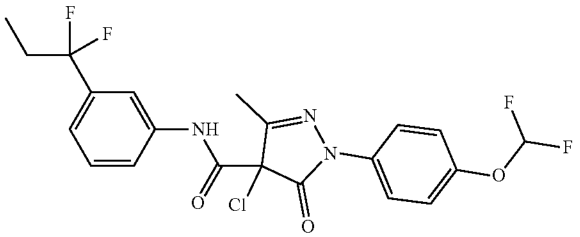

To a 10 mL round-bottom flask equipped with a magnetic stir bar was added 163-A (30.0 mg, 60.9 umol, 1.0 eq) followed by the addition of tetrahydrofuran (1 mL). Then reagent 1-chloropyrrolidine-2,5-dione (9.16 mg, 68.6 umol, 1.1 eq) was added into the mixture at 25° C. The mixture was stirred at 25° C. for 10 min. The mixture was concentrated under reduced pressure to give a residue. The residue was purified by prep-HPLC (column: Phenomenex Synergi Max-RP 150*50 mm*10 um; mobile phase: [water (0.225% formic acid)-acetonitrile]; B %: 50%-80%, 10 min) to give 20.0 mg (66% yield) of 163 as a yellow oil.

LCMS: (ESI) m/z: 438.2 $[M+H]^+$.

$^1$H NMR (400 MHz, MeOD-$d_4$) δ: 8.82 (br s, 1H), 7.86-7.98 (m, 2H), 7.62-7.70 (m, 2H), 7.44 (t, J=8.0 Hz, 1H), 7.31 (br d, J=7.2 Hz, 1H), 7.21 (d, J=9.2 Hz, 2H), 6.29-6.77 (m, 1H), 2.47 (s, 3H), 2.08-2.23 (m, 2H), 1.00 (t, J=7.6 Hz, 3H).

Synthesis of 162

Step 1: Synthesis of ethyl 1-(4-(difluoromethoxy)phenyl)-3-methyl-5-(methylamino)-1H-pyrazole-4-carboxylate (162-A)

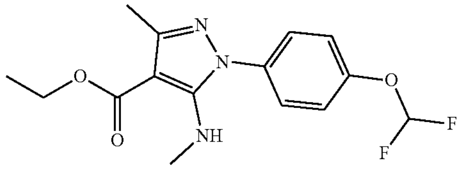 [SMILES: CCOC(=O)c1c(C)nn(-c2ccc(OC(F)F)cc2)c1NC]

162-A was obtained via similar procedure of 168-A from 171-B and iodomethane.

LCMS: (ESI) m/z: 326.1 [M+H]$^+$.

Step 2: Synthesis of 1-(4-(difluoromethoxy)phenyl)-3-methyl-5-(methylamino)-1H-pyrazole-4-carboxylic acid (162-B)

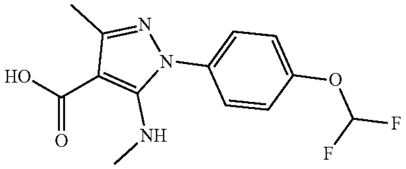 [SMILES: CNc1c(C(=O)O)c(C)nn1-c1ccc(OC(F)F)cc1]

162-B was obtained via similar procedure of 168-B from 162-A and sodium hydroxide.

LCMS: (ESI) m/z: 298.0 [M+H]$^+$.

Step 3: Synthesis of N-(3-(1,1-difluoroethyl)phenyl)-1-(4-(difluoromethoxy)phenyl)-3-methyl-5-(methylamino)-1H-pyrazole-4-carboxamide (162)

Compound ID: 162

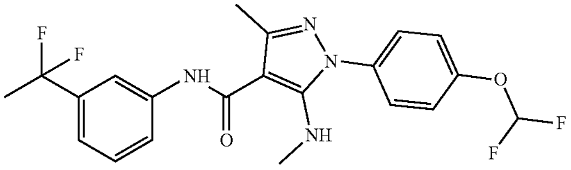

To a solution of 162-B (300 mg, 970 umol, 1.0 eq) and 1H-benzo[d][1,2,3]triazol-1-ol (576 mg, 1.51 mmol, 1.6 eq) in N,N-dimethylformamide (10 mL) was N,N-diisopropylethylamine (261 mg, 2.02 mmol, 2.1 eq), the solution was stirred at 30° C. for 15 mins. Then 3-(1,1-difluoroethyl)aniline (159 mg, 1.01 mmol, 1.0 eq) was added into the solution and the mixture was stirred at 80° C. for 12 h. The solution was concentrated. The residue was purified by prep-HPLC (column: Waters Xbridge 150*25 5 u; mobile phase: [water (10 mM ammonium bicarbonate)-acetonitrile]; B %: 42%-72%, 10 min) to give 129 mg (31% yield) of 162 as a gray solid.

LCMS: (ESI) m/z: 437.2 [M+H]$^+$.

$^1$H NMR (400 Hz, DMSO-d) δ: 9.46 (s, 1H), 7.96 (s, 1H), 7.72 (d, J=8.4 Hz, 1H), 7.58-7.55 (m, 2H), 7.43 (t, J=8.0 Hz, 1H), 7.32 (d, J=8.8 Hz, 2H), 7.31 (t, J=74.0 Hz, 1H), 7.23 (d, J=7.6 Hz, 1H), 6.19 (dd, J=10.8 Hz, 5.6 Hz, 1H), 2.55 (s, 3H), 2.35 (s, 3H), 1.96 (t, J=18.8 Hz, 3H).

Synthesis of 161

Step 1: Synthesis of 2-bromo-1-methoxy-4-nitrobenzene (161-A)

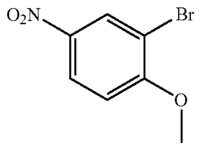

To a solution of 2-bromo-4-nitro-phenol (50.0 g, 229 mmol, 1.0 eq) and potassium carbonate (63.4 g, 459 mmol, 2.0 eq) in N,N-dimethylformamide (300 mL) was added iodomethane (130 g, 917 mmol, 4.0 eq) dropwise at 25° C., and the reaction mixture was stirred at 50° C. for 12 hr. To the reaction mixture was added water (500 mL). The suspension was filtrated and the filter cake was washed with water (300 mL). The solid was concentrated under reduced pressure to give 80.0 g (crude) of 161-A as a white solid.

$^1$H NMR (400 MHz, $CDCl_3$-d) δ: 8.48 (d, J=2.8 Hz, 1H), 8.21-8.24 (m, 1H), 6.97 (d, J=9.2 Hz, 1H), 4.02 (s, 3H).

Step 2: Synthesis of 2-methoxy-5-nitro-1,1'-biphenyl (161-B)

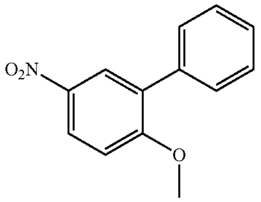 [SMILES: COc1ccc([N+](=O)[O-])cc1-c1ccccc1]

To a solution of 161-A (10.0 g, 43.1 mmol, 1.0 eq) and phenylboronic acid (21.0 g, 172 mmol, 4.0 eq) in dioxane (150 mL) was added a solution of potassium carbonate (11.9 g, 86.2 mmol, 2.0 eq) in water (15 mL) and 1,1-bis(diphenylphosphino)ferrocene]dichloropalladium(II) (1.58 g, 2.15 mmol, 0.050 eq). The suspension was degassed under vacuum and purged with nitrogen several times. The mixture was stirred under nitrogen at 80° C. for 16 hr. To the reaction mixture was added water (200 mL), and the reaction mixture was extracted with ethyl acetate (200 mL×3). The combined organic layer was dried over with sodium sulfate, filtered, concentrated under reduced pressure to give a residue. The crude product was purified by silica gel column chromatography (petroleum ether/ethyl acetate, from 1/0 to 10/1) to give 6.28 g (63% yield) of 161-B as a light brown solid.

LCMS: (ESI) m/z: 230.2 [M+H]$^+$.

Step 3: Synthesis of 5-nitro-[1,1'-biphenyl]-2-ol (161-C)

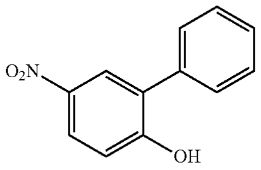 [SMILES: O=[N+]([O-])c1ccc(O)c(-c2ccccc2)c1]

To a solution of 161-B (6.28 g, 27.1 mmol, 1.0 eq) in N,N-dimethylacetamide (60 mL) was added lithium chloride (9.17 g, 216 mmol, 8.0 eq) at 25° C., the reaction mixture was stirred at 145° C. for 48 hr. To the reaction mixture was added water (300 mL), the mixture was extracted with ethyl acetate (300 mL×3), the combined organic layer was washed with brine (200 mL×3), dried over with sodium sulfate, filtered, concentrated under reduced pressure to give a residue. The crude product was purified by silica gel column chromatography (petroleum ether/ethyl acetate, from 10/1 to 5/1) to give 5.50 g (69% yield) of 161-C as a yellow solid.

LCMS: (ESI) m/z: 216.1 $[M+H]^+$.

Step 4: Synthesis of 3-iodo-5-nitro-[1,1'-biphenyl]-2-ol (161-D)

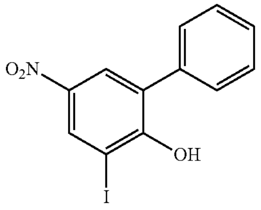 [SMILES: O=[N+]([O-])c1cc(I)c(O)c(-c2ccccc2)c1]

To a solution of 161-C (5.50 g, 18.7 mmol, 1.0 eq) in dimethyl sulfoxide (50 mL) was added iodine (13.0 g, 51.1 mmol, 2.7 eq), then the reaction mixture was stirred at 110° C. for 4 hr. To the reaction mixture was added saturated sodium thiosulfate (50 mL), and the mixture was extracted with ethyl acetate (30 mL×3). The combined organic layer was washed with brine (50 mL×3), dried over with sodium sulfate, filtered, concentrated under reduced pressure to give a residue. The crude product was purified by silica gel column chromatography (petroleum ether/ethyl acetate, from 1/0 to 10/1) to give 6.50 g (crude) of 161-D as yellow oil.

LCMS: (ESI) m/z: 342.0 $[M+H]^+$.

Step 5: Synthesis of 3-iodo-2-methoxy-5-nitro-1,1'-biphenyl (161-E)

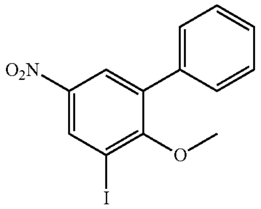 [SMILES: COc1c(I)cc([N+](=O)[O-])cc1-c1ccccc1]

To a solution of 161-D (5.00 g, 14.7 mmol, 1.0 eq) in N,N-dimethylformamide (50 mL) was added iodomethane (6.24 g, 44.0 mmol, 3.0 eq) and potassium carbonate (6.08 g, 44.0 mmol, 3.0 eq), the solution was stirred at 50° C. for 12 h. The solution was poured into water (100 mL), extracted with ethyl acetate (100 mL×3). The combined organic phase was washed with brine (100 mL), dried with anhydrous sodium sulfate, filtered and concentrated. The residue was purified by silica gel column chromatography (petroleum ether/ethyl acetate, from 1/0 to 10/1) to give 5.00 g (95% yield) of 161-E as a white solid.

LCMS: (ESI) m/z: 356.0 $[M+H]^+$.

$^1H$ NMR (400 Hz, $CDCl_3$-d) δ: 8.63 (d, J=2.4 Hz, 1H), 8.23 (d, J=2.8 Hz, 1H), 7.59-7.56 (m, 2H), 7.51-7.46 (m, 3H), 3.47 (s, 3H).

Step 6: Synthesis of 3-allyl-2-methoxy-5-nitro-1,1'-biphenyl (161-F)

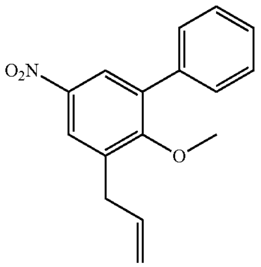 [SMILES: C=CCc1cc([N+](=O)[O-])cc(-c2ccccc2)c1OC]

A solution of 161-E (2.00 g, 5.57 mmol, 1.0 eq), cesium fluoride (3.39 g, 22.3 mmol, 4.0 eq) and tetrakis(triphenylphosphine)platinum (644 mg, 557 umol, 0.10 eq) in tetrahydrofuran (20 mL) was stirred at 20° C. under nitrogen for 30 mins. Then 2-allyl-4,4,5,5-tetramethyl-1,3,2-dioxaborolane (2.34 g, 13.9 mmol, 2.5 eq) in tetrahydrofuran (3 mL) was added. The suspension was stirred at 75° C. for 10 h. The reaction was concentrated in vacuo. The residue was purified by silica gel column chromatography (ethyl acetate/petroleum ether, from 0/1 to 1/2) to afford 1.05 g (70% yield) of 161-F as off-white solid.

$^1H$ NMR (400 MHz, $CDCl_3$-d) δ: 8.13 (d, J=2.8, 1H), 8.08 (d, J=2.8, 1H), 7.59-7.57 (m, 2H), 7.50-7.46 (m, 2H), 7.44-7.41 (m, 1H), 6.05-5.99 (m, 1H), 5.22-5.15 (m, 2H), 3.54 (d, J=6.4 Hz, 2H), 3.42 (s, 3H).

Step 7: Synthesis of 6-methoxy-5-propyl-[1,1'-biphenyl]-3-amine (161-G)

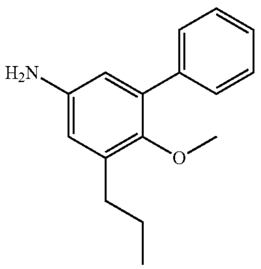 [SMILES: CCCc1cc(N)cc(-c2ccccc2)c1OC]

To a solution of 161-F (1.00 g, 3.71 mmol, 1.0 eq) in methanol (20 mL) was added Pd/C (0.100 g, 371 umol, 10% purity, 0.10 eq). The suspension was degassed and purged with hydrogen for three times. The reaction was stirred at 20° C. under hydrogen (15 psi) for 1 h. The suspension was filtered and the filtrate concentrated in vacuo. The residue was purified by silica gel column chromatography (ethyl acetate/petroleum ether=1/5) to give 0.750 g (75% yield) of 161-G as a yellow oil.

LCMS: (ESI) m/z: 242.1 $[M+H]^+$.

Step 8: Synthesis of 5-iodo-2-methoxy-3-propyl-1,1'-biphenyl (161-H)

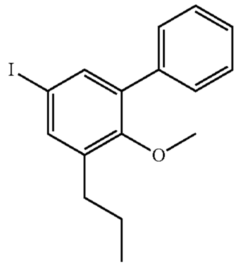 [SMILES: CCCc1cc(I)cc(-c2ccccc2)c1OC]

To a suspension of 161-G (0.750 g, 2.80 mmol, 1.0 eq) in hydrochloric acid (3 M, 2.93 mL, 3.14 eq) and acetonitrile (5 mL) was added sodium nitrite (289 mg, 4.20 mmol, 1.5 eq) in water (10 mL) at 0° C. The mixture was stirred at 0° C. for 10 mins. Then potassium iodide (2.32 g, 14.0 mmol, 5.0 eq) in water (5 mL) was added. The suspension was stirred at 0° C. for 20 min and at 60° C. for 1 h. The reaction was extracted with ethyl acetate (15 mL×3), the combined organic layer was washed with saturated aqueous sodium bisulfite solution (20 mL) and concentrated in vacuo. The residue was purified by silica gel column chromatography (petroleum ether/ethyl acetate, 1/10) to afford 0.850 g (86% yield) of 161-H as yellow oil.

$^1H$ NMR (400 MHz, $CDCl_3$-d) δ: 7.56-7.51 (m, 2H), 7.50 (q, J=2.4 Hz, 2H), 7.44-7.39 (m, 2H), 7.38-7.33 (m, 1H), 3.32 (s, 3H), 2.65-2.57 (t, J=7.6 Hz, 2H), 1.67 (m, 2H), 1.01 (t, J=7.2 Hz, 3H)

Step 9: Synthesis of tert-butyl 1-(6-methoxy-5-propyl-[1,1'-biphenyl]-3-yl)hydrazinecarboxylate (161-I)

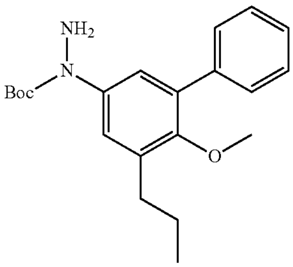 [SMILES: CCCc1cc(N(N)C(=O)OC(C)(C)C)cc(-c2ccccc2)c1OC]

To a solution of 161-H (0.500 g, 1.42 mmol, 1.0 eq), tert-butyl N-aminocarbamate (225 mg, 1.70 mmol, 1.2 eq) and cesium carbonate (694 mg, 2.13 mmol, 1.5 eq) in N,N-dimethylformamide (5 mL) was added cuprous iodide (27.0 mg, 142 umol, 0.10 eq) and 1,10-phenanthroline (51.2 mg, 284 umol, 0.20 eq). The reaction was stirred at 80° C. for 10 h. The reaction was diluted with ethyl acetate (10 mL) and filtered, the filtrate was concentrated in vacuo. The residue was purified by silica gel column chromatography (ethyl acetate/petroleum ether, 1/5) to afford 0.210 g (42% yield) of 161-I as yellow oil.

$^1H$ NMR (400 MHz, MeOD-$d_4$) δ: 7.56 (d, J=7.2 Hz, 2H), 7.42 (t, J=7.2 Hz, 2H), 7.38-7.31 (m, 1H), 7.22 (d, J=6.0 Hz, 2H), 3.31 (br s, 3H), 2.73-2.62 (m, 2H), 1.70 (qd, J=7.2, 15.2 Hz, 2H), 1.50 (s, 9H), 1.02 (t, J=7.2 Hz, 3H).

Step 10: Synthesis of (6-methoxy-5-propyl-[1,1'-biphenyl]-3-yl)hydrazine (161-J)

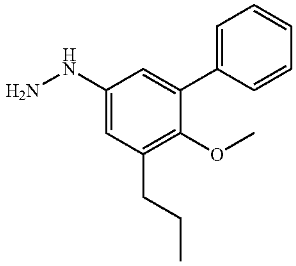 [SMILES: CCCc1cc(NN)cc(-c2ccccc2)c1OC]

A solution of 161-I (0.200 g, 561 umol, 1.0 eq) in hydrogen chloride/ethyl acetate (4 M, 1 mL, 7.1 eq) and ethyl acetate (4 mL) was stirred at 30° C. for 0.5 h. The mixture was stirred at 30° C. for another 2 h. The reaction mixture was concentrated in vacuo to give 0.180 g (crude, hydrochloride) of 161-J as light-yellow oil.

LCMS: (ESI) m/z: 257.1 $[M+H]^+$.

Step 11: Synthesis of 1-(6-methoxy-5-propyl-[1,1'-biphenyl]-3-yl)-3-methyl-1H-pyrazol-5(4H)-one (161-K)

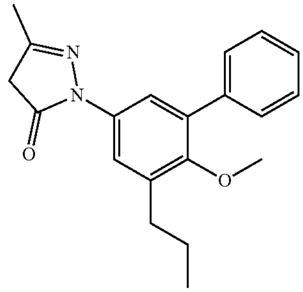 [SMILES: CCCc1cc(N2N=C(C)CC2=O)cc(-c2ccccc2)c1OC]

161-K was obtained via general procedure II from 161-J $^1H$ NMR (400 MHz, $CDCl_3$-d) δ: 7.68-7.55 (m, 2H), 7.45-7.27 (m, 5H), 3.43-3.27 (m, 3H), 2.74-2.54 (m, 2H), 2.33-2.08 (m, 3H), 1.73-1.64 (m, 2H), 1.05-0.91 (m, 3H).

Step 12: Synthesis of 4-nitrophenyl 1-(6-methoxy-5-propyl-[1,1'-biphenyl]-3-yl)-3-methyl-5-oxo-4,5-dihydro-1H-pyrazole-4-carboxylate (161-L)

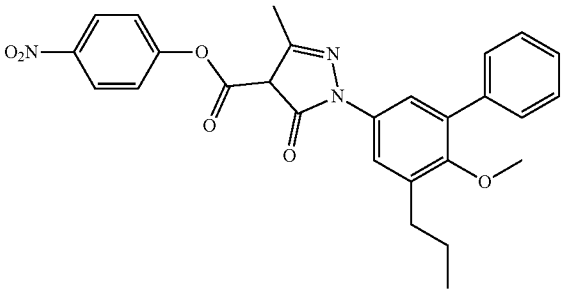 [SMILES: CCCc1cc(N2N=C(C)C(C(=O)Oc3ccc([N+](=O)[O-])cc3)C2=O)cc(-c2ccccc2)c1OC]

161-L was obtained via general procedure III from 161-K LCMS: (ESI) m/z: 488.0 $[M+H]^+$.

Step 13: Synthesis of N-(3-(1,1-difluoroethyl)phenyl)-1-(6-methoxy-5-propyl-[1,1'-biphenyl]-3-yl)-3-methyl-5-oxo-4,5-dihydro-1H-pyrazole-4-carboxamide (161)

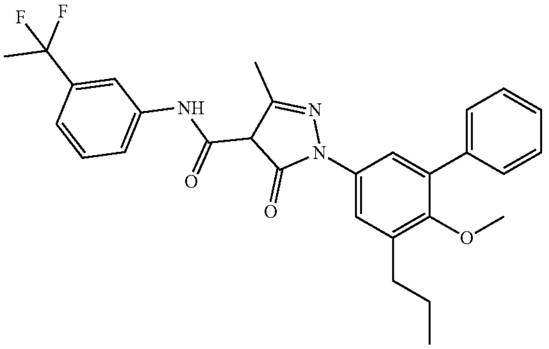 [SMILES: CCCc1cc(N2N=C(C)C(C(=O)Nc3cccc(C(C)(F)F)c3)C2=O)cc(-c2ccccc2)c1OC]

161 was obtained via general procedure from 161-L and 3-(1,1-difluoroethyl)aniline LCMS: (ESI) m/z: 506.5 $[M+H]^+$.

$^1$H NMR (400 MHz, MeOD-$d_4$) δ: 7.92 (s, 1H), 7.66-7.62 (m, 3H), 7.58 (br s, 2H), 7.46-7.41 (m, 2H), 7.40-7.33 (m, 2H), 7.18 (br d, J=7.6 Hz, 1H), 3.34 (s, 3H), 2.77 (t, J=7.6 Hz, 2H), 2.48 (s, 3H), 1.92 (t, J=18.4 Hz, 3H), 1.79-1.69 (m, 2H), 1.04 (t, J=7.2 Hz, 3H).

Synthesis of 160

Step 1: Synthesis of 1-methoxy-2-methyl-4-nitrobenzene (160-A)

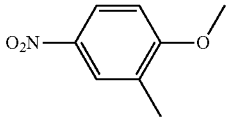

To a solution of 2-methyl-4-nitro-phenol (4.00 g, 26.1 mmol, 1.0 eq) and potassium carbonate (7.22 g, 52.2 mmol, 2.0 eq) in N,N-dimethylformamide (200 mL) was added iodomethane (14.8 g, 104 mmol, 4.0 eq) dropwise at 25° C., and the reaction mixture was stirred at 50° C. for 12 hr. To the reaction mixture was added water (500 mL). The suspension was filtrated and the filter cake was washed with water (300 mL). The solid was concentrated under reduced pressure to give 3.20 g (crude) of 160-A as an off-white solid.

LCMS: (ESI) m/z: 168.1 $[M+H]^+$.

Step 2: Synthesis of 1-iodo-2-methoxy-3-methyl-5-nitrobenzene (160-B)

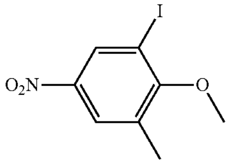

To a solution of 160-A (3.20 g, 19.1 mmol, 1.0 eq) and iodine (7.29 g, 28.7 mmol, 1.5 eq) in dichloromethane (30 mL) was added oxo((trifluoromethyl)sulfonyl)silver (7.38 g, 28.7 mmol, 1.5 eq) at 25° C., then the reaction was stirred at 30° C. for 12 hr. The reaction mixture was filtered, the filtrate was washed with saturated sodium thiosulfate (100 mL×2), and the water phase was extracted with dichloromethane (80 mL×3). The combined organic layer was washed with brine (100 mL×2), dried over with anhydrous sodium sulfate, filtered, concentrated under reduced pressure to give a residue. The crude product was purified by silica gel column chromatography (petroleum ether/ethyl acetate, from 10/1 to 5/1) to give 5.60 g (97% yield) of 160-B as a light brown solid.

LCMS: (ESI) m/z: 294.0 $[M+H]^+$.

Step 3: Synthesis of 2-methoxy-3-methyl-5-nitro-1,1'-biphenyl (160-C)

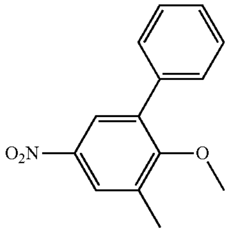 [SMILES: COc1c(C)cc([N+](=O)[O-])cc1-c1ccccc1]

To a solution of 160-B (5.60 g, 18.7 mmol, 1.0 eq) and phenylboronic acid (4.55 g, 37.3 mmol, 2.0 eq) in dioxane (50 mL) was added a solution of sodium bicarbonate (3.13 g, 37.3 mmol, 2.0 eq) in water (5 mL) and 1,1-bis(diphenylphosphino)ferrocene]dichloropalladium(II) (1.37 g, 1.87 mmol, 0.10 eq). The suspension was degassed under vacuum and purged with nitrogen several times. The mixture was stirred under nitrogen at 80° C. for 12 hr. To the reaction mixture was added water (100 mL), and the reaction mixture was extracted with ethyl acetate (100 mL×3). The combined organic phase was washed with brine, dried over with anhydrous sodium sulfate, filtered, concentrated under reduced pressure to give a residue. The crude product was purified by silica gel column chromatography (petroleum ether/ethyl acetate, from 1/0 to 10/1) to give 3.20 g (67% yield) of 160-C as a light yellow oil.

LCMS: (ESI) m/z: 244.1 $[M+H]^+$.

Step 4: Synthesis of 3-(bromomethyl)-2-methoxy-5-nitro-1,1'-biphenyl (160-D)

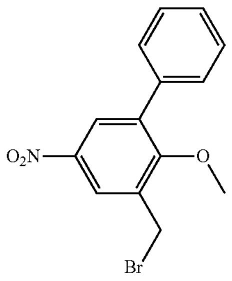 [SMILES: COc1c(CBr)cc([N+](=O)[O-])cc1-c1ccccc1]

To a solution of 160-C (3.20 g, 12.5 mmol, 1.0 eq) in carbon tetrachloride (30 mL) was added dropwise a solution of benzoyl peroxide (605 mg, 2.50 mmol, 0.20 eq) and 1-bromopyrrolidine-2,5-dione (3.34 g, 18.7 mmol, 1.5 eq) in carbon tetrachloride (30 mL) at 0° C., the reaction mixture was stirred at 80° C. for 12 hr. The reaction was washed with water (25 mL×2), the combined aqueous layer was extracted with dichloromethane (25 mL×3). The combined organic layer was washed with brine (100 mL), dried over with anhydrous sodium sulfate, filtered, concentrated under reduced pressure to give a residue. The crude product was purified by silica gel column chromatography (petroleum ether/ethyl acetate, from 1/0 to 10/1) to give 3.50 g (87% yield) of 160-D as a light yellow oil.

LCMS: (ESI) m/z: 324.1 $[M+H]^+$.

Step 5: Synthesis of 1-((2-methoxy-5-nitro-[1,1'-biphenyl]-3-yl)methyl)-1H-imidazole (160-E)

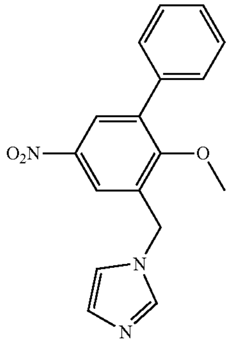

To a solution of 160-D (3.50 g, 10.9 mmol, 1.0 eq) in dichloromethane (10 mL) was added imidazole (7.40 g, 109 mmol, 10 eq) at 25° C., then the reaction mixture was stirred at 25° C. for 12 hr. To the reaction mixture was added water (10 mL), then the mixture was extracted with dichloromethane (20 mL×3). The combined organic layer was washed with brine (30 mL), dried over anhydrous sodium sulfate, filtered, concentrated under reduced pressure to give a residue. The crude product was purified by silica gel column chromatography (ethyl acetate/methanol, from 1/0 to 3/1) to give 1.50 g (45% yield) of 160-E as a light yellow oil.

LCMS: (ESI) m/z: 310.0 $[M+H]^+$.

Step 6: Synthesis of 5-((1H-imidazol-1-yl)methyl)-6-methoxy-[1,1'-biphenyl]-3-amine (160-F)

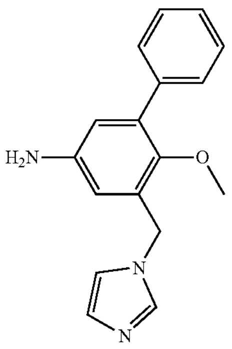 [SMILES: COc1c(Cn2ccnc2)cc([N+](=O)[O-])cc1-c1ccccc1]

To a solution of 160-E (1.50 g, 4.85 mmol, 1.0 eq) in ethanol (20 mL)/water (5 mL) was added iron powder (1.35 g, 24.3 mmol, 5.0 eq) and ammonium chloride (1.30 g, 24.3 mmol, 5.0 eq). The suspension was stirred at 50° C. for 2 hours. The suspension was filtered and the filtrate was concentrated to give a residue. The residue was partitioned between ethyl acetate (40 mL) and water (40 mL). The aqueous layer was extracted with ethyl acetate (30 mL×2). The combined organic layer was washed with brine (50 mL), dried over anhydrous sodium sulfate, filtered and concentrated to give 900 mg (64% yield) of 160-F as a yellow oil.

LCMS: (ESI) m/z: 280.1 $[M+H]^+$.

Step 7: Synthesis of 1-((5-hydrazinyl-2-methoxy-[1,1'-biphenyl]-3-yl)methyl)-1H-imidazole (160-G)

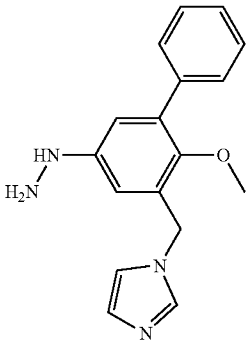 [SMILES: COc1c(Cn2ccnc2)cc(NN)cc1-c1ccccc1]

160-G was obtained via general procedure I from 160-F.

LCMS: (ESI) m/z: 295.1 $[M+H]^+$.

Step 8: Synthesis of 1-(5-((1H-imidazol-1-yl)methyl)-6-methoxy-[1,1'-biphenyl]-3-yl)-3-methyl-1H-pyrazol-5(4H)-one (160-H)

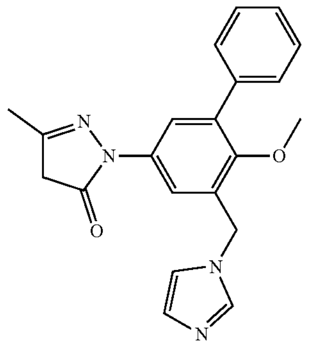

160-H was obtained via general procedure II from 160-G. LCMS: (ESI) m/z: 361.4 $[M+H]^+$.

Step 9: Synthesis of 4-nitrophenyl 1-(5-((1H-imidazol-1-yl)methyl)-6-methoxy-[1,1'-biphenyl]-3-yl)-3-methyl-5-oxo-4,5-dihydro-1H-pyrazole-4-carboxylate (160-I)

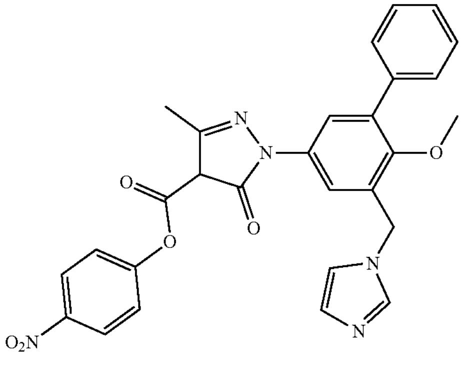 [SMILES: COc1c(Cn2ccnc2)cc(N2N=C(C)C(C(=O)Oc3ccc([N+](=O)[O-])cc3)C2=O)cc1-c1ccccc1]

160-I was obtained via general procedure III from 160-H. LCMS: (ESI) m/z: 526.1 $[M+H]^+$.

Step 10: Synthesis of 1-(5-((1H-imidazol-1-yl)methyl)-6-methoxy-[1,1'-biphenyl]-3-yl)-N-(3-(1,1-difluoroethyl)phenyl)-3-methyl-5-oxo-4,5-dihydro-1H-pyrazole-4-carboxamide (160)

Compound ID: 160

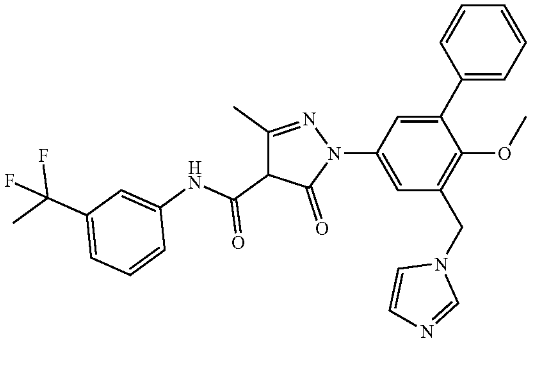

160 was obtained via general procedure IV from 160-I. LCMS: (ESI) m/z: 544.4 $[M+H]^+$.

$^1$H NMR (400 MHz, DMSO-d) δ: 11.26 (s, 1H), 8.21 (s, 3H), 7.90-7.87 (m, 2H), 7.77 (s, 1H), 7.57-7.55 (m, 2H), 7.48 (t, J=7.6 Hz, 2H), 7.39 (t, J=3.2 Hz, 1H), 7.34-7.26 (m, 2H), 7.19 (s, 1H), 7.04 (d, J=7.6 Hz, 1H), 6.91 (s, 1H), 5.24 (s, 2H), 3.19 (s, 3H), 2.24 (s, 3H), 1.94 (t, J=21.6 Hz, 3H).

Synthesis of 159

Step 1: Synthesis of N-(3-(1,1-difluoroethyl)phenyl)-1-(4-(difluoromethoxy)phenyl)-4-ethyl-3-methyl-5-oxo-4,5-dihydro-1H-pyrazole-4-carboxamide (159)

Compound ID: 159

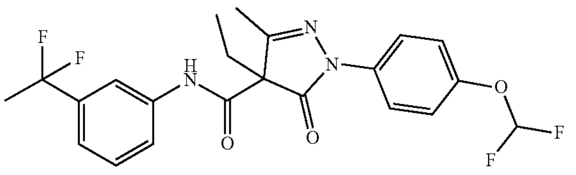

To a solution of 172 (0.100 g, 183 umol, 1.0 eq) in tetrahydrofuran (2 mL) was ethylmagnesium bromide (1 M, 275 uL, 1.5 eq) at −78° C. The mixture was stirred at −78° C. for 0.5 hr. The mixture was quenched with saturated ammonium chloride aqueous (10 mL) and extracted with ethyl acetate (10 mL×2). The combined organic layer was washed with brine (10 mL), dried over sodium sulfate, filtered and concentrated. The residue was purified by prep-TLC (petroleum ether/ethyl acetate, 5/1) to give 3.00 mg (4% yield) of 159 as a yellow oil.

LCMS: (ESI) m/z: 452.2 $[M+H]^+$.

$^1$H NMR: (400 MHz, MeOD-$d_4$) δ: 7.97 (d, J=8.0 Hz, 2H), 7.78 (s, 1H), 7.62 (d, J=8.4 Hz, 1H), 7.41 (t, J=8.0 Hz, 1H), 7.31 (d, J=7.6 Hz, 1H), 7.22 (d, J=9.2 Hz, 2H), 6.82 (t, J=74.0 Hz, 1H), 2.43-2.36 (m, 1H), 2.33 (s, 3H), 2.32-2.22 (m, 1H), 1.90 (t, J=18.4 Hz, 3H), 0.86 (t, J=7.2 Hz, 3H).

Synthesis of 158

Step 1: Synthesis of 4-allyl-N-(3-(1,1-difluoroethyl)phenyl)-1-(4-(difluoromethoxy)phenyl)-3-methyl-5-oxo-4,5-dihydro-1H-pyrazole-4-carboxamide (158-A)

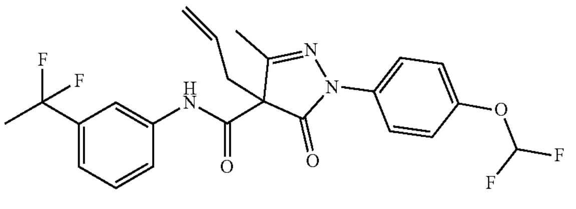 [SMILES: C=CCC1(C(=O)Nc2cccc(C(C)(F)F)c2)C(=O)N(c2ccc(OC(F)F)cc2)N=C1C]

A mixture of 298i (100 mg, 236 umol, 1.0 eq), 3-iodoprop-1-ene (59.5 mg, 354 umol, 1.5 eq) and tetrabutylammonium fluoride (1 M, 354 uL, 1.5 eq) in tetrahydrofuran (5 mL) was stirred at 10° C. for 12 h. The mixture was diluted with water (20 mL) and extracted with ethyl acetate (20 mL×2). The combined organic layer was washed with brine (20 mL), dried over sodium sulfate, filtered and concentrated. The residue was purified by silica gel column chromatography (petroleum ether/ethyl acetate, 20/1) to afford 60.0 mg impure product. The impure product was purified by prep-HPLC (column: Phenomenex Synergi C18 150*30 mm*4 um; mobile phase: [water (0.225% formic acid)-acetonitrile]; B %: 55%-85%, 10 min) to give 10.0 mg (9% yield) of 158-A as a white solid.

LCMS: (ESI) m/z: 464.2 $[M+H]^+$.

Step 2: Synthesis of N-(3-(1,1-difluoroethyl)phenyl)-1-(4-(difluoromethoxy)phenyl)-3-methyl-5-oxo-4-propyl-4,5-dihydro-1H-pyrazole-4-carboxamide (158)

Compound ID: 158

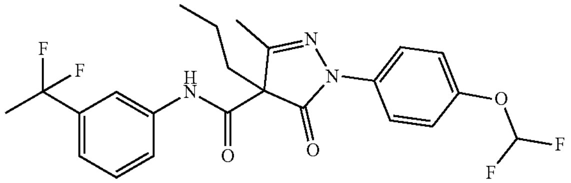

To a solution of 158-A (20.0 mg, 43.2 umol, 1.0 eq) in methanol (3 mL) was added Pd/C (10.0 mg, 10% purity) under nitrogen atmosphere. The suspension was degassed and purged with hydrogen for 3 times. The mixture was stirred under hydrogen (15 psi) at 20° C. for 1 hr. The mixture was filtered and the filtrate was concentrated. The residue was purified by prep-HPLC (column: Phenomenex Synergi C18 150*25*10 um; mobile phase: [water (0.225% formic acid)-acetonitrile]; B %: 68%-98%, 9 min) to give 2.00 mg (10% yield) of 158 as a yellow oil.

LCMS: (ESI) m/z: 466.2 $[M+H]^+$.

$^1H$ NMR: (400 MHz, MeOD-$d_4$) δ: 7.96 (d, J=9.2 Hz, 2H), 7.78 (s, 1H), 7.63 (d, J=8.4 Hz, 1H), 7.42 (t, J=8.0 Hz, 1H), 7.31 (d, J=7.2 Hz, 1H), 7.22 (d, J=9.2 Hz, 2H), 6.82 (t, J=74.0 Hz, 1H), 2.35-2.19 (m, 5H), 1.90 (t, J=18.4 Hz, 3H), 1.28-1.13 (m, 2H), 0.97 (t, J=7.2 Hz, 3H).

Synthesis of 157

Step 1: Synthesis of N-(3-chloro-5-methyl-phenyl)-1-[4-(difluoromethoxy)phenyl]-3,4-dimethyl-5-oxo-pyrazole-4-carboxamide (157)

Compound ID: 157

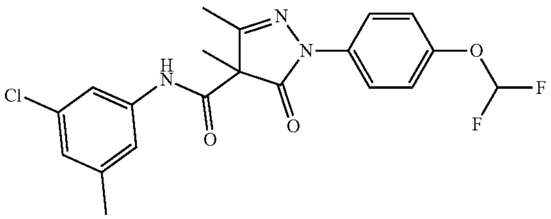

157 was obtained via similar procedure of 167 from 393-A and iodomethane

LCMS: (ESI) m/z: 422.0 $[M+H]^+$.

$^1H$ NMR (400 MHz, MeOD-$d_4$) δ: 7.96 (d, J=8.8 Hz, 2H), 7.51 (s, 1H), 7.27 (s, 1H), 7.21 (d, J=9.2 Hz, 2H), 6.99 (s, 1H), 6.82 (t, J=74 Hz, 1H), 2.32 (s, 3H), 2.29 (s, 3H), 1.75 (s, 3H)

Synthesis of N-(3-(1,1-difluoroethyl)phenyl)-1-(4-(difluoromethoxy)phenyl)-5-ethyl-3-methyl-1H-pyrazole-4-carboxamide (156)

Compound ID: 156

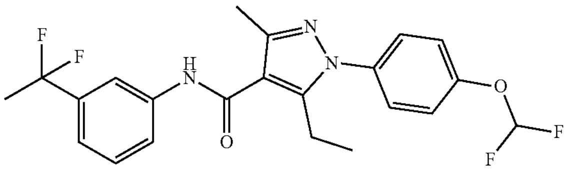

156 was obtained via similar procedure of 179 from 156-C and 3-(1,1-difluoroethyl)aniline LCMS: (ESI) m/z: 436.0 $[M+H]^+$.

$^1H$ NMR (400 MHz, MeOD-$d_4$) δ: 7.88 (s, 1H), 7.71 (d, J=8.0 Hz, 1H), 7.51-7.53 (m, 2H), 7.45 (t, J=8.0 Hz, 1H), 7.29-7.35 (m, 3H), 6.94 (t, J=73.6 Hz, 1H), 2.87 (q, J=7.6 Hz, 2H), 2.42 (s, 3H), 1.93 (t, J=18.22 Hz, 3H), 1.27 (t, J=7.6 Hz, 3H).

Synthesis of 155

Step 1: Synthesis of ethyl 1-(4-(difluoromethoxy)phenyl)-3-ethyl-5-methyl-1H-pyrazole-4-carboxylate (155-A)

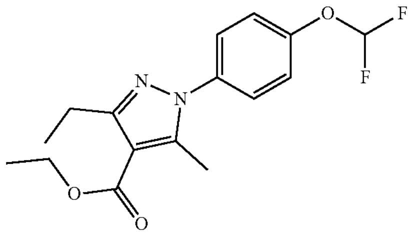 [SMILES: CCOC(=O)c1c(CC)nn(-c2ccc(OC(F)F)cc2)c1C]

155-A was obtained via similar procedure of 156-B from 156-A and (4-(difluoromethoxy)phenyl)hydrazine LCMS: (ESI) m/z: 325.1 $[M+H]^+$.

Step 2: Synthesis of 1-(4-(difluoromethoxy)phenyl)-3-ethyl-5-methyl-1H-pyrazole-4-carboxylic acid (155-B)

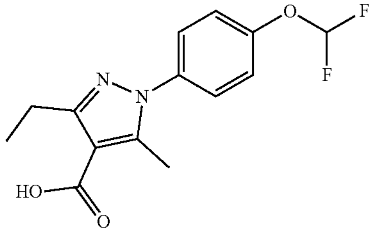 [SMILES: CCc1nn(-c2ccc(OC(F)F)cc2)c(C)c1C(=O)O]

155-B was obtained via similar procedure of 156-C from 156-B and sodium hydroxide.

LCMS: (ESI) m/z: 297.5 [M+H]+.

Step 3: Synthesis of N-(3-(1,1-difluoroethyl)phenyl)-1-(4-(difluoromethoxy)phenyl)-3-ethyl-5-methyl-1H-pyrazole-4-carboxamide (155)

Compound ID : 155

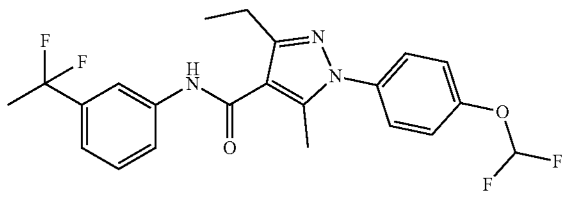

155 was obtained via similar procedure of 179 from 155-B and 3-(1,1-difluoroethyl)aniline LCMS: (ESI) m/z: 436.2 [M+H]+.

$^1$H NMR (400 MHz, MeOD-$d_4$) δ: 7.89 (s, 1H), 7.71 (d, J=8.0 Hz, 1H), 7.49-7.52 (m, 2H), 7.45 (t, J=8.0 Hz, 1H), 7.29-7.36 (m, 3H), 6.96 (t, J=73.6 Hz, 1H), 2.87 (q, J=7.6 Hz, 2H), 2.44 (s, 3H), 1.94 (t, J=18.0 Hz, 3H), 1.08 (t, J=7.6 Hz, 3H).

Synthesis of 154

Step 1: Synthesis of ethyl 2-(cyclopentanecarbonyl)-3-oxo-butanoate (154-A)

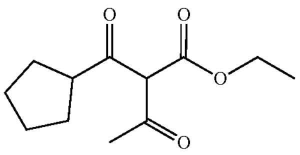 [SMILES: CCOC(=O)C(C(C)=O)C(=O)C1CCCC1]

To a solution of ethyl 3-oxobutanoate (5.00 g, 38.4 mmol, 1.0 eq) in dichloromethane (50 mL) was added magnesium chloride (7.32 g, 76.8 mmol, 2.0 eq) and pyridine (6.08 g, 76.8 mmol, 2.0 eq). The suspension was degassed under vacuum and purged with nitrogen several times. The mixture was stirred under nitrogen at 0° C. for 1 hr. Then to the reaction mixture was added a solution of cyclopentanecarbonyl chloride (5.09 g, 38.4 mmol, 1.0 eq) in dichloromethane (25 mL) dropwise at 0° C., the mixture was stirred at 20° C. under nitrogen for 1 hr. The solution was poured into water (100 mL), extracted with dichloromethane (100 mL×3). The combined organic phase was washed with brine (100 mL), dried with anhydrous sodium sulfate, filtered and concentrated. The residue was purified by silica column (petroleum ether/ethyl acetate, from 1/0 to 10/1) to give 3.00 g (34% yield) of 154-A as a yellow oil.

LCMS: (ESI) m/z: 272.2 [M+H]+.

Step 2: Synthesis of ethyl 2-(cyclopentanecarbonyl)-3-oxo-butanoate (154-B)

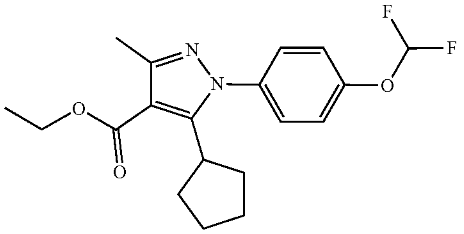 [SMILES: CCOC(=O)c1c(C)nn(-c2ccc(OC(F)F)cc2)c1C1CCCC1]

154-B was obtained via general procedure II from 154-A

LCMS: (ESI) m/z: 365.2 [M+H]+.

$^1$H NMR: (400 MHz, $CDCl_3$-d) δ:7.39-7.35 (m, 2H), 7.26-7.23 (m, 2H), 6.57 (t, J=73.2 Hz, 1H), 4.33 (dd, J=14.4 Hz, 6.8 Hz, 2H), 3.15-3.05 (m, 1H), 2.47 (s, 3H), 2.27-2.08 (m, 2H), 1.90-1.79 (m, 4H), 1.60-1.54 (m, 2H), 1.39 (t, J=6.8 Hz, 3H).

Step 3: Synthesis of 5-cyclopentyl-1-[4-(difluoromethoxy)phenyl]-3-methyl-pyrazole-4-carboxylic acid (154-C)

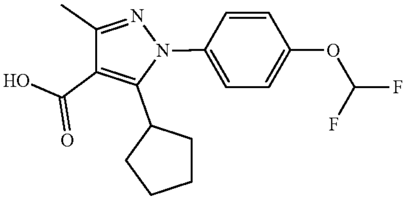 [SMILES: Cc1nn(-c2ccc(OC(F)F)cc2)c(C2CCCC2)c1C(=O)O]

To a solution of 154-B (250 mg, 663 umol, 1.0 eq) in methanol (4 mL) and water (4 mL) was added sodium hydroxide (265 mg, 6.63 mmol, 10 eq), the solution was stirred at 50° C. for 12 h. The solution was concentrated. The residue was diluted with water (10 mL), the pH of the mixture was adjusted to 2 with hydrochloric acid (1 M). The suspension was filtered and washed with water (10 mL×3). The filter cake was dried in vacuum. The residue was purified by silica column (petroleum ether/ethyl acetate, from 3/1 to 1/1) to give 160 mg (71% yield) of 154-C as a white solid.

LCMS: (ESI) m/z: 337.1 [M+H]+.

Step 4: Synthesis of 5-cyclopentyl-N-[3-(1,1-difluoroethyl)phenyl]-1-[4-(difluoromethoxy)phenyl]-3-methyl-pyrazole-4-carboxamide (154)

Compound ID: 154

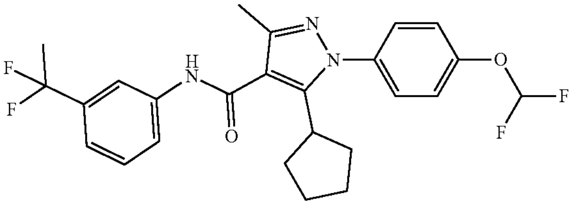

To a solution of 154-C (160 mg, 476 umol, 1.0 eq) in pyridine (5 mL) was added 3-(1,1-difluoroethyl)aniline (150 mg, 951 umol, 2.0 eq) and N-[3-(dimethylamino)propyl]-N-ethylcarbodiimide hydrochloride (182 mg, 951 umol, 2.0 eq), the solution was stirred at 70° C. for 5 h. The solution was concentrated. The residue was purified by prep-HPLC (column: Phenomenex Synergi C18 150*25*10 um; mobile phase: [water (0.225% formic acid)-acetonitrile]; B %: 54%-84%, 10 min) to give 25.6 mg (11% yield) of 154 as a white solid.

LCMS: (ESI) m/z: 476.1 $[M+H]^+$.

$^1$H NMR: (400 MHz, MeOD-$d_4$) δ: 7.87 (s, 1H), 7.71 (d, J=8.4 Hz, 1H), 7.47-7.42 (m, 3H), 7.35-7.30 (m, 3H), 6.95 (t, J=73.2 Hz, 1H), 3.06-2.97 (m, 1H), 2.36 (s, 3H), 1.98-1.89 (m, 7H), 1.79-1.69 (m, 2H), 1.56-1.48 (m, 2H).

Synthesis of 153

Step 1: Synthesis of ethyl 2-(4-methoxyphenyl)-5-methyloxazole-4-carboxylate (153-A)

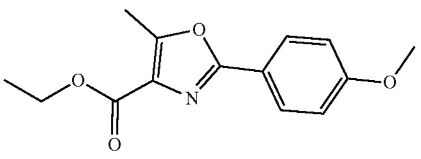 [SMILES: CCOC(=O)c1nc(-c2ccc(OC)cc2)oc1C]

To a solution of (4-methoxyphenyl)methanamine (2.00 g, 14.6 mmol, 1.5 eq) in N, N-dimethyl-formamide (20 mL) was added ethyl 3-oxobutanoate (1.26 g, 9.72 mmol, 1.0 eq), copper acetate monohydrate (194 mg, 972 umol, 0.10 eq), tert-butyl hydroperoxide (1.75 g, 19.4 mmol, 2.0 eq) and iodine (2.96 g, 11.7 mmol, 1.2 eq), the suspension was stirred at 25° C. for 4 h. The solution was poured into water (20 mL), extracted with ethyl acetate (30 mL×3). The combined organic phase was washed with brine (50 mL), dried with anhydrous sodium sulfate, filtered and concentrated. The residue was purified by silica column (petroleum ether/ethyl acetate, from 10/1 to 5/1) to give 600 mg (19% yield) of 153-A as a white solid.

LCMS: (ESI) m/z: 262.2 $[M+H]^+$.

$^1$H NMR: (400 MHz, $CDCl_3$-d) δ: 8.01-7.99 (m, 2H), 6.96-6.94 (m, 2H), 4.41 (dd, J=14.4 Hz, 7.2 Hz, 2H), 3.86 (s, 3H), 2.68 (s, 3H), 1.41 (t, J=7.2 Hz, 3H).

Step 2: Synthesis of 2-(4-methoxyphenyl)-5-methyl-oxazole-4-carboxylic acid (153-B)

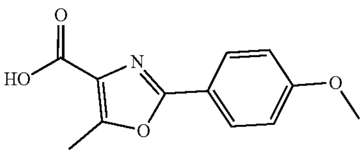 [SMILES: COc1ccc(-c2nc(C(=O)O)c(C)o2)cc1]

153-B was obtained via similar procedure of 154-C from 153-A and sodium hydroxide.

LCMS: (ESI) m/z: 234.2 $[M+H]^+$.

Step 3: Synthesis of N-[3-(1,1-difluoroethyl)phenyl]-2-(4-methoxyphenyl)-5-methyl-oxazole-4-carboxamide (153)

Compound ID: 153

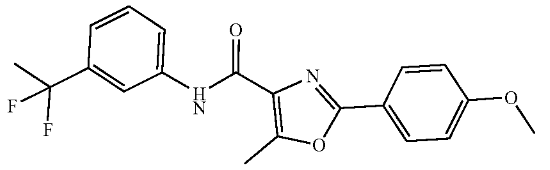

153 was obtained via similar procedure of 154 from 153-B.

LCMS: (ESI) m/z: 373.1 $[M+H]^+$.

$^1$H NMR: (400 MHz, DMSO-d) δ: 10.11 (s, 1H), 8.13 (s, 1H), 8.01 (d, J=8.8 Hz, 2H), 7.96 (d, J=8.0 Hz, 1H), 7.47 (t, J=12.0 Hz, 1H), 7.29 (d, J=7.6 Hz, 1H), 7.13 (d, J=8.8 Hz, 2H), 3.85 (s, J=3H), 2.70 (s, 3H), 1.98 (t, J=18.8 Hz, 3H).

Synthesis of 152

Step 1: Synthesis of ethyl 1-[3-bromo-4-(difluoromethoxy)phenyl]-5-ethyl-3-methyl-pyrazole-4-carboxylate (152-A)

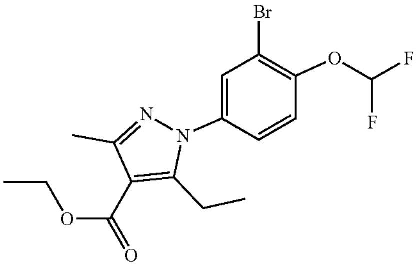 [SMILES: CCOC(=O)c1c(C)nn(-c2ccc(OC(F)F)c(Br)c2)c1CC]

A mixture of 156-A (2.00 g, 10.7 mmol, 1.0 eq) and 179-B (3.73 g, 12.9 mmol, 1.2 eq, hydrochloride) was dissolved in acetic acid (20 mL). It was stirred at 50° C. for 30 min. The mixture was concentrated under reduced pressure to give a residue. The residue was purified by column chromatography on silica gel (petroleum ether/ethyl acetate=1/0 to 10/1) to obtain 3.00 g (61% yield) of 152-A as a red solid.

$^1$H NMR (400 MHz, MeOD-$d_4$) δ: 7.82 (d, J=2.0 Hz, 1H), 7.49 (d, J=2.4 Hz, 1H), 7.47 (s, 1H), 7.00 (t, J=72.8 Hz, 1H), 4.33 (q, J=7.2 Hz, 2H), 2.90 (q, J=7.2 Hz, 2H), 2.44 (s, 3H), 1.38 (t, J=7.2 Hz, 3H), 1.14 (t, J=7.6 Hz, 3H)

Step 2: Synthesis of ethyl 1-[4-(difluoromethoxy)-3-(3-pyridyl)phenyl]-5-ethyl-3-methyl-pyrazole-4-carboxylate (152-B)

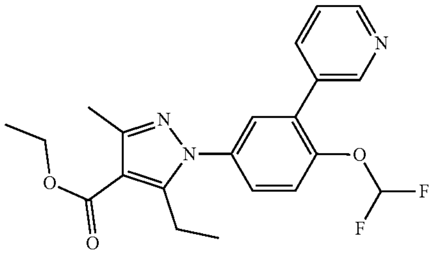 [SMILES: CCOC(=O)c1c(C)nn(-c2ccc(OC(F)F)c(-c3cccnc3)c2)c1CC]

A mixture of 152-A (400 mg, 878 umol, 1.0 eq), 3-(4,4,5,5-tetramethyl-1,3,2-dioxaborolan-2-yl)pyridine (269 mg, 1.31 mmol, 1.5 eq), 1,1-bis(diphenylphosphino)ferrocene] dichloropalladium(II) (32.0 mg, 43.8 umol, 0.050 eq), sodium hydrogen carbonate (147 mg, 1.75 mmol, 2.0 eq) in water (2 mL) and dioxane (10 mL) was stirred at 90° C. for 12 h under nitrogen. The reaction was diluted with water (40 mL). Then it was extracted with ethyl acetic (50 mL×2) and the organic layer was washed with water (100 mL×3) and brine (100 mL). The organic layer was dried over sodium sulfate, filtered and concentrated to obtain the crude product. The residue was purified by column chromatography on silica gel (petroleum ether/ethyl acetate, from 1/0 to 10/1). The residue was further purified by prep-HPLC (column: Waters Xbridge 150*25 mm*5 um; mobile phase: [water (0.05% ammonia hydroxide v/v)-acetonitrile]; B %: 53%-55%, 10 min). Then it was extracted with dichloromethane (20 mL×2) and dried over sodium sulfate, filtered and concentrated to obtain 190 mg (54% yield) of 152-B as a yellow solid.

$^1$H NMR (400 MHz, MeOD-$d_4$) δ: 8.73 (d, J=1.6 Hz, 1H), 8.58 (dd, J=1.6, 3.6 Hz, 1H), 8.05~8.03 (m, 1H), 7.61~7.53 (m, 4H), 6.94 (t, J=73.2 Hz, 2H), 4.33 (q, J=7.2 Hz, 2H), 2.95 (q, J=7.2 Hz, 2H), 2.46 (s, 3H), 1.38 (t, J=7.2 Hz, 3H), 1.17 (t, J=7.6 Hz, 3H).

Step 3: Synthesis of 1-[4-(difluoromethoxy)-3-(3-pyridyl)phenyl]-5-ethyl-3-methyl-pyrazole-4-carboxylic acid (152-C)

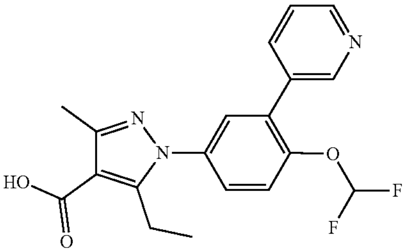 [SMILES: CCc1c(C(=O)O)c(C)nn1-c1ccc(OC(F)F)c(-c2cccnc2)c1]

A mixture of 152-B (190 mg, 473 umol, 1.0 eq) and sodium hydroxide (94.7 mg, 2.37 mmol, 5.0 eq) in ethanol (3 mL) and water (1 mL) was stirred at 50° C. for 12 h. The reaction mixture was diluted with water (40 mL) and adjusted pH to 7 with hydrochloric acid (1 M). Then it was extracted with ethyl acetic (30 mL×2) and the organic layer was washed with brine (100 mL). The organic layer was dried over sodium sulfate, filtered and concentrated to obtain 140 mg (crude) of 152-C as a yellow solid.

LCMS: (ESI) m/z: 374.1 [M+H]$^+$.

Step 4: Synthesis of N-[3-(1,1-difluoroethyl)phenyl]-1-[4-(difluoromethoxy)-3-(3-pyridyl)phenyl]-5-ethyl-3-methyl-pyrazole-4-carboxamide (152)

Compound ID: 152

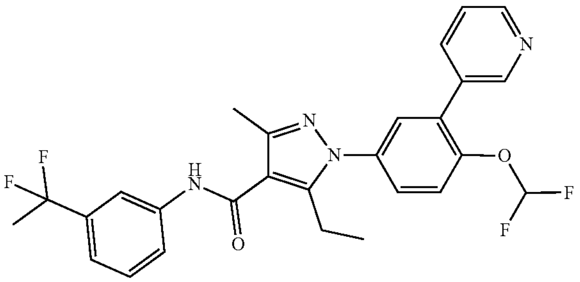

To a solution of 152-C (140 mg, 375 umol, 1.0 eq) and 3-(1,1-difluoroethyl)aniline (58.93 mg, 375 umol, 1.0 eq) in pyridine (3 mL) was added N-[3-(Dimethylamino)propyl]-N-ethylcarbodiimide hydrochloride (108 mg, 562 umol, 1.5 eq). It was stirred at 70° C. for 12 h. The mixture was concentrated under reduced pressure to remove pyridine. Then it was diluted with water (30 mL) and extracted with ethyl acetic (30 mL×2). The organic layer was washed with water (50 mL×3) and brine (50 mL). The organic layer was dried over sodium sulfate, filtered and concentrated to obtain the crude product. The residue was purified by prep-HPLC (column: Waters Xbridge 150*25 5 um; mobile phase: [water (10 mM ammonium bicarbonate)-acetonitrile]; B %: 36%-66%, 10 min). Then it was freeze-dried to obtain 42.5 mg (22% yield) of 152 as a white solid.

LCMS: (ESI) m/z: 513.2 [M+H]$^+$.

$^1$H NMR (400 MHz, MeOD-$d_4$) δ: 8.74 (d, J=1.6 Hz, 1H), 8.59 (dd, J=4.8, 1.2 Hz, 1H), 8.05 (dt, J=8.4, 2.0 Hz, 1H), 7.89 (s, 1H), 7.72 (d, J=8.0 Hz, 1H), 7.62~7.52 (m, 4H), 7.45 (t, J=8.0 Hz, 1H), 7.31 (d, J=7.6 Hz, 1H), 6.94 (t, J=72.8 Hz, 1H), 2.94 (q, J=7.6 Hz, 2H), 2.45 (s, 3H), 1.94 (t, J=18.4 Hz, 3H), 1.13 (t, J=7.6 Hz, 3H).

Synthesis of 151

Step 1: Synthesis of ethyl 1-[4-(difluoromethoxy)-3-phenyl-phenyl]-5-ethyl-3-methyl-pyrazole-4-carboxylate (151-A)

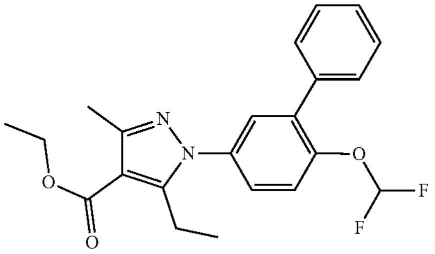 [SMILES: CCOC(=O)c1c(C)nn(-c2ccc(OC(F)F)c(-c3ccccc3)c2)c1CC]

151-A was obtained via similar procedure of 152-B from 152-A and phenylboronic acid.

$^1$H NMR (400 MHz, MeOD-$d_4$) δ: 7.55~7.39 (m, 8H), 6.82 (t, J=73.2 Hz, 2H), 4.33 (q, J=7.2 Hz, 2H), 2.94 (q, J=7.2 Hz, 2H), 2.45 (s, 3H), 1.38 (t, J=7.2 Hz, 3H), 1.16 (t, J=7.2 Hz, 3H).

Step 2: Synthesis of 1-[4-(difluoromethoxy)-3-phenyl-phenyl]-5-ethyl-3-methyl-pyrazole-4-carboxylic acid (151-B)

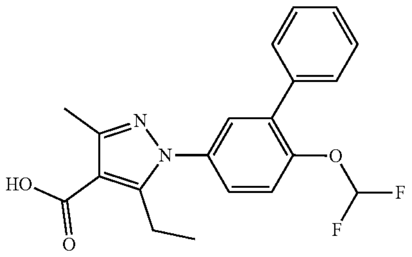

151-B was obtained via similar procedure of 152-C from 151-A and sodium hydroxide.

LCMS: (ESI) m/z: 373.1 [M+H]$^+$.

Step 3: Synthesis of N-[3-(1,1-difluoroethyl)phenyl]-1-[4-(difluoromethoxy)-3-phenyl-phenyl]-5-ethyl-3-methyl-pyrazole-4-carboxamide (151)

Compound ID: 151

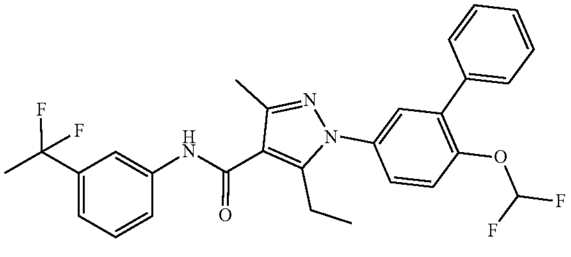

151 was obtained via similar procedure of 152 from 151-C and 3-(1,1-difluoroethyl)aniline.

LCMS: (ESI) m/z: 512.2 [M+H]$^+$.

$^1$H NMR (400 MHz, MeOD-$d_4$) δ: 7.89 (s, 1H), 7.71 (d, J=7.2 Hz, 1H), 7.56~7.41 (m, 9H), 7.31 (d, J=7.2 Hz, 1H), 6.82 (t, J=73.6 Hz, 1H), 2.93 (q, J=7.6 Hz, 2H), 2.45 (s, 3H), 1.94 (t, J=18.0 Hz, 3H), 1.13 (t, J=7.6 Hz, 3H).

Synthesis of 150

Step 1: Synthesis of ethyl 2-acetyl-5-methyl-3-oxohexanoate (150-A)

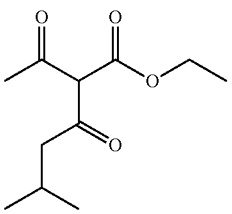

150-A was obtained via similar procedure of 156-A from ethyl 3-oxobutanoate and 3-methylbutanoyl chloride $^1$H NMR (400 MHz, DMSO-$d_4$) δ: 4.18-4.25 (m, 1H), 2.23-2.50 (m, 3H), 1.93-2.07 (m, 4H), 1.19-1.28 (m, 2H), 0.75-0.91 (m, 6H).

Step 2: Synthesis of ethyl 1-(4-(difluoromethoxy)phenyl)-5-isobutyl-3-methyl-1H-pyrazole-4-carboxylate (150-B)

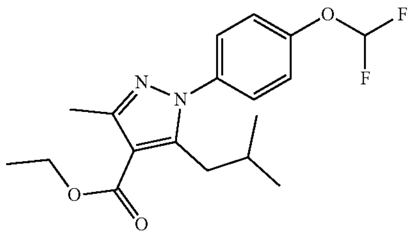 [SMILES: CCOC(=O)c1c(C)nn(-c2ccc(OC(F)F)cc2)c1CC(C)C]

150-B was obtained via similar procedure of 156-B from 150-A and (4-(difluoromethoxy)phenyl)hydrazine LCMS: (ESI) m/z: 353.1 [M+H]$^+$.

Step 3: Synthesis of 1-(4-(difluoromethoxy)phenyl)-5-isobutyl-3-methyl-1H-pyrazole-4-carboxylic acid (150-C)

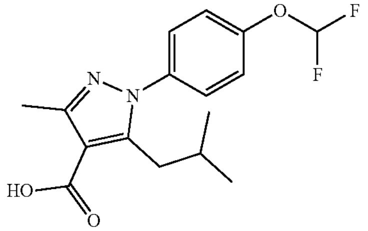 [SMILES: Cc1nn(-c2ccc(OC(F)F)cc2)c(CC(C)C)c1C(=O)O]

150-C was obtained via similar procedure of 156-C from 150-B and sodium hydroxide.

LCMS: (ESI) m/z: 325.1 [M+H]$^+$.

Step 4: Synthesis of N-(3-(1,1-difluoroethyl)phenyl)-1-(4-(difluoromethoxy)phenyl)-5-isobutyl-3-methyl-1H-pyrazole-4-carboxamide (150)

Compound ID : 150

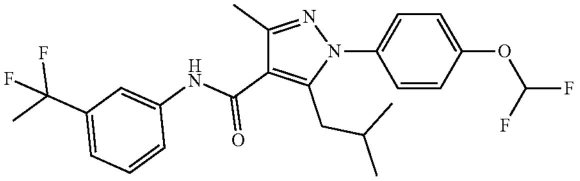

150 was obtained via similar procedure of 179 from 150-C and 3-(1,1-difluoroethyl)aniline LCMS: (ESI) m/z: 464.3 [M+H]$^+$.

$^1$H NMR (400 MHz, MeOD-$d_4$) δ: 7.87 (s, 1H), 7.71 (d, J=8.0 Hz, 1H), 7.43-7.50 (m, 3H), 7.30-7.36 (m, 3H), 6.96

(t, J=73.2 Hz, 1H), 2.78 (d, J=7.2 Hz, 2H), 2.44 (s, 3H), 1.94 (t, J=18.4 Hz, 3H), 1.67-1.73 (m, 1H), 0.76 (d, J=6.8 Hz, 6H).

Synthesis of 149

Step 1: 1-(2-(difluoromethoxy)-5-nitrophenyl)ethanone (149-A)

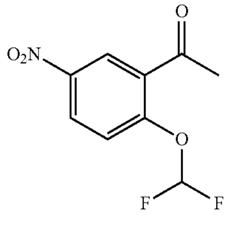 [SMILES: CC(=O)c1cc([N+](=O)[O-])ccc1OC(F)F]

To a mixture of 2-bromo-1-(difluoromethoxy)-4-nitrobenzene (16.0 g, 48.4 mmol, 1.0 eq), tributyl(1-ethoxyvinyl)stannane (22.6 g, 67.7 mmol, 1.4 eq), lithium chloride (4.10 g, 96.7 mmol, 2.0 eq) in dioxane (150 mL) was added tetrakis(triphenylphosphine)platinum (5.59 g, 4.84 mmol, 0.10 eq). The flask was then evacuated and backfilled with nitrogen for three times. The mixture was stirred at 100° C. under an atmosphere of nitrogen for 12 hr. To the mixture was added hydrochloric acid (6M, 100 mL), the result mixture was stirred at 25° C. for 15 min. The mixture was quenched by slow addition of saturated aqueous potassium fluoride (50 mL). The resulting mixture was transferred to a separatory funnel, and the aqueous layer mixture was extracted with ethyl acetate (100 mL×3). The combined organic layer was washed with brine (200 mL), dried over anhydrous sodium sulfate, filtered, and concentrated under reduced pressure affording the residue as a yellow oil. The crude product was purified by silica gel column chromatography (petroleum ether/ethyl acetate, from 20/1 to 5/1) to give 11.0 g (98% yield) of 149-A as a yellow oil.

LCMS: (ESI) m/z: 291.1 $[M+H]^+$.

$^1H$ NMR (400 MHz, $CDCl_3$-$d_4$) δ: 8.57 (d, J=2.8 Hz, 1H), 8.31 (dd, J=9.2, 2.9 Hz, 1H), 7.29 (d, J=9.2 Hz, 1H), 6.41-6.93 (m, 1H), 2.52-2.67 (m, 1H), 2.52-2.72 (m, 3H)

Step 2: 2-bromo-1-(2-(difluoromethoxy)-5-nitrophenyl)ethanone (149-B)

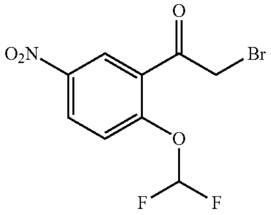 [SMILES: O=C(CBr)c1cc([N+](=O)[O-])ccc1OC(F)F]

To a 250 mL round-bottom flask equipped with a magnetic stir bar and a reflux condenser was added 149-A (11.0 g, 47.6 mmol, 1.0 eq) followed by the addition of acetonitrile (100 mL). Then 1-bromopyrrolidine-2,5-dione (10.2 g, 57.1 mmol, 1.2 eq) and 4-methylbenzenesulfonic acid (1.64 g, 9.52 mmol, 0.20 eq) were added into the mixture at 25° C. The mixture was heated to 70° C. and stirred for 12 h. The mixture was diluted by slow addition of water (20 mL). The mixture was quenched by slow addition of saturated aqueous ammonium chloride (200 mL). The resulting mixture was transferred to a separatory funnel, and the aqueous layer mixture was extracted with ethyl acetate (80 mL×3). The combined organic layer was washed with brine (200 mL), dried over anhydrous sodium sulfate, filtered, and concentrated under reduced pressure affording the residue as a yellow oil. The crude product was purified by silica gel column chromatography (petroleum ether/ethyl acetate, from 20/1 to 5/1) to give 14.0 g (95% yield) of 149-B as a yellow oil.

$^1H$ NMR (400 MHz, $CDCl_3$-d) δ: 8.67-8.77 (m, 1H), 8.41-8.51 (m, 1H), 7.34-7.48 (m, 1H), 6.58-6.99 (m, 2H), 4.26-4.77 (m, 2H).

Step 3: 4-(2-(difluoromethoxy)-5-nitrophenyl)oxazole (149-C)

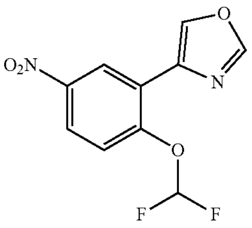 [SMILES: O=[N+]([O-])c1ccc(OC(F)F)c(-c2cocn2)c1]

To a 10 mL round-bottom flask equipped with a magnetic stir bar and a reflux condenser was added 149-B (4.00 g, 12.9 mmol, 1.0 eq) followed by the addition of formamide (5.65 g, 125 mmol, 9.7 eq) at 25° C. The mixture was heated to 100° C. and stirred for 2 h. The mixture was concentrated under reduced pressure affording the crude product as yellow solid. The crude product was purified by silica gel column chromatography (petroleum ether/ethyl acetate, from 20/1 to 5/1) to give 1.90 g (46% yield) of 149-C as a yellow solid.

LCMS: (ESI) m/z: 257.0 $[M+H]^+$.

$^1H$ NMR (400 MHz, $CDCl_3$-$d_4$) δ: 9.01 (d, J=2.8 Hz, 1H), 8.18 (d, J=1.2 Hz, 1H), 8.13 (dd, J=9.0, 2.8 Hz, 1H), 7.93 (d, J=0.8 Hz, 1H), 7.21 (d, J=9.2 Hz, 1H), 6.46-6.89 (m, 2H).

Step 4: 4-(difluoromethoxy)-3-(oxazol-4-yl)aniline (149-D)

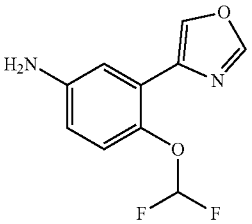

To a solution of 149-C (1.90 g, 7.42 mmol, 1.0 eq) in methanol (10 mL) was added Pd/C (1.00 g, 10% purity) under hydrogen atmosphere. The suspension was degassed and purged with hydrogen for 3 times. The mixture was stirred under hydrogen (15 psi) at 25° C. for 2 hr. The mixture was filtered, the filtrate was concentrated under reduced pressure to give a yellow oil. The crude product was purified by silica gel column chromatography (petroleum ether/ethyl acetate, from 20/1 to 5/1) to give 1.40 g (46% yield) of 149-D as a yellow solid.

LCMS: (ESI) m/z: 227.1 $[M+H]^+$ $^1$H NMR (400 MHz, DMSO-d) δ: 8.59 (s, 2H), 8.44 (s, 1H), 8.04 (d, J=2.4 Hz, 1H), 7.12-7.63 (m, 3H).

Step 5: 4-(2-(difluoromethoxy)-5-hydrazinylphenyl) oxazole (149-E)

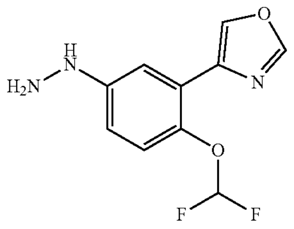 [SMILES: NNc1ccc(OC(F)F)c(-c2cocn2)c1]

149-E was obtained via general procedure I from 149-D

LCMS: (ESI) m/z: 242.3 $[M+H]^+$.

Step 6: ethyl 2-(4-(difluoromethoxy)-3-(oxazol-4-yl)phenyl)hydrazinecarboxylate (149-F)

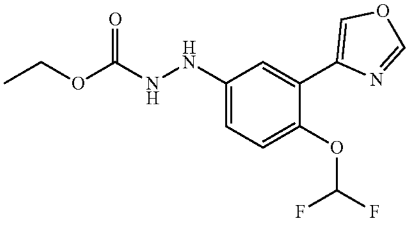 [SMILES: CCOC(=O)NNc1ccc(OC(F)F)c(-c2cocn2)c1]

149-F was obtained via similar procedure of 186-A from 149-E and ethyl carbonochloridate LCMS: (ESI) m/z: 314.0 $[M+H]^+$.

Step 7: ethyl 1-(4-(difluoromethoxy)-3-(oxazol-4-yl)phenyl)-3-methyl-1H-pyrazole-4-carboxylate (149-G)

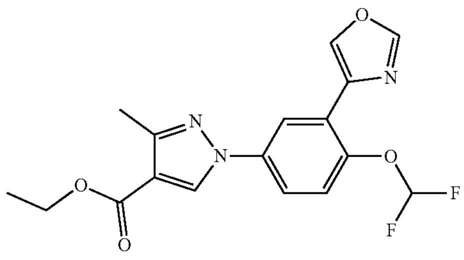 [SMILES: CCOC(=O)c1cn(-c2ccc(OC(F)F)c(-c3cocn3)c2)nc1C]

149-G was obtained via similar procedure of 186-B from 149-F and ethyl (2E)-2-(methoxymethylene)-3-oxo-butanoate LCMS: (ESI) m/z: 364.1 $[M+H]^+$.

Step 8: 1-(4-(difluoromethoxy)-3-(oxazol-4-yl)phenyl)-3-methyl-1H-pyrazole-4-carboxylic acid (149-H)

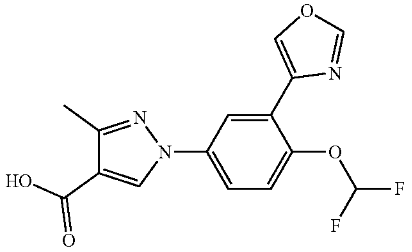 [SMILES: Cc1nn(-c2ccc(OC(F)F)c(-c3cocn3)c2)cc1C(=O)O]

149-H was obtained via similar procedure of 186-D from 176-G and sodium hydroxide
LCMS: (ESI) m/z: 336.0$[M+H]^+$.

Step 9: N-(3-(1,1-difluoroethyl)phenyl)-1-(4-(difluoromethoxy)-3-(oxazol-4-yl)phenyl)-3-methyl-1H-pyrazole-4-carboxamide (149)

Compound ID : 149

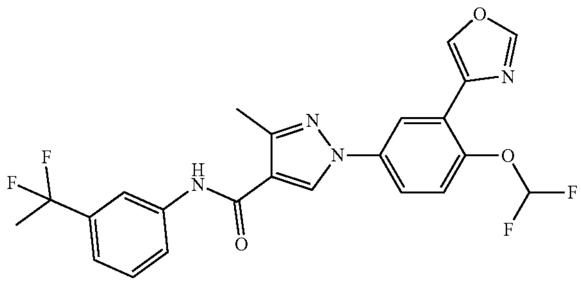

149 was obtained via similar procedure of 186 from 149-H and 3-(1,1-difluoroethyl)aniline
LCMS: (ESI) m/z: 475.1 $[M+H]^+$.
$^1$H NMR (400 MHz, MeOD-$d_4$) δ: 8.89 (s, 1H), 8.56 (d, J=2.76 Hz, 1H), 8.39 (s, 1H), 8.32 (d, J=0.64 Hz, 1H), 7.94 (s, 1H), 7.74-7.85 (m, 2H), 7.40-7.50 (m, 2H), 7.30 (d, J=7.64 Hz, 1H), 6.89-7.28 (m, 1H), 2.59 (s, 3H), 1.96 (t, J=18.24 Hz, 3H).

Synthesis of 148

Step 1: Synthesis of ethyl 1-[4-(difluoromethoxy)-3-(2-pyridyl)phenyl]-5-ethyl-3-methyl-pyrazole-4-carboxylate (148-A)

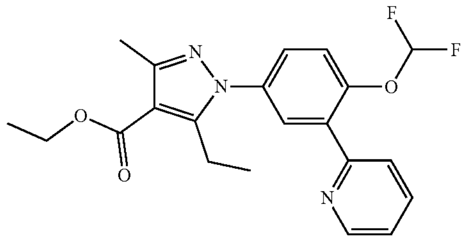 [SMILES: CCOC(=O)c1c(C)nn(-c2ccc(OC(F)F)c(-c3ccccn3)c2)c1CC]

148-A was obtained via similar procedure of 2-[4-(difluoromethoxy)-3-(2-pyridyl)phenyl]-5-methyl-4H-pyrazol-3-one from [4-(difluoromethoxy)-3-(2-pyridyl)phenyl]hydrazine and 156-A.

LCMS: (ESI) m/z: 402.2 $[M+H]^+$.

Step 2: Synthesis of 1-[4-(difluoromethoxy)-3-(2-pyridyl)phenyl]-5-ethyl-3-methyl-pyrazole-4-carboxylic acid (148-B)

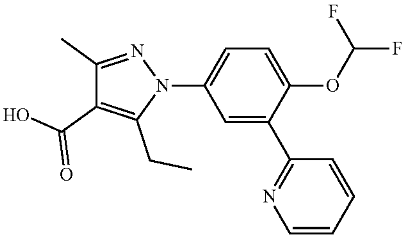 [SMILES: CCc1c(C(=O)O)c(C)nn1-c1ccc(OC(F)F)c(-c2ccccn2)c1]

148-B was obtained via similar procedure of 154-C from 148-A and sodium hydroxide.

LCMS: (ESI) m/z: 374.1 $[M+H]^+$.

Step 3: Synthesis of N-[3-(1,1-difluoroethyl)phenyl]-1-[4-(difluoromethoxy)-3-(2-pyridyl)phenyl]-5-ethyl-3-methyl-pyrazole-4-carboxamide (148)

Compound ID: 148

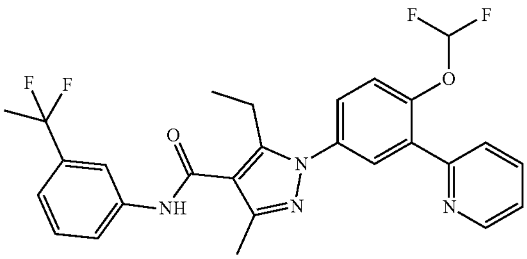

148 was obtained via similar procedure of 154 from 148-B and 3-(1,1-difluoroethyl)aniline.

LCMS: (ESI) m/z: 513.2 $[M+H]^+$.

$^1$H NMR: (400 MHz, DMSO-d) δ: 10.09 (s, 1H), 8.80-8.63 (m, 1H), 8.00 (s, 1H), 7.97-7.92 (m, 1H), 7.89 (d, J=2.8 Hz, 1H), 7.88-7.84 (m, 1H), 7.79-7.73 (m, 1H), 7.65 (dd, J=2.8, 8.8 Hz, 1H), 7.55 (s, 1H), 7.50 (d, J=8.8 Hz, 1H), 7.48-7.45 (m, 1H), 7.44 (td, J=1.2, 3.0, 4.4 Hz, 1H), 7.37 (s, 1H), 7.26 (d, J=7.8 Hz, 1H), 7.19 (s, 1H), 2.88 (q, J=7.4 Hz, 2H), 2.37 (s, 3H), 1.96 (t, J=18.8 Hz, 3H), 1.04 (t, J=7.4 Hz, 3H).

Synthesis of 147

Step 1: Synthesis of 2-(4-(difluoromethoxy)phenyl)-6-methylpyrimidine-4-carboxylic acid (147-A)

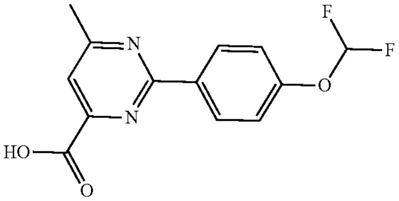 [SMILES: Cc1cc(C(=O)O)nc(-c2ccc(OC(F)F)cc2)n1]

147-A was obtained via similar procedure of 173-C from 173-A and methyl 2-chloro-6-methyl-pyrimidine-4-carboxylate LCMS: (ESI) m/z: 281.1 $[M+H]^+$.

Step 2: Synthesis of N-(3-(1,1-difluoroethyl)phenyl)-2-(4-(difluoromethoxy)phenyl)-6-methylpyrimidine-4-carboxamide (147)

Compound ID: 147

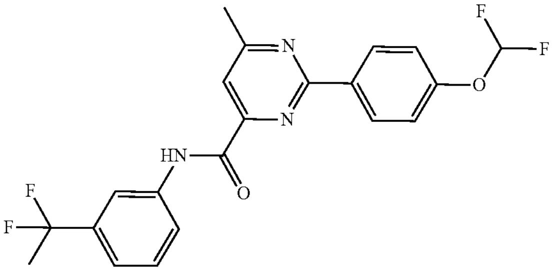

147 was obtained via similar procedure of 173 from 147-A and 3-(1,1-difluoroethyl)aniline LCMS: (ESI) m/z: 420.0 $[M+H]^+$.

$^1$H NMR (400 MHz, MeOD-$d_4$) δ: 8.66-8.71 (m, 2H), 8.09 (s, 1H), 7.91-7.97 (m, 2H), 7.50 (t, J=8.0 Hz, 1H), 7.37 (d, J=7.6 Hz, 1H), 7.29 (d, J=8.8 Hz, 2H), 6.96 (t, J=74.0 Hz, 1H), 2.70 (s, 3H), 1.96 (t, J=18.4 Hz, 3H).

Synthesis of 146

Step 1: Synthesis of ethyl 2-acetyl-4-methyl-3-oxo-pentanoate (146-A)

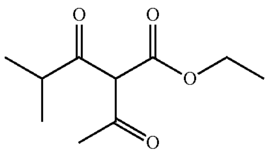

146-A was obtained via similar procedure of 154-A.

LCMS: (ESI) m/z: 201.2 $[M+H]^+$.

Step 2: Synthesis of ethyl 1-(4-(difluoromethoxy)phenyl)-5-isopropyl-3-methyl-1H-pyrazole-4-carboxylate (146-B)

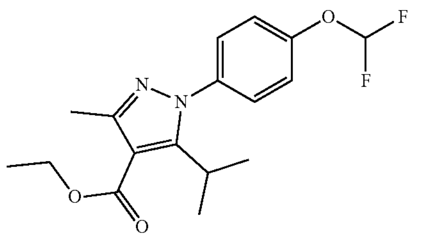 [SMILES: CCOC(=O)c1c(C)nn(-c2ccc(OC(F)F)cc2)c1C(C)C]

146-B was obtained via similar procedure of 154-B from 146-A and (4-(difluoromethoxy)phenyl)hydrazine LCMS: (ESI) m/z: 339.1 $[M+H]^+$.

$^1H$ NMR: (400 MHz, $CDCl_3$-d) δ: 7.41-7.31 (m, 2H), 7.24 (d, J=8.8 Hz, 2H), 6.77-6.36 (m, 1H), 4.34 (q, J=7.2 Hz, 2H), 3.28 (td, J=7.2, 14.2 Hz, 1H), 2.47 (s, 3H), 1.40 (t, J=7.2 Hz, 3H), 1.32 (d, J=7.2 Hz, 6H).

Step 3: Synthesis of 1-[4-(difluoromethoxy)phenyl]-5-isopropyl-3-methyl-pyrazole-4-carboxylic acid (146-C)

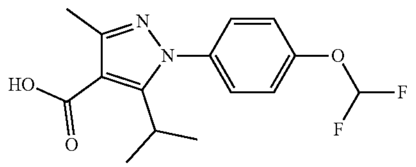 [SMILES: Cc1nn(-c2ccc(OC(F)F)cc2)c(C(C)C)c1C(=O)O]

146-C was obtained via similar procedure of 154-C from 146-B and sodium hydroxide.

LCMS: (ESI) m/z: 311.1 $[M+H]^+$.

Step 4: Synthesis of N-[3-(1,1-difluoroethyl)phenyl]-1-[4-(difluoromethoxy)phenyl]-5-isopropyl-3-methyl-pyrazole-4-carboxamide (146)

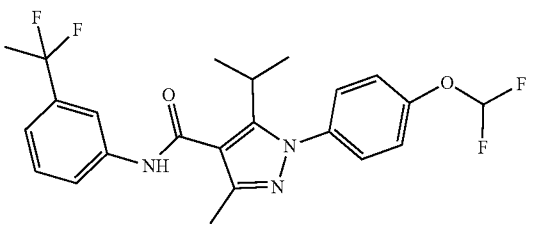 [SMILES: Cc1nn(-c2ccc(OC(F)F)cc2)c(C(C)C)c1C(=O)Nc1cccc(C(C)(F)F)c1]

146 was obtained via similar procedure of 154 from 146-C and 3-(1,1-difluoroethyl)aniline.

LCMS: (ESI) m/z: 450.2 $[M+H]^+$.

$^1H$ NMR: (400 MHz, DMSO-d) δ: 10.35 (s, 1H), 8.02 (s, 1H), 7.77 (br d, J=8.2 Hz, 1H), 7.57-7.53 (m, 1H), 7.51-7.41 (m, 3H), 7.36 (s, 2H), 7.27 (d, J=7.6 Hz, 1H), 7.22-7.16 (m, 1H), 2.97 (q, J=7.0 Hz, 1H), 2.29 (s, 3H), 1.96 (t, J=18.8 Hz, 3H), 1.25 (d, J=7.0 Hz, 6H).

Synthesis of 145

Step 1: Synthesis of ethyl 2-(cyclopropanecarbonyl)-3-oxo-butanoate (145-A)

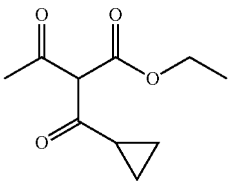

A mixture of ethyl 3-oxobutanoate (5.0 g, 38.4 mmol, 1.0 eq), magnesium chloride (7.32 g, 76.8 mmol, 2.0 eq) and pyridine (6.08 g, 76.8 mmol, 2.0 eq) in dichloromethane (30 mL) was degassed and purged with nitrogen for 3 times, and then the mixture was stirred at 0° C. for 1 h under nitrogen atmosphere, then the mixture was added cyclopropanecarbonyl chloride (4.00 g, 38.4 mmol, 1.0 eq) in dichloromethane (10 mL) dropwise at 0° C. The mixture was stirred at 20° C. for 1 h under an atmosphere of nitrogen. The mixture was cooled to 0° C. To the mixture was added 6 M hydrochloric acid (40 mL), the resulting mixture was stirred at 0° C. for 10 min and then transferred to a separatory funnel, and the aqueous layer mixture was extracted with dichloromethane (40 mL×2), the combined organic layer was washed with brine (80 mL), dried over anhydrous sodium sulfate, filtered and concentrated under reduced pressure affording the residue. The residue was purified by silica gel column chromatography (petroleum ether/ethyl acetate, from 100/1 to 20/1) to give 6.50 g (58% yield) of 145-A as a light yellow liquid.

LCMS: (ESI) m/z: 199.09 $[M+H]^+$.

$^1H$ NMR: (400 MHz, $CDCl_3$-d) δ: 4.32-4.28 (m, 2H), 2.49-2.40 (m, 1H), 2.31 (s, 3H), 1.35-1.32 (m, 3H), 1.23-1.20 (m, 2H), 1.01-0.97 (m, 2H).

Step 2: Synthesis of ethyl 5-cyclopropyl-1-[4-(difluoromethoxy)phenyl]-3-methyl-pyrazole-4-carboxylate (145-B)

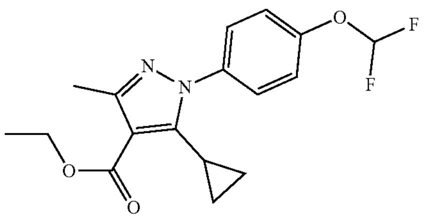 [SMILES: CCOC(=O)c1c(C)nn(-c2ccc(OC(F)F)cc2)c1C1CC1]

To a solution of (4-(difluoromethoxy)phenyl)hydrazine (2.70 g, 12.5 mmol, 1.2 eq, hydrochloride) in acetic acid (30 mL) was added 145-A (3.00 g, 10.3 mmol, 1.0 eq). The mixture was stirred at 50° C. for 1 h. The mixture was concentrated in vacuum directly to give a residue. The residue was purified by silica gel column chromatography (petroleum ether/ethyl acetate, from 50/1 to 5/1) to give the crude product, then the crude product was purified by prep-HPLC, column (Phenomenex Synergi C18 150*25*10 um; mobile phase:[water (0.2% formic acid)-acetonitrile]; B %: 50%-80%, 11 min) to give 0.100 g (3% yield) of 145-B as a light yellow oil.

$^1H$ NMR: (400 MHz, $CDCl_3$-d) δ: 7.53-7.50 (m, 2H), 7.22 (d, J=8.8 Hz, 2H), 6.57 (s, 1H), 4.35 (q, J=7.2 Hz, 2H), 2.48 (s, 3H), 2.00-1.97 (m, 1H), 1.40 (t, J=7.2 Hz, 3H), 0.92 (dd, J=6.8 Hz, 2H), 0.50-0.44 (m, 2H).

Step 3: Synthesis of 5-cyclopropyl-1-[4-(difluoromethoxy)phenyl]-3-methyl-pyrazole-4-carboxylic acid (145-C)

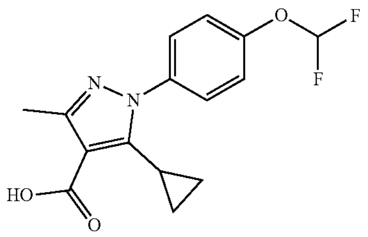 [SMILES: Cc1nn(-c2ccc(OC(F)F)cc2)c(C2CC2)c1C(=O)O]

To a solution of 145-B (0.100 g, 297 umol, 1.0 eq) in ethanol (1 mL) was added sodium hydroxide (0.120 g, 2.97 mmol, 10 eq) and water (1 mL). The mixture was stirred at 80° C. for 2 h. The mixture was diluted with water (30 mL), and extracted with ethyl acetate (10 mL×3), then the pH of aqueous phase was adjusted to 2 by hydrochloric acid (1 M). Next extracted with ethyl acetate (10 mL×3), the combined organic layer was washed with brine (20 mL×1), dried over anhydrous sodium sulfate, filtered and concentrated under reduced pressure to give 1.60 g (crude) of 145-C as a light yellow solid.

LCMS: (ESI) m/z: 309.10 $[M+H]^+$.

Step 4: Synthesis of 5-cyclopropyl-N-[3-(1,1-difluoroethyl)phenyl]-1-[4-(difluoromethoxy)phenyl]-3-methyl-pyrazole-4-carboxamide (145)

Compound ID: 145

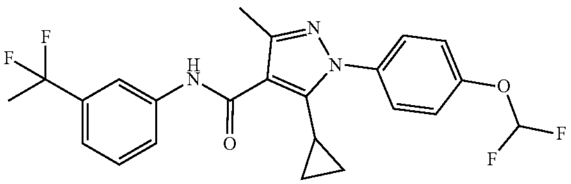

To a solution of 145-C (65.0 mg, 211 umol, 1.0 eq) in pyridine (1 mL) was added N-[3-(dimethylamino)propyl]-N-ethylcarbodiimide hydrochloride (61.0 mg, 316 umol, 1.5 eq) and 3-(1,1-difluoroethyl)aniline (40.0 mg, 253 umol, 1.2 eq). The mixture was stirred at 50° C. for 1 h. The mixture was concentrated in vacuum to give a residue. The residue was purified by prep-HPLC (column: Boston Green ODS 150*30 mm*5 um; mobile phase: [water (0.225% formic acid)-acetonitrile]; B %: 50%-80%, 10 min) to give 16.6 mg (17% yield) of 145 as a yellow solid.

LCMS: (ESI) m/z: 447.9 $[M+H]^+$ $^1H$ NMR: (400 MHz, MeOD-$d_4$) δ: 7.92 (s, 1H), 7.73 (d, J=8.4 Hz, 1H), 7.62 (d, J=9.2 Hz, 2H), 7.46 (t, J=8.0 Hz 1H), 7.35-7.29 (m, 3H), 6.94 (t, J=74.0 Hz, 1H), 2.40 (s, 3H), 2.14-2.05 (m, 1H), 1.94 (t, J=18.4 Hz, 3H), 0.89 (dd, J=8.4, 1.6 Hz, 2H), 0.51 (dd, J=5.6, 1.6 Hz, 2H).

Synthesis of 144

Step 1: Synthesis of ethyl 2-[4-(difluoromethoxy)phenyl]-4-methyl-pyrimidine-5-carboxylate (144-A)

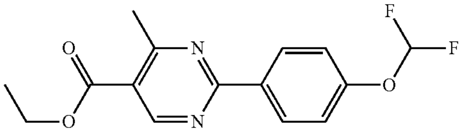 [SMILES: CCOC(=O)c1cnc(-c2ccc(OC(F)F)cc2)nc1C]

144-A was obtained via similar procedure of 152-B from 173-A and ethyl 2-chloro-4-methylpyrimidine-5-carboxylate.

$^1H$ NMR (400 MHz, MeOD-$d_4$) δ: 9.18 (s, 1H), 8.55 (d, J=8.8 Hz, 2H), 7.27 (d, J=8.8 Hz, 2H), 6.97 (t, J=73.6 Hz, 1H), 4.43 (q, J=7.2 Hz, 2H), 2.87 (s, 3H), 1.43 (t, J=7.2 Hz, 3H).

Step 2: Synthesis of 2-[4-(difluoromethoxy)phenyl]-4-methyl-pyrimidine-5-carboxylic acid (4-B)

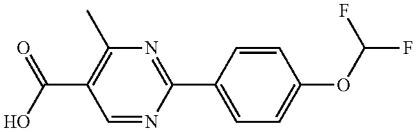

144-B was obtained via similar procedure of 152-C from 144-A and lithium hydroxide hydrate.

LCMS: (ESI) m/z: 281.1 $[M+H]^+$.

Step 3: Synthesis of N-[3-(1,1-difluoroethyl)phenyl]-2-[4-(difluoromethoxy)phenyl]-4-methyl-pyrimidine-5-carboxamide (144)

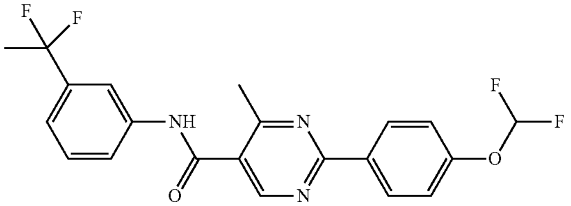 [SMILES: Cc1nc(-c2ccc(OC(F)F)cc2)ncc1C(=O)Nc1cccc(C(C)(F)F)c1]

To a solution of 144-B (75.0 mg, 268 umol, 1.0 eq) in N,N-dimethylformamide (5 mL) was added 1H-benzo[d][1,2,3]triazol-1-ol (102 mg, 268 umol, 1.0 eq) and N,N-diisopropylethylamine (69.2 mg, 535 umol, 2.0 eq). It was stirred at 10° C. for 30 min. Then 3-(1,1-difluoroethyl)aniline (42.1 mg, 268 umol, 1.0 eq) was added into the mixture. It was stirred at 10° C. for 12 h. The mixture was concentrated under reduced pressure to give a residue. The residue was purified by prep-HPLC (column: Boston Green ODS 150*30 mm*5 um; mobile phase: [water (0.225% formic acid)-acetonitrile]; B %: 50%-80%, 10 min). Then it was freeze-dried to obtain 25.6 mg (23% yield) of 144 as a yellow solid.

LCMS: (ESI) m/z: 420.1 $[M+H]^+$.

$^1$H NMR (400 MHz, MeOD-$d_4$) δ: 8.90 (s, 1H), 8.54 (d, J=8.8 Hz, 2H), 7.95 (s, 1H), 7.78 (d, J=8.0 Hz, 1H), 7.47 (t, J=8.0 Hz, 1H), 7.34 (dd, J=8.0, 0.8 Hz, 1H), 7.27 (d, J=8.8 Hz, 2H), 6.96 (t, J=74.0 Hz, 1H), 2.74 (s, 3H), 1.94 (t, J=18.4 Hz, 3H).

Synthesis of 143

Step 1: Synthesis of 2-[4-(difluoromethoxy)phenyl]-N-[3-(1,1-difluoropropyl)phenyl]-4-methyl-pyrimidine-5-carboxamide (143)

Compound ID: 143

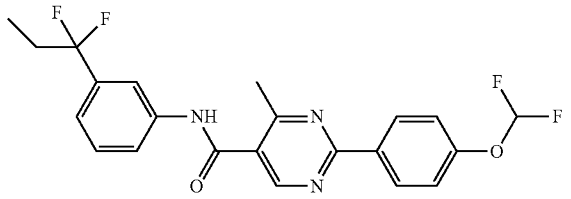

143 was obtained via similar procedure of 144 from 144-B and 3-(1,1-difluoropropyl)aniline.

LCMS: (ESI) m/z: 433.9 [M+H]$^+$.

$^1$H NMR (400 MHz, MeOD-$d_4$) a: 8.90 (s, 1H), 8.54 (d, J=8.8 Hz, 2H), 7.90 (s, 1H), 7.79 (d, J=8.4 Hz, 1H), 7.48 (t, J=8.0 Hz, 1H), 7.32-7.25 (m, 3H), 6.96 (t, J=74.0 Hz, 1H), 2.74 (s, 3H), 2.20 (td, J=16.0, 7.6 Hz, 2H), 0.99 (t, J=7.6 Hz, 3H).

Synthesis of 142

Step 1: Synthesis of ethyl 2-(4-methoxyphenyl)-4-methyloxazole-5-carboxylate (142-A)

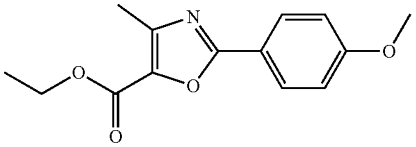 [SMILES: CCOC(=O)c1oc(-c2ccc(OC)cc2)nc1C]

To a 10 mL round-bottom flask equipped with a magnetic stir bar and a reflux condenser was added 4-methoxybenzamide (500 mg, 3.31 mmol, 1.0 eq) followed by the addition of ethyl 2-chloro-3-oxo-butanoate (1.63 g, 9.92 mmol, 3.0 eq). The mixture was heated to 130° C. and stirred for 12 hr. The mixture was quenched by slow addition of brine (5 mL). The resulting mixture was transferred to a separatory funnel, and the aqueous layer mixture was extracted with ethyl acetate (3 mL×3). The combined organic layer was washed with brine (4 mL), dried over anhydrous sodium sulfate, filtered, and concentrated under reduced pressure affording the residue. The residue was purified by silica gel column chromatography (petroleum ether/ethyl acetate, from 20/1 to 10/1) to give 460 mg (49% yield) of 142-A as a yellow solid.

LCMS: (ESI) m/z: 262.2 [M+H]$^+$.

Step 2: Synthesis of 2-(4-methoxyphenyl)-4-methyloxazole-5-carboxylic acid (142-B)

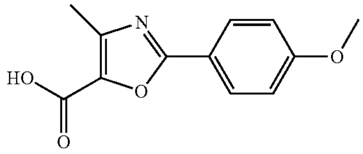 [SMILES: COc1ccc(-c2nc(C)c(C(=O)O)o2)cc1]

To a 50 mL round-bottom flask equipped with a magnetic stir bar and a reflux condenser was added 142-A (200 mg, 707 umol, 1.0 eq) followed by the addition of ethanol (5 mL) and water (5 mL). Then sodium hydroxide (283 mg, 7.07 mmol, 10 eq) was added into the mixture. The mixture was heated to 80° C. and stirred for 2 hr. The mixture was concentrated under reduced pressure to give a residue. The residue was dissolved in water (5 mL). The pH of the mixture was adjusted to 3 by hydrogen chloride solution (6M). The mixture was extracted with ethyl acetate (5 mL×2). The combined organic layer was washed with brine (4 mL), dried over anhydrous sodium sulfate, filtered and concentrated to give 170 mg (95% yield) of 142-B as a light yellow solid.

LCMS: (ESI) m/z: 233.8 [M+H]+.

Step 3: Synthesis of N-(3-(1,1-difluoroethyl)phenyl)-2-(4-methoxyphenyl)-4-methyloxazole-5-carboxamide (142)

Compound ID : 142

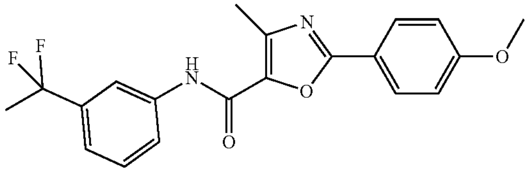

142 was obtained via similar procedure of 173 from 142-B and 3-(1,1-difluoroethyl)aniline.

LCMS: (ESI) m/z: 373.1 [M+H]$^+$.

$^1$H NMR (400 MHz, MeOD-$d_4$) δ: 8.16-8.18 (m, 2H), 7.96 (s, 1H), 7.82-7.84 (m, 1H), 7.46 (t, J=8.0 Hz, 1H), 7.33 (dd, J=0.8, 7.6 Hz, 1H), 7.08-7.11 (m, 2H), 3.89 (s, 3H), 2.55 (s, 3H), 1.94 (t, J=18.4 Hz, 3H).

Synthesis of 141

Step 1: Synthesis of ethyl 2-(4-hydroxyphenyl)-4-methyloxazole-5-carboxylate (141-A)

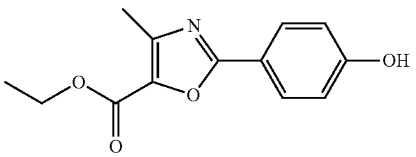 [SMILES: CCOC(=O)c1oc(-c2ccc(O)cc2)nc1C]

141-A was obtained via similar procedure of 142-A from 4-hydroxybenzamide and ethyl 2-chloro-3-oxo-butanoate.

LCMS: (ESI) m/z: 248.2 [M+H]+.

Step 2: Synthesis of ethyl 2-(4-(difluoromethoxy) phenyl)-4-methyloxazole-5-carboxylate (141-B)

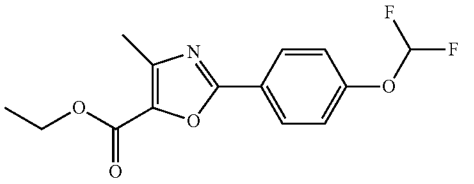 [SMILES: CCOC(=O)c1oc(-c2ccc(OC(F)F)cc2)nc1C]

To a 100 mL round-bottom flask equipped with a magnetic stir bar and a reflux condenser was added 141-A (2.00 g, 7.02 mmol, 1.0 eq), sodium; 2-chloro-2,2-difluoro-acetate (1.60 g, 10.5 mmol, 1.5 eq) followed by the addition of N,N-dimethylformamide (20 mL). Then sodium carbonate (1.49 g, 14.0 mmol, 2.0 eq) was added into the mixture. The mixture was heated to 100° C. and stirred for 2 hr. The mixture was concentrated under reduced pressure to give a residue. The residue was dissolved in ethyl acetate (30 mL) and water (50 mL). The resulting mixture was transferred to a separatory funnel, and the aqueous layer mixture was extracted with ethyl acetate (30 mL×2). The combined organic layer was washed with brine (40 mL), dried over anhydrous sodium sulfate, filtered, and concentrated under reduced pressure affording the residue. The residue was purified by silica gel column chromatography (petroleum ether/ethyl acetate, from 15/1 to 10/1) to give 1.09 g (50% yield) of 141-B as a white solid.

LCMS: (ESI) m/z: 298.1 [M+H]+.

Step 3: Synthesis of 2-(4-(difluoromethoxy)phenyl)-4-methyloxazole-5-carboxylic acid (141-C)

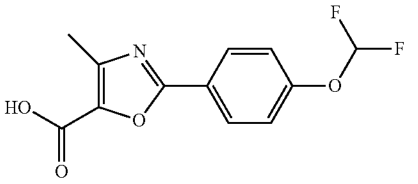 [SMILES: Cc1nc(-c2ccc(OC(F)F)cc2)oc1C(=O)O]

141-C was obtained via similar procedure of 142-B from 141-B and sodium hydroxide.

LCMS: (ESI) m/z: 270.0 [M+H]+.

Step 4: Synthesis of N-(3-(1,1-difluoroethyl)phenyl)-2-(4-(difluoromethoxy)phenyl)-4-methyloxazole-5-carboxamide (141)

Compound ID : 141

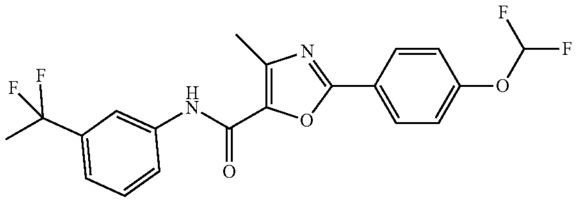

141 was obtained via similar procedure of 142 from 141-C and 3-(1,1-difluoroethyl)aniline.

LCMS: (ESI) m/z: 409.1 [M+H]+.

$^1$H NMR (400 MHz, MeOD-$d_4$) δ: 8.25-8.28 (m, 2H), 7.95 (s, 1H), 7.83 (d, J=8.4 Hz, 1H), 7.46 (t, J=7.6 Hz, 1H), 7.30-7.34 (m, 3H), 6.98 (t, J=73.2 Hz, 1H), 2.56 (s, 3H), 1.94 (t, J=18.4 Hz, 3H).

Synthesis of 140

Step 1: Synthesis of 2-(4-(difluoromethoxy)phenyl)-N-(3-(1,1-difluoropropyl)phenyl)-4-methyloxazole-5-carboxamide (140)

Compound ID : 140

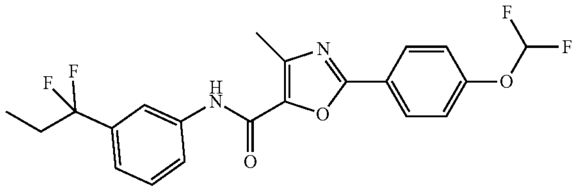

140 was obtained via similar procedure of 142 from 141-C and 3-(1,1-difluoropropyl)aniline.

LCMS: (ESI) m/z: 423.1 [M+H]+.

1H NMR (400 MHz, MeOD-$d_4$) δ: 8.25-8.29 (m, 2H), 7.91 (s, 1H), 7.84 (d, J=8.4 Hz, 1H), 7.46 (t, J=8.0 Hz, 1H), 7.27-7.32 (m, 3H), 6.98 (t, J=73.6 Hz, 1H), 2.56 (s, 3H), 2.15-2.25 (m, 2H), 1.00 (t, J=7.2 Hz, 3H).

Synthesis of 139

Step 1: Synthesis of ethyl 2-[4-(difluoromethoxy)-3-phenyl-phenyl]-4-methyl-pyrimidine-5-carboxylate (139-A)

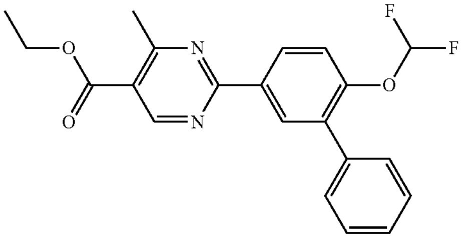 [SMILES: CCOC(=O)c1cnc(-c2ccc(OC(F)F)c(-c3ccccc3)c2)nc1C]

139-A was obtained via similar procedure of 152-B from 127-C and ethyl 2-chloro-4-methylpyrimidine-5-carboxylate.

LCMS: (ESI) m/z: 385.0 $[M+H]^+$.

Step 2: Synthesis of 2-[4-(difluoromethoxy)-3-phenyl-phenyl]-4-methyl-pyrimidine-5-carboxylic acid (139-B)

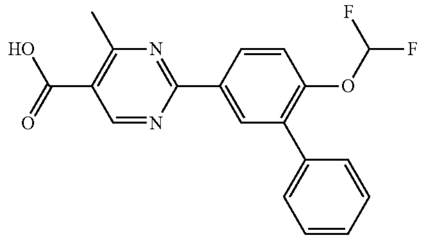 [SMILES: Cc1nc(-c2ccc(OC(F)F)c(-c3ccccc3)c2)ncc1C(=O)O]

139-B was obtained via similar procedure of 144-B from 139-A and lithium hydroxide hydrate.

LCMS: (ESI) m/z: 357.0 $[M+H]^+$.

Step 3: Synthesis of N-[3-(1,1-difluoroethyl)phenyl]-2-[4-(difluoromethoxy)-3-phenyl-phenyl]-4-methyl-pyrimidine-5-carboxamide (139)

Compound ID: 139

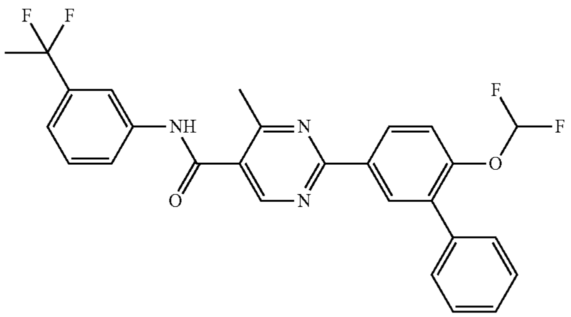

139 was obtained via similar procedure of 144 rom 9-B and 3-(1,1-difluoroethyl)aniline.

LCMS: (ESI) m/z: 496.1 $[M+H]^+$.

$^1$H NMR (400 MHz, MeOD-$d_4$) δ: 8.91 (s, 1H), 8.56 (d, J=2.0 Hz, 1H), 8.54-8.51 (m, 1H), 7.95 (s, 1H), 7.78 (d, J=8.0 Hz, 1H), 7.57-7.54 (m, 2H), 7.50-7.45 (m, 3H), 7.43-7.38 (m, 2H), 7.34 (d, J=8.4 Hz, 1H), 6.84 (t, J=74.0 Hz, 1H), 2.75 (s, 3H), 1.94 (t, J=18.4 Hz, 3H)

Synthesis of 138

Step 1: Synthesis of 2-[4-(difluoromethoxy)-3-phenyl-phenyl]-N-[3-(1,1-difluoropropyl)phenyl]-4-methyl-pyrimidine-5-carboxamide (138)

Compound ID : 138

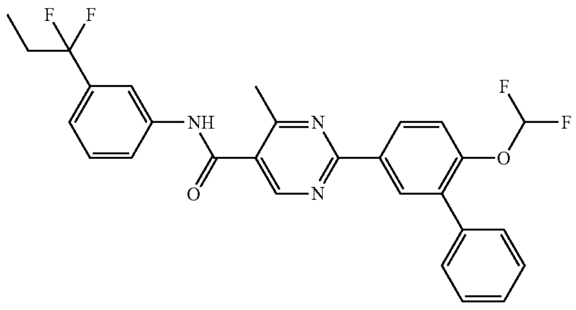

138 was obtained via similar procedure of 139 from 139-B and 3-(1,1-difluoropropyl)aniline.

LCMS: (ESI) m/z: 509.9 $[M+H]^+$.

$^1$H NMR (400 MHz, MeOD-$d_4$) δ: 8.91 (s, 1H), 8.56 (d, J=2.0 Hz, 1H), 8.54-8.51 (m, 1H), 7.90 (s, 1H), 7.79 (d, J=8.4 Hz, 1H), 7.57-7.54 (m, 2H), 7.50-7.45 (m, 3H), 7.43-7.39 (m, 2H), 7.30 (d, J=8.0 Hz, 1H), 6.84 (t, J=73.6 Hz, 1H), 2.75 (s, 3H), 2.27-2.12 (m, 2H), 0.99 (t, J=7.2 Hz, 3H).

Synthesis of 137

Step 1: Synthesis of 2-(4-(difluoromethoxy)phenyl)-N-(3-(1,1-difluoropropyl)phenyl)-6-methylpyrimidine-4-carboxamide (137)

Compound ID : 137

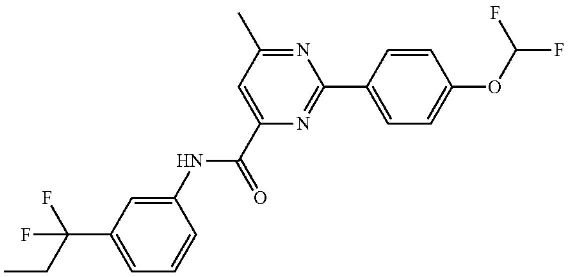

137 was obtained via similar procedure of 147 from 147-A and 3-(1,1-difluoropropyl)aniline LCMS: (ESI) m/z: 434.0 $[M+H]^+$.

$^1$H NMR (400 MHz, MeOD-$d_4$) δ: 8.68-8.72 (m, 2H), 8.06 (s, 1H), 7.93-7.95 (m, 2H), 7.50 (t, J=8.0 Hz, 1H), 7.29-7.34 (m, 3H), 6.96 (t, J=73.6 Hz, 1H), 2.71 (s, 3H), 2.17-2.27 (m, 2H), 1.01 (t, J=7.6 Hz, 3H).

Synthesis of 136

Step 1: Synthesis of N-(3-(1,1-difluoropropyl)phenyl)-2-(4-methoxyphenyl)-4-methyloxazole-5-carboxamide (136)

Compound ID : 136

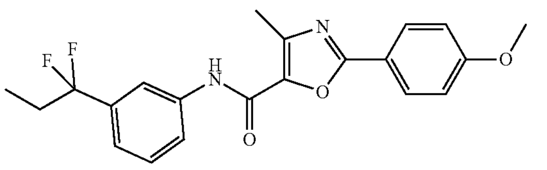

136 was obtained via similar procedure of 142 from 142-C and 3-(1,1-difluoropropyl)aniline LCMS: (ESI) m/z: 387.1 $[M+H]^+$.

$^1$H NMR (400 MHz, MeOD-$d_4$) δ: 8.16 (d, J=8.8 Hz, 2H), 7.91 (s, 1H), 7.83 (d, J=8.0 Hz, 1H), 7.46 (t, J=8.0 Hz, 1H), 7.28 (d, J=8.0 Hz, 1H), 7.08 (d, J=9.2 Hz, 2H), 3.89 (s, 3H), 2.55 (s, 3H), 2.15-2.25 (m, 2H), 1.00 (t, J=7.2 Hz, 3H).

Synthesis of 135

Step 1: Synthesis of methyl 3-methyl-4-oxido-pyrazin-4-ium-2-carboxylate (135-A)

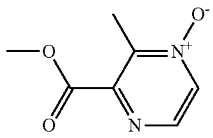

To a solution of methyl 3-methylpyrazine-2-carboxylate (4.00 g, 26.3 mmol, 1.0 eq) in dichloromethane (100 mL) was added hydrogen peroxide (4.17 g, 36.8 mmol, 1.4 eq) (30% aqueous) at 0° C., following added trifluoroacetic anhydride (7.18 g, 34.2 mmol, 1.3 eq). The mixture was stirred at 0° C. for 1 h, then it was stirred at 25° C. for 16 h. The mixture was quenched with saturated sodium sulfite aqueous (100 mL) and extracted with dichloromethane (100 mL×2). The combined organic extracts were dried over sodium sulfate, filtered and concentrated in vacuum to give 5.50 g (crude, mixture) of 135-A as a yellow solid.

LCMS: (ESI) m/z: 169.0 $[M+H]^+$.

Step 2: Synthesis of methyl 5-chloro-3-methyl-pyrazine-2-carboxylate (135-B)

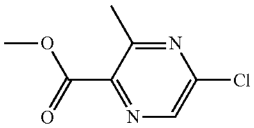

To a solution of 135-A (5.50 g, 32.7 mmol, 1.0 eq) in toluene (50 mL) was added phosphorous oxychloride (10.0 g, 65.4 mmol, 2.0 eq), following added dimethyl formamide (239 mg, 3.27 mmol, 0.10 eq). The mixture was stirred at 65° C. for 12 h. The mixture was cooled to room temperature, diluted with ethyl acetate (100 mL) and washed with saturated sodium hydrogen carbonate solution (100 mL). The aqueous layer was back-extracted with ethyl acetate (100 mL). The combined organic extracts were dried over sodium sulfate, filtered and concentrated in vacuum. The residue was purified by column chromatography on silica gel (petroleum ether/ethyl acetate, from 20/1 to 10/1) to give 400 mg (7% yield) of 135-B1 as a white solid.

$^1$H NMR: (400 MHz, $CDCl_3$-d) δ: 8.52 (s, 1H), 4.02 (s, 3H), 2.86 (s, 3H).

Step 3: Synthesis of methyl 5-[4-(difluoromethoxy)-3-phenyl-phenyl]-3-methyl-pyrazine-2-carboxylate (135-C)

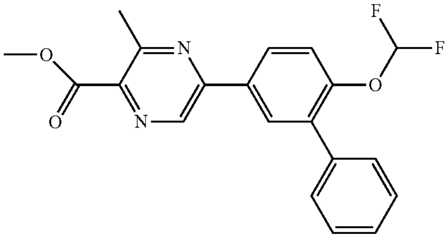 [SMILES: COC(=O)c1ncc(-c2ccc(OC(F)F)c(-c3ccccc3)c2)nc1C]

135-C was obtained via similar procedure of 152-B from 135-B and 127-C.

$^1$H NMR (400 MHz, $CDCl_3$-d) δ: 8.95 (s, 1H), 8.17 (d, J=2.4 Hz, 1H), 8.10 (dd, J=8.4, 2.4 Hz, 1H), 7.58-7.54 (m, 2H), 7.52-7.47 (m, 2H), 7.45-7.39 (m, 2H), 6.43 (t, J=73.6 Hz, 1H), 4.04 (s, 3H), 2.94 (s, 3H)

Step 4: Synthesis of 5-[4-(difluoromethoxy)-3-phenyl-phenyl]-3-methyl-pyrazine-2-carboxylic acid (135-D)

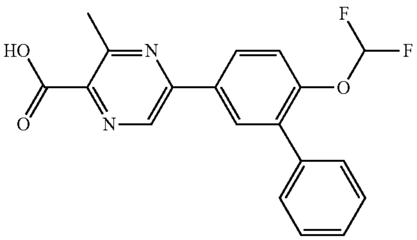 [SMILES: Cc1nc(-c2ccc(OC(F)F)c(-c3ccccc3)c2)cnc1C(=O)O]

135-D was obtained via similar procedure of 144-B from 135-C and lithium hydroxide hydrate.

LCMS: (ESI) m/z: 357.1 $[M+H]^+$.

Step 5: Synthesis of N-[3-(1,1-difluoroethyl)phenyl]-5-[4-(difluoromethoxy)-3-phenyl-phenyl]-3-methyl-pyrazine-2-carboxamide (135)

Compound ID: 135

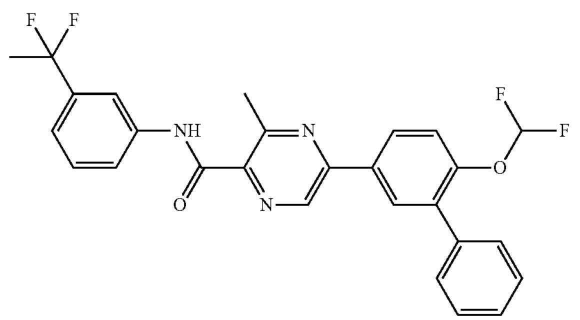

135 was obtained via similar procedure of 144 from 135-D and 3-(1,1-difluoroethyl)aniline.

LCMS: (ESI) m/z: 496.2 $[M+H]^+$.

$^1$H NMR (400 MHz, MeOD-$d_4$) δ: 9.10 (s, 1H), 8.27-8.22 (m, 2H), 8.04 (s, 1H), 7.85 (dd, J=8.0, 1.2 Hz, 1H), 7.58-7.55 (m, 2H), 7.51-7.41 (m, 5H), 7.32 (dd, J=7.6, 0.8 Hz, 1H), 6.84 (t, J=73.6, 1H), 2.99 (s, 3H), 1.95 (t, J=18.3 Hz, 3H).

Synthesis of 134

Step 1: Synthesis of 5-[4-(difluoromethoxy)-3-phenyl-phenyl]-N-[3-(1,1-difluoropropyl)phenyl]-3-methyl-pyrazine-2-carboxamide (134)

Compound ID: 134

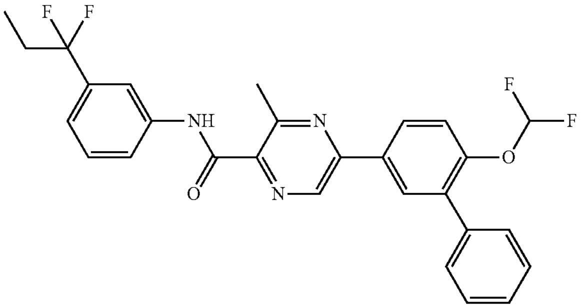

134 was obtained via similar procedure of 135 from 135-D and 3-(1,1-difluoropropyl)aniline LCMS: (ESI) m/z: 510.2 $[M+H]^+$.

$^1$H NMR (400 MHz, MeOD-$d_4$) δ: 9.08 (s, 1H), 8.26-8.21 (m, 2H), 7.99 (s, 1H), 7.84 (dd, J=8.0, 0.8 Hz, 1H), 7.58-7.55 (m, 2H), 7.50-7.41 (m, 5H), 7.27 (dd, J=7.6, 0.8 Hz, 1H), 6.84 (t, J=73.6 Hz, 1H), 2.98 (s, 3H), 2.28-2.13 (m, 2H), 1.00 (t, J=7.4 Hz, 3H).

Synthesis of 133

Step 1: Synthesis of methyl 5-(4-(difluoromethoxy)phenyl)-3-methylpyrazine-2-carboxylate (133-A)

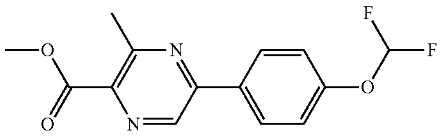 [SMILES: COC(=O)c1ncc(-c2ccc(OC(F)F)cc2)nc1C]

A mixture of 135-B (150 mg, 803 umol, 1.0 eq), 173-A (327 mg, 965 umol, 1.2 eq), 1,1-bis(diphenylphosphino)ferrocene]dichloropalladium(II) (29.4 mg, 40.2 umol, 0.05 eq), sodium bicarbonate (135 mg, 1.6 mmol, 2.0 eq) in dioxane (4 mL) and water (1 mL) was degassed and purged with nitrogen for 3 times, and then the mixture was stirred at 90° C. for 2 h under nitrogen atmosphere. The mixture was diluted with water (20 mL) and extracted with ethyl acetate (20 mL×2). The combined organic layer was washed with brine (30 mL×1), dried over sodium sulfate, filtered and concentrated. The residue was purified by silica gel column chromatography (petroleum ether/ethyl acetate, from 20/1 to 5/1) to give 0.160 g (66% yield) of 133-A as a white solid. LCMS: (ESI) m/z: 295.0 $[M+H]^+$.

Step 2: Synthesis of 5-(4-(difluoromethoxy)phenyl)-3-methylpyrazine-2-carboxylic acid (133-B)

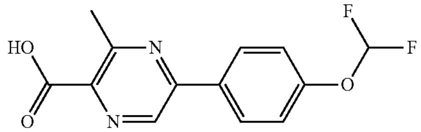 [SMILES: Cc1nc(-c2ccc(OC(F)F)cc2)cnc1C(=O)O]

To a solution of 133-A (0.240 g, 816 umol, 1.0 eq) in tetrahydrofuran (3 mL), methanol (3 mL) and water (3 mL) was added lithium hydroxide hydrate (103 mg, 2.45 mmol, 3.0 eq). The mixture was stirred at 25° C. for 1 h. The mixture was concentrated in vacuum. The residue was diluted with water (30 mL), and adjusted with hydrochloric acid aqueous (1 M) to pH=5, then extracted with ethyl acetate (30 mL×3). The combined organic layer was washed with brine (30 mL), dried over sodium sulfate, filtered and concentrated to give 0.210 g (crude) of 133-B as a white solid.

LCMS: (ESI) m/z: 281.1 $[M+H]^+$.

Step 3: Synthesis of N-(3-(1,1-difluoroethyl)phenyl)-5-(4-(difluoromethoxy)phenyl)-3-methylpyrazine-2-carboxamide (133)

Compound ID: 133

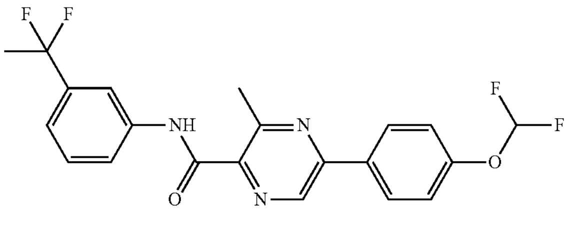

To a solution of 133-B (70.0 mg, 249.8 umol, 1.0 eq) in N,N-dimethylformamide (3 mL) was added 1H-benzo[d][1,2,3]triazol-1-ol (104 mg, 274 umol, 1.1 eq) and N,N-diisopropylethylamine (64.6 mg, 500 umol, 2.0 eq). The mixture was stirred at 20° C. for 0.5 h. Then 3-(1,1-difluoroethyl)aniline (39.3 mg, 250 umol, 1.0 eq) was added. The mixture was stirred at 20° C. for another 1 h. The mixture was concentrated in vacuo. The residue was purified by prep-HPLC (column: Boston Green ODS 150*30 mm*5 um; mobile phase: [water (0.225% formic acid)-acetonitrile]; B %: 62%-92%, 10 min) to give 41.8 mg (40% yield) of 133 as a white solid.

LCMS: (ESI) m/z: 420.1 $[M+H]^+$.

$^1$H NMR: (400 MHz, MeOD-$d_4$) δ: 9.05 (s, 1H), 8.26 (d, J=8.8 Hz, 2H), 8.04 (s, 1H), 7.85 (d, J=8.0 Hz, 1H), 7.47 (t, J=8.0 Hz, 1H), 7.32 (d, J=8.8 Hz, 3H), 6.96 (t, J=74.0 Hz, 1H), 2.99 (s, 3H), 1.95 (t, J=18.4 Hz, 3H).

Synthesis of 132

Step 1: Synthesis of 5-(4-(difluoromethoxy)phenyl)-N-(3-(1,1-difluoropropyl)phenyl)-3-methylpyrazine-2-carboxamide (132)

Compound ID: 132

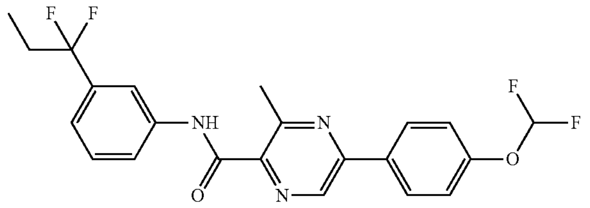

132 was obtained via similar procedure of 133 from 133-B and 3-(1,1-difluoropropyl)aniline.

LCMS: (ESI) m/z: 434.1 $[M+H]^+$.

$^1$H NMR: (400 MHz, MeOD-$d_4$) δ: 9.04 (s, 1H), 8.26 (d, J=8.8 Hz, 2H), 7.99 (s, 1H), 7.85 (d, J=8.0 Hz, 1H), 7.47 (t, J=8.0 Hz, 1H), 7.32 (d, J=8.8 Hz, 2H), 7.28 (d, J=8.0 Hz, 1H), 6.96 (t, J=74.0 Hz, 1H), 2.98 (s, 3H), 2.21 (dt, J=7.6, 16.0 Hz, 2H), 1.00 (t, J=7.6 Hz, 3H).

Synthesis of 131

Step 1: 4-(2-(difluoromethoxy)-5-nitrophenyl)-2-methyloxazole (131-A)

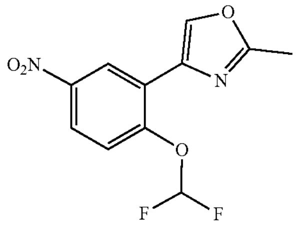 [SMILES: Cc1nc(-c2cc([N+](=O)[O-])ccc2OC(F)F)co1]

131-A was obtained via similar procedure of 149-C from 149-B and acetamide.

LCMS: (ESI) m/z: 271.0 $[M+H]^+$.

$^1$H NMR (400 MHz, CDCl-d) δ: 9.04 (d, J=2.8 Hz, 1H), 8.18 (dd, J=9.2, 2.9 Hz, 1H), 8.10 (s, 1H), 7.24-7.27 (m, 1H), 6.52-6.93 (m, 1H), 2.55 (s, 3H).

Step 2: 4-(difluoromethoxy)-3-(2-methyloxazol-4-yl)aniline (131-B)

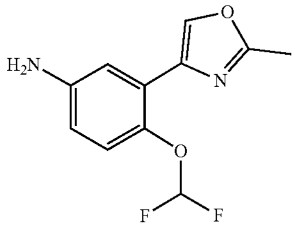

131-B was obtained via similar procedure of 149-D from 149-A and hydrogen

LCMS: (ESI) m/z: 241.1 $[M+H]^+$.

Step 3: 4-(2-(difluoromethoxy)-5-hydrazinylphenyl)-2-methyloxazole (131-C)

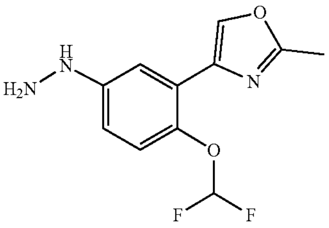 [SMILES: Cc1nc(-c2cc(NN)ccc2OC(F)F)co1]

131-C was obtained via general procedure I from 131-B

LCMS: (ESI) m/z: 256.1 $[M+H]^+$.

Step 4: ethyl 2-(4-(difluoromethoxy)-3-(2-methyloxazol-4-yl)phenyl)hydrazinecarboxylate (131-D)

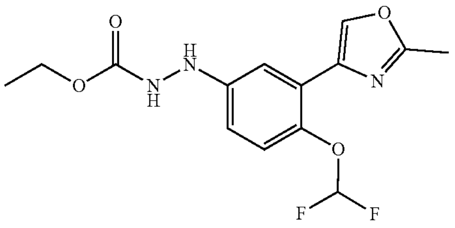 [SMILES: CCOC(=O)NNc1ccc(OC(F)F)c(-c2coc(C)n2)c1]

131-D was obtained via similar procedure of 186-A from 131-C and ethyl carbonochloridate LCMS: (ESI) m/z: 328.1 $[M+H]^+$.

$^1$H NMR (400 MHz, $CDCl_3$-d) δ: 7.95 (s, 1H), 7.50 (br d, J=2.6 Hz, 1H), 6.97 (d, J=8.8 Hz, 1H), 6.68 (dd, J=8.8, 2.9 Hz, 1H), 6.09-6.55 (m, 2H), 4.12 (q, J=7.2 Hz, 2H), 2.39-2.47 (m, 3H), 1.15-1.21 (m, 3H).

Step 5: ethyl 1-(4-(difluoromethoxy)-3-(2-methyloxazol-4-yl)phenyl)-3-methyl-1H-pyrazole-4-carboxylate (131-E)

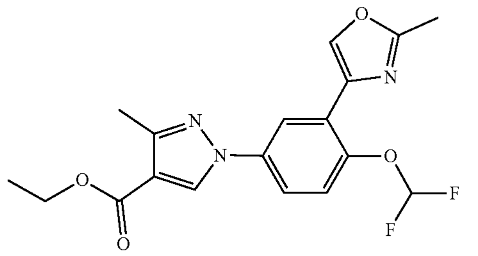 [SMILES: CCOC(=O)c1cn(-c2ccc(OC(F)F)c(-c3coc(C)n3)c2)nc1C]

131-E was obtained via similar procedure of 186-B from 131-D and (2E)-2-(ethoxymethylene)-3-oxo-butanoate.

LCMS: (ESI) m/z: 378.1 $[M+H]^+$.

Step 6: 1-(4-(difluoromethoxy)-3-(2-methyloxazol-4-yl)phenyl)-3-methyl-1H-pyrazole-4-carboxylic acid (131-F)

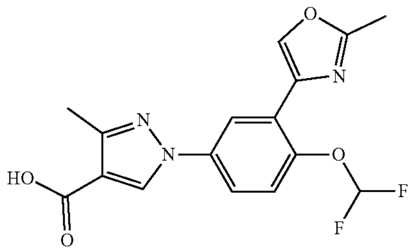 [SMILES: Cc1nc(-c2cc(-n3cc(C(=O)O)c(C)n3)ccc2OC(F)F)co1]

131-F was obtained via similar procedure of 186-D from 131-E and sodium hydroxide LCMS: (ESI) m/z: 350.1 $[M+H]^+$.

Step 7: N-(3-(1,1-difluoroethyl)phenyl)-1-(4-(difluoromethoxy)-3-(2-methyloxazol-4-yl)phenyl)-3-methyl-1H-pyrazole-4-carboxamide (131)

Compound ID : 131

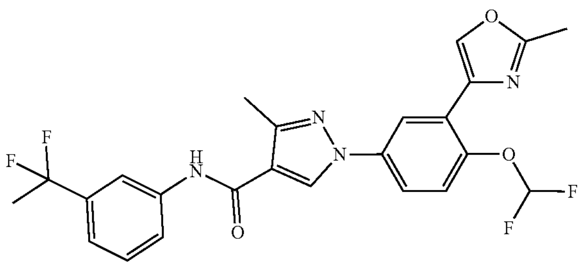

131 was obtained via similar procedure of 186 from 131-F and 3-(1,1-difluoroethyl)aniline LCMS: (ESI) m/z: 489.1 $[M+H]^+$.

$^1$H NMR (400 MHz, MeOD-$d_4$) δ: 8.88 (s, 1H), 8.50 (d, J=2.8 Hz, 1H), 8.24 (s, 1H), 7.94 (s, 1H), 7.75-7.82 (m, 2H), 7.40-7.49 (m, 2H), 7.28-7.33 (m, 1H), 6.85-7.27 (m, 1H), 2.59 (s, 3H), 2.56 (s, 3H), 1.96 (t, J=18.4 Hz, 3H).

Synthesis of 130

Step 1: N-(3-(1,1-difluoroethyl)phenyl)-2-(6-(difluoromethoxy)-[1,1'-biphenyl]-3-yl)-6-methylpyrimidine-4-carboxamide (130)

Compound ID: 130

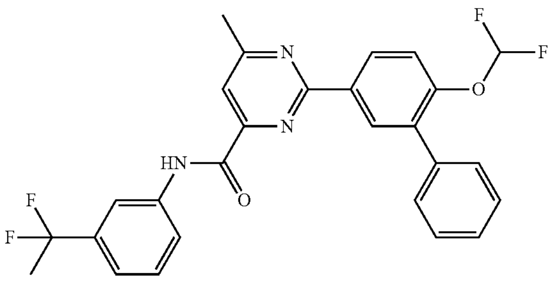

130 was obtained via similar procedure of 173 from 127-D and 3-(1,1-difluoroethyl)aniline LCMS: (ESI) m/z: 496.1 $[M+H]^+$.

$^1$H NMR (400 MHz, MeOD-$d_4$) δ: 8.72 (dd, J=2.0, 8.4 Hz, 1H), 8.69 (d, J=2.0 Hz, 1H), 8.07 (s, 1H), 7.96 (s, 1H), 7.91 (d, J=8.0 Hz, 1H), 7.63-7.58 (m, 2H), 7.52-7.35 (m, 6H), 6.85 (t, J=73.6 Hz, 1H), 2.72 (s, 3H), 1.96 (t, J=18.0 Hz, 3H).

Synthesis of 129

Step 1: Synthesis of N'-(cyclohexylidenemethyl)-4-methylbenzenesulfonohydrazide (129-A)

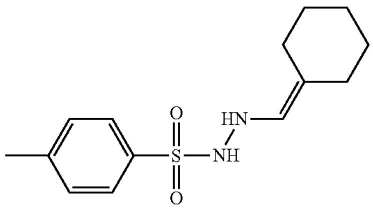 [SMILES: Cc1ccc(S(=O)(=O)NNC=C2CCCCC2)cc1]

To a solution of 4-methylbenzenesulfonohydrazide (8.30 g, 44.6 mmol, 1.0 eq) in methanol (50 mL) was added cyclohexanecarbaldehyde (5.00 g, 44.6 mmol, 1.0 eq). The solution was stirred at 20° C. for 3 h. The reaction was cooled down to 0° C. and the resulting precipitate was filtered and the filter cake was dried in vacuo to afford 5.10 g (41% yield) of 129-A as an off-white solid.

$^1$H NMR (400 MHz, $CDCl_3$-d) δ: 7.7.82 (d, J=8.4 Hz, 2H), 7.60 (br s, 1H), 7.33 (d, J=8.0 Hz, 2H), 7.08 (d, J=5.2 Hz, 1H), 2.45 (s, 3H), 2.28-2.15 (m, 1H), 1.80-1.65 (m, 5H), 1.29-1.07 (m, 5H).

Step 2: Synthesis of 3-(cyclohexylidenemethyl)-2-methoxy-5-nitro-1,1'-biphenyl (129-B)

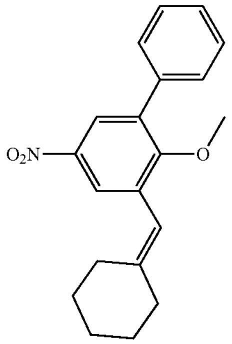 [SMILES: COc1c(C=C2CCCCC2)cc([N+](=O)[O-])cc1-c1ccccc1]

To a suspension of 161-E (1.00 g, 2.82 mmol, 1.0 eq), 129-A (1.18 g, 4.22 mmol, 1.5 eq) in dioxane (15 mL), which was phrased with nitrogen for three times, was added tri(dibenzylideneaceton)dipalladium(0) (258 mg, 282 umol, 0.10 eq), dicyclohexyl-[2-[2,4,6-tri(propan-2-yl)phenyl] phenyl]phosphane (268 mg, 563 umol, 0.20 eq) and lithium; 2-methylpropan-2-olate (789 mg, 9.86 mmol, 3.5 eq). The reaction mixture was stirred at 85° C. under an atmosphere of nitrogen for 10 h. The reaction was diluted with ethyl acetate (50 mL). The suspension was filtered and washed with ethyl acetate (30 mL×3). The combined filtrate was concentrated in vacuo. The residue was purified by silica gel column chromatography (ethyl acetate/petroleum ether, 1/60) to afford 2.50 g (79% yield) of 129-B was obtained as a yellow oil.

LCMS: (ESI) m/z: 324.2 $[M+H]^+$.

Step 3: Synthesis of 5-(cyclohexylmethyl)-6-methoxy-[1,1'-biphenyl]-3-amine (129-C)

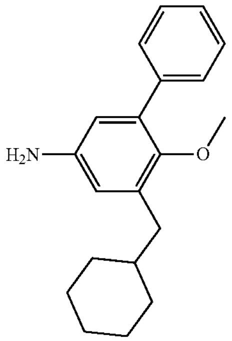 [SMILES: COc1c(CC2CCCCC2)cc(N)cc1-c1ccccc1]

129-C was obtained via similar procedure of 161-G from 129-B and hydrogen.

LCMS: (ESI) m/z: 296.2 $[M+H]^+$.

Step 4: Synthesis of 3-(cyclohexylmethyl)-5-iodo-2-methoxy-1,1'-biphenyl (129-D)

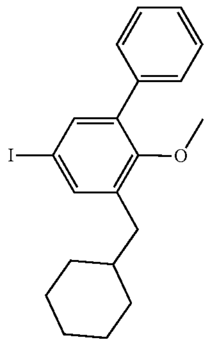 [SMILES: COc1c(CC2CCCCC2)cc(I)cc1-c1ccccc1]

129-D was obtained via similar procedure of 161-H from 129-C and sodium nitrite, potassium iodide $^1$H NMR (400 MHz, $CDCl_3$-d) δ: 7.56-7.49 (m, 3H), 7.46-7.40 (m, 3H), 7.38-7.33 (m, 1H), 3.30 (s, 3H), 2.50 (d, J=7.2 Hz, 2H), 1.80-1.52 (m, 7H), 1.24-1.20 (m, 2H), 1.09-0.96 (m, 2H).

Step 5: Synthesis of tert-butyl 1-(5-(cyclohexylmethyl)-6-methoxy-[1,1'-biphenyl]-3-yl)hydrazinecarboxylate (129-E)

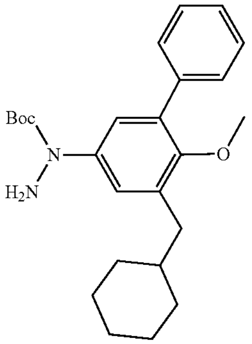 [SMILES: COc1c(CC2CCCCC2)cc(N(N)C(=O)OC(C)(C)C)cc1-c1ccccc1]

129-E was obtained via similar procedure of 161-I from 129-D and tert-butyl hydrazinecarboxylate LCMS: (ESI) m/z: 338.2 $[M-tBuO]^+$.

Step 6: Synthesis of (5-(cyclohexylmethyl)-6-methoxy-[1,1'-biphenyl]-3-yl)hydrazine (129-F)

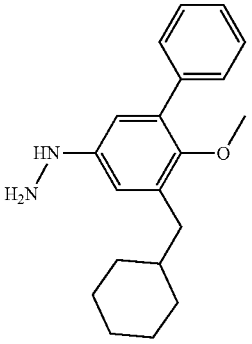 [SMILES: COc1c(CC2CCCCC2)cc(NN)cc1-c1ccccc1]

129-F was obtained via similar procedure of 161-J from 129-E and hydrogen chloride/ethyl acetate LCMS: (ESI) m/z: 311.2 [M+H]+.

Step 7: Synthesis of 1-(5-(cyclohexylmethyl)-6-methoxy-[1,1'-biphenyl]-3-yl)-3-methyl-1H-pyrazol-5(4H)-one (129-G)

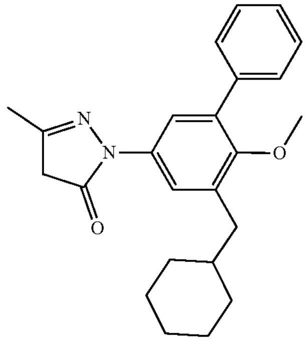

129-G was obtained via general procedure II from 129-F

LCMS: (ESI) m/z: 377.2 [M+H]+.

$^1$H NMR (400 MHz, MeOD-$d_4$) δ: 7.66-7.59 (m, 2H), 7.56-7.32 (m, 5H), 3.34 (s, 3H), 2.64 (d, J=7.6 Hz, 2H), 2.30 (s, 3H), 1.81-1.68 (m, 5H), 1.36-1.26 (m, 4H), 1.14-1.02 (m, 2H).

Step 8: Synthesis of 4-nitrophenyl 1-(5-(cyclohexylmethyl)-6-methoxy-[1,1'-biphenyl]-3-yl)-3-methyl-5-oxo-4,5-dihydro-1H-pyrazole-4-carboxylate (129-H)

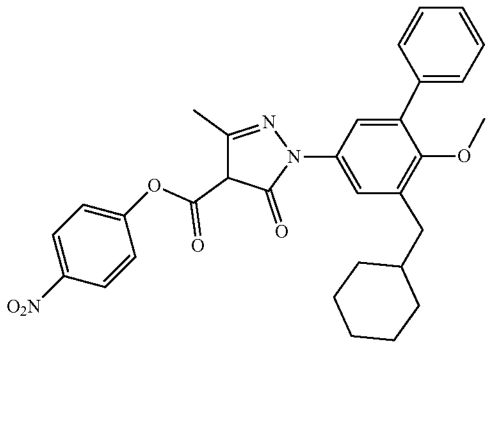 [SMILES: COc1c(CC2CCCCC2)cc(N2N=C(C)C(C(=O)Oc3ccc([N+](=O)[O-])cc3)C2=O)cc1-c1ccccc1]

129-H was obtained via general procedure III from 129-G

LCMS: (ESI) m/z: 542.2 [M+H]+.

Step 9: Synthesis of 1-(5-(cyclohexylmethyl)-6-methoxy-[1,1'-biphenyl]-3-yl)-N-(3-(1,1-difluoroethyl)phenyl)-3-methyl-5-oxo-4,5-dihydro-1H-pyrazole-4-carboxamide (129)

Compound ID: 129

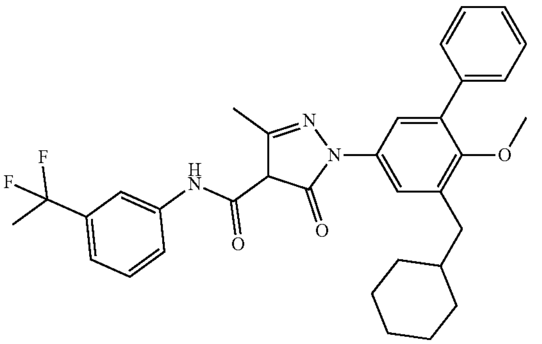

129 was obtained via general procedure IV from 129-H and 3-(1,1-difluoroethyl)aniline LCMS: (ESI) m/z: 560.3 [M+H]+.

$^1$H NMR (400 MHz, MeOD-$d_4$) δ: 7.81 (br s, 1H), 7.56-7.48 (m, 3H), 7.42-7.23 (m, 6H), 7.12 (d, J=7.6 Hz, 1H), 3.22 (s, 3H), 2.51 (d, J=7.2 Hz, 2H), 2.46 (s, 3H), 1.88-1.77 (d, J=28.0 Hz, 3H), 1.67-1.58 (m, 6H), 1.20-1.11 (m, 3H), 1.01-0.90 (m, 2H).

Synthesis of 128

Step 1: Synthesis of 1-(5-(cyclohexylmethyl)-6-methoxy-[1,1'-biphenyl]-3-yl)-N-(3-(1,1-difluoropropyl)phenyl)-3-methyl-5-oxo-4,5-dihydro-1H-pyrazole-4-carboxamide (128)

Compound ID: 128

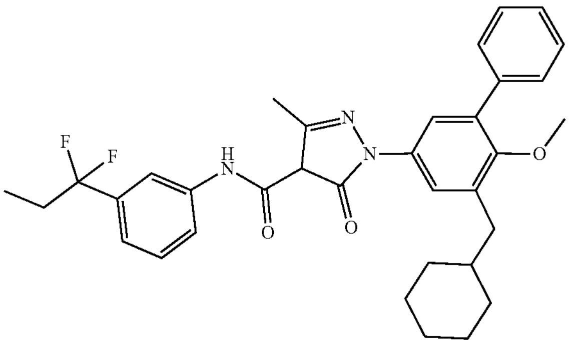

128 was obtained via general procedure IV from 129-H and 3-(1,1-difluoropropyl)aniline LCMS: (ESI) m/z: 574.3 [M+H]+.

$^1$H NMR (400 MHz, MeOD-$d_4$) δ: 7.77 (br s, 1H), 7.54-7.51 (bm, 3H), 7.39-7.23 (m, 6H), 7.10 (d, J=7.6 Hz, 1H), 3.24 (s, 3H), 2.59-2.42 (m, 5H), 2.08 (qt, J=7.8, 15.6 Hz, 2H), 1.71-1.54 (m, 6H), 1.26-1.09 (m, 3H), 1.03-0.91 (m, 2H), 0.88 (t, J=7.6 Hz, 3H).

Synthesis of 127

Step 1: Synthesis of 5-bromo-[1,1'-biphenyl]-2-ol (127-A)

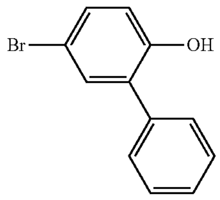 [SMILES: Oc1ccc(Br)cc1-c1ccccc1]

To a 50 mL round-bottom flask equipped with a magnetic stir bar was added 2-phenylphenol (4.00 g, 23.5 mmol, 1.0 eq) followed by the addition of dichloromethane (10 mL). The solution was cooled to −20° C. Next, bromine (3.76 g, 23.5 mmol, 1.0 eq) in dichloromethane (5 mL) was added dropwise. The mixture was allowed to warm to 25° C. and stir for 12 hr. The mixture was diluted by dichloromethane to 80 mL. The mixture was quenched by slow addition of saturated aqueous ammonium sodium sulfite (50 mL). The resulting mixture was transferred to a separatory funnel, and the aqueous layer mixture was extracted with saturated aqueous dichloromethane (80 mL×3). The combined organic layer was washed with brine (80 mL), dried over anhydrous sodium sulfate, filtered, and concentrated under reduced pressure affording the residue as a yellow oil. The crude product was purified by silica gel column chromatography (petroleum ether/ethyl acetate, from 20/1 to 10/1) to give 5.50 g (86% yield) of 127-A as a colorless oil.

LCMS: (ESI) m/z: 249.0 $[M+H]^+$.

Step 2: Synthesis of 5-bromo-2-(difluoromethoxy)-1,1'-biphenyl (127-B)

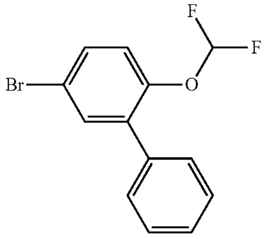 [SMILES: FC(F)Oc1ccc(Br)cc1-c1ccccc1]

To a 50 mL round-bottom flask equipped with a magnetic stir bar and a reflux condenser was added 127-A (3.30 g, 12.2 mmol, 1.0 eq) followed by the addition of acetonitrile (15 mL) and water (6 mL). Then reagent potassium hydroxide (6.84 g, 122 mmol, 10 eq) and 1-[[bromo(difluoro)methyl]-ethoxy-phosphoryl]oxyethane (3.25 g, 12.2 mmol, 1.0 eq) was added into the mixture at 0° C. The mixture was heated to 25° C. and stirred for 2 hr. The mixture was quenched by slow addition of water (100 mL). The resulting mixture was transferred to a separatory funnel, and the aqueous layer mixture was extracted with ethyl acetate (50 mL×3). The combined organic layer was washed with brine (50 mL), dried over anhydrous sodium sulfate, filtered, and concentrated under reduced pressure affording the residue as a colorless oil. The crude product was purified by silica gel column chromatography (petroleum ether/ethyl acetate, from 1/0 to 1/0) to give 2.00 g (55% yield) of 127-B as a colorless oil.

$^1H$ NMR (400 MHz, $CDCl_3$-d) δ: 7.57 (d, J=2.4 Hz, 1H), 7.36-7.51 (m, 6H), 7.15 (d, J=8.8 Hz, 1H), 6.04-6.53 (m, 1H).

Step 3: Synthesis of 2-(6-(difluoromethoxy)-[1,1'-biphenyl]-3-yl)-4,4,5,5-tetramethyl-1,3,2-dioxaborolane (127-C)

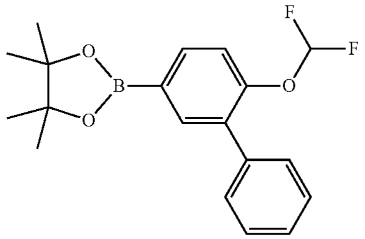 [SMILES: CC1(C)OB(c2ccc(OC(F)F)c(-c3ccccc3)c2)OC1(C)C]

To a 100 mL round-bottom flask equipped with a magnetic stir bar was added 127-B (2.00 g, 6.69 mmol, 1.0 eq), 4,4,5,5-tetramethyl-2-(4,4,5,5-tetramethyl-1,3,2-dioxaborolan-2-yl)-1,3,2-dioxaborolane (3.40 g, 13.4 mmol, 2.0 eq), potassium acetate (1.31 g, 13.4 mmol, 2.0 eq) followed by the addition of dioxane (20 mL). Then 1,1-bis(diphenylphosphino)ferrocene]dichloropalladium(II) (489 mg, 668 umol, 0.10 eq) was added into the mixture at 25° C. The flask was then evacuated and backfilled with nitrogen for three times. The mixture was stirred at 85° C. under an atmosphere of nitrogen for 12 hr. The mixture was filtered, the filtrate was concentrated under reduced pressure to give a residue. The residue was purified by silica gel column chromatography (petroleum ether/ethyl acetate, from 50/1 to 25/1) to give 3.00 g (98% yield) of 127-C as a yellow oil.

LCMS: (ESI) m/z: 347.2 $[M+H]^+$.

Step 4: Synthesis of 2-(6-(difluoromethoxy)-[1,1'-biphenyl]-3-yl)-6-methylpyrimidine-4-carboxylic acid (127-D)

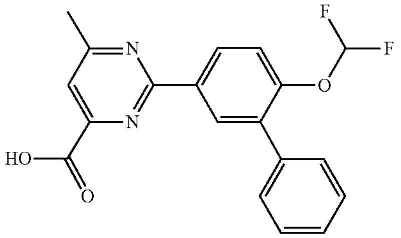 [SMILES: Cc1cc(C(=O)O)nc(-c2ccc(OC(F)F)c(-c3ccccc3)c2)n1]

To a 50 mL round-bottom flask equipped with a magnetic stir bar and a reflux condenser was added 127-C (244 mg, 536 umol, 1.0 eq), methyl 2-chloro-6-methyl-pyrimidine-4-carboxylate (100 mg, 536 umol, 1.0 eq), 1,1-bis(diphenylphosphino)ferrocene]dichloropalladium(II) (39.2 mg, 53.6 umol, 0.10 eq) followed by the addition of dioxane (10 mL) and water (3 mL). Then reagent sodium bicarbonate (90.0 mg, 1.07 mmol, 2.0 eq) was added into the mixture. The mixture was heated to 90° C. and stirred for 12 hr. The mixture was filtered, the filtrate was diluted with water (50 ml), the pH of the mixture was adjusted to 10 by sodium hydroxide solution (1 M). The resulting mixture was transferred to a separatory funnel, and the aqueous layer mixture was extracted with ethyl acetate (50 mL×2). The pH of the aqueous phase was adjusted to 4 by hydrogen chloride solution (6 M). The mixture was extracted with ethyl acetate (40 mL×3). The combined organic layer was washed with brine (30 mL), dried over anhydrous sodium sulfate, filtered and concentrated to give 150 mg (71% yield) of 127-D as a yellow oil.

LCMS: (ESI) m/z: 357.0 $[M+H]^+$.

Step 4: Synthesis of 2-(6-(difluoromethoxy)-[1,1'-biphenyl]-3-yl)-N-(3-(1,1-difluoropropyl)phenyl)-6-methylpyrimidine-4-carboxamide (127)

Compound ID : 127

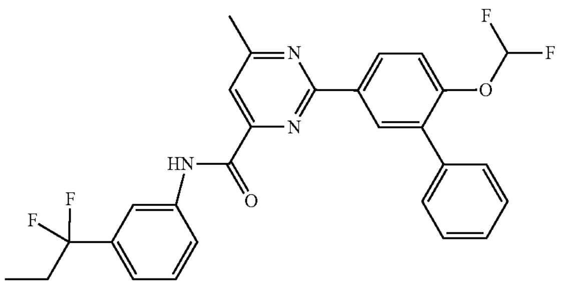

127 was obtained via similar procedure of 173 from 127-D and 3-(1,1-difluoropropyl)aniline LCMS: (ESI) m/z: 510.2 $[M+H]^+$.

$^1$H NMR (400 MHz, MeOD-$d_4$) δ: 8.66-8.69 (m, 2H), 8.02 (s, 1H), 7.88-7.92 (m, 2H), 7.57-7.59 (m, 2H), 7.46-7.51 (m, 3H), 7.39-7.43 (m, 2H), 7.32 (d, J=7.6 Hz, 1H), 6.82 (t, J=74.0 Hz, 1H), 2.70 (s, 3H), 2.13-2.28 (m, 2H), 1.00 (t, J=7.6 Hz, 3H).

Synthesis of 126

Step 1: Synthesis of 6-(4-(difluoromethoxy)phenyl)-3-methylpyrazine-2-carboxylic acid (126-A)

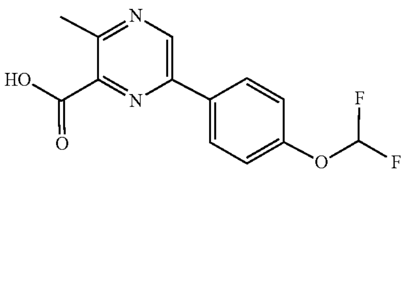 [SMILES: Cc1ncc(-c2ccc(OC(F)F)cc2)nc1C(=O)O]

126-A was obtained via similar procedure of 173-C from 173-A and 118-B.

LCMS: (ESI) m/z: 280.8 $[M+H]^+$.

Step 2: Synthesis of N-(3-(1,1-difluoroethyl)phenyl)-6-(4-(difluoromethoxy)phenyl)-3-methylpyrazine-2-carboxamide (126)

Compound ID : 126

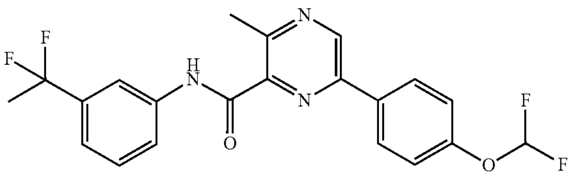

126 was obtained via similar procedure of 173 from 126-A and 3-(1,1-difluoroethyl)aniline LCMS: (ESI) m/z: 420.1 $[M+H]^+$.

$^1$H NMR (400 MHz, MeOD-$d_4$) δ: 9.18 (s, 1H), 8.26-8.34 (m, 2H), 8.06 (s, 1H), 7.88 (br d, J=8.4 Hz, 1H), 7.50 (t, J=8.0 Hz, 1H), 7.31-7.39 (m, 3H), 6.76-7.18 (m, 1H), 2.93 (s, 3H), 1.97 ppm (t, J=18.4 Hz, 3H).

Synthesis of 125

Step 1: Synthesis of 6-(4-(difluoromethoxy)phenyl)-N-(3-(1,1-difluoropropyl)phenyl)-3-methylpyrazine-2-carboxamide (125)

Compound ID: 125

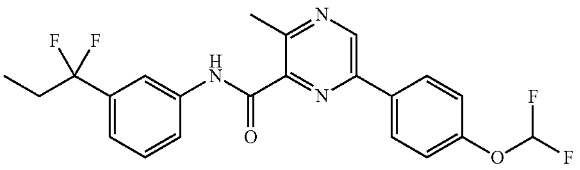

125 was obtained via similar procedure of 173 from 126-A and 3-(1,1-difluoropropyl)aniline LCMS: (ESI) m/z: 434.1 $[M+H]^+$.

$^1$H NMR (400 MHz, MeOD-$d_4$) δ: 9.18 (s, 1H), 8.23-8.37 (m, 2H), 8.02 (s, 1H), 7.88 (d, J=8.4 Hz, 1H), 7.45-7.56 (m, 1H), 7.27-7.38 (m, 3H), 6.71-7.22 (m, 1H), 2.93 (s, 3H), 2.14-2.31 (m, 2H), 1.02 (t, J=7.6 Hz, 3H).

Synthesis of 124

Step 1: Synthesis of N-[3-(1,1-difluoroethyl)phenyl]-2-[4-(difluoromethoxy)-3-phenyl-phenyl]-5-methyl-oxazole-4-carboxamide (124)

Compound ID:124

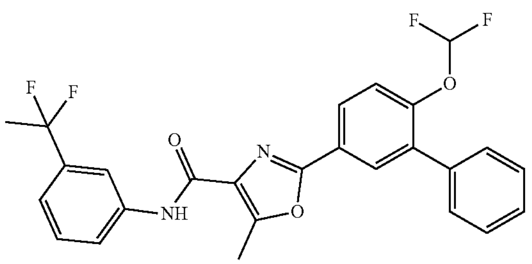

124 was obtained via similar procedure of 154 from 123-E and 3-(1,1-difluoroethyl)aniline.

LCMS: (ESI) m/z: 485.3 $[M+H]^+$.

$^1H$ NMR: (400 MHz, MeOD-$d_4$) δ: 8.17 (d, J=2.4 Hz, 1H), 8.12 (dd, J=2.4, 8.5 Hz, 1H), 7.99 (s, 1H), 7.80 (dd, J=1.0, 8.2 Hz, 1H), 7.58-7.53 (m, 2H), 7.52-7.40 (m, 5H), 7.31 (dd, J=0.8, 7.7 Hz, 1H), 7.03-6.63 (m, 1H), 2.76 (s, 3H), 1.94 (t, J=18.4 Hz, 3H).

Synthesis of 123

Step 1: Synthesis of 3-bromo-4-(difluoromethoxy)benzonitrile (123-A)

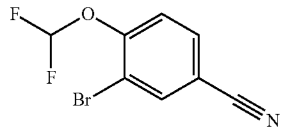 [SMILES: N#Cc1ccc(OC(F)F)c(Br)c1]

To a solution of 3-bromo-4-hydroxy-benzonitrile (10.0 g, 50.5 mmol, 1.0 eq) and (2-chloro-2,2-difluoro-acetyl)oxy-sodium (11.6 g, 75.8 mmol, 1.5 eq) in N,N-dimethylformamide (100 mL) was added sodium carbonate (8.03 g, 75.8 mmol, 1.5 eq), the solution was stirred at 100° C. for 12 h. The mixture was quenched by slow addition of saturated aqueous water (200 mL). The resulting mixture was transferred to a separatory funnel, and the aqueous layer mixture was extracted with ethyl acetate (100 mL×3). The combined organic layers were washed with brine (200 mL), dried over anhydrous sodium sulfate, filtered, and concentrated under reduced pressure affording the residue. The crude product was purified by silica gel column chromatography (petroleum ether/ethyl acetate, from 20/1 to 10/1) to give 6.00 g (48% yield) of 123-A as a white solid.

LCMS: (ESI) m/z: 247.9, 249.9 $[M+H]^+$.

Step 2: Synthesis of 4-(difluoromethoxy)-3-phenyl-benzonitrile (123-B)

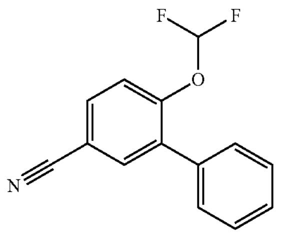 [SMILES: N#Cc1ccc(OC(F)F)c(-c2ccccc2)c1]

To a solution of 123-A (1.50 g, 6.05 mmol, 1.0 eq) and phenylboronic acid (1.47 g, 12.1 mmol, 2.0 eq) in dioxane (20 mL) was added a solution of potassium carbonate (1.67 g, 12.1 mmol, 2.0 eq) in water (4 mL) and 1,1-bis(diphenylphosphino)ferrocene]dichloropalladium(II) (443 mg, 605 umol, 0.10 eq). The suspension was degassed under vacuum and purged with nitrogen several times. The mixture was stirred under nitrogen at 80° C. for 12 hr. To the reaction mixture was added water (20 mL), the mixture was extracted with ethyl acetate (20 mL×3). The combined organic layer was washed with brine (50 mL), dried over anhydrous sodium sulfate, filtered, and concentrated under reduced pressure. The crude product was purified by silica gel column chromatography (petroleum ether/ethyl acetate, from 1/0 to 10/1) to give 1.50 g (99% yield) of 123-B as a light yellow solid.

LCMS: (ESI) m/z: 246.1 $[M+H]^+$.

Step 3: Synthesis of [4-(difluoromethoxy)-3-phenyl-phenyl]methanamine (123-C)

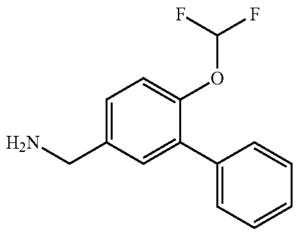 [SMILES: NCc1ccc(OC(F)F)c(-c2ccccc2)c1]

To a solution of 123-B (1.50 g, 5.99 mmol, 1.0 eq) in saturated ammonia/methanol (10 mL) was added raney nickel (524 mg, 6.12 mmol, 1.0 eq). The suspension was degassed under vacuum and purged with hydrogen several times. The mixture was stirred under hydrogen (15 psi) at 25° C. for 1 hr. The mixture was filtered, concentrated under reduced pressure. The crude product was purified by silica gel column chromatography (petroleum ether/ethyl acetate, from 10/1 to 5/1) to give 1.40 g (78% yield) of 123-C as a light green oil.

LCMS: (ESI) m/z: 250.1 $[M+H]^+$.

Step 4: Synthesis of ethyl 2-(6-(difluoromethoxy)-[1,1'-biphenyl]-3-yl)-5-methyloxazole-4-carboxylate (123-D)

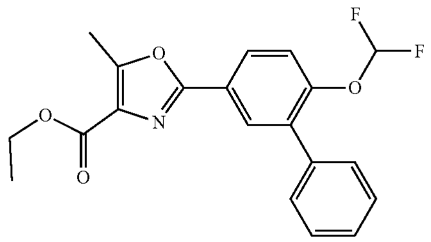 [SMILES: CCOC(=O)c1nc(-c2ccc(OC(F)F)c(-c3ccccc3)c2)oc1C]

123-D was obtained via similar procedure of 153-A from 123-C.

LCMS: (ESI) m/z: 374.1 $[M+H]^+$.

Step 5: Synthesis of 2-[4-(difluoromethoxy)-3-phenyl-phenyl]-5-methyl-oxazole-4-carboxylic acid (123-E)

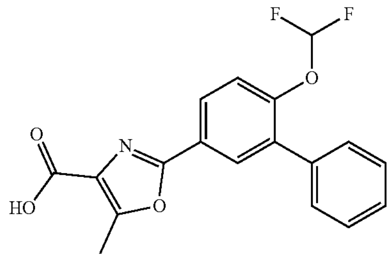 [SMILES: Cc1oc(-c2ccc(OC(F)F)c(-c3ccccc3)c2)nc1C(=O)O]

123-E was obtained via similar procedure of 154-C from 123-D and sodium hydroxide.

LCMS: (ESI) m/z: 346.0 $[M+H]^+$.

Step 6: Synthesis of 2-[4-(difluoromethoxy)-3-phenyl-phenyl]-N-[3-(1,1-difluoropropyl)phenyl]-5-methyl-oxazole-4-carboxamide (123)

Compound ID: 123

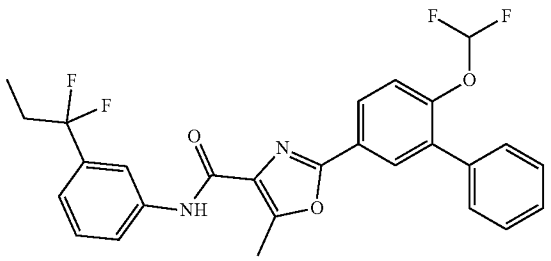

123 was obtained via similar procedure of 154 from 123-E and 3-(1,1-difluoropropyl)aniline.

LCMS: (ESI) m/z: 499.3 $[M+H]^+$.

$^1$H NMR: (400 MHz, MeOD-$d_4$) δ: 8.17 (d, J=2.4 Hz, 1H), 8.11 (dd, J=2.4, 8.5 Hz, 1H), 7.95 (s, 1H), 7.80 (d, J=8.4 Hz, 1H), 7.58-7.53 (m, 2H), 7.51-7.39 (m, 5H), 7.26 (d, J=7.8 Hz, 1H), 7.03-6.63 (m, 1H), 2.76 (s, 3H), 2.29-2.10 (m, 2H), 0.99 (t, J=7.6 Hz, 3H).

Synthesis of 122

Step 1: Synthesis of 2-benzyl-4,4,5,5-tetramethyl-1,3,2-dioxaborolane (122-A)

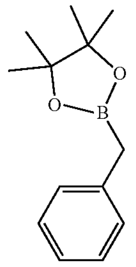 [SMILES: CC1(C)OB(Cc2ccccc2)OC1(C)C]

To a solution of 4,4,5,5-tetramethyl-2-(4,4,5,5-tetramethyl-1,3,2-dioxaborolan-2-yl)-1,3,2-dioxaborolane (44.5 g, 175 mmol, 1.5 eq), triphenylphosphine (3.99 g, 15.2 mmol, 0.13 eq), lithium methanolate (4 M, 58.5 mL, 2.0 eq) and copper iodide (2.23 g, 11.7 mmol, 0.10 eq) in N,N-dimethylformamide (100 mL) was added a solution of bromomethylbenzene (20.0 g, 117 mmol, 1.0 eq) in N,N-dimethylformamide (200 mL). The suspension was degassed under vacuum and purged with nitrogen several times. The mixture was stirred under nitrogen at 20° C. for 12 hours. The suspension was filtered and the filtrate was concentrated. The residue was purified by silica column (petroleum ether/ethyl acetate, from 1/0 to 10/1) to give 5.00 g (20% yield) of 122-A as a white solid.

$^1$H NMR: (400 MHz, $CDCl_3$-d) δ: 7.17-7.04 (m, 5H), 2.22 (s, 2H), 1.15 (s, 12H).

Step 2: Synthesis of 3-benzyl-2-methoxy-5-nitro-1,1'-biphenyl (122-B)

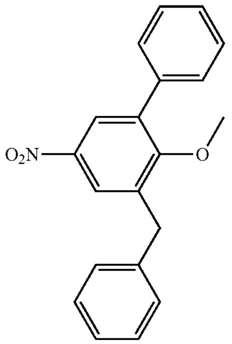 [SMILES: COc1c(Cc2ccccc2)cc([N+](=O)[O-])cc1-c1ccccc1]

To a solution of 161-E (3.00 g, 8.45 mmol, 1.0 eq) and sodium carbonate (1.79 g, 16.9 mmol, 2.0 eq) in dioxane (30 mL)/water (6 mL) was added 122-A (4.85 g, 22.2 mmol, 2.6 eq) and 1,1-bis(diphenylphosphino)ferrocene]dichloropalladium(II) (618 mg, 845 umol, 0.10 eq). The suspension was degassed under vacuum and purged with nitrogen several times. The mixture was stirred under nitrogen at 90° C. for 12 hours. The solution was poured into water(50 mL), extracted with ethyl acetate(50 mL×3), the combined organic phase was washed with brine(50 mL), dried with anhydrous sodium sulfate, filtered and concentrated. The residue was purified by silica column (petroleum ether/ethyl acetate, from 1/0 to 10/1) to give 5.00 g (62% yield) of 122-B as a white solid.

Step 3: Synthesis of 5-benzyl-6-methoxy-[1,1'-biphenyl]-3-amine (122-C)

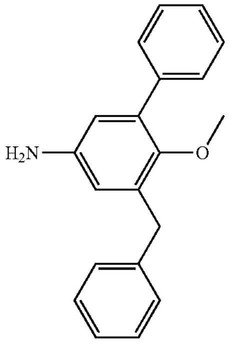 [SMILES: COc1c(Cc2ccccc2)cc(N)cc1-c1ccccc1]

To a solution of 122-B (5.00 g, 15.7 mmol, 1.0 eq) in methanol (50 mL) was added Pd/C (500 mg, 10% purity). The suspension was degassed under vacuum and purged with hydrogen several times. The mixture was stirred under hydrogen (15 psi) at 20° C. for 12 hours. The suspension was filtered and the filtrate was concentrated to give 4.00 g (76% yield) of 122-C as a colorless oil.

LCMS: (ESI) m/z: 290.1 $[M+H]^+$.

Step 4: Synthesis of 3-benzyl-5-iodo-2-methoxy-1,1'-biphenyl (122-D)

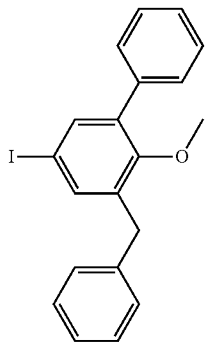 [SMILES: COc1c(Cc2ccccc2)cc(I)cc1-c1ccccc1]

To a solution of 122-C (3.00 g, 8.98 mmol, 1.0 eq) in hydrochloric acid (3 M, 40 mL, 13 eq) was added dropwise a solution of sodium nitrite (858 mg, 12.4 mmol, 1.4 eq) in water (10 mL) at 0° C., the solution was stirred at 0° C. for 30 min. Then potassium iodide (8.61 g, 51.9 mmol, 5.8 eq) was added into the solution and the mixture was stirred at 20° C. for 2 h. The solution was poured into water (20 mL), extracted with ethyl acetate (20 mL×3). The combined organic phase was washed with brine (20 mL), dried with anhydrous sodium sulfate, filtered and concentrated. The residue was purified by silica column (petroleum ether) to give 1.70 g (47% yield) of 122-D as a brown oil.

LCMS: (ESI) m/z: 273.1 $[M-I]^+$.

Step 5: Synthesis of tert-butyl 1-(5-benzyl-6-methoxy-[1,1'-biphenyl]-3-yl)hydrazinecarboxylate (122-E)

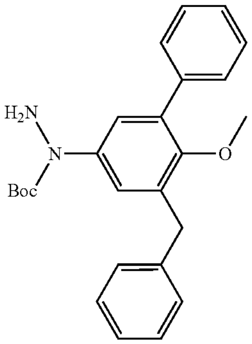

A mixture of 122-D (850 mg, 2.12 mmol, 1.0 eq), tert-butyl N-aminocarbamate (337 mg, 2.55 mmol, 1.2 eq), 1,10-phenanthroline (38.3 mg, 212 umol, 0.10 eq), copper iodide (40.5 mg, 212 umol, 0.10 eq) and cesium carbonate (1.38 g, 4.25 mmol, 2.0 eq) in N,N-dimethylformamide (20 mL) was degassed and purged with nitrogen for 3 times, and then the mixture was stirred at 80° C. for 12 hr under nitrogen atmosphere. The solution was poured into water (30 mL), extracted with ethyl acetate (30 mL×3). The combined organic phase was washed with brine (50 mL), dried with anhydrous sodium sulfate, filtered and concentrated. The residue was purified by silica column (petroleum ether/ethyl acetate, from 10/1 to 5/1 to give 1.30 g (72% yield) of 122-E as a light yellow oil.

LCMS: (ESI) m/z: 427.3 $[M+Na]^+$.

Step 6: Synthesis of (5-benzyl-6-methoxy-[1,1'-biphenyl]-3-yl)hydrazine (122-F)

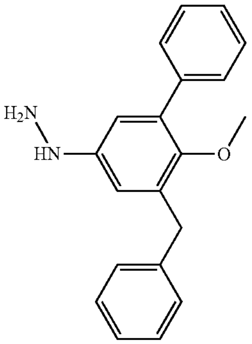 [SMILES: COc1c(Cc2ccccc2)cc(NN)cc1-c1ccccc1]

To a solution of 122-E (1.25 g, 2.96 mmol, 1.0 eq) in ethyl acetate (10 mL) was added hydrogen chloride/ethyl acetate (4 M, 10 mL, 14 eq). The solution was stirred at 25° C. for 1 h. The solution was concentrated to give 1.00 g (90% yield, hydrochloride) of 122-F as a white solid.

LCMS: (ESI) m/z: 305.2 $[M+H]^+$.

Step 7: Synthesis of 1-(5-benzyl-6-methoxy-[1,1'-biphenyl]-3-yl)-3-methyl-1H-pyrazol-5(4H)-one (122-G)

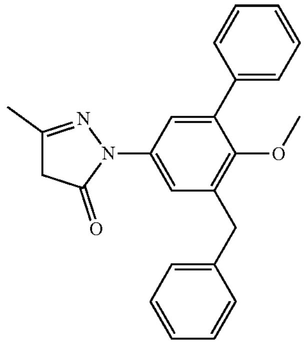 [SMILES: COc1c(Cc2ccccc2)cc(N2N=C(C)CC2=O)cc1-c1ccccc1]

122-G was obtained via general procedure II from 122-F

LCMS: (ESI) m/z: 371.2 $[M+H]^+$.

Step 8: Synthesis of 4-nitrophenyl 1-(5-benzyl-6-methoxy-[1,1'-biphenyl]-3-yl)-3-methyl-5-oxo-4,5-dihydro-1H-pyrazole-4-carboxylate (122-H)

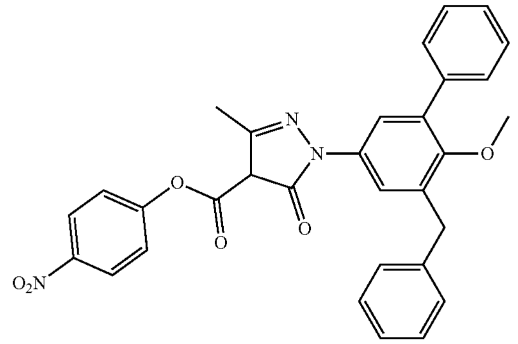 [SMILES: COc1c(Cc2ccccc2)cc(N2N=C(C)C(C(=O)Oc3ccc([N+](=O)[O-])cc3)C2=O)cc1-c1ccccc1]

122-H was obtained via general procedure III from 122-G

LCMS: (ESI) m/z: 536.2 $[M+H]^+$.

Step 9: Synthesis of 1-(5-benzyl-6-methoxy-[1,1'-biphenyl]-3-yl)-N-(3-(1,1-difluoroethyl)phenyl)-3-methyl-5-oxo-4,5-dihydro-1H-pyrazole-4-carboxamide (122)

Compound ID: 122

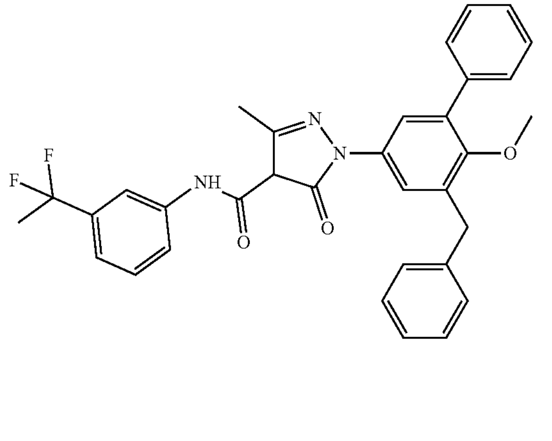

122 was obtained via general procedure IV from 122-H and 3-(1,1-difluoroethyl)aniline LCMS: (ESI) m/z: 554.3 $[M+H]^+$.

$^1$H NMR: (400 MHz, DMSO-d) δ: 10.91 (s, 1H), 7.93 (s, 1H), 7.70-7.58 (m, 5H), 7.49 (t, J=7.2 Hz, 2H), 7.42-7.37 (m, 2H), 7.34-7.28 (m, 4H), 7.22-7.16 (m, 2H), 4.06 (s, 2H), 3.18 (s, 3H), 2.48 (s, 3H), 1.95 (t, J=18.8 Hz, 3H).

Synthesis of 121

Step 1: Synthesis of 1-(5-benzyl-6-methoxy-[1,1'-biphenyl]-3-yl)-N-(3-(1,1-difluoropropyl)phenyl)-3-methyl-5-oxo-4,5-dihydro-1H-pyrazole-4-carboxamide (121)

Compound ID: 121

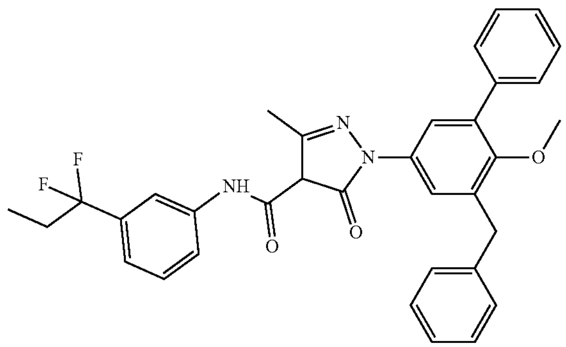

121 was obtained via general procedure IV from 122-H and 3-(1,1-difluoropropyl)aniline LCMS: (ESI) m/z: 568.3 $[M+H]^+$.

$^1$H NMR: (400 MHz, DMSO-d) δ: 10.88 (s, 1H), 7.89 (s, 1H), 7.69-7.59 (m, 5H), 7.49 (t, J=7.6 Hz, 2H), 7.43-7.38 (m, 2H), 7.34-7.28 (m, 4H), 7.22-7.12 (m, 2H), 4.06 (s, 2H), 3.18 (s, 3H), 2.51 (s, 3H), 2.24-2.14 (m, 2H), 0.91 (t, J=7.6 Hz, 3H).

Synthesis of 120

Step 1: Synthesis of 2-(3-bromophenyl)pyridine (120-A)

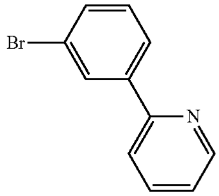 [SMILES: Brc1cccc(-c2ccccn2)c1]

A mixture of (3-bromophenyl)boronic acid (5.00 g, 24.9 mmol, 1.0 eq), 2-bromopyridine (3.93 g, 24.9 mmol, 1.0 eq), tetrakis(triphenylphosphine)platinum (288 mg, 249 umol, 0.010 eq), sodium carbonate (5.81 g, 54.8 mmol, 2.2 eq) in 1,2-dimethoxyethane (63 mL), ethanol (20 mL) and water (28 mL) was degassed and purged with nitrogen for 3 times, and then the mixture was stirred at 90° C. for 18 h under nitrogen atmosphere. The reaction mixture was diluted with water (100 mL) and extracted with ethyl acetate (100 mL×2). The combined organic layer was washed with brine (100 mL), dried over sodium sulfate, filtered and concentrated. The residue was purified by silica gel column chromatography (petroleum ether/ethyl acetate, from 10/1 to 5/1) to give 5.60 g (83% yield) of 120-A as a yellow oil.

LCMS: (ESI) m/z: 234.0, 236.0 $[M+H]^+$.

Step 2: Synthesis of 4-bromo-2-(pyridin-2-yl)phenol (120-B)

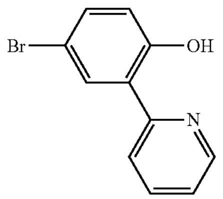 [SMILES: Oc1ccc(Br)cc1-c1ccccn1]

A mixture of 120-A (2.30 g, 8.45 mmol, 1.0 eq), tert-butyl hydroperoxide (6.53 g, 50.70 mmol, 6.0 eq) and palladium acetate (94.9 mg, 422 umol, 0.050 eq) in dichloroethane (30 mL) was stirred at 115° C. for 36 h in a 100 mL of sealed tube. The mixture was quenched with saturated sodium sulfite aqueous (50 mL) and extracted with dichloromethane (50 mL×2). The combined organic layer was dried over magnesium sulfate, filtered and concentrated. The residue was purified by silica gel column chromatography (petroleum ether/ethyl acetate, from 20/1 to 5/1) to give 0.530 g (25% yield) of 120-B as a yellow solid.

LCMS: (ESI) m/z: 250.0 $[M+H]^+$.

$^1$H NMR: (400 MHz, $CDCl_3$-d) δ: 14.40 (br s, 1H), 8.54 (dt, J=5.2, 1.2 Hz, 1H), 7.92-7.87 (m, 3H), 7.39 (dd, J=2.4, 8.8 Hz, 1H), 7.34-7.28 (m, 1H), 6.93 (d, J=8.8 Hz, 1H).

Step 3: Synthesis of 2-(5-bromo-2-(difluoromethoxy)phenyl)pyridine (120-C)

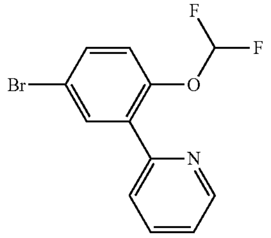 [SMILES: FC(F)Oc1ccc(Br)cc1-c1ccccn1]

To a solution of 120-B (1.05 g, 4.18 mmol, 1.0 eq) in acetonitrile (15 mL) and water (5 mL) was added potassium hydroxide (2.35 g, 41.8 mmol, 10 eq) and 1-[[bromo(difluoro)methyl]-ethoxy-phosphoryl]oxyethane (2.23 g, 8.36 mmol, 2.0 eq). The mixture was stirred at 20° C. for 12 h. The reaction mixture was partitioned between ethyl acetate (30 mL) and water (30 mL). The organic phase was separated, washed with brine (30 mL), dried over sodium sulfate, filtered and concentrated. The residue was purified by silica gel column chromatography (petroleum ether/ethyl acetate, from 20/1 to 5/1) to give 0.890 g (57% yield) of 120-C as a yellow oil.

LCMS: (ESI) m/z: 301.7 $[M+H]^+$.

Step 4: Synthesis of 2-(2-(difluoromethoxy)-5-(4,4,5,5-tetramethyl-1,3,2-dioxaborolan-2-yl)phenyl)pyridine (120-D)

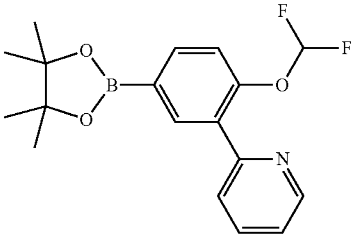 [SMILES: CC1(C)OB(c2ccc(OC(F)F)c(-c3ccccn3)c2)OC1(C)C]

A mixture of 120-C (0.790 g, 2.13 mmol, 1.0 eq), 4,4,5,5-tetramethyl-2-(4,4,5,5-tetramethyl-1,3,2-dioxaborolan-2-yl)-1,3,2-dioxaborolane (1.08 g, 4.26 mmol, 2.0 eq), 1,1-bis(diphenylphosphino)ferrocene]dichloropalladium(II) (78.0 mg, 107 umol, 0.050 eq), potassium acetate (419 mg, 4.26 mmol, 2.0 eq) in dioxane (15 mL) was degassed and purged with nitrogen for 3 times, and then the mixture was stirred at 90° C. for 12 h under nitrogen atmosphere. The reaction mixture was diluted with water (30 mL) and extracted with ethyl acetate (30 mL×2). The combined organic layer was washed with brine (50 mL×2), dried over sodium sulfate, filtered and concentrated. The residue was purified by silica gel column chromatography (petroleum ether/ethyl acetate, from 20/1 to 5/1) to give 0.760 g (75% yield) of 120-D as a colorless oil.

LCMS: (ESI) m/z: 348.1 $[M+H]^+$.

Step 5: Synthesis of ethyl 2-(4-(difluoromethoxy)-3-(pyridin-2-yl)phenyl)-4-methylpyrimidine-5-carboxylate (120-E)

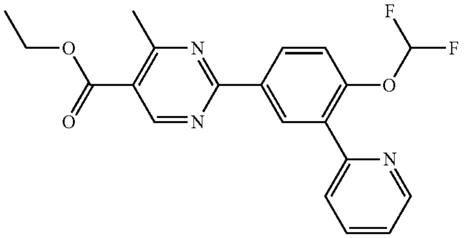 [SMILES: CCOC(=O)c1cnc(-c2ccc(OC(F)F)c(-c3ccccn3)c2)nc1C]

120-E was obtained via similar procedure of 133-A from 120-D and ethyl 2-chloro-4-methylpyrimidine-5-carboxylate.

LCMS: (ESI) m/z: 386.1 $[M+H]^+$.

$^1$H NMR: (400 MHz, $CDCl_3$-d) δ: 9.21 (s, 1H), 8.96 (d, J=2.0 Hz, 1H), 8.78 (d, J=4.8 Hz, 1H), 8.60 (d, J=8.4 Hz, 1H), 7.82-7.74 (m, 2H), 7.36 (d, J=8.8 Hz, 1H), 7.32 (d, J=2.0 Hz, 1H), 6.61 (t, J=74.4 Hz, 1H), 4.44 (q, J=7.2 Hz, 2H), 2.90 (s, 3H), 1.44 (t, J=7.2 Hz, 3H).

Step 6: Synthesis of 2-(4-(difluoromethoxy)-3-(pyridin-2-yl)phenyl)-4-methylpyrimidine-5-carboxylic acid (120-F)

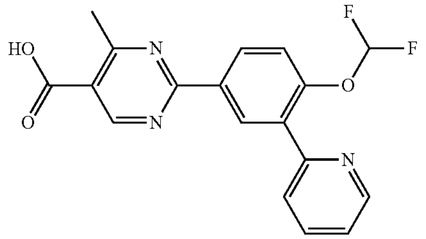 [SMILES: Cc1nc(-c2ccc(OC(F)F)c(-c3ccccn3)c2)ncc1C(=O)O]

120-F was obtained via similar procedure of 133-B from 120-E.

LCMS: (ESI) m/z: 358.0 $[M+H]^+$.

Step 7: Synthesis of N-(3-(1,1-difluoroethyl)phenyl)-2-(4-(difluoromethoxy)-3-(pyridin-2-yl)phenyl)-4-methylpyrimidine-5-carboxamide (120)

Compound ID: 120

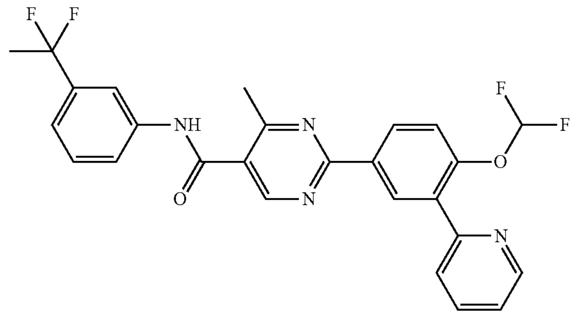

120 was obtained via similar procedure of 133 from 120-F and 3-(1,1-difluoroethyl)aniline.

LCMS: (ESI) m/z: 497.2 $[M+H]^+$.

$^1$H NMR: (400 MHz, MeOD-$d_4$) δ: 8.92 (s, 1H), 8.83 (d, J=2.0 Hz, 1H), 8.69 (d, J=4.8 Hz, 1H), 8.64 (dd, J=2.4, 8.8 Hz, 1H), 7.98-7.93 (m, 2H), 7.82-7.77 (m, 2H), 7.50-7.44 (m, 3H), 7.35 (d, J=7.6 Hz, 1H), 6.97 (t, J=73.6 Hz, 1H), 2.75 (s, 3H), 1.94 (t, J=18.4 Hz, 3H).

Synthesis of 119

Step 1: Synthesis of 2-(4-(difluoromethoxy)-3-(pyridin-2-yl)phenyl)-N-(3-(1,1-difluoropropyl)phenyl)-4-methylpyrimidine-5-carboxamide (119)

Compound ID: 119

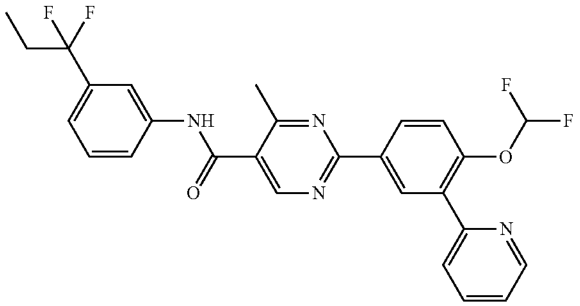

119 was obtained via similar procedure of 133 from 120-F and 3-(1,1-difluoropropyl)aniline.

LCMS: (ESI) m/z: 511.3 $[M+H]^+$.

$^1$H NMR: (400 MHz, MeOD-$d_4$) δ: 8.91 (s, 1H), 8.83 (d, J=2.4 Hz, 1H), 8.69 (d, J=4.4 Hz, 1H), 8.62 (dd, J=2.4, 8.8 Hz, 1H), 7.97-7.93 (m, 1H), 7.90 (s, 1H), 7.82-7.77 (m, 2H), 7.50-7.44 (m, 3H), 7.30 (d, J=7.6 Hz, 1H), 6.96 (t, J=73.6 Hz, 1H), 2.75 (s, 3H), 2.23-2.13 (m, 2H), 1.94 (t, J=7.6 Hz, 3H).

Synthesis of 118

Step 1: Synthesis of 2-(methoxycarbonyl)-3-methylpyrazine 1-oxide (118-A)

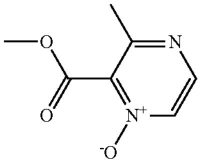

118-A was obtained via similar procedure of 135-A from methyl 3-methylpyrazine-2-carboxylate and hydrogen peroxide LCMS: (ESI) m/z: 169.0 $[M+H]^+$.

Step 2: Synthesis of methyl 6-chloro-3-methylpyrazine-2-carboxylate (118-B)

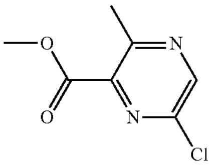

118-B was obtained via similar procedure of 135-B from 118-A and phosphoryl trichloride $^1$H NMR: (400 MHz, $CDCl_3$-d) δ: 8.64 (s, 1H), 4.01 (s, 3H), 2.84 (s, 3H).

Step 3: Synthesis of methyl 6-[4-(difluoromethoxy)-3-phenyl-phenyl]-3-methyl-pyrazine-2-carboxylate (118-C)

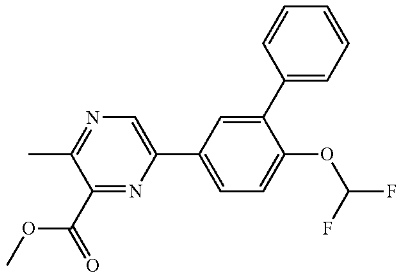 [SMILES: COC(=O)c1nc(-c2ccc(OC(F)F)c(-c3ccccc3)c2)cnc1C]

118-C was obtained via similar procedure of 135-C from 118-B and 127-C.

$^1$H NMR: (400 MHz, $CDCl_3$-d) δ: 9.03 (s, 1H), 8.08 (d, J=2.0 Hz, 1H), 8.02 (dd, J=8.4, 2.4 Hz, 1H), 7.57-7.53 (m, 2H), 7.51-7.37 (m, 4H), 6.41 (t, J=73.6 Hz, 1H), 4.03 (s, 3H), 2.86 (s, 3H).

Step 4: Synthesis of 6-[4-(difluoromethoxy)-3-phenyl-phenyl]-3-methyl-pyrazine-2-carboxylic acid (118-D)

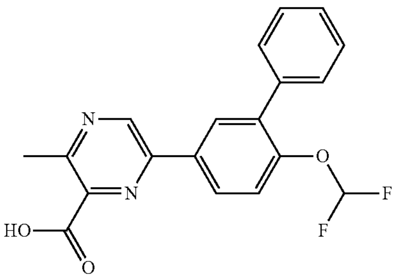 [SMILES: Cc1ncc(-c2ccc(OC(F)F)c(-c3ccccc3)c2)nc1C(=O)O]

118-D was obtained via similar procedure of 135-D from 118-C and lithium hydroxide hydrate.

LCMS: (ESI) m/z: 357.2 $[M+H]^+$.

Step 5: Synthesis of N-[3-(1,1-difluoroethyl)phenyl]-6-[4-(difluoromethoxy)-3-phenyl-phenyl]-3-methyl-pyrazine-2-carboxamide (118)

Compound ID: 118

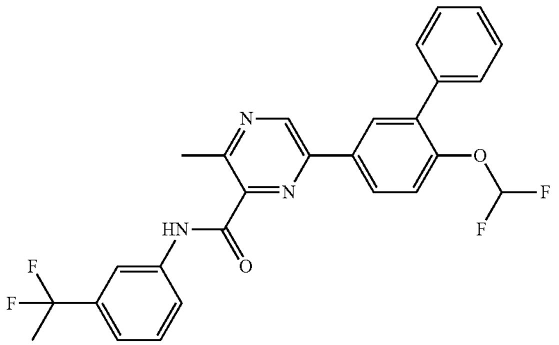

118 was obtained via similar procedure of 135 from 118-D and 3-(1,1-difluoroethyl)aniline.

LCMS: (ESI) m/z: 496.3 $[M+H]^+$.

$^1$H NMR: (400 MHz, MeOD-$d_4$) δ: 9.22 (s, 1H), 8.31-8.27 (m, 2H), 8.01 (s, 1H), 7.86-7.83 (m, 1H), 7.61-7.58 (m, 2H), 7.50-7.45 (m, 4H), 7.43-7.38 (m, 1H), 7.34 (dd, J=7.6, 0.8 Hz, 1H), 6.82 (t, J=73.6 Hz, 1H), 2.91 (s, 3H), 1.95 (t, J=18.4 Hz, 3H).

Synthesis of 117

Step 1: Synthesis of 6-[4-(difluoromethoxy)-3-phenyl-phenyl]-N-[3-(1,1-difluoropropyl)phenyl]-3-methyl-pyrazine-2-carboxamide (117)

Compound ID: 117

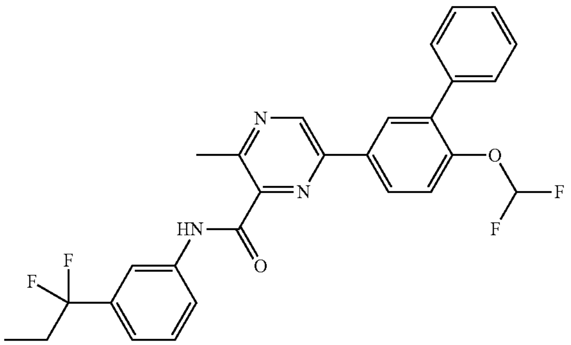

117 was obtained via similar procedure of 118 from 118-D and 3-(1,1-difluoropropyl)aniline.

LCMS: (ESI) m/z: 510.3 $[M+H]^+$.

$^1$H NMR: (400 MHz, MeOD-$d_4$) δ: 9.23 (s, 1H), 8.30-8.27 (m, 2H), 7.97 (s, 1H), 7.87~7.83 (m, 1H), 7.61~7.58 (m, 2H), 7.50~7.45 (m, 4H), 7.43~7.38 (m, 1H), 7.30 (d, J=7.2 Hz, 1H), 6.82 (t, J=74 Hz, 1H), 2.92 (s, 3H), 2.28~2.13 (m, 2H), 1.00 (t, J=7.6 Hz, 3H).

Synthesis of 116

Step 1: Synthesis of ethyl 2-(4-methoxyphenyl)-5-methyloxazole-4-carboxylate (116-A)

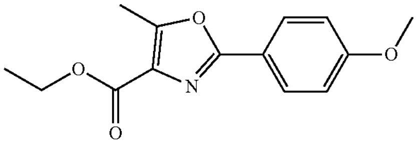 [SMILES: CCOC(=O)c1nc(-c2ccc(OC)cc2)oc1C]

To a solution of (4-methoxyphenyl)methanamine (1.50 g, 10.9 mmol, 1.0 eq) and ethyl 3-oxobutanoate (1.42 g, 10.9 mmol, 1.0 eq) in N,N-dimethylformamide (10 mL) was added iodine (3.33 g, 13.12 mmol, 1.2 eq), copper acetate (199 mg, 1.09 mmol, 0.10 eq) and tert-butyl hydroperoxide (1.97 g, 21.8 mmol, 2.0 eq). The mixture was stirred at 50° C. for 12 hr. The mixture was quenched by slow addition of saturated sodium bisulfite solution. The resulting mixture was transferred to a separatory funnel, and aqueous layer mixture was extracted with ethyl acetate (5 mL×3). The combined organic layer was washed with brine (15 mL), dried over anhydrous sodium sulfate, filtered, and concentrated under reduced pressure affording a light yellow oil. The crude product was purified by silica gel column chromatography (petroleum ether/ethyl acetate, from 30/1 to 20/1) to give 107 mg (1% yield) of 116-A as a light yellow oil.

LCMS: (ESI) m/z: 262.1 $[M+H]^+$.

Step 2: Synthesis of 2-(4-methoxyphenyl)-5-methyloxazole-4-carboxylic acid (116-B)

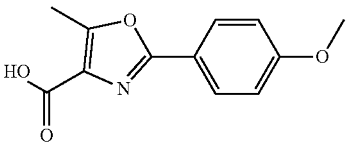 [SMILES: COc1ccc(-c2nc(C(=O)O)c(C)o2)cc1]

To a solution of 116-A (107 mg, 207 umol, 1.0 eq) in ethanol (1 mL) and water (0.2 mL) was added sodium hydroxide (41.5 mg, 1.04 mmol, 5.0 eq). Then the mixture was stirred at 50° C. for 4 hr. The reaction mixture was concentrated under reduced pressure to remove ethanol. The pH of mixture was adjusted to 2 by using hydrochloric acid (1 M), the crude product was separate out to give 50.0 mg (50% yield) of 116-B as a light yellow solid.

LCMS: (ESI) m/z: 234.0 $[M+H]^+$.

Step 3: Synthesis of N-(3-(1,1-difluoropropyl)phenyl)-2-(4-methoxyphenyl)-5-methyloxazole-4-carboxamide (116)

Compound ID: 116

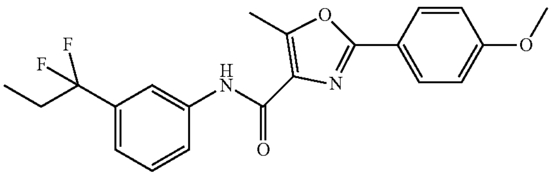

To a solution of 116-B (50.0 mg, 103 umol, 1.0 eq) and 3-(1,1-difluoropropyl)aniline (17.7 mg, 103 umol, 1.0 eq) in pyridine (0.5 mL) was added N-[3-(Dimethylamino)propyl]-N-ethylcarbodiimide hydrochloride (39.6 mg, 207 umol, 2.0 eq). Then the mixture was stirred at 25° C. for 12 hr. The mixture was concentrated under reduced pressure to remove pyridine. The crude product was purified by preparative TLC (petroleum ether/ethyl acetate=3/1) to give a crude product. The crude product was purified by preparative HPLC (Phenomenex luna C18 column (250×50 mm, 10 um); flow rate: 25 mL/min; gradient: 68%-98% B over 9 min; mobile phase A: 0.075% aqueous trifluoroacetic acid, mobile phase B: acetonitrile) to give 3.90 mg (10% yield) of 116 as a yellow solid LCMS: (ESI) m/z: 387.4 $[M+H]^+$.

$^1$H NMR (400 MHz, MeOD-$d_4$) δ: 8.07-7.99 (dt, 2H), 7.96-7.93 (s, 1H), 7.85-7.75 (dd, 1H), 7.49-7.41 (t, 1H), 7.30-7.23 (d, 1H), 7.12-7.03 (dt, 2H), 3.92-3.83 (s, 3H), 2.78-2.68 (s, 3H), 2.27-2.12 (td, 2H), 1.05-0.94 (t, 3H).

Synthesis of 115

Step 1: Synthesis of 3-bromo-4-hydroxybenzamide (115-A)

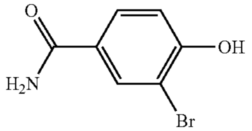

To a 50 mL round-bottom flask equipped with a magnetic stir bar and a reflux condenser was added 3-bromo-4-hydroxy-benzonitrile (2.00 g, 10.1 mmol, 1.0 eq) followed by the addition of sulfuric acid (98%, 20 mL). Then the mixture was heated to 80° C. and stirred for 2 h. The solution was poured into water (100 mL), the mixture was extracted with ethyl acetate (40 mL×3). The combined organic layer was washed with brine (60 mL), dried over anhydrous sodium sulfate, filtered and concentrated to give 1.40 g (55% yield) of 115-A as a yellow solid.

LCMS: (ESI) m/z: 216.0 $[M+H]^+$.

Step 2: Synthesis of ethyl 2-(3-bromo-4-hydroxyphenyl)-4-methyloxazole-5-carboxylate (115-B)

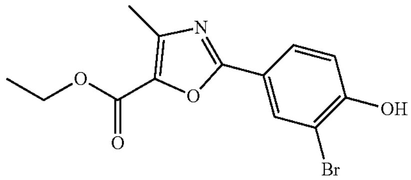 [SMILES: CCOC(=O)c1oc(-c2ccc(O)c(Br)c2)nc1C]

To a 10 mL round-bottom flask equipped with a magnetic stir bar and a reflux condenser was added 115-A (1.20 g, 5.01 mmol, 1.0 eq) followed by the addition of ethyl 2-chloro-3-oxo-butanoate (1.24 g, 7.51 mmol, 1.5 eq). The mixture was heated to 130° C. and stirred for 12 h. The mixture was quenched by slow addition of saturated sodium chloride solution (50 mL). The resulting mixture was transferred to a separatory funnel, and the aqueous layer mixture was extracted with ethyl acetate (50 mL×3). The combined organic layer was washed with brine (40 mL), dried over anhydrous sodium sulfate, filtered, and concentrated under reduced pressure affording the residue. The residue was purified by silica gel column chromatography (petroleum ether/ethyl acetate, from 20/1 to 10/1) to give 1.50 g (75% yield) of 115-B as a yellow solid.

LCMS: (ESI) m/z: 326.0 $[M+H]^+$.

Step 3: Synthesis of ethyl 2-(3-bromo-4-(difluoromethoxy)phenyl)-4-methyloxazole-5-carboxylate 115-C)

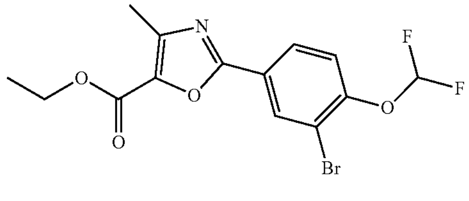 [SMILES: CCOC(=O)c1oc(-c2ccc(OC(F)F)c(Br)c2)nc1C]

To a 50 mL round-bottom flask equipped with a magnetic stir bar and a reflux condenser was added 115-B (1.30 g, 3.27 mmol, 1.0 eq), sodium; 2-chloro-2,2-difluoro-acetate (747 mg, 4.90 mmol, 1.5 eq) followed by the addition of N,N-dimethylformamide (8 mL). Then sodium carbonate (693 mg, 6.54 mmol, 2.0 eq) was added into the mixture. The mixture was heated to 100° C. and stirred for 2 h. The mixture was concentrated under reduced pressure to give a residue. The residue was dissolved in ethyl acetate (80 mL) and water (80 mL). The resulting mixture was transferred to a separatory funnel, and the aqueous layer mixture was extracted with ethyl acetate (50 mL×2). The combined organic layer was washed with brine (50 mL), dried over anhydrous sodium sulfate, filtered, and concentrated under reduced pressure affording the residue. The residue was purified by silica gel column chromatography (petroleum ether/ethyl acetate, from 15/1 to 10/1) to give 600 mg (44% yield) of 115-C as a white solid.

LCMS: (ESI) m/z: 376.0 $[M+H]^+$.

Step 4: Synthesis of ethyl 2-(6-(difluoromethoxy)-[1,1'-biphenyl]-3-yl)-4-methyloxazole-5-carboxylate (115-D)

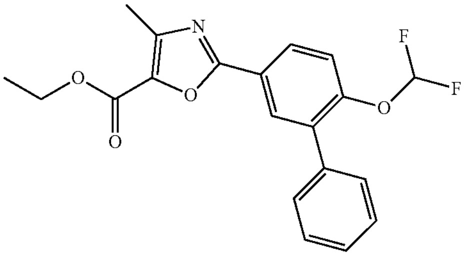 [SMILES: CCOC(=O)c1oc(-c2ccc(OC(F)F)c(-c3ccccc3)c2)nc1C]

To a solution of 115-C (300 mg, 726 umol, 1.0 eq) and phenylboronic acid (124 mg, 1.02 mmol, 1.4 eq) in dioxane (15 mL) and water (3 mL) was added 1,1-bis(diphenylphosphino)ferrocene]dichloropalladium(II) (53.1 mg, 72.6 umol, 0.10 eq) and sodium bicarbonate (152 mg, 1.81 mmol, 2.5 eq). The solution was stirred at 90° C. for 12 h. The solution was filtered through a celite pad and the filtrate was diluted with ethyl acetate (100 mL). The mixture was washed with brine (100 mL). The organic layer was dried over anhydrous sodium sulfate, filtered and concentrated. The residue was purified by column chromatography on silica gel (petroleum ether/ethyl acetate=10/1) to give 280 mg (99% yield) of 115-D as a yellow solid.

LCMS: (ESI) m/z: 374.0 $[M+H]^+$.

$^1$H NMR: (400 MHz, $CDCl_3$-d) δ: 8.19 (d, J=2.8 Hz, 1H), 8.12 (dd, J=2.4, 8.8 Hz, 1H), 7.57-7.50 (m, 2H), 7.50-7.38 (m, 3H), 7.35 (d, J=8.8 Hz, 1H), 6.44 (t, J=73.6H, 1H), 4.42 (q, J=7.2 Hz, 2H), 2.55 (s, 3H), 1.43 (t, J=7.2 Hz, 3H).

Step 5: Synthesis of 2-(6-(difluoromethoxy)-[1,1'-biphenyl]-3-yl)-4-methyloxazole-5-carboxylic acid (115-E)

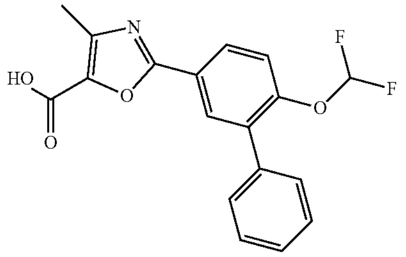 [SMILES: Cc1nc(-c2ccc(OC(F)F)c(-c3ccccc3)c2)oc1C(=O)O]

To a solution of 115-D (280 mg, 724 umol, 1 eq) in ethanol (10 mL) and water (2 mL) was added sodium hydroxide (72.4 mg, 1.81 mmol, 2.5 eq). The solution was stirred at 15° C. for 12 h. The organic solvent was removed under reduced pressure. The residue was diluted with water (50 mL) and acidified by aqueous hydrochloric acid (6 M) to pH=2. The mixture was extracted with ethyl acetate (50 mL×3). The combined organic layer was washed with brine (100 mL), dried over anhydrous sodium sulfate, filtered and concentrated to give 240 mg (96% yield) of 115-E as a white solid.

LCMS: (ESI) m/z: 346.0 $[M+H]^+$.

Step 6: Synthesis of N-(3-(1,1-difluoroethyl)phenyl)-2-(6-(difluoromethoxy)-[1,1'-biphenyl]-3-yl)-4-methyloxazole-5-carboxamide (115)

Compound ID: 115

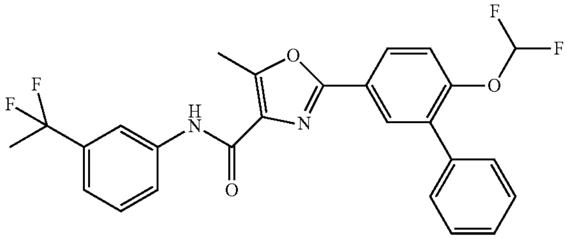

To a solution of 115-E (50.0 mg, 144.8 umol, 1.0 eq) in N,N-dimethylformamide (1 mL) was added [dimethylamino (triazol[4,5-b]pyridin-3-yloxy)methylidene]-dimethylazanium; hexafluorophosphate (60.6 mg, 159 umol, 1.1 eq) and N-ethyl-N-isopropylpropan-2-amine (74.9 mg, 579 umol, 4.0 eq). The solution was stirred at 15° C. for 10 min and then 3-(1,1-difluoroethyl)aniline (29.6 mg, 188 umol, 1.3 eq) was added. The solution was stirred at 15° C. for 2 h. The solution was concentrated. The residue was purified by prep-HPLC (column: Phenomenex Synergi C18 150*25*10 um; mobile phase: [water (0.225% formic acid)-acetonitrile]; B %: 61%-91%, 10 min) to give 43.9 mg (39% yield) of 115 as a yellow solid.

LCMS: (ESI) m/z: 485.2 $[M+H]^+$.

$^1$H NMR: (400 MHz, MeOD-$d_4$) δ: 8.35 (d, J=2.0 Hz, 1H), 8.25 (dd, J=2.0, 8.4 Hz, 1H), 7.93 (s, 1H), 7.81 (d, J=9.2 Hz, 1H), 7.59-7.53 (m, 2H), 7.51-7.38 (m, 5H), 7.33 (dd, J=0.8, 8.0 Hz, 1H), 6.87 (t, J=73.6 Hz, 1H), 2.58 (s, 3H), 1.94 (t, J=18.4 Hz, 3H)

Synthesis of 114

Step 1: Synthesis of 2-(6-(difluoromethoxy)-[1,1'-biphenyl]-3-yl)-N-(3-(1,1-difluoropropyl)phenyl)-4-methyloxazole-5-carboxamide (114)

Compound ID: 114

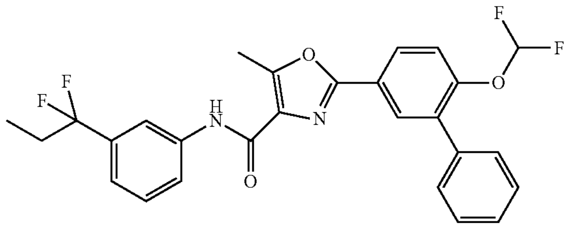

114 was obtained via the similar synthetic method of 115 from 115-E and 3-(1,1-difluoropropyl)aniline.

LCMS: (ESI) m/z: 499.2 $[M+H]^+$.

$^1H$ NMR: (400 MHz, MeOD-$d_4$) δ: 8.35 (d, J=2.0 Hz, 1H), 8.26 (dd, J=2.0, 8.8 Hz, 1H), 7.88 (s, 1H), 7.82 (d, J=8.0 Hz, 1H), 7.60-7.53 (m, 2H), 7.52-7.37 (m, 5H), 7.28 (d, J=7.6 Hz, 1H), 6.87 (t, J=73.2 Hz, 1H), 2.58 (s, 3H), 2.32-2.08 (m, 2H), 0.99 (t, J=7.2 Hz, 3H).

Synthesis of 113

Step 1: Synthesis of 4-(difluoromethoxy)benzonitrile (113-A)

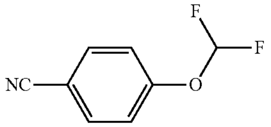 [SMILES: N#Cc1ccc(OC(F)F)cc1]

113-A was obtained via similar procedure of 123-A from 4-hydroxybenzonitrile and (2-chloro-2,2-difluoro-acetyl) oxysodium LCMS: (ESI) m/z: 170.1 $[M+H]^+$.

Step 2: Synthesis of (4-(difluoromethoxy)phenyl)methanamine (113-B)

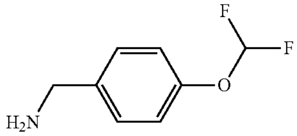

113-B was obtained via similar procedure of 123-C from 113-A and hydrogen

LCMS: (ESI) m/z: 174.1 $[M+H]^+$.

Step 3: Synthesis of ethyl 2-(4-(difluoromethoxy) phenyl)-5-methyloxazole-4-carboxylate (113-C)

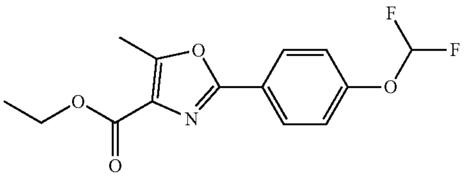 [SMILES: CCOC(=O)c1nc(-c2ccc(OC(F)F)cc2)oc1C]

To a solution of 113-B (1.23 g, 7.11 mmol, 1.9 eq) in ethyl acetate (15 mL) was added ethyl 3-oxobutanoate (500 mg, 3.84 mmol, 1.0 eq), tertbutylammoniumiodide (284 mg, 768 umol, 0.20 eq) and tert-butyl hydroperoxide (1.38 g, 15.4 mmol, 4.0 eq), the solution was stirred at 40° C. for 10 h. The reaction was poured into water (20 mL), extracted with ethyl acetate (20 mL×3). The combined organic phase was washed with brine (20 mL), dried with anhydrous sodium sulfate, filtered and concentrated. The residue was purified by silica column (petroleum ether/ethyl acetate, from 5/1 to 1/1) to give 220 mg (16% yield) of 113-C as a gray solid LCMS: (ESI) m/z: 297.8 $[M+H]^+$.

Step 4: Synthesis of ethyl 2-(4-(difluoromethoxy) phenyl)-5-methyloxazole-4-carboxylic acid (113-D)

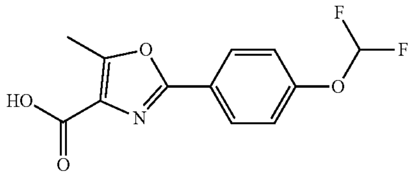 [SMILES: Cc1oc(-c2ccc(OC(F)F)cc2)nc1C(=O)O]

113-D was obtained via similar procedure of 116-B from 113-C and sodium hydroxide LCMS: (ESI) m/z: 270.0 $[M+H]^+$.

Step 5: Synthesis of N-(3-(1,1-difluoroethyl)phenyl)-2-(4-(difluoromethoxy)phenyl)-5-methyloxazole-4-carboxamide (113)

Compound ID: 113

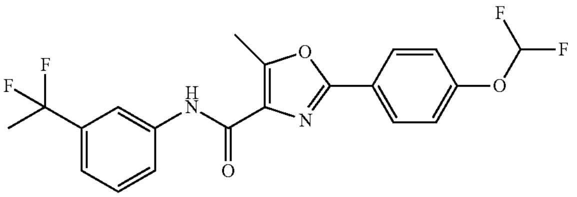

113 was obtained via similar procedure of 116 from 113-D and 3-(1,1-difluoroethyl)aniline LCMS: (ESI) m/z: 409.0 $[M+H]^+$.

$^1H$ NMR (400 MHz, MeOD-$d_4$) δ: 8.17-8.12 (m, 2H), 8.02-7.98 (s, 1H), 7.83-7.79 (d, J=8.4 Hz, 1H), 7.49-7.43 (t, J=8.0 Hz, 1H), 7.34-7.28 (m, 3H), 7.16-6.77 (t, J=73.4 Hz 1H), 2.76 (s, 3H), 1.95 (t, J=18.2 Hz, 3H).

Synthesis of 112

Step 1: Synthesis of 2-(4-(difluoromethoxy)phenyl)-N-(3-(1,1-difluoropropyl)phenyl)-5-methyloxazole-4-carboxamide (112)

Compound ID : 112

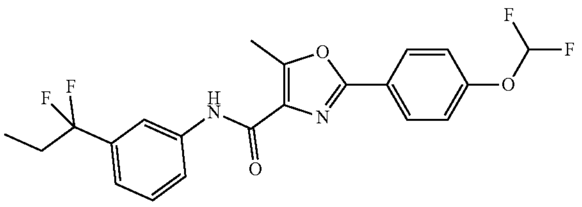

112 was obtained via similar procedure of 116 from 113-D and 3-(1,1-difluoropropyl)aniline LCMS: (ESI) m/z: 423.1 $[M+H]^+$.

$^1$H NMR (400 MHz, MeOD-$d_4$) δ: 8.08-8.17 (td, 2H) 7.95 (s, 1H) 7.80 (dd, J=8.12, 1.16 Hz, 1H) 7.45 (t, J=7.96 Hz, 1H) 7.24-7.33 (td, 3H) 6.75-7.15 (t, 1H) 2.74 (s, 3H) 2.12-2.27 (td, 2H) 1.00 (t, J=7.52 Hz, 3H).

N-(3-(1,1-difluoroethyl)phenyl)-1-(6-(difluoromethoxy)-[1,1'-biphenyl]-3-yl)-3-methyl-5-oxo-4,5-dihydro-1H-pyrazole-4-carboxamide (312i)

Compound ID: 312i

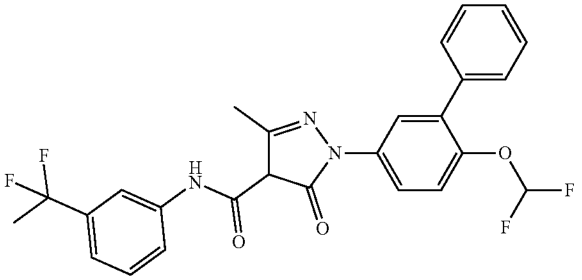

Compound 312i was obtained via general procedure IV from 4-nitrophenyl 1-(4-(difluoromethoxy)phenyl)-3-methyl-5-oxo-4,5-dihydro-1H-pyrazole-4-carboxylate and 3-(1,1-difluoroethyl)aniline.

LCMS: (ESI) m/z: 500.1 $[M+H]^+$.

$^1$H NMR: (400 MHz, MeOD-$d_4$) δ: 7.92 (s, 1H), 7.80 (d, J=2.4 Hz, 1H), 7.72 (dd, J=2.8, 8.8 Hz, 1H), 7.63 (d, J=8.4 Hz, 1H), 7.56 (d, J=8.0 Hz, 2H), 7.46 (t, J=7.2 Hz, 2H), 7.42-7.38 (m, 3H), 7.22 (d, J=8.0 Hz, 1H), 6.71 (t, J=74.0 Hz, 1H), 2.59 (s, 3H), 1.92 (t, J=18.4 Hz, 3H).

Synthesis of 111

Step 1: Synthesis of 4-allyl-N-(3-(1,1-difluoroethyl)phenyl)-1-(6-(difluoromethoxy)-[1,1'-biphenyl]-3-yl)-3-methyl-5-oxo-4,5-dihydro-1H-pyrazole-4-carboxamide (111-A)

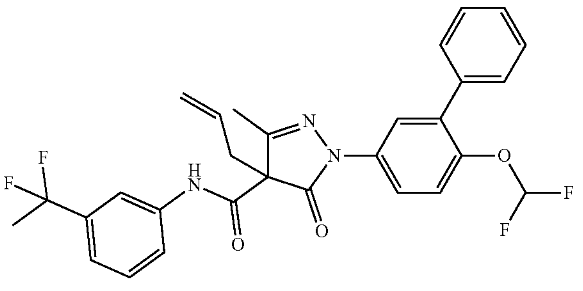 [SMILES: C=CCC1(C(=O)Nc2cccc(C(C)(F)F)c2)C(=O)N(c2ccc(OC(F)F)c(-c3ccccc3)c2)N=C1C]

111-A was obtained via similar procedure of 158-A from 312i and 3-iodoprop-1-ene.

LCMS: (ESI) m/z: 540.2 $[M+H]^+$.

Step 2: Synthesis of N-(3-(1,1-difluoroethyl)phenyl)-1-(6-(difluoromethoxy)-[1,1'-biphenyl]-3-yl)-3-methyl-5-oxo-4-propyl-4,5-dihydro-1H-pyrazole-4-carboxamide (111)

Compound ID: 111

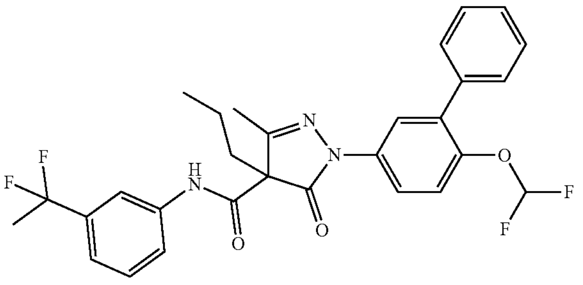

111 was obtained via similar procedure of 158 from 111-A.

LCMS: (ESI) m/z: 542.3 $[M+H]^+$.

$^1$H NMR: (400 MHz, MeOD-$d_4$) δ: 8.01 (s, 1H), 7.96 (d, J=9.2 Hz, 1H), 7.79 (s, 1H), 7.62 (d, J=7.6 Hz, 1H), 7.53-7.49 (m, 2H), 7.47-7.38 (m, 4H), 7.35-7.29 (m, 2H), 6.66 (t, J=74.0 Hz, 1H), 2.35-2.20 (m, 5H), 1.90 (t, J=18.4 Hz, 3H), 1.27-1.14 (m, 2H), 0.97 (t, J=7.2 Hz, 3H).

Synthesis of 410

Step 1: Synthesis of 6-bromo-1-(p-tolylsulfonyl)indole (410i-A)

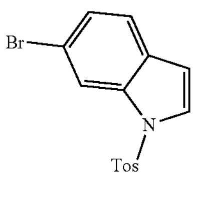

To a suspension of sodium hydride (4.10 g, 102 mmol, 60% purity, 2.0 eq) in N,N-dimethyl formamide (50 mL) was added dropwise a solution of 6-bromo-1H-indole (10.0 g, 51.0 mmol, 1.0 eq) in N,N-dimethyl formamide (50 mL) at 0° C. The mixture was warmed to 20° C. and stirred for 1 h. Then the mixture was re-cooled to 0° C., and a solution of 4-methylbenzene-1-sulfonyl chloride (15.0 g, 76.5 mmol, 1.5 eq) in N,N-dimethyl formamide (50 mL) was added dropwise. After the addition, the mixture was warmed to 20° C. and stirred for another 12 h. The two batches were combined, then poured into cool saturated ammonium chloride (1.5 L), then filtered. The filter cake was collected and dried in vacuo to give 35.0 g (crude) of 410i-A as brown solid.

$^1H$ NMR: (400 MHz, DMSO-d) δ: 8.05 (s, 1H), 7.88 (d, J=8.0 Hz, 2H), 7.84 (d, J=3.6 Hz, 1H), 7.58 (d, J=8.4 Hz, 1H), 7.45-7.37 (m, 3H), 6.86 (d, J=3.6 Hz, 1H), 2.32 (s, 3H).

Step 2: Synthesis of tert-butyl N-(tert-butoxycarbonylamino)-N-[1-(p-tolylsulfonyl)indol-6-yl]carbamate (410i-B)

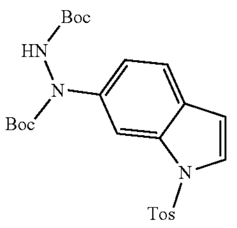

A mixture of 410i-A (8.00 g, 22.8 mmol, 1.0 eq), tert-butyl N-(tert-butoxycarbonylamino)carbamate (7.40 g, 32.0 mmol, 1.4 eq), cesium carbonate (15.0 g, 45.7 mmol, 2.0 eq) and 1,10-phenanthroline (1.20 g, 6.85 mmol, 0.30 eq) and copper iodide (4.40 g, 22.9 mmol, 1.0 eq) in N,N-dimethyl formamide (30 mL) was degassed and purged with nitrogen for 3 times, and then the mixture was stirred at 80° C. for 12 hr under nitrogen atmosphere. The mixture was concentrated in vacuum directly to give a residue, then the residue was diluted with ethyl acetate (100 mL) and filtered, the filtrate was concentrated under reduced pressure to give the crude. The crude product was purified by silica gel column chromatography (petroleum ether/ethyl acetate, from 30/1 to 5/1) to give 29.0 g (79% yield) of 410i-B as a yellow oil.

$^1H$ NMR: (400 MHz, $CDCl_3$-d) a: 8.08 (s, 1H), 7.77 (d, J=7.6 Hz, 2H), 7.53 (d, J=3.2 Hz, 1H), 7.43 (d, J=8.4 Hz, 1H), 7.22 (d, J=8.0 Hz, 2H), 6.86 (br s, 1H), 6.60 (d, J=3.6 Hz, 1H), 2.34 (s, 3H), 1.55-1.51 (m, 18H).

Step 3: Synthesis of [1-(p-tolylsulfonyl)indol-6-yl]hydrazine (410i-C)

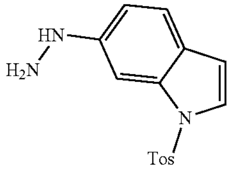

To a solution of 410i-B (29.0 g, 57.8 mmol, 1.0 eq) in ethyl acetate (100 mL) was added ethyl acetate/hydrochloride (4 M, 100 mL, 6.9 eq). The mixture was stirred at 30° C. for 1 h. The mixture was concentrated in vacuum directly to give 16.0 g (crude, hydrochloride) 410i-C as a brown solid.

LCMS: (ESI) m/z: 302.09 $[M+H]^+$.

Step 4: Synthesis of 5-methyl-2-[1-(p-tolylsulfonyl)indol-6-yl]-4H-pyrazol-3-one (410i-D)

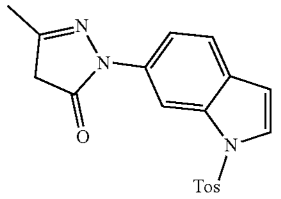

410i-D was obtained via general procedure II from 410i-C $^1H$ NMR: (400 MHz, MeOD-$d_4$) δ: 8.30 (d, J=1.6 Hz, 1H), 7.86 (d, J=8.4 Hz, 2H), 7.77 (d, J=3.6 Hz, 1H), 7.70 (d, J=8.4 Hz, 1H), 7.45 (dd, J=8.4, 2.0 Hz, 1H), 7.33 (d, J=8.4 Hz, 2H), 6.80 (d, J=3.6 Hz, 1H), 2.37 (s, 3H), 2.35 (s, 3H).

Step 5: Synthesis of (4-nitrophenyl) 3-methyl-5-oxo-1-[1-(p-tolylsulfonyl)indol-6-yl]-4H-pyrazole-4-carboxylate (410i-E)

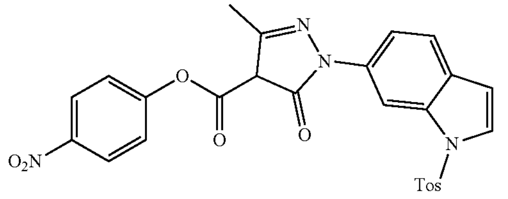

410i-E was obtained via general procedure III from 410i-D

LCMS: (ESI) m/z: 533.1 $[M+H]^+$.

Step 6: Synthesis of N-[3-(1,1-difluoroethyl)phenyl]-3-methyl-5-oxo-1-[1-(p-tolylsulfonyl)indol-6-yl]-4H-pyrazole-4-carboxamide (410i-F)

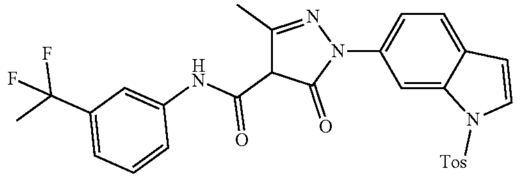

410i-F was obtained via general procedure IV from 410i-E

LCMS: (ESI) m/z: 550.9 $[M+H]^+$.

Step 7: Synthesis of N-[3-(1,1-difluoroethyl)phenyl]-1-(1H-indol-6-yl)-3-methyl-5-oxo-4H-pyrazole-4-carboxamide (410i)

Compound ID: 410i

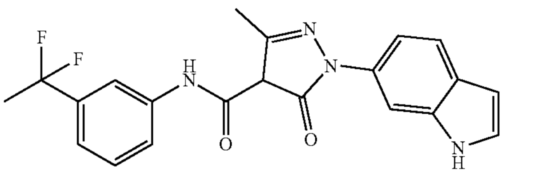

To a solution of 410i-F (4.40 g, 6.23 mmol, 1.0 eq) in ethanol (30 mL) was added potassium hydroxide (1.40 g, 24.0 mmol, 3.9 eq) and water (3 mL). The mixture was stirred at 70° C. for 4 hr. The mixture was concentrated in vacuum to give a residue, the residue diluted with ethyl acetate (300 mL), then washed with hydrochloride (200 mL×1, 1 M), the organic layer was washed was brine (200 mL), dried over anhydrous sodium sulfate, filtered and concentrated under reduced pressure to give the crude product. The crude product was purified by reversed-phase HPLC [water(0.1% formic acid)-acetonitrile]; B %: 10%-60%, 60 min), then the cutter stock was concentrated under reduced pressure to give the impure product. The impure product was triturated with methyl tertiary butyl ether (30 mL) at 20° C. for 15 min, filtered and the filter cake was concentrated under reduced pressure to give 3.20 g (63% yield) of 410i as a yellow solid.

LCMS: (ESI) m/z: 397.4 $[M+H]^+$.

$^1$H NMR: (400 MHz, MeOD-$d_4$) δ: 7.92 (s, 1H), 7.71 (d, J=8.4 Hz, 1H), 7.65 (s, 2H), 7.44-7.36 (m, 2H), 7.25 (d, J=0.4 Hz, 1H), 7.18 (dd, J=8.4, 2.0 Hz, 1H), 6.54 (dd, J=3.2, 0.8 Hz, 1H), 2.63 (s, 3H), 1.92 (t, J=18.0 Hz, 3H).

Synthesis of 367i

Step 1: Synthesis of 1-(1-benzylindol-6-yl)-N-[3-(1,1-difluoroethyl)phenyl]-3-methyl-5-oxo-4H-pyrazole-4-carboxamide (367i)

Compound ID: 367i

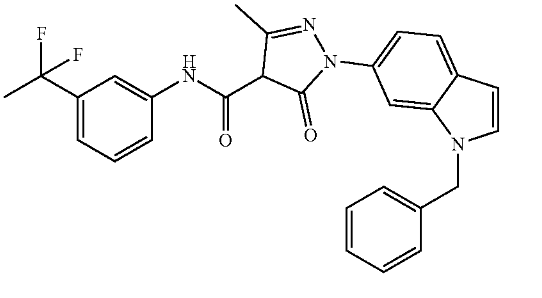

To a solution of 410i (100 mg, 227 umol, 1.0 eq) in N,N-dimethyl formadide (5 mL) was added sodium hydride (12.9 mg, 322 umol, 60% purity, 1.4 eq) at 0° C. slowly under nitrogen, the mixture was stirred 0.5 h, then the (bromomethyl)benzene (36.7 mg, 214 umol, 9.5e-1.0 eq) was injected and the mixture was stirred at 20° C. for 0.5 h. The mixture was quenched with water (30 mL), then extracted with ethyl acetate (20 mL×3), the combined organic layer was washed with brine (30 mL×1), dried over anhydrous sodium sulfate, filtered and concentrated under reduced pressure to give a residue. The residue was purified by prep-TLC (dichloromethane/methanol=10/1) to give a crude product, then the crude product was purified by column: (Boston Green ODS 150*30 mm*5 um; mobile phase: [water (0.225% formic acid)-acetonitrile]; B %: 55%-85%, 10 min) to give 23.1 mg (21% yield) of 367i as a white solid.

LCMS: (ESI) m/z: 487.2$[M+H]^+$.

$^1$H NMR: (400 MHz, DMSO-d) δ: 10.95 (s, 1H), 7.95 (s, 1H), 7.81 (s, 1H), 7.69 (d, J=8.4 Hz, 1H), 7.60 (s, 1H), 7.58 (d, J=3.2 Hz, 1H), 7.42 (s, 1H), 7.36-7.29 (m, 3H), 7.28-7.23 (m, 1H), 7.22-7.16 (m, 3H), 6.58 (d, J=3.2 Hz, 1H), 5.46 (s, 2H), 2.53 (s, 3H), 1.96 (t, J=18.8 Hz, 3H).

Synthesis of 108

Step 1: Synthesis of 1-benzyl-N-[3-(1,1-difluoroethyl)phenyl]-2-(1H-indol-6-yl)-5-methyl-3-oxo-pyrazole-4-carboxamide (108)

Compound ID: 108

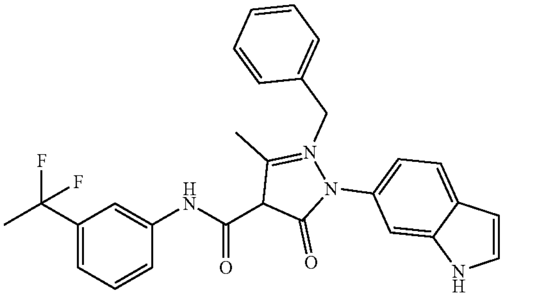

108 was obtained via similar procedure of 367i from 410i and (bromomethyl)benzene.

LCMS: (ESI) m/z: 487.3$[M+H]^+$.

$^1$H NMR: (400 MHz, DMSO-$d_6$) δ: 11.37 (br s, 1H), 11.00 (s, 1H), 7.92 (s, 1H), 7.64 (d, J=8.4 Hz, 1H), 7.58 (d, J=6.8 Hz, 1H), 7.50 (t, J=2.8 Hz, 1H), 7.43 (t, J=8.0 Hz, 1H), 7.33-7.26 (m, 4H), 7.22 (d, J=7.6 Hz, 1H), 6.91 (d, J=6.4 Hz, 2H), 6.84 (dd, J=8.4, 1.6 Hz, 1H), 6.53 (br s, 1H), 5.10 (s, 2H), 2.74 (s, 3H), 1.95 (t, J=18.8 Hz, 3H).

Synthesis of 107

Step 1: Synthesis of 1-(p-tolylsulfonyl)indole-6-carbonitrile (107-A)

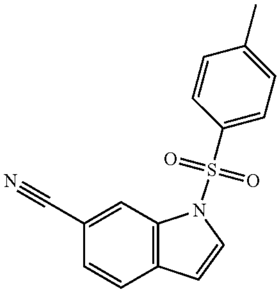 [SMILES: Cc1ccc(S(=O)(=O)n2ccc3ccc(C#N)cc32)cc1]

To a solution of 6-bromo-1-(p-tolylsulfonyl)indole (4.50 g, 12.9 mmol, 1.0 eq) in dry N,N-dimethyl-formamide (80 mL) was added dicyanozinc (1.13 g, 9.64 mmol, 0.75 eq), the reaction was stirred at 25° C. for 20 min under nitrogen. Then to the reaction mixture was added tetrakis(triphenylphosphine)platinum (1.48 g, 1.28 mmol, 0.10 eq), the suspension was degassed under vacuum and purged with nitrogen several times. The mixture was stirred under nitrogen at 95° C. for 16 hr. After cooling to room temperature, the mixture was poured into aqueous saturated sodium carbonate solution (50 mL) and extracted with ethyl acetate (20 mL×4). Combined organic extracts were washed with brine and dried over sodium sulfate, filtered, concentrated under reduced pressure. The crude product was purified by silica gel column chromatography (petroleum ether/ethyl acetate, from 1/0 to 9/1) to give 3.50 g (83% yield) of 107-A as a light yellow solid.

LCMS: (ESI) m/z: 297.1 $[M+H]^+$.

Step 2: Synthesis of [1-(p-tolylsulfonyl)indol-6-yl]methanamine (107-B)

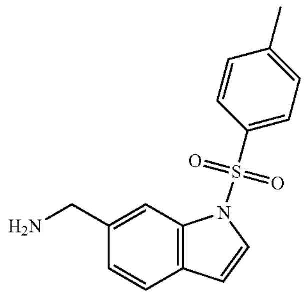 [SMILES: Cc1ccc(S(=O)(=O)n2ccc3ccc(CN)cc32)cc1]

107 was obtained via similar procedure of 123-C from 107-A and hydrogen.

LCMS: (ESI) m/z: 284.2 $[M+H]^+$.

Step 3: Synthesis of ethyl 5-methyl-2-[1-(p-tolylsulfonyl)indol-6-yl]oxazole-4-carboxylate (107-C)

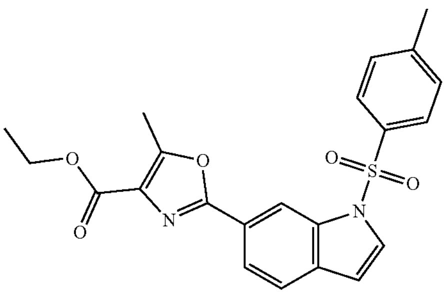 [SMILES: CCOC(=O)c1nc(-c2ccc3ccn(S(=O)(=O)c4ccc(C)cc4)c3c2)oc1C]

To a solution of 107-B (2.20 g, 7.32 mmol, 1.0 eq) in ethyl acetate (30 mL) was added ethyl 3-oxobutanoate (477 mg, 3.66 mmol, 0.50 eq), tert-butyl hydroperoxide (2.64 g, 29.3 mmol, 4.0 eq), tetrabutylammonium; iodide (541 mg, 1.46 mmol, 0.20 eq), the suspension was stirred at 40° C. for 12 h. The reaction was washed with water (50 mL), the aqueous layer mixture was extracted with ethyl acetate (50 mL×2). The combined organic layers were washed with brine (100 mL), dried over anhydrous sodium sulfate, filtered, and concentrated under reduced pressure. The crude product was purified by silica gel column chromatography (petroleum ether/ethyl acetate, from 10/1 to 3/1) to give 600 mg (17% yield) of 107-C as a light yellow solid.

LCMS: (ESI) m/z: 425.0 $[M+H]^+$.

$^1H$ NMR: (400 MHz, DMSO-$d_6$) δ: 8.56-8.48 (m, 1H), 7.97 (d, J=3.8 Hz, 1H), 7.90-7.83 (m, 3H), 7.76 (d, J=8.4 Hz, 1H), 7.40 (d, J=8.0 Hz, 2H), 6.94 (dd, J=0.8, 3.7 Hz, 1H), 4.33 (q, J=7.2 Hz, 2H), 2.71 (s, 3H), 2.31 (s, 3H), 1.34 (t, J=7.2 Hz, 3H).

Step 4: Synthesis of 5-methyl-2-[1-(p-tolylsulfonyl)indol-6-yl]oxazole-4-carboxylic acid (107-D)

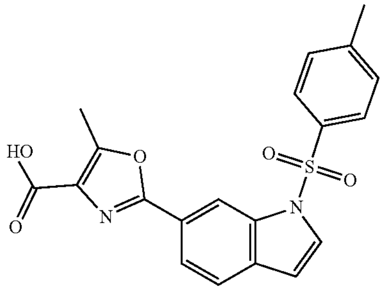 [SMILES: Cc1ccc(S(=O)(=O)n2ccc3ccc(-c4nc(C(=O)O)c(C)o4)cc32)cc1]

107-D was obtained via similar procedure of 154-C from 107-C and sodium hydroxide.

LCMS: (ESI) m/z: 397.1 $[M+H]^+$.

Step 5: Synthesis of N-[3-(1,1-difluoroethyl)phenyl]-2-(1H-indol-6-yl)-5-methyl-oxazole-4-carboxamide (107)

Compound ID: 107

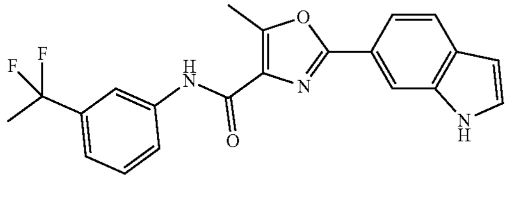

107 was obtained via similar procedure of 154 from 107-D and 3-(1,1-difluoroethyl)aniline.

LCMS: (ESI) m/z: 382.2 $[M+H]^+$.

$^1H$ NMR: (400 MHz, DMSO-$d_6$) δ: 11.48 (br s, 1H), 10.14 (s, 1H), 8.14 (d, J=13.2 Hz, 2H), 7.98 (d, J=8.0 Hz, 1H), 7.78-7.74 (m, 1H), 7.73-7.69 (m, 1H), 7.56 (t, J=2.8 Hz, 1H), 7.47 (t, J=8.0 Hz, 1H), 7.29 (d, J=7.8 Hz, 1H), 6.54 (t, J=2.0 Hz, 1H), 2.73 (s, 3H), 1.98 (t, J=18.8 Hz, 3H).

Synthesis of 106

Step 1: Synthesis of N-[3-(1,1-difluoroethyl)phenyl]-2-[4-(difluoromethoxy)-3-phenyl-phenyl]-5-methyl-oxazole-4-carboxamide (106)

Compound ID: 106

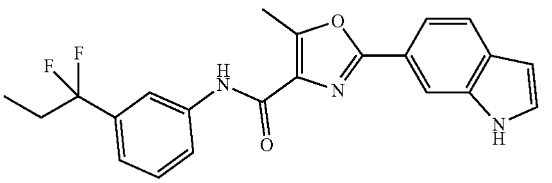

106 was obtained via similar procedure of 154 from 107-D and 3-(1,1-difluoropropyl)aniline.

LCMS: (ESI) m/z: 396.2 $[M+H]^+$.

$^1$H NMR: (400 MHz, DMSO-d) δ: 8.11 (d, J=5.8 Hz, 2H), 7.98 (d, J=8.4 Hz, 1H), 7.78-7.74 (m, 1H), 7.73-7.69 (m, 1H), 7.56 (t, J=2.8 Hz, 1H), 7.47 (t, J=8.0 Hz, 1H), 7.24 (d, J=8.0 Hz, 1H), 6.54 (t, J=1.8 Hz, 1H), 2.73 (s, 3H), 2.29-2.15 (m, 2H), 0.94 (t, J=7.4 Hz, 3H).

Synthesis of 105

Step 1: Synthesis of 3-(4-(difluoromethoxy)phenyl)-2,5-dimethylpyrazine (105-A)

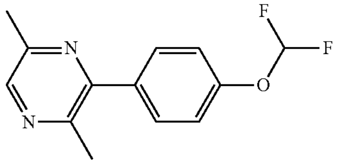 [SMILES: Cc1cnc(C)c(-c2ccc(OC(F)F)cc2)n1]

To a solution of 3-chloro-2,5-dimethyl-pyrazine (1.00 g, 7.01 mmol, 1.0 eq) in dioxane (10 mL)/water (2 mL) was added 173-A (2.84 g, 10.5 mmol, 1.5 eq), 1,1-bis(diphenylphosphino)ferrocene]dichloropalladium(II) (513 mg, 701 umol, 0.10 eq) and sodium bicarbonate (1.18 g, 14.0 mmol, 2.0 eq). The suspension was degassed under vacuum and purged with nitrogen several times. The mixture was stirred under nitrogen at 80° C. for 2 hours. The solution was poured into water (10 mL), extracted with ethyl acetate (10 mL×3). The combined organic phase was washed with brine (20 mL), dried with anhydrous sodium sulfate, filtered and concentrated. The residue was purified by silica column (petroleum ether/ethyl acetate, from 20/1 to 10/1) to give 1.00 g (55% yield) of 105-A as a white solid.

LCMS: (ESI) m/z: 251.1 $[M+H]^+$.

Step 2: Synthesis of 3-(4-(difluoromethoxy)phenyl)-2,5-dimethylpyrazine 1-oxide (105-B)

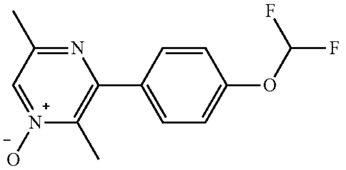 [SMILES: Cc1c[n+]([O-])c(C)c(-c2ccc(OC(F)F)cc2)n1]

To a solution of 105-B (1.00 g, 3.82 mmol, 1.0 eq) in dichloromethane (15 mL) was added a solution of hydrogen peroxide (883 mg, 7.79 mmol, 30% purity, 2.0 eq) and trifluoroaceticanhydride (1.23 g, 5.86 mmol, 1.5 eq) at 0° C. The solution was stirred at 40° C. for 12 hours. The solution was poured into saturated sodium sulfite solution (15 mL), extracted with ethyl acetate (15 mL×3). The combined organic phase was washed with brine (15 mL), dried with anhydrous sodium sulfate, filtered and concentrated. The residue was purified by silica column (petroleum ether/ethyl acetate, from 10/1 to 5/1) to give 105-B as a white solid.

LCMS: (ESI) m/z: 267.1 $[M+H]^+$.

Step 3: Synthesis of 2-chloro-5-(4-(difluoromethoxy)phenyl)-3,6-dimethylpyrazine (105-C)

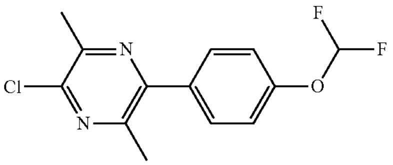 [SMILES: Cc1nc(-c2ccc(OC(F)F)cc2)c(C)nc1Cl]

To a solution of 105-B (800 mg, 2.90 mmol, 1.0 eq) in toluene (10 mL) was added phosphoryl trichloride (1.33 g, 8.69 mmol, 3.0 eq) and N,N-dimethylformamide (21.2 mg, 290 umol, 0.10 eq), the solution was stirred at 60° C. for 12 h. The solution was poured into ice-water (20 mL), extracted with ethyl acetate (20 mL×3). The combined organic phase was washed with saturated sodium bicarbonate solution (20 mL) and brine (20 mL). The organic phase was dried with anhydrous sodium sulfate, filtered and concentrated to give 300 mg (36% yield) of 105-C as a white solid.

$^1$H NMR: (400 MHz, $CDCl_3$-d) δ: 7.60-7.57 (m, 2H), 7.24 (d, J=8.8 Hz, 2H), 6.58 (t, J=73.6 Hz, 1H), 2.67 (s, 3H), 2.58 (s, 3H).

Step 4: Synthesis of 5-(4-(difluoromethoxy)phenyl)-N-(3-(1,1-difluoropropyl)phenyl)-3,6-dimethylpyrazine-2-carboxamide (105)

Compound ID: 105

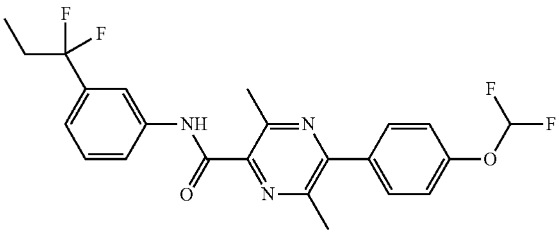

To a solution of 105-C (100 mg, 351 umol, 1.0 eq) and 3-(1,1-difluoropropyl)aniline (60.1 mg, 351 umol, 1.0 eq) in N,N-dimethylformamide (1 mL) was added molybdenumhexacarbonyl (46.4 mg, 176 umol, 0.50 eq), palladium acetate (2.37 mg, 10.5 umol, 0.030 eq), bis(1-adamantyl)-butyl-phosphane (7.56 mg, 21.1 umol, 0.060 eq) and 1,8-diazabicyclo[5.4.0]undec-7-ene (80.2 mg, 527 umol, 1.5 eq) under nitrogen. The suspension was degassed under vacuum and purged with nitrogen several times. The mixture was stirred under nitrogen at 130° C. for 2 hours under microwave (2 bar). The solution was poured into water (5 mL), extracted with ethyl acetate (5 mL×3). The combined organic phase was washed with brine (10 mL), dried with anhydrous sodium sulfate, filtered and concentrated. The crude product was purified by prep-HPLC (column: Boston Green ODS 150*30 mm*5 um; mobile phase: [water (0.225% formic acid)-acetonitrile]; B %: 65%-95%, 10 min) to give 11.0 mg (7% yield) of 105 as a white solid.

LCMS: (ESI) m/z: 448.1 $[M+H]^+$.

$^1$H NMR: (400 MHz, DMSO-$d_6$) δ: 10.78 (s, 1H), 8.06 (s, 1H), 7.96 (d, J=8.4 Hz, 1H), 7.80 (d, J=8.4 Hz, 1H), 7.51 (t, J=8.0 Hz, 1H), 7.38 (t, J=74.0 Hz, 1H), 7.34 (d, J=8.8 Hz, 2H), 7.27 (d, J=8.0 Hz, 1H), 2.78 (s, 3H), 2.67 (s, 3H), 2.29-2.15 (m, 2H), 0.94 (t, J=7.2 Hz, 3H).

Synthesis of 104

Step 1: Synthesis of 3-(6-(difluoromethoxy)-[1,1'-biphenyl]-3-yl)-2,5-dimethylpyrazine (104-A)

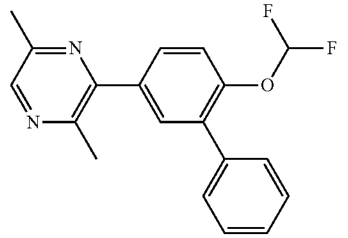 [SMILES: Cc1cnc(C)c(-c2ccc(OC(F)F)c(-c3ccccc3)c2)n1]

104-A was obtained via similar procedure of 105-A from 127-C and 3-chloro-2,5-dimethyl-pyrazine.

LCMS: (ESI) m/z: 327.1 $[M+H]^+$.

Step 2: Synthesis of 3-(6-(difluoromethoxy)-[1,1'-biphenyl]-3-yl)-2,5-dimethylpyrazine 1-oxide (104-B)

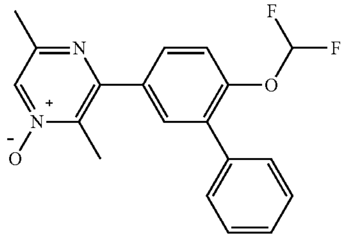 [SMILES: Cc1c[n+]([O-])c(C)c(-c2ccc(OC(F)F)c(-c3ccccc3)c2)n1]

104-B was obtained via similar procedure of 105-B from 104-A and hydrogen peroxide.

LCMS: (ESI) m/z: 343.1 $[M+H]^+$.

Step 3: Synthesis of 2-chloro-5-(6-(difluoromethoxy)-[1,1'-biphenyl]-3-yl)-3,6-dimethylpyrazine (104-C)

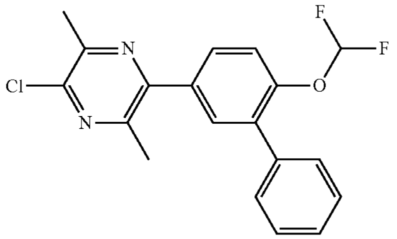 [SMILES: Cc1nc(-c2ccc(OC(F)F)c(-c3ccccc3)c2)c(C)nc1Cl]

104-C was obtained via similar procedure of 105-C from 104-B and phosphoryl trichloride.

LCMS: (ESI) m/z: 361.0 $[M+H]^+$.

$^1$HNMR (400 MHz, $CDCl_3$-d) δ: 7.63 (d, J=2.4 Hz, 1H), 7.58-7.52 (m, 3H), 7.48-7.44 (m, 2H), 7.42-7.36 (m, 2H), 6.40 (t, J=74.0 Hz, 1H), 2.68 (s, 3H), 2.63 (s, 3H).

Step 4: Synthesis of N-(3-(1,1-difluoroethyl)phenyl)-5-(6-(difluoromethoxy)-[1,1'-biphenyl]-3-yl)-3,6-dimethylpyrazine-2-carboxamide (104)

Compound ID: 104

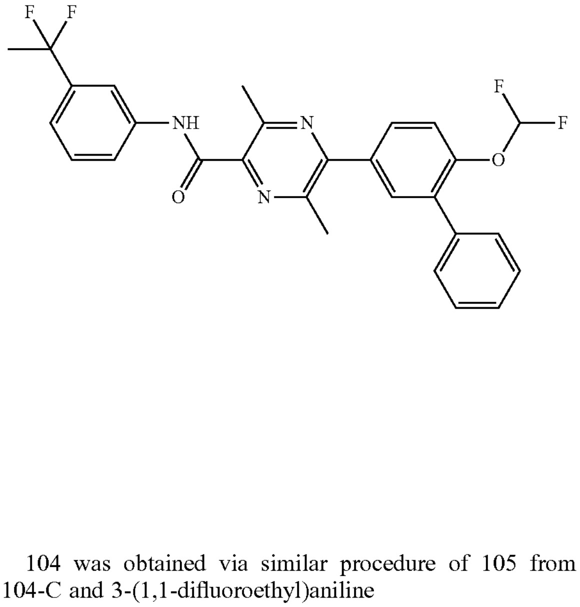

104 was obtained via similar procedure of 105 from 104-C and 3-(1,1-difluoroethyl)aniline LCMS: (ESI) m/z: 510.2 $[M+H]^+$.

$^1$H NMR: (400 MHz, DMSO-d) δ: 10.79 (s, 1H), 8.11 (s, 1H), 7.96 (d, J=8.0 Hz, 1H), 7.82 (dd, J=8.4 Hz, J=2.4 Hz, 1H), 7.78 (d, J=2.0 Hz, 1H), 7.56-7.48 (m, 6H), 7.45-7.41 (m, 1H), 7.32 (d, J=8.0 Hz, 1H), 7.31 (t, J=73.6 Hz, 1H), 2.79 (s, 3H), 2.73 (s, 3H), 1.99 (t, J=18.8 Hz, 3H).

Synthesis of 103

Step 1: Synthesis of 5-(6-(difluoromethoxy)-[1,1'-biphenyl]-3-yl)-N-(3-(1,1-difluoropropyl)phenyl)-3,6-dimethylpyrazine-2-carboxamide (103)

Compound ID: 103

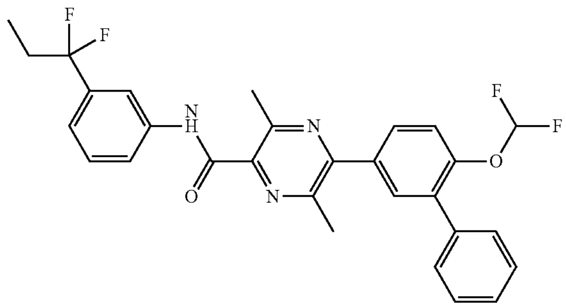

103 was obtained via similar procedure of 105 from 104-C and 3-(1,1-difluoropropyl)aniline LCMS: (ESI) m/z: 524.2 $[M+H]^+$.

$^1H$ NMR: (400 MHz, DMSO-d) δ: 10.78 (s, 1H), 8.06 (s, 1H), 7.96 (d, J=8.4 Hz, 1H), 7.82 (dd, J=8.4 Hz, J=2.4 Hz, 1H), 7.78 (d, J=2.0 Hz, 1H), 7.56-7.48 (m, 6H), 7.46-7.41 (m, 1H), 7.31 (t, J=38.0 Hz, 1H), 2.79 (s, 3H), 2.73 (s, 3H), 2.27-2.15 (m, 2H), 0.94 (t, J=7.2 Hz, 3H).

Synthesis of 102

Step 1: Synthesis of methyl 2-[4-(difluoromethoxy)phenyl]-6-methyl-pyridine-4-carboxylate (102-A)

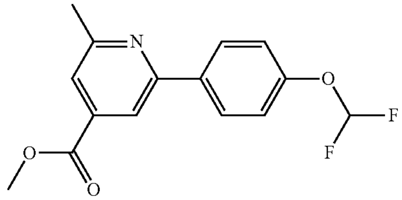 [SMILES: COC(=O)c1cc(C)nc(-c2ccc(OC(F)F)cc2)c1]

102-A was obtained via similar procedure of 144-A from 173-A and methyl 2-chloro-6-methylisonicotinate.

$^1H$ NMR: (400 MHz, $CDCl_3$-d) δ: 8.10-8.05 (m, 3H), 7.66 (d, J=0.8 Hz, 1H), 7.23 (d, J=8.8 Hz, 2H), 6.58 (t, J=73.6 Hz, 1H), 3.99 (s, 3H), 2.70 (s, 3H)

Step 2: Synthesis of 2-[4-(difluoromethoxy)phenyl]-6-methyl-pyridine-4-carboxylic acid (102-B)

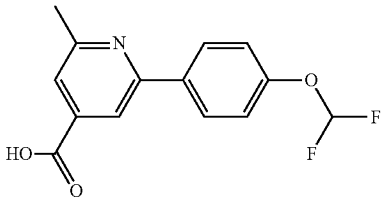 [SMILES: Cc1cc(C(=O)O)cc(-c2ccc(OC(F)F)cc2)n1]

102-B was obtained via similar procedure of 144-B from 152-B and lithium hydroxide hydrate.

LCMS: (ESI) m/z: 280.1 $[M+H]^+$.

Step 3: Synthesis of 2-[4-(difluoromethoxy)phenyl]-N-[3-(1,1-difluoropropyl)phenyl]-6-methyl-pyridine-4-carboxamide (102)

Compound ID: 102

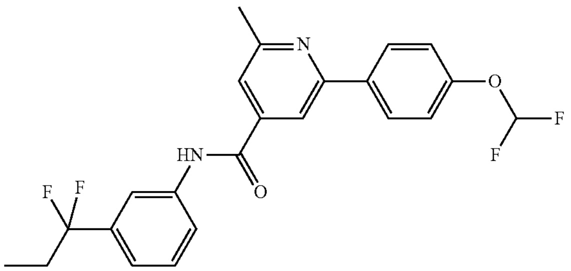

102 was obtained via similar procedure of 144 from 102-B and 3-(1,1-difluoropropyl)aniline LCMS: (ESI) m/z: 433.3 $[M+H]^+$.

$^1H$ NMR (400 MHz, MeOD) δ: 8.14-8.11 (m, 2H), 8.10-8.09 (m, 1H), 7.95-7.91 (m, 1H), 7.85 (d, J=8.4 Hz, 1H), 7.68 (d, J=0.8 Hz, 1H), 7.48 (t, J=8.0 Hz, 1H), 7.30 (s, 1H), 7.28 (d, J=8.8 Hz, 2H), 2.69 (s, 3H), 2.27-2.12 (m, 2H), 0.99 (t, J=7.6 Hz, 3H).

Synthesis of 101

Step 1: Synthesis of cyclobutyl(3-nitrophenyl)methanone (101-A)

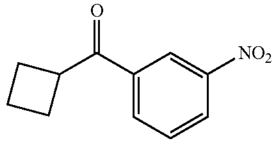 [SMILES: O=C(c1cccc([N+](=O)[O-])c1)C1CCC1]

101-A as obtained via similar procedure of 2-methyl-1-(3-nitrophenyl)propan-1-one from cyclobutyl(phenyl) methanone and nitric acid.

$^1H$ NMR (400 MHz, $CDCl_3$-d) δ: 8.70 (t, J=2.0 Hz, 1H), 8.41 (ddd, J=1.2, 2.4, 8.2 Hz, 1H), 8.24 (td, J=1.2, 8.0 Hz, 1H), 7.67 (t, J=8.0 Hz, 1H), 4.08-4.00 (m, 1H), 2.49-2.35 (m, 4H), 2.21-2.10 (m, 1H), 2.02-1.92 (m, 1H)

Step 2: Synthesis of 1-(cyclobutyldifluoromethyl)-3-nitrobenzene (101-B)

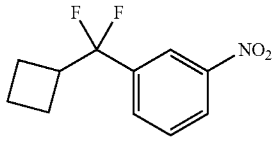 [SMILES: Nc1cccc(C(F)(F)C2CCC2)c1]

101-B was obtained via similar procedure of 1-(1,1-difluoro-2-methylpropyl)-3-nitrobenzene from 101-A and diethylaminosulfur trifluoride.

$^1$H NMR (400 MHz, $CDCl_3$-d) δ: 8.34-8.28 (m, 2H), 7.79 (d, J=7.6 Hz, 1H), 7.62 (t, J=8.0 Hz, 1H), 3.07-2.91 (m, 1H), 2.29-2.17 (m, 2H), 2.06-1.83 (m, 4H).

Step 3: Synthesis of 3-(cyclobutyldifluoromethyl)aniline (101-C)

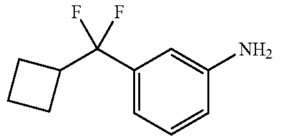

101-C was obtained via similar procedure of 3-(1,1-difluoro-2-methylpropyl)aniline from 101-B and iron powder.

LCMS: (ESI) m/z: 198.1 $[M+H]^+$.

Step 4: Synthesis of N-(3-(cyclobutyldifluoromethyl)phenyl)-1-(4-(difluoromethoxy)phenyl)-3-methyl-5-oxo-4,5-dihydro-1H-pyrazole-4-carboxamide (101)

Compound ID: 101

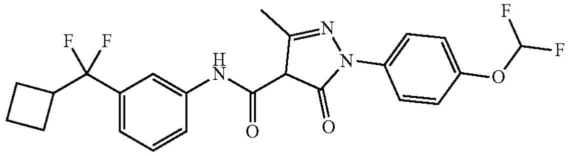

101 was obtained via general procedure IV from 4-nitrophenyl 1-(4-(difluoromethoxy)phenyl)-3-methyl-5-oxo-4,5-dihydro-1H-pyrazole-4-carboxylate and 101-C LCMS: (ESI) m/z: 464.2 $[M+H]^+$.

$^1$H NMR (400 MHz, MeOD-$d_4$) δ: 7.82 (br s, 3H), 7.63 (br d, J=8.0 Hz, 1H), 7.35 (br s, 1H), 7.26-7.07 (m, 3H), 6.80 (t, J=74.4 Hz, 1H), 3.28-2.99 (m, 1H), 2.45 (br s, 3H), 2.31-2.10 (m, 2H), 2.05-1.88 (m, 3H), 1.88-1.78 (m, 1H).

Synthesis of 100

Step 1: Synthesis of 4-chloro-N-(3-(1,1-difluoroethyl)phenyl)-1-(6-(difluoromethoxy)-[1,1'-biphenyl]-3-yl)-3-methyl-5-oxo-4,5-dihydro-1H-pyrazole-4-carboxamide (100-A)

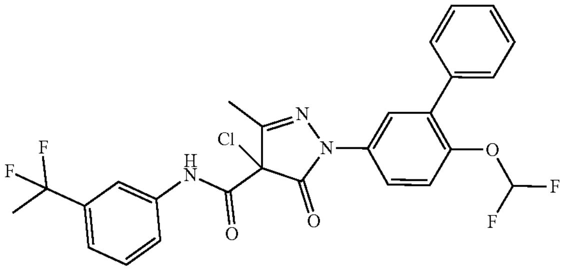 [SMILES: CC1=NN(c2ccc(OC(F)F)c(-c3ccccc3)c2)C(=O)C1(Cl)C(=O)Nc1cccc(C(C)(F)F)c1]

100-A was obtained via similar procedure of 172 from 312i.

LCMS: (ESI) m/z: 551.1 $[M+NH_4]^+$.

Step 2: Synthesis of N-(3-(1,1-difluoroethyl)phenyl)-1-(6-(difluoromethoxy)-[1,1'-biphenyl]-3-yl)-4-ethyl-3-methyl-5-oxo-4,5-dihydro-1H-pyrazole-4-carboxamide (100)

Compound ID: 100

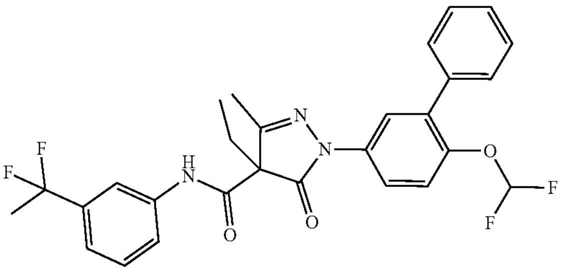

100 was obtained via similar procedure of 158 from 100-A.

LCMS: (ESI) m/z: 528.3 $[M+H]^+$.

$^1$H NMR: (400 MHz, MeOD-$d_4$) δ: 8.02 (d, J=2.8 Hz, 1H), 7.96 (dd, J=2.8, 8.8 Hz, 1H), 7.78 (s, 1H), 7.62 (d, J=7.6 Hz, 1H), 7.53-7.48 (m, 2H), 7.46-7.37 (m, 4H), 7.35-7.29 (m, 2H), 6.65 (t, J=74.0 Hz, 1H), 2.41-2.35 (m, 1H), 2.33 (s, 3H), 2.32-2.28 (m, 1H), 1.89 (t, J=18.4 Hz, 3H), 0.87 (t, J=7.6 Hz, 3H).

Synthesis of 213

Step 1: Synthesis of 4-(difluoromethoxy)-3-(4,4,5,5-tetramethyl-1,3,2-dioxaborolan-2-yl)benzonitrile (213-A)

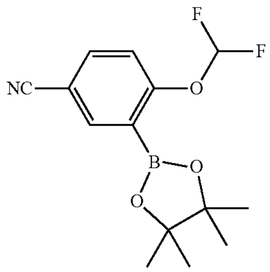 [SMILES: CC1(C)OB(c2cc(C#N)ccc2OC(F)F)OC1(C)C]

To a solution of 123-A (1.5 g, 6.05 mmol, 1.0 eq) and 4,4,5,5-tetramethyl-2-(4,4,5,5-tetramethyl-1,3,2-dioxaborolan-2-yl)-1,3,2-dioxaborolane (2.00 g, 7.86 mmol, 1.3 eq) in dioxane (25 mL) was added 1,1-bis(diphenylphosphino) ferrocene]dichloropalladium(II) (443 mg, 605 umol, 0.10 eq) followed by potassium acetate (1.48 g, 15.1 mmol, 2.5 eq). The solution was stirred at 90° C. for 12 h under nitrogen atmosphere. The solution was filtered and the filtrate was concentrated. The residue was purified by column chromatography on silica gel (petroleum ether/ethyl acetate=50/1 to 20/1) to give 2.25 g (crude) of 213-B as a yellow oil.

LCMS: (ESI) m/z: 214.1 $[M-82]^+$.

Step 2: Synthesis of 4-(difluoromethoxy)-3-(pyridin-2-yl)benzonitrile (213-B)

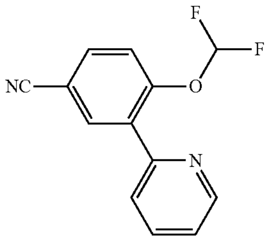 [SMILES: N#Cc1ccc(OC(F)F)c(-c2ccccn2)c1]

To a solution of 213-A (2.24 g, 7.60 mmol, 1.5 eq) and 2-bromopyridine (800 mg, 5.06 mmol, 1.0 eq) in dioxane (30 mL) and water (6 mL) was added 1,1-bis(diphenylphosphino)ferrocene]dichloropalladium(II) (371 mg, 506 umol, 0.10 eq) and potassium carbonate (2.10 g, 15.2 mmol, 3.0 eq). The solution was stirred at 90° C. for 12 h. The solution was partitioned between ethyl acetate (150 mL) and water (150 mL). The aqueous layer was extracted with ethyl acetate (100 mL). The combined organic layer was washed with brine (150 mL), dried over anhydrous sodium sulfate, filtered and concentrated. The residue was purified by prep-TLC (petroleum ether/ethyl acetate=3/1) to give 1.33 g (83% yield) of 213-B as a white solid.

LCMS: (ESI) m/z: 247.0 $[M+H]^+$.

Step 3: Synthesis of 4-(difluoromethoxy)-3-(pyridin-2-yl)benzamide (213-C)

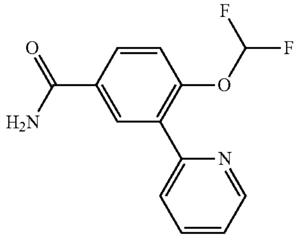 [SMILES: NC(=O)c1ccc(OC(F)F)c(-c2ccccn2)c1]

To a solution of 213-B (1.33 g, 4.20 mmol, 1.0 eq) in dimethylsulfoxide (15 mL) was added potassium carbonate (1.12 g, 8.10 mmol, 1.9 eq) followed by hydrogen peroxide (919 mg, 8.10 mmol, 30% purity, 1.9 eq). The solution was stirred at 20° C. for 15 min. To the solution was added saturated sodium sulfite (20 mL) and the mixture was stirred at 20° C. for 30 min. The solution was partitioned between water (100 mL) and ethyl acetate (100 mL). The aqueous layer was extracted with ethyl acetate (50 mL). The combined organic layers were washed with brine (80 mL), dried over anhydrous sodium sulfate, filtered and concentrated to give 1.10 g (97% yield) of 213-C as a white solid.

LCMS: (ESI) m/z: 265.0 $[M+H]^+$.

Step 4: Synthesis of ethyl 2-(4-(difluoromethoxy)-3-(pyridin-2-yl)phenyl)-4-methyloxazole-5-carboxylate (213-D)

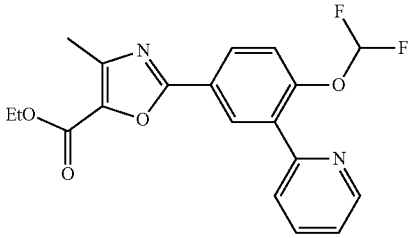 [SMILES: CCOC(=O)c1oc(-c2ccc(OC(F)F)c(-c3ccccn3)c2)nc1C]

To a solution of 213-C (370 mg, 1.38 mmol, 1.0 eq) in N,N-dimethylformamide (1 mL) was added ethyl 2-chloro-3-oxo-butanoate (691 mg, 4.20 mmol, 3.1 eq). The solution was stirred at 130° C. for 20 h. The solution was partitioned between ethyl acetate (100 mL) and water (100 mL). The aqueous layer was extracted with ethyl acetate (50 mL×2). The combined organic layer was washed with brine (100 mL), dried over anhydrous sodium sulfate, filtered and concentrated. The residue was purified by column chromatography on silica gel (petroleum ether/ethyl acetate=5/1) to give 190 mg (30% yield) of 213-D as a brown oil.

LCMS: (ESI) m/z: 375.0 $[M+H]^+$.

Step 5: Synthesis of 2-(4-(difluoromethoxy)-3-(pyridin-2-yl)phenyl)-4-methyloxazole-5-carboxylic acid (213-E)

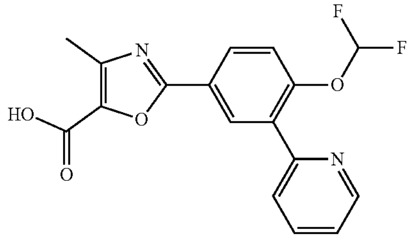 [SMILES: Cc1nc(-c2ccc(OC(F)F)c(-c3ccccn3)c2)oc1C(=O)O]

To a solution of 213-D (180 mg, 391 umol, 1.0 eq) in ethanol (3 mL) and water (1 mL) was added sodium hydroxide (47.0 mg, 1.17 mmol, 3.0 eq). The solution was stirred at 20° C. for 12 h. The solution was partitioned between ethyl acetate (50 mL) and aqueous sodium hydroxide (1 M, 50 mL). The organic layer was separated and the aqueous layer was acidified to pH=3 by addition of aqueous hydrochloric acid (6 M). The mixture was extracted with ethyl acetate (40 mL×3), washed with brine (60 mL), dried over anhydrous sodium sulfate, filtered and concentrated to give 140 mg (90% yield) of 213-E as a yellow solid.

LCMS: (ESI) m/z: 347.0 $[M+H]^+$.

Step 6: Synthesis of N-(3-(1,1-difluoroethyl)phenyl)-2-(4-(difluoromethoxy)-3-(pyridin-2-yl)phenyl)-4-methyloxazole-5-carboxamide (213)

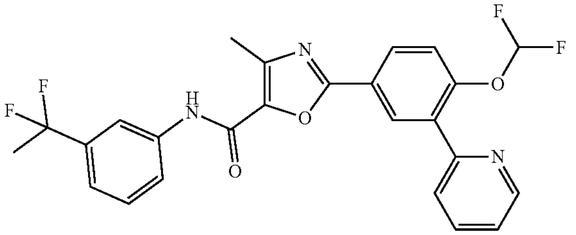 [SMILES: Cc1nc(-c2ccc(OC(F)F)c(-c3ccccn3)c2)oc1C(=O)Nc1cccc(C(C)(F)F)c1]

To a solution of 213-E (30.0 mg, 75.9 umol, 1.0 eq) in N,N-dimethylformamide (0.5 mL) was added [dimethylamino(triazol[4,5-b]pyridin-3-yloxy)methylidene]-dimethylazanium; hexafluorophosphate (40.4 mg, 106 umol, 1.4 eq) and N-ethyl-N-isopropylpropan-2-amine (29.4 mg, 228 umol, 3.0 eq). The solution was stirred at 20° C. for 10 min and then 3-(1,1-difluoroethyl)aniline (16.7 mg, 106 umol, 1.4 eq) was added. The solution was stirred at 20° C. for 5 h. The solution was concentrated. The residue was purified by prep-HPLC (column: Phenomenex Synergi C18 150*25*10 um; mobile phase: [water (0.225% formic acid)-acetonitrile]; B %: 60%-90%, 9 min) to give 41.7 mg (67% yield) of 213 as a yellow solid.

LCMS: (ESI) m/z: 486.3 $[M+H]^+$.

$^1$H NMR: (400 MHz, MeOD-$d_4$) δ: 8.72 (d, J=4.8 Hz, 1H), 8.56 (d, J=2.0 Hz, 1H), 8.34 (dd, J=2.0, 8.4 Hz, 1H), 8.00 (dt, J=2.0, 7.6 Hz, 1H), 7.93 (s, 1H), 7.86-7.78 (m, 2H), 7.54-7.48 (m, 2H), 7.45 (t, J=8.0 Hz, 1H), 7.32 (d, J=78.0 Hz, 1H), 6.99 (t, J=73.2 Hz, 1H), 2.57 (s, 3H), 1.93 (t, J=18.4 Hz, 3H)

Synthesis of 214

Step 1: Synthesis of 2-(4-(difluoromethoxy)-3-(pyridin-2-yl)phenyl)-N-(3-(1,1-difluoropropyl)phenyl)-4-methyloxazole-5-carboxamide (214)

Compound ID: 214

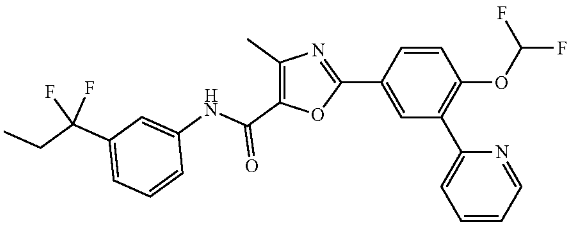

214 was obtained via the similar synthetic method for 213.

LCMS: (ESI) m/z: 500.4 $[M+H]^+$.

$^1$H NMR: (400 MHz, MeOD-$d_4$) δ: 8.73 (d, J=4.8 Hz, 1H), 8.57 (d, J=2.0 Hz, 1H), 8.35 (dd, J=2.0, 8.4 Hz, 1H), 8.03 (dt, J=1.6, 7.6 Hz, 1H), 7.91-7.80 (m, 3H), 7.56-7.49 (m, 2H), 7.46 (t, J=8.0 Hz, 1H), 7.28 (d, J=7.6 Hz, 1H), 7.00 (t, J=73.2, 1H), 2.57 (s, 3H), 2.15-2.11 (m, 2H), 0.99 (t, J=7.6 Hz, 3H)

Synthesis of 215

Step 1: Synthesis of ethyl 2-bromo-5-methyl-1H-imidazole-4-carboxylate (215-A)

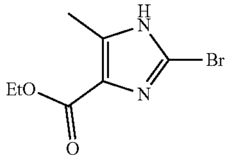

To a solution of ethyl 5-methyl-1H-imidazole-4-carboxylate (3.00 g, 19.5 mmol, 1.0 eq) in acetonitrile (40 mL) was added 1-bromopyrrolidine-2,5-dione (3.64 g, 20.4 mmol, 1.1 eq) portion wises. The mixture was stirred at 20° C. for 12 h. The reaction mixture was concentrated under reduced pressure. The residue was purified by column chromatography on silica gel (petroleum ether/ethyl acetate=5/1) to give 1.90 g (41% yield) of 215-A as a yellow solid.

$^1$H NMR: (400 MHz, $CDCl_3$-d) δ: 10.78 (br s, 1H), 4.31 (q, J=7.2 Hz, 2H), 2.55 (s, 3H), 1.28 (t, J=7.2 Hz, 3H).

Step 2: Synthesis of ethyl 2-(4-(difluoromethoxy)phenyl)-5-methyl-1H-imidazole-4-carboxylate (215-B)

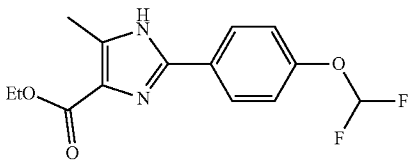 [SMILES: CCOC(=O)c1nc(-c2ccc(OC(F)F)cc2)[nH]c1C]

To a solution of 215-A (300 mg, 1.29 mmol, 1.0 eq) and 173-A (487 mg, 1.80 mmol, 1.4 eq) in dioxane (15 mL) and water (4 mL) was added cesium carbonate (1.05 g, 3.22 mmol, 2.5 eq) and 1,1-bis(diphenylphosphino)ferrocene] dichloropalladium(II) (94.2 mg, 129 umol, 0.10 eq). The solution was stirred at 80° C. for 12 h. The solution was filtered through a celite pad and the filtrate was partitioned between ethyl acetate (80 mL) and water (80 mL). The aqueous layer was extracted with ethyl acetate (50 mL×2). The combined organic layer was washed with brine (80 mL), dried over anhydrous sodium sulfate, filtered and concentrated. The residue was purified by column chromatography on silica gel (petroleum ether/ethyl acetate=5/1) to give 300 mg (78% yield) of 215-B as a white solid.

LCMS: (ESI) m/z: 297.1 $[M+H]^+$.

Step 3: Synthesis of 2-(4-(difluoromethoxy)phenyl)-5-methyl-1H-imidazole-4-carboxylic acid (215-C)

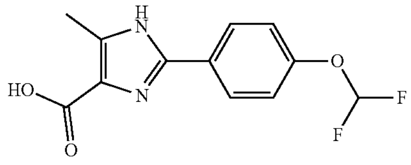 [SMILES: Cc1[nH]c(-c2ccc(OC(F)F)cc2)nc1C(=O)O]

To a mixture of 215-B (300 mg, 1.01 mmol, 1.0 eq) in ethanol (10 mL) and water (3 mL) was added sodium hydroxide (203 mg, 5.06 mmol, 5.0 eq). The mixture was heated to 90° C. and stirred for 12 hours. The organic solvent was removed by reduced pressure and water (2 mL) was added. Then the mixture was adjusted to pH=5 by addition of aqueous hydrochloric acid (1 M) along with precipitate was formed. Filtration and concentration give 250 mg (77% yield) of 215-C as an off-white solid.

LCMS: (ESI) m/z: 269.0 $[M+H]^+$.

Step 4: Synthesis of 2-(4-(difluoromethoxy)phenyl)-N-(3-(1,1-difluoropropyl)phenyl)-5-methyl-1H-imidazole-4-carboxamide (215)

Compound ID 215

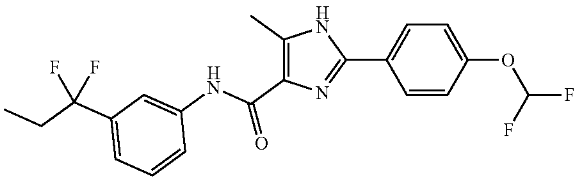

To a solution of 215-C (100 mg, 312 umol, 1.0 eq) in N,N-dimethylformamide (5 mL) was added N-ethyl-N-isopropylpropan-2-amine (202 mg, 1.56 mmol, 5.0 eq), [dimethylamino(triazol[4,5-b]pyridin-3-yloxy)methylidene]-dimethylazanium; hexafluorophosphate (142 mg, 374 umol, 1.2 eq) and N-ethyl-N-isopropylpropan-2-amine (38.1 mg, 312 umol, 1.0 eq). Then the mixture was stirred for 20 minutes, after that it was added 3-(1,1-difluoropropyl)aniline (80.1 mg, 468 umol, 1.5 eq) and stirred at 20° C. for 2 hours. The solution was concentrated. The residue was purified by prep-HPLC (column: Phenomenex Synergi C18 150*25*10 um; mobile phase: [water (0.225% formic acid)-acetonitrile]; B %: 50%-80%, 10 min) to give 26.9 mg (20% yield) of 215 as a white solid.

LCMS: (ESI) m/z: 422.0 $[M+H]^+$.

$^1$H NMR: (400 MHz, MeOD-$d_4$) δ: 8.01-7.90 (m, 3H), 7.75 (d, J=8.0 Hz, 1H), 7.41 (t, J=8.0 Hz, 1H), 7.29-7.16 (m, 3H), 6.89 (t, J=73.6 Hz, 1H), 2.61 (s, 3H), 2.25-2.10 (m, 2H), 0.99 (t, J=7.6 Hz, 1H)

Synthesis of 5-[4-(difluoromethoxy)phenyl]-N-[3-(1,1-difluoropropyl)phenyl]-2-methyl-1H-pyrrole-3-carboxamide (216)

Compound ID: 216

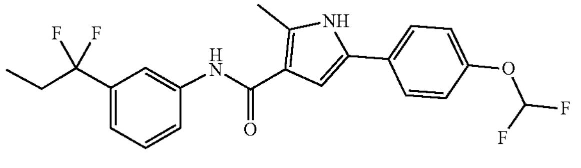

216 was obtained via similar procedure of 152 from 5-[4-(difluoromethoxy)phenyl]-2-methyl-1H-pyrrole-3-carboxylic acid and 3-(1,1-difluoropropyl)aniline LCMS: (ESI) m/z: 421.0 $[M+H]^+$.

$^1$H NMR: (400 MHz, MeOD-$d_4$) δ: 7.88 (s, 1H), 7.74 (dd, J=8.0, 1.2 Hz, 1H), 7.65-7.61 (m, 2H), 7.41 (t, J=8.0 Hz, 1H), 7.21 (d, J=8.0 Hz, 1H), 7.15 (d, J=8.8 Hz, 2H), 6.98 (s, 1H), 6.81 (t, J=74.4 Hz, 1H), 2.58 (s, 3H), 2.19 (m, 2H), 0.99 (t, J=7.6 Hz, 3H).

Synthesis of 5-[4-(difluoromethoxy)-3-phenyl-phenyl]-N-[3-(1,1-difluoropropyl)phenyl]-2-methyl-1H-pyrrole-3-carboxamide (217)

Compound ID 217

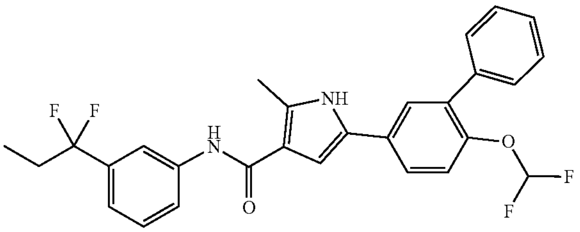

217 was obtained via similar procedure of 216 from 5-[4-(difluoromethoxy)-3-phenyl-phenyl]-2-methyl-1H-pyrrole-3-carboxylic acid and 3-(1,1-difluoropropyl)aniline LCMS: (ESI) m/z: 497.2 $[M+H]^+$.

$^1$H NMR: (400 MHz, MeOD-$d_4$) δ: 7.88 (s, 1H), 7.74 (d, J=9.2 Hz, 1H), 7.69 (d, J=2.4 Hz, 1H), 7.63 (dd, J=8.4, 2.4 Hz, 1H), 7.56~7.53 (m, 2H), 7.47~7.42 (m, 2H), 7.41~7.36 (m, 2H), 7.27 (d, J=8.4 Hz, 1H), 7.20 (dd, J=7.6, 0.8 Hz, 1H), 7.05 (s, 1H), 6.64 (t, J=74.4 Hz, 1H), 2.58 (s, 3H), 2.19 (m, 2H), 0.99 (t, J=7.6 Hz, 3H).

Synthesis of 2-(6-(difluoromethoxy)-[1,1'-biphenyl]-3-yl)-N-(3-(1,1-difluoropropyl)phenyl)-5-methyl-1H-imidazole-4-carboxamide (218)

Compound ID 218

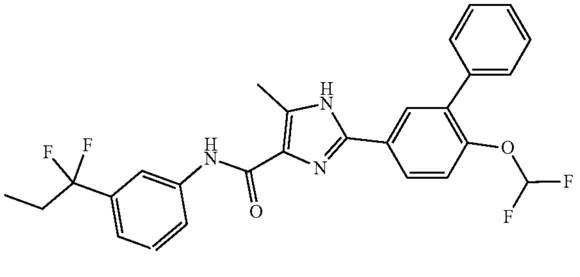

218 was obtained via similar procedure of 173 from 2-(6-(difluoromethoxy)-[1,1'-biphenyl]-3-yl)-5-methyl-1H-imidazole-4-carboxylic acid and 3-(1,1-difluoropropyl)aniline LCMS: (ESI) m/z: 498.2 $[M+H]^+$.

$^1$H NMR (400 MHz, MeOD-$d_4$) δ: 8.06 (d, J=2.4 Hz, 1H), 7.96 (dd, J=2.4, 8.4 Hz, 1H), 7.92 (s, 1H), 7.77 (d, J=8.0 Hz, 1H), 7.55-7.57 (m, 2H), 7.37-7.48 (m, 5H), 7.22 (d, J=8.0 Hz, 1H), 6.76 (t, J=74.0 Hz, 1H), 2.63 (s, 3H), 2.11-2.25 (m, 2H), 0.98 (t, J=7.6 Hz, 3H).

Synthesis of 1-(5-(4-chlorobenzyl)-6-methoxy-[1,1'-biphenyl]-3-yl)-N-(3-(1,1-difluoropropyl)phenyl)-3-methyl-5-oxo-4,5-dihydro-1H-pyrazole-4-carboxamide (236)

Compound ID 236

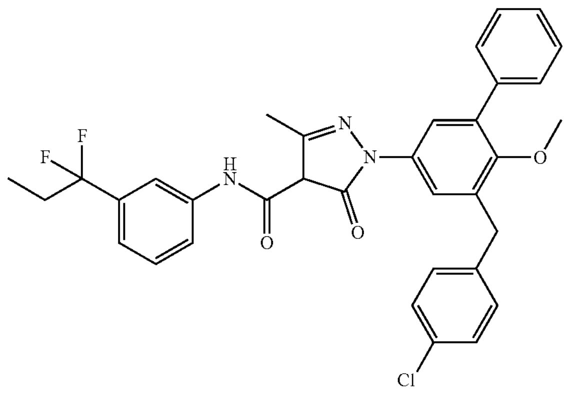

236 was obtained via general procedure IV

LCMS: (ESI) m/z: 602.3 $[M+H]^+$.

$^1$H NMR (400 MHz, MeOD-$d_4$) δ: 7.87 (s, 1H), 7.63 (d, J=7.2 Hz, 3H), 7.39-7.48 (m, 6H), 7.30 (s, 4H), 7.20 (d, J=7.6 Hz, 1H), 4.10 (s, 2H), 3.22 (s, 3H), 2.60 (s, 3H), 2.11-2.23 (m, 2H), 0.98 (t, J=7.2 Hz, 3H).

Synthesis of N-(3-(1,1-difluoroethyl)phenyl)-6-methyl-2-(5-methyl-[1,1'-biphenyl]-3-yl)pyrimidine-4-carboxamide (219)

Compound ID 219

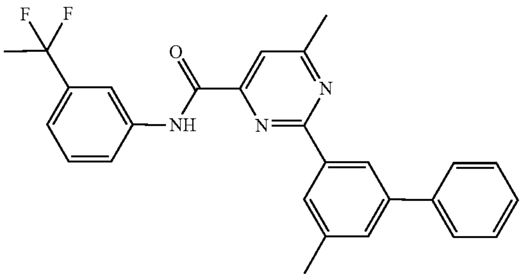

219 was obtained via similar procedure of 133 from 6-methyl-2-(5-methyl-[1,1'-biphenyl]-3-yl)pyrimidine-4-carboxylic acid and 3-(1,1-difluoroethyl)aniline.

LCMS: (ESI) m/z: 444.2 $[M+H]^+$.

$^1$H NMR (400 MHz, $CDCl_3$-d) δ: 10.09 (br s, 1H), 8.53 (s, 1H), 8.29 (s, 1H), 7.98 (s, 1H), 7.96 (s, 1H), 7.88 (d, J=8.0 Hz, 1H), 7.73 (d, J=7.6 Hz, 2H), 7.61 (s, 1H), 7.53-7.47 (m, 3H), 7.42 (d, J=7.6 Hz, 1H), 7.36 (d, J=8.4 Hz, 1H), 2.76 (s, 3H), 2.58 (s, 3H), 1.98 (t, J=18.4 Hz, 3H).

Synthesis of N-(3-(1,1-difluoroethyl)phenyl)-2-(4-(difluoromethoxy)-3-(pyridin-3-yl)phenyl)-5-methyloxazole-4-carboxamide (220)

Compound ID: 220

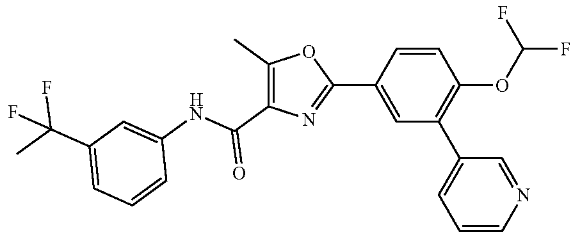

220 was obtained via similar procedure of 123 from 2-(4-(difluoromethoxy)-3-(pyridin-3-yl)phenyl)-5-methyloxazole-4-carboxylic acid and 3-(1,1-difluoroethyl)aniline.

LCMS: (ESI) m/z: 486.3 $[M+H]^+$.

$^1$H NMR (400 MHz, $CDCl_3$-d) δ: 8.92 (s, 1H), 8.84-8.79 (m, 1H), 8.71-8.66 (m, 1H), 8.14 (d, J=2.2 Hz, 1H), 8.10 (dd, J=2.2, 8.6 Hz, 1H), 7.92 (td, J=2.0, 7.8 Hz, 1H), 7.87 (s, 1H), 7.82 (br d, J=8.0 Hz, 1H), 7.46-7.40 (m, 3H), 7.29 (d, J=7.8 Hz, 1H), 6.71-6.33 (m, 1H), 2.81 (s, 3H), 1.96 (t, J=18.2 Hz, 3H).

Synthesis of 2-(4-(difluoromethoxy)-3-(pyridin-3-yl)phenyl)-N-(3-(1,1-difluoropropyl)phenyl)-5-methyloxazole-4-carboxamide (221)

Compound 221

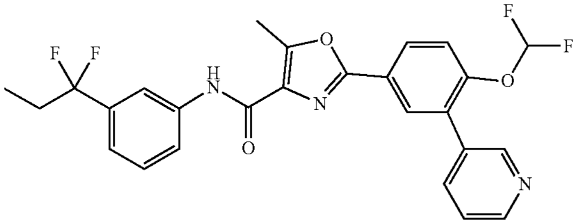

221 was obtained via similar procedure of 123 from 2-(4-(difluoromethoxy)-3-(pyridin-3-yl)phenyl)-5-methyloxazole-4-carboxylic acid and 3-(1,1-difluoropropyl)aniline.

LCMS: (ESI) m/z: 500.3 $[M+H]^+$.

$^1$H NMR (400 MHz, $CDCl_3$-d) δ: 8.91 (s, 1H), 8.87-8.77 (m, 1H), 8.74-8.64 (m, 1H), 8.15 (d, J=2.2 Hz, 1H), 8.10 (dd, J=2.2, 8.6 Hz, 1H), 7.92 (br d, J=8.0 Hz, 1H), 7.83 (br d, J=8.4 Hz, 1H), 7.81 (s, 1H), 7.46-7.40 (m, 3H), 7.24 (s, 1H), 6.71-6.34 (m, 1H), 2.81 (s, 3H), 2.19 (dt, J=7.6, 16.1 Hz, 2H), 1.02 (t, J=7.4 Hz, 3H).

Synthesis of 5-(5-(difluoromethoxy)pyridin-2-yl)-N-(3-(1,1-difluoropropyl)phenyl)-2-methyl-1H-pyrrole-3-carboxamide (222)

Compound ID 222

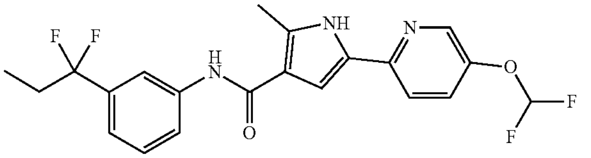

222 was obtained via similar procedure of 216 from 5-(5-(difluoromethoxy)pyridin-2-yl)-2-methyl-1H-pyrrole-3-carboxylic acid and 3-(1,1-difluoropropyl)aniline.

LCMS: (ESI) m/z: 421.9 $[M+H]^+$.

$^1$H NMR (400 MHz, $CDCl_3$-d) δ: 9.50 (br s, 1H), 8.36 (d, J=2.0 Hz, 1H), 7.76 (d, J=8.0 Hz, 1H), 7.68 (s, 1H), 7.57-7.53 (m, 2H), 7.51-7.47 (m, 1H), 7.41 (t, J=8.0 Hz, 1H), 7.22 (d, J=7.6 Hz, 1H), 6.84 (d, J=2.8 Hz, 1H), 6.56 (t, J=72.8 Hz, 1H), 2.68 (s, 3H), 2.25-2.10 (m, 2H), 1.01 (t, J=7.6 Hz, 3H).

Synthesis of 5-(5-(difluoromethoxy)-6-phenylpyridin-2-yl)-N-(3-(1,1-difluoropropyl)phenyl)-2-methyl-1H-pyrrole-3-carboxamide (223)

Compound ID 223

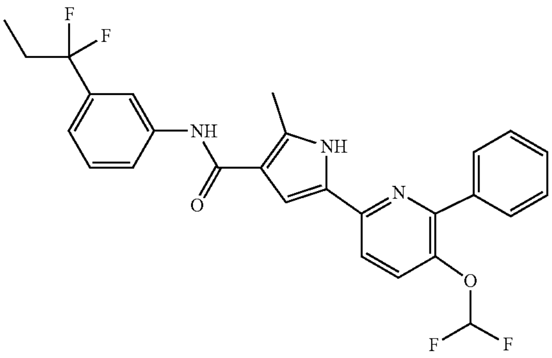

223 was obtained via similar procedure of 222 from 5-(5-(difluoromethoxy)-6-phenylpyridin-2-yl)-2-methyl-1H-pyrrole-3-carboxylic acid and 3-(1,1-difluoropropyl) aniline.

LCMS: (ESI) m/z: 498.1 $[M+H]^+$.

$^1$H NMR (400 MHz, MeOD-$d_4$) δ: 7.96-7.92 (m, 2H), 7.89 (s, 1H), 7.75 (d, J=8.4 Hz, 1H), 7.68 (d, J=0.8 Hz, 2H), 7.51~7.40 (m, 4H), 7.30 (s, 1H), 7.21 (d, J=7.6 Hz, 1H), 6.76 (t, J=73.6 Hz, 1H), 2.60 (s, 3H), 2.27~2.12 (m, 2H), 1.00 (t, J=7.4 Hz, 3H).

Synthesis of 1-(5-(4-chlorobenzyl)-6-methoxy-[1,1'-biphenyl]-3-yl)-N-(3-(1,1-difluoroethyl)phenyl)-3-methyl-5-oxo-4,5-dihydro-1H-pyrazole-4-carboxamide (224)

Compound ID 224

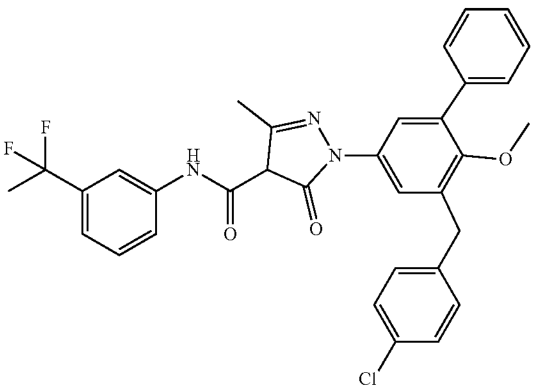

224 was obtained via general procedure IV

LCMS: (ESI) m/z: 588.2 $[M+H]^+$.

$^1$H NMR (400 MHz, MeOD-$d_4$) δ: 7.91 (s, 1H), 7.63 (d, J=7.2 Hz, 3H), 7.54 (d, J=16.4 Hz, 2H), 7.34-7.48 (m, 4H), 7.29 (s, 4H), 7.22 (d, J=8.0 Hz, 1H), 4.09 (s, 2H), 3.21 (s, 3H), 2.56 (s, 3H), 1.92 (t, J=18.4 Hz, 3H).

Synthesis of N-(3-(1,1-difluoropropyl)phenyl)-1-(6-methoxy-5-propyl-[1,1'-biphenyl]-3-yl)-3-methyl-5-oxo-4,5-dihydro-1H-pyrazole-4-carboxamide (225)

Compound ID 225

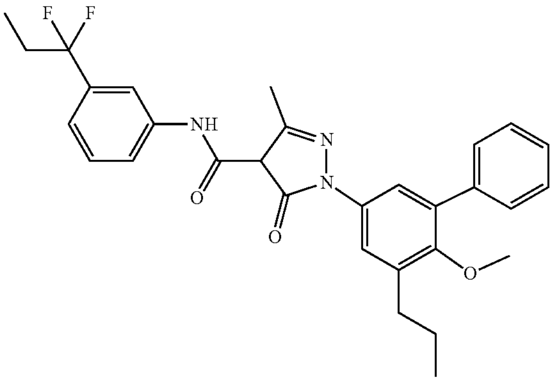

225 was obtained via general procedure IV

LCMS: (ESI) m/z: 520.3 $[M+H]^+$.

$^1$H NMR (400 MHz, MeOD-$d_4$) δ: 7.87 (s, 1H), 7.66-7.61 (m, 3H), 7.48-7.44 (m, 4H), 7.43-7.37 (m, 2H), 7.20 (d, J=8.0 Hz, 1H), 3.36 (s, 3H), 2.75 (t, J=8.0 Hz, 2H), 2.62 (s, 3H), 2.24-2.11 (m, 2H), 1.79-1.70 (m, 2H), 1.05 (t, J=7.6 Hz, 3H), 0.98 (t, J=7.6 Hz, 3H).

Synthesis of N-(3-(1,1-difluoropropyl)phenyl)-6-methyl-2-(5-methyl-[1,1'-biphenyl]-3-yl)pyrimidine-4-carboxamide (226)

Compound ID 226

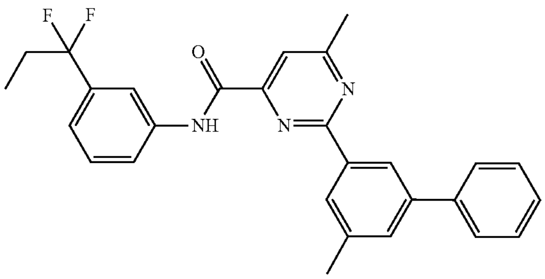

226 was obtained via similar procedure of 133 from 6-methyl-2-(5-methyl-[1,1'-biphenyl]-3-yl)pyrimidine-4-carboxylic acid and 3-(1,1-difluoropropyl)aniline.

LCMS: (ESI) m/z: 458.2 $[M+H]^+$.

$^1$H NMR (400 MHz, $CDCl_3$-d) &: 10.08 (s, 1H), 8.53 (s, 1H), 8.29 (s, 1H), 7.98 (s, 1H), 7.89 (d, J=10.0 Hz, 2H), 7.73 (d, J=7.6 Hz, 2H), 7.61 (s, 1H), 7.53-7.47 (m, 3H), 7.42 (d, J=7.6 Hz, 1H), 7.32 (d, J=8.0 Hz, 1H), 2.76 (s, 3H), 2.58 (s, 3H), 2.27-2.14 (m, 2H), 1.04 (t, J=7.6 Hz, 3H).

Synthesis of 2-(5-(difluoromethoxy)pyridin-2-yl)-N-(3-(1,1-difluoropropyl)phenyl)-5-methyl-1H-imidazole-4-carboxamide (227)

Compound ID 227

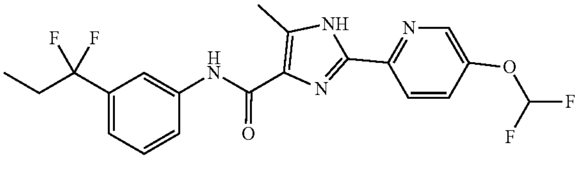

To a 10 mL round-bottom flask equipped with a magnetic stir bar was added 2-(5-(difluoromethoxy)pyridin-2-yl)-5-methyl-1H-imidazole-4-carboxylic acid (50.0 mg, 158 umol, 1.0 eq), 3-(1,1-difluoropropyl)aniline (53.9 mg, 315 umol, 2.0 eq) followed by the addition of N,N-dimethylformamide (4 mL). Then 1H-benzo[d][1,2,3]triazol-1-ol (180 mg, 473 umol, 3.0 eq), N,N-diisopropylethylamine (102 mg, 788 umol, 5.0 eq), N,N-dimethylpyridin-4-amine (38.5 mg, 315 umol, 2.0 eq) was added into the mixture. The mixture was stirred at 25° C. for 12 hr. The mixture was filtered, the filtrate was used for purification directly. The solution was purified by prep-HPLC (column: Phenomenex Synergi C18 150*25*10 um; mobile phase: [water (0.225% formic acid)-acetonitrile]; B %: 48%-78%, min) to give 29.8 mg (45% yield) of 227 as a yellow solid.

LCMS: (ESI) m/z: 423.1 $[M+H]^+$.

$^1$H NMR (MeOD-$d_4$, 400 MHz) δ: 8.49 (s, 1H), 8.18 (dd, J=8.4, 1.2 Hz, 1H), 7.95 (s, 1H), 7.79 (d, J=8.0 Hz, 1H), 7.71 (d, J=8.8 Hz, 1H), 7.44 (t, J=7.6 Hz, 1H), 7.23 (d, J=7.6 Hz, 1H), 6.98 (t, J=72.8 Hz, 1H), 2.64 (s, 3H), 2.12-2.30 (m, 2H), 0.99 (t, J=7.2 Hz, 3H).

Synthesis of N-(3-(1,1-difluoroethyl)phenyl)-2-(4-(difluoromethoxy)-3-(pyridin-2-yl)phenyl)-5-methyloxazole-4-carboxamide (258)

Compound ID 258

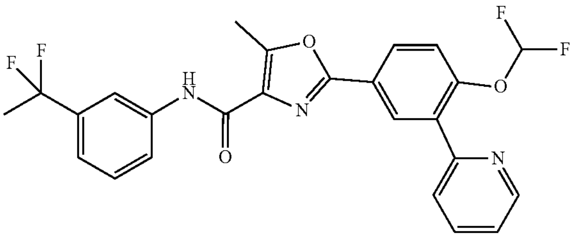

258 was obtained via similar procedure of 220

LCMS: (ESI) m/z: 486.0 $[M+H]^+$.

$^1$H NMR (400 MHz, MeOD-$d_4$) δ: 8.71-8.70 (m, 1H), 8.44 (d, J=2.0 Hz, 1H), 8.20 (dd, J=2.4, 8.8 Hz, 1H), 7.99 (s, 1H), 7.96 (td, J=1.6, 7.6 Hz, 1H), 7.83-7.80 (m, 2H), 7.49-7.43 (m, 3H), 7.31 (dd, J=0.8, 7.6 Hz 1H), 6.97 (t, J=73.2 Hz, 3H), 2.76 (s, 3H), 1.94 (t, J=18.0 Hz, 3H).

Synthesis of 2-(4-(difluoromethoxy)-3-(pyridin-2-yl)phenyl)-N-(3-(1,1-difluoropropyl)phenyl)-5-methyloxazole-4-carboxamide (259)

Compound ID 259

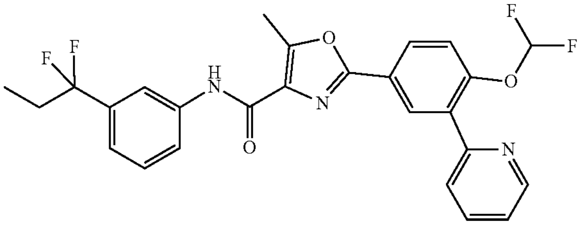

259 was obtained via similar procedure of 258

LCMS: (ESI) m/z: 500.2 $[M+H]^+$.

$^1$H NMR (400 MHz, MeOD-$d_4$) δ: 8.71-8.70 (m, 1H), 8.45 (d, J=2.4 Hz, 1H), 8.20 (dd, J=2.4, 8.8 Hz, 1H), 7.96-7.95 (m, 2H), 7.83-7.81 (m, 2H), 7.50-7.45 (m, 3H), 7.27 (d, J=6.8 Hz, 1H), 6.97 (t, J=73.2 Hz, 1H), 2.79 (s, 3H), 2.27-2.13 (m, 2H), 0.99 (t, J=7.6 Hz, 3H).

Synthesis of 2-(5-(difluoromethoxy)-6-phenylpyridin-2-yl)-N-(3-(1,1-difluoropropyl)phenyl)-5-methyl-1H-imidazole-4-carboxamide (260)

Compound ID 260

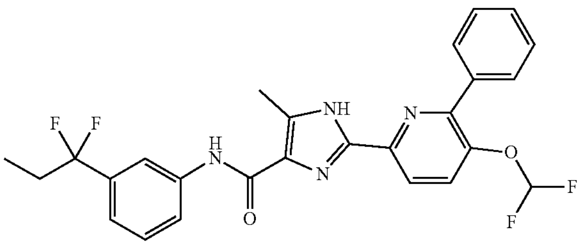

260 was obtained via similar procedure of 227.

LCMS: (ESI) m/z: 499.1 [M+H]$^+$.

$^1$H NMR (400 MHz, MeOD-$d_4$) δ: 8.18 (d, J=8.8 Hz, 1H), 7.99-7.95 (m, 3H), 7.85-7.78 (m, 2H), 7.52-7.42 (m, 4H), 7.24 (d, J=8.0 Hz, 1H), 6.89 (t, J=72.8 Hz, 1H), 2.65 (s, 3H), 2.28-2.14 (m, 2H), 1.00 (t, J=7.6 Hz, 3H).

Synthesis of N-(3-(1,1-difluoroethyl)phenyl)-1-(5-(4-hydroxybenzyl)-6-methoxy-[1,1'-biphenyl]-3-yl)-3-methyl-5-oxo-4,5-dihydro-1H-pyrazole-4-carboxamide (228)

Compound ID: 228

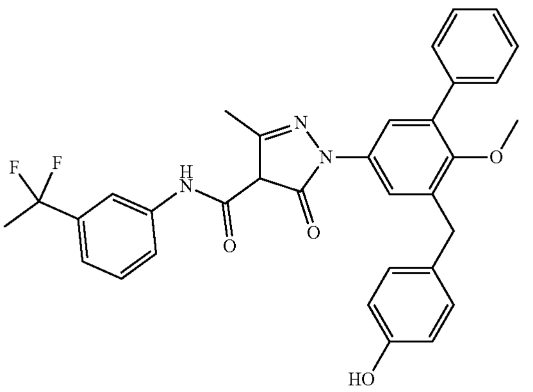

To a solution of 1-(5-(4-(benzyloxy)benzyl)-6-methoxy-[1,1'-biphenyl]-3-yl)-N-(3-(1,1-difluoroethyl)phenyl)-3-methyl-5-oxo-4,5-dihydro-1H-pyrazole-4-carboxamide (30.0 mg, 43.7 umol, 1.0 eq) in methanol (2 mL) was added Pd/C (10.0 mg, 10% purity). The suspension was degassed under vacuum and purged with hydrogen several times. The mixture was stirred under hydrogen (15 psi) at 25° C. for 0.5 h. The suspension was filtered and the filtrate was concentrated to give a residue. The residue was purified by prep-HPLC (column: Phenomenex luna C18 150*25 mm*10 um; mobile phase: [water (0.1% trifluoroacetic acid)-acetonitrile]; B %: 54%-84%, 10 min) to give 12.9 mg (51% yield) of 228 as a yellow solid.

LCMS: (ESI) m/z: 570.3 [M+H]$^+$.

$^1$H NMR (400 Hz, MeOD-$d_4$) δ: 7.90 (s, 1H), 7.61 (d, J=6.8 Hz, 3H), 7.46-7.36 (m, 6H), 7.36-7.10 (m, 1H), 7.09 (d, J=8.4 Hz, 2H), 6.71 (d, J=8.4 Hz, 2H), 3.99 (s, 2H), 3.20 (s, 3H), 2.57 (s, 3H), 1.91 (t, J=16.4 Hz, 3H).

Synthesis of 5-acetyl-N-(3-(1,1-difluoropropyl)phenyl)-1-(4-methoxyphenyl)-3-methyl-1H-pyrazole-4-carboxamide Compound ID: 230

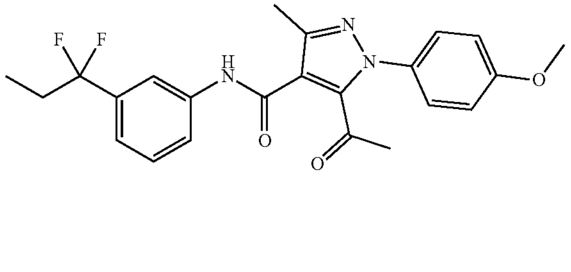

230 was obtained via similar procedure of 193 from 5-acetyl-1-(4-methoxyphenyl)-3-methyl-1H-pyrazole-4-carboxylic acid and 3-(1,1-difluoropropyl)aniline.

LCMS: (ESI) m/z: 428.1 [M+H]$^+$.

$^1$H NMR (400 MHz, $CDCl_3$-d) δ: 9.94 (s, 1H), 7.83 (s, 1H), 7.79 (d, J=8.4 Hz, 1H), 7.41 (t, J=8.0 Hz, 1H), 7.36 (d, J=8.8 Hz, 2H), 7.23 (d, J=8.0 Hz, 1H), 7.04 (d, J=8.8 Hz, 2H), 3.89 (s, 3H), 2.64 (s, 3H), 2.26-2.16 (m, 2H), 2.15 (s, 3H), 1.02 (t, J=7.6 Hz, 3H).

Synthesis of 5-chloro-N-(3-(1,1-difluoropropyl)phenyl)-1-(4-methoxyphenyl)-3-methyl-1H-pyrazole-4-carboxamide (231)

Compound ID: 231

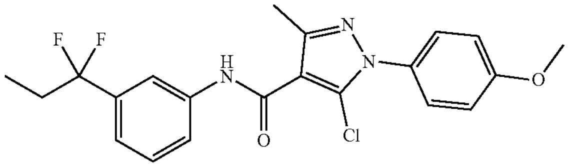

231 was obtained via similar procedure of 222 from 5-chloro-1-(4-methoxyphenyl)-3-methyl-1H-pyrazole-4-carboxylic acid and 3-(1,1-difluoropropyl)aniline.

LCMS: (ESI) m/z: 419.9 [M+H]$^+$.

$^1$H NMR (MeOD-$d_4$, 400 MHz) δ: 7.85 (s, 1H), 7.73 (d, J=8.4 Hz, 1H), 7.43-7.45 (m, 3H), 7.27 (d, J=8.0 Hz, 1H), 7.08-7.09 (m, 2H), 3.88 (s, 3H), 2.45 (s, 3H), 2.19 (m, 2H), 0.99 (t, J=7.6 Hz, 3H).

Synthesis of 4-acetyl-N-(3-(1,1-difluoropropyl)phenyl)-5-(4-methoxyphenyl)-1H-pyrazole-3-carboxamide (232)

Compound ID: 232

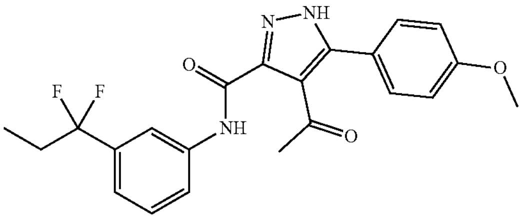

To a solution of 4-acetyl-5-(4-methoxyphenyl)-1H-pyrazole-3-carboxylic acid (45.0 mg, 173 umol, 1.0 eq), 3-(1,1-difluoropropyl)aniline (59.2 mg, 346 umol, 2.0 eq) in pyridine (3 mL) was added N-[3-(dimethylamino)propyl]-N-ethylcarbodiimide hydrochloride (99.4 mg, 519 umol, 3.0 eq), the mixture was stirred at 25° C. for 12 hr. The reaction was concentrated to give a residue. The residue was purified by preparative HPLC column: Shim-pack C18 150*25*10 um; mobile phase: [water (0.225% formic acid)-acetonitrile]; B %: 50%-80%, 10 min to give 41.0 mg (41% yield) of 232 as a yellow solid.

LCMS: (ESI) m/z: 414.2 [M+H]$^+$.

$^1$H NMR (400 MHz, MeOD-$d_4$) δ: 7.95 (s, 1H), 7.79-7.81 (d, J=8.0 Hz, 1H), 7.44-7.49 (m, 3H), 7.26-7.28 (d, J=8.0 Hz, 1H), 7.06-7.08 (d, J=8.0 Hz, 2H), 3.86 (s, 3H), 2.31 (s, 3H), 2.09-2.22 (m, 2H), 0.97-1.00 (t, J=7.6 Hz, 3H).

Synthesis of 4-bromo-N-(4-(1,1-difluoropropyl)phenyl)-5-(4-methoxyphenyl)-1H-pyrazole-3-carboxamide (233)

Compound ID: 233

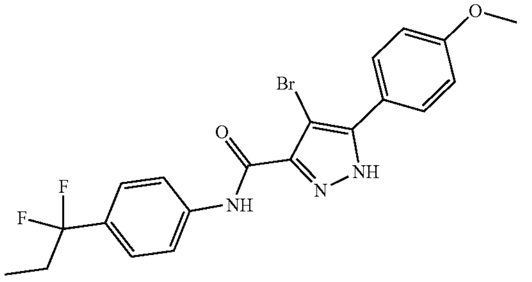

233 was obtained via similar procedure of 258 from 4-bromo-5-(4-methoxyphenyl)-1H-pyrazole-3-carboxylic acid and 3-(1,1-difluoropropyl)aniline.

LCMS: (ESI) m/z: 450.1 $[M+H]^+$.

$^1H$ NMR (400 MHz, MeOD-$d_4$) δ: 7.95 (s, 1H), 7.78 (d, J=8.2 Hz, 1H), 7.69 (d, J=8.8 Hz, 2H), 7.45 (t, J=8.0 Hz, 1H), 7.26 (d, J=8.0 Hz, 1H), 7.08 (d, J=8.8 Hz, 2H), 3.87 (s, 3H), 2.15-2.25 (m, 2H), 1.00 (t, J=7.6 Hz, 3H).

Synthesis of methyl 4-((3-(1,1-difluoropropyl)phenyl)carbamoyl)-1-(4-methoxyphenyl)-3-methyl-1H-pyrazole-5-carboxylate (234)

Compound ID: 234

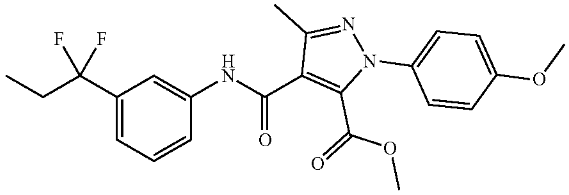

To a solution of 4-((3-(1,1-difluoropropyl)phenyl)carbamoyl)-1-(4-methoxyphenyl)-3-methyl-1H-pyrazole-5-carboxylic acid (65.0 mg, 151 umol, 1.0 eq) and potassium carbonate (41.8 mg, 303 umol, 2.0 eq) in N,N-dimethylformamide (4 mL) was added iodomethane (215 mg, 1.51 mmol, 10 eq), the reaction mixture was stirred at 25° C. for 30 min. The reaction mixture was washed with saturated sodium bicarbonate (20 mL), the aqueous layer was extracted with ethyl acetate (10 mL×3). The combined organic layer was washed with brine (15 mL), dried over anhydrous sodium sulfate, filtered, and concentrated under reduced pressure. The crude product was purified by preparative HPLC: (Phenomenex Gemini C18 column: Phenomenex Gemini-NX C18 75*30 mm*3 um; mobile phase: [water (0.225% formic acid)-acetonitrile]; B %: 45%-75%, 7 min) to give 38.1 mg (57% yield) of 234 as a white solid.

LCMS: (ESI) m/z: 444.2 $[M+H]^+$.

$^1H$ NMR (400 MHz, DMSO-d) δ: 10.48 (s, 1H), 7.91 (s, 1H), 7.73 (d, J=8.4 Hz, 1H), 7.46 (t, J=8.0 Hz, 1H), 7.36 (d, J=8.8 Hz, 2H), 7.23 (d, J=7.6 Hz, 1H), 7.04 (d, J=9.2 Hz, 2H), 3.83 (s, 3H), 3.64 (s, 3H), 2.33 (s, 3H), 2.14-2.25 (m, 2H), 0.93 (t, J=7.2 Hz, 3H).

Synthesis of N-(3-(1,1-difluoropropyl)phenyl)-4-hydroxy-5-(4-methoxyphenyl)-2-methyl-1H-pyrrole-3-carboxamide (235)

Compound ID: 235

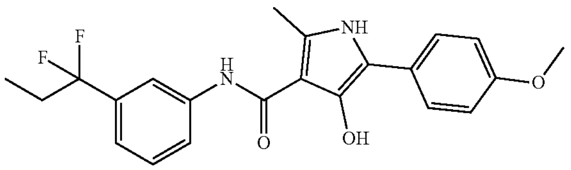

To a solution of 4-hydroxy-5-(4-methoxyphenyl)-2-methyl-1H-pyrrole-3-carboxylic acid (70.0 mg, 283 umol, 1.0 eq) in N,N-dimethylformamide (1 mL) was added 2-(3H-[1,2,3]triazolo[4,5-b]pyridin-3-yl)-1,1,3,3-tetramethylisouronium hexafluorophosphate(V) (161 mg, 425 umol, 1.5 eq), N,N-diisopropylethylamine (110 mg, 849 umol, 3.0 eq), 3-(1,1-difluoropropyl)aniline (58.2 mg, 340 umol, 1.2 eq) at 25° C., and stirred for 12 h. The reaction mixture was quenched with water (10 mL), extracted with ethyl acetate (30 mL). The organic layer was washed with brine (10 mL), dried over sodium sulfate, filtered and the filtrate was concentrated under reduced pressure to give a residue. The residue was purified by prep-TLC (petroleum ether/ethyl acetate=1/1) to give a crude product. The crude product was triturated with methanol (1 mL), filtered and dried over under reduced pressure to give 2.00 mg (2% yield) of 235 as white solid.

LCMS: (ESI) m/z: 401.1 $[M+H]^+$.

$^1H$ NMR (400 MHz, DMSO-d) δ: 10.96-10.82 (br s, 1H), 10.19 (s, 1H), 7.78 (s, 1H), 7.73-7.71 (m, 2H), 7.58-7.43 (m, 1H), 7.43-7.35 (m, 1H), 7.14 (d, J=7.2 Hz, 1H), 6.88 (d, J=8.8 Hz, 2H), 3.70 (s, 3H), 2.52 (s, 3H), 2.22-2.13 (m, 2H), 0.89 (t, J=7.2 Hz, 3H).

Synthesis of 248

Scheme 1

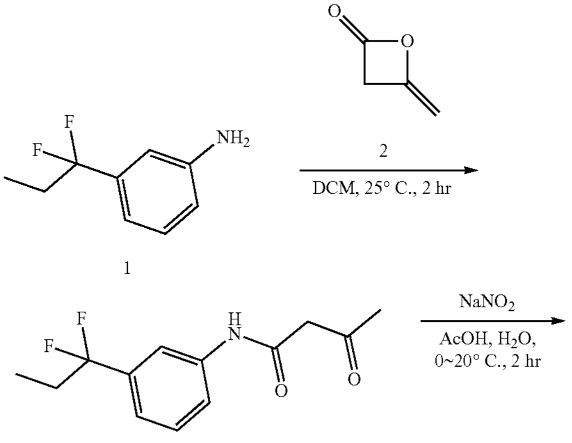

1

3

-continued

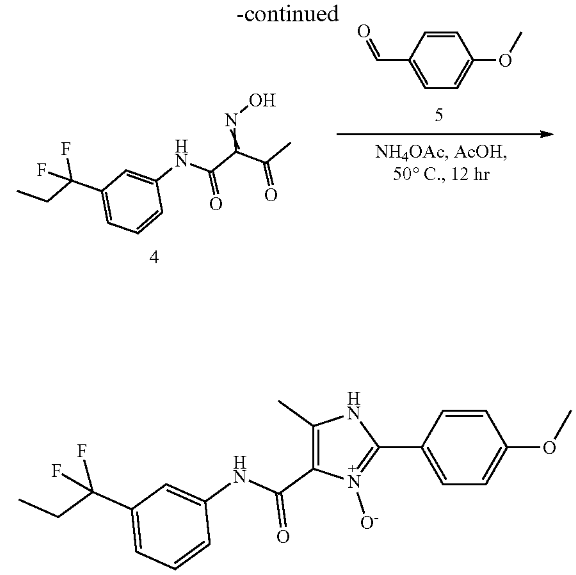

Synthesis of N-(3-(1,1-difluoropropyl)phenyl)-3-oxobutanamide (248-A)

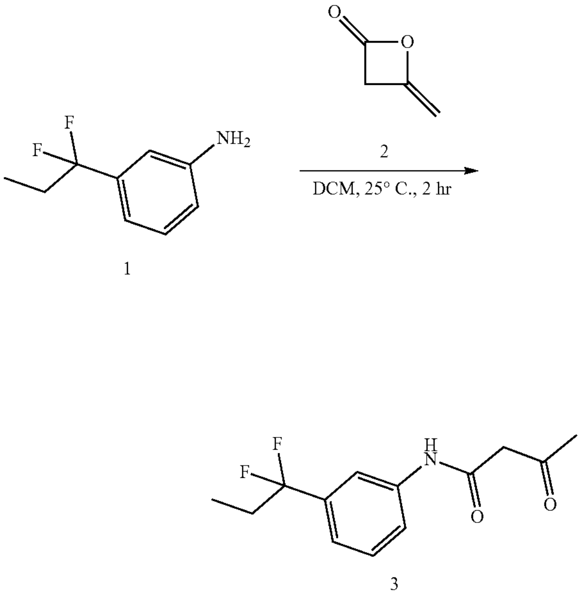

To a solution of 3-(1,1-difluoropropyl)aniline (1.00 g, 5.84 mmol, 1.0 eq) in dichloromethane (10 mL) was added 4-methyleneoxetan-2-one (589 mg, 7.01 mmol, 1.2 eq). The mixture was stirred at 25° C. for 2 h. The reaction mixture was concentrated under reduced pressure. The residue was purified by silica gel column chromatography (petroleum ether/ethyl acetate, from 10/1 to 1/1) to give 350 mg, (22% yield) of 248-A as a yellow gum.

LCMS: (ESI) m/z: 256.1 $[M+H]^+$.

$^1$H NMR (400 MHz, $CDCl_3$-d) δ: 9.30 (s, 1H), 7.71-7.54 (m, 2H), 7.36 (t, J=7.8 Hz, 1H), 7.21 (d, J=7.8 Hz, 1H), 3.59 (s, 2H), 2.31 (s, 3H), 2.19-2.07 (m, 2H), 0.97 (t, J=7.2 Hz, 3H).

Synthesis of N-(3-(1,1-difluoropropyl)phenyl)-2-(hydroxyimino)-3-oxobutanamide (248-B)

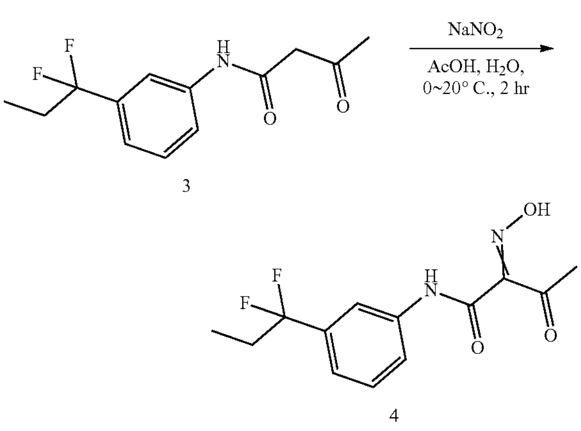

To a solution of 248-A (100 mg, 392 umol, 1.0 eq) in acetic acid (3 mL) was added solution of sodium nitrite (54.1 mg, 784 umol, 2.0 eq) in water (2 mL) at 0° C. It was stirred at 20° C. for 2 hr. The reaction was diluted with water (30 mL) and then extracted with ethyl acetate (30 mL). The organic layer was washed with water (30 mL) and brine (30 mL). The organic layer was dried over anhydrous sodium sulfate, filtered and concentrated to give 110 mg (crude) of 248-B as yellow oil.

LCMS: (ESI) m/z: 285.2 $[M+H]^+$.

Synthesis of 4-((3-(1,1-difluoropropyl)phenyl)carbamoyl)-2-(4-methoxyphenyl)-5-methyl-1H-imidazole 3-oxide (248)

Compound ID: 248

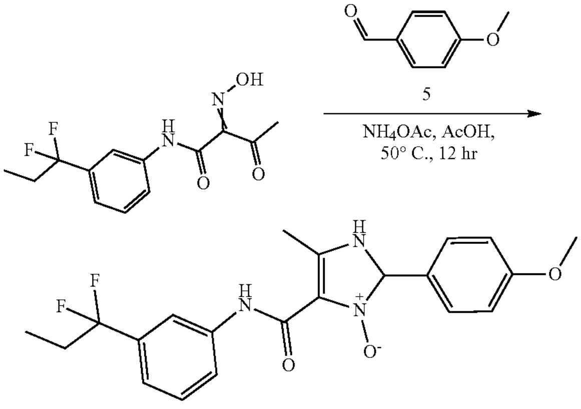

To a solution of 248-B (60.0 mg, 211 umol, 1.0 eq) in acetic acid (2 mL) was added 4-methoxybenzaldehyde (28.7 mg, 211 umol, 1.0 eq) and ammonium acetate (65.1 mg, 844 umol, 4.0 eq). It was stirred at 50° C. for 12 hr. The mixture was concentrated under reduced pressure to give a residue. The residue was purified by prep-HPLC (column: Phenomenex luna C18 150*25 mm*10 um; mobile phase: [water (0.225% formic acid)-acetonitrile]; B %: 42%-72%, 10 min) to give 106 mg (82% yield) of 248 as a yellow solid.

LCMS: (ESI) m/z: 402.1 $[M+H]^+$.

$^1H$ NMR (400 MHz, DMSO-d) δ: 13.77 (s, 1H), 13.21 (s, 1H), 8.39 (d, J=8.4 Hz, 2H), 7.93 (s, 1H), 7.69 (d, J=8.0 Hz, 1H), 7.47 (t, J=7.6 Hz, 1H), 7.22 (d, J=7.6 Hz, 1H), 7.13 (d, J=8.8 Hz, 2H), 3.84 (s, 3H), 2.60 (s, 3H), 2.27-2.17 (m, 2H), 0.93 (t, J=7.2 Hz, 3H).

Synthesis of 249

Scheme 2

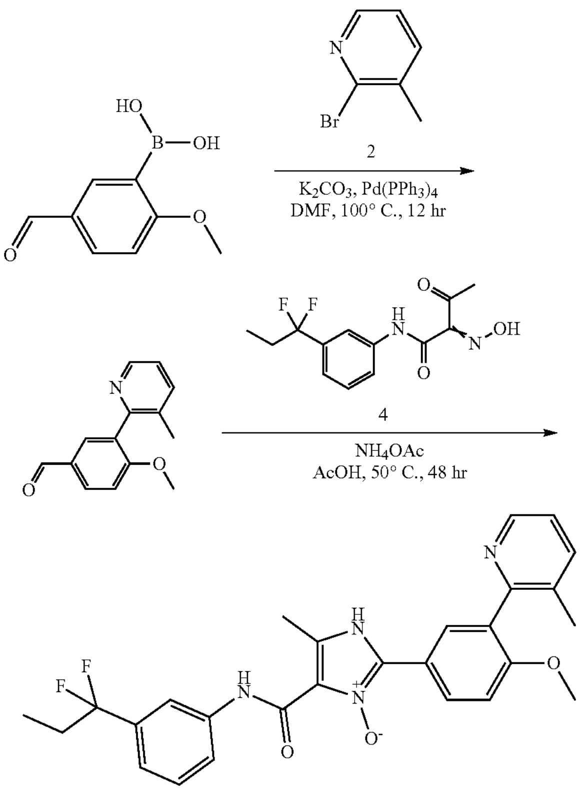

Synthesis of 4-methoxy-3-(3-methylpyridin-2-yl) benzaldehyde (249-A)

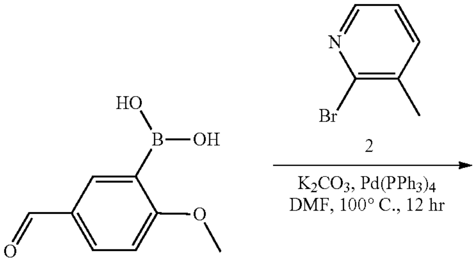

1

-continued

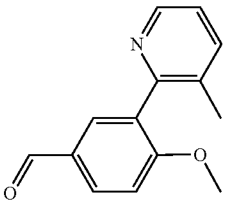

3

To a mixture of 2-bromo-3-methyl-pyridine (500 mg, 2.91 mmol, 1.0 eq) and (5-formyl-2-methoxy-phenyl)boronic acid (628 mg, 3.49 mmol, 1.2 eq) in N,N-dimethylformamide (20 mL) degassed and purged with nitrogen for 3 times, then added potassium carbonate (803 mg, 5.81 mmol, 2.0 eq) and tetrakis(triphenylphosphine)platinum (168 mg, 145 umol, 0.050 eq), the mixture was stirred at 100° C. for 12 hr under nitrogen atmosphere. The reaction mixture was filtered and concentrated under reduced pressure to give a residue. The residue was purified by column chromatography on silica gel (petroleum ether/ethyl acetate, from 1/0 to 2/3) to give 560 mg (85% yield) of 249-A as a colorless oil.

$^1H$ NMR (400 MHz, $CDCl_3$-d) δ: 9.94 (s, 1H), 8.53 (dd, J=1.2, 4.8 Hz, 1H), 7.97 (dd, J=2.0, 8.4 Hz, 1H), 7.83 (d, J=2.4 Hz, 1H), 7.59 (dd, J=0.8, 8.0 Hz, 1H), 7.24 (dd, J=4.8, 7.6 Hz, 1H), 7.11 (d, J=8.4 Hz, 1H), 3.88 (s, 3H), 2.16 (s, 3H).

Synthesis of 4-((3-(1,1-difluoropropyl)phenyl)carbamoyl)-2-(4-methoxy-3-(3-methylpyridin-2-yl) phenyl)-5-methyl-1H-imidazole 3-oxide (249)

Compound ID: 249

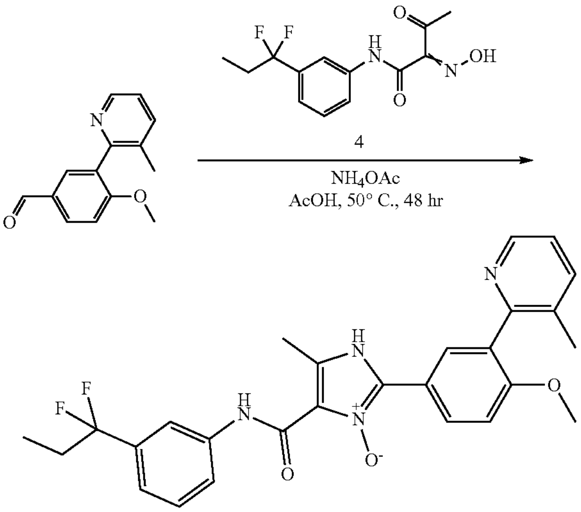

To a mixture of 249-A (40.0 mg, 176 umol, 1.0 eq) and 248-B (50.0 mg, 176 umol, 1.0 eq) in acetic acid (5 mL) was added ammonium acetate (54.2 mg, 704 umol, 4.0 eq), then the mixture was stirred at 50° C. for 48 hr. The reaction mixture was concentrated under reduced pressure to give a residue. The residue was purified by prep-HPLC (column: Boston Green ODS 150*30 mm*5 um; mobile phase: [water (0.225% formic acid)-acetonitrile]; B %: 30%-60%, 7 min) to give 19.8 mg (23% yield) of 249 as a white solid.

LCMS: (ESI) m/z: 493.0 $[M+H]^+$.

$^1$H NMR (400 MHz, DMSO-$d_6$) δ: 12.88 (s, 1H), 12.45 (s, 1H),7.74 (d, J=7.2 Hz, 1H), 7.65 (dd, J=0.08, 4.8 Hz, 1H), 7.50 (s, 1H), 7.10 (s, 1H), 6.88 (d, J=8.4 Hz, 2H), 6.63 (t, J=8.0 Hz, 1H), 6.57-6.49 (m, 2H), 6.39 (d, J=7.8 Hz, 1H), 3.01 (s, 3H), 1.76 (s, 3H), 1.45-1.34 (i, 2H), 1.29 (s, 3H), 0.10 (t, J=7.2 Hz, 3H).

Analytical Data Summary for Compounds of the Invention

| Compound Number | IUPAC Compound name, Mass Spectra and H-NMR data |
|---|---|
| 100 | N-(3-(1,1-difluoroethyl)phenyl)-1-(6-(difluoromethoxy)-[1,1'-biphenyl]-3-yl)-4-ethyl-3-methyl-5-oxo-4,5-dihydro-1H-pyrazole-4-carboxamide<br>LCMS: (ESI) m/z: 528.3 [M + H] +;<br>1H NMR: (400 MHz, MeOD-d4) δ: 8.02 (d, J = 2.8 Hz, 1H), 7.96 (dd, J = 2.8, 8.8 Hz, 1H), 7.78 (s, 1H), 7.62 (d, J = 7.6 Hz, 1H), 7.53 − 7.48 (m, 2H), 7.46 − 7.37 (m, 4H), 7.35 − 7.29 (m, 2H), 6.65 (t, J = 74.0 Hz, 1H), 2.41 − 2.35 (m, 1H), 2.33 (s, 3H), 2.32 − 2.28 (m, 1H), 1.89 (t, J = 18.4 Hz, 3H), 0.87 (t, J = 7.6 Hz, 3H). |
| 101 | N-(3-(cyclobutyldifluoromethyl)phenyl)-1-(4-(difluoromethoxy)phenyl)-3-methyl-5-oxo-4,5-dihydro-1H-pyrazole-4-carboxamide<br>LCMS: (ESI) m/z: 464.2 [M + H] +;<br>1H NMR (400 MHz, MeOD-d4) δ: 7.82 (br s, 3H), 7.63 (br d, J = 8.0 Hz, 1H), 7.35 (br s, 1H), 7.26 − 7.07 (m, 3H), 6.80 (t, J = 74.4 Hz, 1H), 3.28 − 2.99 (m, 1H), 2.45 (br s, 3H), 2.31 − 2.10 (m, 2H), 2.05 − 1.88 (m, 3H), 1.88 − 1.78 (m, 1H). |
| 102 | 2-[4-(difluoromethoxy)phenyl]-N-[3-(1,1-difluoropropyl)phenyl]-6-methyl-pyridine-4-carboxamide<br>LCMS: (ESI) m/z: 433.3 [M + H] +;<br>1H NMR (400 MHz, MeOD) δ: 8.14 − 8.11 (m, 2H), 8.10 − 8.09 (m, 1H), 7.95 − 7.91 (m, 1H), 7.85 (d, J = 8.4 Hz, 1H), 7.68 (d, J = 0.8 Hz, 1H), 7.48 (t, J = 8.0 Hz, 1H), 7.30 (s, 1H), 7.28 (d, J = 8.8 Hz, 2H), 2.69 (s, 3H), 2.27 − 2.12 (m, 2H), 0.99 (t, J = 7.6 Hz, 3H). |
| 103 | 5-(6-(difluoromethoxy)-[1,1'-biphenyl]-3-yl)-N-(3-(1,1-difluoropropyl)phenyl)-3,6-dimethylpyrazine-2-carboxamide<br>LCMS: (ESI) m/z: 524.2 [M + H] +;<br>1H NMR: (400 MHz, DMSO-d6) δ: 10.78(s, 1H), 8.06(s, 1H), 7.96(d, J = 8.4 Hz, 1H), 7.82(dd, J = 8.4 Hz, J = 2.4 Hz, 1H), 7.78(d, J = 2.0 Hz, 1H), 7.56 − 7.48(m, 6H), 7.46 − 7.41(m, 1H), 7.31(t, J = 38.0 Hz, 1H), 2.79(s, 3H), 2.73(s, 3H), 2.27 − 2.15(m, 2H), 0.94(t, J = 7.2 Hz, 3H). |
| 104 | N-(3-(1,1-difluoroethyl)phenyl)-5-(6-(difluoromethoxy)-[1,1'-biphenyl]-3-yl)-3,6-dimethylpyrazine-2-carboxamide<br>LCMS: (ESI) m/z: 510.2 [M + H] +;<br>1H NMR: (400 MHz, DMSO-d6) δ: 10.79(s, 1H), 8.11(s, 1H), 7.96(d, J = 8.0 Hz, 1H), 7.82(dd, J = 8.4 Hz, J = 2.4 Hz, 1H), 7.78(d, J = 2.0 Hz, 1H), 7.56 − 7.48(m, 6H), 7.45 − 7.41(m, 1H), 7.32(d, J = 8.0 Hz, 1H), 7.31(t, J = 73.6 Hz, 1H), 2.79(s, 3H), 2.73(s, 3H), 1.99(t, J = 18.8 Hz, 3H). |
| 105 | 5-(4-(difluoromethoxy)phenyl)-N-(3-(1,1-difluoropropyl)phenyl)-3,6-dimethylpyrazine-2-carboxamide<br>LCMS: (ESI) m/z: 448.1 [M + H] +;<br>1H NMR: (400 MHz, DMSO-d6) δ: 10.78(s, 1H), 8.06(s, 1H), 7.96(d, J = 8.4 Hz, 1H), 7.80(d, J = 8.4 Hz, 1H), 7.51(t, J = 8.0 Hz, 1H), 7.38(t, J = 74.0 Hz, 1H), 7.34(d, J = 8.8 Hz, 2H), 7.27(d, J = 8.0 Hz, 1H), 2.78(s, 3H), 2.67(s, 3H), 2.29 − 2.15(m, 2H), 0.94(t, J = 7.2 Hz, 3H). |
| 106 | N-[3-(1,1-difluoroethyl)phenyl]-2-[4-(difluoromethoxy)-3-phenyl-phenyl]-5-methyl-oxazole-4-carboxamide<br>LCMS: (ESI) m/z: 396.2 [M + H] +;<br>1H NMR (400 MHz, DMSO-d6) δ: 8.11 (d, J = 5.8 Hz, 2H), 7.98 (d, J = 8.4 Hz, 1H), 7.78 − 7.74 (m, 1H), 7.73 − 7.69 (m, 1H), 7.56 (t, J = 2.8 Hz, 1H), 7.47 (t, J = 8.0 Hz, 1H), 7.24 (d, J = 8.0 Hz, 1H), 6.54 (t, J = 1.8 Hz, 1H), 2.73 (s, 3H), 2.29 − 2.15 (m, 2H), 0.94 (t, J = 7.4 Hz, 3H). |
| 107 | N-(3-(1,1-difluoroethyl)phenyl)-2-(1H-indol-6-yl)-5-methyloxazole-4-carboxamide<br>LCMS: (ESI) m/z: 382.2 [M + H] +;<br>1H NMR: (400 MHz, DMSO-d6) δ: 11.48 (br s, 1H), 10.14 (s, 1H), 8.14 (d, J = 13.2 Hz, 2H), 7.98 (d, J = 8.0 Hz, 1H), 7.78 − 7.74 (m, 1H), 7.73 − 7.69 (m, 1H), 7.56 (t, J = 2.8 Hz, 1H), 7.47 (t, J = 8.0 Hz, 1H), 7.29 (d, J = 7.8 Hz, 1H), 6.54 (t, J = 2.0 Hz, 1H), 2.73 (s, 3H), 1.98 (t, J = 18.8 Hz, 3H). |
| 108 | 1-benzyl-N-[3-(1,1-difluoroethyl)phenyl]-2-(1H-indol-6-yl)-5-methyl-3-oxo-pyrazole-4-carboxamide<br>LCMS: (ESI) m/z: 487.3[M + H] +;<br>1H NMR: (400 MHz, DMSO-d6) δ: 11.37 (br s, 1H), 11.00 (s, 1H), 7.92 (s, 1H), 7.64 (d, J = 8.4 Hz, 1H), 7.58 (d, J = 6.8 Hz, 1H), 7.50 (t, J = 2.8 Hz, 1H), 7.43 (t, J = 8.0 Hz, 1H), 7.33 − 7.26 (m, 4H), 7.22 (d, J = 7.6 Hz, 1H), 6.91 (d, J = 6.4 Hz, 2H), 6.84 (dd, J = 8.4, 1.6 Hz, 1H), 6.53 (br s, 1H), 5.10 (s, 2H), 2.74 (s, 3H), 1.95 (t, J = 18.8 Hz, 3H). |
| 111 | N-(3-(1,1-difluoroethyl)phenyl)-1-(6-(difluoromethoxy)-[1,1'-biphenyl]-3-yl)-3-methyl-5-oxo-4-propyl-4,5-dihydro-1H-pyrazole-4-carboxamide<br>LCMS: (ESI) m/z: 542.3 [M + H] +;<br>1H NMR: (400 MHz, MeOD-d4) δ: 8.01 (s, 1H), 7.96 (d, J = 9.2 Hz, 1H), 7.79 (s, 1H), 7.62 (d, J = 7.6 Hz, 1H), 7.53 − 7.49 (m, 2H), 7.47 − 7.38 (m, 4H), 7.35 − 7.29 (m, 2H), 6.66 (t, J = 74.0 Hz, 1H), 2.35 − 2.20 (m, 5H), 1.90 (t, J = 18.4 Hz, 3H), 1.27 − 1.14 (m, 2H), 0.97 (t, J = 7.2 Hz, 3H). |
| 112 | 2-(4-(difluoromethoxy)phenyl)-N-(3-(1,1-difluoropropyl)phenyl)-5-methyloxazole-4-carboxamide<br>LCMS: (ESI) m/z: 423.1 [M + H] +;<br>1H NMR (400 MHz, MeOD-d4) δ: 8.08 − 8.17 (td, 2 H) 7.95 (s, 1 H) 7.80 (dd, J = 8.12, |

-continued

| Compound Number | IUPAC Compound name, Mass Spectra and H-NMR data |
|---|---|
| | 1.16 Hz, 1 H) 7.45 (t, J = 7.96 Hz, 1 H) 7.24 − 7.33 (td, 3 H) 6.75 − 7.15 (t, 1 H) 2.74 (s, 3 H) 2.12 − 2.27 (td, 2 H) 1.00 (t, J = 7.52 Hz, 3 H). |
| 113 | N-(3-(1,1-difluoroethyl)phenyl)-2-(4-(difluoromethoxy)phenyl)-5-methyloxazole-4-carboxamide<br>LCMS: (ESI) m/z: 409.0 [M + H] +.<br>1H NMR (400 MHz, MeOD-d4) δ: 8.17 − 8.12 (m, 2H), 8.02 − 7.98 (s, 1H), 7.83 − 7.79 (d, J = 8.4 Hz, 1H), 7.49 − 7.43 (t, J = 8.0 Hz, 1H), 7.34 − 7.28 (m, 3H), 7.16 − 6.77 (t, J = 73.4 Hz 1H), 2.76 (s, 3H), 1.95 (t, J = 18.2 Hz, 3H). |
| 114 | 2-(6-(difluoromethoxy)-[1,1'-biphenyl]-3-yl)-N-(3-(1,1-difluoropropyl)phenyl)-4-methyloxazole-5-carboxamide<br>LCMS: (ESI) m/z: 499.2 [M + H] +;<br>1H NMR: (400 MHz, MeOD-d4) δ: 8.35 (d, J = 2.0 Hz, 1H), 8.26 (dd, J = 2.0, 8.8 Hz, 1H), 7.88 (s, 1H), 7.82 (d, J = 8.0 Hz, 1H), 7.60 − 7.53 (m, 2H), 7.52 − 7.37 (m, 5H), 7.28 (d, J = 7.6 Hz, 1H), 6.87 (t, J = 73.2 Hz, 1H), 2.58 (s, 3H), 2.32 − 2.08 (m, 2H), 0.99 (t, J = 7.2 Hz, 3H). |
| 115 | N-(3-(1,1-difluoroethyl)phenyl)-2-(6-(difluoromethoxy)-[1,1'-biphenyl]-3-yl)-4-methyloxazole-5-carboxamide<br>LCMS: (ESI) m/z: 485.2 [M + H] +;<br>1H NMR: (400 MHz, MeOD-d4) δ: 8.35 (d, J = 2.0 Hz, 1H), 8.25 (dd, J = 2.0, 8.4 Hz, 1H), 7.93 (s, 1H), 7.81 (d, J = 9.2 Hz, 1H), 7.59 − 7.53 (m, 2H), 7.51 − 7.38 (m, 5H), 7.33 (dd, J = 0.8, 8.0 Hz, 1H), 6.87 (t, J = 73.6 Hz, 1H), 2.58 (s, 3H), 1.94 (t, J = 18.4 Hz, 3H). |
| 116 | N-(3-(1,1-difluoropropyl)phenyl)-2-(4-methoxyphenyl)-5-methyloxazole-4-carboxamide<br>LCMS: (ESI) m/z: 387.4 [M + H] +;<br>1H NMR (400 MHz, MeOD-d4) δ: 8.07 − 7.99 (dt, 2H), 7.96 − 7.93 (s, 1H), 7.85 − 7.75 (dd, 1H), 7.49 − 7.41 (t, 1H), 7.30 − 7.23 (d, 1H), 7.12 − 7.03 (dt, 2H), 3.92 − 3.83 (s, 3H), 2.78 − 2.68 (s, 3H), 2.27 − 2.12 (td, 2H), 1.05 − 0.94 (t, 3H). |
| 117 | 6-[4-(difluoromethoxy)-3-phenyl-phenyl]-N-[3-(1,1-difluoropropyl)phenyl]-3-methyl-pyrazine-2-carboxamide<br>LCMS: (ESI) m/z: 510.3 [M + H] +;<br>1H NMR: (400 MHz, MeOD-d4) δ: 9.23 (s, 1H), 8.30 − 8.27 (m, 2H), 7.97 (s, 1H), 7.87 − 7.83 (m, 1H), 7.61 − 7.58 (m, 2H), 7.50 − 7.45 (m, 4H), 7.43 − 7.38 (m, 1H), 7.30 (d, J = 7.2 Hz, 1H), 6.82 (t, J = 74 Hz, 1H), 2.92 (s, 3H), 2.28 − 2.13 (m, 2H), 1.00 (t, J = 7.6 Hz, 3H). |
| 118 | N-[3-(1,1-difluoroethyl)phenyl]-6-[4-(difluoromethoxy)-3-phenyl-phenyl]-3-methyl-pyrazine-2-carboxamide<br>LCMS: (ESI) m/z: 496.3 [M + H] +;<br>1H NMR: (400 MHz, MeOD-d4) δ: 9.22 (s, 1H), 8.31 − 8.27 (m, 2H), 8.01 (s, 1H), 7.86 − 7.83 (m, 1H), 7.61 − 7.58 (m, 2H), 7.50 − 7.45 (m, 4H), 7.43 − 7.38 (m, 1H), 7.34 (dd, J = 7.6, 0.8 Hz, 1H), 6.82 (t, J = 73.6 Hz, 1H), 2.91 (s, 3H), 1.95 (t, J = 18.4 Hz, 3H). |
| 119 | 2-(4-(difluoromethoxy)-3-(pyridin-2-yl)phenyl)-N-(3-(1,1-difluoropropyl)phenyl)-4-methylpyrimidine-5-carboxamide<br>LCMS: (ESI) m/z: 511.3 [M + H] +;<br>1H NMR: (400 MHz, MeOD-d4) δ: 8.91 (s, 1H), 8.83 (d, J = 2.4 Hz, 1H), 8.69 (d, J = 4.4 Hz, 1H), 8.62 (dd, J = 2.4, 8.8 Hz, 1H), 7.97 − 7.93 (m, 1H), 7.90 (s, 1H), 7.82 − 7.77 (m, 2H), 7.50 − 7.44 (m, 3H), 7.30 (d, J = 7.6 Hz, 1H), 6.96 (t, J = 73.6 Hz, 1H), 2.75 (s, 3H), 2.23 − 2.13 (m, 2H), 1.94 (t, J = 7.6 Hz, 3H). |
| 120 | N-(3-(1,1-difluoroethyl)phenyl)-2-(4-(difluoromethoxy)-3-(pyridin-2-yl)phenyl)-4-methylpyrimidine-5-carboxamide<br>LCMS: (ESI) m/z: 497.2 [M + H] +;<br>1H NMR: (400 MHz, MeOD-d4) δ: 8.92 (s, 1H), 8.83 (d, J = 2.0 Hz, 1H), 8.69 (d, J = 4.8 Hz, 1H), 8.64 (dd, J = 2.4, 8.8 Hz, 1H), 7.98 − 7.93 (m, 2H), 7.82 − 7.77 (m, 2H), 7.50 − 7.44 (m, 3H), 7.35 (d, J = 7.6 Hz, 1H), 6.97 (t, J = 73.6 Hz, 1H), 2.75 (s, 3H), 1.94 (t, J = 18.4 Hz, 3H). |
| 121 | 1-(5-benzyl-6-methoxy-[1,1'-biphenyl]-3-yl)-N-(3-(1,1-difluoropropyl)phenyl)-3-methyl-5-oxo-4,5-dihydro-1H-pyrazole-4-carboxamide<br>LCMS: (ESI) m/z: 568.3 [M + H] +;<br>1H NMR: (400 MHz, DMSO-d6) δ: 10.88(s, 1H), 7.89(s, 1H), 7.69 − 7.59(m, 5H), 7.49(t, J = 7.6 Hz, 2H), 7.43 − 7.38(m, 2H), 7.34 − 7.28(m, 4H), 7.22 − 7.12(m, 2H), 4.06(s, 2H), 3.18(s, 3H), 2.51(s, 3H),2.24 − 2.14(m, 2H), 0.91(t, J = 7.6 Hz, 3H). |
| 122 | 1-(5-benzyl-6-methoxy-[1,1'-biphenyl]-3-yl)-N-(3-(1,1-difluoroethyl)phenyl)-3-methyl-5-oxo-4,5-dihydro-1H-pyrazole-4-carboxamide<br>LCMS: (ESI) m/z: 554.3 [M + H] +;<br>1H NMR: (400 MHz, DMSO-d6) δ: 10.91(s, 1H), 7.93(s, 1H), 7.70 − 7.58(m, 5H), 7.49(t, J = 7.2 Hz, 2H), 7.42 − 7.37(m, 2H), 7.34 − 7.28(m, 4H), 7.22 − 7.16(m, 2H), 4.06(s, 2H), 3.18(s, 3H), 2.48(s, 3H), 1.95(t, J = 18.8 Hz, 3H). |
| 123 | 2-[4-(difluoromethoxy)-3-phenyl-phenyl]-N-[3-(1,1-difluoropropyl)phenyl]-5-methyl-oxazole-4-carboxamide<br>LCMS: (ESI) m/z: 499.3 [M + H] +;<br>1H NMR: (400 MHz, MeOD-d4) δ: 8.17 (d, J = 2.4 Hz, 1H), 8.11 (dd, J = 2.4, 8.5 Hz, 1H), 7.95 (s, 1H), 7.80 (d, J = 8.4 Hz, 1H), 7.58 − 7.53 (m, 2H), 7.51 − 7.39 (m, 5H), 7.26 (d, J = 7.8 Hz, 1H), 7.03 − 6.63 (m, 1H), 2.76 (s, 3H), 2.29 − 2.10 (m, 2H), 0.99 (t, J = 7.6 Hz, 3H). |
| 124 | N-[3-(1,1-difluoroethyl)phenyl]-2-[4-(difluoromethoxy)-3-phenyl-phenyl]-5-methyl-oxazole-4-carboxamide |

-continued

| Compound Number | IUPAC Compound name, Mass Spectra and H-NMR data |
|---|---|
| | LCMS: (ESI) m/z: 485.3 [M + H] +; 1H NMR: (400 MHz, MeOD-d4) δ: 8.17 (d, J = 2.4 Hz, 1H), 8.12 (dd, J = 2.4, 8.5 Hz, 1H), 7.99 (s, 1H), 7.80 (dd, J = 1.0, 8.2 Hz, 1H), 7.58 − 7.53 (m, 2H), 7.52 − 7.40 (m, 5H), 7.31 (dd, J = 0.8, 7.7 Hz, 1H), 7.03 − 6.63 (m, 1H), 2.76 (s, 3H), 1.94 (t, J = 18.4 Hz, 3H). |
| 125 | 6-(4-(difluoromethoxy)phenyl)-N-(3-(1,1-difluoropropyl)phenyl)-3-methylpyrazine-2-carboxamide LCMS: (ESI) m/z: 434.1 [M + H] +; 1H NMR (400 MHz, MeOD-d4) δ : 9.18 (s, 1H), 8.23 − 8.37 (m, 2H), 8.02 (s, 1H), 7.88 (d, J = 8.4 Hz, 1H), 7.45 − 7.56 (m, 1H), 7.27 − 7.38 (m, 3H), 6.71 − 7.22 (m, 1H), 2.93 (s, 3H), 2.14 − 2.31 (m, 2H), 1.02 (t, J = 7.6 Hz, 3H). |
| 126 | N-(3-(1,1-difluoroethyl)phenyl)-6-(4-(difluoromethoxy)phenyl)-3-methylpyrazine-2-carboxamide LCMS: (ESI) m/z: 420.1 [M + H] +; 1H NMR (400 MHz, MeOD-d4) δ: 9.18 (s, 1H), 8.26 − 8.34 (m, 2H), 8.06 (s, 1H), 7.88 (br d, J = 8.4 Hz, 1H), 7.50 (t, J = 8.0 Hz, 1H), 7.31 − 7.39 (m, 3H), 6.76 − 7.18 (m, 1H), 2.93 (s, 3H), 1.97(t, J = 18.4 Hz, 3H). |
| 127 | 2-(6-(difluoromethoxy)-[1,1'-biphenyl]-3-yl)-N-(3-(1,1-difluoropropyl)phenyl)-6-methylpyrimidine-4-carboxamide LCMS: (ESI) m/z: 510.2 [M + H] +; 1H NMR (400 MHz, MeOD-d4) δ: 8.66 − 8.69 (m, 2H), 8.02 (s, 1H), 7.88 − 7.92 (m, 2H), 7.57 − 7.59 (m, 2H), 7.46 − 7.51 (m, 3H), 7.39 − 7.43 (m, 2H), 7.32 (d, J = 7.6 Hz, 1H), 6.82 (t, J = 74.0 Hz, 1H), 2.70 (s, 3H), 2.13 − 2.28 (m, 2H), 1.00 (t, J = 7.6 Hz, 3H). |
| 128 | 1-(5-(cyclohexylmethyl)-6-methoxy-[1,1biphenyl]-3-yl)-N-(3-(1,1-difluoropropyl)phenyl)-3-methyl-5-oxo-4,5-dihydro-1H-pyrazole-4-carboxamide LCMS: (ESI) m/z: 574.3 [M + H] +; 1H NMR (400 MHz, MeOD-d4) δ: 7.77 (br s, 1H), 7.54 − 7.51 (bm, 3H), 7.39 − 7.23 (m, 6H), 7.10 (d, J = 7.6 Hz, 1H), 3.24 (s, 3H), 2.59 − 2.42 (m, 5H), 2.08 (qt, J = 7.8, 15.6 Hz, 2H), 1.71 − 1.54 (m, 6H), 1.26 − 1.09 (m, 3H), 1.03 − 0.91 (m, 2H), 0.88 (t, J = 7.6 Hz, 3H). |
| 129 | 1-(5-(cyclohexylmethyl)-6-methoxy-[1,1biphenyl]-3-yl)-N-(3-(1,1-difluoroethyl)phenyl)-3-methyl-5-oxo-4,5-dihydro-1H-pyrazole-4-carboxamide LCMS: (ESI) m/z: 560.3 [M + H] +; 1H NMR (400 MHz, MeOD-d4) δ: 7.81 (br s, 1H), 7.56 − 7.48 (m, 3H), 7.42 − 7.23 (m, 6H), 7.12 (d, J = 7.6 Hz, 1H), 3.22 (s, 3H), 2.51 (d, J = 7.2 Hz, 2H), 2.46 (s, 3H), 1.88 − 1.77 (d, J = 28.0 Hz, 3H), 1.67 − 1.58 (m, 6H), 1.20 − 1.11 (m, 3H), 1.01 − 0.90 (m, 2H). |
| 130 | N-(3-(1,1-difluoroethyl)phenyl)-2-(6-(difluoromethoxy)-[1,1'-biphenyl]-3-yl)-6-methylpyrimrdine-4-carboxamide LCMS: (ESI) m/z: 496.1[M + H] +; 1H NMR (400 MHz, MeOD-d4) δ: 8.72 (dd, J = 2.0, 8.4 Hz, 1 H), 8.69 (d, J = 2.0 Hz, 1H), 8.07 (s, 1H), 7.96 (s, 1H), 7.91 (d, J = 8.0 Hz, 1H), 7.63 − 7.58 (m, 2H), 7.52 − 7.35 (m, 6H), 6.85 (t, J = 73.6 Hz, 1H), 2.72 (s, 3H), 1.96 (t, J = 18.0 Hz, 3H). |
| 131 | N-(3-(1,1-difluoroethyl)phenyl)-1-(4-(difluoromethoxy)-3-(2-methyloxazol-4-yl)phenyl)-3-methyl-1H-pyrazole-4-carboxamide LCMS: (ESI) m/z: 489.1[M + H] +; 1H NMR (400 MHz, MeOD-d4) δ: 8.88 (s, 1H), 8.50 (d, J = 2.8 Hz, 1H), 8.24 (s, 1H), 7.94 (s, 1H), 7.75 − 7.82 (m, 2H), 7.40 − 7.49 (m, 2H), 7.28 − 7.33 (m, 1H), 6.85 − 7.27 (m, 1H), 2.59 (s, 3H), 2.56 (s, 3H), 1.96 (t, J = 18.4 Hz, 3H). |
| 132 | 5-(4-(difluoromethoxy)phenyl)-N-(3-(1,1-difluoropropyl)phenyl)-3-methylpyrazine-2-carboxamide LCMS: (ESI) m/z: 434.1 [M + H] +; 1H NMR: (400 MHz, MeOD-d4) δ: 9.04 (s, 1H), 8.26 (d, J = 8.8 Hz, 2H), 7.99 (s, 1H), 7.85 (d, J = 8.0 Hz, 1H), 7.47 (t, J = 8.0 Hz, 1H), 7.32 (d, J = 8.8 Hz, 2H), 7.28 (d, J = 8.0 Hz, 1H), 6.96 (t, J = 74.0 Hz, 1H), 2.98 (s, 3H), 2.21 (dt, J = 7.6, 16.0 Hz, 2H), 1.00 (t, J = 7.6 Hz, 3H). |
| 133 | N-(3-(1,1-difluoroethyl)phenyl)-5-(4-(difluoromethoxy)phenyl)-3-methylpyrazine-2-carboxamide LCMS: (ESI) m/z: 420.1 [M + H] +; 1H NMR: (400 MHz, MeOD-d4) δ: 9.05 (s, 1H), 8.26 (d, J = 8.8 Hz, 2H), 8.04 (s, 1H), 7.85 (d, J = 8.0 Hz, 1H), 7.47 (t, J = 8.0 Hz, 1H), 7.32 (d, J = 8.8 Hz, 3H), 6.96 (t, J = 74.0 Hz, 1H), 2.99 (s, 3H), 1.95 (t, J = 18.4 Hz, 3H). |
| 134 | 5-[4-(difluoromethoxy)-3-phenyl-phenyl]-N-[3-(1,1-difluoropropyl)phenyl]-3-methyl-pyrazine-2-carboxamide LCMS: (ESI) m/z: 510.2 [M + H] +. 1H NMR (400 MHz, MeOD-d4) δ: 9.08 (s, 1H), 8.26 − 8.21 (m, 2H), 7.99 (s, 1H), 7.84 (dd, J = 8.0, 0.8 Hz, 1H), 7.58 − 7.55 (m, 2H), 7.50 − 7.41 (m, 5H), 7.27 (dd, J = 7.6, 0.8 Hz, 1H), 6.84 (t, J = 73.6 Hz, 1H), 2.98 (s, 3H), 2.28 − 2.13 (m, 2H), 1.00 (t, J = 7.4 Hz, 3H). |
| 135 | N-[3-(1,1-difluoroethyl)phenyl]-5-[4-(difluoromethoxy)-3-phenyl-phenyl]-3-methyl-pyrazine-2-carboxamide LCMS: (ESI) m/z: 496.2 [M + H] +; 1H NMR (400 MHz, MeOD-d4) δ: 9.10 (s, 1H), 8.27 − 8.22 (m, 2H), 8.04 (s, 1H), 7.85 (dd, J = 8.0, 1.2 Hz, 1H), 7.58 − 7.55 (m, 2H), 7.51 − 7.41 (m, 5H), 7.32 (dd, J = 7.6, 0.8 Hz, 1H), 6.84 (t, J = 73.6, 1H), 2.99 (s, 3H), 1.95 (t, J = 18.4 Hz, 3H). |
| 136 | N-(3-(1,1-difluoropropyl)phenyl)-2-(4-methoxyphenyl)-4-methyloxazole-5-carboxamide |

-continued

| Compound Number | IUPAC Compound name, Mass Spectra and H-NMR data |
|---|---|
| | LCMS: (ESI) m/z: 387.1 [M + H] +;<br>1H NMR (400 MHz, MeOD-d4) δ: 8.16 (d, J = 8.8 Hz, 2H), 7.91 (s, 1H), 7.83 ( d, J = 8.0 Hz, 1H), 7.46 (t, J = 8.0 Hz, 1H), 7.28 (d, J = 8.0 Hz, 1H), 7.08 (d, J = 9.2 Hz, 2H), 3.89 (s, 3H), 2.55 (s, 3H), 2.15 − 2.25 (m, 2H), 1.00 (t, J = 7.2 Hz, 3H). |
| 137 | 2-(4-(difluoromethoxy)phenyl)-N-(3-(1,1-difluoropropyl)phenyl)-6-methylpyrimidine-4-carboxamide<br>LCMS: (ESI) m/z: 434.0 [M + H] +;<br>1H NMR (400 MHz, MeOD-d4) δ: 8.68 − 8.72 (m, 2H), 8.06 (s, 1H), 7.93 − 7.95 (m, 2H), 7.50 (t, J = 8.0 Hz, 1H), 7.29 − 7.34 (m, 3H), 6.96 (t, J = 73.6 Hz, 1H), 2.71 (s, 3H), 2.17 - 2.27 (m, 2H), 1.01 (t, J = 7.6 Hz, 3H). |
| 138 | 2-[4-(difluoromethoxy)-3-phenyl-phenyl]-N-[3-(1,1-difluoropropyl)phenyl]-4-methyl-pyrimidine-5-carboxamide<br>LCMS: (ESI) m/z: 509.9 [M + H] +;<br>1H NMR (400 MHz, MeOD-d4) δ: 8.91 (s, 1H), 8.56 (d, J = 2.0 Hz, 1H), 8.54 − 8.51 (m, 1H), 7.90 (s, 1H), 7.79 (d, J = 8.4 Hz, 1H), 7.57 − 7.54 (m, 2H), 7.50 − 7.45 (m, 3H), 7.43 − 7.39 (m, 2H), 7.30 (d, J = 8.0 Hz, 1H), 6.84 (t, J = 73.6 Hz, 1H), 2.75 (s, 3H), 2.27 − 2.12 (m, 2H), 0.99 (t, J = 7.2 Hz, 3H). |
| 139 | N-[3-(1,1-difluoroethyl)phenyl]-2-[4-(difluoromethoxy)-3-phenyl-phenyl]-4-methyl-pyrimidine-5-carboxamide<br>LCMS: (ESI) m/z: 496.1 [M + H] +;<br>1H NMR (400 MHz, MeOD-d4) δ: 8.91 (s, 1H), 8.56 (d, J = 2.0 Hz, 1H), 8.54 − 8.51 (m, 1H), 7.95 (s, 1H), 7.78 (d, J = 8.0 Hz, 1H), 7.57 − 7.54 (m, 2H), 7.50 − 7.45 (m, 3H), 7.43 − 7.38 (m, 2H), 7.34 (d, J = 8.4 Hz, 1H), 6.84 (t, J = 74.0 Hz, 1H), 2.75 (s, 3H), 1.94 (t, J = 18.4 Hz, 3H). |
| 140 | 2-(4-(difluoromethoxy)phenyl)-N-(3-(1,1-difluoropropyl)phenyl)-4-methyloxazole-5-carboxamide<br>LCMS: (ESI) m/z: 423.1 [M + H] +.<br>1H NMR (400 MHz, MeOD-d4) δ: 8.25 − 8.29 (m, 2H), 7.91 (s, 1H), 7.84 (d, J = 8.4 Hz, 1H), 7.46 (t, J = 8.0 Hz, 1H), 7.27 − 7.32 (m, 3H), 6.98 (t, J = 73.6 Hz, 1H), 2.56 (s, 3H), 2.15 − 2.25 (m, 2H), 1.00 (t, J = 7.2 Hz, 3H). |
| 141 | N-(3-(1,1-difluoroethyl)phenyl)-2-(4-(difluoromethoxy)phenyl)-4-methyloxazole-5-carboxamide<br>LCMS: (ESI) m/z: 409.1 [M + H] +;<br>1H NMR (400 MHz, MeOD-d4) δ: 8.25 − 8.28 (m, 2H),7.95 (s, 1H), 7.83 (d, J = 8.4 Hz, 1H), 7.46 (t, J = 7.6 Hz, 1H), 7.30 − 7.34 (m, 3H), 6.98 (t, J = 73.2 Hz, 1H), 2.56 (s, 3H), 1.94 (t, J = 18.4 Hz, 3H). |
| 142 | N-(3-(1,1-difluoroethyl)phenyl)-2-(4-methoxyphenyl)-4-methyloxazole-5-carboxamide<br>LCMS: (ESI) m/z: 373.1 [M + H] +;<br>1H NMR (400 MHz, MeOD-d4) δ: 8.16 − 8.18 (m, 2H), 7.96 (s, 1H), 7.82 − 7.84 (m, 1H), 7.46 (t, J = 8.0 Hz, 1H), 7.33 (dd, J = 0.8, 7.6 Hz, 1H), 7.08 − 7.11 (m, 2H), 3.89 (s, 3H), 2.55 (s, 3H), 1.94 (t, J = 18.4 Hz, 3H). |
| 143 | 2-[4-(difluoromethoxy)phenyl]-N-[3-(1,1-difluoropropyl)phenyl]-4-methyl-pyrimidine-5-carboxamide<br>LCMS: (ESI) m/z: 433.9 [M + H] +;<br>1H NMR (400 MHz, MeOD-d4) δ: 8.90 (s, 1H), 8.54 (d, J = 8.8 Hz, 2H), 7.90 (s, 1H), 7.79 (d, J = 8.4 Hz, 1H), 7.48 (t, J = 8.0 Hz, 1H), 7.32 − 7.25 (m, 3H), 6.96 (t, J = 74.0 Hz, 1H), 2.74 (s, 3H), 2.20 (td, J = 16.0, 7.6 Hz, 2H), 0.99 (t, J = 7.6 Hz, 3H). |
| 144 | N-[3-(1,1-difluoroethyl)phenyl]-2-[4-(difluoromethoxy)phenyl]-4-methyl-pyrimidine-5-carboxamide<br>LCMS: (ESI) m/z: 420.1 [M + H] +;<br>1H NMR (400 MHz, MeOD-d4) δ: 8.90 (s, 1H), 8.54 (d, J = 8.8 Hz, 2H), 7.95 (s, 1H), 7.78 (d, J = 8.0 Hz, 1H), 7.47 (t, J = 8.0 Hz, 1H), 7.34 (dd, J = 8.0, 0.8 Hz, 1H), 7.27 (d, J = 8.8 Hz, 2H), 6.96 (t, J = 74.0 Hz, 1H), 2.74 (s, 3H), 1.94 (t, J = 18.4 Hz, 3H). |
| 145 | 5-cyclopropyl-N-[3-(1,1-difluoroethyl)phenyl]-1-[4- (difluoromethoxy)phenyl]-3-methyl-pyrazole-4-carboxamide<br>LCMS: (ESI) m/z: 447.9 [M + H] +;<br>1H NMR: (400 MHz, MeOD-d4) δ: 7.92 (s, 1H), 7.73 (d, J = 8.4 Hz, 1H), 7.62 (d, J = 9.2 Hz, 2H), 7.46 (t, J = 8.0 Hz 1H), 7.35 − 7.29 (m, 3H), 6.94 (t, J = 74.0 Hz, 1H), 2.40 (s, 3H), 2.14 − 2.05 (m, 1H), 1.94 (t, J = 18.4 Hz, 3H), 0.89 (dd, J = 8.4, 1.6 Hz, 2H), 0.51 (dd, J = 5.6, 1.6 Hz, 2H). |
| 146 | N-[3-(l,l-difluoroethyl)phenyl]-l-[4-(difluoromethoxy)phenyl]-5-isopropyl-3-methyl-pyrazole-4-carboxamide<br>LCMS: (ESI) m/z: 450.2 [M+H]+;<br>1H NMR: (400 MHz, DMSO-d6) δ: 10.35 (s, 1H), 8.02 (s, 1H), 7.77 (br d, J = 8.2 Hz, 1H), 7.57 - 7.53 (m, 1H), 7.51 - 7.41 (m, 3H), 7.36 (s, 2H), 7.27 (d, J = 7.6 Hz, 1H), 7.22 - 7.16 (m, 1H), 2.97 (q, J = 7.0 Hz, 1H), 2.29 (s, 3H), 1.96 (t, J = 18.8 Hz, 3H), 1.25 (d, J = 7.0 Hz, 6H). |
| 147 | N-(3-(1,1-difluoroethyl)phenyl)-2-(4-(difluoromethoxy)phenyl)-6-methylpyrimidine-4-carboxamide<br>LCMS: (ESI) m/z: 420.0 [M + H] +;<br>1H NMR (400 MHz, MeOD-d4) δ: 8.66 − 8.71 (m, 2H), 8.09 (s, 1H), 7.91 − 7.97 (m, 2H), 7.50 (t, J = 8.0 Hz, 1H), 7.37 (d, J = 7.6 Hz, 1H), 7.29 (d, J = 8.8 Hz, 2H), 6.96 (t, J = 74.0 Hz, 1H), 2.70 (s, 3H), 1.96 (t, J = 18.4 Hz, 3H). |
| 148 | N-[3-(1,1-difluoroethyl)phenyl]-1-[4-(difluoromethoxy)-3-(2-pyridyl)phenyl]-5-ethyl-3-methyl-pyrazole-4-carboxamide<br>LCMS: (ESI) m/z: 513.2 [M + H] +. |

-continued

| Compound Number | IUPAC Compound name, Mass Spectra and H-NMR data |
|---|---|
| | 1H NMR: (400 MHz, DMSO-d6) δ: 10.09 (s, 1H), 8.80 − 8.63 (m, 1H), 8.00 (s, 1H), 7.97 − 7.92 (m, 1H), 7.89 (d, J = 2.8 Hz, 1H), 7.88 − 7.84 (m, 1H), 7.79 − 7.73 (m, 1H), 7.65 (dd, J = 2.8, 8.8 Hz, 1H), 7.55 (s, 1H), 7.50 (d, J = 8.8 Hz, 1H), 7.48 − 7.45 (m, 1H), 7.44 (td, J = 1.2, 3.0, 4.4 Hz, 1H), 7.37 (s, 1H), 7.26 (d, J = 7.8 Hz, 1H), 7.19 (s, 1H), 2.88 (q, J = 7.4 Hz, 2H), 2.37 (s, 3H), 1.96 (t, J = 18.8 Hz, 3H), 1.04 (t, J = 7.4 Hz, 3H). |
| 149 | N-(3-(1,1-difluoroethyl)phenyl)-1-(4-(difluoromethoxy)-3-(oxazol-4-yl)phenyl)-3-methyl-1 H-pyrazole-4-carboxamide<br>LCMS: (ESI) m/z: 475.1[M + H] +;<br>1H NMR (400 MHz, MeOD-d4) δ: 8.89 (s, 1H), 8.56 (d, J = 2.76 Hz, 1H), 8.39 (s, 1H), 8.32 (d, J = 0.64 Hz, 1H), 7.94 (s, 1H), 7.74 − 7.85 (m, 2H), 7.40 − 7.50 (m, 2H), 7.30 (d, J = 7.64 Hz, 1H), 6.89 − 7.28 (m, 1H), 2.59 (s, 3H), 1.96 (t, J = 18.24 Hz, 3H). |
| 150 | N-(3-(1,1-difluoroethyl)phenyl)-1-(4-(difluoromethoxy)phenyl)-5-isobutyl-3-methyl-1 H-pyrazole-4-carboxamide<br>LCMS: (ESI) m/z: 464.3 [M + H] +;<br>1H NMR (400 MHz, MeOD-d4) δ: 7.87 (s, 1H), 7.71 (d, J = 8.0 Hz, 1H), 7.43 − 7.50 (m, 3H), 7.30 − 7.36 (m, 3H), 6.96 (t, J = 73.2 Hz, 1H), 2.78 (d, J = 7.2 Hz, 2H), 2.44 (s, 3H), 1.94 (t, J = 18.4 Hz, 3H), 1.67 − 1.73 (m, 1H), 0.76 (d, J = 6.8 Hz, 6H). |
| 151 | N-[3-(1,1-difluoroethyl)phenyl]-1-[4-(difluoromethoxy)-3-phenyl-phenyl]-5-ethyl-3-methyl-pyrazole-4-carboxamide<br>LCMS: (ESI) m/z: 512.2 [M + H] +;<br>1H NMR (400 MHz, MeOD-d4) δ: 7.89 (s, 1H), 7.71 (d, J = 7.2 Hz, 1H), 7.56 − 7.41 (m, 9H), 7.31 (d, J = 7.2 Hz, 1H), 6.82 (t, J = 73.6 Hz, 1H), 2.93 (q, J = 7.6 Hz, 2H), 2.45 (s, 3H), 1.94 (t, J = 18.0 Hz, 3H), 1.13 (t, J = 7.6 Hz, 3H). |
| 152 | N-[3-(1,1-difluoroethyl)phenyl]-1-[4-(difluoromethoxy)-3-(3-pyridyl)phenyl]-5-ethyl-3-methyl-pyrazole-4-carboxamide<br>LCMS: (ESI) m/z: 513.2 [M + H] +;<br>1H NMR (400 MHz, MeOD-d4) δ: 8.74 (d, J = 1.6 Hz, 1H), 8.59 (dd, J = 4.8, 1.2 Hz, 1H), 8.05 (dt, J = 8.4, 2.0 Hz, 1H), 7.89 (s, 1H), 7.72 (d, J = 8.0 Hz, 1H), 7.62 − 7.52 (m, 4H), 7.45 (t, J = 8.0 Hz, 1H), 7.31 (d, J = 7.6 Hz, 1H), 6.94 (t, J = 72.8 Hz, 1H), 2.94 (q, J = 7.6 Hz, 2H), 2.45 (s, 3H), 1.94 (t, J = 18.4 Hz, 3H), 1.13 (t, J = 7.6 Hz, 3H). |
| 153 | N-[3-(1,1-difluoroethyl)phenyl]-2-(4-methoxyphenyl)-5-methyl-oxazole-4-carboxamide<br>LCMS: (ESI) m/z: 373.1 [M + H] +;<br>1H NMR: (400 MHz, DMSO-d6) δ: 10.11(s, 1H), 8.13(s, 1H), 8.01(d, J = 8.8 Hz, 2H), 7.96(d, J = 8.0 Hz, 1H), 7.47(t, J = 12.0 Hz, 1H), 7.29(d, J = 7.6 Hz, 1H), 7.13(d, J = 8.8 Hz, 2H), 3.85(s, J = 3H), 2.70(s, 3H), 1.98(t, J = 18.8 Hz, 3H). |
| 154 | 5-cyclopentyl-N-[3-(1,1-difluoroethyl)phenyl]-1-[4-(difluoromethoxy)phenyl]-3-methyl-pyrazole-4-carboxamide<br>LCMS: (ESI) m/z: 476.1 [M + H] +;<br>1H NMR: (400 MHz, MeOD-d4) δ: 7.87(s, 1H), 7.71(d, J = 8.4 Hz, 1H), 7.47 − 7.42(m, 3H), 7.35 − 7.30(m, 3H), 6.95(t, J = 73.2 Hz, 1H), 3.06 − 2.97(m, 1H), 2.36(s, 3H), 1.98 − 1.89(m, 7H), 1.79 − 1.69(m, 2H), 1.56 − 1.48(m, 2H). |
| 155 | N-(3-(1,1-difluoroethyl)phenyl)-1-(4-(difluoromethoxy)phenyl)-3-ethyl-5-methyl-1H-pyrazole-4-carboxamide<br>LCMS: (ESI) m/z: 436.2 [M + H] +;<br>1H NMR (400 MHz, MeOD-d4) δ: 7.89 (s, 1H), 7.71 (d, J = 8.0 Hz, 1H), 7.49 − 7.52 (m, 2H), 7.45 (t, J = 8.0 Hz, 1H), 7.29 − 7.36 (m, 3H), 6.96 (t, J = 73.6 Hz, 1H), 2.87 (q, J = 7.6 Hz, 2H), 2.44 (s, 3H), 1.94 (t, J = 18.0 Hz, 3H), 1.08 (t, J = 7.6 Hz, 3H). |
| 156 | N-(3-(1,1-difluoroethyl)phenyl)-1-(4-(difluoromethoxy)phenyl)-5-ethyl-3-methyl-1H-pyrazole-4-carboxamide<br>LCMS: (ESI) m/z: 436.0 [M + H] +;<br>1H NMR (400 MHz, MeOD-d4) δ: 7.88 (s, 1H), 7.71 (d, J = 8.0 Hz, 1H), 7.51 − 7.53 (m, 2H), 7.45 (t, J = 8.0 Hz, 1H), 7.29 − 7.35 (m, 3H), 6.94 (t, J = 73.6 Hz, 1H), 2.87 (q, J = 7.6 Hz, 2H), 2.42 (s, 3H), 1.93 (t, J = 18.22 Hz, 3H), 1.27 (t, J = 7.6 Hz, 3H). |
| 157 | N-(3-chloro-5-methyl-phenyl)-1-[4-(difluoromethoxy)phenyl]-3,4-dimethyl-5-oxo-pyrazole-4-carboxamide<br>LCMS: (ESI) m/z: 422.0 [M + H] +;<br>1H NMR (400 MHz, MeOD-d4) δ: 7.96 (d, J = 8.8 Hz, 2H), 7.51 (s, 1H), 7.27 (s, 1H), 7.21 (d, J = 9.2 Hz, 2H), 6.99 (s, 1H), 6.82 (t, J = 74 Hz, 1H), 2.32 (s, 3H), 2.29 (s, 3H), 1.75 (s, 3H). |
| 158 | N-(3-(1,1-difluoroethyl)phenyl)-1-(4-(difluoromethoxy)phenyl)-3-methyl-5-oxo-4-propyl-4,5-dihydro-1H-pyrazole-4-carboxamide<br>LCMS: (ESI) m/z: 466.2 [M + H] +;<br>1H NMR: (400 MHz, MeOD-d4) δ: 7.96 (d, J = 9.2 Hz, 2H), 7.78 (s, 1H), 7.63 (d, J = 8.4 Hz, 1H), 7.42 (t, J = 8.0 Hz, 1H), 7.31 (d, J = 7.2 Hz, 1H), 7.22 (d, J = 9.2 Hz, 2H), 6.82 (t, J = 74.0 Hz, 1H), 2.35 − 2.19 (m, 5H), 1.90 (t, J = 18.4 Hz, 3H), 1.28 − 1.13 (m, 2H), 0.97 (t, J = 7.2 Hz, 3H). |
| 159 | N-(3-(1,1-difluoroethyl)phenyl)-1-(4-(difluoromethoxy)phenyl)-4-ethyl-3-methyl-5-oxo-4,5-dihydro-1H-pyrazole-4-carboxamide<br>LCMS: (ESI) m/z: 452.2 [M + H] +;<br>1H NMR: (400 MHz, MeOD-d4) δ: 7.97 (d, J = 8.0 Hz, 2H), 7.78 (s, 1H), 7.62 (d, J = 8.4 Hz, 1H), 7.41 (t, J = 8.0 Hz, 1H), 7.31 (d, J = 7.6 Hz, 1H), 7.22 (d, J = 9.2 Hz, 2H), 6.82 (t, J = 74.0 Hz, 1H), 2.43 − 2.36 (m, 1H), 2.33 (s, 3H), 2.32 − 2.22 (m, 1H), 1.90 (t, J = 18.4 Hz, 3H), 0.86 (t, J = 7.2 Hz, 3H). |

-continued

| Compound Number | IUPAC Compound name, Mass Spectra and H-NMR data |
|---|---|
| 160 | 1-(5-((1 H-imidazol-1-yl)methyl)-6-methoxy-[1,1'-biphenyl]-3-yl)-N-(3-(1,1-difluoroethyl)phenyl)-3-methyl-5-oxo-4,5-dihydro-1H-pyrazole-4-carboxamide<br>LCMS: (ESI) m/z: 544.4 [M + H] +;<br>1H NMR (400 MHz, DMSO-d6) δ: 11.26(s, 1H), 8.21(s, 3H), 7.90 – 7.87(m, 2H), 7.77(s, 1H), 7.57 – 7.55(m, 2H), 7.48(t, J = 7.6 Hz, 2H), 7.39(t, J = 3.2 Hz, 1H), 7.34 – 7.26(m, 2H), 7.19(s, 1H), 7.04(d, J = 7.6 Hz, 1H), 6.91(s, 1H), 5.24(s, 2H), 3.19(s, 3H), 2.24(s, 3H), 1.94(t, J = 21.6 Hz, 3H). |
| 161 | N-(3-(1,1-difluoroethyl)phenyl)-1-(6-methoxy-5-propyl-[1,1'-biphenyl]-3-yl)-3-methyl-5-oxo-4,5-dihydro-1H-pyrazole-4-carboxamide<br>LCMS: (ESI) m/z: 506.5 [M + H] +;<br>1H NMR (400 MHz, MeOD-d4) δ: 7.92 (s, 1H), 7.66 – 7.62 (m, 3H), 7.58 (br s, 2H), 7.46 – 7.41 (m, 2H), 7.40 – 7.33 (m, 2H), 7.18 (br d, J = 7.6 Hz, 1H), 3.34 (s, 3H), 2.77 (t, J = 7.6 Hz, 2H), 2.48 (s, 3H), 1.92 (t, J = 18.4 Hz, 3H), 1.79 – 1.69 (m, 2H), 1.04 (t, J = 7.2 Hz, 3H). |
| 162 | N-(3-(1,1-difluoroethyl)phenyl)-1-(4-(difluoromethoxy)phenyl)-3-methyl-5-(methylamino)-1 H-pyrazole-4-carboxamide<br>LCMS: (ESI) m/z: 437.2 [M + H] +;<br>1H NMR(400Hz, DMSO-d6) δ: 9.46(s, 1H), 7.96(s, 1H), 7.72(d, J = 8.4 Hz, 1H), 7.58 – 7.55(m, 2H), 7.43(t, J = 8.0Hz, 1H), 7.32(d, J = 8.8Hz, 2H), 7.31(t, J = 74.0 Hz, 1H), 7.23(d, J = 7.6Hz, 1H), 6.19(dd, J = 10.8Hz, 5.6Hz, 1H), 2.55(s, 3H), 2.35(s, 3H), 1.96(t, J = 18.8Hz, 3H). |
| 163 | 4-chloro-1-(4-(difluoromethoxy)phenyl)-N-(3-(1,1-difluoropropyl)phenyl)-3-methyl-5-oxo-4,5-dihydro-1H-pyrazole-4-carboxamide<br>LCMS: (ESI) m/z: 438.2 [M + H] +;<br>1H NMR (400 MHz, MeOD-d4) δ: 8.82 (br s, 1H), 7.86-7.98 (m, 2H), 7.62 – 7.70 (m, 2H), 7.44 (t, J = 8.0 Hz, 1H), 7.31 (br d, J = 7.2 Hz, 1H), 7.21 (d, J = 9.2 Hz, 2H), 6.29 – 6.77 (m, 1H), 2.47 (s, 3H), 2.08 – 2.23 (m, 2H), 1.00 (t, J = 7.6 Hz, 3H). |
| 164 | N-(3-(1,1-difluoroethyl)phenyl)-2-(4-(difluoromethoxy)phenyl)-5-methyl-2H-1,2,3-triazole-4-carboxamide<br>LCMS: (ESI) m/z: 409.0 [M + H] +;<br>1H NMR (400 MHz, DMSO-d6) δ: 10.54 (s, 1H), 8.15 – 8.19 (m, 2H), 8.08 (s, 1H), 7.95 (d, J = 8.0 Hz, 1H), 7.49 (t, J = 7.6 Hz, 1H), 7.44 (d, J = 9.2 Hz, 2H), 7.35 (t, J = 73.6 Hz, 1H), 7.32 (d, J = 8.0 Hz, 1H), 2.59 (s, 3H), 1.98 (t, J = 18.8 Hz, 3H). |
| 165 | N-(3,5-dichloro-4-fluoro-phenyl)-1-[4-(difluoromethoxy)phenyl]-3,4-dimethyl-5-oxo-pyrazole-4-carboxamide<br>LCMS: (ESI) m/z: 460.1 [M + H] +;<br>1H NMR (400 MHz, MeOD-d4) δ: 7.95 (d, J = 9.2 Hz, 2H), 7.75 (s, 1H), 7.73 (s, 1H), 7.21 (d, J = 9.2 Hz, 2H), 6.82 (t, J = 74.0 Hz, 1H), 2.28 (s, 3H), 1.74 (s, 3H). |
| 166 | N-(3-chloro-5-fluoro-phenyl)-1-[4-(difluoromethoxy)phenyl]-3,4-dimethyl-5-oxo-pyrazole-4-carboxamide<br>LCMS: (ESI) m/z: 425.9 [M + H] +;<br>1H NMR (400 MHz, MeOD-d4) δ: 7.95 (d, J = 8.8 Hz, 2H), 7.51 (s, 1H), 7.46 – 7.43 (m, 1H), 7.21 (d, J = 8.8 Hz, 2H), 6.98-6.96 (m, 1H), 6.82 (t, J = 74.0 Hz, 1H), 2.28 (s, 3H), 1.75 (s, 3H). |
| 167 | N-(3-chlorophenyl)-1-[4-(difluoromethoxy)phenyl]-3,4-dimethyl-5-oxo-pyrazole-4-carboxamide<br>LCMS: (ESI) m/z: 408.2 [M + H] +;<br>1H NMR (400 MHz, MeOD-d4) δ: 7.96 (d, J = 9.2 Hz, 2H), 7.72 (t, J = 2.0 Hz, 1H), 7.46 – 7.44 (m, 1H), 7.30 (t, J = 8.0 Hz, 1H), 7.21 (d, J = 9.2 Hz, 2H), 7.16 – 7.14 (m, 1H), 6.82 (t, J = 74.0 Hz, 1H), 2.29 (s, 3H), 1.75 (s, 3H). |
| 168 | N-(3-(1,1-difluoroethyl)phenyl)-1-(4-(difluoromethoxy)phenyl)-5-(dimethylamino)-3-methyl-1 H-pyrazole-4-carboxamide<br>LCMS: (ESI) m/z: 451.2 [M + H] +;<br>1H NMR: (400 MHz, DMSO-d6) δ: 10.22(s, 1H), 7.99(s, 1H), 7.73(d, J = 7.2 Hz, 1H), 7.65 – 7.63(m, 2H), 7.44(t, J = 8.0 Hz, 1H), 7.33 – 7.30(m, 2H), 7.31(t, J = 74.0 Hz, 1H), 7.26(d, J = 7.6 Hz ,1H), 2.70 – 2.65(m, 6H), 2.28(s, 3H), 1.96(t, J = 18.8 Hz, 3H). |
| 169 | (4R)-N-(3-(1,1-difluoroethyl)phenyl)-1-(4-(difluoromethoxy)phenyl)-3,4-dimethyl-5-oxo-4,5-dihydro-1H-pyrazole-4-carboxamide<br>LCMS: (ESI) m/z: 438.3 [M + H] +;<br>1H NMR: (400 MHz, MeOD-d4) δ: 7.97 (d, J = 9.2 Hz, 2H), 7.78 (s, 1H), 7.64 (d, J = 8.0 Hz, 1H), 7.42 (t, J = 8.0 Hz, 1H), 7.31 (d, J = 7.6 Hz, 1H), 7.21 (d, J = 9.2 Hz, 2H), 6.82 (t, J = 74.4 Hz, 1H), 2.30 (s, 3H), 1.90 (t, J = 18.4 Hz, 3H), 1.76 (s, 3H). |
| 170 | (4S)-N-(3-(1,1-difluoroethyl)phenyl)-1-(4-(difluoromethoxy)phenyl)-3,4-dimethyl-5-oxo-4,5-dihydro-1H-pyrazole-4-carboxamide<br>LCMS: (ESI) m/z: 438.3 [M + H] +;<br>1H NMR: (400 MHz, MeOD-d4) δ: 7.97 (d, J = 9.2 Hz, 2H), 7.78 (s, 1H), 7.64 (d, J = 8.0 Hz, 1H), 7.42 (t, J = 8.0 Hz, 1H), 7.31 (d, J = 7.6 Hz, 1H), 7.21 (d, J = 9.2 Hz, 2H), 6.82 (t, J = 74.4 Hz, 1H), 2.30 (s, 3H), 1.90 (t, J = 18.4 Hz, 3H), 1.76 (s, 3H). |
| 171 | 5-amino-N-(3-(1,1-difluoroethyl)phenyl)-1-(4-(difluoromethoxy)phenyl)-3-methyl-1H-pyrazole-4-carboxamide<br>LCMS: (ESI) m/z: 423.2 [M + H] +;<br>1H NMR(400MHz, DMS0-d6) δ: 8.92(s, 1H), 7.91(s, 1H), 7.73(d, J = 8.4Hz, 1H), 7.62 – 7.59(m, 2H), 7.44(t, J = 7.6Hz, 1H), 7.31(d, J = 4.4Hz, 2H), 7.23(d, J = 7.6Hz, 1H), 7.34(t, J = 60.4Hz, 1H), 2.44(s, 3H), 1.97(t, J = 18.8Hz, 3H). |
| 172 | 4-chloro-N-(3-(1,1-difluoroethyl)phenyl)-1-(4-(difluoromethoxy)phenyl)-3-methyl-5-oxo-4,5-dihydro-1H-pyrazole-4-carboxamide |

-continued

| Compound Number | IUPAC Compound name, Mass Spectra and H-NMR data |
|---|---|
| | LCMS: (ESI) m/z: 480.0 [M + Na] +;<br>1H NMR (400MHz, CDC13-d) δ: 8.82 (br s, 1H), 7.91 (d, J = 9.2 Hz, 2H), 7.73 (s, 1H), 7.64 (d, J = 8.0 Hz, 1H), 7.44 (t, J = 8.0 Hz, 1H), 7.36 (d, J = 8.0 Hz, 1H), 7.21 (d, J = 9.2 Hz, 2H), 6.52 (t, J = 73.6 Hz, 1H), 2.47 (s, 3H), 1.93 (t, J = 18.4 Hz, 3H). |
| 173 | N-(3-(1,1-difluoroethyl)phenyl)-2-(4-(difluoromethoxy)phenyl)pyrimidine-5-carboxamide<br>LCMS: (ESI) m/z 406.1 [M + H] +;<br>1H NMR (400 MHz, MeOD-d4) δ: 9.32 (s, 2H), 8.56 - 8.58 (m, 2H), 7.97 (s, 1H), 7.83 (d, J = 8.00 Hz, 1H), 7.48 (t, J = 7.6 Hz, 1H), 7.35 (d, J = 7.2 Hz, 1H), 7.29 (d, J = 8.8 Hz, 2H), 6.97 (t, J = 73.6 Hz, 1H), 1.94 (t, J = 18.4 Hz, 3H). |
| 174 | N-(3-(1,1-difluoroethyl)phenyl)-1-(4-(difluoromethoxy)phenyl)-3,4-dimethyl-5-oxo-4,5-dihydro-1 H-pyrazole-4-carboxamide<br>LCMS: (ESI) m/z: 438.2 [M + H] +;<br>1H NMR: (400 MHz, MeOD-d4) δ: 7.97 (d, J = 9.2 Hz, 2H), 7.78 (s, 1H), 7.64 (d, J = 8.0 Hz, 1H), 7.42 (t, J = 8.0 Hz, 1H), 7.31 (d, J = 7.6 Hz, 1H), 7.21 (d, J = 9.2 Hz, 2H), 6.82 (t, J = 74.4 Hz, 1H), 2.30 (s, 3H), 1.90 (t, J = 18.4 Hz, 3H), 1.76 (s, 3H). |
| 175 | N-[3-(1,1-difluoroethyl)phenyl]-1-[4-(difluoromethoxy)-3-(2-pyridyl)phenyl]-3-methyl-pyrazole-4-carboxamide<br>LCMS: (ESI) m/z: 485.2[M + H] +;<br>1H NMR: (400MHz, MeOD-d4) δ: 8.87 (s, 1H), 8.71 - 8.69 (m, 1H), 8.13 (d, J = 3.2 Hz, 1H), 7.97 - 7.89 (m, 3H), 7.84 (d, J = 8.0 Hz, 1H), 7.75 (d, J = 8.4 Hz, 1H), 7.50 - 7.41 (m, 3H), 7.29 (d, J = 8.0 Hz, 1H), 6.87 (t, J = 73.6 Hz, 1H), 2.56 (s, 3H), 1.93 (t, J = 18.4 Hz, 3H). |
| 176 | N-(3-(1,1-difluoroethyl)phenyl)-1-(2'-(difluoromethoxy)-[1,1':3',1'-terphenyl]-5'-yl)-3-methyl-1H-pyrazole-4-carboxamide<br>LCMS: (ESI) m/z: 560.3[M + H] +;<br>1H NMR (400 MHz, MeOD-d4) δ: 8.95 (s, 1H), 7.90 (s, 1H), 7.83 (s, 2H), 7.74 (d, J = 8.4 Hz, 1H), 7.68 - 7.61 (m, 4H), 7.55 - 7.47 (m, 4H), 7.47 - 7.38 (m, 3H), 7.28 (d, J = 7.6 Hz, 1H),5.90 (t, J = 73.2 Hz, 1H), 2.57 (s, 3H), 1.93 (t, J = 18.0 Hz, 3H). |
| 177 | N-(3-(1,1-difluoroethyl)phenyl)-1-(4-(difluoromethoxy)-3-(pyridin-2-yl)phenyl)-3,5-dimethyl-1 H-pyrazole-4-carboxamide<br>LCMS: (ESI) m/z: 499.3 [M + H] +;<br>1H NMR (400 MHz, MeOD-d4) δ: 8.67 ( d, J = 4.4 Hz, 1H), 7.82 - 7.96 (m, 4H), 7.72 (d, J = 8.4 Hz, 1H), 7.62 (dd, J = 2.4, 8.8 Hz, 1H), 7.43 - 7.52 (m, 3H), 7.30 (d, J = 7.6 Hz, 1H), 6.94 (t, J = 73.2 Hz 1H), 2.48 (d, J = 19.8 Hz, 6H), 1.93 (t, J = 18.0 Hz, 3H). |
| 178 | N-(3-(1,1-difluoroethyl)phenyl)-1-(4-(difluoromethoxy)-3-(pyridin-3-yl)phenyl)-3,5-dimethyl-1 H-pyrazole-4-carboxamide<br>LCMS: (ESI) m/z: 498.2 [M + H] +;<br>1H NMR (400 MHz, MeOD-d4) δ: 7.89 (s, 1H), 7.72 (d, J = 7.6 Hz, 1H), 7.38 - 7.58 (m, 9H), 7.30 (d, J = 8.0 Hz, 1H), 6.80 (t, J = 73.6 Hz, 1H), 2.47 (d, J = 13.6 Hz, 6H), 1.93 (t, J = 18.4 Hz, 3H). |
| 179 | N-(3-(1,1-difluoroethyl)phenyl)-1-(4-(difluoromethoxy)-3-(pyridin-3-yl)phenyl)-3,5-dimethyl-1 H-pyrazole-4-carboxamide<br>LCMS: (ESI) m/z: 499.1 [M + H] +;<br>1H NMR (400 MHz, MeOD-d4) δ: 8.74 (s, 1H), 8.58 (d, J = 4.4 Hz, 1H), 7.96 ( d, J = 8.0 Hz, 1H), 7.71 (s, 1H), 7.64 (d, J = 8.4 Hz, 1H), 7.63 - 7.59 ( m, 4H), 7.54 (t, J = 8.8 Hz, 1H), 7.44 - 7.31 (m, 1H), 6.92 (t, J = 73.2 Hz, 1H), 1.93 (d, J = 16.4 Hz, 6H), 1.93 (t, J = 18.4Hz, 3H). |
| 180 | N-[3-(1,1-difluoroethyl)phenyl]-1-(4-methoxy-3-methyl-5-phenyl-phenyl)-3-methyl-5-oxo-4H-pyrazole-4-carboxamide<br>LCMS: (ESI) m/z: 478.3 [M + H] +;<br>1H NMR: (400 MHz, CDC13-d) δ: 7.77(s, 1H), 7.58(d, J = 8.0 Hz, 1 H), 7.47(d, J = 7.2 Hz, 2H), 7.36 - 7.30(m, 5 H), 7.23 - 7.21(m, 2 H), 3.32(s, 3 H), 2.49(s, 3 H), 2.27(s, 3 H), 1.90(t, J = 18.0 Hz, 3H). |
| 181 | N-(3-(1,1-difluoroethyl)phenyl)-1-(4-(difluoromethoxy)-3-(pyridin-4-yl)phenyl)-3-methyl-1 H-pyrazole-4-carboxamide<br>LCMS: (ESI) m/z: 485.2[M + H] +;<br>1H NMR (400 MHz, MeOD-d4) δ: 8.89 (s, 1H), 8.66 (d, J = 5.6 Hz, 2H), 7.95 - 7.90 (m, 3H), 7.75 (d, J = 7.6 Hz, 1H), 7.67 (d, J = 6.0 Hz, 2H), 7.51 (d, J = 8.8 Hz, 1H), 7.43 (t, J = 8.0 Hz, 1H), 7.28 (d, J = 7.6 Hz, 1H), 6.87 (t, J = 73.2 Hz, 1H), 2.56 (s, 3H), 1.93 (t, J = 18.0 Hz, 3H). |
| 182 | N-(3-(1,1-difluoroethyl)phenyl)-1-(4-(difluoromethoxy)-3-(pyridin-3-yl)phenyl)-3-methyl-1 H-pyrazole-4-carboxamide<br>LCMS: (ESI) m/z: 485.2 [M + H] +;<br>1H NMR (400 MHz, MeOD-d4) δ: 8.89 (s, 1H), 8.76 (d, J = 1.6 Hz, 1H), 8.63 - 8.56 (m, 1H), 8.08 (d, J = 8.4 Hz, 1H), 7.95 - 7.86 (m, 3H), 7.75 (d, J = 7.6 Hz, 1H), 7.58 - 7.50 (m, 1H), 7.51 (d, J = 8.8 Hz, 1H), 7.44 (t, J = 7.6 Hz, 1H), 7.29 (d, J =8.4 Hz, 1H), 6.86 (t, J = 73.6 Hz, 1H), 2.57 (s, 3H), 1.93 (t, J = 18.0 Hz, 3H). |
| 183 | 4-((3-(1,1-difluoroethyl)phenyl)carbamoyl)-1-(4-(difluoromethoxy)-3-(pyridin-3-yl)phenyl)-3-methyl-1H-pyrazol-5-yl 4-(1-hydroxy-2-methylpropan-2-yl)piperazine-1-carboxylate |

-continued

| Compound Number | IUPAC Compound name, Mass Spectra and H-NMR data |
|---|---|
| | LCMS: (ESI) m/z: 685.6 [M + H] +; 1H NMR: (400 MHz, MeOD-d4) δ: 8.73 (s, 1H), 8.53 (dd, J = 1.2 Hz, 4.8 Hz, 1H), 8.05 − 8.02 (m, 2H), 7.99 (d, J = 2.4 Hz, 1H), 7.56 − 7.45 (m, 2H), 7.47 (d, J = 8.0 Hz, 1H), 7.44 − 7.38 (m, 2H), 7.34 − 7.28 (m, 1H), 6.73 (t, J = 74.0 Hz, 1H), 3.74 (br s, 2H), 3.58 − 3.42 (m, 4H), 3.21 − 2.83 (m, 4H), 2.33 (s, 3H), 1.91 (t, J = 18.0 Hz, 3H), 1.13 (s, 6H). |
| 184 | N-(3-(1,1-difluoroethyl)phenyl)-1-(4-(difluoromethoxy)phenyl)-3,5-dimethyl-1H-pyrazole-4-carboxamide LCMS: (ESI) m/z: 422.0 [M + H] +; 1H NMR: (400 MHz, MeOD-d4) δ: 7.91 (s, 1H), 7.74 (d, J = 8.0 Hz, 1H), 7.54 (d, J = 8.8 Hz, 2H), 7.47 (t, J = 7.6 Hz, 1H), 7.40 − 7.30 (m, 3H), 6.96 (t, J = 74.0 Hz, 1H), 2.46 (s, 3H), 2.45 (s, 3H), 1.95 (t, J = 18.0 Hz, 3H). |
| 185 | 4-((3-(1,1-difluoroethyl)phenyl)carbamoyl)-1-(4-(difluoromethoxy)phenyl)-3-methyl-1H-pyrazol-5-yl 4-(1-hydroxy-2-methylpropan-2-yl)piperazine-1-carboxylate LCMS: (ESI) m/z: 608.4 [M + H] +; 1H NMR (400 MHz, MeOD-d4) δ: 7.78 (d, J = 8.8 Hz, 2H), 7.42 − 7.52 (m, 2H), 7.32 (s, 1H), 7.26 (d, J = 8.0 Hz, 1H), 7.14 (d, J = 8.8 Hz, 2H), 6.78 (t, J = 74.4, 1H), 4.13 ( s, 2H), 3.58 (s, 2H), 3.20 (s, 6H ), 2.33 (s, 3H), 1.93 (t, J = 18.4 Hz, 3H), 1.29 (s, 6H). |
| 186 | N-(3-(1,1-difluoroethyl)phenyl)-1-(6-(difluoromethoxy)-[1,1'-biphenyl]-3-yl)-3-methyl-1H-pyrazole-4-carboxamide LCMS: (ESI) m/z: 484.1 [M + H] +; 1H NMR (400 MHz, MeOD-d4) δ: 8.87 (s, 1H), 7.94 (s, 1H), 7.87 (d, J = 2.8 Hz, 1H), 7.83 (dd, J = 2.8, 8.8 Hz, 1H), 7.78 (d, J = 8.8 Hz, 1H), 7.64 − 7.58 (m, 2H), 7.54 − 7.43 (m, 5H), 7.32 (d, J = 7.8 Hz, 1H), 6.973 (t, J = 68.0, 1H), 2.60 (s, 3H), 1.97 (t, J = 18.4 Hz, 3H). |
| 187 | 4-((3-(1,1-difluoroethyl)phenyl)carbamoyl)-1-(4-(difluoromethoxy)-3-(pyridin-3-yl)phenyl)-3-methyl-1H-pyrazol-5-yl 4-(2-hydroxyethyl)piperazine-1-carboxylate LCMS: (ESI) m/z: 657.6 [M + H] +; 1H NMR: (400 MHz, MeOD-d4) δ: 8.74 (d, J = 1.6 Hz, 1H), 8.53 (d, J = 1.6 Hz, 1H), 8.12 (d, J = 1.6 Hz, 1H), 8.05 (d, J = 8.0 Hz, 1H), 7.96 (d, J = 1.6 Hz, 1H), 7.60 − 7.55 (m, 1H), 7.53 (d, J = 8.0 Hz, 1H), 7.46 (d, J = 8.0 Hz, 1H), 7.40 − 7.30 (m, 2H), 7.32 (d, J = 8.0 Hz, 1H), 6.74 (t, J = 73.6 Hz, 1H), 3.72 − 3.59 (m, 6H), 3.30 − 2.40 (m, 6H), 2.82 (s, 3H), 1.91 (t, J = 18.4 Hz, 3H). |
| 188 | 4-((3-(1,1-difluoroethyl)phenyl)carbamoyl)-1-(4-methoxyphenyl)-3-methyl-1H-pyrazol-5-yl [1,4'-bipiperidine]-1'-carboxylate LCMS: (ESI) m/z: 582.4 [M + H] +; 1H NMR (400 MHz, MeOD-d4) δ: 7.54 − 7.58 (m, 2H), 7.43 (t, J = 7.6 Hz, 1H), 77.39 −.41 (m, 1H), 7.31 (s, 1H), 7.26 ( d, J = 8.0 Hz, 1H), 6.92 − 6.95 (m, 2H), 4.20 ( d, J = 12.4 Hz, 2H), 3.80 (s, 3H), 3.02 − 3.14 (m, 5H), 2.81 (t, J = 12.0 Hz, 2H), 2.30 (s, 3H), 1.93 (t, J = 11.2 Hz, 3H) 1.76 − 1.83 (m, 6H), 1.60 (s, 2H), 1.43 (d, J = 8.8 Hz, 2H). |
| 189 | 4-((3-(1,1-difluoroethyl)phenyl)carbamoyl)-1-(4-(difluoromethoxy)phenyl)-3-methyl-1 H-pyrazol-5-yl [1,4'-bipiperidine]-1'-carboxylate LCMS: (ESI) m/z: 618.5 [M + H] +; 1H NMR (400 MHz, MeOD-d4) δ: 7.77 − 7.80 (m, 2H), 7.49 (t, J = 7.6 Hz, 1H), 7.41 − 7.423(m, 1H), 7.33 (s, 1H), 7.27 ( d, J = 8.0 Hz, 1H), 7.15 (d, J = 9.2 Hz , 2H), 6.79 (t, J = 74.0 Hz, 1H), 4.20 ( d, J = 14.4 Hz, 2H), 3.04 − 3.20 (m, 5H), 3.14 (t, J = 12.8 Hz, 2H), 2.33 ( s, 3H), 1.93 (t, J = 18.4 Hz, 3H), 1.78 − 1.89(m, 6H), 1.63 (s, 2H), 1.48 (d, J = 9.2 Hz, 2H). |
| 190 | 4-((3-(1,1-difluoroethyl)phenyl)carbamoyl)-1-(4-(difluoromethoxy)-3-(pyridin-3-yl)phenyl)-3-methyl-1 H-pyrazol-5-yl [1,4'-bipiperidine]-1'-carboxylate LCMS: (ESI) m/z: 695.4 [M + H] +; 1H NMR: (400 MHz, MeOD-d4) δ: 8.74 (d, J = 1.6 Hz, 1H), 8.54 (d, J = 1.6 Hz, 1H), 8.04 (d, J = 8.8 Hz, 1H), 7.95 (s, 1H), 7.86 (d, J = 8.8 Hz, 1H), 7.65 − 7.55 (m, 1H), 7.46 (d, J = 7.6 Hz, 1H), 7.42 − 7.40 (m, 1H), 7.33 − 7.32 (m, 2H), 7.31 (d, J = 3.6 Hz, 1H), 6.74 (t, J = 74.0 Hz, 1H), 4.20 (d, J = 13.2 Hz, 2H), 2.87 − 2.80 (m, 4H), 2.33 (s, 3H), 1.91 (t, J = 18.4 Hz, 3H), 1.81 − 1.80 (m, 2H), 1.80 − 1.78 (m, 4H), 1.70 − 1.69 (m, 2H), 1.69 − 1.29 (m, 5H). |
| 191 | 4-((3-(1,1-difluoroethyl)phenyl)carbamoyl)-1-(4-(difluoromethoxy)phenyl)-3-methyl-1H-pyrazol-5-yl 4-(2-hydroxyethyl)piperazine-l-carboxylate LCMS: (ESI) m/z: 580.5 [M + H] +; 1H NMR (400MHz, MeOD-d4) δ: 7.74 (d, J = 8.8 Hz, 2H), 7.52 − 7.46 (m, 1H), 7.45 − 7.40 (m, 1H), 7.32 (s, 1H), 7.26 (br d, J = 8.4 Hz, 1H), 7.16 (d, J = 8.8 Hz, 2H), 6.97 (s, 1H), 6.79 (s, 1H), 6.60 (s, 1H), 3.83 − 3.75 (m, 2H), 3.75 − 3.45 (m, 4H), 3.18 − 2.87 (m, 6H), 2.32 (s, 3H), 1.98 − 1.87 (m, 3H). |
| 192 | N-(3-(1,1-difluoroethyl)phenyl)-1-(4-(difluoromethoxy)phenyl)-3-methyl-5-(trifluoromethyl)-1 H-pyrazole-4-carboxamide LCMS: (ESI) m/z: 476.0 [M + H] +; 1H NMR (400 MHz, MeOD-d4) δ: 7.90 (s, 1H)), 7.75 − 7.73 (d, J = 8 Hz, 1H), 7.57 − 7.55 (d, J = 8.8 Hz, 1H), 7.48 (t, J = 7.6 Hz, 1H), 7.37 − 7.35 (d, J = 8.8 Hz, 3H), 6.991 (t, J = 73.2, 1H), 2.428 (s, 3H), 1.953 (t, J = 18.4 Hz, 3H). |
| 193 | 5-acetyl-N-(3-(1,1-difluoroethyl)phenyl)-1-(4-(difluoromethoxy)phenyl)-3-methyl-1H-pyrazole-4-carboxamide LCMS: (ESI) m/z: 450.3 [M + H] +; 1H NMR: (400 MHz, CDC13-d) δ: 9.66 (br s, 1H), 7.83 (s, 1H), 7.72 (br d, J = 8.2 Hz, 1H), 7.48 − 7.33 (m, 3H), 7.27 (s, 3H), 6.79 − 6.31 (m, 1H), 2.59 (s, 3H), 2.16 (s, 3H), 1.91 (t, J = 18.2 Hz, 3H). |

-continued

| Compound Number | IUPAC Compound name, Mass Spectra and H-NMR data |
|---|---|
| 194 | N-[3-(1,1-difluoroethyl)phenyl]-1-[4-(difluoromethoxy) phenyl]-5-(hydroxymethyl)-3-methyl-pyrazole-4-carboxamide<br>LCMS: (ESI) m/z: 438.1 [M + H] +;<br>1H NMR: (400 MHz, CDC13-d) δ: 8.23 (br s, 1H), 7.73 − 7.63 (m, 2H), 7.49 − 7.34 (m, 3H), 7.27 (s, 3H), 6.75 − 6.30 (m, 1H), 4.66 (br d, J = 4.4 Hz, 2H), 4.31 (br s, 1H), 2.58 (s, 3H), 2.00 − 1.83 (m, 4H). |
| 195 | 1-(4-(difluoromethoxy)phenyl)-3-methyl-4-(1-((4-(methylsulfonyl)phenyl)amino)-1H-1,2,3-triazol-4-yl)-1H-pyrazol-5(4H)-one<br>LCMS: (ESI) m/z: 477.3 [M + H] +;<br>1H NMR (400 MHz, MeOD-d4) δ: 7.77 (d, J = 8.8 Hz, 2H), 7.52 (s, 1H), 7.40 − 7.24 (m, 4H), 7.08 (d, J = 8.0 Hz, 1H), 7.11 − 6.67 (t, J = 74.0 Hz, 1H), 2.35 (s, 3H), 2.00 (s, 3H). |
| 213 | N-(3-(1,1-difluoroethyl)phenyl)-2-(4-(difluoromethoxy)-3-(pyridin-2-yl)phenyl)-4-methyloxazole-5-carboxamide<br>LCMS: (ESI) m/z: 486.3 [M + H] +;<br>1H NMR: (400 MHz, MeOD-d4) δ: 8.72 (d, J = 4.8 Hz, 1H), 8.56 (d, J = 2.0 Hz, 1H), 8.34 (dd, J = 2.0, 8.4 Hz, 1H), 8.00 (dt, J = 2.0, 7.6 Hz, 1H), 7.93 (s, 1H), 7.86 − 7.78 (m, 2H), 7.54 − 7.48 (m, 2H), 7.45 (t, J = 8.0 Hz, 1H), 7.32 (d, J = 78.0 Hz, 1H), 6.99 (t, J = 73.2 Hz, 1H), 2.57 (s, 3H), 1.93 (t, J = 18.4 Hz, 3H) |
| 214 | 2-(4-(difluoromethoxy)-3-(pyridin-2-yl)phenyl)-N-(3-(1,1-difluoropropyl)phenyl)-4-methyloxazole-5-carboxamide<br>LCMS: (ESI) m/z: 500.4 [M + H] +;<br>1H NMR: (400 MHz, MeOD-d4) δ: 8.73 (d, J = 4.8 Hz, 1H), 8.57 (d, J = 2.0 Hz, 1H), 8.35 (dd, J = 2.0, 8.4 Hz, 1H), 8.03 (dt, J = 1.6, 7.6 Hz, 1H), 7.91 − 7.80 (m, 3H), 7.56 − 7.49 (m, 2H), 7.46 (t, J = 8.0 Hz, 1H), 7.28 (d, J = 7.6 Hz, 1H), 7.00 (t, J = 73.2, 1H), 2.57 (s, 3H), 2.15 − 2.11 (m, 2H), 0.99 (t, J = 7.6 Hz, 3H) |
| 215 | 2-(4-(difluoromethoxy)phenyl)-N-(3-(1,1-difluoropropyl)phenyl)-5-methyl-1H-imidazole-4-carboxamide<br>LCMS: (ESI) m/z: 422.0 [M + H] +;<br>1H NMR: (400 MHz, MeOD-d4) δ: 8.01 − 7.90 (m, 3H), 7.75 (d, J = 8.0 Hz, 1H), 7.41 (t, J = 8.0 Hz, 1H), 7.29 − 7.16 (m, 3H), 6.89 (t, J = 73.6 Hz, 1H), 2.61 (s, 3H), 2.25 − 2.10 (m, 2H), 0.99 (t, J = 7.6 Hz, 1H). |
| 216 | 5-[4-(difluoromethoxy)phenyl]-N-[3-(1,1-difluoropropyl)phenyl]-2-methyl-1H-pyrrole-3-carboxamide<br>LCMS: (ESI) m/z: 421.0 [M + H] +;<br>1H NMR: (400 MHz, MeOD-d4) δ: 7.88 (s, 1H), 7.74 (dd, J = 8.0, 1.2 Hz, 1H), 7.65 − 7.61 (m, 2H), 7.41 (t, J = 8.0 Hz, 1H), 7.21 (d, J = 8.0 Hz, 1H), 7.15 (d, J = 8.8 Hz, 2H), 6.98 (s, 1H), 6.81 (t, J = 74.4 Hz, 1H), 2.58 (s, 3H), 2.19 (m, 2H), 0.99 (t, J = 7.6 Hz, 3H). |
| 217 | 5-[4-(difluoromethoxy)-3-phenyl-phenyl]-N-[3-(1,1-difluoropropyl)phenyl]-2-methyl-1H-pyrrole-3-carboxamide<br>LCMS: (ESI) m/z: 497.2 [M + H] +;<br>1H NMR: (400 MHz, MeOD-d4) δ: 7.88 (s, 1H), 7.74 (d, J = 9.2 Hz, 1H), 7.69 (d, J = 2.4 Hz, 1H), 7.63 (dd, J = 8.4, 2.4 Hz, 1H), 7.56 − 7.53 (m, 2H), 7.47 − 7.42 (m, 2H), 7.41 -7.36 (m, 2H), 7.27 (d, J = 8.4 Hz, 1H), 7.20 (dd, J = 7.6, 0.8 Hz, 1H), 7.05 (s, 1H), 6.64 (t, J = 74.4 Hz, 1H), 2.58 (s, 3H), 2.19 (m, 2H), 0.99 (t, J = 7.6 Hz, 3H). |
| 218 | 2-(6-(difluoromethoxy)-[1,1'-biphenyl]-3-yl)-N-(3-(1,1-difluoropropyl)phenyl)-5-methyl-1 H-imidazole-4-carboxamide<br>LCMS: (ESI) m/z: 498.2 [M + H] +;<br>1H NMR (400 MHz, MeOD-d4) δ: 8.06 (d, J = 2.4 Hz, 1H), 7.96 (dd, J = 2.4, 8.4 Hz, 1H), 7.92 (s, 1H), 7.77 (d, J = 8.0 Hz, 1H), 7.55 − 7.57 (m, 2H), 7.37 − 7.48 (m, 5H), 7.22 (d, J = 8.0 Hz, 1H), 6.76 (t, J = 74.0 Hz, 1H), 2.63 (s, 3H), 2.11-2.25 (m, 2H), 0.98 (t, J = 7.6 Hz, 3H). |
| 219 | N-(3-(1,1-difluoroethyl)phenyl)-6-methyl-2-(5-methyl-[1,1'-biphenyl]-3-yl)pyrimidine-4-carboxamide<br>LCMS: (ESI) m/z: 444.2 [M + H] +;<br>1H NMR (400 MHz, CDC13-d) δ: 10.09 (br s, 1H), 8.53 (s, 1H), 8.29 (s, 1H), 7.98 (s, 1H), 7.96 (s, 1H), 7.88 (d, J = 8.0 Hz, 1H), 7.73 (d, J = 7.6 Hz, 2H), 7.61 (s, 1H), 7.53 − 7.47 (m, 3H), 7.42 (d, J = 7.6 Hz, 1H), 7.36 (d, J = 8.4 Hz, 1H), 2.76 (s, 3H), 2.58 (s, 3H), 1.98 (t, J = 18.4 Hz, 3H). |
| 220 | N-(3-(1,1-difluoroethyl)phenyl)-2-(4-(difluoromethoxy)-3-(pyridin-3-yl)phenyl)-5-methyloxazole-4-carboxamide<br>LCMS: (ESI) m/z: 486.3 [M + H] +;<br>1H NMR (400 MHz, CDC13-d) δ: 8.92 (s, 1H), 8.84 − 8.79 (m, 1H), 8.71 − 8.66 (m, 1H), 8.14 (d, J = 2.2 Hz, 1H), 8.10 (dd, J = 2.2, 8.6 Hz, 1H), 7.92 (td, J = 2.0, 7.8 Hz, 1H), 7.87 (s, 1H), 7.82 (br d, J = 8.0 Hz, 1H), 7.46 − 7.40 (m, 3H), 7.29 (d, J = 7.8 Hz, 1H), 6.71 − 6.33 (m, 1H), 2.81 (s, 3H), 1.96 (t, J = 18.2 Hz, 3H). |
| 221 | 2-(4-(difluoromethoxy)-3-(pyridin-3-yl)phenyl)-N-(3-(1,1-difluoropropyl)phenyl)-5-methyloxazole-4-carboxamide<br>LCMS: (ESI) m/z: 500.3 [M + H] +;<br>1H NMR (400 MHz, CDC13-d) δ: 8.91 (s, 1H), 8.87 − 8.77 (m, 1H), 8.74 − 8.64 (m, 1H), 8.15 (d, J = 2.2 Hz, 1H), 8.10 (dd, J = 2.2, 8.6 Hz, 1H), 7.92 (br d, J = 8.0 Hz, 1H), 7.83 (br d, J = 8.4 Hz, 1H), 7.81 (s, 1H), 7.46 − 7.40 (m, 3H), 7.24 (s, 1H), 6.71 − 6.34 (m, 1H), 2.81 (s, 3H), 2.19 (dt, J = 7.6, 16.1 Hz, 2H), 1.02 (t, J = 7.4 Hz, 3H). |

-continued

| Compound Number | IUPAC Compound name, Mass Spectra and H-NMR data |
|---|---|
| 222 | 5-(5-(difluoromethoxy)pyridin-2-yl)-N-(3-(1,1-difluoropropyl)phenyl)-2-methyl-1H-pyrrole-3-carboxamide<br>LCMS: (ESI) m/z: 421.9 [M + H] +;<br>1H NMR (400 MHz, CDC13-d) δ: 9.50 (br s, 1H), 8.36 (d, J = 2.0 Hz, 1H), 7.76 (d, J = 8.0 Hz, 1H), 7.68 (s, 1H), 7.57 − 7.53 (m, 2H), 7.51 − 7.47 (m, 1H), 7.41 (t, J = 8.0 Hz, 1H), 7.22 (d, J = 7.6 Hz, 1H), 6.84 (d, J = 2.8 Hz, 1H), 6.56 (t, J = 72.8 Hz, 1H), 2.68 (s, 3H), 2.25-2.10 (m, 2H), 1.01 (t, J = 7.6 Hz, 3H). |
| 223 | 5-(5-(difluoromethoxy)-6-phenylpyridin-2-yl)-N-(3-(1,1-difluoropropyl)phenyl)-2-methyl-1H-pyrrole-3-carboxamide<br>LCMS: (ESI) m/z: 498.1 [M + H] +;<br>1H NMR (400 MHz, MeOD-d4) δ: 7.96 − 7.92 (m, 2H), 7.89 (s, 1H), 7.75 (d, J = 8.4 Hz, 1H), 7.68 (d, J = 0.8 Hz, 2H), 7.51 − 7.40 (m, 4H), 7.30 (s, 1H), 7.21 (d, J = 7.6 Hz, 1H), 6.76 (t, J = 73.6 Hz, 1H), 2.60 (s, 3H), 2.27 − 2.12 (m, 2H), 1.00 (t, J = 7.4 Hz, 3H). |
| 224 | 1-(5-(4-chlorobenzyl)-6-methoxy-[1,1'-biphenyl]-3-yl)-N-(3-(1,1-difluoroethyl)phenyl)-3-methyl-5-oxo-4,5-dihydro-1H-pyrazole-4-carboxamide<br>LCMS: (ESI) m/z: 588.2 [M + H] +;<br>1H NMR (400 MHz, MeOD-d4) δ: 7.91 (s, 1H), 7.63 (d, J = 7.2 Hz, 3H), 7.54 (d, J = 16.4 Hz, 2H), 7.34 − 7.48 (m, 4H), 7.29 (s, 4H), 7.22 (d, J = 8.0 Hz, 1H), 4.09 (s, 2H), 3.21 (s, 3H), 2.56 (s, 3H), 1.92 (t, J = 18.4 Hz, 3H). |
| 225 | N-(3-(1,1-difluoropropyl)phenyl)-1-(6-methoxy-5-propyl-[1,1'-biphenyl]-3-yl)-3-methyl-5-oxo-4,5-dihydro-1H-pyrazole-4-carboxamide<br>LCMS: (ESI) m/z: 520.3 [M + H] +;<br>1H NMR (400 MHz, MeOD-d4) δ: 7.87 (s, 1H), 7.66 − 7.61 (m, 3H), 7.48 − 7.44 (m, 4H), 7.43 − 7.37 (m, 2H), 7.20 (d, J = 8.0 Hz, 1H), 3.36 (s, 3H), 2.75 (t, J = 8.0 Hz, 2H), 2.62 (s, 3H), 2.24 - 2.11 (m, 2H), 1.79 - 1.70 (m, 2H), 1.05 (t, J = 7.6 Hz, 3H), 0.98 (t, J = 7.6 Hz, 3H). |
| 226 | N-(3-(1,1-difluoropropyl)phenyl)-6-methyl-2-(5-methyl-[1,1'-biphenyl]-3-yl)pyrimidine-4-carboxamide<br>LCMS: (ESI) m/z: 458.2 [M + H] +;<br>1H NMR (400 MHz, CDC13-d) δ: 10.08 (s, 1H), 8.53 (s, 1H), 8.29 (s, 1H), 7.98 (s, 1H), 7.89 (d, J = 10.0 Hz, 2H), 7.73 (d, J = 7.6 Hz, 2H), 7.61 (s, 1H), 7.53 − 7.47 (m, 3H), 7.42 (d, J = 7.6 Hz, 1H), 7.32 (d, J = 8.0 Hz, 1H), 2.76 (s, 3H), 2.58 (s, 3H), 2.27 − 2.14 (m, 2H), 1.04 (t, J = 7.6 Hz, 3H). |
| 227 | 2-(5-(difluoromethoxy)pyridin-2-yl)-N-(3-(1,1-difluoropropyl)phenyl)-5-methyl-1H-imidazole-4-carboxamide<br>LCMS: (ESI) m/z: 423.1 [M + H] +;<br>1H NMR (MeOD-d4, 400 MHz) δ: 8.49 (s, 1H), 8.18 (dd, J = 8.4, 1.2 Hz, 1H), 7.95 (s, 1H), 7.79 ( d, J = 8.0 Hz, 1H), 7.71 (d, J = 8.8 Hz, 1H), 7.44 (t, J = 7.6 Hz, 1H), 7.23 (d, J = 7.6 Hz, 1H), 6.98 (t, J = 72.8 Hz, 1H), 2.64 (s, 3H), 2.12 − 2.30 (m, 2H), 0.99 (t, J = 7.2 Hz, 3H). |
| 228 | N-(3-(1,1-difluoroethyl)phenyl)-1-(5-(4-hydroxybenzyl)-6-methoxy- [1,1'-biphenyl]-3-yl)-3-methyl-5-oxo-4,5-dihydro-1H-pyrazole-4-carboxamide<br>LCMS: (ESI) m/z: 570.3 [M + H] +;<br>1H NMR (400Hz, MeOD-d4) δ: 7.90(s ,1H), 7.61(d, J = 6.8 Hz, 3H), 7.46 − 7.38(m, 6H),7.36 − 7.10 (m, 1H), 7.09(d, J = 8.4 Hz, 2H), 6.71(d, J = 8.4 Hz, 2H), 3.99(s, 2H), 3.20(s, 3H), 2.57(s, 3H), 1.91(t, J = 16.4 Hz, 3H). |
| 229 | N-(3-(1,1-difluoropropyl)phenyl)-5-fluoro-1-(4-methoxyphenyl)-3-methyl-1H-pyrazole-4-carboxamide<br>LCMS: (ESI) m/z: 404.2 [M + H] +;<br>1H NMR (400 MHz, CDC13-d) δ: 7.74 − 7.65 (m, 2H), 7.53 (br d, J = 8.4 Hz, 3H), 7.42 (br t, J = 7.6 Hz, 1H), 7.26 − 7.22 (m, 1H), 7.06 − 6.98 (m, 2H), 3.92 − 3.81 (m, 3H), 2.58 (s, 3H), 2.17 (dt, J = 8.0, 16.0 Hz, 2H), 1.01 (br t, J = 7.6 Hz, 3H). |
| 230 | 5-acetyl-N-(3-(1,1-difluoropropyl)phenyl)-1-(4-methoxyphenyl)-3-methyl-1H-pyrazole-4-carboxamide<br>LCMS: (ESI) m/z: 428.1 [M + H] +;<br>1H NMR (400 MHz, CDC13-d) δ: 9.94 (s, 1H), 7.83 (s, 1H), 7.79 (d, J = 8.4 Hz, 1H), 7.41 (t, J = 8.0 Hz, 1H), 7.36 (d, J = 8.8 Hz, 2H), 7.23 (d, J = 8.0 Hz, 1H), 7.04 (d, J = 8.8 Hz, 2H), 3.89 (s, 3H), 2.64 (s, 3H), 2.26 − 2.16 (m, 2H), 2.15 (s, 3H), 1.02 (t, J = 7.6 Hz, 3H). |
| 231 | 5-chloro-N-(3-(1,1-difluoropropyl)phenyl)-1-(4-methoxyphenyl)-3-methyl-1H-pyrazole-4-carboxamide<br>LCMS: (ESI) m/z: 419.9 [M + H] +;<br>1H NMR (MeOD-d4, 400 MHz) δ: 7.85 (s, 1H), 7.73 (d, J = 8.4 Hz, 1H), 7.43 − 7.45 (m, 3H), 7.27 (d, J = 8.0 Hz, 1H), 7.08 − 7.09 (m, 2H), 3.88 (s, 3H), 2.45 (s, 3H), 2.19 (m, 2H), 0.99 (t, J = 7.6 Hz, 3H). |
| 232 | 4-acetyl-N-(3-(1,1-difluoropropyl)phenyl)-5-(4-methoxyphenyl)-1 H-pyrazole-3-carboxamide<br>LCMS: (ESI) m/z: 414.2 [M + H] +;<br>1H NMR (400 MHz, MeOD-d4) δ: 7.95(s, 1H), 7.79 − 7.81 (d, J = 8.0 Hz, 1H), 7.44 − 7.49 (m, 3H), 7.26 − 7.28 (d, J = 8.0 Hz, 1H), 7.06 − 7.08 (d, J = 8.0 Hz, 2H), 3.86(s, 3H), 2.31(s, 3H), 2.09 − 2.22 (m, 2H), 0.97 − 1.00 (t, J = 7.6 Hz, 3H). |

-continued

| Compound Number | IUPAC Compound name, Mass Spectra and H-NMR data |
|---|---|
| 233 | 4-bromo-N-(4-(1,1-difluoropropyl)phenyl)-5-(4-methoxyphenyl)-1H-pyrazole-3-carboxamide<br>LCMS: (ESI) m/z: 450.1[M + H] +;<br>1H NMR (400 MHz, MeOD-d4) δ: 7.95 (s, 1H), 7.78 (d, J = 8.2 Hz, 1H), 7.69 (d, J = 8.8 Hz, 2H), 7.45 (t, J = 8.0 Hz, 1H), 7.26 (d, J = 8.0 Hz, 1H), 7.08 (d, J = 8.8 Hz, 2H), 3.87 (s, 3H), 2.15 − 2.25 (m, 2H), 1.00 (t, J = 7.6 Hz, 3H). |
| 234 | methyl 4-((3-(1,1-difluoropropyl)phenyl)carbamoyl)-1-(4-methoxyphenyl)-3-methyl-1H-pyrazole-5-carboxylate<br>LCMS: (ESI) m/z: 444.2 [M + H] +;<br>1H NMR (400 MHz, DMSO-d6) δ: 10.48 (s, 1H), 7.91 (s, 1H), 7.73 (d, J = 8.4 Hz, 1H), 7.46 (t, J = 8.0 Hz, 1H), 7.36 (d, J = 8.8 Hz, 2H), 7.23 (d, J = 7.6 Hz, 1H), 7.04 (d, J = 9.2 Hz, 2H), 3.83 (s, 3H), 3.64 (s, 3H), 2.33 (s, 3H), 2.14 − 2.25 (m, 2H), 0.93 (t, J = 7.2 Hz, 3H). |
| 235 | N-(3-(1,1-difluoropropyl)phenyl)-4-hydroxy-5-(4-methoxyphenyl)-2-methyl-1H-pyrrole-3-carboxamide<br>LCMS: (ESI) m/z: 401.1 [M + H] +;<br>1H NMR (400 MHz, DMSO-d6) δ: 10.96 − 10.82 (bs, 1H), 10.19 (s, 1H), 7.78(s, 1H), 7.73 − 7.71 (m, 2H), 7.58 − 7.43 (m, 1H), 7.43 − 7.35 (m, 1H), 7.14 (d, J = 7.2 Hz, 1H), 6.88 (d, J = 8.8 Hz, 2H), 3.70 (s, 3H), 2.52(s, 3H), 2.22 - 2.13 (m, 2H), 0.89 (t, J = 7.2 Hz, 3H). |
| 236 | 1-(5-(4-chlorobenzyl)-6-methoxy-[1,1'-biphenyl]-3-yl)-N-(3-(1,1-difluoropropyl)phenyl)-3-methyl-5-oxo-4,5-dihydro-1H-pyrazole-4-carboxamide<br>LCMS: (ESI) m/z: 602.3 [M + H] +;<br>1H NMR (400 MHz, MeOD-d4) δ: 7.87 (s, 1H), 7.63 (d, J = 7.2 Hz, 3H), 7.39 − 7.48 (m, 6H), 7.30 (s, 4H), 7.20 (d, J = 7.6 Hz, 1H), 4.10 (s, 2H), 3.22 (s, 3H), 2.60 (s, 3H), 2.11 − 2.23 (m, 2H), 0.98 (t, J = 7.2 Hz, 3H). |
| 247 | N-(3-(1,1-difluoroethyl)phenyl)-2-(4-methoxyphenyl)-5-methylpyrimidine-4-carboxamide<br>LCMS: (ESI) m/z: 384.2 [M + H] +;<br>1H NMR (400 MHz, CDC13-d) δ: 10.27 (br s, 1H), 8.79 (s, 1H), 8.41 (dd, J = 7.2,2.0 Hz, 2H), 7.93 (s, 1H), 7.86(s, 1 H), 7.49 (d, J = 8.0 Hz, 1H), 7.33 (d, J = 7.6 Hz, 1H), 7.07 (dd, J = 7.2, 2.4 Hz, 2H), 3.92 (s, 3 H), 2.78 (s, 3H), 1.99(t, J = 18.4 Hz, 3H). |
| 248 | 4-((3-(1,1-difluoropropyl)phenyl)carbamoyl)-2-(4-methoxyphenyl)-5-methyl-1H-imidazole 3-oxide<br>LCMS: (ESI) m/z: 402.1 [M + H] +;<br>1H NMR (400 MHz, DMSO-d6) δ: 13.77 (s, 1H), 13.21 (s, 1H), 8.39 (d, J = 8.4 Hz, 2H), 7.93 (s, 1H), 7.69 (d, J = 8.0 Hz, 1H), 7.47 (t, J = 7.6 Hz, 1H), 7.22 (d, J = 7.6 Hz, 1H), 7.13 (d, J = 8.8 Hz, 2H), 3.84 (s, 3H), 2.60 (s, 3H), 2.27 − 2.17 (m, 2H), 0.93 (t, J = 7.2 Hz, 3H). |
| 249 | 4-((3-(1,1-difluoropropyl)phenyl)carbamoyl)-2-(4-methoxy-3-(3-methylpyridin-2-yl)phenyl)-5-methyl-1H-imidazole 3-oxide<br>LCMS: (ESI) m/z: 493.0 [M + H] +;<br>1H NMR (400 MHz, DMSO-d6) δ: 12.88 (s, 1H), 12.45(s, 1H), 7.74 (d, J = 7.2 Hz, 1H), 7.65 (dd, J = 0.08, 4.8 Hz, 1H), 7.50 (s, 1H), 7.10 (s, 1H), 6.88 (d, J = 8.4 Hz, 2H), 6.63 (t, J = 8.0 Hz, 1H), 6.57 − 6.49 (m, 2H), 6.39 (d, J = 7.8 Hz, 1H), 3.01 (s, 3H), 1.76 (s, 3H), 1.45 − 1.34 (m, 2H), 1.29 (s, 3H), 0.10 (t, J = 7.2 Hz, 3H). |
| 250 | 4-((3-(1,1-difluoropropyl)phenyl)carbamoyl)-2-(4-methoxyphenyl)-5-methyloxazole 3-oxide<br>LCMS: (ESI) m/z: 403.0 [M + H] +;<br>1H NMR (400 MHz, DMSO-d6) δ: 12.81 (s, 1H), 8.42 − 8.39 (m, 2H), 7.94 (s, 1H), 7.72 (d, J = 8.0 Hz, 1H), 7.52 (t, J = 8.0 Hz, 1H), 7.30 (d, J = 7.6 Hz, 1H), 7.19 (d, J = 9.2 Hz, 2H), 3.87 (s, 3H), 2.74 (s, 3H), 2.28 − 2.18 (m, 2H), 0.93 (t, J = 7.6 Hz, 3H). |
| 251 | 4-((3-(1,1-difluoropropyl)phenyl)carbamoyl)-2-(4-methoxy-3-(3-methylpyridin-2-yl)phenyl)-5-methyloxazole 3-oxide<br>LCMS: (ESI) m/z: 494.2 [M + H] +;<br>1H NMR (400 MHz, DMSO-d6) δ: 12.75 (s, 1H), 8.49 − 8.44 (m, 2H), 8.35 (d, J = 2.4 Hz, 1H), 7.92 (s, 1H), 7.75 − 7.70 (m, 2H), 7.50 (t, J = 8.0 Hz, 1H), 7.40 (d, J = 8.8 Hz, 1H), 7.35 (dd, J = 4.8, 7.6 Hz, 1H), 7.29 (d, J = 8.4 Hz, 1H), 3.86 (s, 3H), 2.74 (s, 3H), 2.27 − 2.17 (m, 2H), 2.10 (s, 3H), 0.92 (t, J = 7.2 Hz, 3H). |
| 253 | 5-((3-(1,1-difluoropropyl)phenyl)carbamoyl)-2-(4-methoxyphenyl)-4-methyl-2H-1,2,3-triazole 1-oxide<br>LCMS: (ESI) m/z: 403.2 [M + H] +;<br>1H NMR (400 MHz, MeOD-d4) δ: 8.21 − 8.15 (m, 1H), 8.10 − 8.03 (m, 2H), 8.00 − 7.93 (m, 1H), 7.75 − 7.68 (m, 1H), 7.54 (d, J = 7.8 Hz, 1H), 7.43 − 7.35 (m, 2H), 4.5(s, 3H), 2.89 (s, 3H), 2.51 − 2.38 (m, 2H), 1.26 − 1.21 (m, 3H). |
| 257 | 5'-(difluoromethoxy)-N-(3-(1,1-difluoropropyl)phenyl)-6-methyl-[2,2'-bipyridine]-4-carboxamide<br>LCMS: (ESI) m/z: 434.0 [M + H] +;<br>1H NMR (MeOD-d4, 400 MHz) δ: 8.58 (s, 1H), 8.54 (d, J = 2.8 Hz, 1H), 8.47 (d, J = 8.8 Hz, 1H), 7.91-7.97 (m, 1H), 7.84 ( d, J = 8.0 Hz, 1H), 7.68 − 7.77 (m, 2H), 7.47 (t, J = 8.0 Hz, 1H), 7.29 (d, J = 7.6 Hz, 1H), 7.01 (t, J = 73.2 Hz, 1H), 2.69 (s, 3H), 2.11 − 2.28 (m, 2H), 0.99 (t, J = 7.2 Hz, 3H). |

-continued

| Compound Number | IUPAC Compound name, Mass Spectra and H-NMR data |
|---|---|
| 258 | N-(3-(1,1-difluoroethyl)phenyl)-2-(4-(difluoromethoxy)-3-(pyridin-2-yl)phenyl)-5-methyloxazole-4-carboxamide<br>LCMS: (ESI) m/z: 486.0 [M + H] +;<br>1H NMR (400 MHz, MeOD-d4) δ: 8.71 - 8.70 (m, 1H), 8.44 (d, J = 2.0 Hz, 1H), 8.20 (dd, J = 2.4, 8.8 Hz, 1H), 7.99 (s, 1H), 7.96 (td, J = 1.6, 7.6 Hz, 1H), 7.83 - 7.80 (m, 2H), 7.49 - 7.43 (m, 3H), 7.31 (dd, J = 0.8, 7.6 Hz 1H), 6.97 (t, J = 73.2 Hz, 3H), 2.76 (s, 3H), 1.94 (t, J = 18.0 Hz, 3H). |
| 259 | 2-(4-(difluoromethoxy)-3-(pyridin-2-yl)phenyl)-N-(3-(1,1-difluoropropyl)phenyl)-5-methyloxazole-4-carboxamide<br>LCMS: (ESI) m/z: 500.2 [M + H] +;<br>1H NMR (400 MHz, MeOD-d4) δ: 8.71 - 8.70 (m, 1H), 8.45 (d, J = 2.4 Hz, 1H), 8.20 (dd, J = 2.4, 8.8 Hz, 1H), 7.96 - 7.95 (m, 2H), 7.83 - 7.81 (m, 2H), 7.50 - 7.45 (m, 3H), 7.27 (d, J = 6.8 Hz, 1H), 6.97 (t, J = 73.2 Hz, 1H), 2.79 (s, 3H), 2.27 - 2.13 (m, 2H), 0.99 (t, J = 7.6 Hz, 3H). |
| 260 | 2-(5-(difluoromethoxy)-6-phenylpyridin-2-yl)-N-(3-(1,1-difluoropropyl)phenyl)-5-methyl-1 H-imidazole-4-carboxamide<br>LCMS: (ESI) m/z: 499.1 [M + H] +;<br>1H NMR (400 MHz, MeOD-d4) δ: 8.18 (d, J = 8.8 Hz, 1H), 7.99 - 7.95 (m, 3H), 7.85 - 7.78 (m, 2H), 7.52 - 7.42 (m, 4H), 7.24 (d, J = 8.0 Hz, 1H), 6.89 (t, J = 72.8 Hz, 1H), 2.65 (s, 3H), 2.28 - 2.14 (m, 2H), 1.00 (t, J = 7.6 Hz, 3H). |
| 272 | N-(3-(1,1-difluoropropyl)phenyl)-6-methoxy-2-methyl-4-oxo-1,4-dihydroquinoline-3-carboxamide<br>LCMS: (ESI) m/z: 387.1 [M + H] +;<br>1H NMR (400 MHz, MeOD-d4) δ:7.92 (s, 1H), 7.72 (d, J = 2.8 Hz, 2H), 7.55 (d, J = 9.0 Hz, 1H), 7.43 (s, 1H), 7.37 (dd, J = 2.8, 9.0 Hz, 1H), 7.27 - 7.18 (m, 1H), 3.92 (s, 3H), 2.88 (s, 3H), 2.13 - 2.27 (m, 2H), 1.00 (t, J = 7.4 Hz, 3H). |
| 273 | N-(3-(1,1-difluoropropyl)phenyl)-7-methoxy-2-methyl-4-oxo-1,4-dihydroquinoline-3-carboxamide<br>LCMS: (ESI) m/z: 387.1 [M + H] +;<br>1H NMR (400 MHz, MeOD-d4) δ: 8.20 (d, J = 9.0 Hz, 1H), 7.90 (s, 1H), 7.70 (br d, J = 8.3 Hz, 1H), 7.46 - 7.39 (m, 1H), 7.21 (br d, J = 7.8 Hz, 1H), 7.12 - 7.01 (m, 1H), 7.00 - 6.90 (m, 1H), 3.92 (s, 3H), 2.87 (s, 3H), 2.26 - 2.14 (m, 2H), 0.99 (t, J = 7.6 Hz, 3H). |
| 275 | N-(3-(1,1-difluoropropyl)phenyl)-3-hydroxy-1-(4-methoxybenzyl)-2-(4-methoxyphenyl)piperidine-4-carboxamide<br>LCMS: (ESI) m/z: 525.4 [M + H] +;<br>1H NMR (400 MHz, CDC13-d) δ: 9.22 (s, 0.6H), 8.56 (s, 0.4H), 7.69 - 7.50 (m, 2H), 7.44 - 7.30 (m, 3H), 7.17 - 7.11 (m, 3H), 6.97 - 6.95 (m, 2H), 6.86 - 6.80 (m, 2H), 4.04 (s, 0.6H), 3.88 - 3.78 (m, 7H), 3.64 - 3.60 (m, 0.4H), 3.34 (s, 0.6H), 3.13 - 3.09 (m, 0.6H), 3.03 - 3.01(m, 0.4), 3.00 - 2.90 (m, 1H), 2.83 - 2.80 (m, 0.4H), 2.62 - 2.58 (m, 0.6H), 2.46 - 2.39 (m, 0.4H), 2.19 - 2.01 (m, 5.4H), 1.93 - 1.86 (m, 0.6H), 0.98 - 0.93 (m, 3H). |

Example 2

Biological Activity of Compounds of the Invention

ACSS2 Cell-Free Activity Assay (Cell-Free $IC_{50}$)

The assay is based on a coupling reaction with Pyrophosphatase: ACSS2 is converting ATP+CoA+Acetate=>AMP+pyrophosphate+Acetyl-CoA (Ac-CoA). Pyrophosphatase converts pyrophosphate, a product of the ACSS2 reaction, to phosphate which can be detected by measuring the absorbance at 620 nm after incubation with the Biomol green reagent (Enzo life Science, BML-AK111).

Cell-Free $IC_{50}$ Determination:

10 nM of human ACSS2 protein (OriGene Technologies, Inc) was incubated for 90 minutes at 37 C with various compounds' concentrations in a reaction containing 50 mM Hepes pH 7.5, 10 mM DTT, 90 mM KCl, 0.006% Tween-20, 0.1 mg/ml BSA, 2 mM $MgCl_2$, 10 μM CoA, 5 mM NaAc, 300 μM ATP and 0.5 U/ml Pyrophosphatase (Sigma). At the end of the reaction, Biomol Green was added for 30 minutes at RT and the activity was measured by reading the absorbance at 620 nm. $IC_{50}$ values were calculated using non-linear regression curve fit with 0% and 100% constrains (CDD Vault, Collaborative Drug Discovery, Inc.).

Results:

The results are presented in Table 2 below:

| Compound No. | ACSS2 Biochemical IC50 |
|---|---|
| 100 | + |
| 101 | ++ |
| 102 | + |
| 103 | + |
| 104 | + |
| 105 | + |
| 106 | + |
| 107 | + |
| 108 | + |
| 109 | ++ |
| 110 | ++ |
| 111 | + |
| 112 | ++ |
| 113 | + |
| 114 | + |
| 115 | + |
| 116 | + |
| 117 | + |
| 118 | + |
| 119 | + |
| 120 | + |
| 121 | ++ |
| 122 | +++ |

-continued

| Compound No. | ACSS2 Biochemical IC50 |
|---|---|
| 123 | + |
| 124 | + |
| 125 | + |
| 126 | + |
| 127 | + |
| 128 | ++ |
| 129 | ++ |
| 130 | ++ |
| 131 | + |
| 132 | + |
| 133 | + |
| 134 | + |
| 135 | ++ |
| 136 | ++ |
| 137 | ++ |
| 138 | + |
| 139 | + |
| 140 | + |
| 141 | + |
| 142 | + |
| 143 | + |
| 144 | + |
| 145 | ++ |
| 146 | + |
| 147 | ++ |
| 148 | + |
| 149 | + |
| 150 | + |
| 151 | + |
| 152 | + |
| 153 | + |
| 154 | + |
| 155 | + |
| 156 | + |
| 157 | + |
| 158 | + |
| 159 | ++ |
| 160 | +++ |
| 161 | +++ |
| 162 | ++ |
| 163 | +++ |
| 164 | + |
| 165 | + |
| 166 | + |
| 167 | + |
| 168 | ++ |
| 169 | + |
| 170 | + |
| 171 | + |
| 172 | ++ |
| 173 | + |
| 174 | + |
| 175 | ++ |
| 176 | ++ |
| 177 | ++ |
| 178 | ++ |
| 179 | ++ |
| 180 | ++ |
| 181 | ++ |
| 182 | ++ |
| 183 | + |
| 184 | + |
| 185 | + |
| 186 | ++ |
| 187 | + |
| 188 | ++ |
| 189 | ++ |
| 190 | ++ |
| 191 | ++ |
| 192 | ++ |
| 193 | + |
| 194 | ++ |
| 195 | + |
| 196 | ++ |
| 197 | + |

-continued

| Compound No. | ACSS2 Biochemical IC50 |
|---|---|
| 198 | + |
| 199 | ++ |
| 200 | + |
| 201 | + |
| 202 | ++ |
| 203 | + |
| 204 | +++ |
| 205 | +++ |
| 206 | +++ |
| 207 | +++ |
| 208 | +++ |
| 209 | +++ |
| 213 | + |
| 214 | + |
| 215 | + |
| 216 | + |
| 217 | + |
| 218 | + |
| 219 | + |
| 220 | + |
| 221 | + |
| 222 | + |
| 223 | + |
| 224 | ++ |
| 225 | ++ |
| 226 | + |
| 227 | + |
| 228 | ++ |
| 229 | ++ |
| 230 | + |
| 231 | + |
| 232 | + |
| 233 | + |
| 234 | + |
| 235 | + |
| 236 | ++ |
| 237 | + |
| 247 | ++ |
| 248 | +++ |
| 249 | +++ |
| 250 | + |
| 251 | + |
| 253 | + |
| 254 | + |
| 255 | + |
| 256 | + |
| 257 | + |
| 258 | + |
| 259 | + |
| 260 | + |
| 261 | + |
| 262 | + |
| 263 | + |
| 264 | + |
| 265 | + |
| 266 | + |
| 267 | + |
| 268 | + |
| 269 | + |
| 270 | + |
| 271 | ++ |
| 272 | ++ |
| 273 | ++ |
| 274 | +++ |
| 275 | + |
| 276 | + |
| 277 | +++ |
| 278 | + |
| 279 | + |

(+) $IC_{50}$ >100 nM
(++) $IC_{50}$ 1-100 nM
(+++) $IC_{50}$ <1 nM

What is claimed is:

1. A method of treating, suppressing, reducing the severity, reducing the risk of developing or inhibiting a disease or disorder selected from: cancer, human alcoholism, viral infection, alcoholic steatohepatitis (ASH), non alcoholic fatty liver disease (NAFLD), non-alcoholic steatohepatitis (NASH), metabolic disorder, neuropsychiatric disease, inflammatory condition or autoimmune disease or disorder, comprising administering a compound to a subject suffering from said disease or disorder under conditions effective to treat, suppress, reduce the severity, reduce the risk of developing, or inhibit said disease or disorder, wherein the compound is represented by the structure of formula (II):

(II)

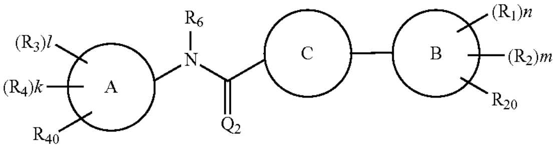

wherein

A and B rings are each independently a single or fused aromatic or heteroaromatic ring system, a single or fused C3-C10 cycloalkyl, a single or fused C3-C10 heterocyclic ring;

C ring is selected from the following (wavy line represents a connection point):

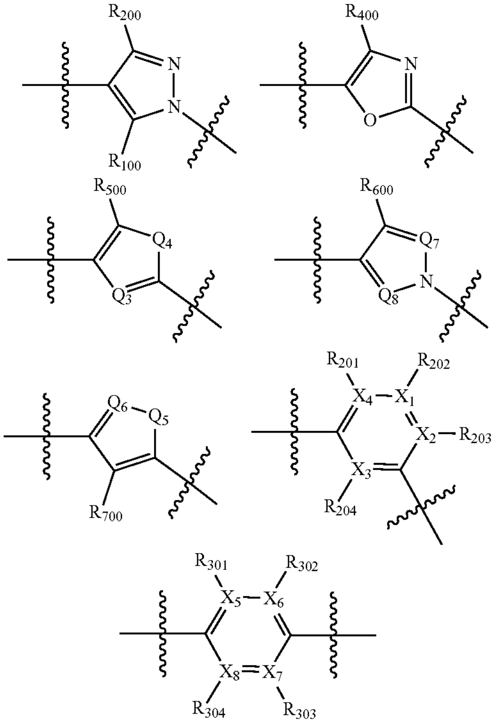

wherein $X_1$, $X_2$, $X_3$, $X_4$, $X_5$, $X_6$, $X_7$ and $X_8$ are each independently N, N—O, or C, wherein at least one of $X_1$, $X_2$, $X_3$, $X_4$, $X_5$, $X_6$, $X_7$ or $X_8$ is N, and wherein if $X_1$, $X_2$, $X_3$, $X_4$, $X_5$, $X_6$, $X_7$ or $X_8$ is N than its respective substituent is nothing;

$Q_3$, $Q_6$, $Q_7$ and $Q_8$ are each independently N, N—O, CH or C(R);

$Q_4$ and $Q_5$ are each independently O, NH or N(R);

$R_{200}$, $R_{400}$, $R_{500}$, and $R_{600}$ are each independently H or a $C_1$-$C_5$ linear or branched, substituted or unsubstituted alkyl;

$R_{201}$, $R_{202}$, $R_{203}$, $R_{204}$, $R_{301}$, $R_{302}$, $R_{303}$, and $R_{304}$ are each independently nothing, H or a $C_1$-$C_5$ linear or branched, substituted or unsubstituted alkyl;

$R_{100}$ and $R_{700}$ are each independently H, F, Cl, Br, I, OH, SH, $R_8$—SH, —$R_8$—O—$R_{10}$, $R_8$—($C_3$-$C_8$ cycloalkyl), $R_8$—($C_3$-$C_8$ heterocyclic ring), $CD_3$, $OCD_3$, CN, $NO_2$, —$R_8$CN, $N(R)_2$, $R_8$—N($R_{10}$)($R_{11}$), $R_9$—$R_8$—N($R_{10}$)($R_{11}$), $B(OH)_2$, —OC(O)—N($R_{10}$)($R_{11}$), —OC(O)$CF_3$, —$OCH_2$Ph, NHC(O)—$R_{10}$, NHCO—N($R_{10}$)($R_{11}$), —C(O)Ph, C(O)O—$R_{10}$, $R_8$—C(O)—$R_{10}$, C(O)—$R_{10}$, $C_1$-$C_5$ linear or branched C(O)-haloalkyl, C(O)NHR, C(O)N($R_{10}$)($R_{11}$), $SO_2R$, $SO_2N$($R_{10}$)($R_{11}$), $C_1$-$C_5$ linear or branched, substituted or unsubstituted alkyl, $C_1$-$C_5$ linear or branched, substituted or unsubstituted alkenyl, $C_1$-$C_5$ linear, branched or cyclic haloalkyl, $C_1$-$C_5$ linear, branched or cyclic alkoxy optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted $C_3$-$C_8$ heterocyclic ring, substituted or unsubstituted aryl, substituted or unsubstituted benzyl, or $CH(CF_3)$(NH—$R_{10}$);

$R_1$, $R_2$ and $R_{20}$ are each independently H, F, Cl, Br, I, OH, SH, $R_8$—SH, —$R_8$—O—$R_{10}$, $R_8$—($C_3$-$C_8$ cycloalkyl), $R_8$—($C_3$-$C_8$ heterocyclic ring), $CD_3$, $OCD_3$, CN, $NO_2$, —$R_8$CN, $N(R)_2$, $R_8$—N($R_{10}$)($R_{11}$), $R_9$—$R_8$—N($R_{10}$)($R_{11}$), $B(OH)_2$, —OC(O)$CF_3$, —$OCH_2$Ph, NHC(O)—$R_{10}$, NHCO—N($R_{10}$)($R_{11}$), —C(O)Ph, C(O)O—$R_{10}$, $R_8$—C(O)—$R_{10}$, C(O)—$R_{10}$, $C_1$-$C_5$ linear or branched C(O)-haloalkyl, C(O)NHR, C(O)N($R_{10}$)($R_{11}$), $SO_2R$, $SO_2N$($R_{10}$)($R_{11}$), $C_1$-$C_5$ linear or branched, substituted or unsubstituted alkyl, $C_1$-$C_5$ linear or branched, substituted or unsubstituted alkenyl, $C_1$-$C_5$ linear, branched or cyclic haloalkyl, $C_1$-$C_5$ linear, branched or cyclic alkoxy, optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted $C_3$-$C_8$ heterocyclic ring, substituted or unsubstituted aryl, substituted or unsubstituted benzyl, $CH(CF_3)$(NH—$R_{10}$);

or $R_2$ and $R_1$ are joint together to form a 5 or 6 membered substituted or unsubstituted, aliphatic or aromatic, carbocyclic or heterocyclic ring;

$R_3$, $R_4$ and $R_{40}$ are each independently H, F, Cl, Br, I, OH, SH, $R_8$—SH, —$R_8$—O—$R_{10}$, $CD_3$, $OCD_3$, CN, $NO_2$, —$R_8$CN, $N(R)_2$, $R_8$—N($R_{10}$)($R_{11}$), $R_9$—$R_8$—N($R_{10}$)($R_{11}$), $B(OH)_2$, —OC(O)$CF_3$, —$OCH_2$Ph, —NHCO—$R_{10}$, NHCO—N($R_{10}$)($R_{11}$), —C(O)Ph, C(O)O—$R_{10}$, $R_8$—C(O)—$R_{10}$, C(O)—$R_{10}$, $C_1$-$C_5$ linear or branched C(O)-haloalkyl, C(O)NHR, C(O)N($R_{10}$)($R_{11}$), $SO_2R$, $SO_2N$($R_{10}$)($R_{11}$), $C_1$-$C_5$ linear or branched, substituted or unsubstituted alkyl, $C_1$-$C_5$ linear, branched or cyclic haloalkyl, $C_1$-$C_5$ linear, branched or cyclic alkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted $C_3$-$C_8$ heterocyclic ring, substituted or unsubstituted aryl, or $CH(CF_3)(NH—R_{10})$;

or $R_3$ and $R_4$ are joint together to form a 5 or 6 membered substituted or unsubstituted, aliphatic or aromatic, carbocyclic or heterocyclic ring;

$R_6$ is H, $C_1$-$C_5$ linear or branched alkyl, C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl, C(O)R, $C(O)(OCH_3)$, or $S(O)_2R$;

or $R_{10}$ and $R_{11}$ are joint to form a substituted or unsubstituted $C_3$-$C_8$ heterocyclic ring;

R is H, $C_1$-$C_5$ linear or branched alkyl, $C_1$-$C_5$ linear or branched alkoxy, aryl or heteroaryl, or two gem R substituents are joint together to form a 5 or 6 membered heterocyclic ring;

m, n, l and k are each independently an integer between 0 and 4;

$Q_2$ is S, O, N—OH, $CH_2$, CH(R), C(R) 2 or N—OMe;

or a pharmaceutically acceptable salt thereof.

2. The method of claim 1, wherein the compound is selected from the following:

| Compound Number | Compound Structure |
|---|---|
| 106 | 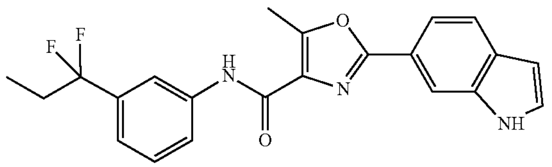 [SMILES: CCC(F)(F)c1cccc(NC(=O)c2nc(-c3ccc4cc[nH]c4c3)oc2C)c1] |
| 107 | 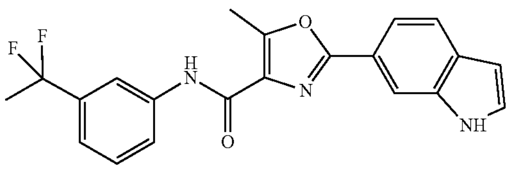 [SMILES: Cc1oc(-c2ccc3cc[nH]c3c2)nc1C(=O)Nc1cccc(C(C)(F)F)c1] |
| 222 | 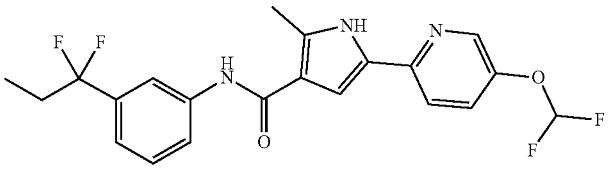 [SMILES: CCC(F)(F)c1cccc(NC(=O)c2cc(-c3ccc(OC(F)F)cn3)[nH]c2C)c1] |
| 223 | 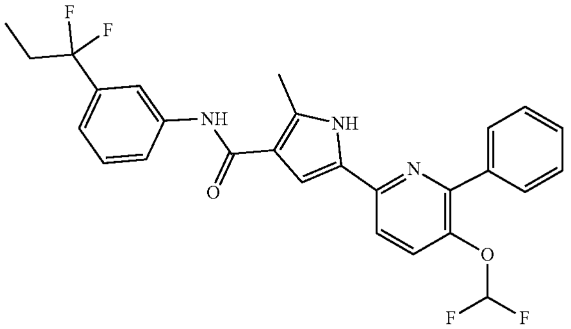 [SMILES: CCC(F)(F)c1cccc(NC(=O)c2cc(-c3ccc(OC(F)F)c(-c4ccccc4)n3)[nH]c2C)c1] |
| 227 | 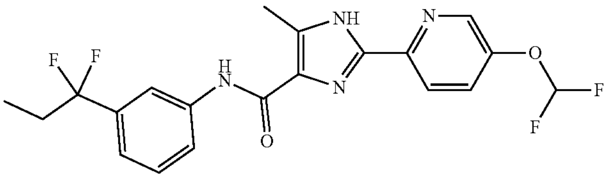 [SMILES: CCC(F)(F)c1cccc(NC(=O)c2nc(-c3ccc(OC(F)F)cn3)[nH]c2C)c1] |

-continued

| Compound Number | Compound Structure |
| --- | --- |
| 254 | 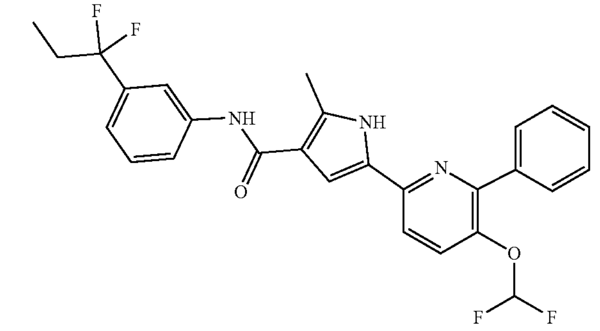 [SMILES: CCC(F)(F)c1cccc(NC(=O)c2cc(-c3ccc(OC(F)F)c(-c4ccccc4)n3)[nH]c2C)c1] |
| 256 | 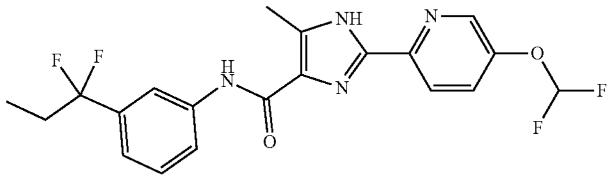 [SMILES: CCC(F)(F)c1cccc(NC(=O)c2nc(-c3ccc(OC(F)F)cn3)[nH]c2C)c1] |
| 257 | 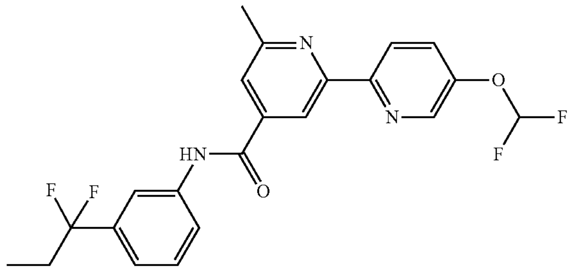 [SMILES: CCC(F)(F)c1cccc(NC(=O)c2cc(C)nc(-c3ccc(OC(F)F)cn3)c2)c1] |
| 260 | 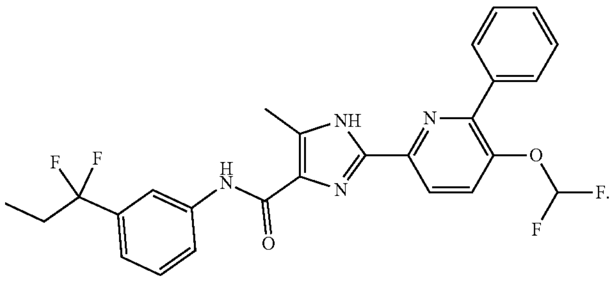 [SMILES: CCC(F)(F)c1cccc(NC(=O)c2nc(-c3ccc(OC(F)F)c(-c4ccccc4)n3)[nH]c2C)c1] |

3. The method of claim 1, wherein the cancer is selected from the list of: hepatocellular carcinoma, melanoma (e.g., BRAF mutant melanoma), glioblastoma, breast cancer (e.g., invasive ductal carcinomas of the breast, triple-negative breast cancer), prostate cancer, liver cancer, brain cancer, ovarian cancer, lung cancer, Lewis lung carcinoma (LLC), colon carcinoma, pancreatic cancer, renal cell carcinoma and mammary carcinoma; wherein the cancer is early cancer, advanced cancer, invasive cancer, metastatic cancer, drug resistant cancer or any combination thereof; wherein the subject has been previously treated with chemotherapy, immunotherapy, radiotherapy, biological therapy, surgical intervention, or any combination thereof; wherein the compound is administered in combination with an anti-cancer therapy, preferably wherein the anti-cancer therapy is chemotherapy, immunotherapy, radiotherapy, biological therapy, surgical intervention, or any combination thereof;

wherein the viral infection is human cytomegalovirus (HCMV) infection;

wherein the metabolic disorder is selected from: obesity, weight gain, hepatic steatosis and fatty liver disease; and/or wherein the neuropsychiatric disease or disorder is selected from: anxiety, depression, schizophrenia, autism and post-traumatic stress disorder.

4. The method of claim 1, wherein the C ring is:

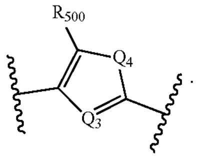

5. The method of claim 4, wherein $Q_4$ is NH and $Q_3$ is N or N—O.

6. The method of claim 4, wherein the B ring is a single or fused pyridine ring.

7. The method of claim 4, wherein the A ring is a phenyl ring, $R_{40}$ is $C_1$-$C_5$ linear, branched or cyclic haloalkyl, and l and k are both 0.

8. A compound of formula (II):

(II)

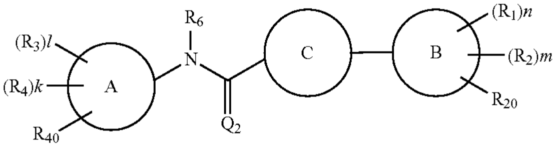

wherein

A is a single or fused aromatic ring system and B is a single or fused heteroaromatic ring system;

C ring is selected from the following (wavy line represents a connection point):

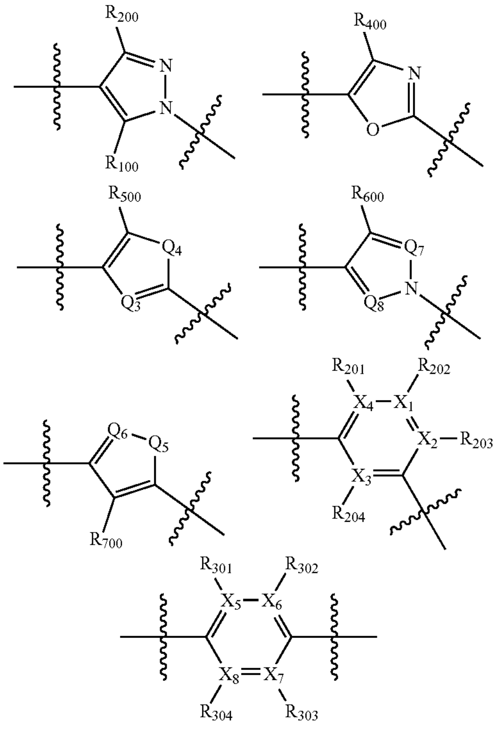

wherein $X_1$, $X_2$, $X_3$, $X_4$, $X_5$, $X_6$, $X_7$ and $X_8$ are each independently N, N—O, or C, wherein at least one of $X_1$, $X_2$, $X_3$, $X_4$, $X_5$, $X_6$, $X_7$, or $X_8$ is N, and wherein if $X_1$, $X_2$, $X_3$, $X_4$, $X_5$, $X_6$, $X_7$ or $X_8$ is N than its respective substituent is nothing;

$Q_3$, $Q_6$, $Q_7$ and $Q_8$ are each independently N, N—O, CH or C(R);

$Q_4$ and $Q_5$ are each independently O, NH or N(R);

$R_{200}$, $R_{400}$, $R_{500}$, and $R_{600}$ are each independently H or a $C_1$-$C_5$ linear or branched, substituted or unsubstituted alkyl;

$R_{201}$, $R_{202}$, $R_{203}$, $R_{204}$, $R_{301}$, $R_{302}$, $R_{303}$, and $R_{304}$ are each independently nothing, H or a $C_1$-$C_5$ linear or branched, substituted or unsubstituted alkyl;

$R_{100}$ and $R_{700}$ are each independently H, F, Cl, Br, I, OH, SH, $R_8$—SH, —$R_8$—θ-$R_{10}$, $R_8$—($C_3$-$C_8$ cycloalkyl), $R_8$—(C3-$C_8$ heterocyclic ring), $CD_3$, $OCD_3$, CN, $NO_2$, —$R_8$CN, $N(R)_2$, $R_8$—$N(R_{10})(R_{11})$, $R_9$—$R_8$—$N(R_{10})(R_{11})$, $B(OH)_2$, —OC(O)—$N(R_{10})(R_{11})$, —OC(O)$CF_3$, —$OCH_2$Ph, NHC(O)—$R_{10}$, NHCO—$N(R_{10})(R_{11})$, —C(O)Ph, C(O)O—$R_{10}$, $R_8$—C(O)—$R_{10}$, C(O)—$R_{10}$, $C_1$-$C_5$ linear or branched C(O)-haloalkyl, C(O) NHR, C(O)$N(R_{10})(R_{11})$, $SO_2R$, $SO_2N(R_{10})(R_{11})$, $C_1$-$C_5$ linear or branched, substituted or unsubstituted alkyl, $C_1$-$C_5$ linear or branched, substituted or unsubstituted alkenyl, $C_1$-$C_5$ linear, branched or cyclic haloalkyl, $C_1$-$C_5$ linear, branched or cyclic alkoxy optionally wherein at least one methylene group ($CH_2$) in the alkoxy is replaced with an oxygen atom, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted $C_3$-$C_8$ heterocyclic ring, substituted or unsubstituted aryl, substituted or unsubstituted benzyl, or $CH(CF_3)(NH—R_{10})$;

$R_1$, $R_2$ and $R_{20}$ are each independently H, F, Cl, Br, I, OH, SH, $R_8$—SH, —$R_8$—O—$R_{10}$, $R_8$—($C_3$-$C_8$ cycloalkyl), $R_8$—($C_3$-$C_8$ heterocyclic ring), $CD_3$, $OCD_3$, CN, $NO_2$, —$R_8$CN, $N(R)_2$, $R_8$—$N(R_{10})(R_{11})$, $R_9$—$R_8$—$N(R_{10})(R_{11})$, $B(OH)_2$, —OC(O) $CF_3$, —$OCH_2$Ph, NHC(O)—$R_{10}$, NHCO—$N(R_{10})(R_{11})$, —C(O)Ph, C(O)O—$R_{10}$, $R_8$—C(O)—$R_{10}$, C(O)—$R_{10}$, $C_1$-$C_5$ linear or branched C(O)-haloalkyl, C(O)NHR, C(O)$N(R_{10})(R_{11})$, $SO_2R$, $SO_2N(R_{10})(R_{11})$, $C_1$-$C_5$ linear or branched, substituted or unsubstituted alkyl, $C_1$-$C_5$ linear or branched, substituted or unsubstituted alkenyl, $C_1$-$C_5$ linear, branched or cyclic haloalkyl, $C_1$-$C_5$ linear, branched or cyclic alkoxy, optionally wherein at least one methylene group ($CH_2$) in the alkoxy is replaced with an oxygen atom, $C_1$-$C_5$ linear or branched alkoxyalkyl, substituted or unsubstituted $C_3$-$C_8$ cycloalkyl, substituted or unsubstituted $C_3$-$C_8$ heterocyclic ring, substituted or unsubstituted aryl, substituted or unsubstituted benzyl, $CH(CF_3)(NH—R_{10})$;

or $R_2$ and $R_1$ are joint together to form a 5 or 6 membered substituted or unsubstituted, aliphatic or aromatic, carbocyclic or heterocyclic ring;

$R_3$, $R_4$ and $R_{40}$ are each independently H, F, Cl, Br, I, OH, SH, $R_8$—SH, —$R_8$—O—$R_{10}$, $CD_3$, $OCD_3$, CN, $NO_2$, —$R_8$CN, $N(R)_2$, $R_8$—$N(R_{10})(R_{11})$, $R_9$—$R_8$—$N(R_{10})(R_{11})$, $B(OH)_2$, —OC(O)$CF_3$, —$OCH_2$Ph, —NHCO—$R_{10}$, NHCO—$N(R_{10})(R_{11})$, —C(O)Ph, C(O)O—$R_{10}$, $R_8$—C(O)—$R_{10}$, C(O)—$R_{10}$, $C_1$-$C_5$ linear or branched C(O)-haloalkyl, C(O)NHR, C(O)$N(R_{10})(R_{11})$, $SO_2R$, $SO_2N(R_{10})(R_{11})$, $C_1$-$C_5$ linear or branched, substituted or unsubstituted alkyl, $C_1$-$C_5$ linear, branched or cyclic haloalkyl, $C_1$-$C_5$ linear, branched or cyclic alkoxy, $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl, substituted or unsubstituted $C_3$-$C_8$ heterocyclic ring, substituted or unsubstituted aryl, or $CH(CF_3)(NH—R_{10})$;

or $R_3$ and $R_4$ are joint together to form a 5 or 6 membered substituted or unsubstituted, aliphatic or aromatic, carbocyclic or heterocyclic ring;

$R_6$ is H, $C_1$-$C_5$ linear or branched alkyl, C(O)R, or $S(O)_2R$;

$R_8$ is $[CH_2]_p$ wherein p is between 1 and 10;

$R_9$ is $[CH]_q$, $[C]_q$ wherein q is between 2 and 10;

$R_{10}$ and $R_{11}$ are each independently H, CN, $C_1$-$C_5$ linear or branched alkyl, C(O)R, C(O)($OCH_3$), or $S(O)_2R$;

or $R_{10}$ and Ru are joint to form a substituted or unsubstituted $C_3$-$C_8$ heterocyclic ring;

R is H, $C_1$-$C_5$ linear or branched alkyl, $C_1$-$C_5$ linear or branched alkoxy, aryl or heteroaryl, or two gem R substituents are joint together to form a 5 or 6 membered heterocyclic ring;

m, n, l and k are each independently an integer between 0 and 4;

$Q_2$ is S, O, N—OH, $CH_2$, CH(R), $C(R)_2$ or N—OMe;

or a pharmaceutically acceptable salt thereof.

9. The compound of claim 8, wherein the C ring is:

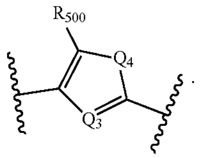

10. The compound of claim 9, wherein $Q_4$ is NH and $Q_3$ is N or N—O.

11. The compound of claim 8, wherein the B ring is a single or fused pyridine ring.

12. The compound of claim 8, wherein $R_{40}$ is $C_1$-$C_5$ linear, branched or cyclic haloalkyl, and l and k are both 0.

13. The compound of claim 8, wherein n and m are both 1, $R_{20}$ is selected from H, F, Cl, Br, I, $C_1$-$C_5$ linear, branched or cyclic alkoxy, and substituted or unsubstituted aryl, $R_1$ is selected from F, Cl, Br, I, $C_1$-$C_5$ linear, branched or cyclic alkoxy, and substituted or unsubstituted aryl, and $R_2$ is selected from F, Cl, Br, I, $C_1$-$C_5$ linear, branched or cyclic alkoxy, and substituted or unsubstituted aryl.

* * * * *